US012595284B2

(12) United States Patent
McDonagh et al.

(10) Patent No.:    US 12,595,284 B2
(45) Date of Patent:         Apr. 7, 2026

(54) AMATOXIN ANTIBODY-DRUG CONJUGATES AND USES THEREOF

(71) Applicant: Heidelberg Pharma Research GmbH, Ladenburg (DE)

(72) Inventors: Charlotte Fenton McDonagh, Winchester, MA (US); Rajiv Panwar, Acton, MA (US); Torsten Hechler, Ladenburg (DE); Michael Kulke, Ladenburg (DE); Ganapathy N. Sarma, San Ramon, CA (US); Andreas Pahl, Ladenburg (DE); Christoph Mueller, Ladenburg (DE); Werner Simon, Ladenburg (DE); Christian Lutz, Ladenburg (DE); Francesca Gallo, Ladenburg (DE)

(73) Assignee: Heidelberg Pharma Research GmbH, Ladenburg (DE)

( * ) Notice: Subject to any disclaimer, the term of this patent is extended or adjusted under 35 U.S.C. 154(b) by 1095 days.

(21) Appl. No.: 17/605,766

(22) PCT Filed: Apr. 24, 2020

(86) PCT No.: PCT/EP2020/061555
§ 371 (c)(1),
(2) Date: Oct. 22, 2021

(87) PCT Pub. No.: WO2020/216947
PCT Pub. Date: Oct. 29, 2020

(65) Prior Publication Data
US 2023/0135930 A1      May 4, 2023

Related U.S. Application Data

(60) Provisional application No. 62/838,290, filed on Apr. 24, 2019.

(51) Int. Cl.
A61K 47/68        (2017.01)
A61K 45/06        (2006.01)
(Continued)

(52) U.S. Cl.
CPC ................ C07K 7/64 (2013.01); A61K 45/06 (2013.01); A61K 47/6831 (2017.08);
(Continued)

(58) Field of Classification Search
None
See application file for complete search history.

(56) References Cited

U.S. PATENT DOCUMENTS 8,354,509 B2     1/2013  Carven et al.
2012/0100161 A1   4/2012  Faulstich et al.
(Continued)

FOREIGN PATENT DOCUMENTS

JP        2018-513120 A      5/2018
WO     WO 2010/115629 A2   10/2010
(Continued)

OTHER PUBLICATIONS

Japan Patent Office, Office Action in Japanese Patent Application No. 2021-562940 (Nov. 7, 2023).
(Continued)

*Primary Examiner* — Karl J Puttlitz
(74) *Attorney, Agent, or Firm* — Grüneberg Global IP, PLLC

(57)              ABSTRACT

Amatoxins, as well as antibody-drug conjugates (ADCs) comprising an amatoxin are provided, as well as compositions and methods of using the same. The compositions and methods provided herein can be used for cancer therapy. They can also be used to prepare a patient for hematopoietic stem cell transplant therapy and to improve the engraftment of hematopoietic stem cell transplants by selectively deplet- (Continued)

A                              B                              C ing endogenous hematopoietic stem cells prior to the transplant procedure. Methods and compositions for the treatment of various hematopoietic diseases, metabolic disorders, cancers, and autoimmune diseases, as well as prevention of graft-versus-host-disease (GVHD), are provided.

18 Claims, 57 Drawing Sheets

Specification includes a Sequence Listing.

(51) Int. Cl.
  *A61P 35/00* (2006.01)
  *C07K 7/64* (2006.01)
  *C07K 16/28* (2006.01)
(52) U.S. Cl.
  CPC .......... *A61K 47/6867* (2017.08); *A61P 35/00* (2018.01); *C07K 16/2803* (2013.01); *C07K 2317/565* (2013.01); *C07K 2319/55* (2013.01)

(56) References Cited

U.S. PATENT DOCUMENTS

| | | | |
|---|---|---|---|
| 2016/0002298 A1 | 1/2016 | Müller et al. | |
| 2017/0349666 A1 | 12/2017 | Klein et al. | |
| 2018/0043033 A1* | 2/2018 | Anderl ............... | A61K 47/6889 |
| 2019/0218308 A1 | 7/2019 | Chanteux et al. | |
| 2020/0407440 A1 | 12/2020 | McDonagh et al. | |
| 2021/0077571 A1 | 3/2021 | Müller et al. | |
| 2021/0206872 A1* | 7/2021 | Pearse .................. | A61K 35/545 |
| 2022/0133902 A1 | 5/2022 | Kulke et al. | |
| 2022/0370632 A1 | 11/2022 | Hechler et al. | |
| 2023/0355792 A1 | 11/2023 | Kulke et al. | |
| 2024/0165257 A1 | 5/2024 | Hechler et al. | |
| 2024/0307549 A1 | 9/2024 | Kulke et al. | |
| 2025/0009901 A1 | 1/2025 | Kulke et al. | |
| 2025/0064960 A1 | 2/2025 | Hechler et al. | |

FOREIGN PATENT DOCUMENTS

| | | | |
|---|---|---|---|
| WO | 2011/092295 A2 | 8/2011 | |
| WO | WO 2012/041504 A1 | 4/2012 | |
| WO | 2013/088363 A1 | 6/2013 | |
| WO | 2014/135282 A1 | 9/2014 | |
| WO | WO 2016/142049 A1 | 9/2016 | |
| WO | 2017/149077 A1 | 9/2017 | |
| WO | WO 2017/210288 A1 | 12/2017 | |
| WO | WO 2018/115466 A1 | 6/2018 | |
| WO | WO 2018/134787 A2 | 7/2018 | |
| WO | 2019/030171 A1 | 2/2019 | |
| WO | WO 2019/030173 A1 | 2/2019 | |
| WO | 2019/197654 A1 | 10/2019 | |
| WO | 2020/216947 A1 | 10/2020 | |
| WO | 2022/096604 A1 | 5/2022 | |

OTHER PUBLICATIONS

International Property Office of Singapore, Search Report in Singaporean Patent Application No. 11202110287Q (Nov. 26, 2023).
International Property Office of Singapore, Written Opinion in Singaporean Patent Application No. 11202110287Q (Nov. 27, 2023).
Cormedi et al., "Predicting immunotherapy response through genomics", Current opinion in Genetics & Development, vol. 66, Feb. 2021, pp. 1-9.
Drew M. Pardoll, "The blockade of immune checkpoints in cancer immunotherapy", Nat. Rev. Cancer, vol. 12, Apr. 2012, pp. 252-264.
Deckert et al., "A novel anti-CD37 antibody-drug conjugate with multiple anti-tumor mechanisms for the treatment of B-cell malignancies", Blood, vol. 122, No. 20, Nov. 14, 2013, pp. 3500-3510.

Darvin et al., "Immune checkpoint inhibitors: recent progress and potentia biomarkers", Experimental and Molecular Medicine, vol. 50, No. 165, Dec. 13, 2018, pp. 1-11.
Edwards et al., "Current Opinion in Genetics & Development", J. Mol. Biol., vol. 334, No. 1, Nov. 14, 2003, pp. 103-118.
Kroemer et al., "Immunogenic Cell Death in Cancer Therapy", Annu. Rev. Immunol., vol. 31, 2013, pp. 51-72.
Li et al., "A Mini-Review for Cancer Immunotherapy: Molecular Understanding of PD-1/PD-L1 Pathway & Translational Blockade of Immune Checkpoints", Int. J. Mo. Sci., vol. 17, No. 1151, 2016, pp. 1-22.
Lloyd et al., "Modelling the human immune response: performance of a $10^{11}$ human antibody repertoire against a broad panel of therapeutically relevant antigens", Protein Engineering, Design & Selection, vol. 22, No. 3, Oct. 4, 2008, pp. 159-168.
Marshall et al., "Immuno-Oncology: Emerging Targets and Combination Therapies", Frontiers in Oncology, vol. 8, Article 315, Aug. 23, 2018, pp. 1- 29.
Martin E. Hemler, "Specific tetraspanin functions", The Journal of Cell Biology, vol. 155, No. 7, Dec. 24, 2001, pp. 1103-1107.
Martins et al., "Adverse effects of immune-checkpoint inhibitors: epidemiology, management and surveillance", Nat. Rev. Clin. Oncol., vol. 16, No. 9, Sep. 2019, pp. 563-580.
Obeid et al., "Calreticulin exposure dictates the immunogenicity of cancer cell death", Nat. Med., vol. 13, No. 1, Jan. 2007, pp. 54-61.
Office Action received for U.S. Appl. No. 17/518,911, mailed on Jul. 20, 2023, 34 pages.
Office Action received for U.S. Appl. No. 17/697,583, mailed on Aug. 7, 2023, 31 pages.
Office Action received for U.S. Appl. No. 17/697,583, mailed on Feb. 27, 2024, 19 pages.
Office Action received for U.S. Appl. No. 17/518,911, mailed on Mar. 6, 2024, 41 pages.
Office Action received for U.S. Appl. No. 17/697,583, mailed on Nov. 22, 2024, 22 pages.
Pereira et al., "AGS67E, an Anti-CD37 Monomethyl Auristatin E Antibody-Drug Conjugate as a Potential Therapeutic for B/T-Cell Malignancies and AML: A New Role for CD37 in AML", Mol. Cancer Ther., vol. 14, No. 7, Jul. 2015, pp. 1-24.
Qin et al., "Novel immune checkpoint targets: moving beyond PD-1 and CTLA-4", Mol. Cancer, vol. 18, No. 155, Nov. 6, 2019, pp. 1-14.
Sambi et al., "Current Challenges in Cancer Immunotherapy: Multimodal Approaches to Improve Efficacy and Patient Response Rates", J. Oncol., Feb. 28, 2019, pp. 1-13.
Singh et al., "Immune checkpoint inhibitors: a promising anticancer therapy", Drug Discov. Today, vol. 25, No. 1, Jan. 2020, pp. 223-229.
Stathis et al., "Safety, Tolerability, and Preliminary Activity of IMGN529, a CD37-targeted Antibody-Drug Conjugate, in Patients with Relapsed or Refractory B-cell non-Hodgkin Lymphoma: a Dose-escalation, Phase I Study", Invest. New Drugs., vol. 36, No. 5, Feb. 17, 2018, pp. 869-876.
Strop et al., "Location matters: site of conjugation modulates stability and pharmacokinetics of antibody drug conjugates", Chemistry and Biology, vol. 20, Feb. 21, 2013, pp. 161-167.
Taams et al., "Immune checkpoint inhibition: from molecules to clinical application", Clinical and Experimental Immunology., vol. 200, No. 2, 2020, pp. 105-107.
Vaisitti et al., "Anti-CD37 Alpha-Amanitin Conjugated Antibodies as Therapeutic Weapons for Richter's Syndrome", Blood, vol. 138, Suppl. 1, Nov. 5, 2021, pp. 791-792.
Voss et al., "Abstract 915: Preclinical Evaluation of Anti-CD37 Antibody-targeted Amanitin Conjugates (ATAC) in B-cell Malignancies", Cancer Res., vol. 81, Suppl. 13, Jul. 1, 2021, pp. 1-5.
Wei et al., "Fundamental Mechanisms of Immune Checkpoint Blockade Therapy", Cancer Discov., vol. 8, No. 9, Aug. 16, 2018, pp. 1069-1086.
Wieland et al., "Amatoxins, Phallotoxins, Phallolysin, and Antamanide: The Biologically Active Components of Poisonous Amanita Mushroom", Critical Review in Biochem., vol. 5, No. 3, Dec. 1978, pp. 185-260.

(56)     References Cited

OTHER PUBLICATIONS

Witkowska et al., "Investigational therapies targeting CD37 forthe treatment of B-cell lymphoid malignancies", Expert Opinion on Investigational Drugs, vol. 27, No. 2, Jan. 15, 2018, pp. 171-177.

Wu et al., "Humanization of a murine monoclonal antibody by simultaneous optimization of framework and CDR residues", J. Mol. Biol., vol. 294, Issue 1, Nov. 19, 1999, pp. 151-162.

Xu-Monette et al., "Assessment of CD37 B-cell antigen and cell of origin significantly improves risk prediction in diffuse large B-cell lymphoma", Blood., vol. 128, No. 26, Dec. 29, 2016, pp. 3083-3100.

Zou et al., "Expression and Function of Tetraspanins and Their Interacting Partners in B Cells", Front. Immunol., vol. 9, Article 1606, Jul. 18, 2018, pp. 1-17.

U.S. Appl. No. 17/518,911, filed Nov. 4, 2021, 2022/0133902, Kulke et al.

U.S. Appl. No. 17/697,583, filed Mar. 17, 2022, 2022/0370632, Hechler et al.

Barbas III et al., "Assembly of combinatorial antibody libraries on phage surfaces: The gene III site", Proc. Natl. Acad. Sci. USA, vol. 88, Sep. 1991, pp. 7978-7982.

Binz et al., "Engineering novel binding proteins from nonimmunoglobulin domains", Nature Biotechnology, vol. 23, No. 10, Oct. 6, 2005, pp. 1257-1268.

Bird et al., "Single-Chain Antigen-Binding Proteins", Science, vol. 242, Oct. 21, 1988, pp. 423-426.

Bradley A. Katz, "Structural and mechanistic determinants of affinity and specificity of ligands discovered or engineered by phage display", Annu. Rev. Biophys. Biomol. Struct., vol. 26, 1997, pp. 27-45.

Branco et al., "Selective deletion of antigen-specific, activated T Cells by a humanized MAB to CD2 (Medi-507) is mediated by NK Cells", Transplantation, vol. 68, No. 10, Nov. 27, 1999, pp. 1588-1596.

Brian K. Kay, "Biologically displayed random peptides as reagents in mapping protein-protein interactions", Perspective in Drug Discovery and Design, vol. 2, Mar. 9, 1995, pp. 251-268.

Cannons et al., "4-1BB ligand induces cell division, sustains survival, and enhances effector function of CD4 and CD8 T cells with similar efficacy", The Journal of Immunology, May 29, 2001, pp. 1313-1324.

Carl et al., "A novel connector linkage applicable in prodrug design", J. Med. Chem., vol. 24, No. 5, May 1981, pp. 479-480.

Chakravarty et al., "Plasmin-activated prodrugs for cancer chemotherapy. 2. Synthesis and biological activity of peptidyl derivatives of doxorubicin", J. Med. Chem., vol. 26, No. 5, Jun. 28, 1982, pp. 638-644.

Chin et al., "Structure of the 4-1BB/4-1BBL complex and distinct binding and functional properties of utomilumab and urelumab", Nature communications, vol. 9, No. 4679, Nov. 8, 2018, pp. 1-13.

Chiswell et al., "Phage antibodies: will new 'coliclonal' antibodies replace monoclonal antibodies?", Trends Biotechnol., vol. 10, Mar. 1992, pp. 80-84.

Clackson et al., "Making antibody fragments using phage display libraries", Nature, vol. 352, Aug. 15, 1991, pp. 624-628.

Cox et al., "A directory of human germ-line $V_X$ segments reveals a strong bias in their usage", Eur. J. Immunol., vol. 24, Dec. 23, 1993, pp. 827-836.

Dall'Acqua et al., "Properties of human IgG1s engineered for enhanced binding to the neonatal Fc receptor (FcRn)", The Journal of Biological Chemistry, vol. 281, No. 33, Aug. 18, 2006, pp. 23514-23524.

Datta-Mannan et al., "Humanized IgG$_1$ Variants with Differential Binding Properties to the Neonatal Fc Receptor: Relationship to Pharmacokinetics in Mice and Primates", Drug Metab. Dispos., vol. 35, No. 1, Oct. 11, 2006, pp. 86-94.

De Groot et al., "Elongated Multiple Electronic Cascade and Cyclization Spacer Systems in Activatible Anticancer Prodrugs for Enhanced Drug Release", J. Org. Chem., vol. 66, No. 26, Jul. 3, 2001, pp. 8815-8830.

Doronina et al., "Enhanced Activity of Monomethylauristatin F through Monoclonal Antibody Delivery: Effects of Linker Technology on Efficacy and Toxicity", Bioconjugate Chem., vol. 17, Oct. 19, 2005, pp. 114-124.

Dubowchik et al., "Receptor-mediated and enzyme-dependent targeting of cytotoxic anticancer drugs", Pharmacology & Therapeutics, vol. 83, 1999, pp. 67-123.

Dubrot et al., "Treatment with anti-CD137 mAbs causes intense accumulations of liver T cells without selective antitumor immunotherapeutic effects in this organ", Cancer immunology, immunotherapy, vol. 59, Mar. 25, 2010, pp. 1223-1233.

Edelman et al., "The covalent structure of an entire γG immunoglobulin molecule", Proc. N. A. S., vol. 63, Mar. 21, 1969, pp. 78-85.

Felici et al., "Peptide and protein display on the surface of filamentous bacteriophage", Biotechnol. Annual Rev., vol. 1, 1995, pp. 149-183.

Fisher et al., "Targeting of 4-1BB by monoclonal antibody PF-05082566 Enhances T-cell function and promotes anti-tumor activity", Cancer Immunology, Immunotherapy, vol. 61, Mar. 11, 2012, pp. 1721-1733.

Graham et al., "Characteristics of a human cell line transformed by DNA from human adenovirus type 5", J. Gen Virol., vol. 36, Feb. 10, 1977, pp. 59-72.

Greg T. Hermanson, "Bioconjugate Techniques", Second Edition, 2008, pp. 1-1202.

Hay et al., "A 2-nitroimidazole carbamate prodrug of 5-amimo-1-(chloromethyl)-3-[(5,6,7-trimethoxyindol-2-YL)carbonyl]-1,2-dihydro-3H-benz[E]indole (amino-seco-CBI-TMI) for use with ADEPT and GDEPT", Bioorganic & Medicinal Chemistry Letters, vol. 9, Jun. 25, 1999, pp. 2237-2242.

Hermiston et al., "CD45: A critical regulator of signaling thresholds in immune cells", Annu. Rev. Immunol., vol. 21, 2003, pp. 107-137.

Hinton et al., "Engineered Human IgG Antibodies with Longer Serum Half-lives in Primates", The Journal of Biological Chemistry, vol. 279, No. 8, Feb. 20, 2004, pp. 6213-6216.

Hinton et al., "An Engineered Human IgG1 Antibody with Longer Serum Half-Life", The Journal of Immunology, vol. 176, No. 1, Jan. 1, 2006, pp. 346-356.

Holliger et al., ""Diabodies": Small bivalent and bispecific antibody fragments", Proc. Natl. Acad. Sci. USA, vol. 90, Jul. 1993, pp. 6444-6448.

Hoogenboom et al., "Antibody phage display technology and its applications", Immunotechnology, vol. 4, Feb. 13, 1998, pp. 1-20.

Huston et al., "Protein engineering of antibody binding sites: recovery of specific activity in an anti-digoxin single-chain Fv analogue produced in *Escherichia coli*", Proc. Natl. Acad. Sci. USA, vol. 85, Aug. 1988, pp. 5879-5883.

Ishiyama et al., "The increase of CD5$^{LOW+}$ NK Cells in Patients with multiple Myeloma and plasmacytoma", Anticancer Research, vol. 14, Feb. 15, 1994, pp. 725-730.

Jain et al., "Current ADC Linker Chemistry", Pharm. Res., vol. 32, Mar. 11, 2015, pp. 3526-3540.

Jennie P. Mather, "Establishment and characterization of two distinct mouse testicular epithelial cell lines", Biol. Reprod., vol. 23, Apr. 29, 1980, pp. 243-251.

Jones et al., "Isolation of complementary DNA clones encoding the human lymphocyte glycoprotein T1/Leu-1", Nature, vol. 323, Sep. 25, 1986, pp. 346-349.

Junutula et al., "Site-specific conjugation of a cytotoxic drug to an antibody improves the therapeutic index", Nature Biotechnology, vol. 26, No. 8, Aug. 2008, pp. 925-932.

Kabat et al., "Sequences of Proteins of Immunological Interest", Fifth Edition, U.S. Department of Health and Human Services, vol. 1, 1991, 1238 pages.

Kay et al., "High-throughput screening strategies to identify inhibitors of protein-protein interactions", Mol. Divers., vol. 1, 1995, pp. 139-140.

Kim et al., "Mapping the site on human IgG for binding of the MHC class I-related receptor, FcRn", Eur. J. Immunol., vol. 29, 1999, pp. 2819-2825.

(56)    References Cited

OTHER PUBLICATIONS

Laguzza et al., "New antitumor monoclonal antibody-vinca conjugates LY203725 and related compounds: design, preparation, and representative in vivo activity", J. Med. Chem., vol. 32, No. 3, Feb. 26, 1988, pp. 548-555.

Leriche et al., "Cleavable linkers in chemical biology", Bioorg. Med. Chem., vol. 20, Jul. 30, 2011, pp. 571-582.

Li et al., "cGMP production of astatine-211-labeled anti-CD45 antibodies for use in allogeneic hematopoietic cell transplantation for treatment of advanced hematopoietic malignancies", PloS one, vol. 13, Oct. 18, 2018, pp. 1-17.

Liu et al., "New procedures for preparation and isolation of conjugates of proteins and a synthetic copolymer of D-amino acids and immunochemical characterization of such conjugates", Biochemistry, vol. 18, No. 4, 1979, pp. 690-697.

Makkouk et al., "Characterizing CD137 upregulation on NK cells in patients receiving monoclonal antibody therapy", Annals of Oncology, vol. 28, Nov. 9, 2016, pp. 415-420.

Martinez-Forero et al., "T Cell Costimulation with Anti-CD137 Monoclonal Antibodies Is Mediated by K63—Polyubiquitin-Dependent Signals from Endosomes", J. of Immunology, vol. 190, No. 12, Jun. 15, 2013, pp. 6694-6706.

Mather et al., "Culture of testicular cells in hormone-supplemented serum-free medium", Annals N.Y. Acad. Sci., vol. 383, 1982, pp. 44-68.

Matinkhoo et al., "Synthesis of the Death-Cap Mushroom Toxin α-Amanitin", J. Am. Chem. Soc., vol. 140, Mar. 21, 2018, pp. 6513-6517.

McCafferty et al., "Phage antibodies: filamentous phage displaying antibody variable domains", Nature, vol. 348, Dec. 6, 1990, pp. 552-554.

Neville Jr. et al., "Enhancement of immunotoxin efficacy by acid-cleavable cross-linking agents utilizing diphtheria toxin and toxin mutants", Biol. Chem., vol. 264, No. 25, Sep. 5, 1989, pp. 14653-14661.

Orozco et al., "Anti-CD45 radioimmunotherapy without TBI before transplantation facilitates persistent haploidentical donor engraftment", Blood, vol. 127, No. 3, Jan. 21, 2016, pp. 352-359.

Palchaudhuri et al., "Non-genotoxic conditioning for hematopoietic stem cell transplantation using a hematopoietic-cell-specific internalizing immunotoxin", Nature Biotechnology, vol. 34, No. 7, Jul. 2016, pp. 738-749.

Petkova et al., "Enhanced half-life of genetically engineered human IgG1 Antibodies in a humanized FcRn mouse model: potential application in humorally mediated autoimmune disease", International Immunology, vol. 18, No. 12, Oct. 31, 2006, pp. 1759-1769.

Rathanaswami et al., "High-affinity binding measurements of antibodies to cell-surface-expressed antigens", Analytical Biochemistry, vol. 373, Aug. 16, 2007, pp. 52-60.

Riechmann et al., "Reshaping human antibodies for therapy", Nature, vol. 332, Mar. 24, 1988, pp. 323-327.

Seed et al., "Molecular cloning of the CD2 antigen, the T-cell erythrocyte receptor, by a rapid immunoselection procedure", Proc. Natl. Acad. Sci. USA, vol. 84, May 1987, pp. 3365-3369.

Segal et al., "Results from an Integrated Safety Analysis of Urelumab, an Agonist Anti-CD137 Monoclonal Antibody", Clinical Cancer Research, vol. 23, No. 8, Apr. 15, 2017, pp. 1929-1936.

Segal et al., "Phase I Study of Single-Agent Utomilumab (PF-05082566), a 4-1BB/CD137 Agonist, in Patients with Advanced Cancer", Clinical Cancer Research, vol. 24, No. 8, Apr. 15, 2018, pp. 1816-1823.

Sewell et al., "Molecular cloning of the human T-lymphocyte surface CD2 (T11) antigen", Proc. Natl. Acad. Sci. USA, vol. 83, Nov. 1986, pp. 8718-8722.

Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, vol. 276, No. 9, Mar. 2, 2001, pp. 6591-6604.

Söderström et al., "Increased Carotid Artery Lesion Inflammation Upon Treatment With the CD137 Agonistic Antibody 2A", Circ. J., vol. 81, Dec. 2017, pp. 1945-1952.

Sondermann et al., "The 3.2-Å crystal structure of the human IgG1 Fc fragment-FcγRIII complex", Nature, vol. 406, Jul. 20, 2000, pp. 267-273.

Sullivan et al., "Bone Marrow Transplantation for Non-Malignant Disease", American Society of Hematology, 2000, pp. 319-338.

Theodor Wieland, "The toxic peptides from Amanita mushrooms", Int. J. Peptide Protein Res., vol. 22, No. 3, Jan. 15, 1983, pp. 257-276.

Thorpe et al., "New Coupling Agents for the Synthesis of Immunotoxins Containing a Hindered Disulfide Bond with Improved Stability in Vivo", Cancer Research, vol. 47, Nov. 15, 1987, pp. 5924-5931.

Tomlinson et al., "The Repertoire of Human Germline VH Sequences Reveals about Fifty Groups of $V_H$ Segments with Different Hypervariable Loops", J. Mol. Biol., vol. 227, Jun. 3, 1992, pp. 776-798.

Urlaub et al., "Isolation of Chinese hamster cell mutants deficient in dihydrofolate Reductase activity", Proc. Natl. Acad. Sci. USA, vol. 77, No. 7, Jul. 1980, pp. 4216-4220.

Vaccaro et al., "Engineering the Fc region of immunoglobulin G to modulate in vivo antibody levels", Nature Biotechnology, vol. 23, No. 10, Oct. 2005, pp. 1283-1288.

Ward et al., "Binding activities of a repertoire of single immunoglobulin variable domains secreted from *Escherichia coli*", Nature, vol. 341, Oct. 12, 1989, pp. 544-546.

Werner-Favre et al., "Cell surface antigen CD5 is a marker for activated human B cells", Eur. J. Immunol., vol. 19, 1989, pp. 1209-1213.

Williams et al., "Cell-based selection of internalizing fully human antagonistic antibodies directed against FLT3 for suppression of leukemia cell growth", Leukemia, vol. 19, Jun. 2, 2005, pp. 1432-1438.

Yazaki et al., "Expression of Recombinant Antibodies in Mammalian Cell Lines", Methods in Molecular Biology™, vol. 248, Benny K. C. Lo, ed., Humana Press, 2003, pp. 255-268.

Yeung et al., "A Therapeutic Anti-VEGF Antibody with Increased Potency Independent of Pharmacokinetic Half-life", Cancer Research, vol. 70, No. 8, Apr. 15, 2010, pp. 3269-3277.

Zalevsky et al., "Enhanced antibody half-life improves in vivo activity", Nat. Biotechnol., vol. 28, No. 2, Feb. 2010, pp. 157-159.

Zanotti et al., "Synthesis of analogues of amaninamide, an amatoxin from the white Amanita virosa mushroom", Int. J. Peptide Protein Res., vol. 30, Jan. 30, 1987, pp. 450-459.

European Patent Office, International Search Report in International Patent Application No. PCT/EP2020/061555 (Aug. 18, 2020).

European Patent Office, Written Opinion in International Patent Application No. PCT/EP2020/061555 (Aug. 18, 2020).

Office Action received for U.S. Appl. No. 17/046,497, mailed on Mar. 26, 2024, 27 pages.

U.S. Appl. No. 17/046,497, filed Oct. 9, 2020, 2021/0077571, Müller et al.

European Patent Office, Communication pursuant to Article 94(3) EPC in European Patent Application No. 20724752.9 (Jun. 27, 2024).

Japan Patent Office, Office Action in Japanese Patent Application No. 2021-562940 (Aug. 20, 2024).

Office Action received for U.S. Appl. No. 17/046,497, mailed on Mar. 28, 2025, 16 pages.

Office Action issued in Korean Patent Application No. 10-2021-7038138 on Jul. 13, 2025, (with English translation), 17 pages.

* cited by examiner

ADC Conjugate C

Linear, saturating exposure above 1 mg/kg

| Dose (mg/kg) | AUCinf / Dose (hour*kg*ug/mL/mg) | Cmax / Dose (kg*ug/mL/mg) | Half-life (hour) | Cl (mL/hour/kg) | Vss (mL/kg) |
|---|---|---|---|---|---|
| 0.5 | 308 | 20.1 | 10.3 | 3.28 | 50.1 |
| 1 | 278 | 16.9 | 15.5 | 3.77 | 73.0 |
| 2 | 328 | 16.2 | 23.7 | 3.07 | 98.6 |

ADC Conjugate A

Nonlinear, non-saturating exposure below 0.3 mg/kg

| Dose (mg/kg) | AUCinf / Dose (hour*kg*ug/mL/mg) | Cmax / Dose (kg*ug/mL/mg) | Half-life (hour) | Cl (mL/hour/kg) | Vss (mL/kg) |
|---|---|---|---|---|---|
| 0.1 | 151 | 23.9 | 4.31 | 6.82 | 40.1 |
| 0.3 | 310 | 30.2 | 12.4 | 3.3 | 47.5 |
| 0.6 | 268 | 16.0 | 20.7 | 3.74 | 107 |

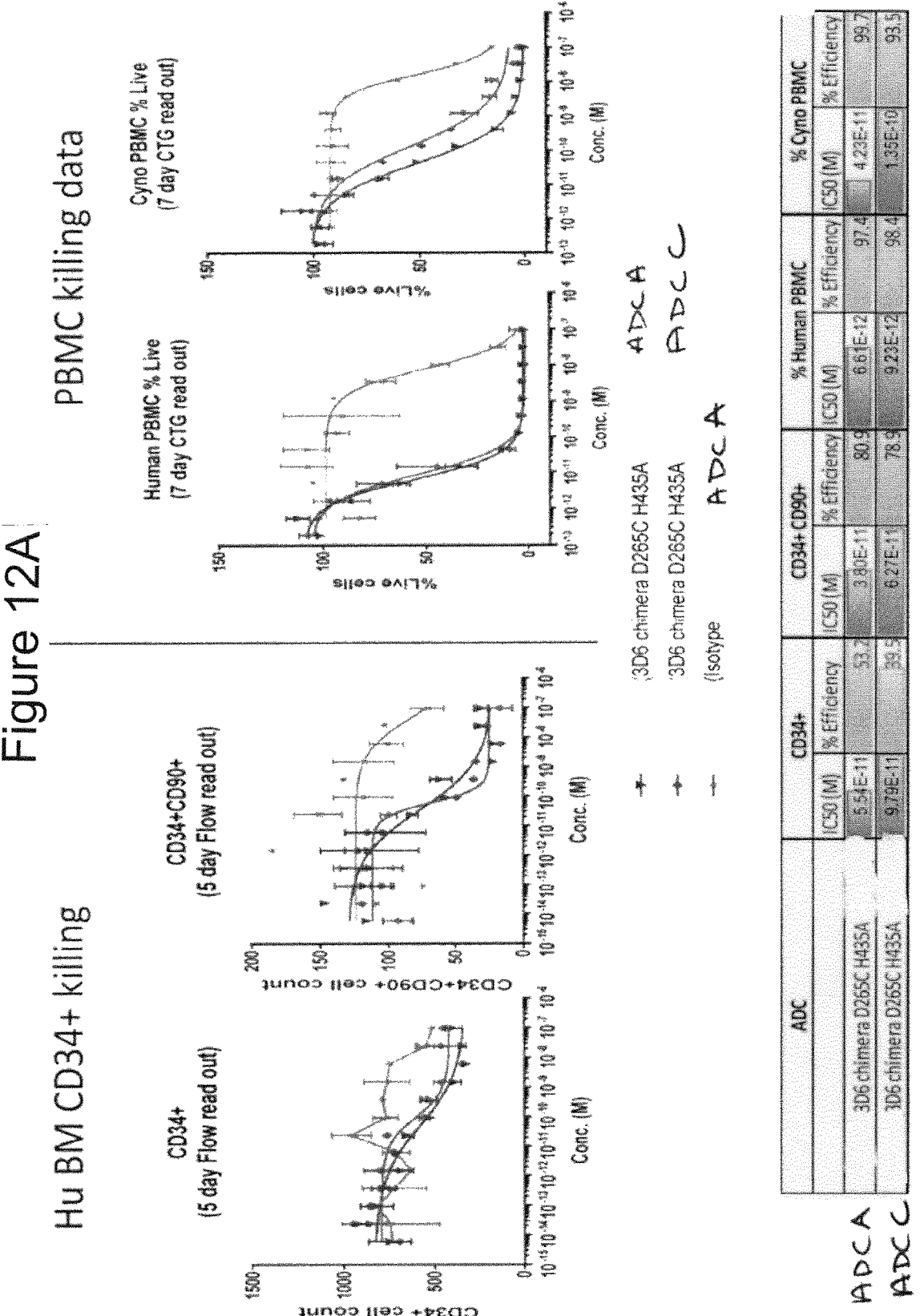

Figure 18

HDP 30.0880

HDP 30.1699

HDP 30.2867

HDP 30.2371

Figure 19

HDP 30.2060

HDP 30.2115

HDP 30.2347

JIMT-1
96h BrdU

| | EC50 |
|---|---|
| T-D265C-30.2867 | 9.944e-010 |
| T-D265C-30.0880 | ~ 1.802e-009 |

C

BT474
96h BrdU

| | EC50 |
|---|---|
| T-D265C-30.2867 | 2.235e-010 |
| T-D265C-30.0880 | 2.632e-010 |

Linker attachment: aa4
96h BrdU on LNCap cells

| | EC50 |
|---|---|
| anti-PSMA-D265C-30.1699 | 2.215e-011 |
| anti-PSMA-D265C-30.2371 | 1.392e-011 |
| anti-PSMA-D265C-30.0880 | 1.069e-010 |
| anti-PSMA-D265C-30.2867 | 4.736e-011 |

A

Linker attachment: aa1
96h BrdU on LNCap cells

| | EC50 |
|---|---|
| anti-PSMA-D265C-30.2060 | ~ 3.201e-011 |
| anti-PSMA-D265C-30.2115 | 2.732e-010 |
| anti-PSMA-D265C-30.2347 | 4.343e-011 |

AMATOXIN ANTIBODY-DRUG CONJUGATES AND USES THEREOF

INCORPORATION-BY-REFERENCE OF MATERIAL SUBMITTED ELECTRONICALLY

Incorporated by reference in its entirety herein is a nucleotide/amino acid sequence listing submitted concurrently herewith and identified as follows: One 460,537 Byte ASCII (Text) file named "757689_ReplacementSequenceListing_ST25," created on Dec. 1, 2021.

FIELD OF THE INVENTION

The present invention relates to amatoxins, Antibody-Drug Conjugates (ADCs) comprising an amatoxin, compositions comprising such ADCs, and methods for using the same.

BACKGROUND OF THE INVENTION

Monoclonal antibodies (mAb) can be conjugated to a therapeutic agent to form an antibody drug conjugate (ADC). ADCs can exhibit increased efficacy, as compared to an unconjugated antibody. The linkage of the antibody to the drug can be direct, or indirect via a linker. An important aspect of successful therapeutic ADCs is that the ADC be not only effective but well-tolerated. Often the cytotoxin impacts both efficacy and tolerability.

ADC have been proposed as therapeutic agents for the treatment of cancer. The use of ADCs for the local delivery of cytotoxic or cytostatic agents, i.e. drugs to kill or inhibit tumor cells in the treatment of cancer theoretically allows targeted delivery of the drug moiety to tumors, and intracellular accumulation therein, where systemic administration of these unconjugated drug agents may result in unacceptable levels of toxicity, also to normal cells.

ADCs have also been proposed as a therapeutic regimen for preparing patients for transplant and stem cell therapy. By conditioning a patient with a cell-specific ADC, stem cells or immune cells can be selectively depleted while leaving the patient's remaining immune system largely intact. For example, Palchaudhuri et al. (2016) *Nat. Biotechnol.* 34, 738-745 describes the use of a single dose of an anti-CD45 ADC where an anti-CD45 antibody was conjugated to saporin, and its ability to enable engraftment of donor cells and for treatment in a sickle-cell anemia model. Unlike irradiation, the CD45-SAP ADC was reported to have avoided neutropenia and anemia, and provided for rapid recovery of T and B cells with minimal overall toxicity. There remains a need for toxins that can be used for non-genotoxic targeted ADC-conditioning where the toxin is potent to the target cells while minimizing patient side effects.

SUMMARY OF THE INVENTION

The present invention provides amatoxins that can be used in antibody drug conjugates (ADC), e.g., for delivery of the amatoxin to a target cell. The present invention further provides particular modifications of antibodies that can be used in antibody drug conjugates for the delivery of the amatoxin to a target cell. The present invention further relates to combinations of said amatoxins and antibodies which have increased efficacy, enhanced tolerability in vivo, and therefore advantageous therapeutic windows.

BRIEF DESCRIPTION OF FIGURES

FIG. 1 depicts the structures of formulae IV (FIG. 1A), VI (FIG. 1B), and IIa (FIG. 1C). "Ab" in FIGS. 1A to 1C represents an antibody. FIGS. 1A, 1B, and 1C represent Conjugates A, B, and C, respectively, referred to in the examples. Conjugates A, B, and C are also referred to as ADC A, ADC B, and ADC C.

FIG. 2 graphically depicts results from in vitro cytoxicity assays using Kasumi-1 cells in the presence of ADC with pre-incubation of ADC in media (A) or 50% human serum (B) to evaluate serum stability of conjugates.

FIGS. 12A and 12B graphically depict results showing anti-CD45 ADCs A or C (FIG. 14A) or anti-CD45 ADCs A or B (FIG. 14B) in in vitro cell killing assays.

FIG. 18 depicts the structures of amanitin-linker constructs HDP30.2867, 30.0880, 30.2371, and 30.1699, respectively.

FIG. 19 depicts the structures of amanitin-linker constructs HDP30.2115, 30.2060, and 30.2347, respectively.

FIG. 35 graphically depicts the cytotoxic activity in vitro of ADC compounds comprising an anti-PSMA antibody with a D265C mutation (h3/F11-D265C-Var16) conjugated to structurally different amanitin derivatives on LNCap cells (A, B).

DETAILED DESCRIPTION

Figure 3:
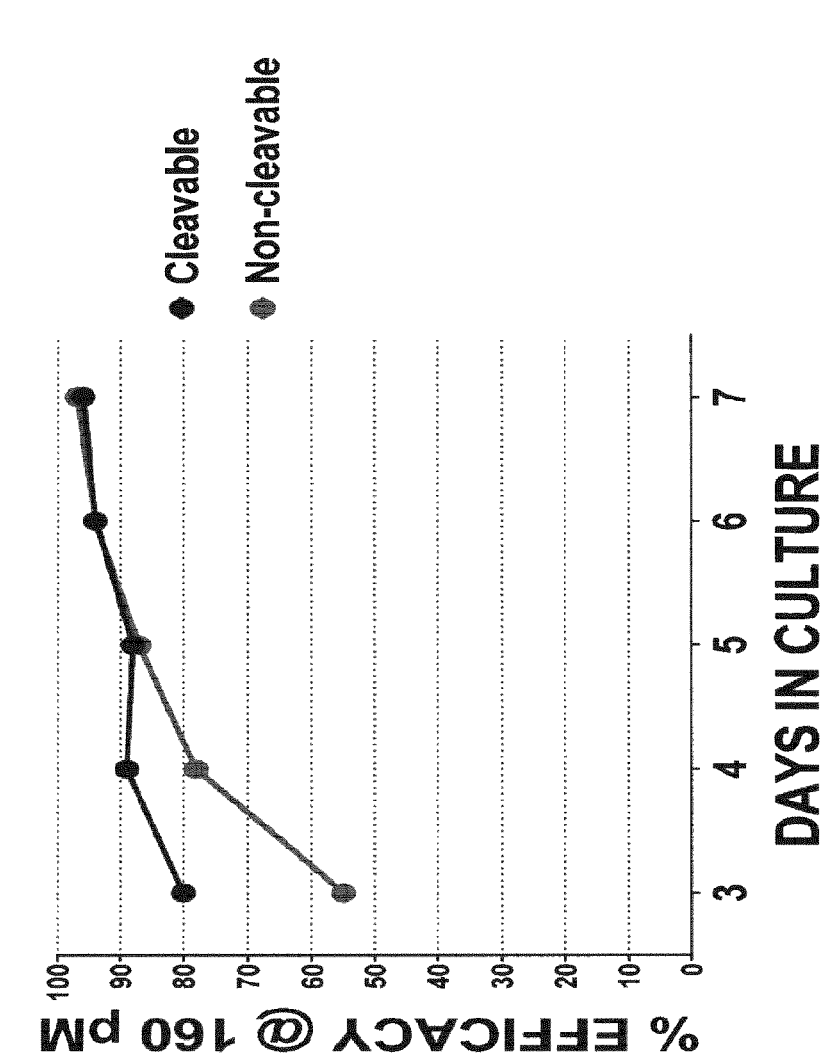
FIG. 3 graphically depicts results from in vitro cytoxicity assays using Kasumi-1 cells in the presence of ADC with iteration on the time of incubation with titrated ADC samples to evaluate differences in the kinetics of cytotoxicity between cleavable and non-cleavable conjugates.
Figure 3:
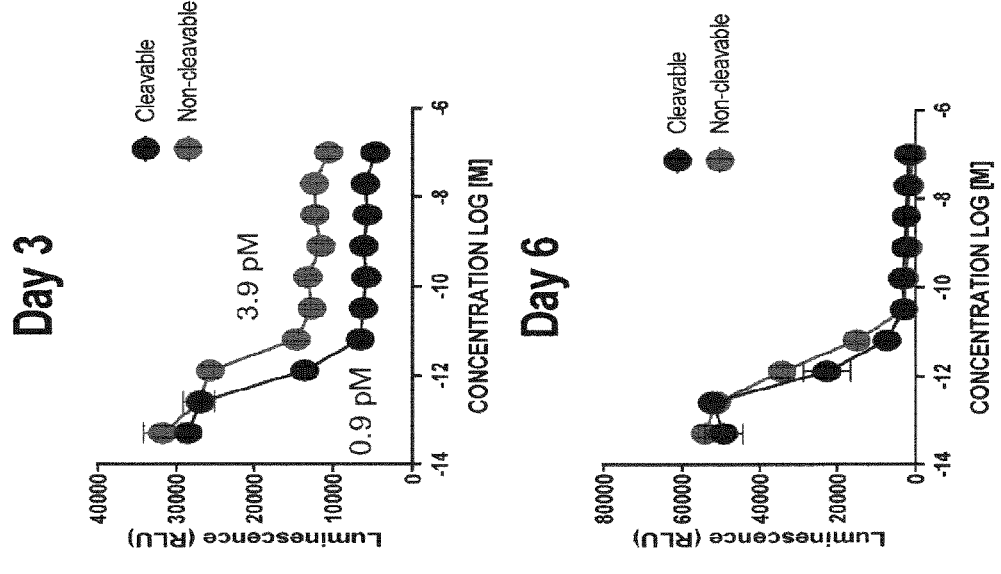

For clarity of disclosure, and not by way of limitation, the detailed description of the invention is divided into the subsections which follow.

The present invention relates to an amatoxin, or derivative or analogue thereof, comprising the structure of formula (An) or formula (Bn)

Formula (An)

Formula (Bn)

wherein n is 2, 3, 4, 5, 6, 7, 8 or 9.

In one embodiment, the invention relates to an amatoxin, or derivative or analogue thereof, comprising the structure of formula (A)

Formula (A) (HDP 30.2867)

or an enantiomer or diastereomer thereof.

In a further embodiment, the invention relates to an amatoxin, or derivative or analogue thereof, comprising the structure of formula (B)

Formula (B) (HDP 30.0880)

or an enantiomer or diastereomer thereof.

Said amatoxins, or derivatives or analogues thereof, can be used in the preparation of an antibody-drug conjugate (ADC).

ADCs according to the present invention have been shown by the inventors to have a particularly high plasma stability and tolerability, and therefore, an improved therapeutic window.

The present invention further relates to an antibody-drug conjugate (ADC) comprising an antibody, or an antigen-binding fragment thereof, conjugated to an amatoxin via a linker, the ADC having the structure of formula (I):

(I)

or a stereoisomer thereof;

wherein:

Q is S or a sulfoxid group;

L is a non-cleavable linker;

Z is a chemical moiety formed by a coupling reaction between a reactive substituent present on L and a reactive substituent present within the antibody, or antigen-binding fragment thereof; and Ab is the antibody, or the antigen binding fragment thereof.

Said ADC may have the structure of formula (Ia):

(Ia)

Said ADC may also have the structure of formula (Ib):

(Ib)

In said ADCs, L can comprise one or more of a bond, $-(C=O)-$, a $-C(O)NH-$ group, an $-OC(O)NH-$ group, $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, a $-(CH_2CH_2O)_p-$ group where p is an integer from 1-6, or a solubility enhancing group;

wherein each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro;

or each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be interrupted by one or more heteroatoms selected from O, S and N.

Said solubility enhancing group may have the formula $-O_a-C(O)NH-SO_2-NR^1-$, wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted or optionally interrupted by one or more heteroatoms selected from O, S and $NR^3$, wherein $R^3$ is independently selected from the group consisting of hydrogen and $C_1$-$C_4$ alkyl.

In said ADCs, L may comprise a $-(CH_2)_n-$ unit, where n is an integer from 2-6. Preferably L is $-(CH_2)_n-$, where n is 6.

In said ADCs, Ab, Z, and L, taken together as Ab-Z-L, can be represented by the formula:

wherein S is the sulfur atom of a cysteine residue present in the antibody, or the antigen-binding fragment thereof.

In one embodiment, the present invention relates to an antibody-drug conjugate (ADC) comprising an antibody, or an antigen-binding fragment thereof, conjugated to an ama-toxin via a linker, the ADC having the structure of formula (I):

(I)

or a stereoisomer thereof;

wherein:

Q is S or a sulfoxid group;

L is a cleavable linker;

Z is a chemical moiety formed by a coupling reaction between a reactive substituent present on L and a reactive substituent present within the antibody, or antigen-binding fragment thereof; and Ab is the antibody, or the antigen binding fragment thereof.

Said ADC can have the structure of formula (Ia):

(Ia)

Said ADC can have the structure of formula (Ib):

(Ib)

In said ADCs, L comprises one or more of a hydrazine, a disulfide, a thioether, an amino acid, a peptide consisting of up to 10 amino acids, a p-aminobenzyl (PAB) group, a heterocyclic self-immolative group, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, heteroaryl, a —(C═O)— group, a —C(O)NH— group, an —OC(O)NH— group, a —(CH$_2$CH$_2$O)$_p$— group where p is an integer from 1-6, or a solubility enhancing group;

wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro;

or each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N.

Said solubility enhancing group may have the formula —$O_a$—C(O)NH—$SO_2$—$NR^1$—, wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted or optionally interrupted by one or more heteroatoms selected from O, S and $NR^3$, wherein $R^3$ is independently selected from the group consisting of hydrogen and $C_1$-$C_4$ alkyl.

According to one embodiment of the present invention, L comprises a peptide selected from the group consisting of Phe-Lys, Val-Lys, Phe-Ala, Phe-Cit, Val-Ala, Val-Cit, and Val-Arg. L may further comprise a PAB group.

In one embodiment, L is represented by the formula:

According to a preferred embodiment, the invention relates to an ADC comprising an antibody conjugated to an amatoxin, the ADC having a structure according to formula (II):

(II)

or a stereoisomer thereof.

Said ADC can have the structure of formula (IIa):

(IIa)

Said ADC can have the structure of formula (IIb):

(IIb)

According to a preferred embodiment of the invention, the antibody, or the antigen binding fragment thereof, specifically binds to an antigen expressed on the cell surface of a cancer cell, or a human stem cell, in particular a hematopoietic stem cell (HSC), or a T cell.

According to a further preferred embodiment of the invention, the antibody, or the antigen binding fragment thereof, specifically binds to human Her2, PSMA, CD37, or CD123.

According to another preferred embodiment of the present invention, the antibody, or the antigen binding fragment thereof, comprises an Fc region comprising at least one mutation selected from the group consisting of D265C, D265A, A118C, H435A, L234A, or L235A (according to EU index).

According to another preferred embodiment of the present invention, the antibody, or antigen binding fragment thereof, specifically binds to PSMA and comprises a CDRH1 according to SEQ ID NO. 378, a CDRH2 according to SEQ ID NO. 379, a CDRH3 according to SEQ ID NO. 380, a CDRL1 according to SEQ ID NO. 381, a CDRL2 according to SEQ ID NO. 382, and a CDRL3 according to SEQ ID NO. 383.

According to another preferred embodiment of the present invention, the antibody, or antigen binding fragment thereof, comprises a heavy chain variable region according to SEQ ID NO. 375 and a light chain variable region according to SEQ ID NO. 377.

According to another preferred embodiment of the present invention, said antibody comprises a heavy chain according to SEQ ID NO. 371, SEQ ID NO. 372, SEQ ID NO. 373, or SEQ ID NO. 374, and a light chain according to SEQ ID NO. 376, or an antigen binding fragment thereof.

The invention further relates to an antibody-drug conjugate (ADC) comprising an antibody, or an antigen-binding fragment thereof, conjugated to an amatoxin, or a derivative or analogue thereof, via a linker, wherein the antibody, or the antigen binding fragment thereof, comprises an Fc region comprising at least two mutations consisting of L234A and L235A (according to EU index).

According to a particularly preferred embodiment, said Fc region is further comprising a mutation consisting of D265C (according to EU index).

According to a preferred embodiment of the present invention, said antibody, or antigen binding fragment thereof, specifically binds to an antigen expressed on the cell surface of a cancer cell, preferably of a human cancer cell.

According to another preferred embodiment of the present invention, said antibody, or antigen binding fragment thereof, specifically binds to prostate-specific membrane antigen (PSMA), preferably human PSMA, or to Her2 antigen, CD37, or CD123.

A preferred embodiment relates to an antibody-drug conjugate (ADC), wherein said antibody, or antigen binding fragment thereof, specifically binds to PSMA and comprises a CDRH1 according to SEQ ID NO. 378, a CDRH2 according to SEQ ID NO. 379, a CDRH3 according to SEQ ID NO. 380, a CDRL1 according to SEQ ID NO. 381, a CDRL2 according to SEQ ID NO. 382, and a CDRL3 according to SEQ ID NO. 383.

According to a preferred embodiment of the present invention, said antibody specifically binding to PSMA, or antigen binding fragment thereof, comprises a heavy chain variable region according to SEQ ID NO. 375 and a light chain variable region according to SEQ ID NO. 377.

According to another preferred embodiment of the present invention, said antibody comprises a heavy chain according to SEQ ID NO. 372, SEQ ID NO. 373, or SEQ ID NO. 374, and a light chain according to SEQ ID NO. 376, or an antigen binding fragment thereof.

In further preferred embodiments, the antibody-drug conjugate (ADC) comprises an antibody, or antigen binding fragment thereof, which is conjugated to any compound which is selected from the group consisting of HDP30.2060, HDP30.2115, HDP30.2347, HDP30.1699, HDP30.2371, HDP30.0880, and HDP30.2867.

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.2060. Most preferrably, in said ADC the compound HDP30.2060 is linked directly to the sulfur atom of cysteine D265C of said antibody (EU numbering).

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.2115. Most preferrably, in said ADC the compound HDP30.2115 is linked directly to the sulfur atom of cysteine D265C of said antibody.

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.2347. Most preferrably, in said ADC the compound HDP30.2347 is linked directly to the sulfur atom of cysteine D265C of said antibody.

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.1699. Most preferrably, in said ADC the compound HDP30.1699 is linked directly to the sulfur atom of cysteine D265C of said antibody.

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.2371. Most preferrably, in said ADC the compound HDP30.2371 is linked directly to the sulfur atom of cysteine D265C of said antibody.

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.0880. Most preferrably, in said ADC the compound HDP30.0880 is linked directly to the sulfur atom of cysteine D265C of said antibody.

The invention further relates to an antibody-drug conjugate (ADC) comprising an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.2867. Most preferrably, in said ADC the compound HDP30.2867 is linked directly to the sulfur atom of cysteine D265C of said antibody.

In said antibody-drug conjugates (ADCs) according to the present invention, the drug antibody ratio (DAR) is about 1, 2, 3, or 4, preferably the DAR is 2.

A further aspect of the present invention relates to said ADCs for use in the treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, hematological cancer, leukemia, and malignant lymphoma.

The invention further relates to the use of any of said ADCs for treatment of cancer in a patient, particularly wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, hematological cancer, leukemia, and malignant lymphoma.

According to another preferred embodiment of the present invention, said antibody-drug conjugate (ADC) comprises an antibody, or antigen binding fragment thereof, that specifically binds to an antigen expressed on the cell surface of a hematopoietic stem cell (HSC), preferably of a human HSC.

A further embodiment of the present invention relates to a method of depleting a population of cells in a human subject, said method comprising administering the said ADC to the subject, wherein the ADC comprises an antibody, or an antigen-binding fragment thereof, that specifically binds to an extracellular antigen expressed by cells in the population of cells.

A further embodiment of the present invention relates to a method of conditioning a human subject for cell transplantation, said method comprising administering said ADC to the human subject such that the endogenous stem or endogenous immune cells in the human subject are depleted, wherein the ADC specifically binds to an extracellular antigen expressed by the endogenous stem or endogenous immune cells.

A further embodiment of the present invention relates to said method, further comprising administering to the human subject allogenic stem cells or allogeneic immune cells.

A further embodiment of the present invention relates to said method, wherein the ADC specifically binds to an extracellular antigen expressed on an immune cell, and wherein the subject has or is at risk of developing graft versus host disease (GVHD).

The invention further relates to a pharmaceutical composition comprising any of said ADCs, or combinations thereof, and at least a pharmaceutically acceptable carrier.

Definitions

Unless stated otherwise, the following terms and phrases as used herein are intended to have the following meanings.

The term "acyl" as used herein refers to —C(=O)R, wherein R is hydrogen ("aldehyde"), $C_1$-$C_{12}$ alkyl, $C_2$-$C_{12}$ alkenyl, $C_2$-$C_{12}$ alkynyl, $C_3$-$C_7$ carbocyclyl, $C_6$-$C_{20}$ aryl, 5-10 membered heteroaryl, or 5-10 membered heterocyclyl, as defined herein. Non-limiting examples include formyl, acetyl, propanoyl, benzoyl, and acryloyl.

The term "$C_1$-$C_{12}$ alkyl" as used herein refers to a straight chain or branched, saturated hydrocarbon having from 1 to 12 carbon atoms. Representative $C_1$-$C_{12}$ alkyl groups include, but are not limited to, -methyl, -ethyl, -n-propyl, -n-butyl, -n-pentyl, and -n-hexyl; while branched $C_1$-$C_{12}$ alkyls include, but are not limited to, -isopropyl, -sec-butyl, -isobutyl, -tert-butyl, -isopentyl, and 2-methylbutyl. A $C_1$-$C_{12}$ alkyl group can be unsubstituted or substituted.

The term "alkenyl" as used herein refers to $C_2$-$C_{12}$ hydrocarbon containing normal, secondary, or tertiary carbon atoms with at least one site of unsaturation, i.e., a carbon-carbon, $sp^2$ double bond. Examples include, but are not limited to: ethylene or vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, and the like. An alkenyl group can be unsubstituted or substituted.

"Alkynyl" as used herein refers to a $C_2$-$C_{12}$ hydrocarbon containing normal, secondary, or tertiary carbon atoms with at least one site of unsaturation, i.e., a carbon-carbon, sp triple bond. Examples include, but are not limited to acetylenic and propargyl. An alkynyl group can be unsubstituted or substituted.

"Aryl" as used herein refers to a $C_6$-$C_{20}$ carbocyclic aromatic group. Examples of aryl groups include, but are not limited to, phenyl, naphthyl and anthracenyl. An aryl group can be unsubstituted or substituted.

"Arylalkyl" as used herein refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms. An alkaryl group can be unsubstituted or substituted.

"Cycloalkyl" as used herein refers to a saturated carbocyclic radical, which may be mono- or bicyclic. Cycloalkyl groups include a ring having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted.

"Cycloalkenyl" as used herein refers to an unsaturated carbocyclic radical, which may be mono- or bicyclic. Cycloalkenyl groups include a ring having 3 to 6 carbon atoms as a monocycle or 7 to 12 carbon atoms as a bicycle. Examples of monocyclic cycloalkenyl groups include 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. A cycloalkenyl group can be unsubstituted or substituted.

"Heteroaralkyl" as used herein refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo[4,5], [5,5], [5,6], or [6,6] system.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl radical comprises 2 to 20 carbon atoms and 1 to 3 heteroatoms selected from N, O, P, and S. A heteroaryl or heterocycloalkyl may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo[4,5], [5,5], [5,6], or [6,6] system. Heteroaryl and heterocycloalkyl can be unsubstituted or substituted.

Heteroaryl and heterocycloalkyl groups are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heteroaryl groups include by way of example and not limitation pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl.

Examples of heterocycloalkyls include by way of example and not limitation dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl.

By way of example and not limitation, carbon bonded heteroaryls and heterocycloalkyls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heteroaryls and heterocycloalkyls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Still more typically, nitrogen bonded heterocycles include 1-aziridyl, 1-azetedyl, 1-pyrrolyl, 1-imidazolyl, 1-pyrazolyl, and 1-piperidinyl.

"Substituted" as used herein and as applied to any of the above alkyl, alkenyl, alkynyl, aryl, arylalkyl, cycloalkyl, heteroaryl, heterocyclyl, and the like, means that one or more hydrogen atoms are each independently replaced with a substituent. Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted. Typical substituents include, but are not limited to, —X, —R, —OH, —OR, —SH, —SR, NH₂, —NHR, —N(R)₂, —N⁺(R)₃, —CX₃, —CN, —OCN, —SCN, —NCO, —NCS, —NO, —NO₂, —N₃, —NC(═O)H, —NC(═O)R, —C(═O)H, —C(═O)R, —C(═O)NH₂, —C(═O)N(R)₂, —SO₃—, —SO₃H, —S(═O)₂R, —OS (═O)₂OR, —S(═O)₂NH₂, —S(═O)₂N(R)₂, —S(═O)R, —OP(═O)(OH)₂, —OP(═O)(OR)₂, —P(═O)(OR)₂, —PO₃, —PO₃H₂, —C(═O)X, —C(═S)R, —CO₂H, —CO₂R, —CO₂—, —C(═S)OR, —C(═O)SR, —C(═S) SR, —C(═O)NH₂, —C(═O)N(R)₂, —C(═S)NH₂, —C(═S)N(R)₂, —C(═NH)NH₂, and —C(═NR)N(R)₂; wherein each X is independently selected for each occasion from F, C, Br, and I; and each R is independently selected for each occasion from $C_1$-$C_{12}$ alkyl, $C_6$-$C_{20}$ aryl, $C_3$-$C_{14}$ heterocycloalkyl or heteroaryl, protecting group and prodrug moiety. Wherever a group is described as "optionally substituted," that group can be substituted with one or more of the above substituents, independently for each occasion.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —CH₂—, —CH₂CH₂—, —CH₂CH(CH₃)CH₂—, and the like. Other radical naming conventions clearly indicate that the radical is a di-radical such as "alkylene," "alkenylene," "arylene," "heterocycloalkylene," and the like.

Wherever a substituent is depicted as a di-radical (i.e., has two points of attachment to the rest of the molecule), it is to be understood that the substituent can be attached in any directional configuration unless otherwise indicated.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers," or sometimes "optical isomers."

A carbon atom bonded to four non-identical substituents is termed a "chiral center." "Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116). A mixture containing equal amounts of individual enantiomeric forms of opposite chirality is termed a "racemic mixture."

The compounds disclosed in this description and in the claims may comprise one or more asymmetric centers, and different diastereomers and/or enantiomers of each of the compounds may exist. The description of any compound in this description and in the claims is meant to include all enantiomers, diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer. Accordingly, enantiomers, optical isomers, and diastereomers of each of the structural formulae of the present disclosure are contemplated herein. In the present specification, the structural formula of the compound represents a certain isomer for convenience in some cases, but the present disclosure includes all isomers, such as geometrical isomers, optical isomers based on an asymmetrical carbon, stereoisomers, tautomers, and the like, it being understood that not all isomers may have the same level of activity. The compounds may occur in different tautomeric forms. The compounds according to the disclosure are meant to include all tautomeric forms, unless stated otherwise. When the structure of a compound is depicted as a specific tautomer, it is to be understood that the invention of the present application is not limited to that specific tautomer.

The compounds of any formula described herein include the compounds themselves, as well as their salts, and their solvates, if applicable. A salt, for example, can be formed between an anion and a positively charged group (e.g., amino) on a compound of the disclosure. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of the disclosure. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. The compounds of the disclosure also include those salts containing quaternary nitrogen atoms.

Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Additionally, the compounds of the present disclosure, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc. "Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$. A hydrate refers to, for example, a mono-hydrate, a di-hydrate, a tri-hydrate, etc.

In addition, a crystal polymorphism may be present for the compounds or salts thereof represented by the formulae disclosed herein. It is noted that any crystal form, crystal form mixture, or anhydride or hydrate thereof, is included in the scope of the present disclosure.

As used herein, the term "about" refers to a value that is within 10% above or below the value being described. For example, the term "about 5 nM" indicates a range of from 4.5 nM to 5.5 nM.

As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Suitable amatoxins and derivatives thereof are further described herein below. As described herein, amatoxins may be conjugated to an antibody, or antigen-binding fragment thereof, for instance, by way of a linker moiety (L) (thus forming a conjugate (i.e., ADC)). Exemplary methods of amatoxin conjugation and linkers useful for such processes are described below.

In the context of the present invention the term "amatoxin" includes all cyclic peptides composed of 8 amino acids as isolated from the genus *Amanita* and described in Wieland, T. and Faulstich H. (Wieland T, Faulstich H., CRC Crit Rev Biochem. 5 (1978) 185-260), further all chemical derivatives thereof; further all semisynthetic analogs thereof; further all synthetic analogs thereof built from building blocks according to the master structure of the natural compounds (cyclic, 8 amino acids), further all synthetic or semisynthetic analogs containing non-hydroxylated amino acids instead of the hydroxylated amino acids, further all synthetic or semisynthetic analogs, in which the sulfoxide moiety is replaced by a sulfone, thioether, or by atoms different from sulfur, e.g., a carbon atom as in a carbanalog of amanitin.

As used herein, a "derivative" of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

As used herein, an "analogue" of a compound is structurally related but not identical to the compound and exhibits at least one activity of the compound. The compound to which the analogue is compared is known as the "parent" compound. The afore-mentioned activities include, without limitation: binding activity to another compound; inhibitory activity, e.g. enzyme inhibitory activity; toxic effects; activating activity, e.g. enzyme-activating activity. It is not required that the analogue exhibits such an activity to the same extent as the parent compound. A compound is regarded as an analogue within the context of the present application, if it exhibits the relevant activity to a degree of at least 1% (more preferably at least 5%, more preferably at least 10%, more preferably at least 20%, more preferably at least 30%, more preferably at least 40%, and more preferably at least 50%) of the activity of the parent compound. Thus, an "analogue of an amatoxin", as it is used herein, refers to a compound that is structurally related to any one of □-amanitin, β-amanitin, γ-amanitin, ε-amanitin, amanin, amaninamide, amanullin, and amanullinic acid and that exhibits at least 1% (more preferably at least 5%, more preferably at least 10%, more preferably at least 20%, more preferably at least 30%, more preferably at least 40%, and more preferably at least 50%) of the inhibitory activity against mammalian RNA polymerase II as compared to at least one of α-amanitin, β-amanitin, γ-amanitin, ε-amanitin, amanin, amaninamide, amanullin, and amanullinic acid. An "analogue of an amatoxin" suitable for use in the present invention may even exhibit a greater inhibitory activity against mammalian RNA polymerase II than any one of α-amanitin, β-amanitin, γ-amanitin, ε-amanitin, amanin, amaninamide, amanullin, or amanullinic acid. The inhibitory activity might be measured by determining the concentration at which 50% inhibition occurs ($IC_{50}$ value). The inhibitory activity against mammalian RNA polymerase II can be determined indirectly by measuring the inhibitory activity on cell proliferation.

A "semisynthetic analogue" refers to an analogue that has been obtained by chemical synthesis using compounds from natural sources (e.g. plant materials, bacterial cultures, fungal cultures or cell cultures) as starting material. Typically, a "semisynthetic analogue" of the present invention has been synthesized starting from a compound isolated from a mushroom of the Amanitaceae family. In contrast, a "synthetic analogue" refers to an analogue synthesized by so-called total synthesis from small (typically petrochemical) building blocks. Usually, this total synthesis is carried out without the aid of biological processes.

According to some embodiments of the present invention, the amatoxin can be selected from the group consisting of α-amanitin, β-amanitin, amanin, amaninamide and analogues, derivatives and salts thereof.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined below.

In the context of the present invention, the term "amanitins" particularly refers to bicyclic structure that are based on an aspartic acid or asparagine residue in position 1, a proline residue, particularly a hydroxyproline residue in position 2, an isoleucine, hydroxyisoleucine or dihydroxyisoleucine in position 3, a tryptophan or hydroxytryptophan residue in position 4, glycine residues in positions 5 and 7, an isoleucine residue in position 6, and a cysteine residue in position 8, particularly a derivative of cysteine that is oxidized to a sulfoxide or sulfone derivative (for the numbering and representative examples of amanitins, see FIG.

1), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in each case wherein any such derivative or analogue is functionally active by inhibiting mammalian RNA polymerase II As used herein, the term "antibody" refers to an immunoglobulin molecule that specifically binds to, or is immunologically reactive with, a particular antigen, and includes monoclonal, genetically engineered, and otherwise modified forms of antibodies, including but not limited to chimeric antibodies, humanized antibodies, heteroconjugate antibodies (e.g., bi-tri- and quad-specific antibodies, diabodies, triabodies, and tetrabodies), and antigen binding fragments of antibodies, including, for example, Fab', $F(ab')_2$, Fab, Fv, rIgG, and scFv fragments. Unless otherwise indicated, the term "monoclonal antibody" (mAb) is meant to include both intact molecules, as well as antibody fragments (including, for example, Fab and $F(ab')_2$ fragments) that are capable of specifically binding to a target protein. As used herein, the Fab and $F(ab')_2$ fragments refer to antibody fragments that lack the Fc fragment of an intact antibody. Examples of these antibody fragments are described herein.

As used herein, the term "monoclonal antibody" refers to an antibody that is derived from a single clone, including any eukaryotic, prokaryotic, or phage clone, and not the method by which it is produced.

The antibodies of the present invention are generally isolated or recombinant. "Isolated," when used herein refers to a polypeptide, e.g., an antibody, that has been separated and/or recovered from a cell or cell culture from which it was expressed. Thus, an "isolated antibody," refers to an antibody which is substantially free of other antibodies having different antigenic specificities. For instance, an isolated antibody that specifically binds to CD117 is substantially free of antibodies that specifically bind antigens other than CD117.

The term "antigen-binding fragment," as used herein, refers a fragment of an antibody that retains the ability to specifically bind to a target antigen. The antigen-binding function of an antibody can be performed by fragments of a full-length antibody. The antibody fragment can be, for example, a Fab, $F(ab')_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a $F(ab')_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al., Nature 341:544-546, 1989); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example, Bird et al., Science 242:423-426, 1988 and Huston et al., Proc. Natl. Acad. Sci. USA 85:5879-5883, 1988). Antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD117 antibody" or "an antibody that binds to CD117" refers to an antibody that is capable of binding CD117, e.g., human CD117, with sufficient affinity such that the antibody is useful as a diagnostic and/or therapeutic agent in targeting CD117. The amino acid sequences of the two main isoforms of human CD117 are provided in SEQ ID NO: 145 (isoform 1) and SEQ ID NO: 146 (isoform 2). An "anti-CD117 ADC" refers to an ADC wherein the antibody is an anti-CD117 antibody.

As used herein, the term "anti-CD45 antibody" or "an antibody that binds to CD45" refers to an antibody that is capable of binding CD45, e.g., human CD117, with sufficient affinity such that the antibody is useful as a diagnostic and/or therapeutic agent in targeting CD45. An "anti-CD45 ADC" refers to an ADC wherein the antibody is an anti-CD45 antibody.

As used herein, the term "anti-CD137 antibody" or "an antibody that binds to CD137" refers to an antibody that is capable of binding CD137, e.g., human CD137, with sufficient affinity such that the antibody is useful as a diagnostic and/or therapeutic agent in targeting CD137. An "anti-CD137 ADC" refers to an ADC wherein the antibody is an anti-CD137 antibody.

As used herein, the term "anti-CD2 antibody" or "an antibody that binds to CD2" refers to an antibody that is capable of binding CD2, e.g., human CD2, with sufficient affinity such that the antibody is useful as a diagnostic and/or therapeutic agent in targeting CD2. An "anti-CD2 ADC" refers to an ADC wherein the antibody is an anti-CD2 antibody.

As used herein, the term "anti-CD5 antibody" or "an antibody that binds to CD5" refers to an antibody that is capable of binding CD5, e.g., human CD5, with sufficient affinity such that the antibody is useful as a diagnostic and/or therapeutic agent in targeting CD5. An "anti-CD5 ADC" refers to an ADC wherein the antibody is an anti-CD5 antibody.

As used herein, the term "bispecific antibody" refers to, for example, a monoclonal, often a human or humanized antibody that is capable of binding at least two different antigens. For instance, one of the binding specificities can be directed towards a hematopoietic stem cell surface antigen, CD117 (e.g., GNNK+ CD117), and the other can specifically bind a different hematopoietic stem cell surface antigen or another cell surface protein, such as a receptor or receptor subunit involved in a signal transduction pathway that potentiates cell growth, among others.

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a p-sheet configuration, connected by three CDRs, which form loops that connect, and in some cases form part of, the p-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, MD, 1987). In certain embodiments, numbering of immunoglobulin amino acid residues is performed according to the immunoglobulin amino acid residue numbering system of Kabat et al., unless otherwise indicated (although any antibody numbering scheme, including, but not limited to IMGT and Chothia, can be utilized).

As used herein, the terms "condition" and "conditioning" refer to processes by which a patient is prepared for receipt of a transplant, e.g., a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an ADC capable of binding an antigen expressed by hematopoietic stem cells, such as CD117 (e.g., GNNK+CD117). Administration of an ADC capable of binding an HSC antigen to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012). Notably, the term "conjugate" (when referring to a compound) is also referred to interchangeably herein as a "drug conjugate", "antibody drug conjugate" or "ADC".

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, or antigen-binding fragment thereof, such as an antibody, antigen-binding fragment thereof, or specific anti-CD117 antibody that binds CD117 (such as GNNK+CD117) known in the art or described herein. Examples of suitably reactive substituents include a nucleophile/electrophile pair (e.g., a thiol/haloalkyl pair, an amine/carbonyl pair, or a thiol/$\alpha$,$\beta$-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, "CRU (competitive repopulating unit)" refers to a unit of measure of long-term engrafting stem cells, which can be detected after in-vivo transplantation.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, "drug-to-antibody ratio" or "DAR" refers to the number of drugs, e.g., amatoxin, attached to the antibody of a conjugate. The DAR of an ADC can range from 1 to 8, although higher loads are also possible depending on the number of linkage sites on an antibody. In certain embodiments, the conjugate has a DAR of 1, 2, 3, 4, 5, 6, 7, or 8.

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not found naturally in a particular organism, such as a human patient. Exogenous substances include those that are provided from an external source to an organism or to cultured matter extracted therefrom.

The terms "Fc", "Fc region," and "Fc domain," as used herein refer to the portion of an IgG antibody that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. An Fc region contains the second constant domain CH2 (e.g., residues at EU positions 231-340 of IgG1) and the third constant domain CH3 (e.g., residues at EU positions 341-447 of human IgG1). As used herein, the Fc region includes the "lower hinge region" (e.g., residues at EU positions 233-239 of IgG1). Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358, and thus slight differences between the sequences presented in the instant application and sequences known in the art can exist. Thus, a "wild type IgG Fc domain" or "WT IgG Fc domain" refers to any naturally occurring IgG Fc region (i.e., any allele). The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively. An example of a "WT" Fc region is provided in SEQ ID NO: 122 (which provides a heavy chain constant region containing an Fc region).

The terms "modified Fc region" or "variant Fc region" as used herein refers to an IgG Fc domain comprising one or more amino acid substitutions, deletions, insertions or modifications introduced at any position within the Fc region.

The terms "full length antibody" and "intact antibody" are used herein interchangeably to refer to an antibody in its substantially intact form, and not an antibody fragment as defined herein. In one embodiment, an ADC described herein comprises an intact antibody. Thus, for an IgG antibody, an intact antibody comprises two heavy chains each comprising a variable region, a constant region and an Fc region, and two light chains each comprising a variable region and a constant region. More specifically, an intact IgG comprises two light chains each comprising a light chain variable region (VL) and a light chain constant region (CL), and comprises two heavy chains each comprising a heavy chain variable region (VH) and three heavy chain constant regions (CH1, CH2, and CH3). CH2 and CH3 represent the Fc region of the heavy chain.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include CD34$^+$ cells. CD34$^+$ cells are immature cells that express the CD34 cell surface marker. In humans, CD34+ cells are believed to include a subpopulation of cells with the stem cell properties defined above, whereas in mice, HSCs are CD34–. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38–, CD45RA–, CD90+, CD49F+, and lin– (negative for mature lineage markers including CD2, CD3, CD4, CD7, CD8, CD10, CD11B, CD19, CD20, CD56, CD235A). In mice, bone marrow LT-HSCs are CD34–, SCA-1+, C-kit+, CD135–, Slamfl/CD150+, CD48–, and lin– (negative for mature lineage markers including Ter119, CD11b, Gr1, CD3, CD4, CD8, B220, IL7ra), whereas ST-HSCs are CD34+, SCA-1+, C-kit+, CD135–, Slamfl/CD150+, and lin– (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self-renewal potential (i.e., they survive throughout adulthood, and can be serially transplanted through successive recipients), whereas ST-HSCs have limited self-renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the term "human antibody" is intended to include antibodies having variable and constant regions derived from human germline immunoglobulin sequences. A human antibody may include amino acid residues not encoded by human germline immunoglobulin sequences (e.g., mutations introduced by random or site-specific mutagenesis in vitro or during gene rearrangement or by somatic mutation in vivo). However, the term "human antibody", as used herein, is not intended to include antibodies in which CDR sequences derived from the germline of another mammalian species, such as a mouse, have been grafted onto human framework sequences. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625, 126; 5,633,425; 5,569,825; 5,661,016; 5,545,806; 5,814, 318; 5,885,793; 5,916,771; and 5,939,598).

A "humanized" antibody refers to an antibody that contains minimal sequences derived from non-human immunoglobulin. Thus, "humanized" forms of non-human (e.g., murine) antibodies are chimeric antibodies that contain minimal sequence derived from the non-human antibody. All or substantially all of the FW regions may also be those of a human immunoglobulin sequence. The humanized antibody can also contain at least a portion of an immunoglobulin constant region (Fc), typically that of a human immunoglobulin consensus sequence. Methods of antibody humanization are known in the art and have been described, for example, in Riechmann et al., Nature 332:323-7, 1988; U.S. Pat. Nos. 5,530,101; 5,585,089; 5,693,761; 5,693,762; and 6,180,370.

As used herein, the term "antibody-like protein" refers to a protein that has been engineered (e.g. by mutagenesis of Ig loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (Binz et al., 2005). Antibody-like proteins can be derived from large libraries of mutants, e.g. by panning from large phage display libraries, and can be isolated in analogy to regular antibodies. Also, antibody-like binding proteins can be obtained by combinatorial mutagenesis of surface-exposed residues in globular proteins.

As used herein, the term "Fab" relates to an IgG fragment comprising the antigen binding region, said fragment being composed of one constant and one variable domain from each heavy and light chain of the antibody.

As used herein, the term "F(ab)$_2$" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually comprising serine (S) and/or glycine (G) residues. This chimeric molecule retains the specificity of the original immunoglobulin, despite removal of the constant regions and the introduction of a linker peptide.

According to one aspect of the present invention, the present invention relates to said conjugate or pharmaceutical composition as described for use in the treatment of cancer.

According to one aspect of the present invention, the present invention relates to said conjugate or pharmaceutical composition as described for use in the treatment of B lymphocyte-associated malignancies or B cell-mediated autoimmune diseases, in particular for use in the treatment of non-Hodgkin's lymphoma, follicular lymphoma, diffuse large B cell non-Hodgkin's lymphoma, chronic lymphocytic leukaemia, rheumatoid arthritis, granulomatosis with polyangiitis and microscopic polyangiitis and pemphigus vulgaris.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or nonspecifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeloblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein a "neutral antibody" refers to an antibody, or an antigen binding fragment thereof, that is not capable of significantly neutralizing, blocking, inhibiting, abrogating, reducing or interfering with the activities of a particular or specified target (e.g., CD117), including the binding of receptors to ligands or the interactions of enzymes with substrates. In one embodiment, a neutral anti-CD117 antibody, or fragment thereof, is an anti-CD117 antibody that does not substantially inhibit SCF-dependent cell proliferation and does not cross block SCF binding to CD117. An example of a neutral antibody is Ab67 (or an antibody having the binding regions of Ab67). In contrast, an "antagonist" anti-CD117 antibody inhibits SCF-dependent proliferation and is able to cross block SCF binding to CD117. An example of an antagonist antibody is Ab55 (or an antibody having the binding regions of Ab55).

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

The terms "specific binding" or "specifically binding", as used herein, refers to the ability of an antibody to recognize and bind to a specific protein structure (epitope) rather than to proteins generally. If an antibody is specific for epitope "A", the presence of a molecule containing epitope A (or free, unlabeled A), in a reaction containing labeled "A" and the antibody, will reduce the amount of labeled A bound to the antibody. By way of example, an antibody "binds specifically" to a target if the antibody, when labeled, can be competed away from its target by the corresponding non-labeled antibody. In one embodiment, an antibody specifically binds to a target, e.g., CD117, CD45, CD2, CD5, CD137, CD134, or CD252, if the antibody has a $K_D$ for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to CD117" or "specifically binds to CD117," as used herein, refers to an antibody or that binds to CD117 and has a dissociation constant ($K_D$) of $1.0 \times 10^{-7}$ M or less, as determined by surface plasmon resonance. In one embodiment, $K_D$ (M) is determined according to standard bio-layer interferometry (BLI). In one embodiment, $K_{off}$ (1/s) is determined according to standard bio-layer interferometry (BLI). It shall be understood, however, that the antibody may be capable of specifically binding to two or more antigens which are related in sequence. For example, in one embodiment, an antibody can specifically bind to both human and a non-human (e.g., mouse or non-human primate) orthologs of CD117, CD45, CD2, CD5, CD137, CD134, or CD252.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to promote the engraftment of exogenous hematopoietic stem cells.

As used herein, the phrase "substantially cleared from the blood" refers to a point in time following administration of a therapeutic agent, e.g., an ADC comprising an amatoxin, to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, or antibody fragments, such as ELISA-based detection assays known in the art or described herein. Additional assays that can be used to detect antibodies, or antibody fragments, include immunoprecipitation techniques and immunoblot assays, among others known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome. Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease. Additional diseases that may be treated using the conditioning and/or transplantation methods described herein include a malignancy, such as a neuroblastoma or a hematologic cancer, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refers to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease. Beneficial or desired clinical results include, but are not limited to, promoting the engraftment of exogenous hematopoietic cells in a patient following antibody conditioning therapy as described herein and subsequent hematopoietic stem cell transplant therapy. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeloblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD117+ leukemic cells) or autoimmune cells (e.g., CD117+ autoimmune lymphocytes, such as a CD117+ T-cell that expresses a T-cell receptor that cross-reacts with a self-antigen). Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state is completely avoided.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

Antibody-Drug Conjugates (ADCs)

Antibodies, and antigen-binding fragments thereof, as described herein can be conjugated (linked) to a cytotoxic molecule (i.e., a cytotoxin), thus forming an antibody-drug conjugate (ADC). As used herein, the terms "cytotoxin", "cytotoxic moiety", and "drug" are used interchangeably.

In particular, the ADCs as disclosed herein include an antibody (including an antigen-binding fragment thereof) conjugated to an amatoxin, e.g., amatoxin set forth in Formula (V), wherein the cytotoxic moiety, when not conjugated to an antibody, has a cytotoxic or cytostatic effect. In various embodiments, the cytotoxic moiety exhibits reduced or no cytotoxicity when bound in a conjugate, but resumes cytotoxicity after cleavage from the linker. In various embodiments, the cytotoxic moiety maintains cytotoxicity without cleavage from the linker. In some embodiments, the cytotoxic molecule is conjugated to a cell internalizing antibody, or antigen-binding fragment thereof as disclosed herein, such that following the cellular uptake of the antibody, or fragment thereof, the cytotoxin may access its intracellular target and, e.g., mediate hematopoietic cell death. ADCs of the present disclosure therefore may be of the general formula $$Ab\text{-}(Z\text{-}L\text{-}Cy)_n,$$

wherein an antibody or antigen-binding fragment thereof (Ab) is conjugated (covalently linked) to linker (L), through a chemical moiety (Z), to a cytotoxic moiety (Cy).

Accordingly, the antibody or antigen-binding fragment thereof may be conjugated to a number of drug moieties as indicated by integer n, which represents the average number of cytotoxins per antibody, which may range, e.g., from about 1 to about 20. Any number of cytotoxins can be conjugated to the antibody, e.g., 1, 2, 3, 4, 5, 6, 7, or 8. In some embodiments, n is from 1 to 4. In some embodiments, n is 1. The average number of drug moieties per antibody in preparations of ADC from conjugation reactions may be characterized by conventional means such as mass spectroscopy, ELISA assay, and HPLC. The quantitative distribution of ADC in terms of n may also be determined. In some instances, separation, purification, and characterization of homogeneous ADC where n is a certain value from ADC with other drug loadings may be achieved by means such as reverse phase HPLC or electrophoresis.

For some antibody-drug conjugates, n may be limited by the number of attachment sites on the antibody. For example, where the attachment is a cysteine thiol, an antibody may have only one or several cysteine thiol groups, or may have only one or several sufficiently reactive thiol groups through which a linker may be attached. Generally, antibodies do not contain many free and reactive cysteine thiol groups which may be linked to a drug moiety; primarily, cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, higher drug loading, e.g. $n>5$, may cause aggregation, insolubility, toxicity, or loss of cellular permeability of certain antibody-drug conjugates.

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Only the most reactive lysine groups may react with an amine-reactive linker reagent. In certain embodiments, an antibody is subjected to denaturing conditions to reveal reactive nucleophilic groups such as lysine or cysteine.

The loading (drug/antibody ratio) of an ADC may be controlled in different ways, e.g., by: (i) limiting the molar excess of drug-linker intermediate or linker reagent relative to antibody, (ii) limiting the conjugation reaction time or temperature, (iii) partial or limiting reductive conditions for cysteine thiol modification, (iv) engineering by recombinant techniques the amino acid sequence of the antibody such that the number and position of cysteine residues is modified for control of the number and/or position of linker-drug attachments.

Cytotoxins

The cytotoxin of the antibody-drug conjugates described herein is an amatoxin or derivative thereof. Amatoxins are potent and selective inhibitors of RNA polymerase II and thereby also inhibit the transcription and protein biosynthesis of the affected cells. As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Amatoxins are rigid bicyclic octapeptides having the basic sequence Ile-Trp-Gly-Ile-Gly-Cys-Asn(or Asp)-Pro, crosslinked by an attachment between the Cys sulfur and position 2 of the Trp indole ring, forming a tryptathionine. Depending on the particular amatoxin, certain amino acid substituents are varied by post-translational modification (i.e. Pro to Hyp; Ile to DHIle; and Trp to 5-OH Trp).

Amatoxins may be isolated from a variety of mushroom species (e.g., *Amanita phalloides, Galerina marginata, Lepiota brunneo-incarnata*) or may be prepared semi-synthetically or synthetically. Different mushroom species contain varying amounts of different amatoxin family members. A member of this family, α-amanitin, is known to be an extremely potent inhibitor of eukaryotic RNA polymerase II and to a lesser degree, RNA polymerase Ill, thereby inhibiting transcription and protein biosynthesis. Wieland, *Int. J. Pept. Protein Res.* 1983, 22(3):257-276.

Structures of the various naturally occurring amatoxins are represented by formula (III) and accompanying Table 1, and are disclosed in, e.g., Zanotti et al., *Int. J. Peptide Protein Res.* 30, 1987, 450-459, which is incorporated by reference herein in its entirety.

(III)

TABLE 1

| Amatoxin structures | | | | | | | |
|---|---|---|---|---|---|---|---|
| Name | $R_1$ | $R_2$ | $R_3, R_4$ | $R_5$ | $R_6, R_7$ | $R_8$ | $R_9$ |
| α-amanitin | OH | OH | H | OH | H | $NH_2$ | OH |
| β-amanitin | OH | OH | H | OH | H | OH | OH |
| γ-amanitin | OH | H | H | OH | H | $NH_2$ | OH |
| ε-amanitin | OH | H | H | OH | H | OH | OH |
| Amanin | OH | OH | H | H | H | OH | OH |
| Amaninamide | OH | OH | H | H | H | $NH_2$ | OH |
| Amanullin | H | H | H | OH | H | $NH_2$ | OH |
| Amanullinic acid | H | H | H | OH | H | OH | OH |
| Proamanullin | H | H | H | OH | H | $NH_2$ | H |

Antibodies, or antigen-binding fragments thereof, that recognize and bind to an antigen expressed on the cell surface of a human stem cell or a T cell can be conjugated to an amatoxin, such as an α-amanitin or a derivative thereof, as described in, for example, U.S. Pat. Nos. 9,233, 173 and 9,399,681 and US Patent Application Publication Nos. 2016/0089450, 2016/0002298, 2015/0218220, 2014/0294865, the disclosure of each of which is incorporated herein by reference as it pertains, for example, to amatoxins, such as α-amanitin, as well as covalent linkers that can be used for covalent conjugation. Exemplary methods of amatoxin conjugation and linkers useful for such processes are described herein. Exemplary linker-containing amatoxins useful for conjugation to an antibody, or antigen-binding fragment, in accordance with the compositions and methods are also described herein.

As used herein, the term "amatoxin derivative" or "amanitin derivative" refers to an amatoxin that has been chemically modified at one or more positions relative to a naturally occurring amatoxin, such as α-amanitin, β-amanitin, γ-amanitin, ε-amanitin, amanin, amaninamide, amanullin, amanullinic acid, or proamanullin. In each instance, the derivative may be obtained by chemical modification of a naturally occurring compound ("semi-synthetic"), or may be obtained from an entirely synthetic source. Synthetic routes to various amatoxin derivatives are disclosed in, for example, U.S. Pat. No. 9,676,702 and in Perrin et al., J. Am. Chem. Soc. 2018, 140, p. 6513-6517, each of which is incorporated by reference herein in their entirety with respect to synthetic methods for preparing and derivatizing amatoxins.

In some embodiments, the amatoxin or derivative thereof is represented by formula (V):

(V)

or an enantiomer or diastereomer thereof.

In some embodiments, Q is S. In some embodiments, Q is a sulfoxid group.

In one embodiment, the amatoxin or derivative thereof is represented by formula (Va):

(Va)

In some embodiments, Q is S. In some embodiments, Q is a sulfoxid group.

In this particular embodiment, the amatoxin or derivative thereof is represented by formula (Vb):

(Vb)

In some embodiments, Q is S. In some embodiments, Q is a sulfoxid group.

Additional amatoxins that may be used for conjugation to an antibody, or antigen-binding fragment thereof, in accordance with the compositions and methods described herein are described, for example, in WO 2016/142049; WO 2016/071856; WO 2017/149077; WO 2018/115466; and WO 2017/046658, the disclosures of which are incorporated herein by reference in their entirety.

Linkers

The term "Linker" as used herein means a divalent chemical moiety comprising a covalent bond or a chain of atoms that covalently attaches an antibody or fragment thereof (Ab) to an amatoxin as described herein, e.g., an amatoxin of formulae (IV), (IVa), (IVb), (V), (Va), or (Vb), to form an antibody-drug conjugate (ADC).

Covalent attachment of the antibody and the amatoxin requires the linker to have two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p. 234-242).

Accordingly, present linkers have two reactive termini, one for conjugation to an antibody and the other for conjugation to an amatoxin. The antibody conjugation reactive terminus of the linker (reactive moiety, defined herein as Z') is typically a chemical moiety that is capable of conjugation to the antibody through, e.g., a cysteine thiol or lysine amine group on the antibody, and so is typically a thiol-reactive group such as a Michael acceptor (as in maleimide), a leaving group, such as a chloro, bromo, iodo, or an R-sulfanyl group, or an amine-reactive group such as a carboxyl group. Conjugation of the linker to the antibody is described more fully herein below.

The amatoxin conjugation reactive terminus of the linker is typically a chemical moiety that is capable of conjugation to the amatoxin through formation of a bond with a reactive substituent within the amatoxin molecule. Non-limiting examples include, for example, formation of an amide bond with a basic amine or carboxyl group on the amatoxin, via a carboxyl or basic amine group on the linker, respectively, or formation of an ether or the like, via alkylation of an OH group on the amatoxin via e.g., a leaving group on the linker.

When the term "linker" is used in describing the linker in conjugated form, one or both of the reactive termini will be absent (such as reactive moiety Z', having been converted to chemical moiety Z, as described herein below) or incomplete (such as being only the carbonyl of the carboxylic acid) because of the formation of the bonds between the linker and/or the amatoxin, and between the linker and/or the antibody or antigen-binding fragment thereof. Such conjugation reactions are described further herein below.

A variety of linkers can be used to conjugate the antibodies, antigen-binding fragments, and ligands described to a cytotoxic molecule. Generally, linkers suitable for the present disclosure may be substantially stable in circulation, but allow for release of the amatoxin within or in close proximity to the target cells. In some embodiments, certain linkers suitable for the present disclosure may be categorized as "cleavable" or "non-cleavable". Generally, cleavable linkers contain one or more functional groups that is cleaved in response to a physiological environment. For example, a cleavable linker may contain an enzymatic substrate (e.g., valine-alanine) that degrades in the presence of an intracellular enzyme (e.g., cathepsin B), an acid-cleavable group (e.g., a hydrozone) that degrades in the acidic environment of a cellular compartment, or a reducible group (e.g., a disulfide) that degrades in an intracellular reducing environment. By contrast, generally, non-cleavable linkers are released from the ADC during degradation (e.g., lysosomal degradation) of the antibody moiety of the ADC inside the target cell.

Non-Cleavable Linkers

Non-cleavable linkers suitable for use herein further may include one or more groups selected from a bond, —(C=O)—, $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, and combinations thereof, each of which may be optionally substituted, and/or may include one or more heteroatoms (e.g., S, N, or O) in place of one or more carbon atoms. Non-limiting examples of such groups include $(CH_2)_p$, $(C=O)(CH_2)_p$, and polyethyleneglycol (PEG; $(CH_2CH_2O)_p$), units, wherein p is an integer from 1-6, independently selected for each occasion.

In some embodiments, the linker L comprises one or more of a bond, —(C=O)—, a —C(O)NH— group, an —OC(O)NH— group, $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, heteroarylene, a —(CH$_2$CH$_2$O)$_p$— group where p is an integer from 1-6, or a solubility enhancing group;

wherein each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro;

In some embodiments, each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be interrupted by one or more heteroatoms selected from O, S and N.

In some embodiments, each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, the linker L comprises a solubility enhancing group of the formula —O$_a$—C(O)NH—SO$_2$—N(R$^1$)—, wherein:

a is 0 or 1;

R$^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted or optionally interrupted by one or more heteroatoms selected from O, S and NR$^3$, wherein R$^3$ is independently selected from the group consisting of hydrogen and $C_1$-$C_4$ alkyl. Such solubility enhancing groups are described in, for example, U.S. Pat. No. 9,636,421 and U.S. Patent Application Publication No. 2017/0298145, the disclosures of each of which are incorporated herein by reference in their entirety.

In some embodiments, the solubility enhancing group of the formula —O$_a$—C(O)NH—SO$_2$—N(R$^1$)— further comprises a $C_1$-$C_6$ alkylene or a —(CH$_2$CH$_2$O)$_p$— group, where p is an integer from 1-6. Non-limiting examples of such solubility enhancing groups include those depicted in Table 2, above.

TABLE 2

| Exemplary solubility enhancing groups |
| --- | m = 1-6

In some embodiments, the non-cleavable linker comprises a —$(CH_2)_n$— unit, where n is an integer from, 2-12, e.g., 2-6. In some embodiments, the non-cleavable linker comprises a —$(CH_2)_n$— where n is 1, 2, 3, 4, 5, or 6. In some embodiments, the non-cleavable linker is —$(CH_2)_n$— where n is 6, represented by the formula:

Cleavable Linkers

In some embodiments, the linker conjugating the antibody or antigen binding fragment thereof and the amatoxin is cleavable under intracellular conditions, such that cleavage of the linker releases the drug unit from the antibody in the intracellular environment. Cleavable linkers are designed to exploit the differences in local environments, e.g., extracellular and intracellular environments, including, for example, pH, reduction potential or enzyme concentration, to trigger the release of the amatoxin in the target cell. Generally, cleavable linkers are relatively stable in circulation, but are particularly susceptible to cleavage in the intracellular environment through one or more mechanisms (e.g., including, but not limited to, activity of proteases, peptidases, and glucuronidases). Cleavable linkers used herein are substantially stable in circulating plasma and/or outside the target cell and may be cleaved at some efficacious rate inside the target cell or in close proximity to the target cell.

Suitable cleavable linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Suitable cleavable linkers may include, for example, chemical moieties such as a hydrazine, a disulfide, a thioether or a dipeptide.

Linkers hydrolyzable under acidic conditions include, for example, hydrazones, semicarbazones, thiosemicarbazones, cis-aconitic amides, orthoesters, acetals, ketals, or the like. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661, the disclosure of each of which is incorporated herein by reference in its entirety as it pertains to linkers suitable for covalent conjugation. Such linkers are relatively stable under neutral pH conditions, such as those in the blood, but are unstable at below pH 5.5 or 5.0, the approximate pH of the lysosome.

Linkers cleavable under reducing conditions include, for example, a disulfide. A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio)toluene), SPDB and SMPT (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935, the disclosure of each of which is incorporated herein by reference in its entirety as it pertains to linkers suitable for covalent conjugation.

Linkers susceptible to enzymatic hydrolysis can be, e.g., a peptide-containing linker that is cleaved by an intracellular peptidase or protease enzyme, including, but not limited to, a lysosomal or endosomal protease. One advantage of using intracellular proteolytic release of the therapeutic agent is that the agent is typically attenuated when conjugated and the serum stabilities of the conjugates are typically high. In some embodiments, the peptidyl linker is at least two amino acids long or at least three amino acids long. Exemplary amino acid linkers include a dipeptide, a tripeptide, a tetrapeptide or a pentapeptide. Examples of suitable peptides include those containing amino acids such as Valine, Alanine, Citrulline (Cit), Phenylalanine, Lysine, Leucine, and Glycine. Amino acid residues which comprise an amino acid linker component include those occurring naturally, as well as minor amino acids and non-naturally occurring amino acid analogs, such as citrulline. Exemplary dipeptides include valine-citrulline (vc or val-cit) and alanine-phenylalanine (af or ala-phe). Exemplary tripeptides include glycine-valine-citrulline (gly-val-cit) and glycine-glycine-glycine (gly-gly-gly). In some embodiments, the linker includes a dipeptide such as Val-Cit, Ala-Val, or Phe-Lys, Val-Lys, Ala-Lys, Phe-Cit, Leu-Cit, Ile-Cit, Phe-Arg, or Trp-Cit. Linkers containing dipeptides such as Val-Cit or Phe-Lys are disclosed in, for example, U.S. Pat. No. 6,214,345, the disclosure of which is incorporated herein by reference in its entirety as it pertains to linkers suitable for covalent conjugation. In some embodiments, the linker comprises a dipeptide selected from Val-Ala and Val-Cit.

Linkers suitable for conjugating the antibodies, antigen-binding fragments, described herein to a cytotoxic molecule include those capable of releasing an amatoxin by a 1,6-elimination process. Chemical moieties capable of this elimination process include the p-aminobenzyl (PAB) group, 6-maleimidohexanoic acid, pH-sensitive carbonates, and other reagents as described in Jain et al., Pharm. Res. 32:3526-3540, 2015, the disclosure of which is incorporated herein by reference in its entirety as it pertains to linkers suitable for covalent conjugation.

In some embodiments, the linker includes a "self-immolative" group such as the afore-mentioned PAB or PABC (para-aminobenzyloxycarbonyl), which are disclosed in, for example, Carl et al., J. Med. Chem. (1981) 24:479-480; Chakravarty et al (1983) J. Med. Chem. 26:638-644; U.S. Pat. No. 6,214,345; US20030130189; US20030096743; U.S. Pat. No. 6,759,509; US20040052793; U.S. Pat. Nos. 6,218,519; 6,835,807; 6,268,488; US20040018194; WO98/13059; US20040052793; U.S. Pat. Nos. 6,677,435; 5,621,002; US20040121940; WO2004/032828). Other such chemical moieties capable of this process ("self-immolative linkers") include methylene carbamates and heteroaryl groups such as aminothiazoles, aminoimidazoles, aminopyrimidines, and the like. Linkers containing such heterocyclic self-immolative groups are disclosed in, for example, U.S. Patent Publication Nos. 20160303254 and 20150079114, and U.S. Pat. No. 7,754,681; Hay et al. (1999) Bioorg. Med. Chem. Lett. 9:2237; US 2005/0256030; de Groot et al (2001) J. Org. Chem. 66:8815-8830; and U.S. Pat. No. 7,223,837. In some embodiments, a dipeptide is used in combination with a self-immolative linker.

In some embodiments, the linker L comprises one or more of a hydrazine, a disulfide, a thioether, an amino acid, a peptide consisting of up to 10 amino acids, a p-aminobenzyl (PAB) group, a heterocyclic self-immolative group, $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, heteroaryl, a —(C=O)— group, a —C(O)NH— group, an —OC(O)NH— group, a —$(CH_2CH_2O)_p$— group where p is an integer from 1-6, or a solubility enhancing group; wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N.

In some embodiments, each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N and may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro.

One of skill in the art will recognize that one or more of the groups listed may be present in the form of a bivalent (diradical) species, e.g., $C_1$-$C_6$ alkylene and the like.

In some embodiments, the linker L comprises a solubility enhancing group of the formula —$O_a$—C(O)NH—$SO_2$—N$(R^1)$—, wherein:

a is 0 or 1;

$R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted or optionally interrupted by one or more heteroatoms selected from O, S and $NR^3$, wherein $R^3$ is independently selected from the group consisting of hydrogen and $C_1$-$C_4$ alkyl. Such solubility enhancing groups are described in, for example, U.S. Pat. No. 9,636,421 and U.S. Patent Application Publication No. 2017/0298145, the disclosures of each of which are incorporated herein by reference in their entirety.

In some embodiments, the solubility enhancing group of the formula $-O_a-C(O)NH-SO_2-N(R^1)-$ further comprises a $C_1$-$C_6$ alkylene or a $-(CH_2CH_2O)_p-$ group, where p is an integer from 1-6. Non-limiting examples of such solubility enhancing groups include those depicted in Table 2, above.

In some embodiments, the linker includes a p-aminobenzyl group (PAB). In one embodiment, the p-aminobenzyl group is disposed between the cytotoxic drug and a protease cleavage site in the linker. In one embodiment, the p-aminobenzyl group is part of a p-aminobenzyloxycarbonyl unit. In one embodiment, the p-aminobenzyl group is part of a p-aminobenzylamido unit.

In some embodiments, the linker comprises a dipeptide selected from the group consisting of Phe-Lys, Val-Lys, Phe-Ala, Phe-Cit, Val-Ala, Val-Cit, and Val-Arg. In some embodiments, the linker comprises one or more of PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a combination of one or more of a peptide, oligosaccharide, $-(CH_2)_p-$, $-(CH_2CH_2O)_p-$, PAB, Val-Cit-PAB, Val-Ala-PAB, Val-Lys(Ac)-PAB, Phe-Lys-PAB, Phe-Lys(Ac)-PAB, D-Val-Leu-Lys, Gly-Gly-Arg, Ala-Ala-Asn-PAB, or Ala-PAB.

In some embodiments, the linker comprises a $-(C=O)(CH_2)_p-$ unit, wherein p is an integer from 1-6.

In some embodiments, the linker comprises PAB-Ala-Val-propionyl, represented by the formula:

In some embodiments, the linker comprises PAB-Cit-Val-propionyl, represented by the formula:

Such PAB-dipeptide-propionyl linkers are disclosed in, e.g., International Patent Application Publication No. WO2017/149077, which is incorporated by reference herein in its entirety. Further, the cytotoxins disclosed in WO2017/149077 are incorporated by reference herein.

It will be recognized by one of skill in the art that any one or more of the chemical groups, moieties and features disclosed herein may be combined in multiple ways to form linkers useful for conjugation of the antibodies and amatoxins as disclosed herein. Further linkers useful in conjunction with the compositions and methods described herein, are described, for example, in U.S. Patent Application Publication No. 2015/0218220, the disclosure of which is incorporated herein by reference in its entirety.

Linker-Amatoxin and Linker-Antibody Conjugation

In certain embodiments, the linker is reacted with an amatoxin or derivative thereof according to any of formulae (V), (Va), or (Vb) under appropriate conditions to form a linker-amatoxin conjugate. In certain embodiments, reactive groups are used on the amatoxin or linker to form a covalent attachment.

The amatoxin-linker conjugate is subsequently reacted with the antibody, derivatized antibody, or antigen-binding fragment thereof, under appropriate conditions to form the ADC. Alternatively, the linker may first be reacted with the antibody, derivatized antibody or antigen-binding fragment thereof, to form a linker-antibody conjugate, and then reacted with the amatoxin to form the ADC. Such conjugation reactions will now be described more fully.

A number of different reactions are available for covalent attachment of linkers or amatoxin-linker conjugates to the antibody or antigen-binding fragment thereof. Suitable attachment points on the antibody molecule include, but are not limited to, the amine groups of lysine, the free carboxylic acid groups of glutamic acid and aspartic acid, the sulfhydryl groups of cysteine, and the various moieties of aromatic amino acids. For instance, non-specific covalent attachment may be undertaken using a carbodiimide reaction to link a carboxy (or amino) group on a linker to an amino (or carboxy) group on an antibody moiety. Additionally, bifunctional agents such as dialdehydes or imidoesters may also be used to link the amino group on a linker to an amino group on an antibody moiety. Also available for attachment of amatoxins to antibody moieties is the Schiff base reaction. This method involves the periodate oxidation of a glycol or hydroxy group on either the antibody or linker, thus forming an aldehyde which is then reacted with the linker or antibody, respectively. Covalent bond formation occurs via formation of a Schiff base between the aldehyde and an amino group. Isothiocyanates may also be used as coupling agents for covalently attaching amatoxins or antibody moieties to linkers. Other techniques are known to the skilled artisan and within the scope of the present disclosure.

Linkers useful in for conjugation to the antibodies or antigen-binding fragments as described herein include, without limitation, linkers containing a chemical moiety Z, formed by a coupling reaction between the antibody and a reactive chemical moiety (referred to herein as a reactive substituent, Z') on the linker as depicted in Table 3, below. Wavy lines designate points of attachment to the antibody or antigen-binding fragment, and the cytotoxic molecule, respectively.

TABLE 3

Exemplary chemical moieties Z formed by coupling reactions in the
formation of antibody-drug conjugates.

| Exemplary Coupling Reactions | Chemical Moiety Z Formed by Coupling Reactions |
| --- | --- |
| [3 + 2] Cycloaddition | |
| [3 + 2] Cycloaddition | |
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |

TABLE 3-continued

Exemplary chemical moieties Z formed by coupling reactions in the
formation of antibody-drug conjugates.

| Exemplary Coupling Reactions | Chemical Moiety Z Formed by Coupling Reactions |
|---|---|
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |

TABLE 3-continued

Exemplary chemical moieties Z formed by coupling reactions in the
formation of antibody-drug conjugates.

| Exemplary Coupling Reactions | Chemical Moiety Z Formed by Coupling Reactions |
|---|---|
| [3 + 2] Cycloaddition, Esterification | |
| [3 + 2] Cycloaddition, Esterification | |
| [3 + 2] Cycloaddition, Etherification | |
| [3 + 2] Cycloaddition | |
| Michael addition | |

TABLE 3-continued

Exemplary chemical moieties Z formed by coupling reactions in the
formation of antibody-drug conjugates.

| Exemplary Coupling Reactions | Chemical Moiety Z Formed by Coupling Reactions |
|---|---|
| Michael addition | |
| Imine condensation, Amidation | |
| Imine condensation | |
| Disulfide formation | |
| Thiol alkylation | |
| Condensation, Michael addition | |

One of skill in the art will recognize that a reactive substituent Z' attached to the linker and a reactive substituent on the antibody or antigen-binding fragment thereof, are engaged in the covalent coupling reaction to produce the chemical moiety Z, and will recognize the reactive substituent Z'. Therefore, antibody-drug conjugates useful in conjunction with the methods described herein may be formed by the reaction of an antibody, or antigen-binding fragment thereof, with a linker or amatoxin-linker conjugate, as described herein, the linker or amatoxin-linker conjugate including a reactive substituent Z', suitable for reaction with a reactive substituent on the antibody, or antigen-binding fragment thereof, to form the chemical moiety Z.

As depicted in Table 3, examples of suitably reactive substituents Z' on the linker and reactive substituents on the antibody or antigen-binding fragment thereof include a nucleophile/electrophile pair (e.g., a thiol/haloalkyl pair, an amine/carbonyl pair, or a thiol/α,β-unsaturated carbonyl pair, and the like), a diene/dienophile pair (e.g., an azide/alkyne pair, or a diene/α,β-unsaturated carbonyl pair, among others), and the like. Coupling reactions between the reactive substitutents to form the chemical moiety Z include, without limitation, thiol alkylation, hydroxyl alkylation, amine alkylation, amine or hydroxylamine condensation, hydrazine formation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein. In some embodiments, the reactive substituent Z' is an electrophilic functional group suitable for reaction with a nucleophilic functional group on the antibody, or antigen-binding fragment thereof.

Reactive substituents that may be present within an antibody, or antigen-binding fragment thereof, as disclosed herein include, without limitation, nucleophilic groups such as (i)N-terminal amine groups, (ii) side chain amine groups, e.g. lysine, (iii) side chain thiol groups, e.g. cysteine, and (iv) sugar hydroxyl or amino groups where the antibody is glycosylated. Reactive substituents that may be present within an antibody, or antigen-binding fragment thereof, as disclosed herein include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. In some embodiments, the reactive substituents present within an antibody, or antigen-binding fragment thereof as disclosed herein include, are amine or thiol moieties. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In some embodiments, the reactive substituent Z' attached to the linker is a nucleophilic group which is reactive with an electrophilic group present on an antibody. Useful electrophilic groups on an antibody include, but are not limited to, aldehyde and ketone carbonyl groups. A nucleophilic group (e.g., a) heteroatom of can react with an electrophilic group on an antibody and form a covalent bond to the antibody. Useful nucleophilic groups include, but are not limited to, hydrazide, oxime, amino, hydroxyl, hydrazine, thiosemicarbazone, hydrazine carboxylate, and arylhydrazide.

In some embodiments, chemical moiety Z is the product of a reaction between reactive nucleophilic substituents present within the antibodies, or antigen-binding fragments thereof, such as amine and thiol moieties, and a reactive electrophilic substituent Z' attached to the linker. For instance, Z' may be a Michael acceptor (e.g., maleimide), activated ester, electron-deficient carbonyl compound, or an aldehyde, among others.

Several representative and non-limiting examples of reactive substituents Z' and the resulting chemical moieties Z are provided in Table 4.

TABLE 4

Complementary reactive substituents and chemical moieties

| Functional Group on Antibody | Z' group | Z group |
| --- | --- | --- |

Naturally Occurring

Synthetically Introduced

TABLE 4-continued

Complementary reactive substituents and chemical moieties

| Functional Group on Antibody | Z' group | Z group |
|---|---|---|
|  R = H or alkyl |  (Y = O or NH) | |

For instance, linkers suitable for the synthesis of linker-antibody conjugates and ADCs include, without limitation, reactive substituents Z' attached to the linker, such as a maleimide or haloalkyl group. These may be attached to the linker by, for example, reagents such as succinimidyl 4-(N-maleimidomethyl)-cyclohexane-L-carboxylate (SMCC), N-succinimidyl iodoacetate (SIA), sulfo-SMCC, m-male-imidobenzoyl-N-hydroxysuccinimidyl ester (MES), sulfo-MES, and succinimidyl iodoacetate, among others described, in for instance, Liu et al., 18:690-697, 1979, the disclosure of which is incorporated herein by reference as it pertains to linkers for chemical conjugation.

In some embodiments, the reactive substituent Z' attached to linker L is a maleimide, azide, or alkyne. An example of a maleimide-containing linker is the non-cleavable male-imidocaproyl-based linker, which is particularly useful for the conjugation of microtubule-disrupting agents such as auristatins. Such linkers are described by Doronina et al., Bioconjugate Chem. 17:14-24, 2006, the disclosure of which is incorporated herein by reference as it pertains to linkers for chemical conjugation.

In some embodiments, the reactive substituent Z' is —(C═O)— or —NH(C═O)—, such that the linker may be joined to the antibody, or antigen-binding fragment thereof, by an amide or urea moiety, respectively, resulting from reaction of the —(C═O)— or —NH(C═O)— group with an amino group of the antibody or antigen-binding fragment thereof.

In some embodiments, the reactive substituent Z' is an N-maleimidyl group, halogenated N-alkylamido group, sulfonyloxy N-alkylamido group, carbonate group, sulfonyl halide group, thiol group or derivative thereof, alkynyl group comprising an internal carbon-carbon triple bond, (hetero)cycloalkynyl group, bicyclo[6.1.0]non-4-yn-9-yl group, alkenyl group comprising an internal carbon-carbon double bond, cycloalkenyl group, tetrazinyl group, azido group, phosphine group, nitrile oxide group, nitrone group, nitrile imine group, diazo group, ketone group, (O-alkyl) hydroxylamino group, hydrazine group, halogenated N-ma-leimidyl group, 1,1-bis (sulfonylmethyl)methylcarbonyl group or elimination derivatives thereof, carbonyl halide group, or an allenamide group, each of which may be optionally substituted. In some embodiments, the reactive substituent comprises a cycloalkene group, a cycloalkyne group, or an optionally substituted (hetero)cycloalkynyl group.

In some embodiments, the chemical moiety Z is selected from Table 3 or Table 4. In some embodiments, the chemical moiety Z is:

where S is a sulfur atom which represents the reactive substituent present within an antibody, or antigen-binding fragment thereof, that specifically binds to an antigen expressed on the cell surface of a human stem cell or a T cell (e.g., from the —SH group of a cysteine residue).

In some embodiments, the linker-reactive substituent group, taken together as L-Z', prior to conjugation with the antibody or antigen binding fragment thereof, has the structure:

where the wavy line indicates the point of attachment to a substituent on the amatoxin. This linker-reactive substituent group L-Z' may alternatively be referred to as N-beta-maleimidopropyl-Val-Ala-para-aminobenzyl (BMP-Val-Ala-PAB). The wavy line at the linker terminus indicates the point of attachment to the amatoxin. In some embodiments, the linker L and the chemical moiety Z, after conjugation to the antibody, taken together as L-Z-Ab, has the structure:

where S is a sulfur atom which represents the reactive substituent present within an antibody, or antigen-binding fragment thereof, that specifically binds to an antigen expressed on the cell surface of a human stem cell or a T cell (e.g., from the —SH group of a cysteine residue. The wavy line at the linker terminus indicates the point of attachment to the amatoxin.

In some embodiments, the linker-reactive substituent group, taken together as L-Z', prior to conjugation with the antibody or antigen binding fragment thereof, has the structure:

This linker-reactive substituent group may alternatively be referred to as 1-n-hexyl-maleimide, which is a non-cleavable linker. The wavy line at the linker terminus indicates the point of attachment to the amatoxin.

In some embodiments, the linker L and the chemical moiety Z, after conjugation to the antibody, taken together as L-Z-Ab, has the structure:

where S is a sulfur atom which represents the reactive substituent present within an antibody, or antigen-binding fragment thereof, that specifically binds to an antigen expressed on the cell surface of a cell, e.g., a tumor cell or a human stem cell or a T cell (e.g., from the —SH group of a cysteine residue). The wavy line at the linker terminus indicates the point of attachment to the amatoxin. One of skill in the art will recognize that in this embodiment, the linker-reactive substituent group structure L-Z', prior to conjugation with the antibody or antigen binding fragment thereof, includes a maleimide as the group Z'. The foregoing linker moieties and amatoxin-linker conjugates, among others useful in conjunction with the compositions and methods described herein, are described, for example, in U.S. Patent Application Publication No. 2015/0218220 and Patent Application Publication No. WO2017/149077, the disclosure of each of which is incorporated herein by reference in its entirety.

In one aspect, the cytotoxin of the ADC as disclosed herein is an amatoxin or derivative thereof as represented by any of formulae (V), (Va), or (Vb). One of skill in the art will recognize that such amatoxins present multiple possibilities for attachment points to the linker.

In some embodiments, the amatoxin has the structure of formula (V), and the linker is attached by an ether bond to the OH group of the hydroxyl tryptophan residue. In such embodiments, the ADC may be represented by formula (I):

(I)

or a stereoisomer thereof;
wherein:
Q is S;
L is a linker;
Z is a chemical moiety formed by a coupling reaction between a reactive substituent present on L and a reactive substituent present within an antibody, or antigen-binding fragment thereof; and
Ab is an antibody,
each as disclosed herein.

In some embodiments, the amatoxin has the structure of formula (Va), and the linker is attached by an ether bond to the OH group of the hydroxyl tryptophan residue. In such embodiments, the ADC may be represented by formula (Ia):

(Ia)

In some embodiments, the amatoxin has the structure of formula (Vb), and the linker is attached by an ether bond to the OH group of the hydroxyl tryptophan residue. In such embodiments, the ADC may be represented by formula (Ib):

(Ib)

In some embodiments, the linker L of the ADC of formula (I), (Ia), or (Ib) is a non-cleavable linker. In some embodiments, the non-cleavable linker L comprises one or more of a bond, —(C=O)—, a —C(O)NH— group, an —OC(O) NH— group, $C_1$-$C_6$ alkylene, $C_1$-$C_6$ heteroalkylene, $C_2$—C alkenylene, $C_2$—C heteroalkenylene, $C_2$—C alkynylene, $C_2$—C heteroalkynylene, $C_3$-$C_6$ cycloalkylene, heterocycloalkylene, arylene, heteroarylene, a —$(CH_2CH_2O)_p$— group where p is an integer from 1-6, or a solubility enhancing group;

wherein each $C_1$-$C_6$ alkylene, $C_1$-$C_6$ heteroalkylene, $C_2$-$C_6$ alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro; or each $C_1$-$C_6$ alkylene, $C_1$-$C_6$ heteroalkylene, $C_2$—C alkenylene, $C_2$-$C_6$ heteroalkenylene, $C_2$-$C_6$ alkynylene, $C_2$-$C_6$ heteroalkynylene, $C_3$-$C_6$ cycloalkylene, heterocycloalkylene, arylene, or heteroarylene may optionally be interrupted by one or more heteroatoms selected from O, S and N.

In some embodiments, the non-cleavable linker L comprises a solubility enhancing group of the formula —$O_a$— C(O)NH—$SO_2$—$NR^1$—, wherein:

a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted, optionally interrupted, or both, by one or more heteroatoms selected from O, S and $NR^3$, wherein $R^3$ is independently selected from the group consisting of hydrogen and $C_1$-$C_4$ alkyl.

In some embodiments, the non-cleavable linker L comprises a —$(CH_2)_n$— unit, where n is an integer from 2-6. In some embodiments, the non-cleavable linker L is —$(CH_2)_n$—, where n is 6.

In some embodiments, Ab, Z, and the non-cleavable linker L, taken together as Ab-Z-L, is represented by the formula:

where S is a sulfur atom which represents the reactive substituent present within the antibody, or antigen-binding fragment thereof, that specifically binds to an antigen expressed on a cell, e.g., surface of a human stem cell or a T cell (e.g., from the —SH group of a cysteine residue). The wavy line at the linker terminus indicates the point of attachment to the amatoxin.

In some embodiments, the ADC according to formula (I) is represented by formula (II):

(II)

a stereoisomer thereof, or a pharmaceutically acceptable salt thereof.

In some embodiments, the ADC according to formula (II) is represented by formula (IIa):

(IIa)

a stereoisomer thereof, or a pharmaceutically acceptable salt thereof.

In some embodiments, the ADC according to formula (II) is represented by formula (IIb):

(IIb)

a stereoisomer thereof, or a pharmaceutically acceptable salt thereof.

Surprisingly, according to the present disclosure, it has been found that ADCs comprising an amatoxin and a non-cleavable linker conjugating the amatoxin to the antibody moiety of the ADC have improved tolerability as compared to an ADC comprising an amatoxin and a cleavable linker. For example, in some embodiments, the improved tolerability may be increased therapeutic index. In some embodiments, the improved tolerability may be a smaller elevation, or absence of elevation, of one or more blood liver enzyme levels (e.g., AST, ALT, ADH, or total bilirubin) at a particular dose of the ADC comprising a non-cleavable linker as compared to an ADC comprising a cleavable linker.

In some embodiments, the linker L of the ADC of formula (I), (Ia), or (Ib) is a cleavable linker. In some embodiments, the cleavable linker L comprises one or more of a hydrazine, a disulfide, a thioether, an amino acid, a peptide consisting of up to 10 amino acids, a p-aminobenzyl (PAB) group, a heterocyclic self-immolative group, $C_1$-$C_6$ alkyl, $C_1$-$C_6$ heteroalkyl, $C_2$—C alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, heteroaryl, a —(C=O)— group, a —C(O)NH— group, an —OC(O)NH— group, a —(CH$_2$CH$_2$O)$_p$— group where p is an integer from 1-6, or a solubility enhancing group;

wherein each $C_1$-$C_6$ alkyl, $C_1$-$C_6$ heteroalkyl, $C_2$-$C_6$ alkenyl, $C_2$-$C_6$ heteroalkenyl, $C_2$-$C_6$ alkynyl, $C_2$-$C_6$ heteroalkynyl, $C_3$-$C_6$ cycloalkyl, heterocycloalkyl, aryl, or heteroaryl group may be optionally substituted with from 1 to 5 substituents independently selected for each occasion from the group consisting of alkyl, alkenyl, alkynyl, cycloalkyl, heterocycloalkyl, alkaryl, alkyl heteroaryl, amino, ammonium, acyl, acyloxy, acylamino, aminocarbonyl, alkoxycarbonyl, ureido, carbamate, aryl, heteroaryl, sulfinyl, sulfonyl, hydroxyl, alkoxy, sulfanyl, halogen, carboxy, trihalomethyl, cyano, hydroxy, mercapto, and nitro;

or each $C_1$-$C_6$ alkyl, $C_1$-$C_6$ heteroalkyl, $C_2$-$C_6$ alkenyl, $C_2$-$C_6$ heteroalkenyl, $C_2$-$C_6$alkynyl, $C_2$-$C_6$ heteroalkynyl, $C_3$-$C_6$ cycloalkyl, heterocycloalkyl, aryl, or heteroaryl group may optionally be interrupted by one or more heteroatoms selected from O, S and N.

In some embodiments, the cleavable linker L comprises a solubility enhancing group of the formula —O$_a$—C(O)NH—SO$_2$—NR$^1$—, wherein:

a is 0 or 1; and

R$^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, each of which may be optionally substituted or optionally interrupted by one or more heteroatoms selected from O, S and NR$^3$, wherein R$^3$ is independently selected from the group consisting of hydrogen and $C_1$-$C_4$ alkyl.

In some embodiments, the cleavable linker L comprises a peptide selected from the group consisting of Phe-Lys, Val-Lys, Phe-Ala, Phe-Cit, Val-Ala, Val-Cit, and Val-Arg.

In some embodiments, the cleavable linker L further comprises a PAB group.

In some embodiments, the cleavable linker L is represented by the formula:

Preparation of Antibody-Drug Conjugates

In the ADCs of formula Ab-(Z-L-Cy)$_n$ as disclosed herein, such as an ADC of any of formulae (I), (Ia), or (Ib), (II), (IIa), or (IIb), an antibody or antigen binding fragment thereof (Ab) is conjugated to one or more cytotoxic drug moieties (Cy; e.g., an amatoxin), for example, from about 1 to about 20 cytotoxic moieties per antibody, through a linker L and a chemical moiety Z, each as disclosed herein. In some embodiments, n is 1. In some embodiments, n is about 1 to about 5, about 1 to about 4, about 1 to about 3, or about 3 to about 5. In some embodiments, n is about 1, about 2, about 3, or about 4.

The ADCs of the present disclosure may be prepared by several routes, employing organic chemistry reactions, conditions, and reagents known to those skilled in the art, including: (1) reaction of a reactive substituent of an antibody or antigen binding fragment thereof with a bivalent linker reagent to form Ab-Z-L as described herein above, followed by reaction with a cytotoxic moiety Cy; or (2) reaction of a reactive substituent of a cytotoxic moiety with a bivalent linker reagent to form Cy-L-Z', followed by reaction with a reactive substituent of an antibody or antigen binding fragment thereof as described herein above, to form an ADC of formula Ab-(Z-L-Cy)$_n$. Additional methods for preparing ADC are described herein.

In one embodiment, the antibody or antigen binding fragment thereof can have one or more carbohydrate groups that can be chemically modified to have one or more sulfhydryl groups. The ADC is then formed by conjugation through the sulfhydryl group's sulfur atom as described herein above.

In another embodiment, the antibody can have one or more carbohydrate groups that can be oxidized to provide an aldehyde (—CHO) group (see, for e.g., Laguzza, et al., J. Med. Chem. 1989, 32(3), 548-55). The ADC is then formed by conjugation through the corresponding aldehyde as described herein above. Other protocols for the modification of proteins for the attachment or association of cytotoxins are described in Coligan et al., Current Protocols in Protein Science, vol. 2, John Wiley & Sons (2002), incorporated herein by reference.

Methods for the conjugation of linker-drug moieties to cell-targeted proteins such as antibodies, immunoglobulins or fragments thereof are found, for example, in U.S. Pat. Nos. 5,208,020; 6,441,163; WO2005037992; WO2005081711; and WO2006/034488, all of which are hereby expressly incorporated by reference in their entirety.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In some embodiments, the ADC of formula (IIa) may be prepared by conjugation of a thiol group on the antibody to the amatoxin-linker conjugate Cy-L-Z', represented by the structure:

This amatoxin-linker conjugate may be prepared according to Schemes 1 to 3, starting from commercially available 6-hydroxytryptophan (1). Compound 1 may be protected with tert-butyloxycarbonyl anhydride ((BOC)$_2$O). Hexahydropyrroloindole 3 may be produced as a mixture of cis and trans isomers upon irradiation of protected hydroxytryptophan 2 in the presence of oxygen and a sensitizer (Rose Bengal). Preparation of compound 3 (as well as procedure for preparation of compounds 2 to Va) are provided in International Patent Application Publication No. WO2019/ 030173, the disclosure of which is incorporated by reference herein in its entirety. Commercial 9-fluorenylmethoxycarbonyl (FMOC) protected 4-hydroxyproline (4) may be alkylated with allyl bromide and subsequently attached to tetrahydropyranyl (THP) polystyrene resin under mild acidic conditions (pyridinium para-toluenesulfonate; PPTS) to give the resin bound allyl ester 5, which may be deprotected with palladium tetrakistriphenylphosphine palladium and dimethyl barbituric acid to give intermediate 6. Protected amino acid 7 may be prepared according to the method reported in International Patent Application Publication No. WO2014/ 009025, the disclosure of which is incorporated herein in its entirety. Protected amine 7 may then be coupled to resin bound hydroxyproline 6 to afford peptide 8.

Scheme 1.

1

2

3

4

-continued

5

6

7

8

Peptide 8 may then be subjected to multiple coupling and deprotection reactions to provide monocyclic intermediate 9 (Scheme 2). Amino acids FmocAsn(Trt)OH, FmocCys(OTrt)OH, FmocGlyOH, FmocIleOH, FmocGlyOH, and hexahydropyrroloindole 3 may be utilized in sequential solid phase coupling reactions to yield intermediate 9. Each amino acid may be coupled using PyBOP/HOBT in dichloromethane and dimethylformamide (DMF) in the presence of diisopropylethylamine (DIEA). Deprotection may be performed with 20% piperidine in DMF.

Scheme 2.

8

9

TFA/triisopropyl silane

10

1. DPPA, DIEA
2. NH₃/MeOH

-continued

11

Following the final coupling reaction, intermediate 9 may be cleaved from the solid phase support resin with trifluoroacetic acid in the presence of triisopropylsilane to give peptide 10. Treatment of 10 with diphenylphosphorylazide (DPPA) and DIEA induced macrocyclization, and deprotection with ammoniacal methanol provided the amatoxin derivative 11 (i.e., formula Va, where Q=S).

The maleimidohexyl amatoxin conjugate 14 may be prepared from compound 11 according to Scheme 3. Diels-Alder adduct 12 may be prepared from maleimide and 2,5-dimethylfuran and then alkylated with 1,6-dibromohexane to give protected linker 13. Compound 11 may be alkylated with compound 13 in dimethyl sulfoxide (DMSO) in the presence of sodium hydroxide, followed by heating to 10000 in DMSO to afford the amatoxin-linker conjugate 14. Procedures for preparing compounds 12 and 13, as well as O-alkylation of a related amatoxin (α-amanitin) have been previously reported in U.S. Patent Application Publication No. 2018/0043033, the disclosure of which is incorporated by reference herein in its entirety.

Scheme 3.

12

-continued

13

14

Antibodies

The ADC compositions and methods disclosed herein comprise an agent to facilitate the selective delivery of such ADCs to a population of cells in the target tissues (e.g., cancer or tumor cells, or hematopoietic stem cells of the bone marrow stem cell niche). The cell target specificity of the ADC is determined by an antigen binding protein such as an antibody, or antigen binding portion thereof.

In one embodiment, the invention includes ADCs comprising antibodies, and antigen-binding fragments thereof, that specifically bind to human CD45, CD49d (VLA-4), CD49f(VLA-6), CD51, CD84, CD90, CD117, CD133, CD134, CD184 (CXCR4), HLA-DR, CD11a, CD18, CD34, CD41/61, CD43, CD58, CD71, CD97, CD162, CD166, CD205 and CD361, CD13, CD33, CD34, CD44, CD4, CD59, CD84/CD150, CD90/Thy1, CD93, CD105/Endoglin, CD123/IL-3R, CD126/IL-6R, CD133, CD135/Flt3 receptor, CD166/ALCAM, Prominin 2, Erythropoietin R, Endothelial Cell-Selective Adhesion Molecule, CD244, Tie1, Tie2, MPL, G-CSFR, CSF3R, IL-1R, gp130, Leukemia inhibitory factor Receptor, oncostatin M receptor, Embigin and IL-18R. Other examples of antigens that can be bound by the ADCs disclosed herein include, but are not limited to, CD7, CDw12, CD13, CD15, CD19, CD21, CD22, CD29, CD30, CD33, CD34, CD36, CD38, CD40, CD41, CD42a, CD42b, CD42c, CD42d, CD43, CD45RA, CD45RB, CD45RC, CD45RO, CD48, CD49b, CD49d, CD49e, CD49f, CD50, CD53, CD55, CD64a, CD68, CD71, CD72, CD73, CD81, CD82, CD85A, CD85K, CD90, CD99, CD104, CD105, CD109, CD110, CD111, CD112, CD114, CD115, CD123, CD124, CD126, CD127, CD130, CD131, CD133, CD135, CD138, CD151, CD157, CD162, CD164, CD168, CD172a, CD173, CD174, CD175, CD175s, CD176, CD183, CD191, CD200, CD201, CD205, CD217, CD220, CD221, CD222, CD223, CD224, CD225, CD226, CD227, CD228, CD229, CD230, CD235a, CD235b, CD236, CD236R, CD238, CD240, CD242, CD243, CD277, CD292, CDw293, CD295, CD298, CD309, CD318, CD324, CD325, CD338, CD344, CD349 or CD350. Other examples of antigens that can be bound by the ADCs disclosed herein include, but are not limited to, CD11a, CD18, CD37, CD47, CD52, CD58, CD62L, CD69, CD74, CD97, CD103, CD132, CD156a, CD179a, CD79b, CD184, CD232, CD244, CD252, CD302, CD305, CD317 and CD361.

In certain embodiments, an antibody, or antigen binding fragment thereof, in an ADC described herein has a certain dissociation rate which is particularly advantageous when used as a part of a conjugate. For example, an anti-CD117 antibody has, in certain embodiments, an off rate constant (Koff) for human CD117 and/or rhesus CD117 of $1 \times 10^{-2}$ to $1 \times 10^{-3}$, $1 \times 10^{-3}$ to $1 \times 10^{-4}$, $1 \times 10^{-5}$ to $1 \times 10^{-6}$, $1 \times 10^{-6}$ to $1 \times 10^{-7}$ or $1 \times 10^{-7}$ to $1 \times 10^{-8}$, as measured by bio-layer interferometry (BLI). In some embodiments, the antibody or antigen-binding fragment thereof binds a cell surface antigen (e.g., human CD117 and/or rhesus CD117) with a $K_D$ of about 100 nM or less, about 90 nM or less, about 80 nM or less, about 70 nM or less, about 60 nM or less, about 50 nM or less, about 40 nM or less, about 30 nM or less, about 20 nM or less, about 10 nM or less, about 8 nM or less, about 6 nM or less, about 4 nM or less, about 2 nM or less, about 1 nM or less as determined by a Bio-Layer Interferometry (BLI) assay.

Anti-CD117 Antibodies

In one embodiment, the present invention includes ADCs comprising antibodies, and antigen-binding fragments thereof, that specifically bind to CD117, such as GNNK+ CD117. Such ADCs may be used as therapeutic agents to, for example, (i) treat cancers and autoimmune diseases characterized by CD117+ cells and (ii) promote the engraftment of transplanted hematopoietic stem cells in a patient in need of transplant therapy. These therapeutic activities can be caused, for instance, by the binding of isolated anti-CD117 antibodies, antigen-binding fragments thereof, that bind to CD117 (e.g., GNNK+ CD117) expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein.

Antibodies and antigen-binding fragments capable of binding human CD117 (also referred to as c-Kit, mRNA NCBI Reference Sequence: NM_000222.2, Protein NCBI Reference Sequence: NP_000213.1), including those capable of binding GNNK+CD117, can be used in conjunction with the compositions and methods described herein in order to condition a patient for hematopoietic stem cell transplant therapy. Polymorphisms affecting the coding region or extracellular domain of CD117 in a significant percentage of the population are not currently well-known in non-oncology indications. There are at least four isoforms of CD117 that have been identified, with the potential of additional isoforms expressed in tumor cells. Two of the CD117 isoforms are located on the intracellular domain of the protein, and two are present in the external juxtamembrane region. The two extracellular isoforms, GNNK+ and GNNK–, differ in the presence (GNNK+) or absence (GNNK–) of a 4 amino acid sequence. These isoforms are reported to have the same affinity for the ligand (SCF), but ligand binding to the GNNK– isoform was reported to increase internalization and degradation. The GNNK+ isoform can be used as an immunogen in order to generate antibodies capable of binding CD117, as antibodies generated against this isoform will be inclusive of the GNNK+ and GNNK– proteins. The amino acid sequences of human CD117 isoforms 1 and 2 are described in SEQ ID Nos: 145 and 146, respectively. In certain embodiments, anti-human CD117 (hCD117) antibodies disclosed herein are able to bind to both isoform 1 and isoform 2 of human CD117.

As described below, a yeast library screen of human antibodies was performed to identify novel anti-CD117 antibodies, and fragments thereof, having diagnostic and therapeutic use. Antibody 54 (Ab54), Antibody 55 (Ab55), Antibody 56 (Ab56), Antibody 57 (Ab57), Antibody 58 (Ab58), Antibody 61 (Ab61), Antibody 66 (Ab66), Antibody 67 (Ab67), Antibody 68 (Ab68), and Antibody 69 (Ab69) were human antibodies that were identified in this screen. These antibodies cross react with human CD117 and rhesus CD117. Further, these antibodies disclosed herein are able to bind to both isoforms of human CD117, i.e., isoform 1 (SEQ ID NO: 145) and isoform 2 (SEQ ID NO: 146).

The amino acid sequences for the various binding regions of anti-CD117 antibodies, including Ab54, Ab55, Ab56, Ab57, Ab58, Ab61, Ab66, Ab67, Ab68, and Ab69 are described in the Sequence Table below. Included in the invention are ADCs comprising human anti-CD117 antibodies comprising the CDRs as set forth in the Sequence Table below, as well as human anti-CD117 antibodies comprising the variable regions set forth in the Sequence Table below.

In one embodiment, the invention provides an ADC comprising an anti-CD117 antibody, or antigen-binding fragment thereof, comprising binding regions, e.g., CDRs, variable regions, corresponding to those of Antibody 55. The heavy chain variable region (VH) amino acid sequence of Antibody 55 (i.e., Ab55) is set forth in SEQ ID NO: 19 (see Sequence Table). The VH CDR domain amino acid sequences of Antibody 55 are set forth in SEQ ID NO: 21 (VH CDR1); SEQ ID NO: 22 (VH CDR2), and SEQ ID NO: 23 (VH CDR3). The light chain variable region (VL) amino acid sequence of Antibody 55 is described in SEQ ID NO: 20 (see Sequence Table). The VL CDR domain amino acid sequences of Antibody 55 are set forth in SEQ ID NO: 24 (VL CDR1); SEQ ID NO: 25 (VL CDR2), and SEQ ID NO: 26 (VL CDR3). The heavy chain constant region of Antibody 55 is set forth in SEQ ID NO: 122. The light chain constant region of Antibody 55 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 21, 22, and 23, and a light chain variable region CDR set as set forth in SEQ ID Nos: 24, 25, and 26. In other embodiments, an anti-CD117 antibody, or antigen-binding portion thereof, comprises a variable light chain comprising the amino acid residues set forth in SEQ ID NO: 20, and a heavy chain variable region as set forth in SEQ ID NO: 19.

In one embodiment, the invention provides an an ADC comprising an anti-CD117 antibody, or antigen-binding fragment thereof, comprising binding regions, e.g., CDRs, variable regions, corresponding to those of Antibody 54. The heavy chain variable region (VH) amino acid sequence of Antibody 54 (i.e., Ab54) is set forth in SEQ ID NO: 29 (see Sequence Table). The VH CDR domain amino acid sequences of Antibody 54 are set forth in SEQ ID NO: 31 (VH CDR1); SEQ ID NO: 32 (VH CDR2), and SEQ ID NO: 33 (VH CDR3). The light chain variable region (VL) amino acid sequence of Antibody 54 is described in SEQ ID NO: 30 (see Sequence Table). The VL CDR domain amino acid sequences of Antibody 54 are set forth in SEQ ID NO: 34 (VL CDR1); SEQ ID NO: 35 (VL CDR2), and SEQ ID NO: 36 (VL CDR3). The heavy chain constant region of Antibody 54 is set forth in SEQ ID NO: 122. The light chain constant region of Antibody 54 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 31, 32, and 33, and a light chain variable region CDR set as set forth in SEQ ID Nos: 34, 35, and 36. In other embodiments, an anti-CD117 antibody, or antigen-binding portion thereof, comprises a variable light chain comprising the amino acid residues set forth in SEQ ID NO: 30, and a heavy chain variable region as set forth in SEQ ID NO: 29.

In one embodiment, the invention provides an ADC comprising an anti-CD117 antibody, or antigen-binding fragment thereof, comprising binding regions, e.g., CDRs, variable regions, corresponding to those of Antibody 56. The heavy chain variable region (VH) amino acid sequence of Antibody 56 (i.e., Ab56) is set forth in SEQ ID NO: 39 (see Sequence Table). The VH CDR domain amino acid sequences of Antibody 56 are set forth in SEQ ID NO: 41 (VH CDR1); SEQ ID NO: 42 (VH CDR2), and SEQ ID NO: 43 (VH CDR3). The light chain variable region (VL) amino acid sequence of Antibody 56 is described in SEQ ID NO: 40 (see Sequence Table). The VL CDR domain amino acid sequences of Antibody 56 are set forth in SEQ ID NO: 44 (VL CDR1); SEQ ID NO: 45 (VL CDR2), and SEQ ID NO: 46 (VL CDR3). The heavy chain constant region of Antibody 56 is set forth in SEQ ID NO: 122. The light chain constant region of Antibody 56 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 41, 42, and 43, and a light chain variable region CDR set as set forth in SEQ ID Nos: 44, 45, and 46. In other embodiments, an anti-CD117 antibody, or antigen-binding portion thereof, comprises a variable light chain comprising the amino acid residues set forth in SEQ ID NO: 40, and a heavy chain variable region as set forth in SEQ ID NO: 39.

In one embodiment, the invention provides an ADC comprising an anti-CD117 antibody, or antigen-binding fragment thereof, comprising binding regions, e.g., CDRs, variable regions, corresponding to those of Antibody 57. The heavy chain variable region (VH) amino acid sequence of Antibody 57 (i.e., Ab57) is set forth in SEQ ID NO: 49 (see Sequence Table). The VH CDR domain amino acid sequences of Antibody 57 are set forth in SEQ ID NO: 51 (VH CDR1); SEQ ID NO: 52 (VH CDR2), and SEQ ID NO: 53 (VH CDR3). The light chain variable region (VL) amino acid sequence of Antibody 57 is described in SEQ ID NO: 50 (see Sequence Table). The VL CDR domain amino acid sequences of Antibody 57 are set forth in SEQ ID NO: 54 (VL CDR1); SEQ ID NO: 55 (VL CDR2), and SEQ ID NO: 56 (VL CDR3). The heavy chain constant region of Antibody 57 is set forth in SEQ ID NO: 122. The light chain constant region of Antibody 57 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 51, 52, and 53, and a light chain variable region CDR set as set forth in SEQ ID Nos: 54, 55, and 56. In other embodiments, an anti-CD117 antibody, or antigen-binding portion thereof, comprises a variable light chain comprising the amino acid residues set forth in SEQ ID NO: 50, and a heavy chain variable region as set forth in SEQ ID NO: 49.

In one embodiment, the invention provides an ADC comprising an anti-CD117 antibody, or antigen-binding fragment thereof, comprising binding regions, e.g., CDRs, variable regions, corresponding to those of Antibody 58. The heavy chain variable region (VH) amino acid sequence of Antibody 58 (i.e., Ab58) is set forth in SEQ ID NO: 59 (see Sequence Table). The VH CDR domain amino acid sequences of Antibody 58 are set forth in SEQ ID NO: 61 (VH CDR1); SEQ ID NO: 62 (VH CDR2), and SEQ ID NO: 63 (VH CDR3). The light chain variable region (VL) amino acid sequence of Antibody 58 is described in SEQ ID NO: 60 (see Sequence Table). The VL CDR domain amino acid sequences of Antibody 58 are set forth in SEQ ID NO: 64 (VL CDR1); SEQ ID NO: 65 (VL CDR2), and SEQ ID NO: 66 (VL CDR3). The heavy chain constant region of Antibody 58 is set forth in SEQ ID NO: 122. The light chain constant region of Antibody 58 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 61, 62, and 63, and a light chain variable region CDR set as set forth in SEQ ID Nos: 64, 65, and 66. In other embodiments, an anti-CD117 antibody, or antigen-binding portion thereof, comprises a variable light chain comprising the amino acid residues set forth in SEQ ID NO: 60, and a heavy chain variable region as set forth in SEQ ID NO: 59.

In one embodiment, the invention provides an ADC comprising an anti-CD117 antibody, or antigen-binding fragment thereof, comprising binding regions, e.g., CDRs, variable regions, corresponding to those of Antibody 61. The heavy chain variable region (VH) amino acid sequence of Antibody 61 (i.e., Ab61) is set forth in SEQ ID NO: 69 (see Sequence Table). The VH CDR domain amino acid sequences of Antibody 61 are set forth in SEQ ID NO: 71 (VH CDR1); SEQ ID NO: 72 (VH CDR2), and SEQ ID NO: 73 (VH CDR3). The light chain variable region (VL) amino acid sequence of Antibody 61 is described in SEQ ID NO: 70 (see Sequence Table). The VL CDR domain amino acid sequences of Antibody 61 are set forth in SEQ ID NO: 74 (VL CDR1); SEQ ID NO: 75 (VL CDR2), and SEQ ID NO: 76 (VL CDR3). The heavy chain constant region of Antibody 61 is set forth in SEQ ID NO: 122. The light chain constant region of Antibody 61 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 71, 72, and 73, and a light chain variable region CDR set as set forth in SEQ ID Nos: 74, 75, and 76. In other embodiments, an anti-CD117 antibody, or antigen-binding portion thereof, comprises a variable light chain comprising the amino acid residues set forth in SEQ ID NO: 70, and a heavy chain variable region as set forth in SEQ ID NO: 69.

In one embodiment, the invention provides an ADC comprising an anti-CD117 antibody, or antigen-binding fragment thereof, comprising binding regions, e.g., CDRs, variable regions, corresponding to those of Antibody 66. The heavy chain variable region (VH) amino acid sequence of Antibody 66 (i.e., Ab66) is set forth in SEQ ID NO: 79 (see Sequence Table). The VH CDR domain amino acid sequences of Antibody 66 are set forth in SEQ ID NO: 81 (VH CDR1); SEQ ID NO: 82 (VH CDR2), and SEQ ID NO: 83 (VH CDR3). The light chain variable region (VL) amino acid sequence of Antibody 66 is described in SEQ ID NO: 80 (see Sequence Table). The VL CDR domain amino acid sequences of Antibody 66 are set forth in SEQ ID NO: 84 (VL CDR1); SEQ ID NO: 85 (VL CDR2), and SEQ ID NO: 86 (VL CDR3). The heavy chain constant region of Antibody 66 is set forth in SEQ ID NO: 122. The light chain constant region of Antibody 66 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 81, 82, and 83, and a light chain variable region CDR set as set forth in SEQ ID Nos: 84, 85, and 86. In other embodiments, an anti-CD117 antibody, or antigen-binding portion thereof, comprises a variable light chain comprising the amino acid residues set forth in SEQ ID NO: 80, and a heavy chain variable region as set forth in SEQ ID NO: 79.

In one embodiment, the invention provides an ADC comprising an anti-CD117 antibody, or antigen-binding fragment thereof, comprising binding regions, e.g., CDRs, variable regions, corresponding to those of Antibody 67. The heavy chain variable region (VH) amino acid sequence of Antibody 67 is set forth in SEQ ID NO: 9 (see Table 2). The VH CDR domain amino acid sequences of Antibody 67 are set forth in SEQ ID NO 11 (VH CDR1); SEQ ID NO: 12 (VH CDR2), and SEQ ID NO: 13 (VH CDR3). The light chain variable region (VL) amino acid sequence of Antibody 67 is described in SEQ ID NO: 10 (see Table 2). The VL CDR domain amino acid sequences of Antibody 67 are set forth in SEQ ID NO 14 (VL CDR1); SEQ ID NO: 15 (VL CDR2), and SEQ ID NO: 16 (VL CDR3). The full length heavy chain (HC) of Antibody 67 is set forth in SEQ ID NO: 110, and the full length heavy chain constant region of Antibody 67 is set forth in SEQ ID NO: 122. The light chain (LC) of Antibody 67 is set forth in SEQ ID NO: 109. The light chain constant region of Antibody 67 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 11, 12, and 13, and a light chain variable region CDR set as set forth in SEQ ID Nos: 14, 15, and 16. In other embodiments, an anti-CD117 antibody, or antigen-binding portion thereof, comprises a variable heavy chain comprising the amino acid residues set forth in SEQ ID NO: 9, and a heavy chain variable region as set forth in SEQ ID NO: 10. In further embodiments, an anti-CD117 antibody comprises a heavy chain comprising SEQ ID NO: 110 and a light chain comprising SEQ ID NO: 109.

In one embodiment, the invention provides an ADC comprising an anti-CD117 antibody, or antigen-binding fragment thereof, comprising binding regions, e.g., CDRs, variable regions, corresponding to those of Antibody 68. The heavy chain variable region (VH) amino acid sequence of Antibody 68 (i.e., Ab68) is set forth in SEQ ID NO: 89 (see Sequence Table). The VH CDR domain amino acid sequences of Antibody 68 are set forth in SEQ ID NO: 91 (VH CDR1); SEQ ID NO: 92 (VH CDR2), and SEQ ID NO: 93 (VH CDR3). The light chain variable region (VL) amino acid sequence of Antibody 68 is described in SEQ ID NO: 90 (see Sequence Table). The VL CDR domain amino acid sequences of Antibody 68 are set forth in SEQ ID NO: 94 (VL CDR1); SEQ ID NO: 95 (VL CDR2), and SEQ ID NO: 96 (VL CDR3). The heavy chain constant region of Antibody 68 is set forth in SEQ ID NO: 122. The light chain constant region of Antibody 68 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 91, 92, and 93, and a light chain variable region CDR set as set forth in SEQ ID Nos: 94, 95, and 96. In other embodiments, an anti-CD117 antibody, or antigen-binding portion thereof, comprises a variable light chain comprising the amino acid residues set forth in SEQ ID NO: 90, and a heavy chain variable region as set forth in SEQ ID NO: 89.

In one embodiment, the invention provides an ADC comprising an anti-CD117 antibody, or antigen-binding fragment thereof, comprising binding regions, e.g., CDRs, variable regions, corresponding to those of Antibody 69. The heavy chain variable region (VH) amino acid sequence of Antibody 69 (i.e., Ab69) is set forth in SEQ ID NO: 99 (see Sequence Table). The VH CDR domain amino acid sequences of Antibody 69 are set forth in SEQ ID NO: 101 (VH CDR1); SEQ ID NO: 102 (VH CDR2), and SEQ ID NO: 103 (VH CDR3). The light chain variable region (VL) amino acid sequence of Antibody 69 is described in SEQ ID NO: 100 (see Sequence Table). The VL CDR domain amino acid sequences of Antibody 69 are set forth in SEQ ID NO: 104 (VL CDR1); SEQ ID NO: 105 (VL CDR2), and SEQ ID NO: 106 (VL CDR3). The heavy chain constant region of Antibody 69 is set forth in SEQ ID NO: 122. The light chain constant region of Antibody 69 is set forth in SEQ ID NO: 121. Thus, in certain embodiments, an anti-CD117 antibody, or antigen-binding portion thereof, comprises a variable heavy chain CDR set (CDR1, CDR2, and CDR3) as set forth in SEQ ID Nos: 101, 102, and 103, and a light chain variable region CDR set as set forth in SEQ ID Nos: 104, 105, and 106. In other embodiments, an anti-CD117 antibody, or antigen-binding portion thereof, comprises a variable light chain comprising the amino acid residues set forth in SEQ ID NO: 100, and a heavy chain variable region as set forth in SEQ ID NO: 99.

Further, the amino acid sequences for the various binding regions of the anti-CD117 antibodies Ab77, Ab79, Ab81, Ab85, Ab86, Ab87, Ab88, and Ab89 are described in the Sequence Table provided below. Anti-CD117 antibodies having these sequences can also be used in the ADCs described herein.

In one embodiment, the invention provides an ADC comprising an anti-CD117 antibody, or antigen-binding fragment thereof, comprising binding regions, e.g., CDRs, variable regions, corresponding to those of Antibody 77. The heavy chain variable region (VH) amino acid sequence of Antibody 77 (i.e., Ab77) is set forth in SEQ ID NO: 147 (see Sequence Table). The VH CDR domain amino acid sequences of Antibody 77 are set forth in SEQ ID NO: 263 (VH CDR1); SEQ ID NO: 2 (VH CDR2), and SEQ ID NO: 3 (VH CDR3). The light chain variable region (VL) amino acid sequence of Antibody 77 is described in SEQ ID NO: 231 (see Sequence Table). The VL CDR domain amino acid sequences of Antibody 77 are set forth in SEQ ID NO: 264 (VL CDR1); SEQ ID NO: 265 (VL CDR2), and SEQ ID NO: 266 (VL CDR3). The heavy chain constant region of Antibody 77 is set forth in SEQ ID NO: 269. The light chain constant region of Antibody 77 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 263, 2, and 3, and a light chain variable region CDR set as set forth in SEQ ID Nos: 264, 265, and 266. In other embodiments, an anti-CD117 antibody, or antigen-binding portion thereof, comprises a variable light chain comprising the amino acid residues set forth in SEQ ID NO: 231, and a heavy chain variable region as set forth in SEQ ID NO: 147.

In one embodiment, the invention provides an ADC comprising an anti-CD117 antibody, or antigen-binding fragment thereof, comprising binding regions, e.g., CDRs, variable regions, corresponding to those of Antibody 79. The heavy chain variable region (VH) amino acid sequence of Antibody 79 (i.e., Ab79) is set forth in SEQ ID NO: 147 (see Sequence Table). The VH CDR domain amino acid sequences of Antibody 79 are set forth in SEQ ID NO: 263 (VH CDR1); SEQ ID NO: 2 (VH CDR2), and SEQ ID NO: 3 (VH CDR3). The light chain variable region (VL) amino acid sequence of Antibody 79 is described in SEQ ID NO: 233 (see Sequence Table). The VL CDR domain amino acid sequences of Antibody 79 are set forth in SEQ ID NO: 267 (VL CDR1); SEQ ID NO: 265 (VL CDR2), and SEQ ID NO: 266 (VL CDR3). The heavy chain constant region of Antibody 79 is set forth in SEQ ID NO: 269. The light chain constant region of Antibody 79 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 263, 2, and 3, and a light chain variable region CDR set as set forth in SEQ ID Nos: 267, 265, and 266. In other embodiments, an anti-CD117 antibody, or antigen-binding portion thereof, comprises a variable light chain comprising the amino acid residues set forth in SEQ ID NO: 233, and a heavy chain variable region as set forth in SEQ ID NO: 147.

In one embodiment, the invention provides an ADC comprising an anti-CD117 antibody, or antigen-binding fragment thereof, comprising binding regions, e.g., CDRs, variable regions, corresponding to those of Antibody 81. The heavy chain variable region (VH) amino acid sequence of Antibody 81 (i.e., Ab81) is set forth in SEQ ID NO: 147 (see Sequence Table). The VH CDR domain amino acid sequences of Antibody 81 are set forth in SEQ ID NO: 263 (VH CDR1); SEQ ID NO: 2 (VH CDR2), and SEQ ID NO: 3 (VH CDR3). The light chain variable region (VL) amino acid sequence of Antibody 81 is described in SEQ ID NO: 235 (see Sequence Table). The VL CDR domain amino acid sequences of Antibody 81 are set forth in SEQ ID NO: 264 (VL CDR1); SEQ ID NO: 268 (VL CDR2), and SEQ ID NO: 266 (VL CDR3). The heavy chain constant region of Antibody 81 is set forth in SEQ ID NO: 269. The light chain constant region of Antibody 81 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 263, 2, and 3, and a light chain variable region CDR set as set forth in SEQ ID Nos: 264, 268, and 266. In other embodiments, an anti-CD117 antibody, or antigen-binding portion thereof, comprises a variable light chain comprising the amino acid residues set forth in SEQ ID NO: 235, and a heavy chain variable region as set forth in SEQ ID NO: 147.

In one embodiment, the invention provides an ADC comprising an anti-CD117 antibody, or antigen-binding fragment thereof, comprising binding regions, e.g., CDRs, variable regions, corresponding to those of Antibody 85. The heavy chain variable region (VH) amino acid sequence of Antibody 85 (i.e., Ab86) is set forth in SEQ ID NO: 243 (see Sequence Table). The VH CDR domain amino acid sequences of Antibody 85 are set forth in SEQ ID NO: 245 (VH CDR1); SEQ ID NO: 246 (VH CDR2), and SEQ ID NO: 247 (VH CDR3). The light chain variable region (VL) amino acid sequence of Antibody 85 is described in SEQ ID NO: 242 (see Sequence Table). The VL CDR domain amino acid sequences of Antibody 85 are set forth in SEQ ID NO: 248 (VL CDR1); SEQ ID NO: 249 (VL CDR2), and SEQ ID NO: 250 (VL CDR3). The heavy chain constant region of Antibody 85 is set forth in SEQ ID NO: 269. The light chain constant region of Antibody 85 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 245, 246, and 247, and a light chain variable region CDR set as set forth in SEQ ID Nos: 248, 249, and 250. In other embodiments, an anti-CD117 antibody, or antigen-binding portion thereof, comprises a variable light chain comprising the amino acid residues set forth in SEQ ID NO: 244, and a heavy chain variable region as set forth in SEQ ID NO: 243.

In one embodiment, the invention provides an ADC comprising an anti-CD117 antibody, or antigen-binding fragment thereof, comprising binding regions, e.g., CDRs, variable regions, corresponding to those of Antibody 86. The heavy chain variable region (VH) amino acid sequence of Antibody 86 (i.e., Ab86) is set forth in SEQ ID NO: 251 (see Sequence Table). The VH CDR domain amino acid sequences of Antibody 86 are set forth in SEQ ID NO: 245 (VH CDR1); SEQ ID NO: 253 (VH CDR2), and SEQ ID NO: 3 (VH CDR3). The light chain variable region (VL) amino acid sequence of Antibody 86 is described in SEQ ID NO: 252 (see Sequence Table). The VL CDR domain amino acid sequences of Antibody 86 are set forth in SEQ ID NO: 254 (VL CDR1); SEQ ID NO: 249 (VL CDR2), and SEQ ID NO: 255 (VL CDR3). The heavy chain constant region of Antibody 86 is set forth in SEQ ID NO: 269. The light chain constant region of Antibody 86 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 245, 253, and 3, and a light chain variable region CDR set as set forth in SEQ ID Nos: 254, 249, and 255. In other embodiments, an anti-CD117 antibody, or antigen-binding portion thereof, comprises a variable light chain comprising the amino acid residues set forth in SEQ ID NO: 252, and a heavy chain variable region as set forth in SEQ ID NO: 251.

In one embodiment, the invention provides an ADC comprising an anti-CD117 antibody, or antigen-binding fragment thereof, comprising binding regions, e.g., CDRs, variable regions, corresponding to those of Antibody 87. The heavy chain variable region (VH) amino acid sequence of Antibody 87 (i.e., Ab87) is set forth in SEQ ID NO: 243 (see Sequence Table). The VH CDR domain amino acid sequences of Antibody 87 are set forth in SEQ ID NO: 245 (VH CDR1); SEQ ID NO: 246 (VH CDR2), and SEQ ID NO: 247 (VH CDR3). The light chain variable region (VL) amino acid sequence of Antibody 87 is described in SEQ ID NO: 256 (see Sequence Table). The VL CDR domain amino acid sequences of Antibody 87 are set forth in SEQ ID NO: 257 (VL CDR1); SEQ ID NO: 5 (VL CDR2), and SEQ ID NO: 255 (VL CDR3). The heavy chain constant region of Antibody 87 is set forth in SEQ ID NO: 269. The light chain constant region of Antibody 87 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 245, 246, and 247, and a light chain variable region CDR set as set forth in SEQ ID Nos: 257, 5, and 255. In other embodiments, an anti-CD117 antibody, or antigen-binding portion thereof, comprises a variable light chain comprising the amino acid residues set forth in SEQ ID NO: 256, and a heavy chain variable region as set forth in SEQ ID NO: 243.

In one embodiment, the invention provides an ADC comprising an anti-CD117 antibody, or antigen-binding fragment thereof, comprising binding regions, e.g., CDRs, variable regions, corresponding to those of Antibody 88. The heavy chain variable region (VH) amino acid sequence of Antibody 88 (i.e., Ab88) is set forth in SEQ ID NO: 258 (see Sequence Table). The VH CDR domain amino acid sequences of Antibody 88 are set forth in SEQ ID NO: 245 (VH CDR1); SEQ ID NO: 259 (VH CDR2), and SEQ ID NO: 3 (VH CDR3). The light chain variable region (VL) amino acid sequence of Antibody 88 is described in SEQ ID NO: 256 (see Sequence Table). The VL CDR domain amino acid sequences of Antibody 88 are set forth in SEQ ID NO: 257 (VL CDR1); SEQ ID NO: 5 (VL CDR2), and SEQ ID NO: 255 (VL CDR3). The heavy chain constant region of Antibody 88 is set forth in SEQ ID NO: 269. The light chain constant region of Antibody 88 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 245, 259, and 3, and a light chain variable region CDR set as set forth in SEQ ID Nos: 257, 5, and 255. In other embodiments, an anti-CD117 antibody, or antigen-binding portion thereof, comprises a variable light chain comprising the amino acid residues set forth in SEQ ID NO: 256, and a heavy chain variable region as set forth in SEQ ID NO: 258.

In one embodiment, the invention provides an ADC comprising an anti-CD117 antibody, or antigen-binding fragment thereof, comprising binding regions, e.g., CDRs, variable regions, corresponding to those of Antibody 89. The heavy chain variable region (VH) amino acid sequence of Antibody 89 (i.e., Ab89) is set forth in SEQ ID NO: 260 (see Sequence Table). The VH CDR domain amino acid sequences of Antibody 89 are set forth in SEQ ID NO: 245 (VH CDR1); SEQ ID NO: 2 (VH CDR2), and SEQ ID NO: 3 (VH CDR3). The light chain variable region (VL) amino acid sequence of Antibody 89 is described in SEQ ID NO: 252 (see Sequence Table). The VL CDR domain amino acid sequences of Antibody 89 are set forth in SEQ ID NO: 254 (VL CDR1); SEQ ID NO: 249 (VL CDR2), and SEQ ID NO: 255 (VL CDR3). The heavy chain constant region of Antibody 89 is set forth in SEQ ID NO: 269. The light chain constant region of Antibody 89 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 245, 2, and 3, and a light chain variable region CDR set as set forth in SEQ ID Nos: 254, 249, and 255. In other embodiments, an anti-CD117 antibody, or antigen-binding portion thereof, comprises a variable light chain comprising the amino acid residues set forth in SEQ ID NO: 252, and a heavy chain variable region as set forth in SEQ ID NO: 260.

In one embodiment, the invention provides an ADC comprising an anti-CD117 antibody, or antigen-binding fragment thereof, comprising binding regions, e.g., CDRs, variable regions, corresponding to those of Antibody 249. The heavy chain variable region (VH) amino acid sequence of Antibody 249 (i.e., Ab249) is set forth in SEQ ID NO: 238 (see Sequence Table). The VH CDR domain amino acid sequences of Antibody 249 are set forth in SEQ ID NO: 286 (VH CDR1); SEQ ID NO: 2 (VH CDR2), and SEQ ID NO: 287 (VH CDR3). The light chain variable region (VL) amino acid sequence of Antibody 249 is described in SEQ ID NO: 242 (see Sequence Table). The VL CDR domain amino acid sequences of Antibody 249 are set forth in SEQ ID NO: 288 (VL CDR1); SEQ ID NO: 249 (VL CDR2), and SEQ ID NO: 289 (VL CDR3). The heavy chain constant region of Antibody 249 is set forth in SEQ ID NO: 269. The light chain constant region of Antibody 249 is set forth in SEQ ID NO: 283. Thus, in certain embodiments, an anti-CD117 antibody, or antigen-binding portion thereof, comprises a variable heavy chain CDR set (CDR1, CDR2, and CDR3) as set forth in SEQ ID Nos: 286, 2, and 287, and a light chain variable region CDR set as set forth in SEQ ID Nos: 288, 249, and 289. In other embodiments, an anti-CD117 antibody, or antigen-binding portion thereof, comprises a variable light chain comprising the amino acid residues set forth in SEQ ID NO: 242, and a heavy chain variable region as set forth in SEQ ID NO: 238.

Further, included in the disclosure is anti-CD117 antibody drug conjugates (ADCs) comprising binding regions (heavy and light chain CDRs or variable regions) as set forth in SEQ ID Nos: 147 to 168. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 148. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 149. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 150. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 151. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 152. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 153. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 154. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 155. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 156. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 157. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 158. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 159. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 160. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 161. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 162. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 163. In one embodiment, the anti-CD117 antibody, or antigen binding portion thereof, comprises a heavy chain variable region as set forth in the amino acid sequence of SEQ ID NO: 164, and a light chain variable region as set forth in the amino acid sequence of SEQ ID NO: 165. In one embodiment, the anti-CD117 antibody, or antigen binding portion thereof, comprises a heavy chain variable region as set forth in the amino acid sequence of SEQ ID NO: 166, and a light chain variable region as set forth in the amino acid sequence of SEQ ID NO: 167. In one embodiment, the anti-CD117 antibody, or antigen binding portion thereof, comprises a heavy chain variable region as set forth in the amino acid sequence of SEQ ID NO: 168, and a light chain variable region as set forth in the amino acid sequence of SEQ ID NO: 169. In one embodiment, the anti-CD117 antibody, or antigen binding portion thereof, comprises a heavy chain variable region as set forth in the amino acid sequence of SEQ ID NO: 170, and a light chain variable region as set forth in the amino acid sequence of SEQ ID NO: 171. In one embodiment, the anti-CD117 antibody, or antigen binding portion thereof, comprises a heavy chain variable region as set forth in the amino acid sequence of SEQ ID NO: 172, and a light chain variable region as set forth in the amino acid sequence of SEQ ID NO: 173. In one embodiment, the anti-CD117 antibody, or antigen binding portion thereof, comprises a heavy chain variable region as set forth in the amino acid sequence of SEQ ID NO: 174, and a light chain variable region as set forth in the amino acid sequence of SEQ ID NO: 175. In one embodiment, the anti-CD117 antibody, or antigen binding portion thereof, comprises a heavy chain variable region as set forth in the amino acid sequence of SEQ ID NO: 176, and a light chain variable region as set forth in the amino acid sequence of SEQ ID NO: 177. In one embodiment, the anti-CD117 antibody, or antigen binding portion thereof, comprises a heavy chain variable region as set forth in the amino acid sequence of SEQ ID NO: 178, and a light chain variable region as set forth in the amino acid sequence of SEQ ID NO: 179. In one embodiment, the anti-CD117 antibody, or antigen binding portion thereof, comprises a heavy chain variable region as set forth in the amino acid sequence of SEQ ID NO: 180, and a light chain variable region as set forth in the amino acid sequence of SEQ ID NO: 181. In one embodiment, the anti-CD117 antibody, or antigen binding portion thereof, comprises a heavy chain variable region as set forth in the amino acid sequence of SEQ ID NO: 172, and a light chain variable region as set forth in the amino acid sequence of SEQ ID NO: 182. In one embodiment, the anti-CD117 antibody, or antigen binding portion thereof, comprises a heavy chain variable region as set forth in the amino acid sequence of SEQ ID NO: 183, and a light chain variable region as set forth in the amino acid sequence of SEQ ID NO: 184. In one embodiment, the anti-CD117 antibody, or antigen binding portion thereof, comprises a heavy chain variable region as set forth in the amino acid sequence of SEQ ID NO: 185, and a light chain variable region as set forth in the amino acid sequence of SEQ ID NO: 186. In one embodiment, the anti-CD117 antibody, or antigen binding portion thereof, comprises a heavy chain variable region as set forth in the amino acid sequence of SEQ ID NO: 187, and a light chain variable region as set forth in the amino acid sequence of SEQ ID NO: 188. In one embodiment, the anti-CD117 antibody, or antigen binding portion thereof, comprises a heavy chain variable region as set forth in the amino acid sequence of SEQ ID NO: 189, and a light chain variable region as set forth in the amino acid sequence of SEQ ID NO: 190. In one embodiment, the anti-CD117 antibody, or antigen binding portion thereof, comprises a heavy chain variable region as set forth in the amino acid sequence of SEQ ID NO: 191, and a light chain variable region as set forth in the amino acid sequence of SEQ ID NO: 192. In one embodiment, the anti-CD117 antibody, or antigen binding portion thereof, comprises a heavy chain variable region as set forth in the amino acid sequence of SEQ ID NO: 193, and a light chain variable region as set forth in the amino acid sequence of SEQ ID NO: 194. In one embodiment, the anti-CD117 antibody, or antigen binding portion thereof, comprises a heavy chain variable region as set forth in the amino acid sequence of SEQ ID NO: 195, and a light chain variable region as set forth in the amino acid sequence of SEQ ID NO: 196. In one embodiment, the anti-CD117 antibody, or antigen binding portion thereof, comprises a heavy chain variable region as set forth in the amino acid sequence of SEQ ID NO: 197, and a light chain variable region as set forth in the amino acid sequence of SEQ ID NO: 198. In one embodiment, the anti-CD117 antibody, or antigen binding portion thereof, comprises a heavy chain variable region as set forth in the amino acid sequence of SEQ ID NO: 199, and a light chain variable region as set forth in the amino acid sequence of SEQ ID NO: 200. In one embodiment, the anti-CD117 antibody, or antigen binding portion thereof, comprises a heavy chain variable region as set forth in the amino acid sequence of SEQ ID NO: 201, and a light chain variable region as set forth in the amino acid sequence of SEQ ID NO: 190. In one embodiment, the anti-CD117 antibody, or antigen binding portion thereof, comprises a heavy chain variable region as set forth in the amino acid sequence of SEQ ID NO: 202, and a light chain variable region as set forth in the amino acid sequence of SEQ ID NO: 203. In one embodiment, the anti-CD117 antibody, or antigen binding portion thereof, comprises a heavy chain variable region as set forth in the amino acid sequence of SEQ ID NO: 204, and a light chain variable region as set forth in the amino acid sequence of SEQ ID NO: 205. In one embodiment, the anti-CD117 antibody, or antigen binding portion thereof, comprises a heavy chain variable region as set forth in the amino acid sequence of SEQ ID NO: 206, and a light chain variable region as set forth in the amino acid sequence of SEQ ID NO: 207. In one embodiment, the anti-CD117 antibody, or antigen binding portion thereof, comprises a heavy chain variable region as set forth in the amino acid sequence of SEQ ID NO: 208, and a light chain variable region as set forth in the amino acid sequence of SEQ ID NO: 209. In one embodiment, the anti-CD117 antibody, or antigen binding portion thereof, comprises a heavy chain variable region as set forth in the amino acid sequence of SEQ ID NO: 210, and a light chain variable region as set forth in the amino acid sequence of SEQ ID NO: 211. In one embodiment, the anti-CD117 antibody, or antigen binding portion thereof, comprises a heavy chain variable region as set forth in the amino acid sequence of SEQ ID NO: 212, and a light chain variable region as set forth in the amino acid sequence of SEQ ID NO: 213. In one embodiment, the anti-CD117 antibody, or antigen binding portion thereof, comprises a heavy chain variable region as set forth in the amino acid sequence of SEQ ID NO: 214, and a light chain variable region as set forth in the amino acid sequence of SEQ ID NO: 215. In one embodiment, the anti-CD117 antibody, or antigen binding portion thereof, comprises a heavy chain variable region as set forth in the amino acid sequence of SEQ ID NO: 216, and a light chain variable region as set forth in the amino acid sequence of SEQ ID NO: 217. In one embodiment, the anti-CD117 antibody, or antigen binding portion thereof, comprises a heavy chain variable region as set forth in the amino acid sequence of SEQ ID NO: 218, and a light chain variable region as set forth in the amino acid sequence of SEQ ID NO: 219. In one embodiment, the anti-CD117 antibody, or antigen binding portion thereof, comprises a heavy chain variable region as set forth in the amino acid sequence of SEQ ID NO: 220, and a light chain variable region as set forth in the amino acid sequence of SEQ ID NO: 221. In one embodiment, the anti-CD117 antibody, or antigen binding portion thereof, comprises a heavy chain variable region as set forth in the amino acid sequence of SEQ ID NO: 222, and a light chain variable region as set forth in the amino acid sequence of SEQ ID NO: 223. In one embodiment, the anti-CD117 antibody, or antigen binding portion thereof, comprises a heavy chain variable region as set forth in the amino acid sequence of SEQ ID NO: 224, and a light chain variable region as set forth in the amino acid sequence of SEQ ID NO: 225. In one embodiment, the anti-CD117 antibody, or antigen binding portion thereof, comprises a heavy chain variable region as set forth in the amino acid sequence of SEQ ID NO: 226, and a light chain variable region as set forth in the amino acid sequence of SEQ ID NO: 227. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 228. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 229. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 230. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 231. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 232. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 233. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 234. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 235. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 236.

In one embodiment, the anti-CD117 antibody, or antigen binding portion thereof, of an ADC described herein comprises a heavy chain variable region as set forth in the amino acid sequence of SEQ ID NO: 147, and a light chain variable region as set forth in the amino acid sequence of SEQ ID NO: 237. In one embodiment, the anti-CD117 antibody, or antigen binding portion thereof, comprises a heavy chain variable region as set forth in the amino acid sequence of SEQ ID NO: 243, and a light chain variable region as set forth in the amino acid sequence of SEQ ID NO: 244. In one embodiment, the anti-CD117 antibody, or antigen binding portion thereof, comprises a heavy chain variable region as set forth in the amino acid sequence of SEQ ID NO: 251, and a light chain variable region as set forth in the amino acid sequence of SEQ ID NO: 252. In one embodiment, the anti-CD117 antibody, or antigen binding portion thereof, comprises a heavy chain variable region as set forth in the amino acid sequence of SEQ ID NO: 243, and a light chain variable region as set forth in the amino acid sequence of SEQ ID NO: 256. In one embodiment, the anti-CD117 antibody, or antigen binding portion thereof, comprises a heavy chain variable region as set forth in the amino acid sequence of SEQ ID NO: 258, and a light chain variable region as set forth in the amino acid sequence of SEQ ID NO: 256. In one embodiment, the anti-CD117 antibody, or antigen binding portion thereof, comprises a heavy chain variable region as set forth in the amino acid sequence of SEQ ID NO: 260, and a light chain variable region as set forth in the amino acid sequence of SEQ ID NO: 252. In one embodiment, the anti-CD117 antibody, or antigen binding portion thereof, comprises a heavy chain variable region as set forth in the amino acid sequence of SEQ ID NO: 238, and a light chain variable region as set forth in the amino acid sequence of SEQ ID NO: 239. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 239. In one embodiment, the anti-CD117 antibody, or antigen binding portion thereof, comprises a heavy chain variable region as set forth in the amino acid sequence of SEQ ID NO: 147, and a light chain variable region as set forth in the amino acid sequence of SEQ ID NO: 240. In one embodiment, the anti-CD117 antibody, or antigen binding portion thereof, comprises a heavy chain variable region as set forth in the amino acid sequence of SEQ ID NO: 238, and a light chain variable region as set forth in the amino acid sequence of SEQ ID NO: 241. In one embodiment, the anti-CD117 antibody, or antigen binding portion thereof, comprises a heavy chain variable region as set forth in the amino acid sequence of SEQ ID NO: 238, and a light chain variable region as set forth in the amino acid sequence of SEQ ID NO: 242.

Certain of the anti-CD117 antibodies described herein are neutral antibodies, in that the antibodies do not substantially inhibit CD117 activity on a CD117 expressing cell. Neutral antibodies can be identified using, for example, an in in vitro stem cell factor (SCF)-dependent cell proliferation assay. In an SCF dependent cell proliferation assay, a neutral CD117 antibody will not kill CD34+ cells that are dependent on SCF to divide, as a neutral antibody will not block SCF from binding to CD117 such as to inhibit CD117 activity.

Neutral antibodies can be used for diagnostic purposes, given their ability to specifically bind to human CD117, but are also effective for killing CD117 expressing cells when conjugated to a cytotoxin, such as those described herein. Typically, antibodies used in conjugates have agonistic or antagonistic activity that is unique to the antibody. Described herein, however, is a unique approach to conjugates, especially in the context wherein the conjugate is being used as a conditioning agent prior to a stem cell transplantation. While antagonistic antibodies alone or in combination with a cytotoxin as a conjugate can be effective given the killing ability of the antibody alone in addition to the cytotoxin, conditioning with a conjugate comprising a neutral anti-CD117 antibody presents an alternative strategy where the activity of the antibody is secondary to the effect of the cytotoxin, but the internalizing and affinity characteristics, e.g., dissociation rate, of the antibody are important for effective delivery of the cytotoxin.

Examples of neutral anti-CD117 antibodies include Ab58, Ab61, Ab66, Ab67, Ab68, and Ab69. A comparison of the amino acid sequences of the CDRs of neutral, anti-CD117 antibody CDRs reveals consensus sequences among two groups of neutral antibodies identified. Ab58 and Ab61 share the same light chain CDRs and HC CDR3, with slight variations in the HC CDR1 and HC CDR2. Consensus sequences for the HC CDR1 and CDR2 are described in SEQ ID Nos: 133 and 134. Ab66, Ab67, Ab68, and Ab69 are also neutral antibodies. While Ab66, Ab67, Ab68, and Ab69 share the same light chain CDRs and the same HC CDR3, these antibodies have variability within their HC CDR1 and HC CDR2 regions. Consensus sequences for these antibodies in the HC CDR1 and HC CDR2 regions are provided in SEQ ID Nos: 139 and 140, respectively.

Antagonist antibodies are also provided herein, including Ab54, Ab55, Ab56, and Ab57. While Ab54, Ab55, Ab56, and Ab57 share the same light chain CDRs and the same HC CDR3, these antibodies have variability within their HC CDR1 and HC CDR2 regions. Consensus sequences for these antibodies in the HC CDR1 and HC CDR2 regions are provided in SEQ ID Nos: 127 and 128, respectively.

In one embodiment, the anti-CD117 antibody, or antigen binding fragment thereof, comprises variable regions having an amino acid sequence that is at least 95%, 96%, 97% or 99% identical to the SEQ ID Nos disclosed herein. Alternatively, the anti-CD117 antibody, or antigen binding fragment thereof, comprises CDRs comprising the SEQ ID Nos disclosed herein with framework regions of the variable regions described herein having an amino acid sequence that is at least 95%, 96%, 97% or 99% identical to the SEQ ID Nos disclosed herein.

The anti-CD117 antibodies described herein can be in the form of full-length antibodies, bispecific antibodies, dual variable domain antibodies, multiple chain or single chain antibodies, and/or binding fragments that specifically bind human CD117, including but not limited to Fab, Fab', (Fab')2, Fv, scFv (single chain Fv), surrobodies (including surrogate light chain construct), single domain antibodies, camelized antibodies and the like. They also can be of, or derived from, any isotype, including, for example, IgA (e.g., IgA1 or IgA2), IgD, IgE, IgG (e.g. IgG1, IgG2, IgG3 or IgG4), or IgM. In some embodiments, the anti-CD117 antibody is an IgG (e.g. IgG1, IgG2, IgG3 or IgG4).

Antibodies for use in conjunction with the methods described herein include variants of those antibodies described above, such as antibody fragments that contain or lack an Fc domain, as well as humanized variants of non-human antibodies described herein and antibody-like protein scaffolds (e.g., $^{10}$Fn3 domains) containing one or more, or all, of the CDRs or equivalent regions thereof of an antibody, or antibody fragment, described herein. Exemplary antigen-binding fragments of the foregoing antibodies include a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv, among others.

In one embodiment, anti-CD117 antibodies comprising one or more radiolabeled amino acids are provided. A radiolabeled anti-CD117 antibody may be used for both diagnostic and therapeutic purposes (conjugation to radiolabeled molecules is another possible feature). Nonlimiting examples of labels for polypeptides include, but are not limited to 3H, 14C, 15N, 35S, 90Y, 99Tc, and 125I, 131I, and 186Re. Methods for preparing radiolabeled amino acids and related peptide derivatives are known in the art (see for instance Junghans et al., in Cancer Chemotherapy and Biotherapy 655-686 (2d edition, Chafner and Longo, eds., Lippincott Raven (1996)) and U.S. Pat. Nos. 4,681,581, 4,735,210, 5,101,827, 5,102,990 (U.S. RE35,500), U.S. Pat. Nos. 5,648,471 and 5,697,902. For example, a radioisotope may be conjugated by a chloramine T method.

Anti-CD45 Antibodies

In one embodiment, the present invention includes ADCs comprising antibodies, and antigen-binding fragments thereof, that specifically bind to a CD45 polypeptide, e.g., a human CD45 polypeptide, and uses thereof. In an exemplary embodiment, the antibody, or antigen-binding fragment thereof, that specifically binds to a CD45 polypeptide comprises a heavy chain variable region and a light chain variable region.

CD45 is a hematopoietic cell-specific transmembrane protein tyrosine phosphatase essential for T and B cell antigen receptor-mediated signaling. CD45 includes a large extracellular domain, and a phosphatase containing cytosolic domain. CD45 may act as both a positive and negative regulator depending on the nature of the stimulus and the cell type involved. Although there are a large number of permutations possible in the CD45 gene, only six isoforms are traditionally identified in humans. The isoforms are RA, RO, RB, RAB, RBC and RABC (Hermiston et al. 2003 "CD45: a critical regulator of signaling thresholds in immune cells." Annu Rev Immunol. 2:107-137). CD45RA is expressed on naïve T cells, and CD45RO is expressed on activated and memory T cells, some B cell subsets, activated monocytes/macrophages, and granulocytes. CD45RB is expressed on peripheral B cells, naïve T cells, thymocytes, weakly on macrophages, and dendritic cells.

In certain embodiments, the anti-CD45 antibody is selected from apamistamab (also known 90Y-BC8, Iomab-B, BC8; as described in, e.g., US20170326259, WO2017155937, and Orozco et al. Blood. 127.3 (2016): 352-359) or BC8-B10 (as described, e.g., in Li et al. PloS one 13.10 (2018): e0205135), each of which is incorporated by reference. Other anti-CD45 antibodies have been described, for example, in WO2003048327, WO2016016442, US20170226209, US20160152733, U.S. Pat. No. 9,701,756; US20110076270, or U.S. Pat. No. 7,825,222, each of which is incorporated by reference.

Anti-CD137 Antibodies

The present invention includes ADCs comprising antibodies, and antigen-binding fragments thereof, that specifically bind to a CD137 polypeptide, e.g., a human CD137 polypeptide, and uses thereof. In an exemplary embodiment, the antibody, or antigen-binding fragment thereof, that specifically binds to a CD137 polypeptide comprises a heavy chain variable region and a light chain variable region.

T cells have been shown to express CD137, as this antigen is a transmembrane TNF receptor superfamily of costimulatory molecules and is expressed on a variety of hematopoietic cells and promotes T cell activation and regulates proliferation and survival of T cells (see, e.g., Cannons et al., J. Immunol. 167:1313-1324, 2001, the disclosure of which is incorporated herein by reference as it pertains to the expression of CD137 by T cells). CD137 is alternatively named tumor necrosis factor receptor superfamily member 9 (TNFRSF9), 4-1BB, or induced by lymphocyte activation (ILA).

In certain embodiments, the anti-CD137 antibody is selected from ADG106 (as described in, e.g., US20190055314, WO2019037711, WO2019036855);

AGEN2373 (as described in, e.g., WO2018191502, US20180344870); ATOR-1017 (as described in, e.g., WO2018091740, US20180118841) PE0166 (as described in, e.g., Song et al. AACR 2019, Abstract 2397/21), ure-lumab (also known as BMS-663513; as described in, e.g., WO2004010947, WO2005035584, US20090068192, U.S. Pat. Nos. 7,659,384, 8,475,790, 8,137,667, US20100183621, U.S. Pat. No. 8,716,452, US20120141494, U.S. Pat. No. 9,382,328, US20140193422, WO2016029073, US20160368998, WO2017181034, US20190062445, Chin et al. Nature communications. 9.1 (2018): 4679; Segal et al. Clinical Cancer Research. 23.8 (2017): 1929-1936); and utomilumab (also known as PF-05082566, MOR-7480; as described in, e.g., WO2012032433, US20120237498, US20140178368, WO2012145183, WO2015119923, WO2015179236, US20160152722, US20190031765, WO2017130076, Chin et al. Nature communications. 9.1 (2018): 4679; Segal et al. Clinical Cancer Research. 24.8 (2018): 1816-1823; Fisher et al. Cancer Immunology, Immunotherapy. 61.10 (2012): 1721-1733), each of which is incorporated by reference.

Other anti-CD137 antibodies have been described, for example, in WO2018134787, WO2019020774, WO2017077085, US20180327504, US20190099488, US2019006045, US20190015508, WO2019014328, US20190071510, WO2018127787, US20180258177, U.S. Ser. No. 10/174,122, WO2016110584, WO2018017761, WO2018098370, US20130149301, WO2019027754, WO2018156740, US20160244528, WO2016134358, U.S. Ser. No. 10/233,251, US20170226215, US20160083474, WO2017049452, US20180282422, WO2015188047, WO2010132389, US20120076722, US20110177104, WO2011031063, US20080305113, US20080008716, U.S. Pat. No. 7,829,088, US20090041763, WO2006126835, Söderström et al. Circulation J. 81.12 (2017): 1945-1952; Makkouk, et al. Annals of Oncology 28.2 (2016): 415-420; Martinez-Forero et al. J. of Immunology. 190.12 (2013): 6694-6706; Dubrot et al. Cancer immunology, immunotherapy. 59.8 (2010): 1223-1233; each of which is incorporated by reference.

In another embodiment, the antibody, or antigen-binding fragment thereof, comprises a heavy chain variable region that comprises an amino acid sequence having at least 95% identity to an anti-CD137 antibody herein, e.g., at least 95%, 96%, 97%, 98%, 99%, or 100% identity to an anti-CD137 antibody herein. In certain embodiments, an antibody comprises a modified heavy chain (HC) variable region comprising an HC variable domain of an anti-CD137 antibody herein, or a variant thereof, which variant (i) differs from the anti-CD137 antibody in 1, 2, 3, 4 or 5 amino acids substitutions, additions or deletions; (ii) differs from the anti-CD137 antibody in at most 5, 4, 3, 2, or 1 amino acids substitutions, additions or deletions; (iii) differs from the anti-CD137 antibody in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to the anti-CD137 antibody, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of the anti-CD137 antibody, while retaining the CD137 binding specificity of the antibody.

In one embodiment, an anti-CD137 antibody that may be used in the methods and compositions (including ADCs) described herein is the murine anti-CD137 antibody BBK2

(Thermo Fisher; MS621 PABX) or an anti-CD137 antibody comprising antigen binding regions corresponding to the BBK2 antibody. The BBK2 antibody (which may also be referred to as a BBK-2 antibody or an anti-4-1BB antibody), is a mouse monoclonal antibody (IgG1, kappa) that binds to the ectodomain of human 4-1BB recombinant protein (4-1BB is also known as CD137). In certain embodiments, the methods and compositions of the disclosure include an anti-CD137 antibody comprising the binding regions (e.g., the CDRs) of the BBK2 antibody. In another embodiment, the methods and compositions of the disclosure comprise an antibody that competitively inhibits the binding of the BBK2 antibody to its epitope on CD137. In certain embodiments, the anti-CD137 antibody is humanized BBK2 or chimeric BBK2.

In one embodiment, the methods and compositions described herein include a chimeric anti-CD137 (ch-BBK2) antibody comprising the variable heavy and light chain regions of BBK2. In certain embodiments, the chimeric BBK2 antibody is an IgG1 antibody comprising human constant regions. The heavy chain amino acid sequence of ch-BBK2 is described in SEQ ID NO: 290, and the light chain amino acid sequence of ch-BBK2 is described in SEQ ID NO: 291. The CDR regions (CDR1, CDR2, and CDR3) of each of the heavy and light chain sequences are described in bold below. The CDR regions of BBK2 can be defined according to Kabat numbering. CDRs as defined by Kabat numbering are described below for each of the heavy and light chain sequences (described in bold below). The variable regions of BBK2 are italicized.

SAVYYCTRNGVEGYPHYYAMEYWGQGTSV TVSS. The light chain variable region of BBK2 is set forth in SEQ ID NO: 299 as DIQMTQTTSAL-SASLGDRVTIGCRASQDLSNH-LYWYQQKPDGTVKLLIYYTSRLHSGVPSR FSGSGSGTDYSLTIRNLEQEDVATYFCQQGYTLPY-TFGGGTKLEIK. Anti-CD137 antibodies (including anti-CD137 ADCs) can comprise the heavy and light chain variable region amino acid sequences as set forth in SEQ ID Nos: 298 and 299, respectively.

In one embodiment, the anti-CD137 antibody, e.g., a chimeric (ch-BBK2) antibody or a humanized BBK2 antibody, comprises a heavy chain variable region comprising a CDR1 comprising the amino acid sequence of SEQ ID NO: 292, a CDR2 comprising the amino acid sequence of SEQ ID NO: 293, and a CDR3 comprising the amino acid sequence of SEQ ID NO: 294; and comprises a light chain variable region comprising a CDR1 comprising the amino acid sequence of SEQ ID NO: 295, a CDR2 comprising the amino acid sequence of SEQ ID NO: 296, and a CDR3 comprising the amino acid sequence of SEQ ID NO: 297.

In one embodiment, the anti-CD137 antibody, e.g., a chimeric (ch-BBK2) antibody or a humanized BBK2 antibody, comprises a heavy chain variable region comprising a CDR1 comprising the amino acid sequence of SEQ ID NO: 292, a CDR2 comprising the amino acid sequence of SEQ ID NO: 293, and a CDR3 comprising the amino acid sequence of SEQ ID NO: 294; and comprises a light chain variable region comprising a CDR1 comprising the amino acid sequence of SEQ ID NO: 295, a CDR2 comprising the

```
                    (ch-BBK2 heavy chain; SEQ ID NO: 290)
QVQLQQPGAELVRPGASVKLSCKASGYTFTSYWINWVKQRPGQGLEWIGNIYPSDSYTNY

NQKFKDKATLTVDKSSNTVYMQLNSPTSEDSAVYYCTRNGVEGYPHYYAMEYWGQGTSV

TVSSASTKGPSVFPLAPSSKSTSGGTAALGCLVKDYFPEPVTVSWNSGALTSGVHTFPAVL

QSSGLYSLSSVVTVPSSSLGTQTYICNVNHKPSNTKVDKKVEPKSCDKTHTCPPCPAPELL

GGPSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRW

QQGNVFSCSVMHEALHNHYTQKSLSLSPGK (ch-BBK2 light chain; SEQ ID NO: 291)
DIQMTQTTSALSASLGDRVTIGCRASQDLSNHLYWYQQKPDGTVKLLIYTSRLHSGVPSR

FSGSGSGTDYSLTIRNLEQEDVATYFCQQGYTLPYTFGGGTKLEIKRTVAAPSVFIFPPSDE

QLKSGTASVVCLLNNFYPREAKVQWKVDNALQSGNSQESVTEQDSKDSTYSLSSTLTLSK

ADYEKHKVYACEVTHQGLSSPVTKSFNRGEC
```

Thus, in one embodiment, the VH CDR amino acid sequences of anti-CD137 antibody BBK2 (including ch-BBK2) are as follows: SYWIN (VH CDR1; SEQ ID NO: 292); NIYPSDSYTNYNQKFKD (VH CDR2; SEQ ID NO: 293) and NGVEGYPHYYAMEY (VH CDR3; SEQ ID NO: 294), and the VL CDR amino acid sequences of anti-CD137 antibody BBK2 (including ch-BBK2) are as follows: RASQDLSNHLY (VL CDR1; SEQ ID NO: 295); YTSRLHS (VL CDR2; SEQ ID NO: 296) and QQGYTLPYT (VL CDR3; SEQ ID NO: 297).

The heavy chain variable region of BBK2 is set forth in SEQ ID NO: 298 as QVQLQQPGAELVRPGASVKLSCK-ASGYTFTSYWINWVKQRPGQGLEWIGNIYPSD-SYTNY NQKFKDKATLTVDKSSNTVYMQLNSPTSEDamino acid sequence of SEQ ID NO: 296, and a CDR3 comprising the amino acid sequence of SEQ ID NO: 297.

Thus, BBK2, humanized BBK2, or chimeric BBK2 antibodies can be used in the anti-CD137 ADCs and methods described herein. Each of these antibodies can be conjugated to any of the cytotoxin described below using methods known in the art and those described herein.

Anti-CD5 Antibodies

In certain embodiments, compositions and methods described herein include an ADC comprising an antibody, or fragment thereof, that specifically binds to human CD5. Human CD5 is also referred to as LEU1 or T1. Human CD5 is a type-I transmembrane glycoprotein found on the surface of thymocytes, T lymphocytes and a subset of B lymphocytes. Two isoforms of human CD5 have been identified. Isoform 1 contains 438 amino acids and is described in Jones. et al. (1988) *Nature* 323 (6086), 346-349 and below (NCBI Reference Sequence: NP_001333385.1):

cifically bind to a CD5 polypeptide, e.g., a human CD5 polypeptide, and uses thereof. In an exemplary embodiment, the antibody, or antigen-binding fragment thereof, that specifically binds to a CD5 polypeptide comprises a heavy chain variable region and a light chain variable region.

```
                                                 (SEQ ID NO: 363)
MVCSQSWGRS SKQWEDPSQASKVCQRLNCG VPLSLGPFLV TYTPQSSIICYGQL

GSFSNCSHSRNDMCHS LGLTCLEPQKTTPPTTRPPPTTTPEPTAPP

RLQLVAQSGG QHCAGVVEFYSGSLGGTISY EAQDKTQDLE NFLCNNLQCG

SFLKHLPETE AGRAQDPGEP REHQPLPIQWKIQNSSCTSL EHCFRKIKPQ

KSGRVLALLC SGFQPKVQSR LVGGSSICEG TVEVRQGAQWAALCDSSSAR

SSLRWEEVC REQQCGSVNSY RVLDAGDPTS RGLFCPHQKL

SQCHELWERNSYCKKVFVTCQDPNPAGLAAGTVASIILAL VLLVVLLVVC

GPLAYKKLVK KFRQKKQRQWIGPTGMNQNM SFHRNHTATV RSHAENPTAS

HVDNEYSQPP RNSHLSAYPA LEGALHRSSMQPDNSSDSDY DLHGAQRL
```

T cells have been shown to express CD5, which is a cell adhesion molecule and has been implicated both in the proliferative response of activated T cells and in T cell helper function. It has also been shown to function as a receptor, delivering co-stimulatory signals to T cells by interacting with CD72, a cell surface protein exclusive to B cells. Antibodies, or antigen-binding fragments thereof, that bind CD5 may suppress T cell activation and T cell-mediated immune responses against hematopoietic stem cell grafts, for example, by inhibiting the interaction between CD5 and CD72. Antibodies, and antigen-binding fragments thereof, that bind CD5 can also be used to kill CD5+ T cells directly, for instance, by conjugating the antibody, or antigen-binding fragment thereof, to a cytotoxin (such as a cytotoxin described herein or known in the art) or by using an unconjugated antibody, or antigen-binding fragment thereof, capable of recruiting complement proteins to the T cell.

Additionally, subsets of activated B cells have been shown to express CD5, and this expression pattern is particularly common among autoreactive B cells (Werner-Favre et al., European Journal of Immunology 19:1209-1231 (1989), the disclosure of which is incorporated herein by reference in its entirety). CD5 has also been shown to be expressed by subsets of NK cells; particularly among patients that have multiple myeloma have been shown to harbor populations of low density CD5+(CD5LOW+) NK cells, and this surface antigen has been implicated in NK cell activation (Ishiyama et al., Anticancer Research 14:725-730 (1994), the disclosure of which is incorporated herein by reference in its entirety). Antibodies, or antigen-binding fragments thereof, that specifically bind CD5 can thus be used to attenuate the activation of B cells and NK cells. Antibodies, or antigen-binding fragments thereof, that bind CD5 can also be used to kill CD5+ B cells and NK cells directly, for instance, by conjugating the antibody, or antigen-binding fragment thereof, to a cytotoxin (such as a cytotoxin described herein or known in the art) or by using an unconjugated antibody, or antigen-binding fragment thereof, capable of recruiting complement proteins to the B cell or NK cell.

The present invention encompasses ADCs comprising antibodies, and antigen-binding fragments thereof, that spe- In one embodiment, an ADC comprises an antibody comprising the heavy chain variable region comprises one or more complementarity determining regions (CDRs). In one embodiment, the heavy chain variable region comprises a VH CDR1 comprising the amino acid sequence of SEQ ID NO: 341. In one embodiment, the heavy chain variable region comprises a VH CDR2 comprising the amino acid sequence of SEQ ID NO: 342. In one embodiment, the heavy chain variable region comprises a VH CDR3 comprising the amino acid sequence of SEQ ID NO: 343. In one embodiment, the heavy chain variable region comprises one or more VH CDRs selected from the group consisting of SEQ ID NO: 341, SEQ ID NO: 342, and SEQ ID NO: 343. In one embodiment, the heavy chain variable region comprises two or more VH CDRs selected from the group consisting of SEQ ID NO: 341, SEQ ID NO: 342, and SEQ ID NO: 343. In one embodiment, the heavy chain variable region comprises a VH CDR1 comprising SEQ ID NO: 341, a VH CDR2 comprising SEQ ID NO: 342, and a VH CDR3 comprising SEQ ID NO: 343.

In one embodiment, an ADC comprises an antibody comprising the light chain variable region comprises one or more complementarity determining regions (CDRs). In one embodiment, the light chain variable region comprises a VL CDR1 comprising the amino acid sequence of SEQ ID NO: 344. In one embodiment, the light chain variable region comprises a VL CDR2 comprising the amino acid sequence of SEQ ID NO: 345. In one embodiment, the light chain variable region comprises a VL CDR3 comprising the amino acid sequence of SEQ ID NO: 346. In one embodiment, the light chain variable region comprises one or more VL CDRs selected from the group consisting of SEQ ID NO: 344, SEQ ID NO: 345, and SEQ ID NO: 346. In one embodiment, the light chain variable region comprises two or more VL CDRs selected from the group consisting of SEQ ID NO: 344, SEQ ID NO: 345, and SEQ ID NO: 346. In one embodiment, the light chain variable region comprises a VL CDR1 comprising SEQ ID NO: 344, a VL CDR2 comprising SEQ ID NO: 345, and a VL CDR3 comprising SEQ ID NO: 346.

In an exemplary embodiment, the antibody, or antigen-binding fragment thereof, comprises a heavy chain variable region that comprises a VH CDR1 comprising SEQ ID NO: 341, a VH CDR2 comprising SEQ ID NO: 342, and a VH CDR3 comprising SEQ ID NO: 343, and a light chain variable region that comprises a VL CDR1 comprising SEQ ID NO: 344, a VL CDR2 comprising SEQ ID NO: 345, and a VL CDR3 comprising SEQ ID NO: 346.

In certain embodiments, one or more of the CDRs (i.e., one or more heavy chain CDRs having SEQ ID NOs: 341-343, and/or one or more light chain CDRs having SEQ ID NOs: 344-346) can comprise a conservative amino acid substitution (or 2, 3, 4, or 5 amino acid substitutions) while retaining the CD5 specificity of the antibody (i.e., specificity similar to an antibody, or antigen-binding fragment thereof, comprising heavy chain CDRs of SEQ ID NOs: 341 to 343, and light chain CDRs of SEQ ID NOs:344 to 346).

In certain embodiments, the anti-CD5 antibody, or antigen binding fragment thereof, is murine antibody 5D7, or a humanized version thereof. Murine antibody 5D7 binds to human CD5 and is described in US Patent Publication No. 20008/0245027, the contents of which relating to the antibody sequences disclosed therein are incorporated by reference herein. SEQ ID Nos: 353 to 358 described in the sequence summary table correspond to the CDRs of murine anti-CD5 antibody 5D7. A humanized version of anti-CD5 antibody 5D7 is described in SEQ ID NO: 359 (humanized heavy chain variable region) and SEQ ID NO: 360 (humanized light chain variable region). In one embodiment, the ADCs and uses thereof described herein include an antibody comprising the CDRs set forth in SEQ ID Nos: 353 to 358. In one embodiment, the ADCs and uses thereof described herein include an antibody comprising the heavy and light chain variable regions as set forth in SEQ ID Nos: 359 and 360, respectively.

In one embodiment, the antibody, or antigen-binding fragment thereof, comprises a heavy chain variable region that comprises the amino acid sequence set forth in SEQ ID NO: 359. In another embodiment, the antibody, or antigen-binding fragment thereof, comprises a heavy chain variable region that comprises an amino acid sequence having at least 95% identity to SEQ ID NO: 359, e.g., at least 95%, 96%, 97%, 98%, 99%, or 100% identity to SEQ ID NO: 359. In certain embodiments, an antibody comprises a modified heavy chain (HC) variable region comprising an HC variable domain comprising SEQ ID NO: 359, or a variant of SEQ ID NO: 359, which variant (i) differs from SEQ ID NO: 359 in 1, 2, 3, 4 or 5 amino acids substitutions, additions or deletions; (ii) differs from SEQ ID NO: 359 in at most 5, 4, 3, 2, or 1 amino acids substitutions, additions or deletions; (iii) differs from SEQ ID NO: 359 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 359, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of SEQ ID NO: 359, while retaining the CD5 binding specificity of the antibody, i.e. has a binding specificity similar to an antibody, or antigen-binding fragment thereof, comprising SEQ ID NO: 359.

In one embodiment, the antibody, or antigen-binding fragment thereof, comprises a light chain variable region that comprises the amino acid sequence set forth in SEQ ID NO: 360. In another embodiment, the antibody, or antigen-binding fragment thereof, comprises a light chain variable region that comprises an amino acid sequence having at least 95% identity to SEQ ID NO: 360, e.g., at least 95%, 96%, 97%, 98%, 99%, or 100% identity to SEQ ID NO: 360. In certain embodiments, an antibody comprises a modified light chain (LC) variable region comprising an LC variable domain comprising SEQ ID NO: 360, or a variant of SEQ ID NO: 360, which variant (i) differs from SEQ ID NO: 360 in 1, 2, 3, 4 or 5 amino acids substitutions, additions or deletions; (ii) differs from SEQ ID NO: 360 in at most 5, 4, 3, 2, or 1 amino acids substitutions, additions or deletions; (iii) differs from SEQ ID NO: 360 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 360, wherein in any of (i)-(iv), an amino acid substitution may be a conservative amino acid substitution or a non-conservative amino acid substitution; and wherein the modified light chain variable region can have an enhanced biological activity relative to the light chain variable region of SEQ ID NO: 360, while retaining the CD5 binding specificity of the antibody, i.e., has a binding specificity similar to an antibody, or antigen-binding fragment thereof, comprising SEQ ID NO: 360.

In an exemplary embodiment, the antibody, or antigen-binding fragment thereof, comprises a heavy chain variable region that comprises an amino acid sequence having at least 95% identity to SEQ ID NO: 359, e.g., at least 95%, 96%, 97%, 98%, 99%, or 100% identity to SEQ ID NO: 359, and a light chain variable region that comprises an amino acid sequence having at least 95% identity to SEQ ID NO: 360, e.g., at least 95%, 96%, 97%, 98%, 99%, or 100% identity to SEQ ID NO: 360. In one embodiment, the antibody, or antigen-binding fragment thereof, comprises a heavy chain variable region that comprises SEQ ID NO: 359, and a light chain variable region that comprises SEQ ID NO: 360.

In another embodiment, the anti-CD5 antibody, or antigen-binding fragment thereof, can contain a heavy chain variable region that comprises a VH CDR1 comprising the amino acid sequence of SEQ ID NO: 353. In one embodiment, the heavy chain variable region comprises a VH CDR2 comprising the amino acid sequence of SEQ ID NO: 354. In one embodiment, the heavy chain variable region comprises a VH CDR3 comprising the amino acid sequence of SEQ ID NO: 355. In one embodiment, the heavy chain variable region comprises one or more VH CDRs selected from the group consisting of SEQ ID NO: 353, SEQ ID NO: 354, and SEQ ID NO: 355. In one embodiment, the heavy chain variable region comprises two or more VH CDRs selected from the group consisting of SEQ ID NO: 353, SEQ ID NO: 354, and SEQ ID NO: 355. In one embodiment, the heavy chain variable region comprises a VH CDR1 comprising SEQ ID NO: 353, a VH CDR2 comprising SEQ ID NO: 354, and a VH CDR3 comprising SEQ ID NO: 355.

In one embodiment, the light chain variable region comprises one or more complementarity determining regions (CDRs). In one embodiment, the light chain variable region comprises a VL CDR1 comprising the amino acid sequence of SEQ ID NO: 356. In one embodiment, the light chain variable region comprises a VL CDR2 comprising the amino acid sequence of SEQ ID NO: 357. In one embodiment, the light chain variable region comprises a VL CDR3 comprising the amino acid sequence of SEQ ID NO: 358. In one embodiment, the light chain variable region comprises one or more VL CDRs selected from the group consisting of SEQ ID NO: 356, SEQ ID NO: 357, and SEQ ID NO: 358. In one embodiment, the light chain variable region comprises two or more VL CDRs selected from the group consisting of SEQ ID NO: 356, SEQ ID NO: 357, and SEQ ID NO: 358. In one embodiment, the light chain variable region comprises a VL CDR1 comprising SEQ ID NO: 356, a VL CDR2 comprising SEQ ID NO: 357, and a VL CDR3 comprising SEQ ID NO: 358.

In an exemplary embodiment, the antibody, or antigen-binding fragment thereof, comprises a heavy chain variable region that comprises a VH CDR1 comprising SEQ ID NO: 353, a VH CDR2 comprising SEQ ID NO: 354, and a VH CDR3 comprising SEQ ID NO: 355, and a light chain variable region that comprises a VL CDR1 comprising SEQ ID NO: 356, a VL CDR2 comprising SEQ ID NO: 357, and a VL CDR3 comprising SEQ ID NO: 358.

In certain embodiments, one or more of the CDRs (i.e., one or more heavy chain CDRs having SEQ ID NOs: 353-355, and/or one or more light chain CDRs having SEQ ID NOs: 356-358) can comprise a conservative amino acid substitution (or 2, 3, 4, or 5 amino acid substitutions) while retaining the CD5 specificity of the antibody (i.e., specificity similar to an antibody, or antigen-binding fragment thereof, comprising heavy chain CDRs of SEQ ID NOs: 353 to 355, and light chain CDRs of SEQ ID NOs:356 to 358).

Antibodies and antigen-binding fragments thereof capable of binding CD5 antigen can be identified using techniques known in the art and described herein, such as by immunization, computational modeling techniques, and in vitro selection methods, such as the phage display and cell-based display platforms described below.

Anti-CD5 antibodies that can be used in conjunction with the compositions and methods described herein include those that have one or both of the following variable regions, or an amino acid sequence having at least 85% sequence identity thereto (e.g., an amino acid sequence having 85%, 90%, 95%, 97%, 98%, 99%, or more, sequence identity thereto):

```
a V_L having the amino acid sequence
                          (SEQ ID NO: 325)
DIQMTQSPSSMSASLGDRVTITCRASQDINSYLSWFQQKPGKSPKTLIY
RANRLVDGVPSRFSGSGSGTDYTLTISSLQYEDFGIYYCQQYDESPWTF
GGGTKLEIK;
and a V_H having the amino acid sequence
                          (SEQ ID NO: 326)
QIQLVQSGPGLKKPGGSVRISCAASGYTFTNYGMNWWKQAPGKGLRWMG
WNTHTGEPTYADDFKGRFTFSLDTSKSTAYLQINSLRAEDTATYFCTRR
GYDWYFDVWGQGTTVTVSS.
```

Antibodies and antigen-binding fragments thereof containing the foregoing V_L and V_H sequences are described, e.g., in U.S. Pat. No. 5,869,619, the disclosure of which is incorporated herein by reference as it pertains to anti-CD5 antibodies and antigen-binding fragments thereof, such as the he1 antibody. In some embodiments, the anti-CD5 antibody or antigen-binding fragment thereof includes the V_L and V_H chains of SEQ ID NO: 325 and SEQ ID NO: 326. In some embodiments, the anti-CD5 antibody or antigen-binding fragment thereof includes the CDRs contained in the V_L and V_H chains of SEQ ID NO: 325 and SEQ ID NO: 326. In some embodiments, the anti-CD5 antibody or antigen-binding fragment thereof includes the CDRs contained in the V_L and V_H chains of SEQ ID NO: 325 and SEQ ID NO: 326 and the remainder of the V_L and V_H sequences have at least 85% sequence identity (e.g., 85%, 90%, 95%, 97%, 98%, 99%, or greater sequence identity) to the V_L and V_H sequences of SEQ ID NO: 325 and SEQ ID NO: 326.

In some embodiments, the anti-CD5 antibody or antigen-binding fragment thereof includes the following CDRs:

```
a CDR-H1 having the amino acid sequence
                          (SEQ ID NO: 327)
GYTFTNY;

a CDR-H2 having the amino acid sequence
                          (SEQ ID NO: 328)
NTHTGE;

a CDR-H3 having the amino acid sequence
                          (SEQ ID NO: 329)
RGYDWYFDV;

a CDR-L1 having the amino acid sequence
                          (SEQ ID NO: 330)
RASQDINSYLS;

a CDR-L2 having the amino acid sequence
                          (SEQ ID NO: 331)
RANRLVD;
and a CDR-L3 having the amino acid sequence
                          (SEQ ID NO: 332)
QQYDESPWT.
```

Additional anti-CD5 antibodies that can be used in conjunction with the compositions and methods described herein include those that have one or both of the following variable regions, or an amino acid sequence having at least 85% sequence identity thereto (e.g., an amino acid sequence having 85%, 90%, 95%, 97%, 98%, 99%, or more, sequence identity thereto):

```
a V_L having the amino acid sequence
                          (SEQ ID NO: 333)
DIQMTQSPSSLSASVGDRVTITCRASQDINSYLSWFQQKPGKAPKTLIY
RANRLESGVPSRFSGSGSGTDYTLTIS SLQYEDFGIYYCQQYDESPWT
FGGGTKLEIK;
and a V_H having the amino acid sequence
                          (SEQ ID NO: 334)
EIQLVQSGGGLVKPGGSVRISCAASGYTFTNYGMNWVRQAPGKGLEWMG
WINTHYGEPTYADSFKGTRTFSLDDSKNTAYLQINSLRAEDTAVYFCTR
RGYDWYFDVWGQGGTTVTVSS.
```

Antibodies and antigen-binding fragments thereof containing the foregoing V_L and V_H sequences are described, e.g., in U.S. Pat. No. 5,869,619, the disclosure of which is incorporated herein by reference as it pertains to anti-CD5 antibodies and antigen-binding fragments thereof, such as the he3 antibody. In some embodiments, the anti-CD5 antibody or antigen-binding fragment thereof includes the CDRs contained in the V_L and V_H chains of the antibody that includes the V_L and V_H chains of SEQ ID NO:327 and SEQ ID NO: 328. In some embodiments, the anti-CD5 antibody or antigen-binding fragment thereof includes the CDRs contained in the V_L and V_H chains of SEQ ID NO:327 and SEQ ID NO: 328 and the remainder of the V_L and V_H sequences have at least 85% sequence identity (e.g., 85%, 90%, 95%, 97%, 98%, 99%, or greater sequence identity) to the V_L and V_H sequences of SEQ ID NO:327 and SEQ ID NO: 328.

In some embodiments, the anti-CD5 antibody or antigen-binding fragment thereof includes the following CDRs:

```
a CDR-H1 having the amino acid sequence
                          (SEQ ID NO: 335)
GYTFTNY;
```

-continued

```
a CDR-H2 having the amino acid sequence
                                 (SEQ ID NO: 336)
NTHYGE;

a CDR-H3 having the amino acid sequence
                                 (SEQ ID NO: 337)
RRGYDWYFDV;

a CDR-L1 having the amino acid sequence
                                 (SEQ ID NO: 338)
RASQDINSYLS;

a CDR-L2 having the amino acid sequence
                                 (SEQ ID NO: 339)
RANRLES;
and a CDR-L3 having the amino acid sequence
                                 (SEQ ID NO: 340)
QQYDESPWT.
```

Antibodies and antigen-binding fragments thereof containing the foregoing CDR sequences are described, e.g., in U.S. Pat. No. 5,869,619, the disclosure of which is incorporated herein by reference as it pertains to anti-CD5 antibodies and antigen-binding fragments thereof.

Other anti-CD5 antibodies that can be used in conjunction with the compositions and methods described herein include, for instance, anti-CD5 antibodies that are described in U.S. Pat. Nos. 5,821,123; 5,766,886; 5,770,196; 7,153,932; 5,621,083; 6,649,742; 6,146,631; 5,756,699; 5,744,580; 6,376,217; 5,837,491; and 6,146,850, the disclosures of each of which are incorporated herein by reference as they pertain to anti-CD5 antibodies and antigen-binding fragments thereof.

Other anti-CD5 antibodies that can be used in conjunction with the compositions and methods described herein include, for instance, those produced by the hybridoma cell line deposited as ATCC CRL 8000 (anti-CD5 murine antibody OKT1). Such antibodies are described in U.S. Pat. Nos. 4,515,894; 4,657,760; and 4,363,799, the disclosures of each of which are incorporated herein by reference as they pertains to anti-CD5 antibodies and antigen-binding fragments thereof.

Anti-CD5 antibodies that can be used in conjunction with the compositions and methods described herein include those that have one or more, or all, of the following CDRs:

```
a CDR-H1 having the amino acid sequence
                                 (SEQ ID NO: 341)
GYSITSGYY;

a CDR-H2 having the amino acid sequence
                                 (SEQ ID NO: 342)
ISYSGFT;

a CDR-H3 having the amino acid sequence
                                 (SEQ ID NO: 343)
AGDRTGSWFAY;

a CDR-L1 having the amino acid sequence
                                 (SEQ ID NO: 344)
QDISNY;

a CDR-L2 having the amino acid sequence
                                 (SEQ ID NO: 345)
ATS;
and a CDR-L3 having the amino acid sequence
                                 (SEQ ID NO: 346)
LQYASYPFT.
```

Antibodies and antigen-binding fragments thereof containing the foregoing CDR sequences are described, e.g., in U.S. Pat. No. 8,679,500, the disclosure of which is incorporated herein by reference as it pertains to anti-CD5 antibodies and antigen-binding fragments thereof.

Anti-CD5 antibodies that can be used in conjunction with the compositions and methods described herein include those that have one or more, or all, of the following CDRs:

```
a CDR-H1 having the amino acid sequence
                                 (SEQ ID NO: 347)
GYIFTNYG;

a CDR-H2 having the amino acid sequence
                                 (SEQ ID NO: 348)
INTYNGEP;

a CDR-H3 having the amino acid sequence
                                 (SEQ ID NO: 349)
ARGDYYGYEDY;

a CDR-L1 having the amino acid sequence
                                 (SEQ ID NO: 350)
QGISNY;

a CDR-L2 having the amino acid sequence
                                 (SEQ ID NO: 351)
YTS;
and a CDR-L3 having the amino acid sequence
                                 (SEQ ID NO: 352)
QQYSKLPWT.
```

Antibodies and antigen-binding fragments thereof containing the foregoing CDR sequences are described, e.g., in U.S. Pat. No. 8,679,500.

Anti-CD5 antibodies that can be used in conjunction with the compositions and methods described herein include those that have one or more, or all, of the following CDRs:

```
a CDR-H1 having the amino acid sequence
                                 (SEQ ID NO: 353)
FSLSTSGMG;

a CDR-H2 having the amino acid sequence
                                 (SEQ ID NO: 354)
WWDDD;

a CDR-H3 having the amino acid sequence
                                 (SEQ ID NO: 355)
RRATGTGFDY;

a CDR-L1 having the amino acid sequence
                                 (SEQ ID NO: 356)
QDVGTA;

a CDR-L2 having the amino acid sequence
                                 (SEQ ID NO: 357)
WTSTRHT;
and a CDR-L3 having the amino acid sequence
                                 (SEQ ID NO: 358)
YNSYNT.
```

Antibodies and antigen-binding fragments thereof containing the foregoing CDR sequences are described, e.g., in US Patent Application Publication No. 2008/0254027, the disclosure of which is incorporated herein by reference as it pertains to anti-CD5 antibodies and antigen-binding fragments thereof.

Other anti-CD5 antibodies that can be used in conjunction with the compositions and methods described herein include, for instance, anti-CD5 antibodies that are described in PCT Application Publication No. WO1992/014491, such as the anti-CD5 antibodies produced by hybridoma cell line deposited at the Institut Pasteur under No. 1-1025 on Jan. 10, 1991. The disclosure of PCT Application Publication No. WO1992/014491 is incorporated herein by reference as it pertains to anti-CD5 antibodies and antigen-binding fragments thereof.

Other anti-CD5 antibodies that can be used in conjunction with the compositions and methods described herein include, for instance, anti-CD5 antibodies that are described in U.S. Pat. Nos. 6,010,902 and 7,192,736, US Patent Application Publication Nos. 2011/0250203 and 2017/0129128, and PCT Application Publication Nos. WO2016/172606; WO1994/023747; and WO1996/041608; the disclosures of each of which are incorporated herein by reference as they pertain to anti-CD5 antibodies and antigen binding fragments thereof.

In some embodiments, the anti-CD5 antibodies that can be used in conjunction with the compositions and methods described herein include those that contain a combination of CDR-H1, CDR-H2, CDR-H3, CDR-L1, CDR-L2, and CDR-L3 regions set forth in the table below.

TABLE 5

| Ab No. | Name | CDRH1 | CDRH2 | CDRH3 |
|---|---|---|---|---|
| 1 | 1D8 | SGYSFTGYTM | LINPYNGGTT | CARDYYGSSPDFDYW |
| 2 | 3I21 | SGYSFTDYTM | LINPYNGGTM | CARDNYGSSPDFDYW |
| 3 | 4H10 | SGYSFTGYTM | LINPYNGGTM | CARDNYGSSPYFDYW |
| 4 | 8J23 | SGYSFTGYTM | LINPYNGGTM | CARDNYGSSPYFDYW |
| 5 | 504 | SGYSFTGYTM | LINPYNGGTT | CARDYYGSSPDFDYW |
| 6 | 4H2 | SGFTFSNYAM | SISSGGNTF | CVRYYYGVTYWYFDVW |
| 7 | 5G2 | SGFTFSSYAM | SISSGGSTY | CVRYYYGIRYWYFDVW |
| 8 | 8G8 | SGYSFTAYNI | SIDPYYGDTK | CARRMITMGDWYFDVW |
| 9 | 6M4 | SGYSFTAYSM | SIDPYYGDTK | CARRMITTGDWYFDVW |
| 10 | 2E3 | SGYTFTNFAI | LISSNSGDVS | CARHYGAHNYFDYW |
| 11 | 4E24 | SGYTFTNFAI | LISTSSGDVS | CARHYGANNYFDYW |
| 12 | 4F10 | SGYTFTNFAI | LISSNSGDVS | CARHYGAHNYFDYW |
| 13 | 7J9 | SGYTFTNFAI | LISSNSGDVS | CARHYGAHNYFDYW |
| 14 | 7P9 | SGFNIKDTYM | RIDPANGNTK | CAREENYYGTYYFDYW |
| 15 | 8E24 | SGYSFTSYWM | MIHPSDSETR | CARWGDHDDAMDFW |
| 16 | 6L18 | SGFSLTNYDV | VIWSGGNTD | CARNHGDGYFNWYFDVW |
| 17 | 7H7 | SGFSLTNYDV | VIWSGGNTD | CARNHGDGYYNWYFDVW |
| 18 | 1E7 | SGFTFSNYGM | AINSNGDITY | CARGTAWFTYW |
| 19 | 8J21 | SGYSFTGYTM | LINPYNGGTR | CARDGDDGWDIDVW |
| 20 | 7I11 | SGYIFANYGM | WINTYTGEPT | CARRGTYWHFDVW |
| 21 | 8M9 | SGYNFTNYGM | WINTYTGEPT | CARRGSYWHFDVW |
| 22 | 1P21 | SGYTFTNYGM | WINTYTGEPT | CARRSTLVFDYW |
| 23 | 2H11 | SGYTFTDYYI | WIYPGGGNTR | CARNGYWYFDVW |
| 24 | 3M22 | SGYTFTDYYI | WIYPGGGNTR | CARNGYWYFDVW |
| 25 | 5M6 | SGNTFTNFYL | CIYPGNVKTK | CAKEGDYDGTAYFDYW |
| 26 | 5H8 | SGYTFTNYGM | WINTYTGEPT | CARRRDGNFDYW |
| 27 | 7I19 | SEFTFSNYAM | TISSGGSYTY | CVRHGYFDVW |
| 28 | 1A20 | SGYTFTSYRM | RIDPYDSGTH | CAFYDGAYW |
| 29 | 8E15 | SGFNIKDTYM | RIDPANGNTK | CASYDPDYW |
| 30 | 8C10 | SGYSFTDYTM | LINPYNGGTR | CARDTTATYYFDYW |
| 31 | 3P16 | SGYMFTNHGM | WINTYTGEPT | CARRVATYFDVW |

TABLE 5-continued

| 32 | 4F3 | SGYMFTNYGM | WINTYTGEPT | CTRRSHITLDYW |
| 33 | 5M24 | SGYIFTNYGM | WINTYTGEPT | CARRRTTAFDYW |
| 34 | 5O24 | SGFNIKDYYI | WIDPENGRTE | CNNGNYVRHYYFDYW |
| 35 | 7B16 | SGYTFINYGM | WINTYTGEPT | CTRRREITFDYW |
| 36 | 1E8 | SGYTFTDYFI | EIYPGSSNTY | CARSGISPFTYW |
| 37 | 2H16 | SGYIFTGYNI | AVYPGNGDTS | CAKYDRFFASW |

| Ab No. | Name | CDRH1 | CDRH2 | CDRH3 |
|---|---|---|---|---|
| 1 | 1D8 | SQGISNHL | YFTSS | CQQYSNLPYTF |
| 2 | 3I21 | SQGIRNYL | YFTSS | CQQYSNLPYTF |
| 3 | 4H10 | SQGISNHL | YFTSS | CQQYSNLPYTF |
| 4 | 8J23 | SQGINNYL | YYTSS | CQQYSKIPYTC |
| 5 | 5O4 | SQGISNHL | YFTSS | CQQYSNLPYTF |
| 6 | 4H2 | SQSVDHDGDSYM | YAASN | CQQNYEDPTF |
| 7 | 5G2 | SQSVDYDGDSYM | YAASN | CQQSNEDPTF |
| 8 | 8G8 | SQDISNYL | YYTSR | CQQGDALPWTF |
| 9 | 6M4 | SQDISTYL | FYTSR | CQQGNSLPFTF |
| 10 | 2E3 | TSSISSSYL | YGTSN | CQQWSSRPPTF |
| 11 | 4E24 | NSSVSSSYL | YGTSN | CQQYSGYPLTF |
| 12 | 4F10 | TSSISSSYL | YGTSN | CQQYSDYPLTF |
| 13 | 7J9 | TSSISSSYL | YGTSN | CQQRSYFPFTF |
| 14 | 7P9 | SENIYYNL | YNANS | CKQVYDVPFTF |
| 15 | 8E24 | SENIYGYF | YNAKT | CQHHYGTPFTF |
| 16 | 6L18 | SQDINNYI | HYTST | CLQYDNLWTF |
| 17 | 7H7 | SQDINKYI | HYTST | CLQYDNLWTF |
| 18 | 1E7 | SENIYSYL | YNAKT | CQHHYGYPYTF |
| 19 | 8J21 | SQGIRNYL | YHTST | CQQYSNLPLTF |
| 20 | 7I11 | SQDVRTDV | YSASF | CQQHYTSPWTF |
| 21 | 8M9 | SQDVITAV | YSASY | CQQHYSTPWTF |
| 22 | 1P21 | SQSIGTSI | KSASE | CQQSNRWPLTF |
| 23 | 2H11 | SSQSLLNQKNYL | YWAST | CQNDYDYPYTF |
| 24 | 3M22 | SSSVSSSYL | YSTSN | CHQYHRSPLTF |
| 25 | 5M6 | SENIYYNL | YNANS | CQQTFDVPWTF |
| 26 | 5H8 | SQTIGTSI | KNASE | CQQSNSWPLTY |
| 27 | 7I19 | SQSLLYSSDQKNYL | YWAST | CQQYYNYPLTF |
| 28 | 1A20 | NSSVSYM | YDTSK | CQQWSSNPFTF |
| 29 | 8E15 | SENIYYNL | YNANS | CKQAYDVPWTF |
| 30 | 8O10 | SSSLSYM | YDTSN | CQQWSSFPPTF |
| 31 | 3P16 | SQRIGTSM | KSASE | CQQSNSWPLTF |
| 32 | 4F3 | SQSIGTSI | KSASE | CQQSNSWPLTF |
| 33 | 5M24 | SQNIGTSI | KDASE | CQQSDSWPLTF |

TABLE 5-continued

| 34 | 5O24 | ISSVSYM | YATSN | CQQWSSNPRTF |
| 35 | 7B16 | SQTIATSI | KNASE | CQQSNSWPLTF |
| 36 | 1E8 | SQSLVHSNGNTYL | YKVSN | CWQNTHFPQTF |
| 37 | 2H16 | NESVEYSGTSLM | SAASN | CQQSRQVPLTF |

Antibodies and antigen-binding fragments thereof containing the foregoing CDR sequences of the table above are described, e.g., in US Patent Application Publication No. 2011/0250203, the disclosure of which is incorporated herein by reference as it pertains to anti-CD5 antibodies and antigen binding fragments thereof.

Anti-CD2 Antibodies

Compositions and methods described herein include, in certain embodiments, an antibody, or fragment thereof, that specifically binds to human CD2. Human CD2 is also referred to as T-cell Surface Antigen T11/Leu-5, T11, CD2 antigen (p50), and Sheep Red Blood Cell Receptor (SRBC). CD2 is expressed on T cells. Two isoforms of human CD2 have been identified. Isoform 1 contains 351 amino acids is described in Seed, B. et al. (1987) 84: 3365-69 (see also Sewell et al. (1986) 83: 8718-22) and below (NCBI Reference Sequence: NP_001758.2):

(SEQ ID NO: 312)
```
msfpckfvas fllifnvssk gavskeitna letwgalgqd inldipsfqm sddiddikwe ktsdkkkiaq frkeketfke kdtyklfkng tlkikhlktd dqdiykvsiy dtkgknvlek ifdlkiqerv skpkiswtci nttltcevmn gtdpelnlyq dgkhlklsqr vithkwttsl sakfkctagn kvskessvep vscpekgldi yliigicggg sllmvfvall vfyitkrkkq rsrrndeele trahrvatee rgrkphqipa stpqnpatsq hpppppghrs qapshrpppp ghrvghqpqk rppapsgtqv hqqkgpplpr prvqpkpphg aaenslspss n
```

A second isoform of CD2 is 377 amino acids and is identified herein as NCBI Reference Sequence: NP_001315538.1.

T cells and NK cells have been shown to express CD2, which is a cell adhesion molecule and specific marker for such lymphocytes. For instance, CD2 interacts with other adhesion molecules, such as lymphocyte function-associated antigen-3 (LFA-3/CD58), to potentiate T cell activation. Antibodies and antigen-binding fragments thereof capable of binding CD2 may suppress T cell activation and T cell-mediated immune responses against hematopoietic stem cell grafts, for example, by inhibiting the interaction between CD2 and LFA-3. Antibodies and antigen-binding fragments thereof that bind to this cell-surface antigen can be identified using techniques known in the art and described herein, including immunization, computational modeling techniques, and in vitro selection methods, such as the phage display and cell-based display platforms described below.

In certain embodiments, the present invention encompasses an ADC comprising an antibody, or antigen-binding fragment thereof, that specifically binds to a CD2 polypeptide, e.g., a human CD2 polypeptide, and uses thereof.

In one embodiment, an ADC comprises an anti-CD2 antibody comprising a heavy chain variable region comprises one or more complementarity determining regions (CDRs). In one embodiment, the heavy chain variable region comprises a VH CDR1 comprising the amino acid sequence of SEQ ID NO:300. In one embodiment, the heavy chain variable region comprises a VH CDR2 comprising the amino acid sequence of SEQ ID NO:301. In one embodiment, the heavy chain variable region comprises a VH CDR3 comprising the amino acid sequence of SEQ ID NO:302. In one embodiment, the heavy chain variable region comprises one or more VH CDRs selected from the group consisting of SEQ ID NO:300, SEQ ID NO:301, and SEQ ID NO:302. In one embodiment, the heavy chain variable region comprises two or more VH CDRs selected from the group consisting of SEQ ID NO:300, SEQ ID NO:301, and SEQ ID NO:302. In one embodiment, the heavy chain variable region comprises a VH CDR1 comprising SEQ ID NO:300, a VH CDR2 comprising SEQ ID NO:301, and a VH CDR3 comprising SEQ ID NO:302.

In one embodiment, an ADC comprises an anti-CD2 antibody comprising light chain variable region comprises one or more complementarity determining regions (CDRs). In one embodiment, the light chain variable region comprises a VL CDR1 comprising the amino acid sequence of SEQ ID NO:303. In one embodiment, the light chain variable region comprises a VL CDR2 comprising the amino acid sequence of SEQ ID NO:304. In one embodiment, the light chain variable region comprises a VL CDR3 comprising the amino acid sequence of SEQ ID NO:305. In one embodiment, the light chain variable region comprises one or more VL CDRs selected from the group consisting of SEQ ID NO:303, SEQ ID NO:304, and SEQ ID NO:305. In one embodiment, the light chain variable region comprises two or more VL CDRs selected from the group consisting of SEQ ID NO:303, SEQ ID NO:304, and SEQ ID NO:305. In one embodiment, the light chain variable region comprises a VL CDR1 comprising SEQ ID NO:303, a VL CDR2 comprising SEQ ID NO:304, and a VL CDR3 comprising SEQ ID NO:305.

In an exemplary embodiment, the anti-CD2 antibody, or antigen-binding fragment thereof, comprises a heavy chain variable region that comprises a VH CDR1 comprising SEQ ID NO:300, a VH CDR2 comprising SEQ ID NO:301, and a VH CDR3 comprising SEQ ID NO:302, and a light chain variable region that comprises a VL CDR1 comprising SEQ ID NO:303, a VL CDR2 comprising SEQ ID NO:304, and a VL CDR3 comprising SEQ ID NO:305.

In certain embodiments, one or more of the CDRs (i.e., one or more heavy chain CDRs having SEQ ID NOs: 300-302, and/or one or more light chain CDRs having SEQ ID NOs: 303-305) can comprise a conservative amino acid substitution (or 2, 3, 4, or 5 amino acid substitutions) while retaining the CD2 specificity of the antibody (i.e., specificity similar to an antibody, or antigen-binding fragment thereof, comprising heavy chain CDRs of SEQ ID NOs: 300 to 302, and light chain CDRs of SEQ ID NOs:303 to 305).

In one embodiment, the antibody, or antigen-binding fragment thereof, comprises a heavy chain variable region that comprises the amino acid sequence set forth in SEQ ID NO: 306. In another embodiment, the antibody, or antigen-binding fragment thereof, comprises a heavy chain variable region that comprises an amino acid sequence having at least 95% identity to SEQ ID NO: 306, e.g., at least 95%, 96%, 97%, 98%, 99%, or 100% identity to SEQ ID NO: 306. In certain embodiments, an antibody comprises a modified heavy chain (HC) variable region comprising an HC variable domain comprising SEQ ID NO: 306, or a variant of SEQ ID NO: 306, which variant (i) differs from SEQ ID NO: 306 in 1, 2, 3, 4 or 5 amino acids substitutions, additions or deletions; (ii) differs from SEQ ID NO: 306 in at most 5, 4, 3, 2, or 1 amino acids substitutions, additions or deletions; (iii) differs from SEQ ID NO: 306 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 306, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of SEQ ID NO: 306, while retaining the CD2 binding specificity of the antibody, i.e. has a binding specificity similar to an antibody, or antigen-binding fragment thereof, comprising SEQ ID NO: 306. In one embodiment, the antibody, or antigen-binding fragment thereof, comprises a heavy chain variable region that differs from the amino acid sequence set forth in SEQ ID NO: 306 at one, two, three or four amino acids. For example, the antibody, or antigen-binding fragment thereof, can comprise a heavy chain variable region that differs from the amino acid sequence set forth in SEQ ID NO: 306 at one, two, three, or four of positions 12, 13, 28, and/or 48. In one embodiment, the heavy chain variable region differs from the amino acid sequence set forth in SEQ ID NO:306 at positions 12, 13, 28, and 48. In one embodiment, the heavy chain variable region comprises one, two, three, or four of the following substitutions with respect to the sequence set forth in SEQ ID NO:306: K12Q; K13R; T281; and M48V. In one embodiment, the heavy chain variable region comprises the substitutions K12Q; K13R; T281; and M48V with respect to SEQ ID NO:306.

In one embodiment, the antibody, or antigen-binding fragment thereof, comprises a light chain variable region that comprises the amino acid sequence set forth in SEQ ID NO:307. In another embodiment, the antibody, or antigen-binding fragment thereof, comprises a light chain variable region that comprises an amino acid sequence having at least 95% identity to SEQ ID NO:307, e.g., at least 95%, 96%, 97%, 98%, 99%, or 100% identity to SEQ ID NO:307. In certain embodiments, an antibody comprises a modified light chain (LC) variable region comprising an LC variable domain comprising SEQ ID NO: 307, or a variant of SEQ ID NO: 307, which variant (i) differs from SEQ ID NO: 307 in 1, 2, 3, 4 or 5 amino acids substitutions, additions or deletions; (ii) differs from SEQ ID NO: 307 in at most 5, 4, 3, 2, or 1 amino acids substitutions, additions or deletions; (iii) differs from SEQ ID NO: 307 in 1-5, 1-3, 1-2, 2-5 or 3-5 amino acids substitutions, additions or deletions and/or (iv) comprises an amino acid sequence that is at least about 75%, 80%, 85%, 90%, 95%, 96%, 97%, 98% or 99% identical to SEQ ID NO: 307, wherein in any of (i)-(iv), an amino acid substitution may be a conservative amino acid substitution or a non-conservative amino acid substitution; and wherein the modified light chain variable region can have an enhanced biological activity relative to the light chain variable region of SEQ ID NO:307, while retaining the CD2 binding specificity of the antibody, i.e., has a binding specificity similar to an antibody, or antigen-binding fragment thereof, comprising SEQ ID NO:307.

In an exemplary embodiment, the antibody, or antigen-binding fragment thereof, comprises a heavy chain variable region that comprises an amino acid sequence having at least 95% identity to SEQ ID NO: 306, e.g., at least about 95%, about 96%, about 97%, about 98%, about 99%, or 100% identity to SEQ ID NO: 306, and a light chain variable region that comprises an amino acid sequence having at least about 95% identity to SEQ ID NO:307, e.g., at least about 95%, about 96%, about 97%, about 98%, about 99%, or 100% identity to SEQ ID NO:307. In one embodiment, the antibody, or antigen-binding fragment thereof, comprises a heavy chain variable region that comprises SEQ ID NO: 306, and a light chain variable region that comprises SEQ ID NO:307. In one embodiment, the antibody is an Ab1 antibody that comprises a heavy chain variable region comprising SEQ ID NO:306, and a light chain variable region comprising SEQ ID NO:307.

In one embodiment, the antibody, or antigen-binding fragment thereof, comprises a heavy chain variable region that comprises the amino acid sequence set forth in SEQ ID NO:308. In another embodiment, the antibody, or antigen-binding fragment thereof, comprises a heavy chain variable region that comprises an amino acid sequence having at least 95% identity to SEQ ID NO:308, e.g., at least about 95%, about 96%, about 97%, about 98%, about 99%, or 100% identity to SEQ ID NO:308. In an exemplary embodiment, the antibody, or antigen-binding fragment thereof, comprises a heavy chain variable region that comprises an amino acid sequence having at least 95% identity to SEQ ID NO:308, e.g., at least about 95%, about 96%, about 97%, about 98%, about 99%, or 100% identity to SEQ ID NO:308, and a light chain variable region that comprises an amino acid sequence having at least about 95% identity to SEQ ID NO:309, e.g., at least about 95%, about 96%, about 97%, about 98%, about 99%, or 100% identity to SEQ ID NO:309. In one embodiment, the antibody, or antigen-binding fragment thereof, comprises a heavy chain variable region that comprises SEQ ID NO:308, and a light chain variable region that comprises SEQ ID NO:309. In one embodiment, the antibody is an Ab1a antibody that comprises a heavy chain variable region comprising SEQ ID NO:308, and a light chain variable region comprising SEQ ID NO:309.

In one embodiment, the heavy chain variable region comprises one or more complementarity determining regions (CDRs). In one embodiment, the heavy chain variable region comprises a VH CDR1 comprising the amino acid sequence of SEQ ID NO:3131. In one embodiment, the heavy chain variable region comprises a VH CDR2 comprising the amino acid sequence of SEQ ID NO:314. In one embodiment, the heavy chain variable region comprises a VH CDR3 comprising the amino acid sequence of SEQ ID NO:315. In one embodiment, the heavy chain variable region comprises one or more VH CDRs selected from the group consisting of SEQ ID NO:313, SEQ ID NO:314, and SEQ ID NO:315. In one embodiment, the heavy chain variable region comprises two or more VH CDRs selected from the group consisting of SEQ ID NO:313, SEQ ID NO:314, and SEQ ID NO:315. In one embodiment, the heavy chain variable region comprises a VH CDR1 comprising SEQ ID NO:313, a VH CDR2 comprising SEQ ID NO:314, and a VH CDR3 comprising SEQ ID NO:315.

In one embodiment, the heavy chain variable region comprises one or more complementarity determining regions (CDRs). In one embodiment, the heavy chain variable region comprises a VH CDR1 comprising the amino acid sequence of SEQ ID NO:313. In one embodiment, the heavy chain variable region comprises a VH CDR2 comprising the amino acid sequence of SEQ ID NO:314. In one embodiment, the heavy chain variable region comprises a VH CDR3 comprising the amino acid sequence of SEQ ID NO:316. In one embodiment, the heavy chain variable region comprises one or more VH CDRs selected from the group consisting of SEQ ID NO:313, SEQ ID NO:314, and SEQ ID NO:316. In one embodiment, the heavy chain variable region comprises two or more VH CDRs selected from the group consisting of SEQ ID NO:313, SEQ ID NO:314, and SEQ ID NO:316. In one embodiment, the heavy chain variable region comprises a VH CDR1 comprising SEQ ID NO:313, a VH CDR2 comprising SEQ ID NO:314, and a VH CDR3 comprising SEQ ID NO:316.

In one embodiment, the light chain variable region comprises one or more complementarity determining regions (CDRs). In one embodiment, the light chain variable region comprises a VL CDR1 comprising the amino acid sequence of SEQ ID NO:317. In one embodiment, the light chain variable region comprises a VL CDR2 comprising the amino acid sequence of SEQ ID NO:318. In one embodiment, the light chain variable region comprises a VL CDR3 comprising the amino acid sequence of SEQ ID NO:319. In one embodiment, the light chain variable region comprises one or more VL CDRs selected from the group consisting of SEQ ID NO:317, SEQ ID NO:318, and SEQ ID NO:319. In one embodiment, the light chain variable region comprises two or more VL CDRs selected from the group consisting of SEQ ID NO:317, SEQ ID NO:318, and SEQ ID NO:319. In one embodiment, the light chain variable region comprises a VL CDR1 comprising SEQ ID NO:317, a VL CDR2 comprising SEQ ID NO:318, and a VL CDR3 comprising SEQ ID NO:319.

In an exemplary embodiment, the antibody, or antigen-binding fragment thereof, comprises a heavy chain variable region that comprises a VH CDR1 comprising SEQ ID NO:313, a VH CDR2 comprising SEQ ID NO:314, and a VH CDR3 comprising SEQ ID NO:315, and a light chain variable region that comprises a VL CDR1 comprising SEQ ID NO:317, a VL CDR2 comprising SEQ ID NO:318, and a VL CDR3 comprising SEQ ID NO:319.

In an exemplary embodiment, the antibody, or antigen-binding fragment thereof, comprises a heavy chain variable region that comprises a VH CDR1 comprising SEQ ID NO:313, a VH CDR2 comprising SEQ ID NO:314, and a VH CDR3 comprising SEQ ID NO:316, and a light chain variable region that comprises a VL CDR1 comprising SEQ ID NO:317, a VL CDR2 comprising SEQ ID NO:318, and a VL CDR3 comprising SEQ ID NO:319.

In certain embodiments, one or more of the CDRs (i.e., one or more heavy chain CDRs having SEQ ID NOs: 313-316, and/or one or more light chain CDRs having SEQ ID NOs: 317-318) can comprise a conservative amino acid substitution (or 2, 3, 4, or 5 amino acid substitutions) while retaining the CD2 specificity of the antibody (i.e., specificity similar to an antibody, or antigen-binding fragment thereof, comprising heavy chain CDRs of SEQ ID NOs: 313 to 315, and light chain CDRs of SEQ ID NOs:18 to 20; or comprising heavy chain CDRs of SEQ ID NOs: 313, 314, 316, and light chain CDRs of SEQ ID NOs:317 to 319).

In one embodiment, the antibody, or antigen-binding fragment thereof, comprises a heavy chain variable region that comprises the amino acid sequence set forth in SEQ ID NO: 320. In another embodiment, the antibody, or antigen-binding fragment thereof, comprises a heavy chain variable region that comprises an amino acid sequence having at least about 95% identity to SEQ ID NO: 320, e.g., at least about 95%, about 96%, about 97%, about 98%, about 99%, or 100% identity to SEQ ID NO: 320. In certain embodiments, an antibody comprises a modified heavy chain (HC) variable region comprising an HC variable domain comprising SEQ ID NO: 320, or a variant of SEQ ID NO: 320, which variant (i) differs from SEQ ID NO: 320 in 1, 2, 3, 4 or 5 amino acids substitutions, additions or deletions; (ii) differs from SEQ ID NO: 320 in at most 5, 4, 3, 2, or 1 amino acids substitutions, additions or deletions; (iii) differs from SEQ ID NO: 320 in 1-5, 1-3, 1-2, 2-5 or 3-5 amino acids substitutions, additions or deletions and/or (iv) comprises an amino acid sequence that is at least about 75%, about 80%, about 85%, about 90%, about 95%, about 96%, about 97%, about 98% or about 99% identical to SEQ ID NO: 320, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of SEQ ID NO: 320, while retaining the CD2 binding specificity of the antibody, i.e. has a binding specificity similar to an antibody, or antigen-binding fragment thereof, comprising SEQ ID NO: 320.

In one embodiment, the antibody, or antigen-binding fragment thereof, comprises a heavy chain variable region that comprises the amino acid sequence set forth in SEQ ID NO: 321. In another embodiment, the antibody, or antigen-binding fragment thereof, comprises a heavy chain variable region that comprises an amino acid sequence having at least about 95% identity to SEQ ID NO: 321, e.g., at least about 95%, about 96%, about 97%, about 98%, about 99%, or 100% identity to SEQ ID NO: 321. In certain embodiments, an antibody comprises a modified heavy chain (HC) variable region comprising an HC variable domain comprising SEQ ID NO: 320, or a variant of SEQ ID NO: 321, which variant (i) differs from SEQ ID NO: 321 in 1, 2, 3, 4 or 5 amino acids substitutions, additions or deletions; (ii) differs from SEQ ID NO: 321 in at most 5, 4, 3, 2, or 1 amino acids substitutions, additions or deletions; (iii) differs from SEQ ID NO: 321 in 1-5, 1-3, 1-2, 2-5 or 3-5 amino acids substitutions, additions or deletions and/or (iv) comprises an amino acid sequence that is at least about 75%, about 80%, about 85%, about 90%, about 95%, about 96%, about 97%, about 98% or about 99% identical to SEQ ID NO: 321, wherein in any of (i)-(iv), an amino acid substitution may be a conservative amino acid substitution or a non-conservative amino acid substitution; and wherein the modified heavy chain variable region can have an enhanced biological activity relative to the heavy chain variable region of SEQ ID NO: 321, while retaining the CD2 binding specificity of the antibody, i.e. has a binding specificity similar to an antibody, or antigen-binding fragment thereof, comprising SEQ ID NO: 321.

In one embodiment, the antibody, or antigen-binding fragment thereof, comprises a light chain variable region that comprises the amino acid sequence set forth in SEQ ID NO:322. In another embodiment, the antibody, or antigen-binding fragment thereof, comprises a light chain variable region that comprises an amino acid sequence having at least about 95% identity to SEQ ID NO:322, e.g., at least about about 95%, about 96%, about 97%, about 98%, about 99%, or 100% identity to SEQ ID NO:322. In certain embodiments, an antibody comprises a modified light chain (LC) variable region comprising an LC variable domain comprising SEQ ID NO: 322, or a variant of SEQ ID NO: 322, which variant (i) differs from SEQ ID NO: 322 in 1, 2, 3, 4 or 5 amino acids substitutions, additions or deletions; (ii) differs from SEQ ID NO: 322 in at most 5, 4, 3, 2, or 1 amino acids substitutions, additions or deletions; (iii) differs from SEQ ID NO: 322 in 1-5, 1-3, 1-2, 2-5 or 3-5 amino acids substitutions, additions or deletions and/or (iv) comprises an amino acid sequence that is at least about 75%, about 80%, about 85%, about 90%, about 95%, about 96%, about 97%, about 98% or about 99% identical to SEQ ID NO: 322, wherein in any of (i)-(iv), an amino acid substitution may be a conservative amino acid substitution or a non-conservative amino acid substitution; and wherein the modified light chain variable region can have an enhanced biological activity relative to the light chain variable region of SEQ ID NO:322, while retaining the CD2 binding specificity of the antibody, i.e., has a binding specificity similar to an antibody, or antigen-binding fragment thereof, comprising SEQ ID NO:322.

In an exemplary embodiment, the antibody, or antigen-binding fragment thereof, comprises a heavy chain variable region that comprises an amino acid sequence having at least 95% identity to SEQ ID NO: 320, e.g., at least about 95%, about 96%, about 97%, about 98% or about 99%, or 100% identity to SEQ ID NO: 320, and a light chain variable region that comprises an amino acid sequence having at least about 95% identity to SEQ ID NO:322, e.g., at least about 95%, about 96%, about 97%, about 98% or about 99%, or 100% identity to SEQ ID NO:322. In one embodiment, the antibody, or antigen-binding fragment thereof, comprises a heavy chain variable region that comprises SEQ ID NO: 320, and a light chain variable region that comprises SEQ ID NO:322.

In an exemplary embodiment, the antibody, or antigen-binding fragment thereof, comprises a heavy chain variable region that comprises an amino acid sequence having at least about 95% identity to SEQ ID NO: 321, e.g., at least about 95%, about 96%, about 97%, about 98% or about 99%, or 100% identity to SEQ ID NO: 321, and a light chain variable region that comprises an amino acid sequence having at least about 95% identity to SEQ ID NO:322, e.g., at least about 95%, about 96%, about 97%, about 98% or about 99%, or 100% identity to SEQ ID NO:322. In one embodiment, the antibody, or antigen-binding fragment thereof, comprises a heavy chain variable region that comprises SEQ ID NO: 321, and a light chain variable region that comprises SEQ ID NO:322.

Anti-CD2 antibodies that can be used in conjunction with the compositions and methods described herein include those that have one or more, or all, of the following CDRs:

```
a. a CDR-H1 having the amino acid sequence
                                    (SEQ ID NO: 300)
   EYYMY;

b. a CDR-H2 having the amino acid sequence
                                    (SEQ ID NO: 301)
   RIDPEDGSIDYVEKFKK;

C. a CDR-H3 having the amino acid sequence
                                    (SEQ ID NO: 302)
   GKFNYRFAY;

d. a CDR-L1 having the amino acid sequence
                                    (SEQ ID NO: 303)
   RSSQSLLHSSGNTYLN;

e. a CDR-L2 having the amino acid sequence
                                    (SEQ ID NO: 304)
   LVSKLES;
   and f. a CDR-L3 having the amino acid sequence
                                    (SEQ ID NO: 305)
   MQFTHYPYT.
```

Antibodies and antigen-binding fragments thereof containing the foregoing CDR sequences are described, e.g., in U.S. Pat. No. 6,849,258, the disclosure of which is incorporated herein by reference as it pertains to anti-CD2 antibodies and antigen-binding fragments thereof.

The antibodies and fragments thereof disclosed in U.S. Pat. Nos. 5,730,979; 5,817,311; 5,951,983; and 7,592,006; such as LO-CD2a, BTI-322, and antibodies produced by the hybridoma cell line deposited as ATCC Deposit No. HB 11423 (e.g., antibodies or antigen-binding fragments thereof containing one or more, or all, of the CDR sequences of antibody LO-CD2a isolated from the hybridoma cell line deposited as ATCC Deposit No. HB 11423) can be used in conjunction with the compositions and methods disclosed herein. Exemplary antibodies that may be used in conjunction with the compositions and methods described herein include humanized antibodies containing one or more, or all, of the CDR sequences of an antibody isolated from the hybridoma cell line deposited as ATCC Deposit No. HB 11423, such as MEDI-507. MEDI-507 is a humanized anti-CD2 monoclonal antibody that contains the CDR-H and CDR-L sequences of (a) through (f) above, and is described in Branco et al., Transplantation 68:1588-1596 (1999). MEDI-507 is additionally described in WO99/03502A1 and WO1994/020619A1; U.S. Pat. Nos. 7,592,006, 6,849,258, 5,951,983, 5,817,311, and 5,730,979; and U.S. Patent Publication Nos. US2011/0280868, US2004/0265315 and 2011/0091453, the disclosures of each of which are incorporated herein by reference as they pertain to anti-CD2 antibodies and antigen-binding fragments thereof, such as the anti-CD2 antibody MEDI-507. In one embodiment, the anti-CD2 antibody is Siplizumab, or an antigen-binding fragment thereof.

Other anti-CD2 antibodies that can be used in conjunction with the compositions and methods described herein include, for instance, anti-CD2 antibodies that are described in U.S. Pat. Nos. 6,541,611 and 7,250,167, the disclosures of each of which are incorporated herein by reference as they pertain to anti-CD2 antibodies and antigen-binding fragments thereof, such as the anti-CD2 antibody LO-CD2b and antibodies produced by the hybridoma cell line deposited as ATCC Deposit No. PTA-802. Exemplary antibodies that may be used in conjunction with the compositions and methods described herein include humanized antibodies containing one or more, or all, of the CDR sequences of an antibody isolated from the hybridoma cell line deposited as ATCC Deposit No. PTA-802.

Other anti-CD2 antibodies that can be used in conjunction with the compositions and methods described herein include, for instance, anti-CD2 antibodies that are described in U.S. Pat. Nos. 5,795,572 and 5,807,734, the disclosures of each of which are incorporated herein by reference as they pertains to anti-CD2 antibodies and antigen-binding fragments thereof, such as the anti-CD2 antibody produced by hybridoma cell line deposited as ATCC Deposit No. HB 69277. For instance, anti-CD2 antibodies and antigen-binding fragments thereof that may be used in conjunction with the compositions and methods described herein include those that contain a hinge region having an amino acid sequence of EPKSSDKTHTSPPSP (SEQ ID NO: 316), such as scFv fragments containing a hinge region having the amino acid sequence of EPKSSDKTHTSPPSP (SEQ ID NO: 316). The incorporation of a hinge region having the amino acid sequence of SEQ ID NO: 316 can be beneficial, as this hinge motif has been mutated relative to wild-type hinge region sequences so as to eliminate potentially reactive cysteine residues that may promote undesirable oxidative dimerization of a single-chain antibody fragment, such as a scFv fragment.

Other anti-CD2 antibodies that can be used in conjunction with the compositions and methods described herein include, for instance, anti-CD2 antibodies that are described in U.S. Pat. No. 6,764,688, such as the anti-CD2 antibody TS2/18 and antibodies produced by hybridoma cell line deposited as ATCC Deposit No. HB-195. The disclosure of U.S. Pat. No. 6,764,688 is incorporated herein by reference as it pertains to anti-CD2 antibodies and antigen-binding fragments thereof.

Other anti-CD2 antibodies that can be used in conjunction with the compositions and methods described herein include, for instance, anti-CD2 antibodies that are described in U.S. Pat. Nos. 6,162,432, 6,558,662, 7,408,039, 7,332, 157, 7,638,121, 7,939,062, and 7,115,259, US Patent Application Publication No. 2006/0084107, 2014/0369974, 2002/0051784, and 2013/0183322, and PCT Publication No. WO1992/016563, the disclosures of each of which are incorporated herein by reference as they pertain to anti-CD2 antibodies and antigen binding fragments thereof.

Anti-Her2 Antibodies

Antibodies specific to Her2 antigen are known to the person skilled in the art, e.g., trastuzumab.

Anti-PSMA Antibodies

Antibodies specific to prostate-specific membrane antigen (PSMA) comprised in ADCs according to the present invention have been disclosed in WO2020/025564A1, the disclosure of which is herewith incorporated by reference in its entirety.

Fc Mutations

The antibodies or binding fragments described herein may also include modifications and/or mutations that alter the properties of the antibodies and/or fragments, such as those that increase half-life, increase or decrease ADCC, etc., as is known in the art.

In one embodiment, an antibody, or binding fragment thereof, comprises a variant Fc region, wherein said variant Fc region comprises at least one amino acid modification relative to a wild-type Fc region, such that said molecule has an altered affinity for an FcgammaR. Certain amino acid positions within the Fc region are known through crystallography studies to make a direct contact with FcγR. Specifically amino acids 234-239 (hinge region), amino acids 265-269 (B/C loop), amino acids 297-299 (C'/E loop), and amino acids 327-332 (F/G) loop. (see Sondermann et al., 2000 Nature, 406: 267-273). Thus, the antibodies (e.g., anti-CD117, CD45, CD137, CD2, CD5, CD262, or CD134) described herein may comprise variant Fc regions comprising modification of at least one residue that makes a direct contact with an Fcγ R based on structural and crystallographic analysis. In one embodiment, the Fc region of the antibody (or fragment thereof) comprises an amino acid substitution at amino acid 265 according to the EU index as in Kabat et al., Sequences of Proteins of Immunological Interest, 5th Ed. Public Health Service, NH1, MD (1991), expressly incorporated herein by references. The "EU index as in Kabat" refers to the numbering of the human IgG1 EU antibody. The EU index or EU index as in Kabat or EU numbering scheme refers to the numbering of the EU antibody (Edelman et al., 1969, Proc Natl Acad Sci USA 63:78-85, hereby entirely incorporated by reference.) In one embodiment, the Fc region comprises a D265A mutation. In one embodiment, the Fc region comprises a D265C mutation. In some embodiments, the Fc region of the antibody (or fragment thereof) comprises an amino acid substitution at amino acid 234 according to the EU index as in Kabat. In one embodiment, the Fc region comprises a L234A mutation. In some embodiments, the Fc region of the antibody (or fragment thereof) comprises an amino acid substitution at amino acid 235 according to the EU index as in Kabat. In one embodiment, the Fc region comprises a L235A mutation. In yet another embodiment, the Fc region comprises a L234A and L235A mutation. In a further embodiment, the Fc region of the antibody of an ADC described herein comprises a D265C, L234A, and L235A mutation.

In certain aspects a variant IgG Fc domain comprises one or more amino acid substitutions resulting in decreased or ablated binding affinity for an Fc.gamma.R and/or C1q as compared to the wild type Fc domain not comprising the one or more amino acid substitutions. Fc binding interactions are essential for a variety of effector functions and downstream signaling events including, but not limited to, antibody dependent cell-mediated cytotoxicity (ADCC) and complement dependent cytotoxicity (CDC). Accordingly, in certain aspects, an antibody comprising a modified Fc region (e.g., comprising a L234A, L235A, and a D265C mutation) has substantially reduced or abolished effector functions.

Affinity to an Fc region can be determined using a variety of techniques known in the art, for example but not limited to, equilibrium methods (e.g., enzyme-linked immunoabsorbent assay (ELISA); KinExA, Rathanaswami et al. Analytical Biochemistry, Vol. 373:52-60, 2008; or radioimmunoassay (RIA)), or by a surface plasmon resonance assay or other mechanism of kinetics-based assay (e.g., BIACORE™. analysis or Octet™ analysis (forteBIO)), and other methods such as indirect binding assays, competitive binding assays fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions. One example of a competitive binding assay is a radioimmunoassay comprising the incubation of labeled antigen with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound in the presence of increasing amounts of an unlabeled second antibody.

Antibodies may be further engineered to further modulate antibody half-life by introducing additional Fc mutations, such as those described for example in (Dall'Acqua et al. (2006) J Biol Chem 281: 23514-24), (Zalevsky et al. (2010) Nat Biotechnol 28: 157-9), (Hinton et al. (2004) J Biol Chem 279: 6213-6), (Hinton et al. (2006) J Immunol 176: 346-56), (Shields et al. (2001) J Biol Chem 276: 6591-604), (Petkova et al. (2006) Int Immunol 18: 1759-69), (Datta-Mannan et al. (2007) Drug Metab Dispos 35: 86-94), (Vaccaro et al. (2005) Nat Biotechnol 23: 1283-8), (Yeung et al. (2010) Cancer Res 70: 3269-77) and (Kim et al. (1999) Eur J Immunol 29: 2819-25), and include positions 250, 252, 253, 254, 256, 257, 307, 376, 380, 428, 434 and 435. Exemplary mutations that may be made singularly or in combination are T250Q, M252Y, 1253A, S254T, T256E, P2571, T307A, D376V, E380A, M428L, H433K, N434S, N434A, N434H, N434F, H435A and H435R mutations.

Thus, in one embodiment, the Fc region comprises a mutation resulting in a decrease in half life. An antibody having a short half life may be advantageous in certain instances where the antibody is expected to function as a short-lived therapeutic, e.g., the conditioning step described herein where the antibody is administered followed by HSCs. Ideally, the antibody would be substantially cleared prior to delivery of the HSCs, which also generally express an antigen targeted by an ADC described herein, e.g., CD117, but are not the target of the ADC, unlike the endogenous stem cells. In one embodiment, the Fc regions comprise a mutation at position 435 (EU index according to Kabat). In one embodiment, the mutation is an H435A mutation.

In one embodiment, the antibody described herein has a half life of equal to or less than 24 hours, a half life of equal to or less than 22 hours, a half life of equal to or less than 20 hours, a half life of equal to or less than 18 hours, a half life of equal to or less than 16 hours, a half life of equal to or less than 14 hours, equal to or less than 13 hours, equal to or less than 12 hours, or equal to or less than 11 hours. In one embodiment, the half life of the antibody is 11 hours to 24 hours; 12 hours to 22 hours; 10 hours to 20 hours; 8 hours to 18 hours; or 14 hours to 24 hours.

In some aspects, the Fc region comprises two or more mutations that confer reduced half-life and greatly diminish or completely abolish an effector function of the antibody. In some embodiments, the Fc region comprises a mutation resulting in a decrease in half-life and a mutation of at least one residue that can make direct contact with an FcγR (e.g., as based on structural and crystallographic analysis). In one embodiment, the Fc region comprises a H435A mutation, a L234A mutation, and a L235A mutation. In one embodiment, the Fc region comprises a H435A mutation and a D265C mutation. In one embodiment, the Fc region comprises a H435A mutation, a L234A mutation, a L235A mutation, and a D265C mutation.

In some embodiments, the antibody or antigen-binding fragment thereof is conjugated to a cytotoxin (e.g., amatoxin) by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265. In one embodiment, the Fc region of the anti-CD117 antibody (or fragment thereof) comprises an amino acid substitution at amino acid 265 according to the EU index as in Kabat. In one embodiment, the Fc region comprises a D265C mutation. In one embodiment, the Fc region comprises a D265C and H435A mutation. In one embodiment, the Fc region comprises a D265C, a L234A, and a L235A mutation. In one embodiment, the Fc region comprises a D265C, a L234A, a L235A, and a H435A mutation.

In some embodiments of these aspects, the cysteine residue is naturally occurring in the Fc domain of the antibody or antigen-binding fragment thereof. For instance, the Fc domain may be an IgG Fc domain, such as a human IgG1 Fc domain, and the cysteine residue may be selected from the group consisting of Cys261, Csy321, Cys367, and Cys425.

For example, in one embodiment, the Fc region of Antibody 67 is modified to comprise a D265C mutation (e.g., SEQ ID NO: 111). In another embodiment, the Fc region of Antibody 67 is modified to comprise a D265C, L234A, and L235A mutation (e.g., SEQ ID NO: 112). In yet another embodiment, the Fc region of Antibody 67 is modified to comprise a D265C and H435A mutation (e.g., SEQ ID NO: 113). In a further embodiment, the Fc region of Antibody 67 is modified to comprise a D265C, L234A, L235A, and H435A mutation (e.g., SEQ ID NO: 114).

In regard to Antibody 55, in one embodiment, the Fc region of Antibody 55 is modified to comprise a D265C mutation (e.g., SEQ ID NO: 117). In another embodiment, the Fc region of Antibody 55 is modified to comprise a D265C, L234A, and L235A mutation (e.g., SEQ ID NO: 118). In yet another embodiment, the Fc region of Antibody 55 is modified to comprise a D265C and H435A mutation (e.g., SEQ ID NO: 119). In a further embodiment, the Fc region of Antibody 55 is modified to comprise a D265C, L234A, L235A, and H435A mutation (e.g., SEQ ID NO: 120).

The Fc regions of any one of Antibody 54, Antibody 55, Antibody 56, Antibody 57, Antibody 58, Antibody 61, Antibody 66, Antibody 67, Antibody 68, or Antibody 69 can be modified to comprise a D265C mutation (e.g., as in SEQ ID NO: 123); a D265C, L234A, and L235A mutation (e.g., as in SEQ ID NO: 124); a D265C and H435A mutation (e.g., as in SEQ ID NO: 125); or a D265C, L234A, L235A, and H435A mutation (e.g., as in SEQ ID NO: 126).

The variant Fc domains described herein are defined according to the amino acid modifications that compose them. For all amino acid substitutions discussed herein in regard to the Fc region, numbering is always according to the EU index. Thus, for example, D265C is an Fc variant with the aspartic acid (D) at EU position 265 substituted with cysteine (C) relative to the parent Fc domain. Likewise, e.g., D265C/L234A/L235A defines a variant Fc variant with substitutions at EU positions 265 (D to C), 234 (L to A), and 235 (L to A) relative to the parent Fc domain. A variant can also be designated according to its final amino acid composition in the mutated EU amino acid positions. For example, the L234A/L235A mutant can be referred to as LALA. It is noted that the order in which substitutions are provided is arbitrary.

In one embodiment, the antibody, or antigen binding fragment thereof, comprises variable regions having an amino acid sequence that is at least 95%, 96%, 97% or 99% identical to the SEQ ID Nos disclosed herein. Alternatively, the antibody, or antigen binding fragment thereof, comprises CDRs comprising the SEQ ID Nos disclosed herein with framework regions of the variable regions described herein having an amino acid sequence that is at least 95%, 96%, 97% or 99% identical to the SEQ ID Nos disclosed herein.

In one embodiment, the antibody, or antigen binding fragment thereof, comprises a heavy chain variable region and a heavy chain constant region having an amino acid sequence that is disclosed herein. In another embodiment, the antibody, or antigen binding fragment thereof, comprises a light chain variable region and a light chain constant region having an amino acid sequence that is disclosed herein. In yet another embodiment, the antibody, or antigen binding fragment thereof, comprises a heavy chain variable region, a light chain variable region, a heavy chain constant region and a light chain constant region having an amino acid sequence that is disclosed herein.

Methods of Identifying Antibodies

Provided herein are novel ADCs that may be used, for example, in conditioning methods for stem cell transplantation. In view of the disclosure herein, other antibodies can be identified that can be used in the ADCs and methods of the invention.

Methods for high throughput screening of antibody, or antibody fragment libraries for molecules capable of binding a cell surface antigen (e.g., CD117, CD45, CD2, CD5, CD134, CD252, CD137) can be used to identify and affinity mature antibodies useful for treating cancers, autoimmune diseases, and conditioning a patient (e.g., a human patient) in need of hematopoietic stem cell therapy as described herein. Such methods include in vitro display techniques known in the art, such as phage display, bacterial display, yeast display, mammalian cell display, ribosome display, mRNA display, and cDNA display, among others. The use of phage display to isolate ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules). In addition, functional antibody fragments, such as Fab and scFv fragments, have been expressed in in vitro display formats (see, for example, McCafferty et al., Nature 348:552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies that bind, e.g., CD117, CD45, CD2, CD5, CD134, CD252, CD137 (e.g., GNNK+CD117) that can in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies, and antibody fragments, in silico that bind a cell surface antigen (e.g., CD117, CD45, CD2, CD5, CD134, CD252, CD137). For example, using computational modeling techniques, one of skill in the art can screen libraries of antibodies, and antibody fragments, in silico for molecules capable of binding specific epitopes, such as extracellular epitopes of this antigen. The antibodies, and antigen-binding fragments thereof, identified by these computational techniques can be used in conjunction with the therapeutic methods described herein, such as the cancer and autoimmune disease treatment methods described herein and the patient conditioning procedures described herein.

Additional techniques can be used to identify antibodies, and antigen-binding fragments thereof, that bind a cell surface antigen (e.g., CD117) on the surface of a cell (e.g., a cancer cell, autoimmune cell, or hematopoietic stem cell) and that are internalized by the cell, for instance, by receptor-mediated endocytosis. For example, the in vitro display techniques described above can be adapted to screen for antibodies, and antigen-binding fragments thereof, that bind a cell surface antigen (e.g., CD117) on the surface of a cancer cell, autoimmune cell, or hematopoietic stem cell and that are subsequently internalized. Phage display represents one such technique that can be used in conjunction with this screening paradigm. To identify antibodies, and fragments thereof, that bind a cell surface antigen (e.g., CD117) and are subsequently internalized by cancer cells, autoimmune cells, or hematopoietic stem cells, one of skill in the art can adapt the phage display techniques described, for example, in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, or antibody fragments, covalently bound to the phage particles can be incubated with a cell surface target antigen (e.g., CD117) antigen, for instance, by first incubating the phage library with blocking agents (such as, for instance, milk protein, bovine serum albumin, and/or IgG so as to remove phage encoding antibodies, or fragments thereof, that exhibit non-specific protein binding and phage that encode antibodies or fragments thereof that bind Fc domains, and then incubating the phage library with a population of hematopoietic stem cells. The phage library can be incubated with the target cells, such as cancer cells, autoimmune cells, or hematopoietic stem cells for a time sufficient to allow cell surface antigen specific antibodies, or antigen-binding fragments thereof, (e.g., CD117-specific antibodies, or antigen-binding fragments thereof) to bind cell-surface antigen (e.g., sell-surface CD117) antigen and to subsequently be internalized by the cancer cells, autoimmune cells, or hematopoietic stem cells (e.g., from 30 minutes to 6 hours at 4° C., such as 1 hour at 4° C.). Phage containing antibodies, or fragments thereof, that do not exhibit sufficient affinity for one or more of these antigens so as to permit binding to, and internalization by, cancer cells, autoimmune cells, or hematopoietic stem cells can subsequently be removed by washing the cells, for instance, with cold (4° C.) 0.1 M glycine buffer at pH 2.8. Phage bound to antibodies, or fragments thereof, that have been internalized by the cancer cells, autoimmune cells, or hematopoietic stem cells can be identified, for instance, by lysing the cells and recovering internalized phage from the cell culture medium. The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, or fragments thereof, inserted within the phage genome. The encoded antibodies, or fragments thereof, can subsequently be prepared de novo by chemical synthesis (for instance, of antibody fragments, such as scFv fragments) or by recombinant expression (for instance, of full-length antibodies).

An exemplary method for in vitro evolution of a cell surface antigen antibody (e.g., anti-CD117) antibodies for use with the compositions and methods described herein is phage display. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains). The template antibody-encoding sequence into which these mutations are introduced may be, for example, a naive human germline sequence. These mutations can be performed using standard mutagenesis techniques known in the art. Each mutant sequence thus encodes an antibody corresponding to the template save for one or more amino acid variations. Retroviral and phage display vectors can be engineered using standard vector construction techniques known in the art. P3 phage display vectors along with compatible protein expression vectors can be used to generate phage display vectors for antibody diversification.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its overall molecular structure.

In a typical screen, a phage library may be contacted with and allowed to bind one of the foregoing antigens or an epitope thereof. To facilitate separation of binders and non-binders, it is convenient to immobilize the target on a solid support. Phage bearing a cell surface-binding moiety can form a complex with the target on the solid support, whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means.

The recovered phage can then be amplified through infection of bacterial cells, and the screening process can be repeated with the new pool that is now depleted in non-binding antibodies and enriched for antibodies that bind a target antigen (e.g., CD117). The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof. An increase in the number of phage recovered at each round of selection is an indication that convergence of the library has occurred in a screen.

Another method for identifying antibodies includes using humanizing non-human antibodies that bind a cell surface target antigen (e.g., CD117), for instance, according to the following procedure. Consensus human antibody heavy chain and light chain sequences are known in the art (see e.g., the "VBASE" human germline sequence database; Kabat et al. Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al. Eur. J. Immunol. 24:827-836, 1994, the disclosures of each of which are incorporated herein by reference as they pertain to consensus human antibody heavy chain and light chain sequences. Using established procedures, one of skill in the art can identify the variable domain framework residues and CDRs of a consensus antibody sequence (e.g., by sequence alignment). One can substitute one or more CDRs of the heavy chain and/or light chain variable domains of consensus human antibody with one or more corresponding CDRs of a non-human antibody that binds a cell surface antigen (e.g., CD117) as described herein in order to produce a humanized antibody. This CDR exchange can be performed using gene editing techniques described herein or known in the art.

To produce humanized antibodies, one can recombinantly express a polynucleotide encoding the above consensus sequence in which one or more variable region CDRs have been replaced with one or more variable region CDR sequences of a non-human antibody that binds a cell surface target antigen (e.g., CD117). As the affinity of the antibody for the hematopoietic stem cell antigen is determined primarily by the CDR sequences, the resulting humanized antibody is expected to exhibit an affinity for the hematopoietic stem cell antigen that is about the same as that of the non-human antibody from which the humanized antibody was derived. Methods of determining the affinity of an antibody for a target antigen include, for instance, ELISA-based techniques described herein and known in the art, as well as surface plasmon resonance, fluorescence anisotropy, and isothermal titration calorimetry, among others.

The internalizing capacity of an antibody, or fragment thereof, can be assessed, for instance, using radionuclide internalization assays known in the art. For example, antibodies, or fragments thereof, identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$Cu, $^{67}$Cu, $^{177}$Lu, $^{77}$As, $^{72}$As, $^{86}$Y $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, or fragments thereof, using beads, such as polystyrene beads, containing electrophilic halogen reagents (e.g., Iodination Beads, Thermo Fisher Scientific, Inc., Cambridge, MA). Radiolabeled antibodies, or fragments thereof, can be incubated with cancer cells, autoimmune cells, or hematopoietic stem cells for a time sufficient to permit internalization (e.g., from 30 minutes to 6 hours at 4° C., such as 1 hour at 4° C.). The cells can then be washed to remove non-internalized antibodies, or fragments thereof, (e.g., using cold (4° C.) 0.1 M glycine buffer at pH 2.8). Internalized antibodies, or fragments thereof, can be identified by detecting the emitted radiation (e.g., γ-radiation) of the resulting cancer cells, autoimmune cells, or hematopoietic stem cells in comparison with the emitted radiation (e.g., γ-radiation) of the recovered wash buffer.

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CLL-1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

Vertebrate cells may also be used as hosts. For example, mammalian cell lines that are adapted to grow in suspension may be useful. Other examples of useful mammalian host cell lines are monkey kidney CV1 line transformed by SV40

(COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Pharmaceutical Compositions

According to one aspect of the present invention, the present invention relates to a pharmaceutical composition comprising said conjugate as described.

Said pharmaceutical composition may comprise one or more pharmaceutically acceptable buffers, surfactants, diluents, carriers, excipients, fillers, binders, lubricants, glidants, disintegrants, adsorbents, and/or preservatives.

In aqueous form, said pharmaceutical formulation may be ready for administration, while in lyophilised form said formulation can be transferred into liquid form prior to administration, e.g., by addition of water for injection which may or may not comprise a preservative such as for example, but not limited to, benzyl alcohol, antioxidants like vitamin A, vitamin E, vitamin C, retinyl palmitate, and selenium, the amino acids cysteine and methionine, citric acid and sodium citrate, synthetic preservatives like the parabens methyl paraben and propyl paraben.

Said pharmaceutical formulation may further comprise one or more stabilizer, which may be, e.g., an amino acid, a sugar polyol, a disaccharide and/or a polysaccharide. Said pharmaceutical formulation may further comprise one or more surfactant, one or more isotonizing agents, and/or one or more metal ion chelator, and/or one or more preservative.

The pharmaceutical formulation as described herein can be suitable for at least intravenous, intramuscular or subcutaneous administration. Alternatively, said conjugate according to the present invention may be provided in a depot formulation which allows the sustained release of the biologically active agent over a certain period of time.

In still another aspect of the present invention, a primary packaging, such as a prefilled syringe or pen, a vial, or an infusion bag is provided, which comprises said formulation according to the previous aspect of the invention.

The prefilled syringe or pen may contain the formulation either in lyophilised form (which has then to be solubilised, e.g., with water for injection, prior to administration), or in aqueous form. Said syringe or pen is often a disposable article for single use only, and may have a volume between 0.1 and 20 ml. However, the syringe or pen may also be a multi-use or multi-dose syringe or pen.

Said vial may also contain the formulation in lyophilised form or in aqueous form and may serve as a single or multiple use device. As a multiple use device, said vial can have a bigger volume. Said infusion bag usually contains the formulation in aqueous form and may have a volume between 20 and 5000 ml.

ADCs described herein can be administered to a patient (e.g., a human patient suffering from an immune disease or cancer) in a variety of dosage forms. For instance, ADCs described herein can be administered to a patient suffering from an immune disease or cancer in the form of an aqueous solution, such as an aqueous solution containing one or more pharmaceutically acceptable excipients. Suitable pharmaceutically acceptable excipients for use with the compositions and methods described herein include viscosity-modifying agents. The aqueous solution may be sterilized using techniques known in the art.

Pharmaceutical formulations comprising ADCs as described herein are prepared by mixing such ADC with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Methods of Use

ADCs described herein may be administered by a variety of routes, such as orally, transdermally, subcutaneously, intranasally, intravenously, intramuscularly, intraocularly, or parenterally. The most suitable route for administration in any given case will depend on the particular antibody, or antigen-binding fragment, administered, the patient, pharmaceutical formulation methods, administration methods (e.g., administration time and administration route), the patient's age, body weight, sex, severity of the diseases being treated, the patient's diet, and the patient's excretion rate.

The effective dose of an ADC, antibody, or antigen-binding fragment thereof, described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 µg/mL) of the antibody, antigen-binding fragment thereof. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant. In the case of a conditioning procedure prior to hematopoietic stem cell transplantation, the ADC, antibody, or antigen-binding fragment thereof, can be administered to the patient at a time that optimally promotes engraftment of the exogenous hematopoietic stem cells, for instance, from 1 hour to 1 week (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, or about 7 days) or more prior to administration of the exogenous hematopoietic stem cell transplant.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Comparative Study of Amanitins

Figure 1:
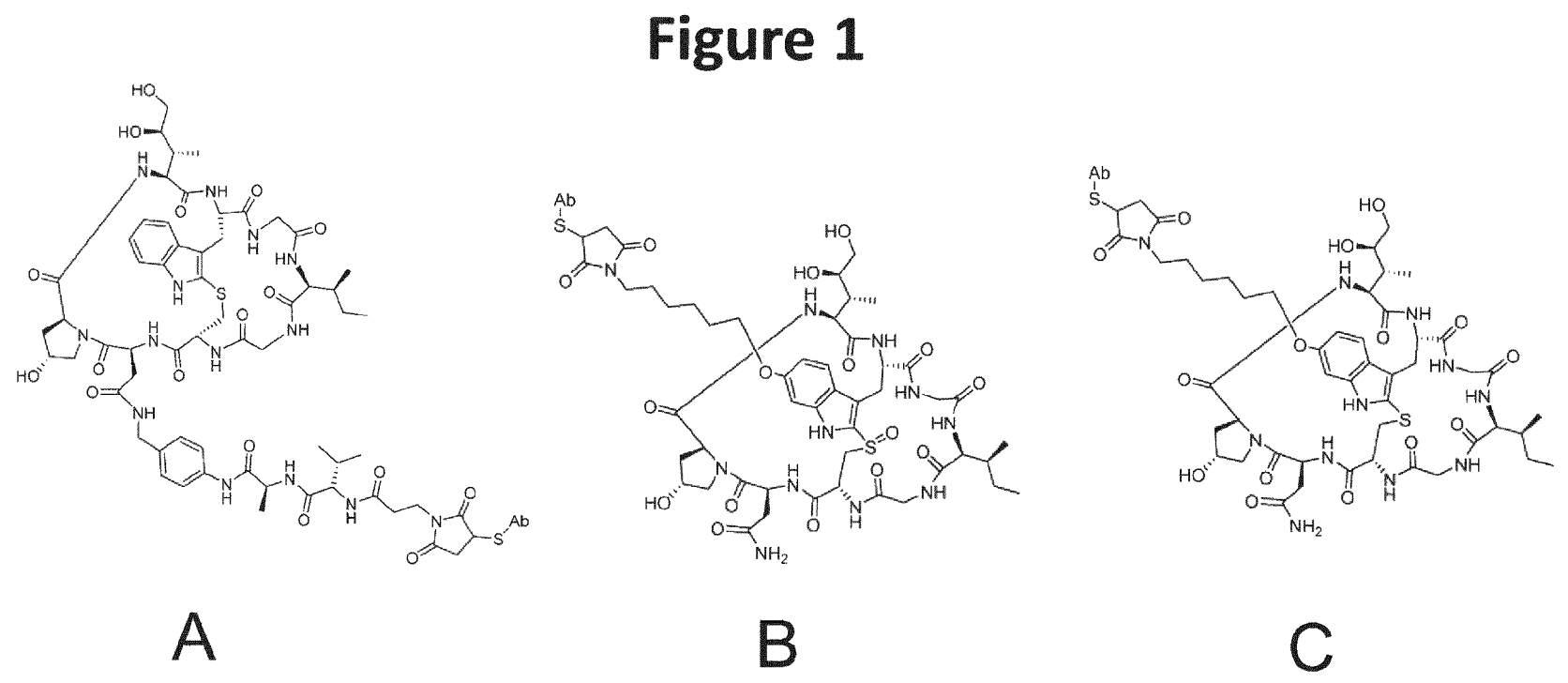

Three different amanitins were tested in parallel to determine their kinetics and tolerability as toxins. FIG. 1 provides the structures of three amanitin/linker conjugates. FIG. 1A provides an amanitin/linker conjugate represented by Formula (IV) (also referred to as "Conjugate A" or "ADC A"), where the amanitin has a cleavable linker (BMP-Val-Ala-PAB) linker on AA1 (Asn). The amanitin in Formula (IV) is based on amatoxin having thiotryptophan moiety. FIG. 1B provides an amanitin/linker conjugate represented by Formula (VI) (also referred to as "Conjugate B" or "ADC B", where the amanitin is conjugated to a non-cleavable linker on indole 6' oxygen. The amanitin described in Formula (VI) is based on amatoxin having 6-hydroxy-tryptophan sulfoxide moiety. FIG. 1C provides an amanitin/linker conjugate described herein in Formula (IIa) (also referred to as "Conjugate C" or "ADC C", including a non-cleavable linker on indole 6' oxygen, where the amanitin is based on amatoxin having 6-hydroxy-thiotryptophan moiety.

Figure 2:
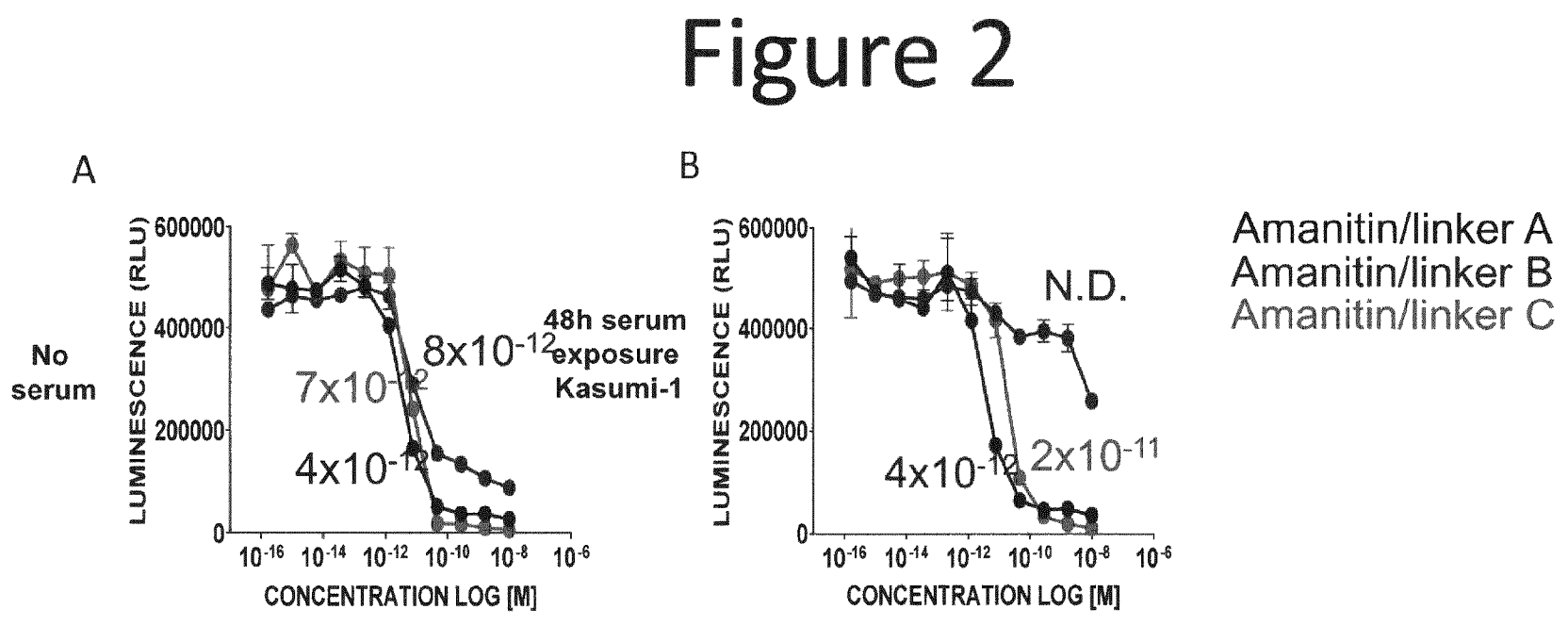

Conjugates A, B and C were tested in parallel for their potency on CD117 expressing cells with or without a pre-incubation in human serum. ADC A, B, and C were either pre-incubated in cell culture media without human serum or 50% human serum at 37 C for 48 hours. The titrated ADC was then added to Kasumi-1 cells and incubated for 3 days at 37 C and cell killing was determined using CellTiter-Glo. As described in FIG. 2, in the absence of serum incubation, cleavable Conjugate A and non-cleavable Conjugate C reached similar efficacy by day 3, with non-cleavable conjugate B demonstrating reduced maximum killing at higher concentrations. Each ADC conjugate demonstrated picomolar IC50 killing. When ADC was pre-incubated for 48 hours in the presence of human serum, potency was significantly decreased for non-cleavable conjugate B but was maintained for cleavable conjugate A and non-cleavable conjugate C. Thus, cleavable and non-cleavable conjugates A and C were serum stable while non-cleavable conjugate B was inactivated in the presence of human serum as measured by in vitro cytotoxicity.

To determine differences in the kinetics of ADC-mediated cytotoxicity, Kasumi-1 cells were incubated with titrations of cleavable conjugate A or non-cleavable conjugate C for 3-7 days at 37 C and cell viability was measured on day 3, 4, 5, 6, and 7 by CellTiter-Glo. As shown in FIG. 3, significant differences were observed in maximum cell killing at high concentrations for cleavable and non-cleavable ADC. When cells were incubated for a total of 6 days at 37

C with ADC, both cleavable conjugate A and non-cleavable conjugate C were able to achieve nearly complete cell killing at high concentrations. Killing of greater than 80% of Kasumi-1 cells in culture with 160 pM non-cleavable conjugate C could only be achieved after incubation of Kasumi-1 cells for 5 days or longer, while a similar threshold was achieved for cleavable conjugate A after 3 days or longer incubation.

In sum, the enzyme cleavable amanitin of FIG. 1A (Conjugate A) and the non-cleavable amanitin (conjugate C in FIG. 1C) showed long term stability in serum, while amanitin/linker B showed instability and inactivation in serum. Non-cleavable conjugate C demonstrated extended kinetics of cytotoxicity as measured in an in vitro assay compared to a similar cleavable amanitin conjugate (conjugate A).

Example 2: Anti-CD117 ADC Demonstrates Potent Killing of AML Cells and Human CD34+ Cells In Vitro, Selectively Depletes Human CD34+ Cells in Humanized Mice, and Demonstrates Anti-AML Activity in Xenograft Models An anti-CD117 antibody (Ab85 having Fc modifications L234A, L235A, D265C, and H435A) was conjugated to Conjugate C forming anti-CD117 ADC C. Anti-CD117 ADC C was tested both in vitro and in vivo for its ability to target and kill cells expressing CD117 and human HSCs.

Figure 4:
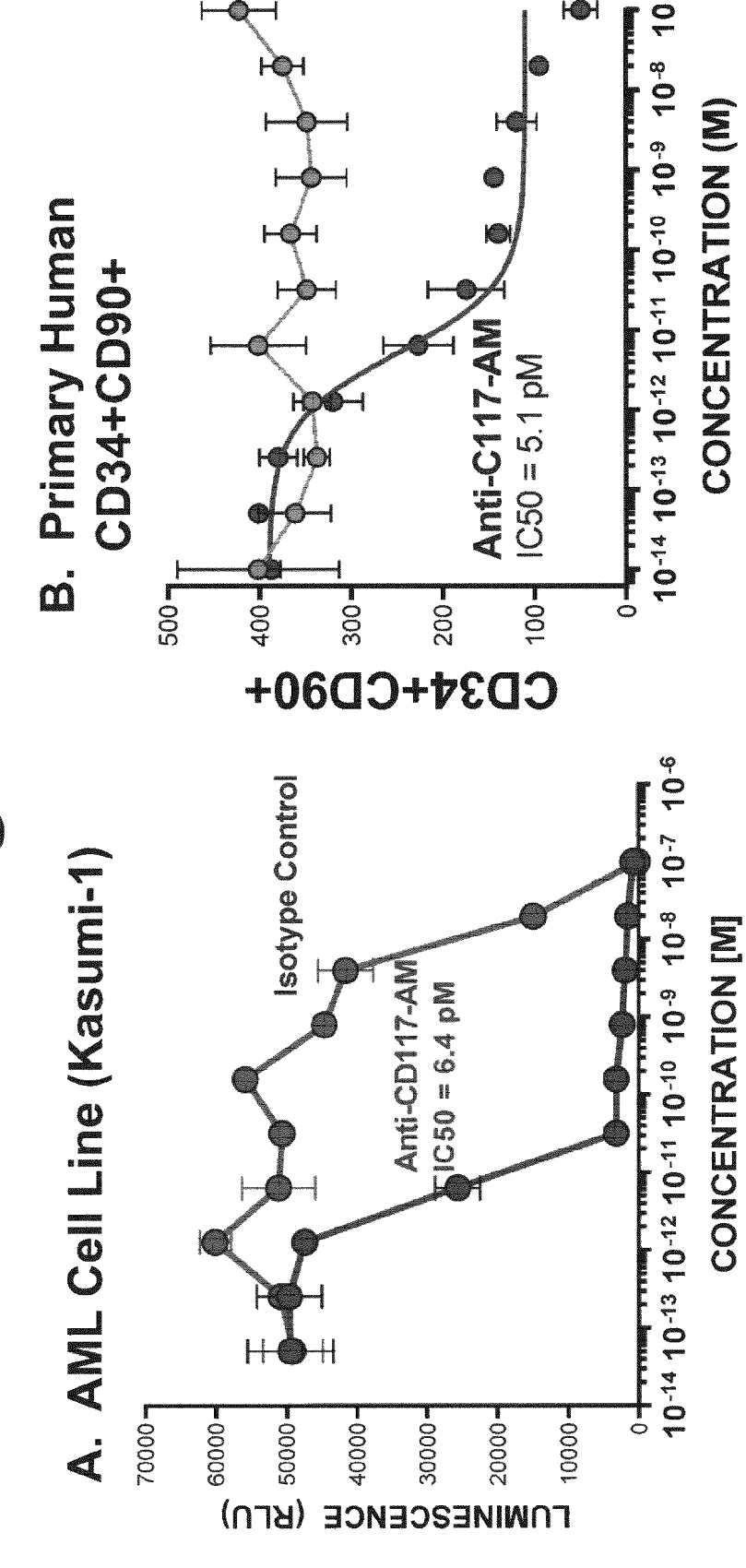
FIG. 4 graphically depicts results from two in vitro cell killing assays using Kasumi-1 cells (4A) and CD34+ cells (4B). The ADC tested was anti-CD117 ADC C.

Two in vitro assays were performed using anti-CD117 ADC C. The first tested the ability of the ADC to kill Kasumi-1 cells (an AML cell line), which express human CD117. As described in FIG. 4A, Anti-CD117 ADC C (referred to as "Anti-CD117-AM" in FIG. 4A) was titrated and incubated with Kasumi-1 cells for 6 days at 37 C and viability was assessed by CellTiter-Glo. The control was a non-specific isotype matched ADC C. Non-cleavable conjugate C demonstrated potent killing of Kasumi-1 cells with an IC50 of 6.4 pM. In FIG. 4B, a similar cytotoxicity assay using Human CD34+ bone marrow cells collected was performed. Human CD34+ bone marrow cells were incubated with non-cleavable conjugate C or a corresponding isotype control ADC for 6 days. Cell killing was determined by flow cytometry. The non-cleavable conjugate C demonstrated potent killing of primary human CD34+CD90+ cells with an IC50 of 5.1 pM.

Figure 5:
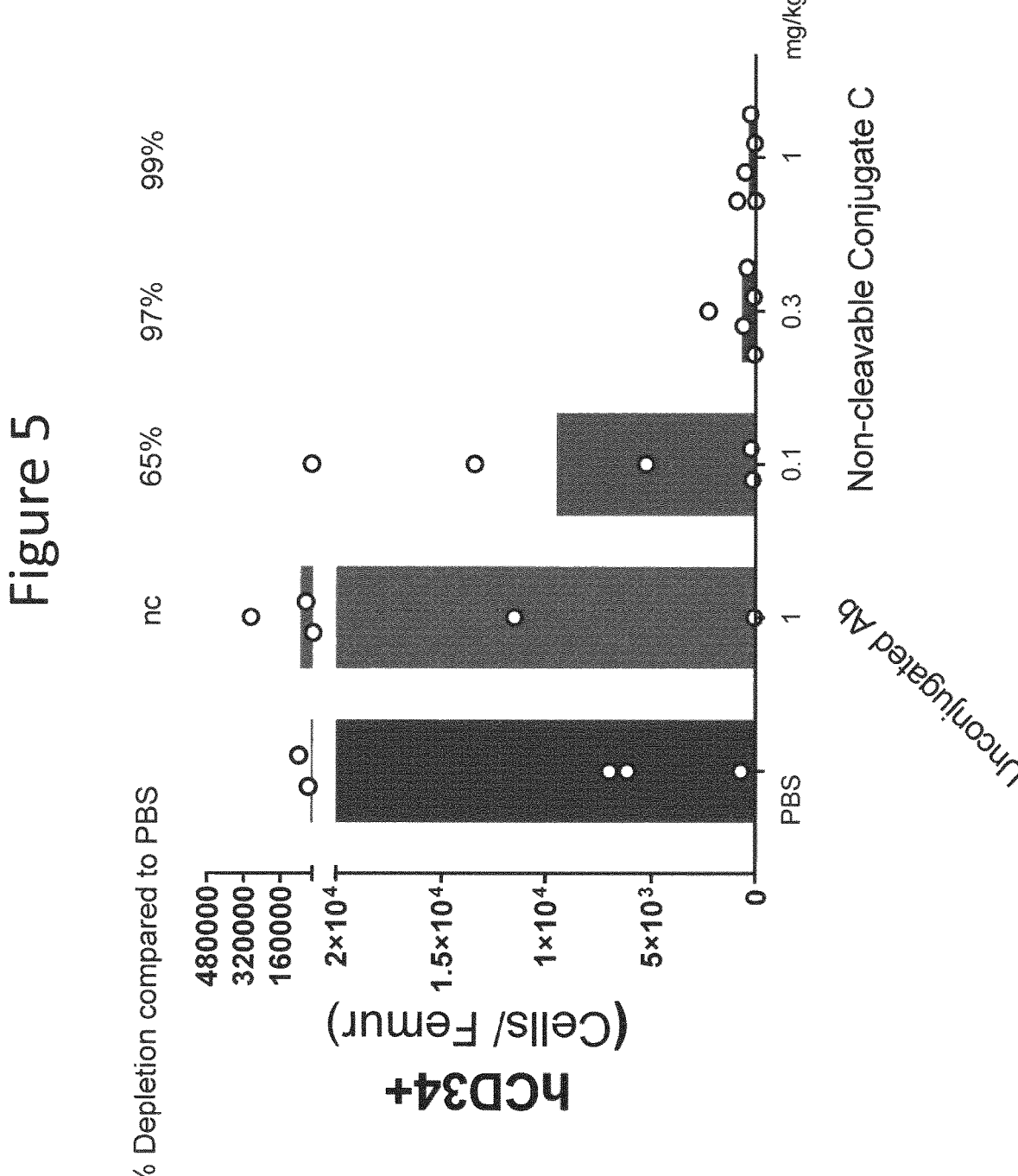
FIG. 5 graphically depicts the ability of anti-CD117 ADC C to potently deplete human CD34+ in the bone marrow of humanized NSG mice.

An in vivo assay was also performed to test the ability of anti-CD117 ADC C to selectively deplete human CD34+ cells. A single dose of 0.1, 0.3, or 1.0 mg/kg of the anti-CD117 ADC C was administered to humanized NSG mice. Controls consisted of a 1 mg/kg dose of the unconjugated antibody that comprised part of non-cleavable conjugate C and vehicle (PBS) treatment. At Day 21, the number of human CD34+ cells were determined by flow cytometry analysis of bone marrow collected from the femur of treated humanized NSG mice. As described in FIG. 5, anti-CD117 ADC C was able to potently deplete human CD34+ cells, achieving greater than 95% depletion compared to PBS for both 0.3 and 1 mg/kg doses. The unconjugated antibody demonstrated no depletion as compared to vehicle control.

Figure 6:
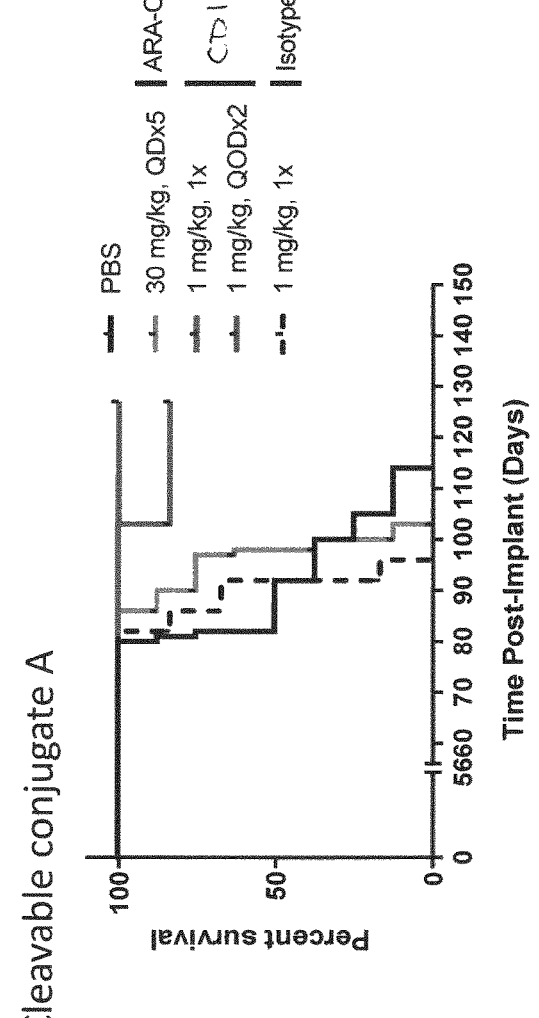
FIG. 6 are Kaplan Meier plots reflecting the survival of Kasumi-1 implanted humanized NSG mice treated with the indicated doses of conjugates or controls.
Figure 6:
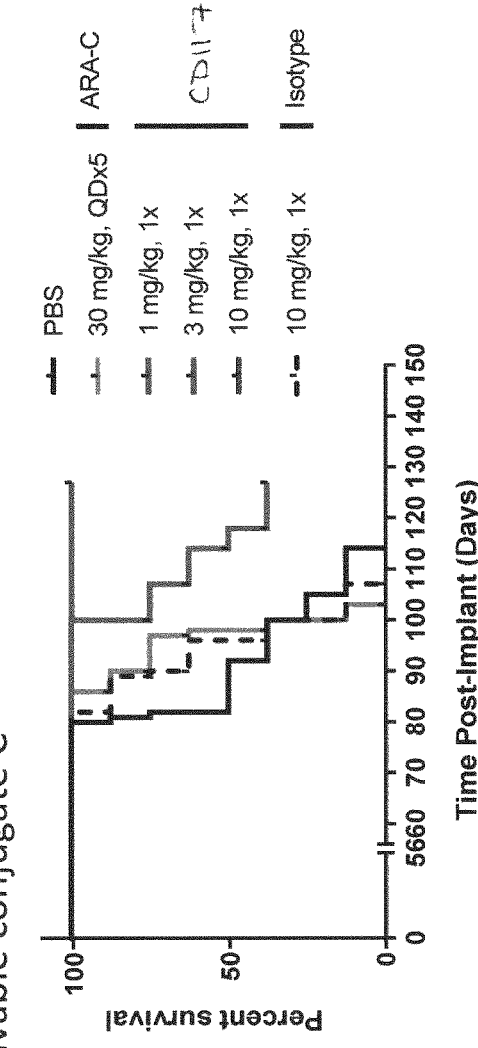
Figure 7:
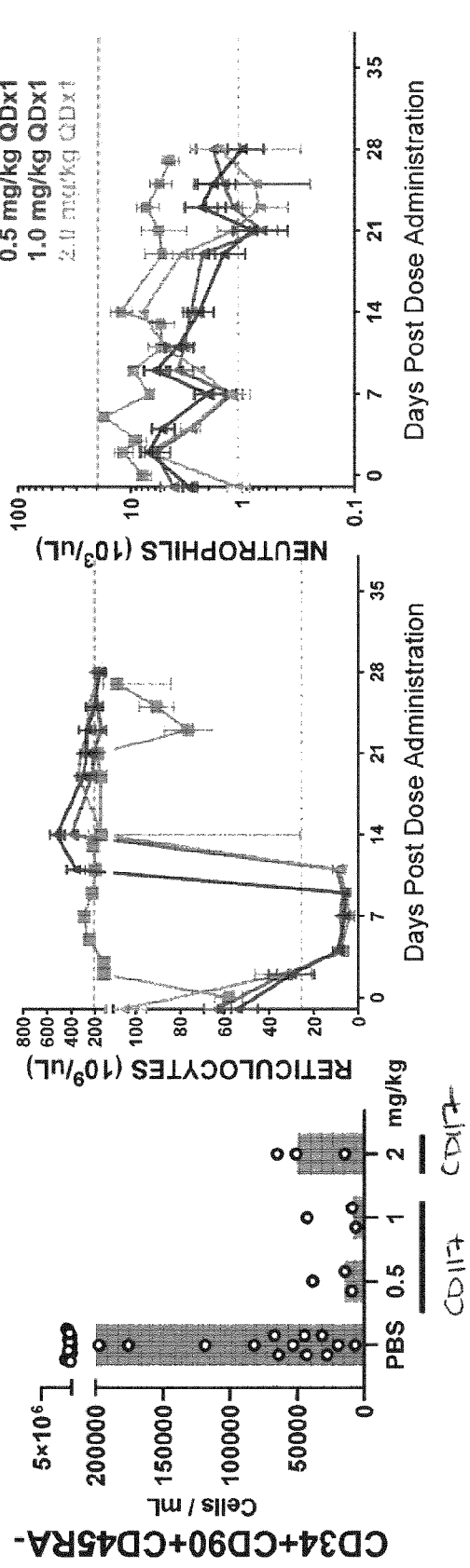
FIG. 7 graphically depicts the efficacy of Conjugate C as evaluated in male cynomolgus monkeys. 2.0 mg/kg dose (LALA) 30.2867 batch issues may have resulted in a decrease in HSC sensitivity FIG. 8 graphically depicts tolerability of ADCs containing either Conjugate A or Conjugate C in male cynomolgus monkeys.

To assess in vivo anti-tumor activity of ADCs, humanized NSG mice were implanted with Kasumi-1 cells and then treated with vehicle, 30 mg/kg QD×5 cytarabine (ARA-C), cleavable conjugate A (1 mg/kg 1×, 1 mg/kg QOD×2) or 10 mg/kg isotype conjugated to cleavable amanitin (FIG. 1A). In addition, Kasumi-1 implanted mice were treated with non-cleavable conjugate C (1 mg/kg 1×, 3 mg/kg 1×, 10 mg/kg 1×) or 10 mg/kg isotype conjugated to non-cleavable amanitin (FIG. 1C). Kaplan-Meier curves demonstrating survival of animals treated as indicated is depicted in FIG. 6. Kasumi-1 implanted mice treated with cleavable conjugate A demonstrate median survival above 50% at day 130 for groups treated with either 1 mg/kg or 1 mg/kg QOD×2 in comparison to isotype, ARA-C, or vehicle treated animals. Mice treated with either 3 mg/kg or 10 mg/kg non-cleavable conjugate C demonstrate full survival at day 130 in comparison to isotype, ARA-C, 1 mg/kg non-cleavable conjugate C, or vehicle treated animals.

In summary, non-cleavable conjugate C demonstrates potent in vitro cell killing of Kasumi-1 cells, an AML cell line, and primary human CD34+CD90+ bone marrow cells. Conjugate C is capable of depleting more than 95% of human CD34+ cells from the bone marrow of humanized NSG mice. Both cleavable and non-cleavable conjugates demonstrated potent anti-tumor activity in vivo.

Example 3: Efficacy and Tolerability of ADC C in Non-Human Primates (NHPs)

To determine the efficacy of non-cleavable conjugate C in non-human primates, male cynomologus monkeys were treated with a single dose of non-cleavable conjugate C at 0.5, 1.0, and 2.0 mg/kg. The 0.5 and 1.0 mg/kg doses were with Ab85 with the following Fc modifications: D265C H435A (EU numbering) conjugated to non-cleavable amanitin C (FIG. 1C). The 2.0 mg/kg dose comprised Ab85 with the following Fc modifications: L234A L235A D265C H435A (EU numbering) conjugated to non-cleavable amanitin C (FIG. 1C). Bone marrow asipirates were collected from treated animals on day 7 and efficacy was assessed by quantitiation of CD34+CD90+CD45RA− populations by flow cytometry. Significant depletion was observed at 0.5 and 1.0 mg/kg doses. Peripheral blood samples were collected throughout the course of the 28 day study. Reticulocyte counts of animals treated at 0.5, 1.0, and 2.0 mg/kg decreased significantly beginning on day 2 with reticulocyte rebound occurring in a dose-dependent manner. This is expected on-target pharmacology as reticulocytes are short-lived and progenitor populations in this hematopoietic lineage strongly express CD117. Neutrophil depletion was observed beginning on day 18 for all treatment groups. This is also expected on-target pharmacology, as neutrophils are dependent on hematopoietic stem cell differentiation for regeneration.

Figure 8:
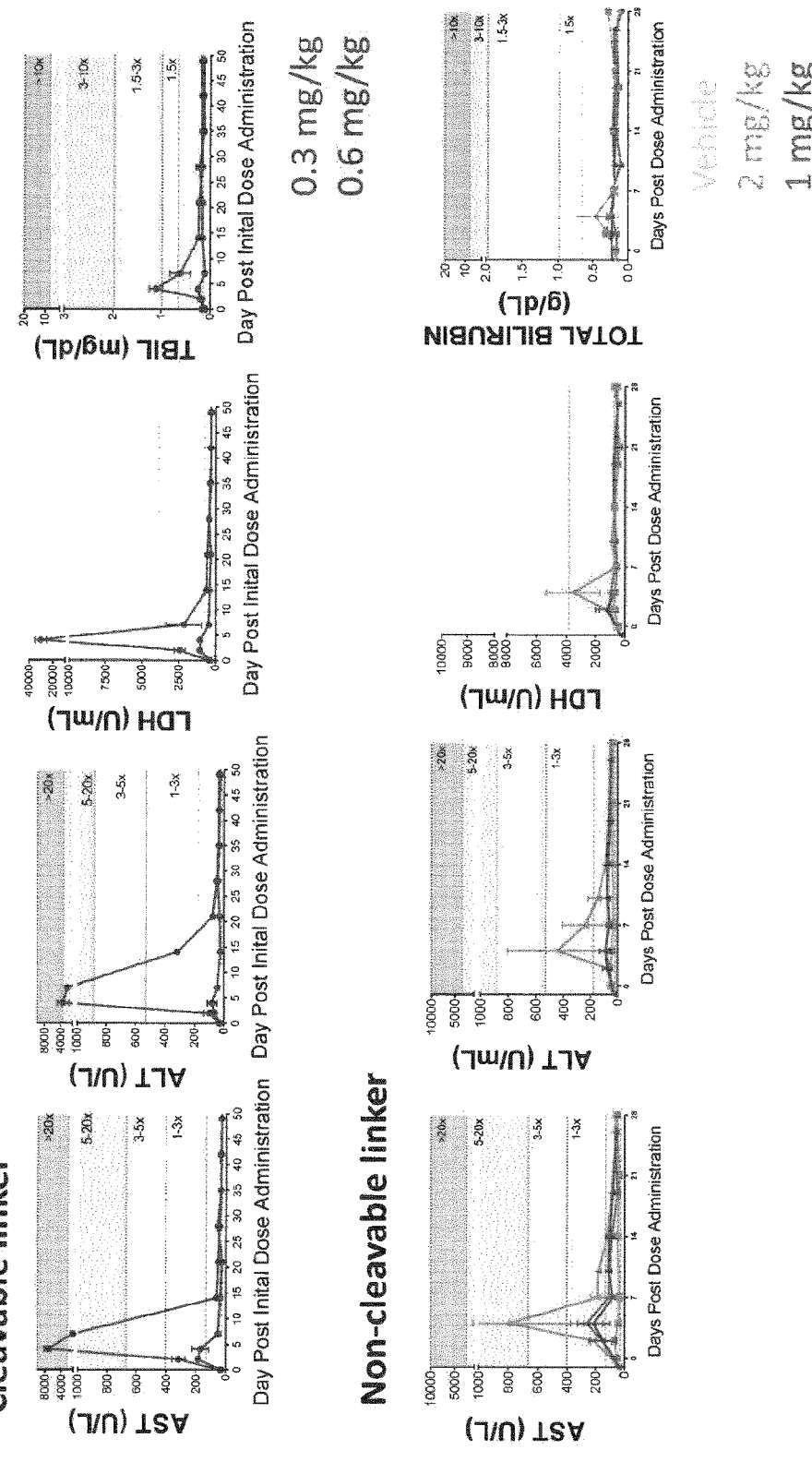

In addition to efficacy, tolerability of ADCs containing either anti-CD117 ADC A or anti-CD117 ADC C were tested in NHPs. As described in FIG. 8, treatment of cynomologus monkeys with a 0.3 mg/kg dose of cleavable conjugate A conjugated to antibody CK6 (Fc modifications D265C and H435A) resulted in mild transient and reversible elevation of aspartate aminotransferase (AST) levels, with no elevation above normal range for alanine aminotransferase (ALT), lactate dehydrogenase (LDH), or total bilirubin (TBIL) over the course of the study. Treatment of animals with a 0.6 mg/kg dose of conjugate A resulted in more significant elevation of AST, ALT, LDH, and TBIL.

In cynomolgus monkeys treated with 0.5 and 1.0 mg/kg non-cleavable conjugate C, Ab85 with the following Fc modifications: D265C H435A (EU numbering) conjugated to non-cleavable amanitin C (FIG. 1C), demonstrated mild transient and reversible elevation in AST with no elevation above normal range for ALT, LDH, and TBIL throughout the course of the study. In animals treated with 2.0 mg/kg non-cleavable conjugate C, Ab85 with the following Fc modifications: L234A L235A D265C H435A (EU number-ing) conjugated to non-cleavable amanitin C (FIG. 1C), more significant elevation was observed for AST and ALT.

Figure 9:
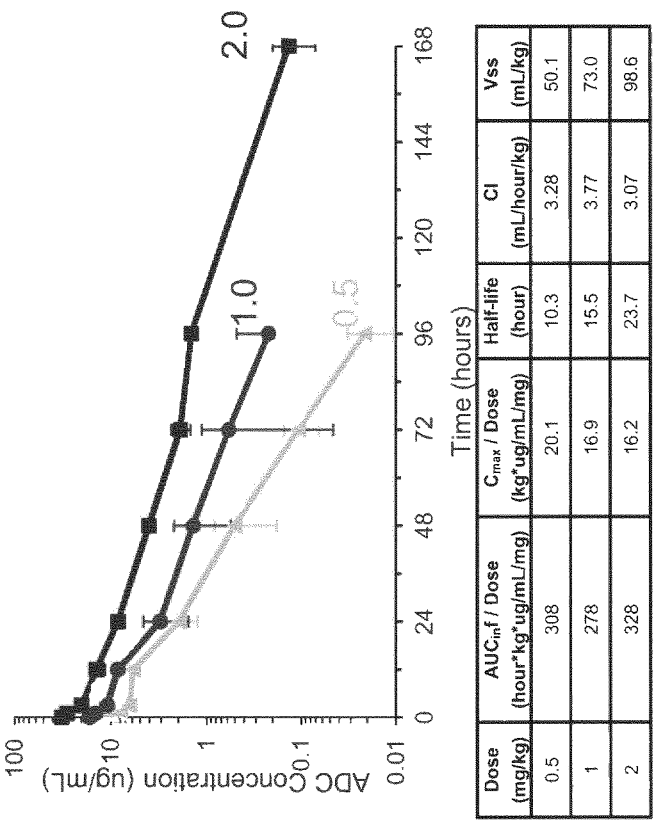
FIG. 9 graphically depicts pharmacokinetic analysis of conjugate A and conjugate C administered to male cynomolgus monkeys.
Figure 9:
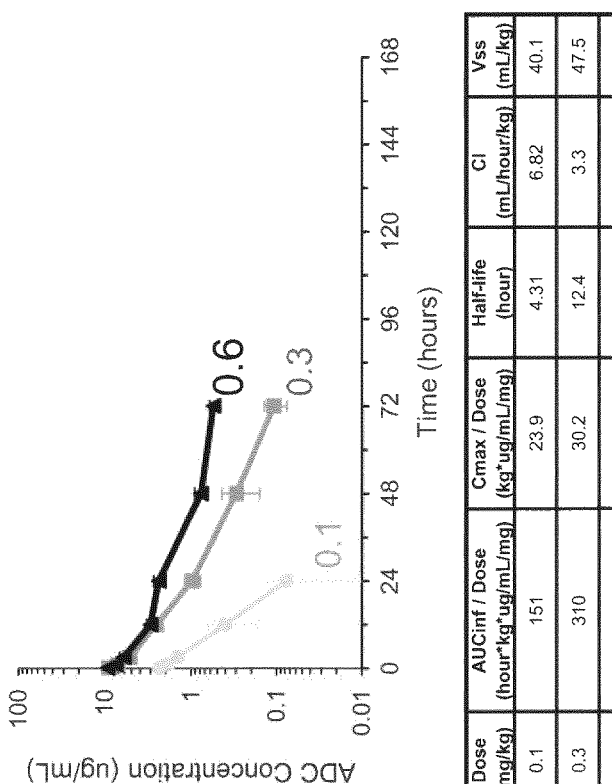

Pharmacokinetic characteristics were also studied in ant-CD117 ADO A vs. C. As described in FIG. 9, well tolerated doses of ADC conjugate C achieved saturating explosures in NHPs compared to ADO Conjugate A. Pharmacokinetic data was also analyzed for ADO conjugate 0 with various Fc mutations. For both anti-D117 ADO A and anti-CD117 ADO 0, ex vivo cytotoxicity assays revealed that for both ADCs there was a loss of efficacy at plasma concentrations below 100 ng/ml (data not shown).

Figure 10:
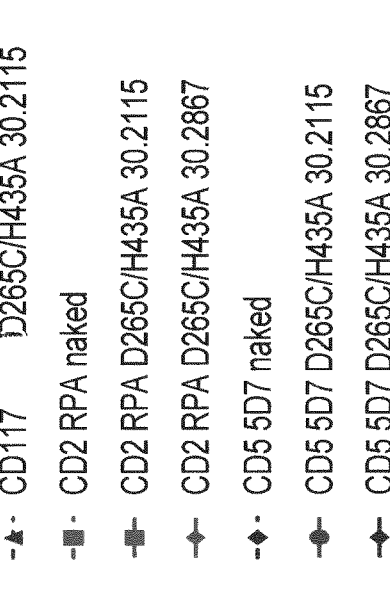
FIG. 10 graphically depicts that anti-CD2 and CD5 ADC C are able to deplete T cells.
Figure 10:
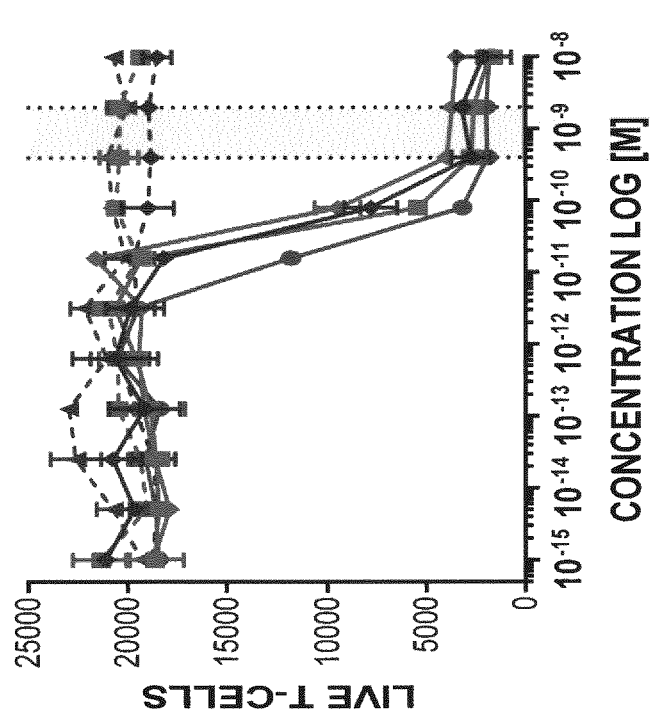
Figure 11:
FIG. 11 graphically depicts that while anti-CD2 ADCs A and C are saturated by Day 5, some cells still express CD5.
Figure 11:
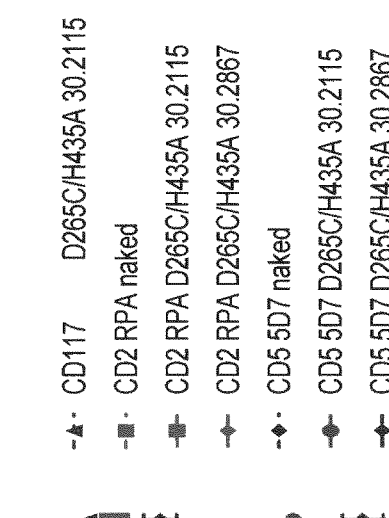
Figure 11:
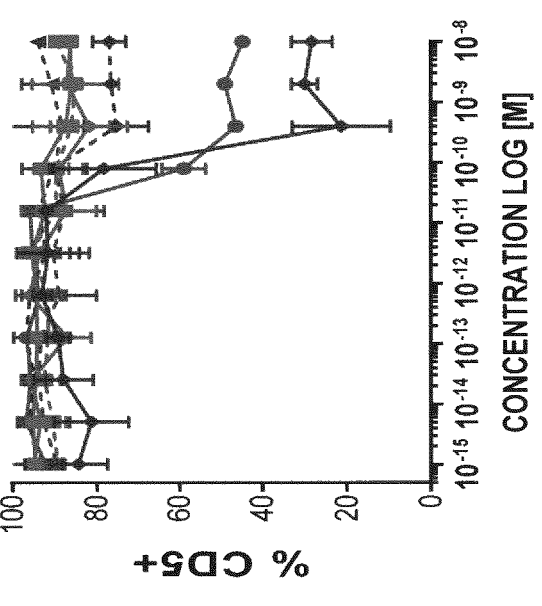
Figure 11:
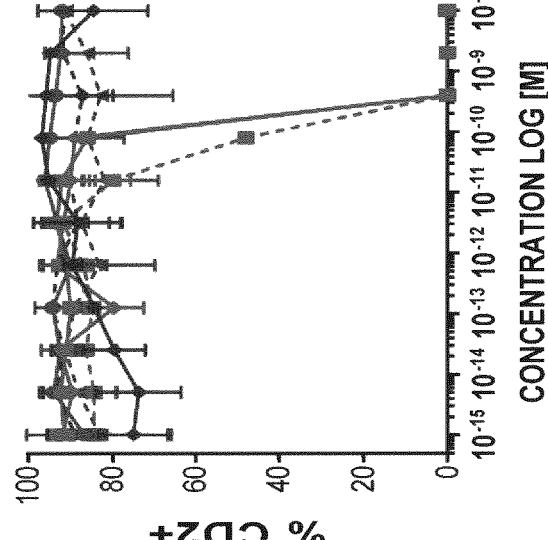

In sum, anti-CD117 ADO 0 demonstrated efficacy at doses as low as 0.5 mg/kg and was tolerated at a single dose of 2.0 mg/kg in cynomologus monkeys while the cleavable conjugate A was efficacious at a dose as low as 0.3 mg/kg but not tolerated at a single dose of 0.6 mg/kg supporting the finding that non-cleavable amanitin (FIG. 10C) is better tolerated.

Example 4: Primary Human T-Cell Killing with Anti-CD2 ADC C and CD5 ADC C

A study was performed to determine if ant-CD2 and anti-CD5 D265 H435A antibodies used in an ADO C (as described above and in FIG. 1) was as efficacious as Conjugate A for killing primary T cells. Thus, an in vitro cell killing assay was used. The protocol of the study is provided below:

---

General Protocol T cell killing assay: 384 well format

---

Coat plate with 0.5 mg/mL anti-CD3 incubate in 37 C. for 2 hours in TC treated low flange 384 well plate
Wash plate
Thaw primary T cells with AIM-V media
Plate 2500 cells per well + 20 ng recombinant human IL-2
Titrate antibodies and add to cells in duplicate for 30 min on ice
Culture for in 37° C. for 5 days
On day 5, stain cells for CD3, Live/Dead marker for 30 min, using Viaflo aspirate volume and add PBS
Run cells on Celesta
Readout: viability, CD2 and CD5 expression by flow

---

Anti-CD2 ADCs A and C included anti-CD2 antibody RPA with FC modifications D265C/H435A. Naked RPA was used as a control. Anti-CD5 ADCs A and C included anti-CD5 antibody 5D7 with Fc modifications D265C/H435A. Naked 5D7 was used as a control. As described in FIG. 12, Conjugate C demonstrated T cell depletion comparable to Conjugate A. Efficacy results are also provide in the table below.

| Label | DAR | IC50 (pM) | % Efficacy |
|---|---|---|---|
| Ab85 D265C/H435A ADC A | 1.9 | — | 0.9 |
| CD2 RPA naked | — | — | 0.0 |
| CD2 RPA2.10 D265C/H435A ADC A | 2.1 | 54.0 | 85.7 |
| CD2 RPA2.10 D265C/H435A ADC C | 2.1 | 86.9 | 78.7 |
| CD5 5D7 naked | — | — | 0.0 |
| CD5 5D7 D265C/H435A ADC A | 2 | 22.1 | 89.4 |
| CD5 5D7 D265C/H435A Ab ADC C | 2.0 | 50.8 | 84.9 |

Figure 13:
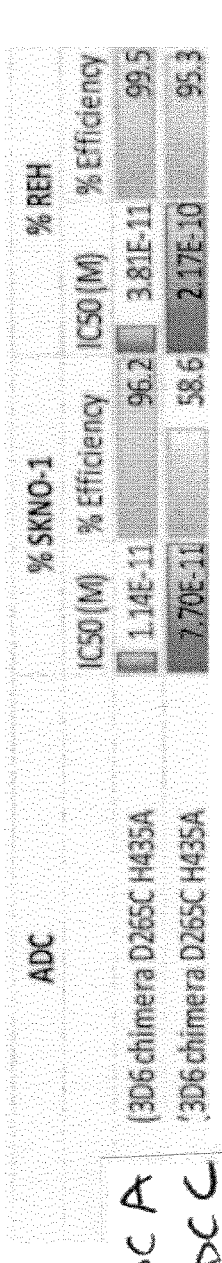
FIG. 13 graphically depicts results showing anti-CD45 ADCs A or C in in vitro cell killing assays.

FIG. 13 provides results showing that CD2 is saturated by day 5, whereas some cells still express CD5.

Figure 12B:
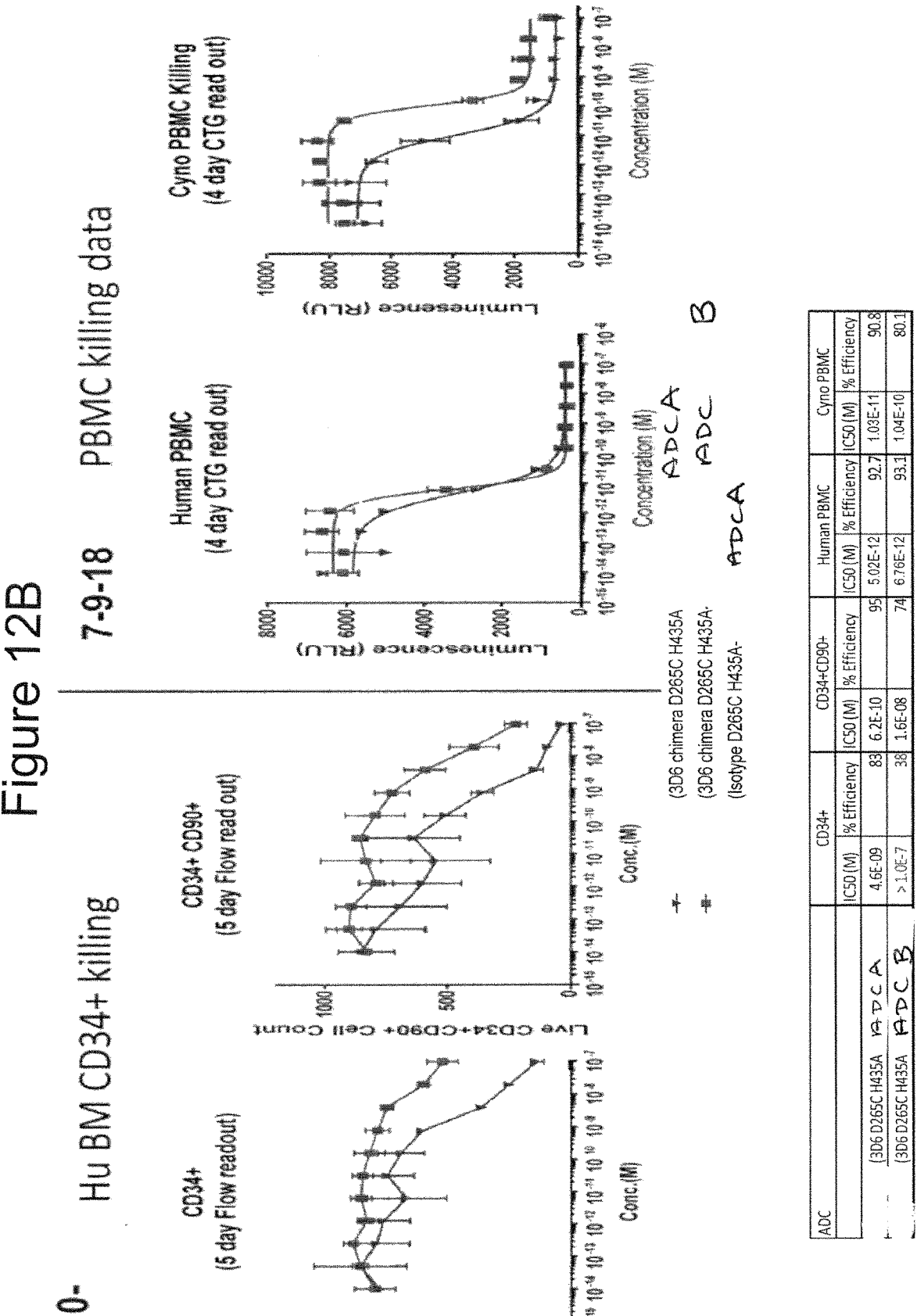

The results above and in FIGS. 12 and 13 show that both anti-CD2 and anti-CD5 ADCs C (D265C H435A) were as efficacious as Conjugate A on primary human T-cells in vitro.

Example 5: Efficacy of Anti-CD45 ADC C

In addition to CD2, CD5, and CD117, Conjugate C was tested in comparison to Conjugate A in the context of anti-CD45 antibodies. A chimeric anti-CD45 antibody 3D6 was used in the below experiments (murine 3D6 variable regions and a human IgG1 framework with Fc modifications D265C and H435A).

Figure 14:
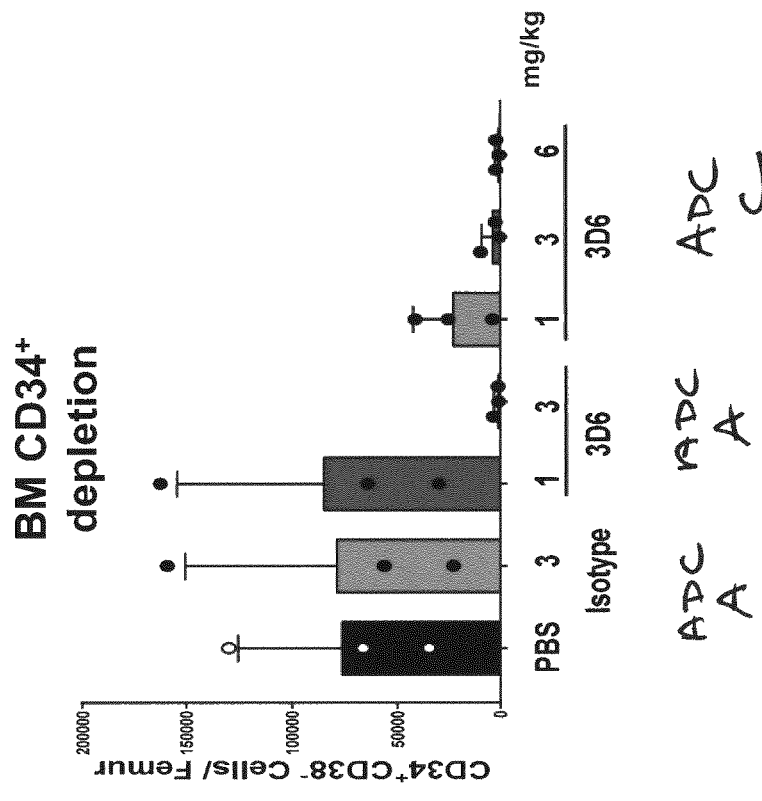
FIG. 14 graphically depicts results of anti-CD45 ADCs A or C in in vivo cell depletion experiments.
Figure 14:
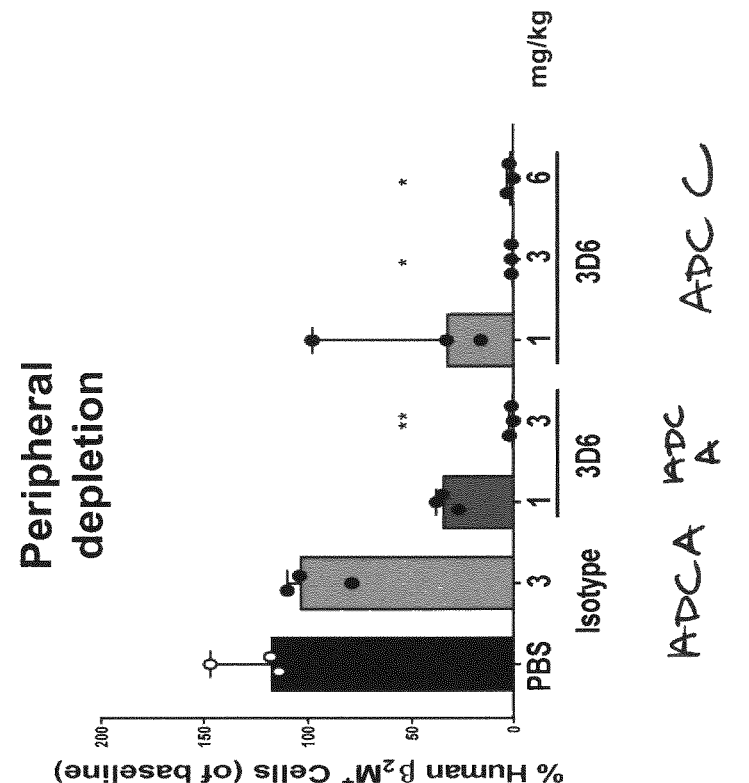

An in vitro cell killing assay was performed comparing anti-CD45 ADC A and anti-CD45 ADC C. As described in FIG. 14A, both ADCs A and C were able to kill human bone marrow CD34+ cells, as well as PBMC. An isotype negative control was also tested. As described in the Table presented in FIG. 14A, both anti-CD45 ADCs A and C were effective at killing CD34+ bone marrow and PBMC cells. This assay was repeated with anti-CD45 ADC A and B, As described in FIG. 14B, anti-CD45 ADC A showed a higher efficiency for killing CD34+ bone marrow cells vs. anti-CD45 ADC B. Both molecules were effective in a similar manner at killing human and cyno PBMCs.

A second in vitro cell killing assay was also performed using anti-CD45 ADCs A and C looking at the ability of each ADC to kill cells expressing either SKNO-1 or REH. The results are provided in FIG. 13 (left panel are the number of live SKNO-1 cells following exposure to anti-CD45 ADC A or C; right panel are the number of live REH cells following exposure to anti-CD45 ADC A or C). The efficiency of each molecule in these assays is described in the table in FIG. 13.

Figure 16:
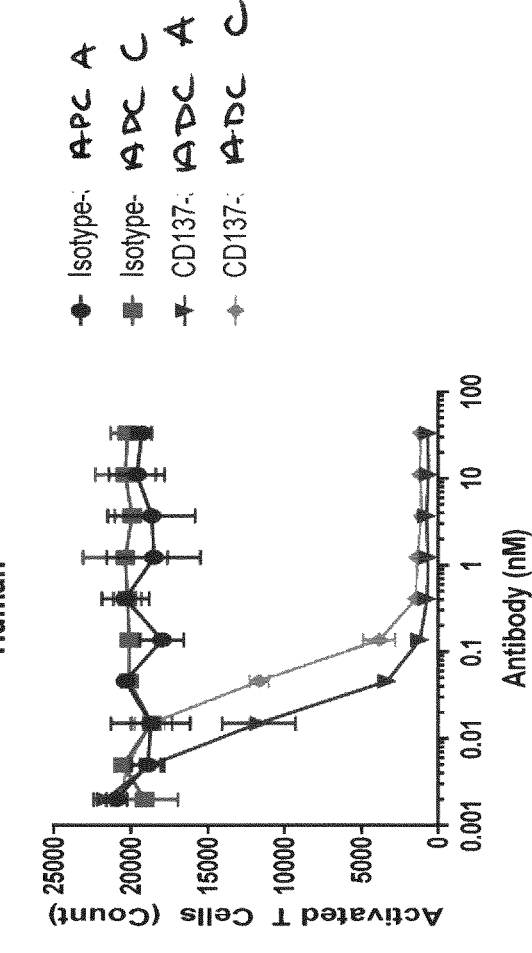
FIG. 16 graphically depicts results showing anti-CD137 ADCs A and C in a T cell killing assay.

Anti-CD45 ADCs A and C were further tested for the ability of each ADC to deplete CD45+ cells in vivo. Both ADC A (cleavable) and ADC C (non-cleavable) were able to deplete CD45+ cells efficiently in a humanized NSG mouse model. The results of the study are provided in FIG. 14. As described in FIG. 16, both ADCs were able to deplete peripheral CD45+ cells as well as bone marrow (BM) CD34+ cells. The maximum total dose in the mice for anti-CD45 ADC A was 3 mg/kg, whereas a much higher dose of ADC C was tolerated for anti-CD45 ADC C at more than 51 mg/kg. Thus, efficacy was observed for both anti-CD45 ADCs, but the ADC C was tolerated by the mice at higher doses.

Figure 15:
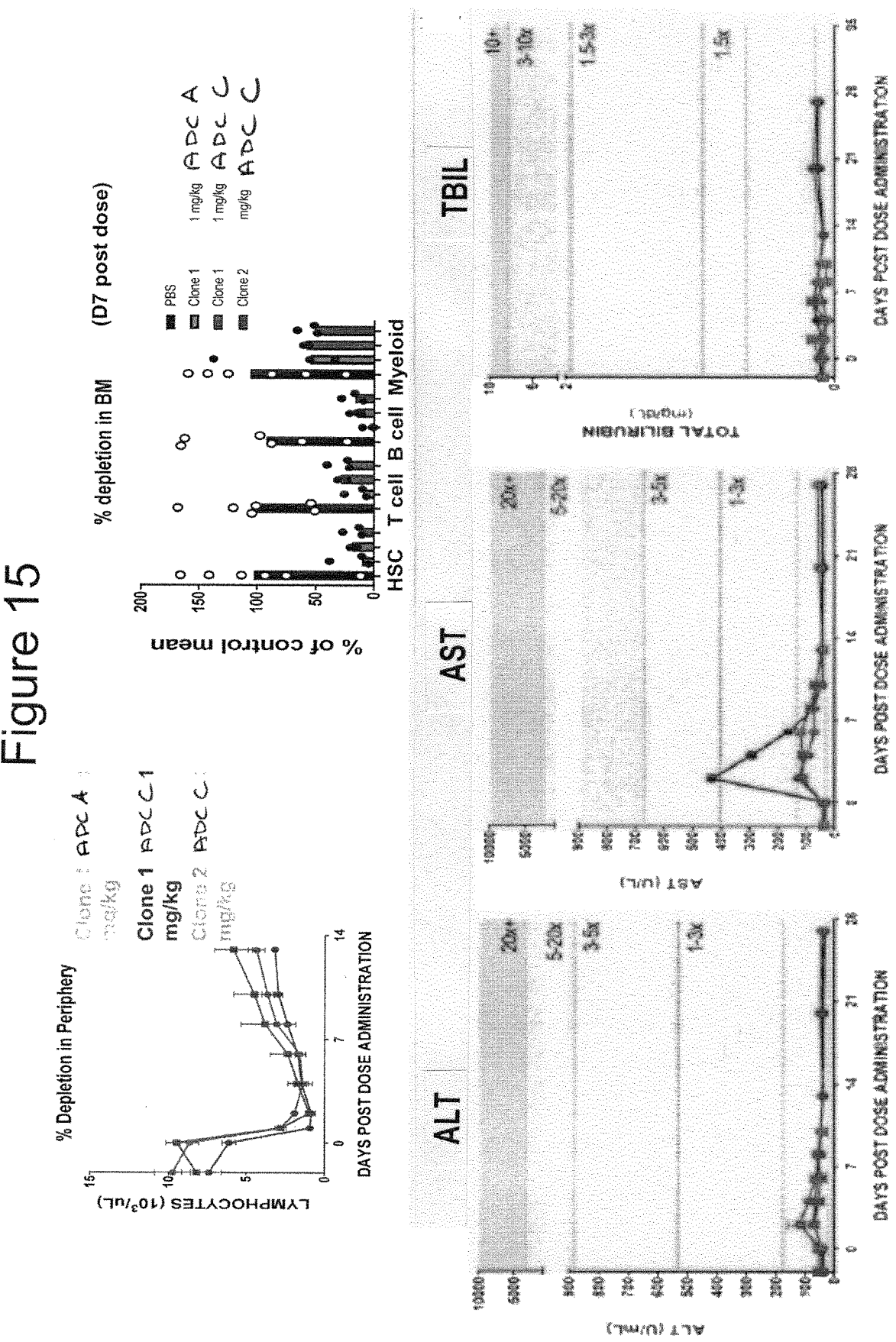
FIG. 15 graphically depicts results from administration of anti-CD45 ADCs A or C to mice at a number of dose amounts. Levels of peripheral lymphocytes, HSCs, and lymphocytes are shown. All ADCs were administered at 1 mg/kg.

Anti-CD45 ADCs A and C were also tested for their ability to deplete peripheral lymphocytes, bone marrow (BM) HSCs and lymphocytes in humanized NSG mice. Anti-CD45 ADCs A and C were each delivered at a dose of 1 mg/kg to the mice. The results from these studies are described in FIG. 15 and show that anti-CD45 ADCs A and C had comparable depletion of peripheral lymphocytes, HSCs, and BM lymphocytes at day 7 post injection at 1 mg/kg. Anti-CD45 ADC A showed mild, transient reversible liver enzyme elevation at 1 mg/kg, while little to no liver enzyme elevation was observed with anti-CD45 ADC C with the same 1 mg/kg dose.

Example 6: Anti-CD137 ADC A and C Characterization

Figure 17:
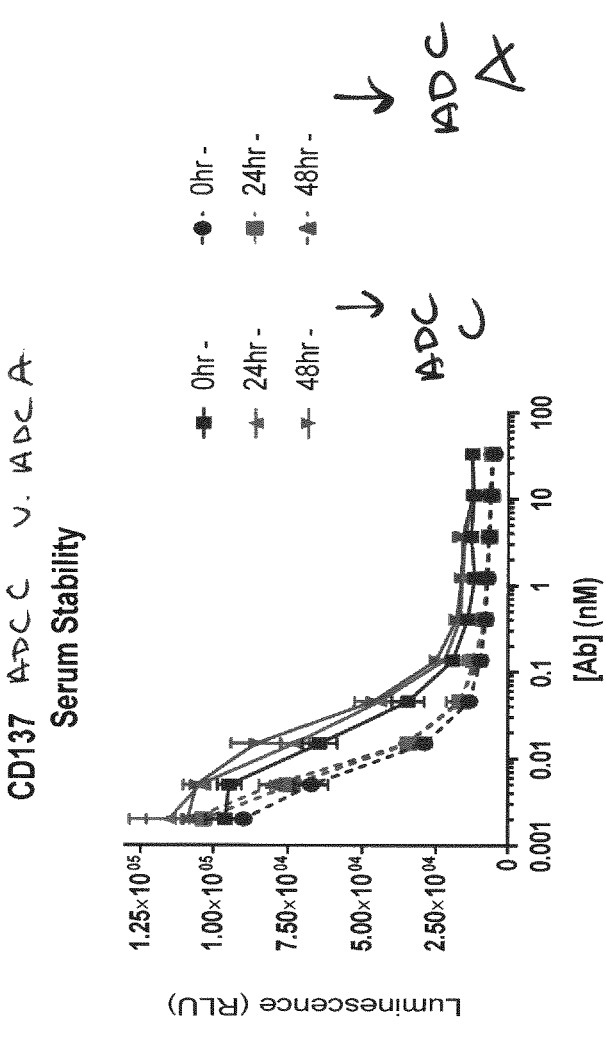
FIG. 17 graphically depicts cell line serum stability of anti-CD137 ADCs A and C over 48 hours.

Anti-CD137 ADC A and ADC C were tested for their ability to kill T cells, as well as for serum stability. Anti-CD137 antibody BBK2 was used in this example. An in vitro T cell killin assay was performed, where the results shown in FIG. 16 demonstrated both anti-CD137 ADC A and C were able to kill activated T cells in comparison to the isotype ADC A and C control. In addition, cell line serum stability was tested for both anti-CD137 ADC A and C over 48 hours, as described in FIG. 17.

Example 7: Synthesis of S-desoxy-5'-hydroxy-amaninamide

The ADCs of formula (IIa) as disclosed herein were prepared from the corresponding linker-amatoxin conjugates according to standard methods known to one of skill in the art. The penultimate amatoxin-linker conjugate to the ADCs of formula (IIa) (compound 14; Scheme 3) may be prepared from amatoxin derivative 11 following the general procedure for O-alkylation of the related amatoxin ($\alpha$-amanitin) disclosed in U.S. Patent Application Publication No. 2018/0043033, the disclosure of which is incorporated by reference herein in its entirety. Amatoxin derivative 11 may be prepared according to the procedures disclosed in International Patent Application Publication No. WO2019/030173, the disclosure of which is incorporated by reference herein in its entirety. Compound 7 (Scheme 1) may be prepared according to the methods reported in International Patent Application Publication No. WO2014/009025, the disclosure of which is incorporated herein in its entirety.

Example 8: Amanitin Derivatives

Figure 18:
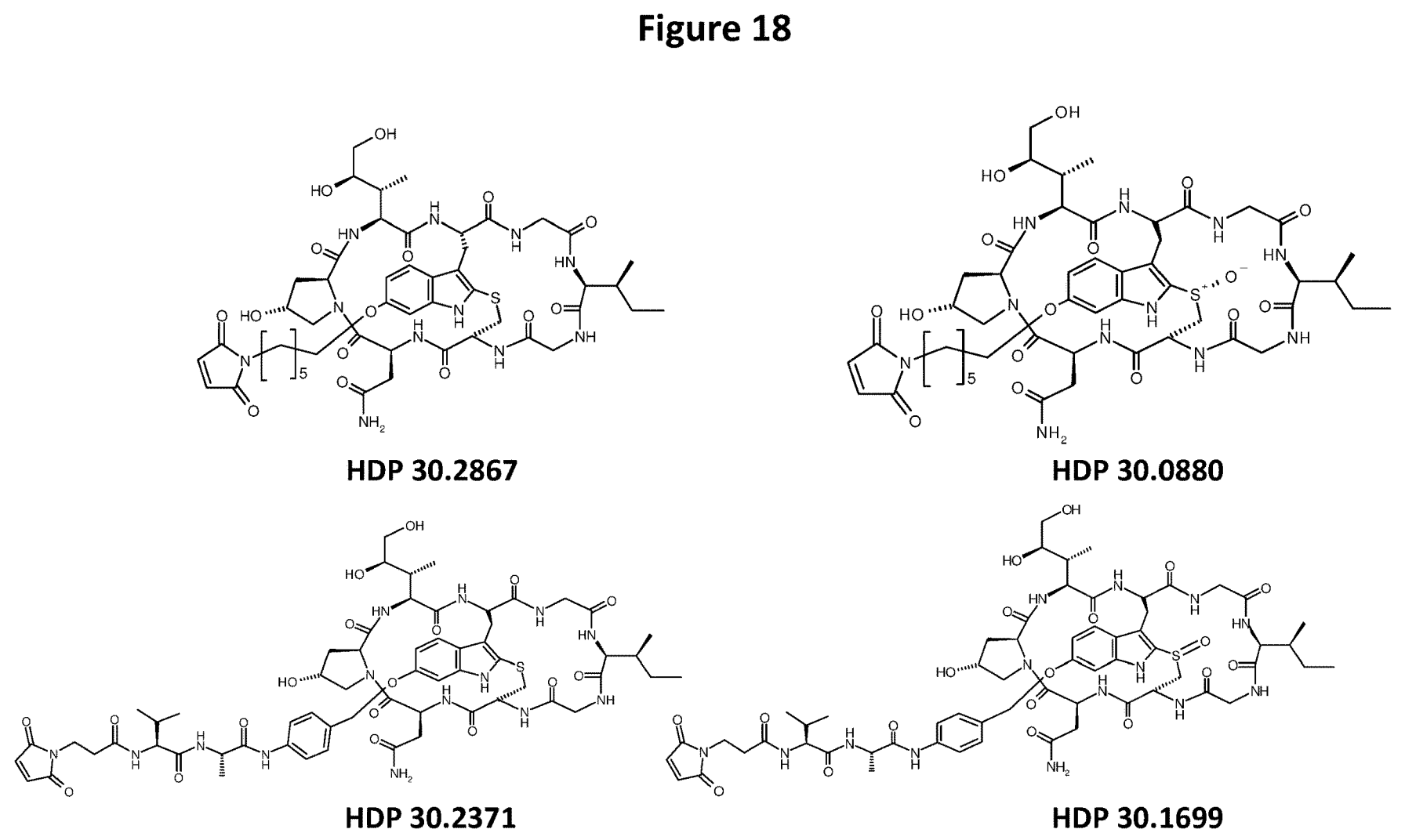
Figure 19:
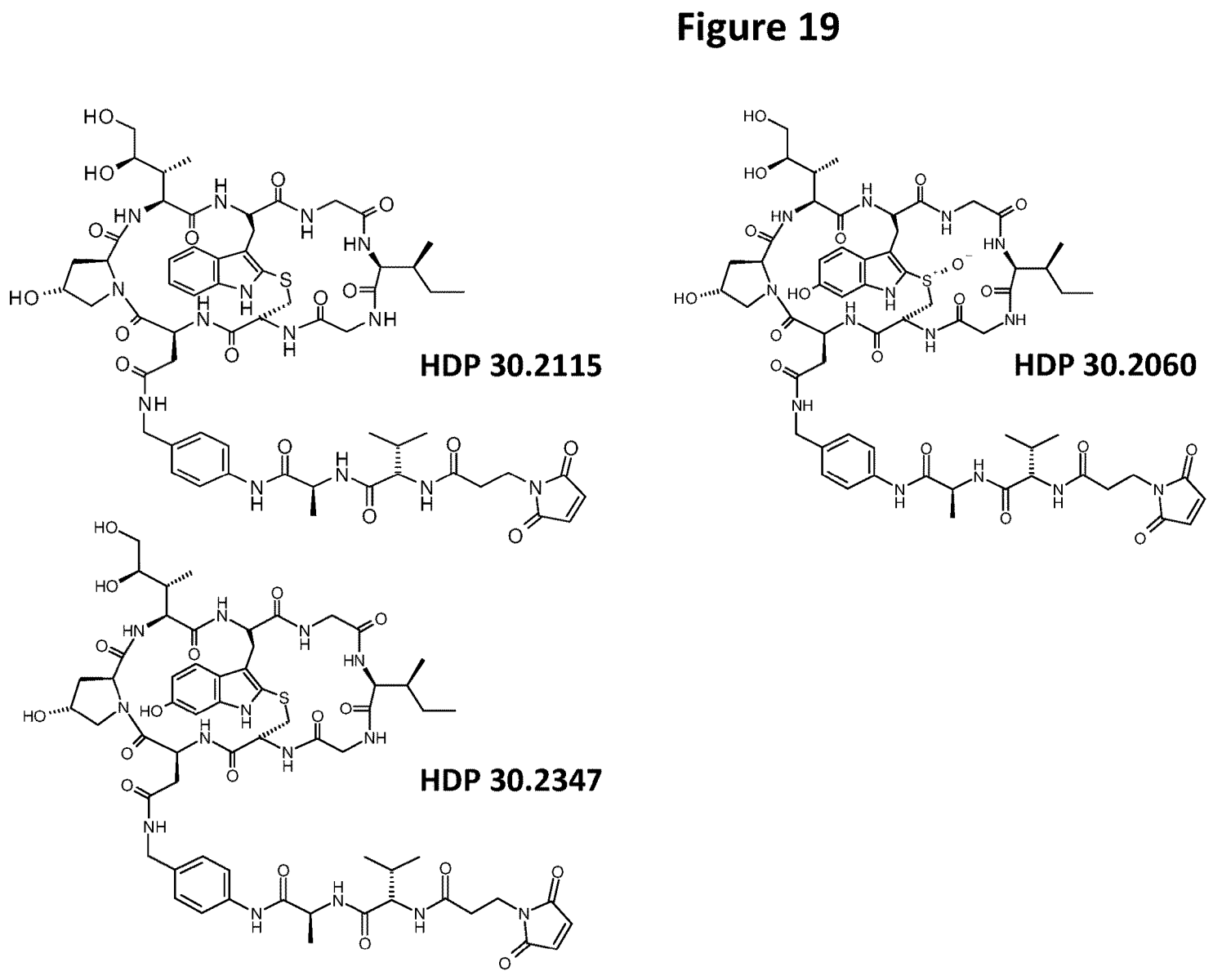

Various amanitin derivatives were used for conjugation with target-specific antibodies (FIG. 18, FIG. 19). They were generated according to the methods as disclosed in WO2018/115466 and WO2019/197654, the disclosures of which are incorporated herein in its entirety.

TABLE 6

| Molecular characteristics of amatoxin-linker constructs | | | | |
|---|---|---|---|---|
| Applicant's identifier | Tryptophan (Trp) | Sulfur bridge | Linker at | Linker |
| 30.2867 | 6-Hydroxy-Trp | thioether | aa4 | stable C6-linker |
| 30.0880 | 6-Hydroxy-Trp | sulfoxide | aa4 | stable C6-linker |
| 30.1699 | 6-Hydroxy-Trp | sulfoxide | aa4 | cleavable Val-Ala |
| 30.2371 | 6-Hydroxy-Trp | thioether | aa4 | cleavable Val-Ala |
| 30.2060 | 6-Hydroxy-Trp | sulfoxide | aa1 | cleavable Val-Ala |
| 30.2115 | Trp | thioether | aa1 | cleavable Val-Ala |
| 30.2347 | 6-Hydroxy-Trp | thioether | aa1 | cleavable Val-Ala |

Example 9: Method of Conjugation

Antibodies directed to Her2 or prostate-specific membrane antigen (PSMA) were conjugated to the amatoxin linker conjugates by means of the so-called Thiomab technology. In this approach, the conjugation takes place by conjugation of the maleimide residue of the toxin linker construct to the free SH group of an engineered cysteine residue in the antibody, as shown in the following reaction scheme:

-continued

The principles of this conjugation method, are disclosed in Junutula et al (2008), the content of which is incorporated herein by reference.

The antibodies directed to Her2 (Trastuzumab) or prostate-specific membrane antigen (PSMA) used in the present experiments comprise a D265C substitution in both Fc domains, in order to provide a cysteine residue that has such free SH group. The respective technology is disclosed in WO2016142049 A1 assigned to the present applicant, the content of which is incorporated herein by reference, and delivers a homogenous product with a fixed drug to antibody ratio ("DAR") of 2 and a site specific conjugation.

Example 10: Cytotoxicity Assay with Anti-Her2-ADCs In Vitro

Cytotoxic activity of anti-Her2 amatoxin conjugates was evaluated in vitro with target-positive tumor cell lines and the chemiluminescent BrdU incorporation assay (Roche Diagnostics). Cell viability was determined after 96 h incubation with different concentrations of conjugates at 37° C. and 5% $CO_2$ by measurement of fixed and permeabilized cells with an anti-BrdU-HRP antibody in a BMG Labtech Optima microplate reader. $EC_{50}$ value of dose-response curve was calculated by Graphpad Prism 4.0 software.

Figure 20:
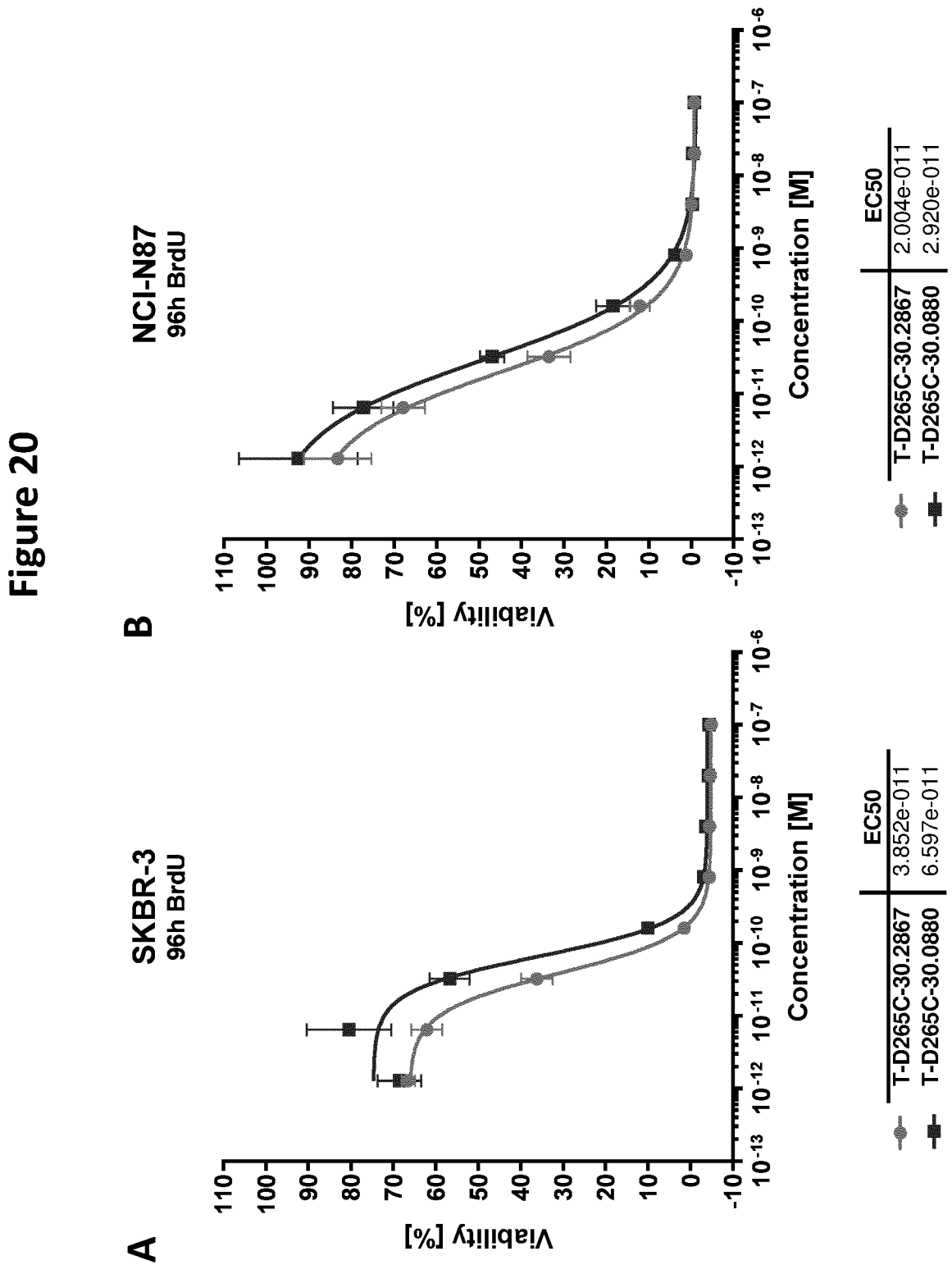
FIG. 20 graphically depicts the cytotoxic activity in vitro of ADC compounds T-D265C-30.2867 and T-D265C-30.0880, respectively, on (A) SKBR-3, (B) NCI-N87, (C) BT474 and (D) JIMT-1 cell lines in 96 h-BrdU assay.

The cytotoxic activity of Trastuzumab carrying a D265C mutation (T-D265C) conjugated to compound 30.2867 (formula (A)), and to compound 30.0880 (formula (B)), respectively, via its D265C residue was tested on SKBR-3, NCI-N87, BT474 and JIMT-1 cell lines (FIG. 20). T-D265C-30.2867 slightly outperformed T-D265C-30.0880 on all tested cell lines.

Figure 21:
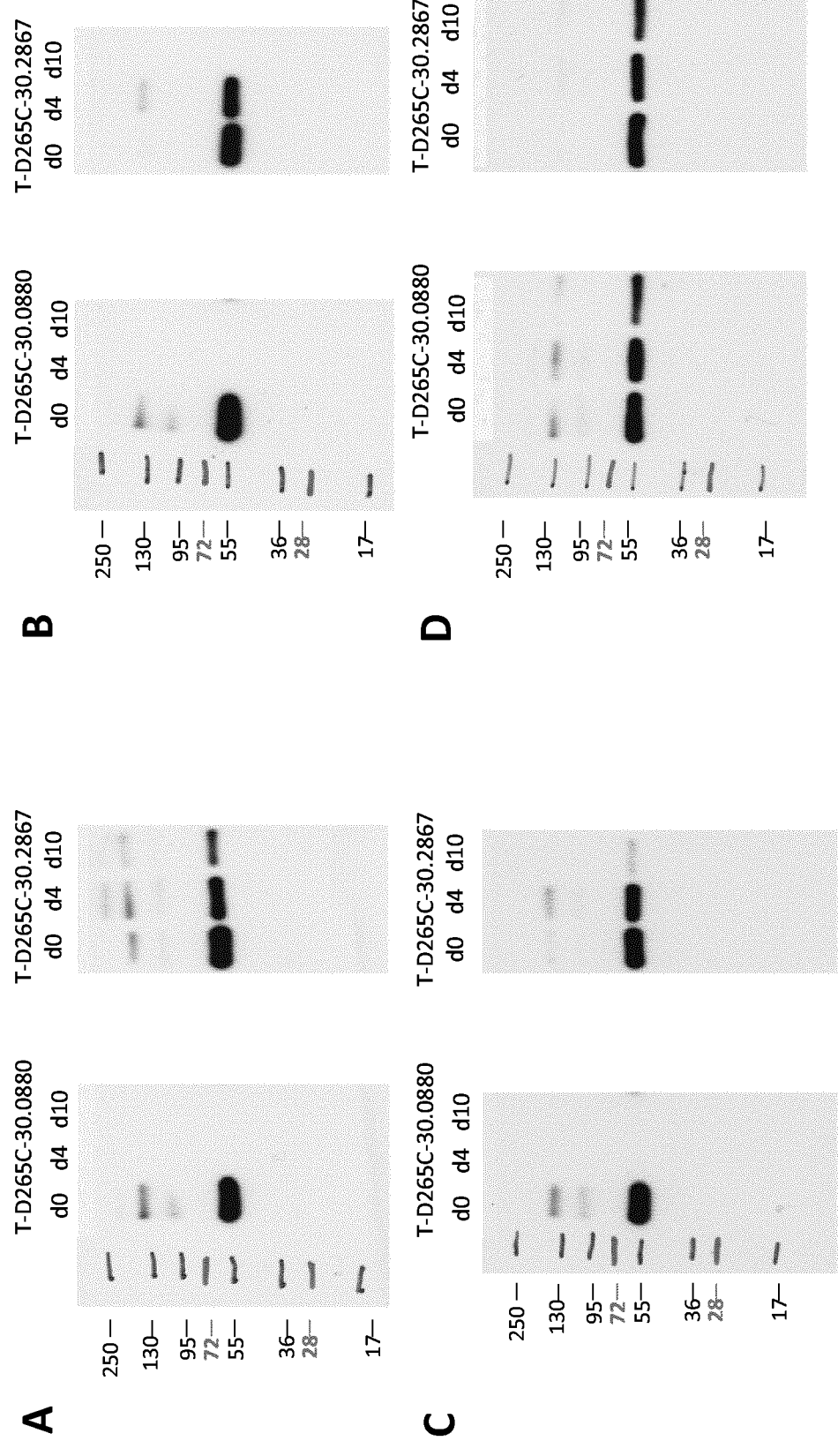
FIG. 21 graphically depicts results of SDS-PAGE/Western Blot analysis of the stability of ADC compounds T-D265C-30.2867 and T-D265C-30.0880, respectively, after incubation for 0, 4 and 10 days, respectively, in (A) human-, (B) mouse-, (C) cynomolgus plasma and (D) PBS (control), respectively.

Example 11: Stability of Anti-Her2-ADCs in Human, Mouse, and Cynomolgus Plasma ADC conjugates T-D265C-30.2867 and T-D265C-30.0880, respectively, directed to Her2 antigen, were incubated with human, mouse, and cynomolgus plasma, and phosphate buffered saline (PBS, control), respectively, for 0, 4, and 10 days. Samples were subjected to sodium dodecyl sulphate (SDS) polyacryl amide (PAA) gel electrophoresis SDS-PAGE), and antibody heavy chain molecules were detected with an amanitin-specific polyclonal antiserum by Western blotting (FIG. 21).

The ADC conjugate T-D265C-30.2867 showed higher plasma stability over all tested species compared to the ADC conjugate T-D265C-30.0880. T-D265C-30.2867 showed lower stability in MP than in HP and CP, respectively.

Figure 23:
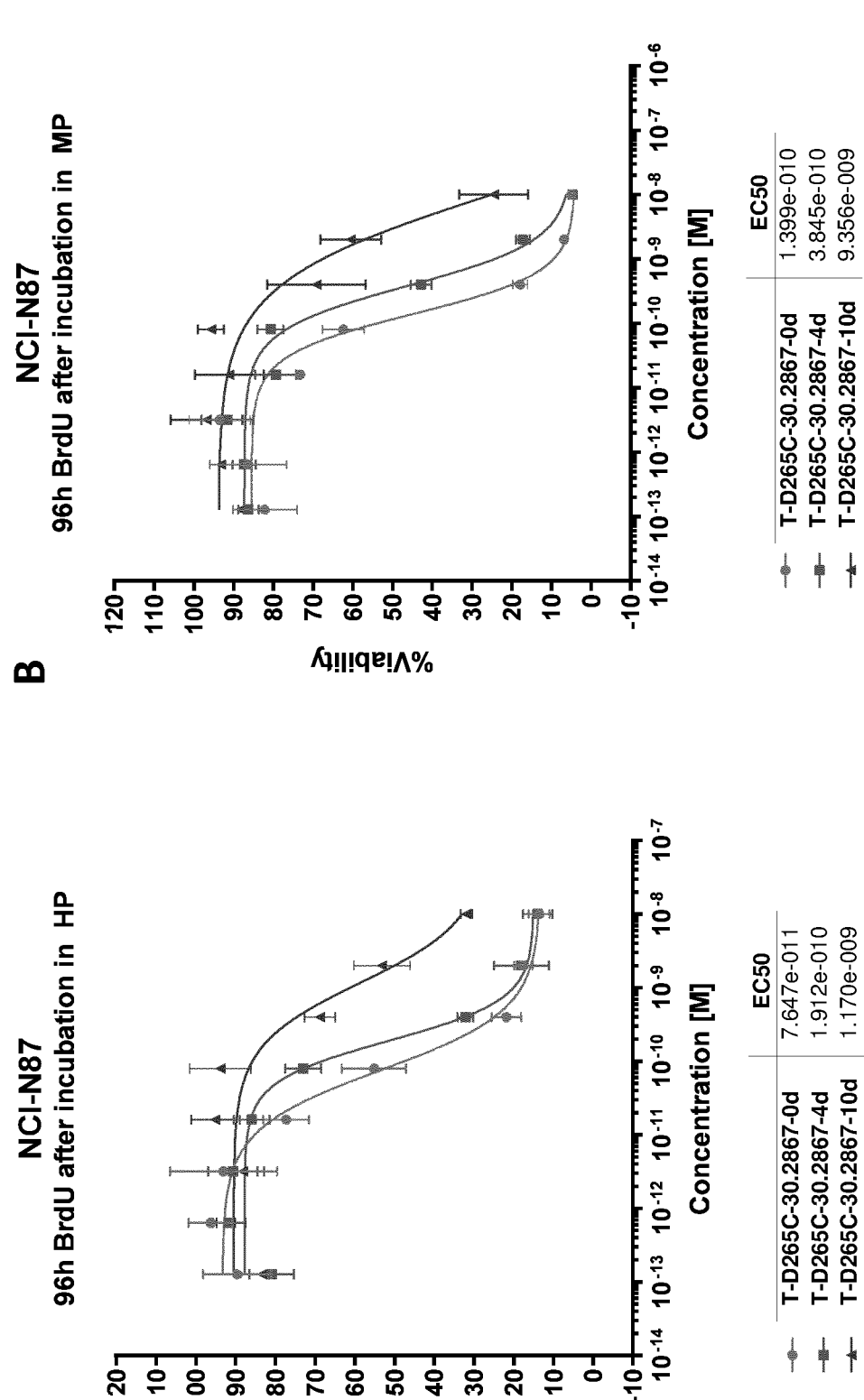
FIG. 23 graphically depicts the cytotoxic activity in vitro of ADC compound T-D265C-30.2867 on NCI-N87 cells after incubation for 0, 4 and 10 days, respectively, in (A) human-, (B) mouse-, (C) cynomolgus plasma and (D) PBS (control), respectively.
Figure 23:
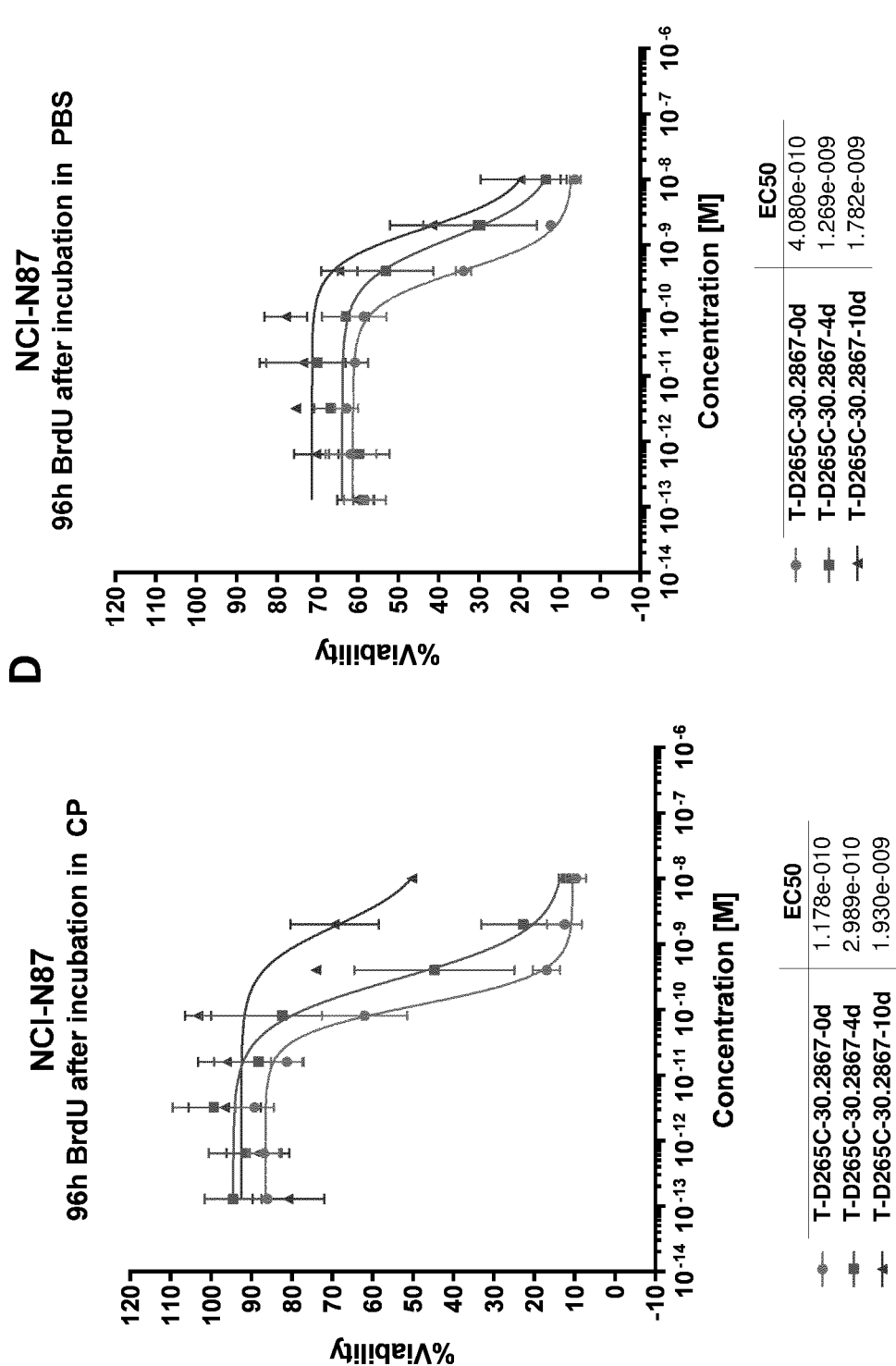
Figure 24:
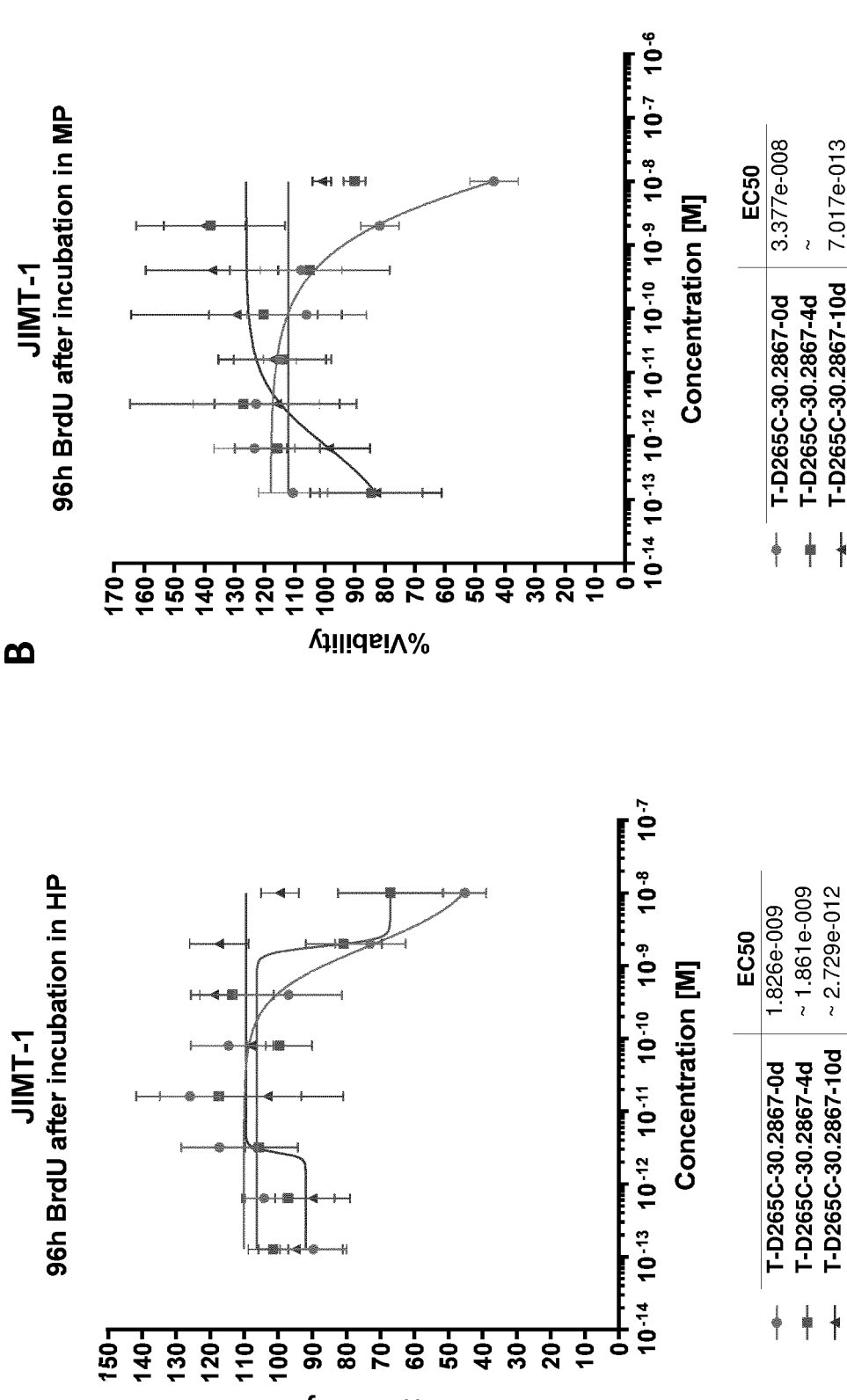
FIG. 24 graphically depicts the cytotoxic activity in vitro of ADC compound T-D265C-30.2867 on JIMT-1 cells after incubation for 0, 4 and 10 days, respectively, in (A) human-, (B) mouse-, (C) cynomolgus plasma and (D) PBS (control), respectively.
Figure 24:
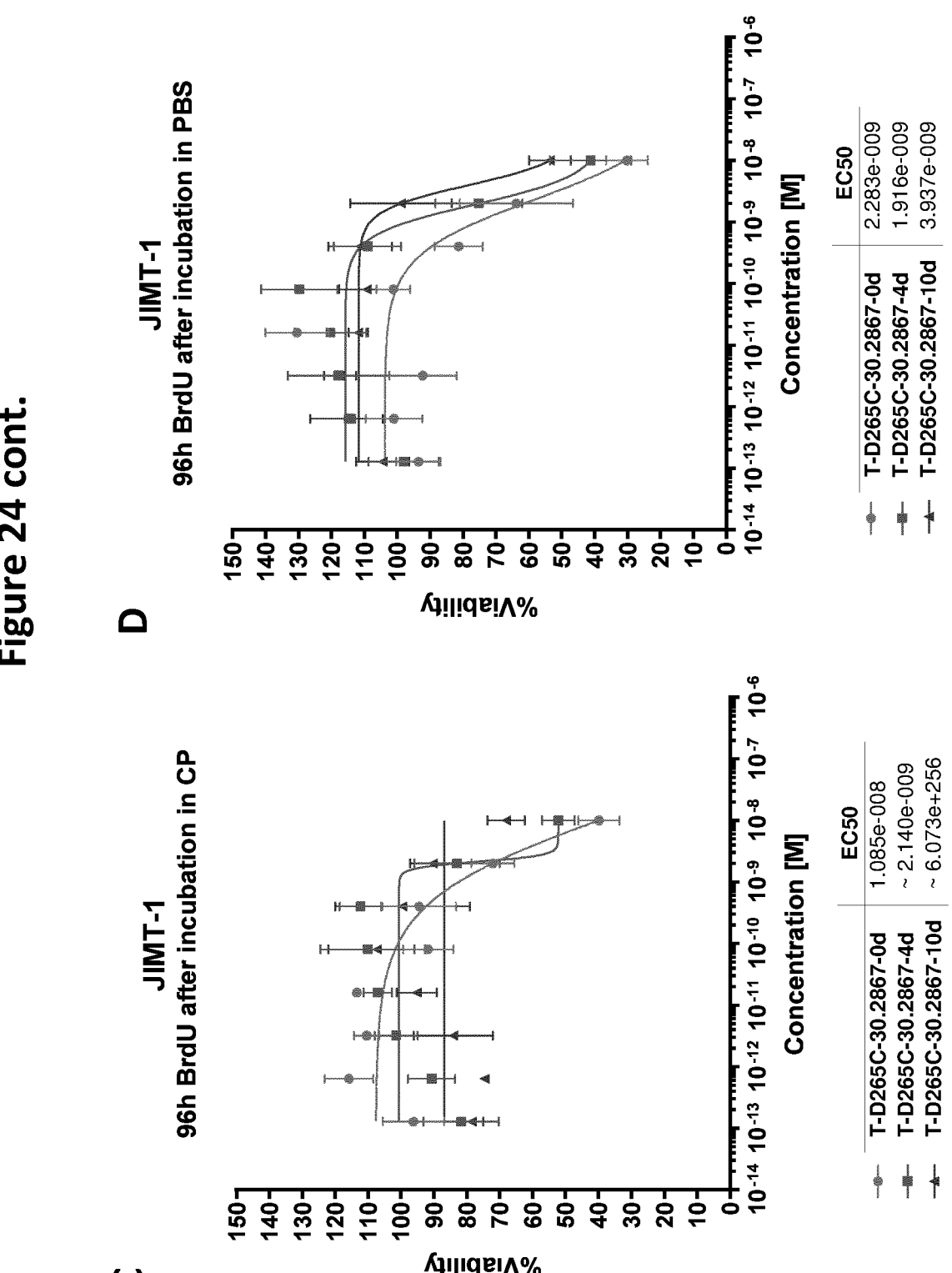

For further assessment of stability, the cytotoxic activity in vitro of ADC compound T-D265C-30.2867 after incubation for 0, 4 and 10 days, respectively, in human plasma, mouse plasma, cynomolgus plasma, and PBS (phosphate buffered saline, control), respectively, was analyzed on SKBR-3 cells (FIG. 22), on NCI-N87 cells (FIG. 23), and on JIMT-1 cells (FIG. 24).

Figure 22:
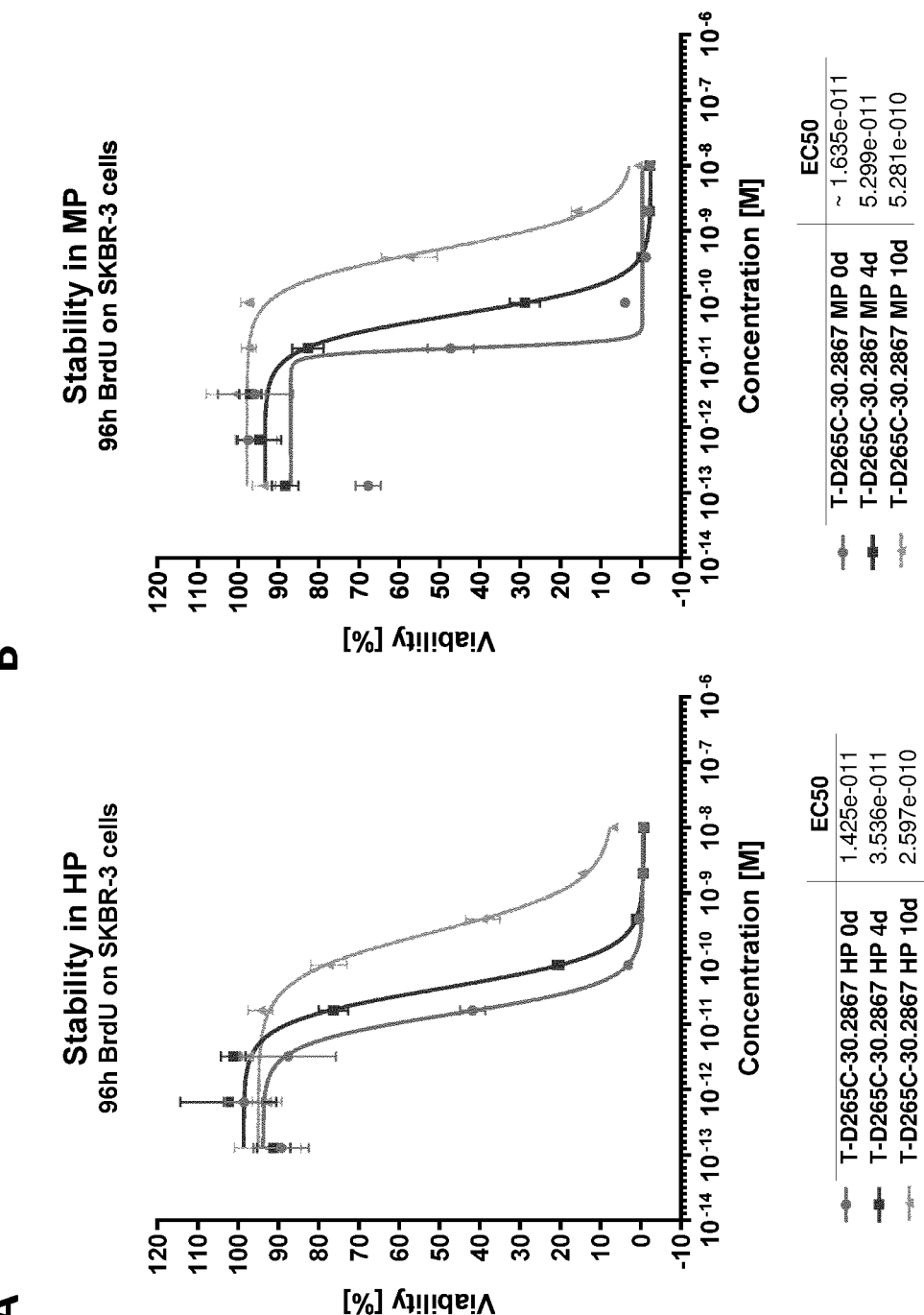
FIG. 22 graphically depicts the cytotoxic activity in vitro of ADC compound T-D265C-30.2867 on SBR-3 cells after incubation for 0, 4 and 10 days, respectively, in (A) human-, (B) mouse-, (C) cynomolgus plasma and (D) PBS (control), respectively.
Figure 22:
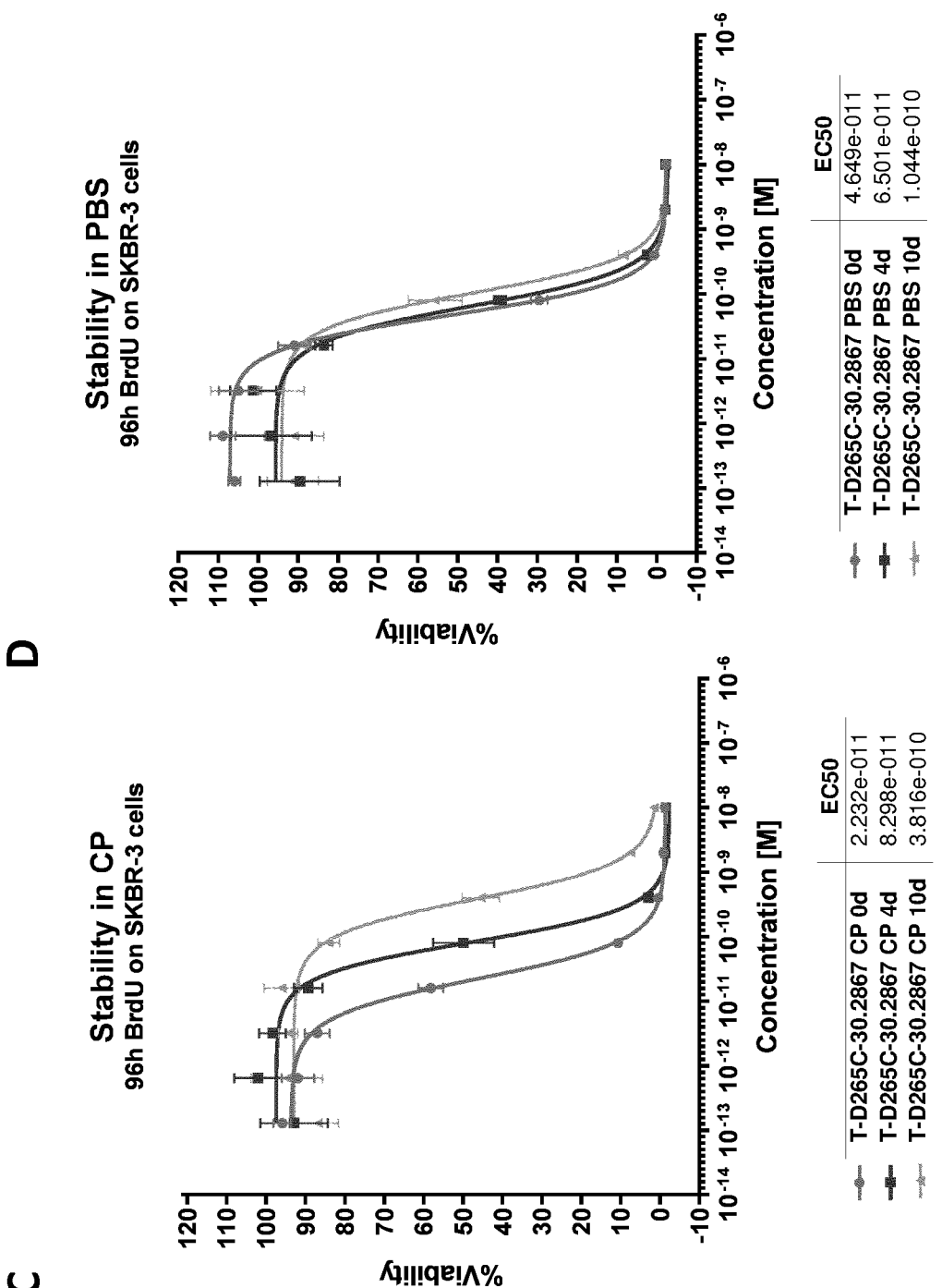

After 4-day incubation in human plasma, mouse plasma, and cynomolgus plasma, respectively, the cytotoxic potential of T-D265C-30.2867 on SKBR-3 cells was only slightly reduced. After 10-day incubation in human plasma and cynomolgus plasma, the cytotoxic potential was reduced by factor 20, in mouse plasma, however, a reduction by factor 33 was observed. Incubation in PBS at 37° C. had almost no effect on cytotoxic potential of T-D265C-30.2867 on SKBR-3 cells (FIG. 22, Table 7).

TABLE 7

Stability and cytotoxic potential on SKBR-3 cells of
T-D265C-30.2867 in human mouse and
cynomolgus plasma; values are EC50 values [nM]

| Matrix | 0 days | 4 days | 10 days | Reduction of cytotoxic potential compared to day 0 |
|---|---|---|---|---|
| Human plasma | 14 | 35 | 260 | 18.6 x |
| Mouse plasma | 16 | 53 | 528 | 33.0 x |
| Cynomolgus plasma | 22 | 83 | 382 | 17.4 x |
| PBS | 46 | 65 | 104 | 2.3 x |

After 4-day incubation in human plasma, mouse plasma and cynomolgus plasma, respectively, the cytotoxic potential of T-D265C-30.2867 on NCI-N87 cells was only slightly reduced. After 10-day incubation in human plasma and cynomolgus plasma, the cytotoxic potential was reduced by factor 15, however, app. 50% residual cell viability was observed after 10-day incubation in cynomolgus plasma. After 10-day incubation in mouse plasma, a reduction by factor 67 was observed. Incubation in PBS at 37° C. had a low effect on cytotoxic potential of T-D265C-30.2867 on NCI-N87 cells (FIG. 23).

After 4-day incubation in human plasma and cynomolgus plasma, the cytotoxic potential of T-D265C-30.2867 on JIMT-1 cells was only slightly reduced. After 4-day incubation in mouse plasma, T-D265C-30.2867 showed no cytotoxic potential at all on JIMT-1 cells. After 10-day incubation in human plasma, mouse plasma and cynomolgus plasma, no cytotoxic potential at all was observed on JIMT-1 cells. Incubation in PBS at 37° C. had almost no effect on cytotoxic potential of T-D265C-30.2867 on JIMT-1 cells (FIG. 24).

Example 12: Efficacy of Anti-Her2-ADCs in Mouse Xenograft Tumor Models In Vivo In the JIMT-1 mouse xenograft model, female NMRI nude mice were inoculated with $5 \times 10^6$ JIMT-1 breast cancer cells per mouse subcutaneously in the right flank. At a mean tumor vol. of ~120 mm$^3$, animals were allocated to three groups on day 0. On the same day, the animals received a single intravenous dose of amanitin-based anti-Her2 antibody drug conjugates (ADCs). The tumor volume and body weight were determined twice per week.

Figure 25:
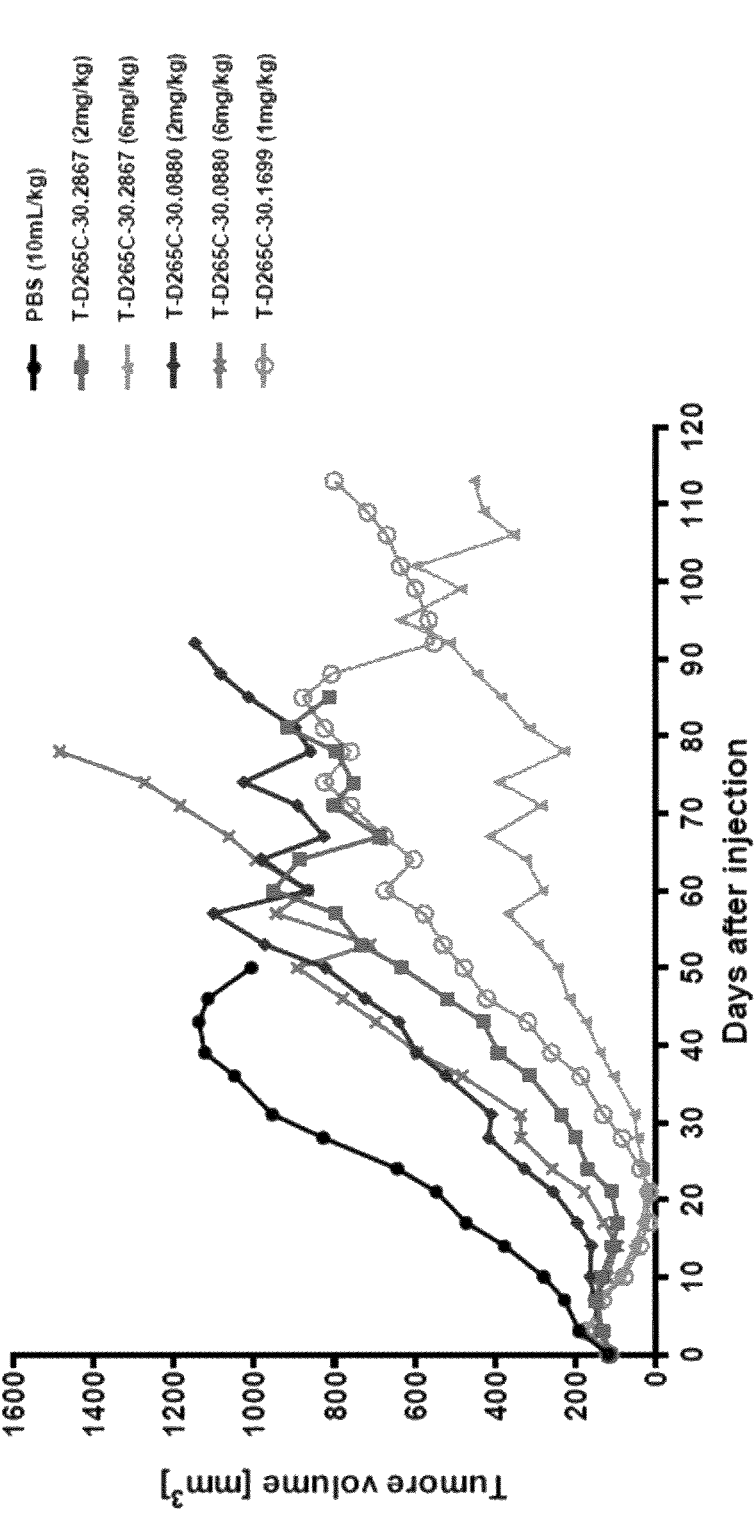
FIG. 25 graphically depicts results of cytotoxic efficacy analysis of Anti-Her2-ADCs in JIMT-1-cell xenograft tumor mouse models in vivo using ADC compounds T-D265C-30.2867, T-D265C-30.0880 and T-D265C-30.1699.

As shown in FIG. 25, the efficacy of T-D265C-30.2867 in vivo was better than that of T-D265C-30.0880. At 113 days after treatment, 0/10 animals which had received a dose of 2 mg/kg, and 4/10 animals which had received a dose of 6 mg/kg T-D265C-30.2867 were alive; in the latter group, 1/4 animals were tumor free. In contrast, at 113 days after treatment, 0/10 animals which had received a dose of 2 mg/kg, and 0/10 animals which had received a dose of 6 mg/kg T-D265C-30.0880 were alive. At 113 days after treatment, 4/10 animals which had received a dose of 1 mg/kg T-D265C-30.1699 were alive, and 1/4 animals was tumor free.

Figure 26:
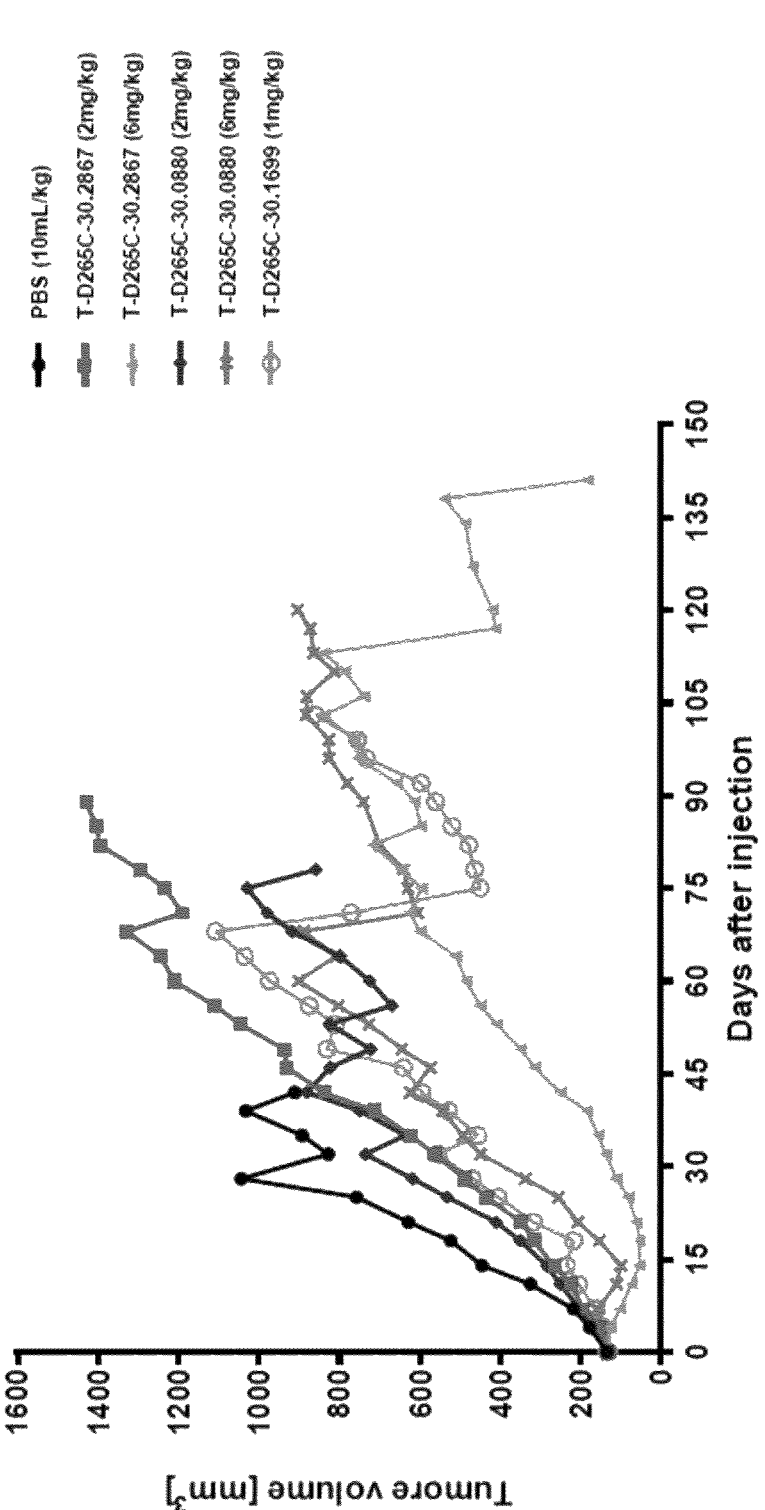
FIG. 26 graphically depicts results of cytotoxic efficacy analysis of Anti-Her2-ADCs in NCI-N87-cell xenograft tumor mouse models in vivo using ADC compounds T-D265C-30.2867, T-D265C-30.0880 and T-D265C-30.1699.

With a respective NCI-N87 mouse tumor xenograft model, as shown in FIG. 26, again, the cytotoxic efficacy of T-D265C-30.2867 in vivo was better than that of T-D265C-30.0880. At 141 days after treatment, 0/10 animals which had received a dose of 2 mg/kg, and 3/10 animals which had received a dose of 6 mg/kg T-D265C-30.2867 were alive; in the latter group, however, 0/3 animals were tumor free. In contrast, at 141 days after treatment, 0/10 animals which had received a dose of 2 mg/kg, and 0/10 animals which had received a dose of 6 mg/kg T-D265C-30.0880 were alive. At 141 days after treatment, 0/10 animals which had received a dose of 1 mg/kg T-D265C-30.1699 was alive either.

Example 13: Cytotoxicity Assay with Anti-PSMA-ADCs In Vitro

Figure 27:
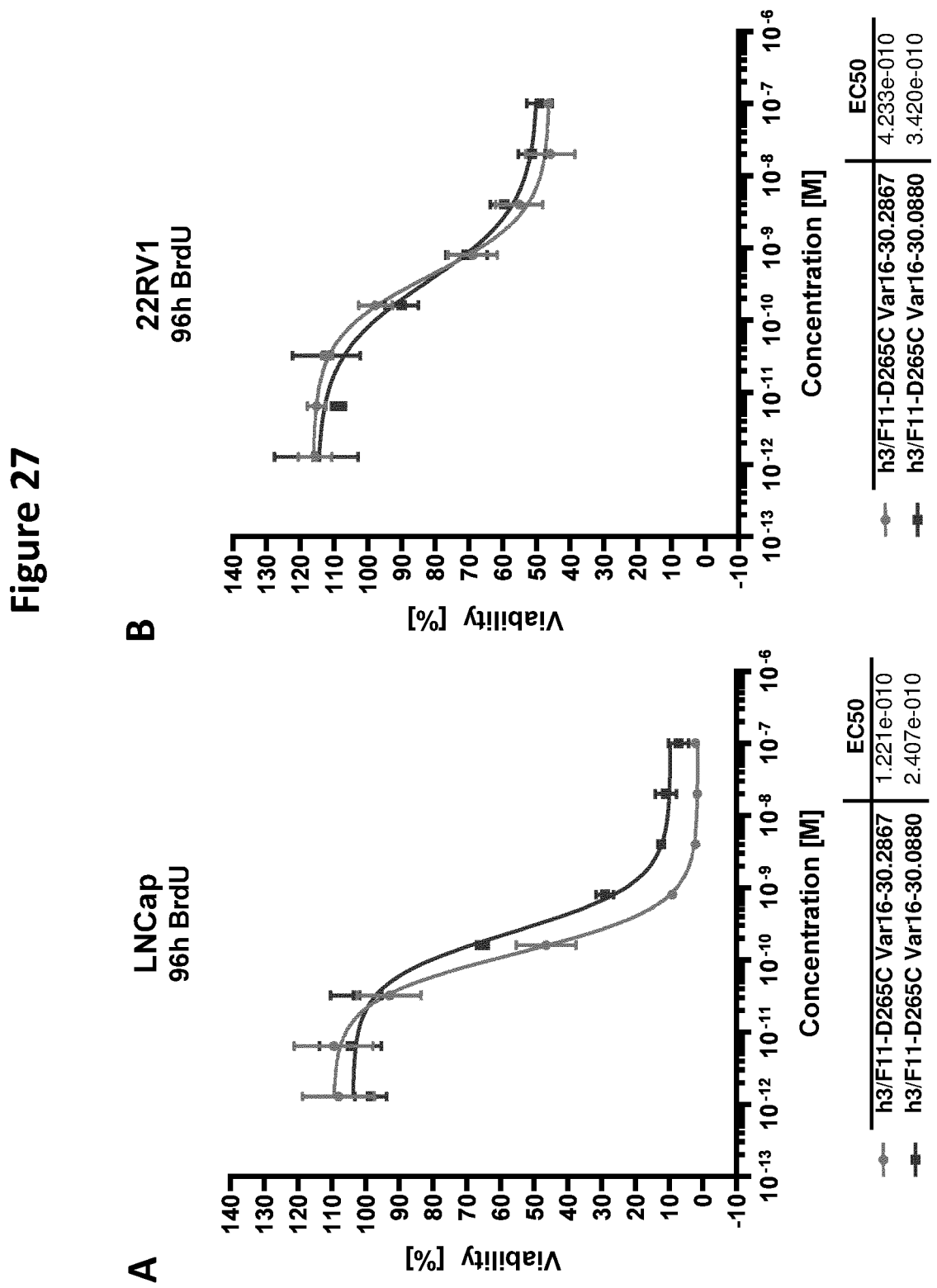
FIG. 27 graphically depicts the cytotoxic activity in vitro of ADC compounds h3/F11-D265C-Var16-30.2867 and h3/F11-D265C-Var16-30.0880, respectively, on (A) LNCap, (B) 22RV1, and (C) PC3 cell lines in 96 h-BrdU assay.
Figure 27:
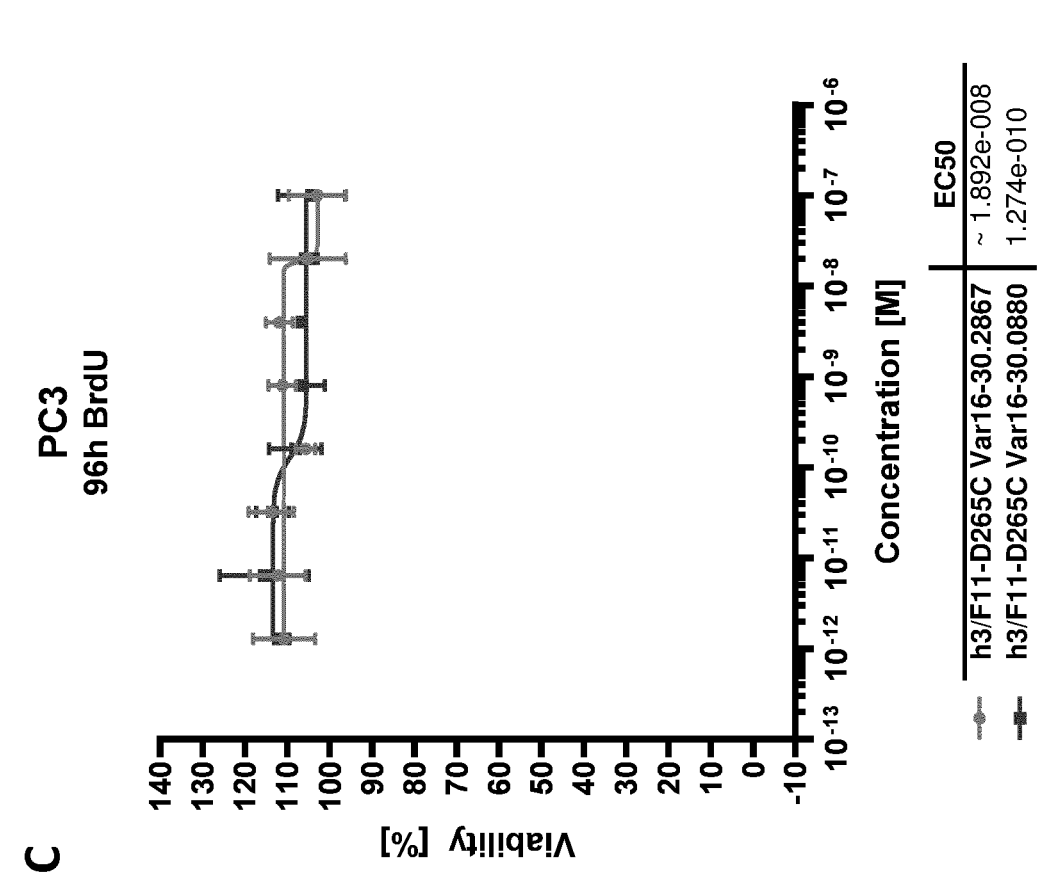

The cytotoxic activity in vitro of an anti-PSMA antibody carrying a D265C mutation (h3/F11-D265C-Var16) conjugated to compound 30.2867 (formula (A)), and to compound 30.0880 (formula (B)), respectively, via its D265C residue was tested on LNCap-, 22RV1-(both PSMA-positive), and PC3 (PSMA-negative) cell lines (FIG. 27). The compound h3/F11-D265C-Var16-30.2867 slightly outperformed h3/F11-D265C-Var16-30.0880 on one out of two tested cell lines. No cytotoxic potential was observed on the PSMA-negative cell line PC3.

Example 14: Stability of Anti-PSMA-ADCs in Human, Mouse, and Cynomolgus Plasma ADC conjugates h3/F11-D265C-Var16-30.2867 and h3/F11-D265C-Var16-30.0880, respectively, directed to PSMA antigen, were incubated in human, mouse, and cynomolgus plasma, and phosphate buffered saline (PBS, control), respectively, for 0, 4, and 10 days. Samples were subjected to sodium dodecyl sulphate (SDS) polyacryl amide (PAA) gel electrophoresis SDS-PAGE), and antibody heavy chain molecules were detected with an amanitin-specific polyclonal antiserum by Western blotting. h3/F11-D265C-Var16-30.2867 showed higher plasma stability over all tested plasma species compared to h3/F11-D265C-Var16-30.0880. h3/F11-D265C-Var16-30.2867 showed lower stability in mouse plasma than in human plasma and cynomolgus plasma, respectively.

Example 15: Efficacy of Anti-PSMA-ADCs in Mouse Xenograft Tumor Model In Vivo In the LNCap xenograft tumor mouse model, male CB17 SCID mice were inoculated with $2.5 \times 10^6$ LNCap prostate carcinoma cells per mouse subcutaneously in the right flank. At a mean tumor vol. of ~150 mm$^3$, animals were allocated to groups on day 0. On the same day, the animals received a single intravenous dose of amanitin-based anti-PSMA antibody drug conjugates (ADCs). Tumor volume and body weight were determined twice per week.

Figure 28:
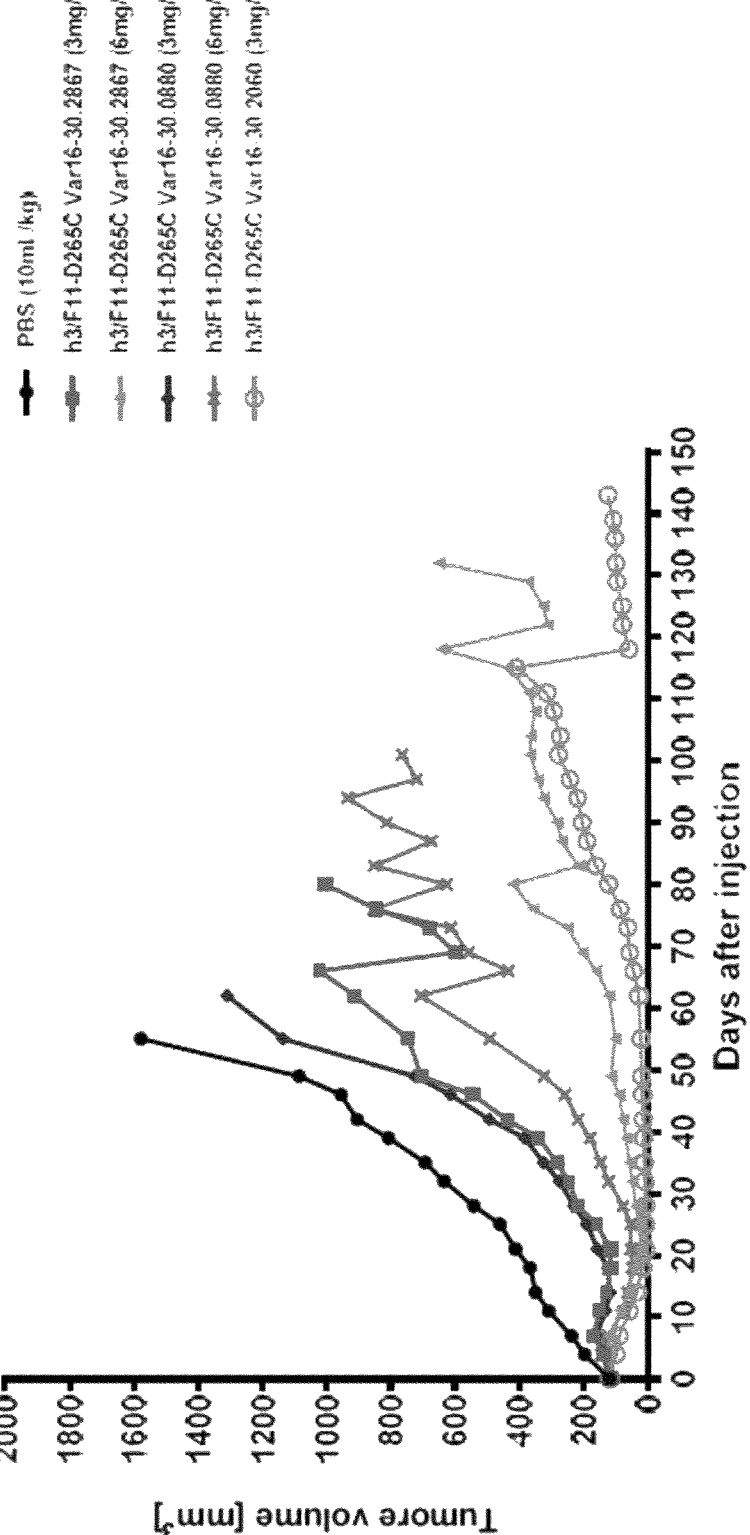
FIG. 28 graphically depicts results of cytotoxic efficacy analysis of Anti-PSMA-ADCs in LNCap-cell xenograft tumor mouse models in vivo using ADC compounds h3/F11-D265C-Var16-30.2867, h3/F11-D265C-Var16-30.0880 and h3/F11-D265C-Var16-30.2060.

As shown in FIG. 28, the efficacy of h3/F11-D265C-Var16-30.2867 in vivo was better than that of h3/F11-D265C-Var16-30.0880.

Example 16: Tolerability Study in Monkeys

Figure 29:
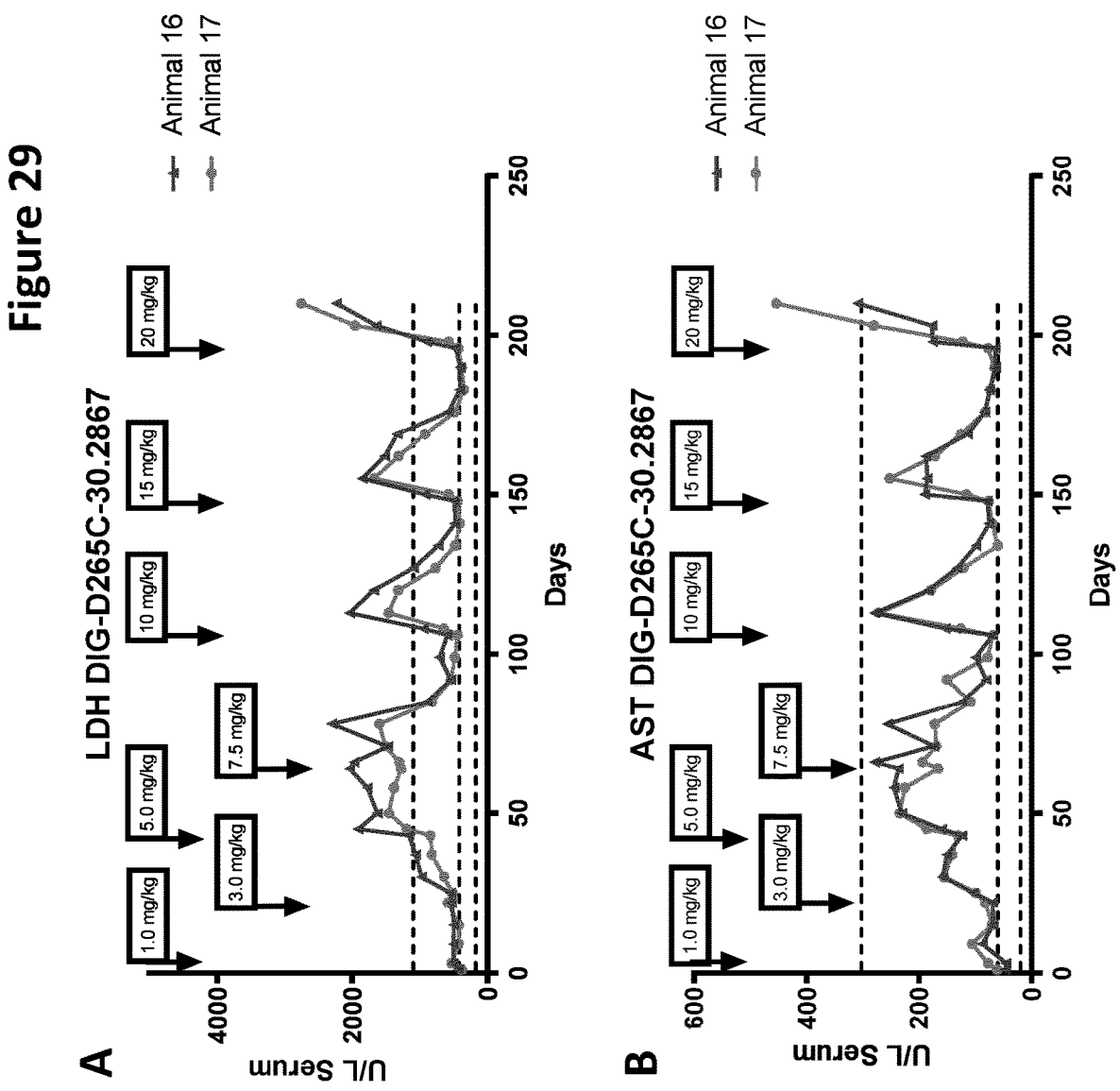
FIG. 29 graphically depicts results of a tolerability study in monkeys using the Anti-Digoxigenin ADC compound DIG-D265C-30.2867 at different doses between 1 mg/kg and 20 mg/kg. Results for assessment of LDH, AST, ALT parameters are shown.
Figure 29:
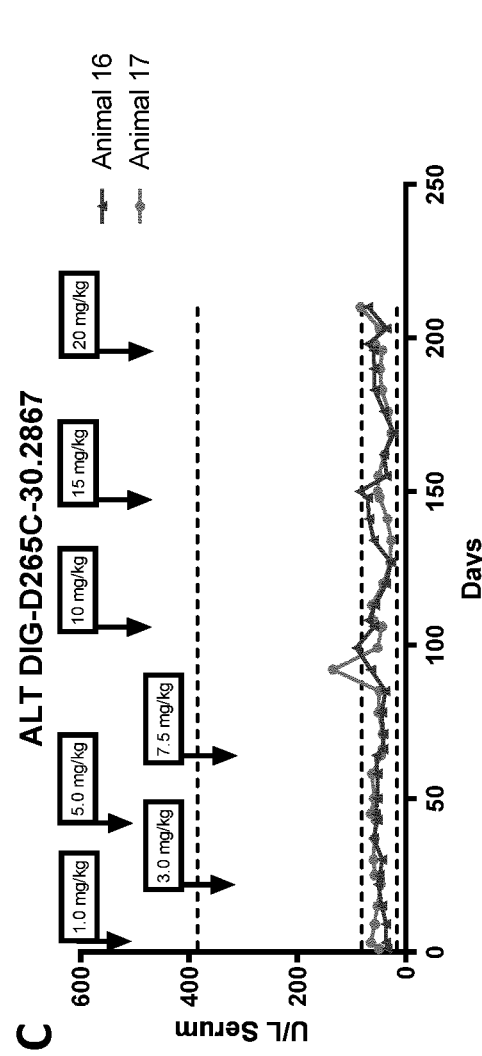
Figure 30:
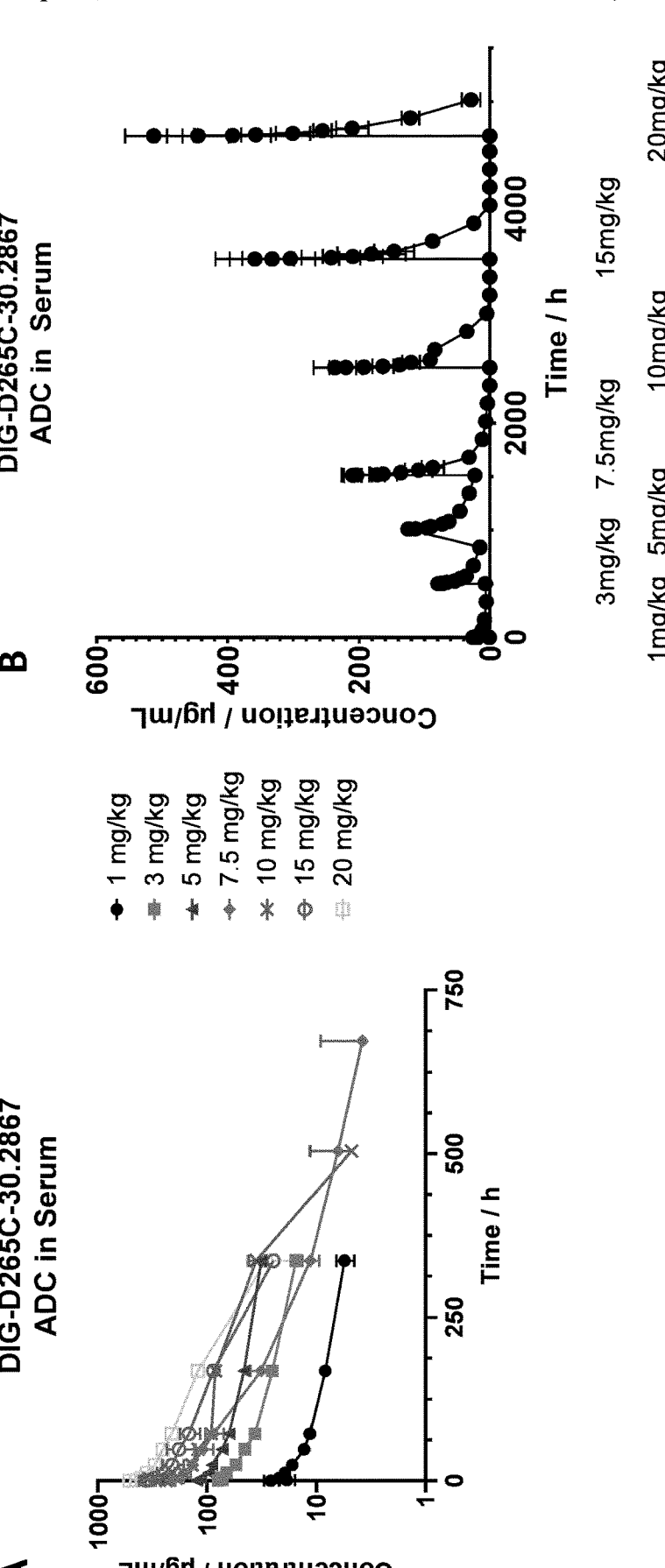
FIG. 30 graphically depicts results of a tolerability study in monkeys using DIG-D265C-30.2867. Pharmacokinetic data for the ADC in serum are shown.
Figure 31:
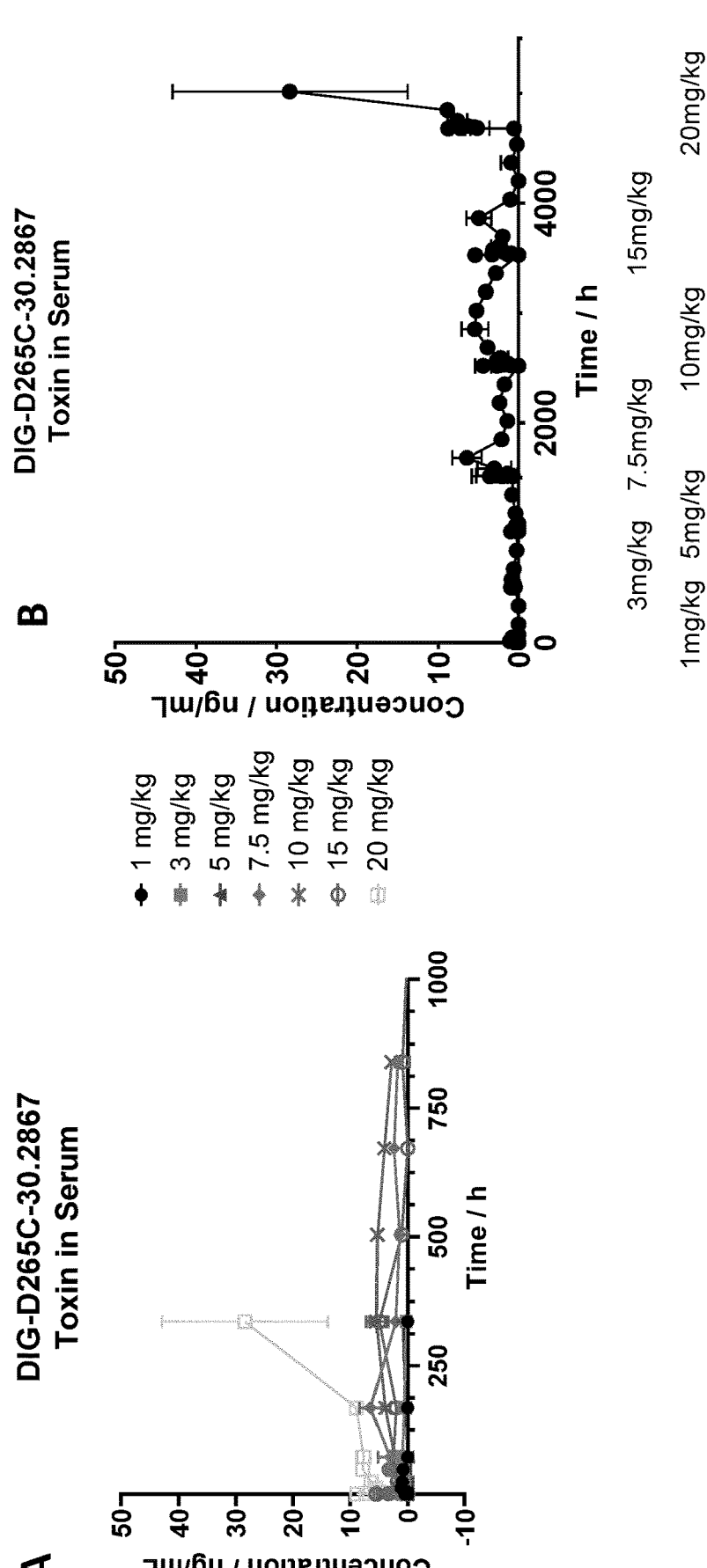
FIG. 31 graphically depicts results of a tolerability study in monkeys using DIG-D265C-30.2867. Pharmacokinetic data for the amatoxin in serum are shown.

A tolerability study in monkeys with a non-binding Anti-Digoxigenin ADC (DIG-D265C-30.2867) using escalating doses from 1 mg/kg to 20 mg/kg was performed. Results for assessment of LDH, AST, ALT parameters indicated a good tolerability (FIG. 29). Pharmacokinetic data for the ADC and the amatoxin in serum are shown in FIG. 30 and FIG. 31, respectively. Both animals died at 15 days and 19 days, respectively, after the last dosing (20 mg/kg). The maximum tolerated dose (MTD) was assessed to be 15 mg/kg<MTD<20 mg/kg.

Example 17: Cytotoxicity Assay In Vitro Using Structurally Different Amanitin Derivatives The cytotoxic activity in vitro of ADCs listed in Table 8, which are comprising an anti-Her2 antibody carrying a D265C mutation (T-D265C, anti-Her2-D265C) conjugated to structurally different amanitin derivatives via its D265C residue was tested on JIMT-1 cells, NCI-N87 cells and SKBR-3 cells.

TABLE 8

Her2-specific ADCs comprising structurally different amanitin derivatives

| ADC Compound | DAR | Specification |
|---|---|---|
| anti-Her2-D265C-30.2060 | 1.92 | SO; 6-OH-Trp; cleavable VA linker at aa1 |
| anti-Her2-D265C-30.2115 | 2.0 | S; Trp; cleavable VA linker at aa1 |
| anti-Her2-D265C-30.2347 | 1.90 | S; 6-OH-Trp; cleavable VA linker at aa1 |
| anti-Her2-D265C-30.1699 | 2.0 | SO; 6-OH-Trp; cleavable VA linker at aa4 |
| anti-Her2-D265C-30.2371 | 2.0 | S; 6-OH-Trp; cleavable VA linker at aa4 |
| anti-Her2-D265C-30.0880 | 2.0 | SO; 6-OH-Trp; C6 linker at aa4 |
| anti-Her2-D265C-30.2867 | 2.0 | S; 6-OH-Trp; C6 linker at aa4 |

Figure 32:
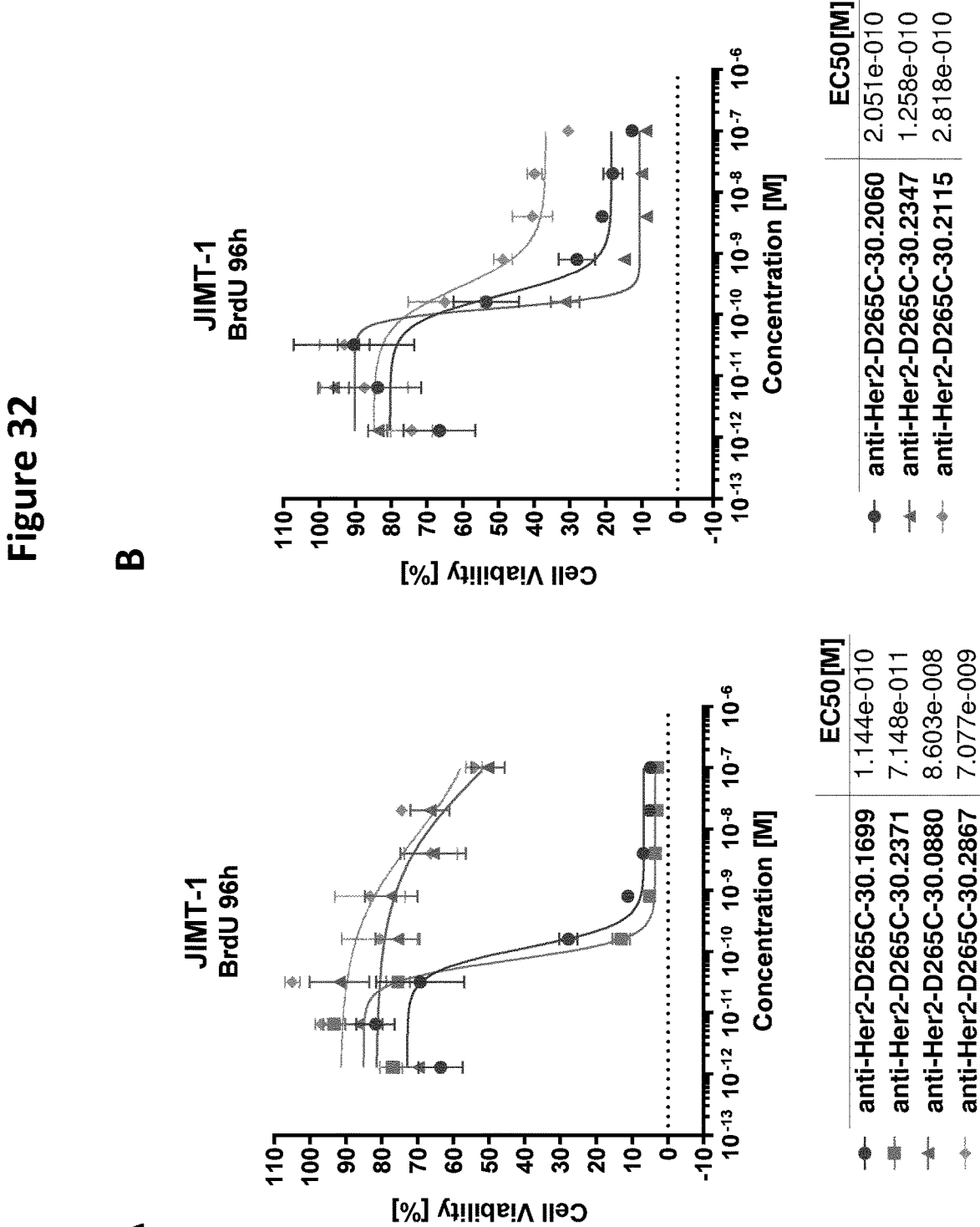
FIG. 32 graphically depicts the cytotoxic activity in vitro of ADC compounds comprising an anti-Her2 antibody with a D265C mutation (T-D265C) conjugated to structurally different amanitin derivatives on JIMT-1 cells (A, B).
Figure 33:
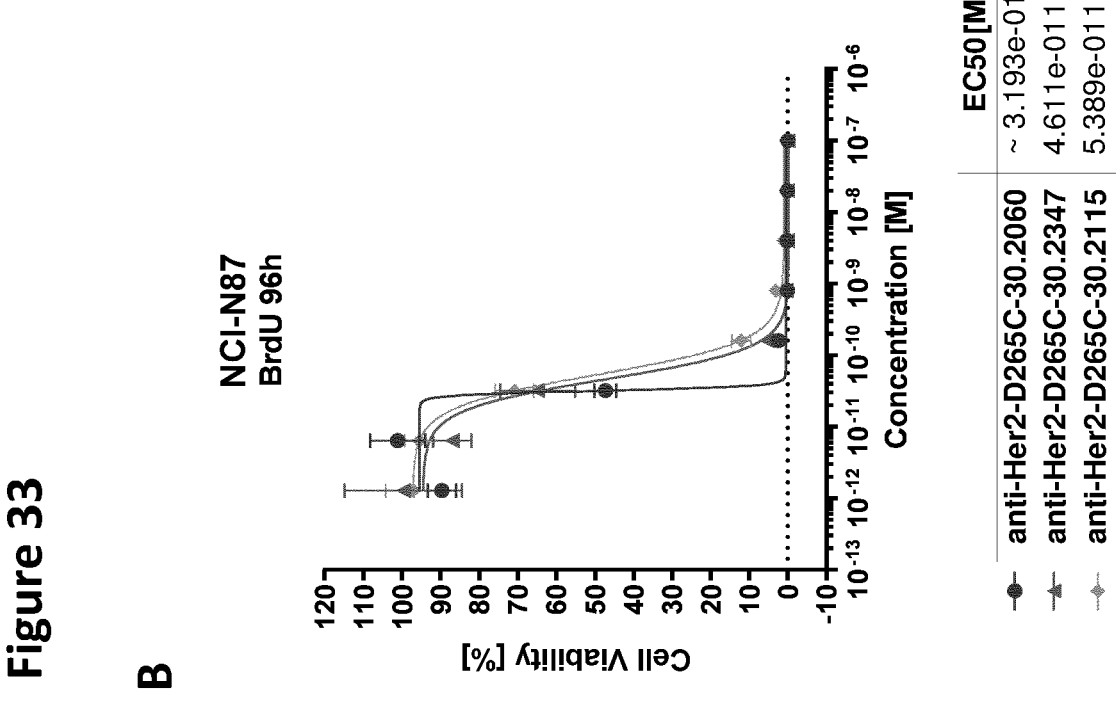
FIG. 33 graphically depicts the cytotoxic activity in vitro of ADC compounds comprising an anti-Her2 antibody with a D265C mutation (T-D265C) conjugated to structurally different amanitin derivatives on NCI-N87 cells (A, B).
Figure 33:
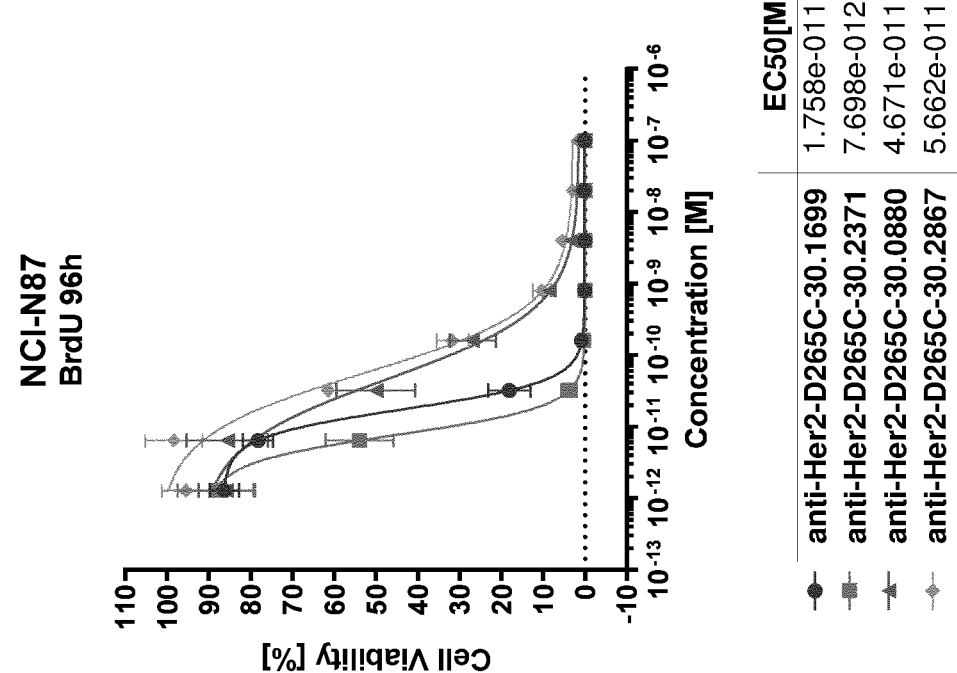
Figure 34:
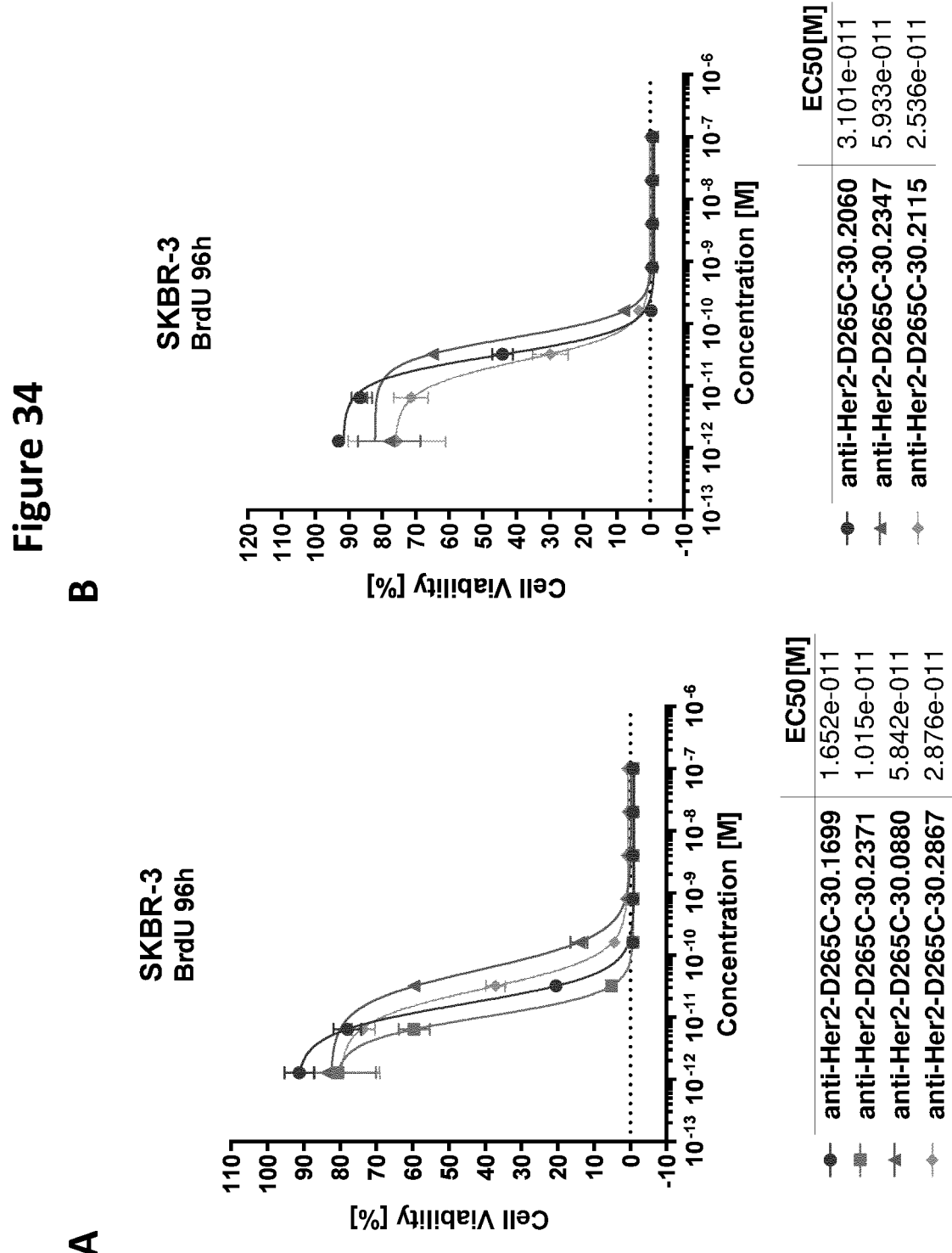
FIG. 34 graphically depicts the cytotoxic activity in vitro of ADC compounds comprising an anti-Her2 antibody with a D265C mutation (T-D265C) conjugated to structurally different amanitin derivatives on SKBR-3 cells (A, B).

Cytotoxic efficacies of respective ADCs on JIMT-1 cells (FIG. 32), NCI-N87 cells (FIG. 33) and SKBR-3 cells (FIG. 34), respectively, are shown in Table 9.

TABLE 9

Cytotoxic activities of Her2-specific ADCs comprising structurally different amanitin derivatives

| ADC Compound | EC50 [pM] on JIMT-1 | EC50 [pM] on NCI-N87 | EC50 [pM] on SKBR-3 | MTD [mg/kg] |
|---|---|---|---|---|
| anti-Her2-D265C-30.2060 | 205 (nfb: 20%) | 32 | 31 | ≥30 |
| anti-Her2-D265C-30.2115 | 282 (nfb: 40%) | 54 | 25 | ≥25 |
| anti-Her2-D265C-30.2347 | 126 (nfb: 10%) | 46 | 59 | ≥10 (<25) |
| anti-Her2-D265C-30.1699 | 114 | 18 | 17 | 15 |
| anti-Her2-D265C-30.2371 | 71 | 8 | 10 | ≥10 (<25) |
| anti-Her2-D265C-30.0880 | 86000 (nfb: 50%) | 47 | 58 | ≥60 |
| anti-Her2-D265C-30.2867 | 7077 (nfb: 50%) | 57 | 29 | ≥80 |

The cytotoxic activity in vitro of ADCs listed in Table 10, which are comprising an anti-PSMA antibody carrying a 0265 mutation (h3/F11-D265C-Var16, anti-PSMA-D265C) conjugated to structurally different amanitin derivatives via its 02650 residue was tested on LNCap- and 22RV1 cell lines (both PSMA-positive).

TABLE 10

PSMA-specific ADCs comprising structurally different amanitin derivatives

| ADC Compound | DAR | Specification |
|---|---|---|
| anti-PSMA-D265C-30.2060 | 1.89 | SO; 6-OH-Trp; cleavable VA linker at aa1 |
| anti-PSMA-D265C-30.2115 | 2.0 | S; Trp; cleavable VA linker at aa1 |
| anti-PSMA-D265C-30.2347 | 1.91 | S; 6-OH-Trp; cleavable VA linker at aa1 |
| anti-PSMA-D265C-30.1699 | 2.0 | SO; 6-OH-Trp; cleavable VA linker at aa4 |
| anti-PSMA-D265C-30.2371 | 2.0 | S; 6-OH-Trp; cleavable VA linker at aa4 |
| anti-PSMA-D265C-30.0880 | 2.0 | SO; 6-OH-Trp; C6 linker at aa4 |
| anti-PSMA-D265C-30.2867 | 2.0 | S; 6-OH-Trp; C6 linker at aa4 |

Figure 36:
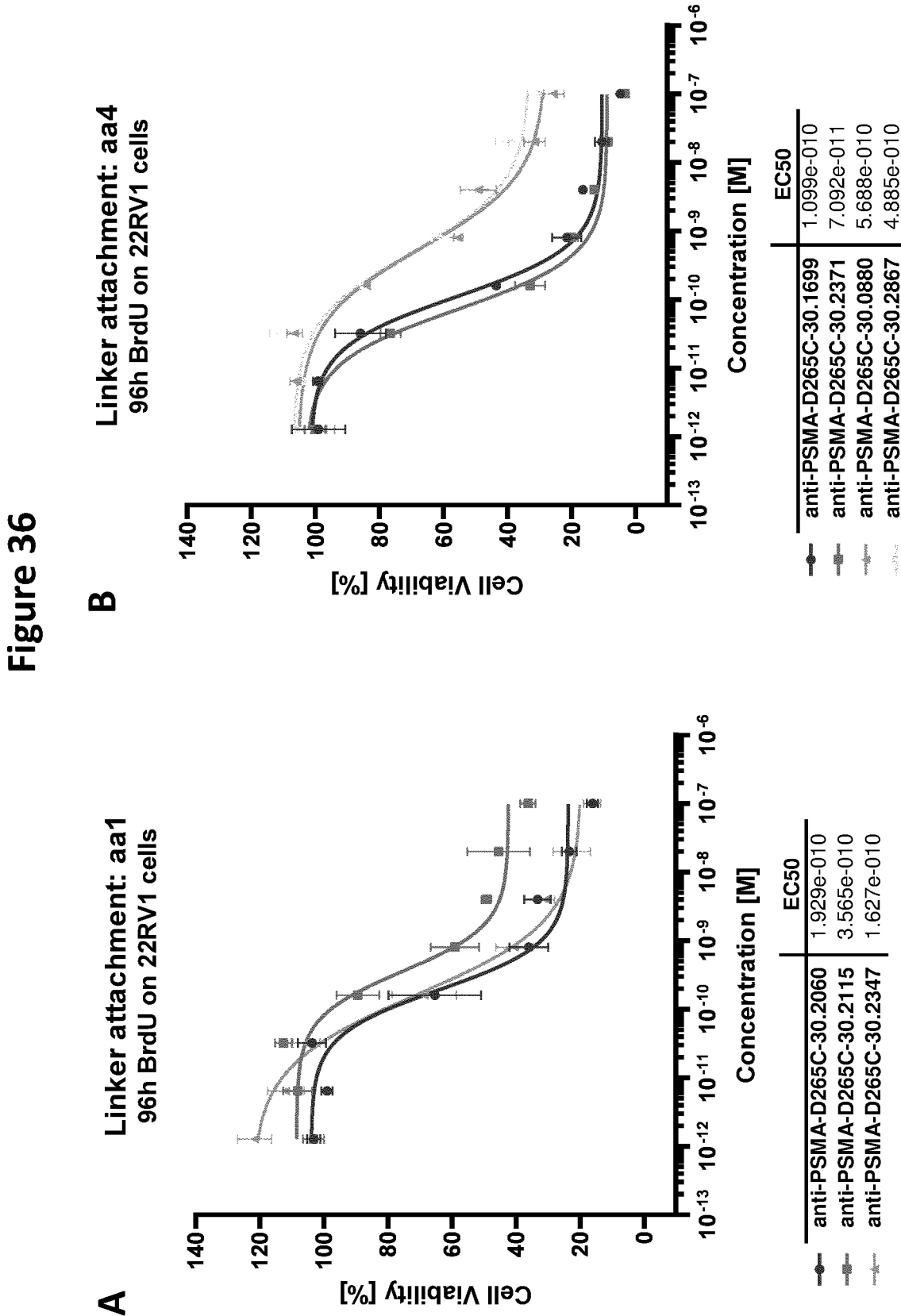
FIG. 36 graphically depicts the cytotoxic activity in vitro of ADC compounds comprising an anti-PSMA antibody with a D265C mutation (h3/F11-D265C-Var16) conjugated to structurally different amanitin derivatives on 22RV1 cells (A, B).
Figure 37:
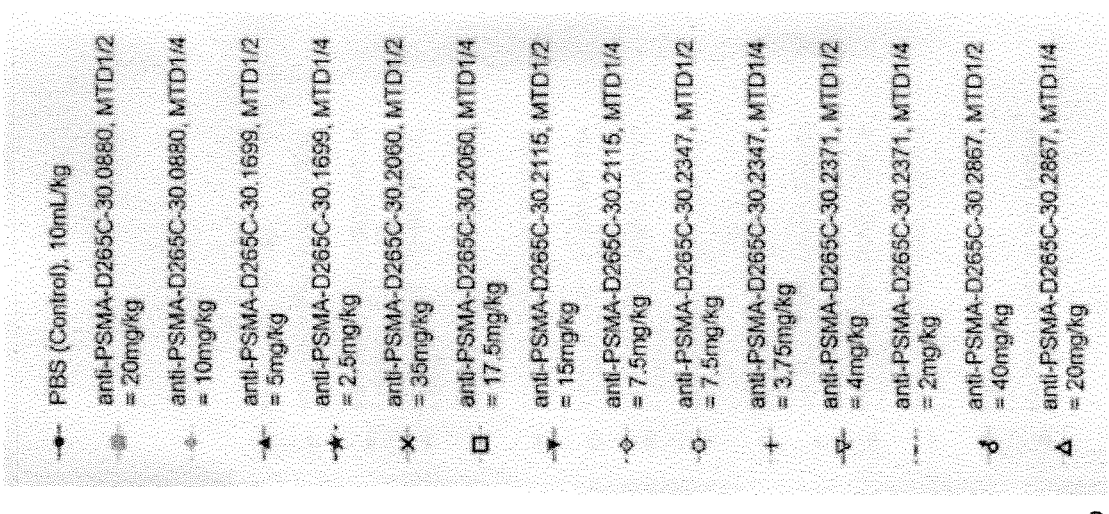
FIG. 37 graphically depicts results of cytotoxic efficacy analysis of various Anti-PSMA-ADCs comprising structurally different amanitin derivatives in an LNCap-cell xenograft tumor mouse model in vivo. Means+/−SEM for all groups at maximum tolerated dose (MTD) ½ and ¼ are shown.
Figure 37:
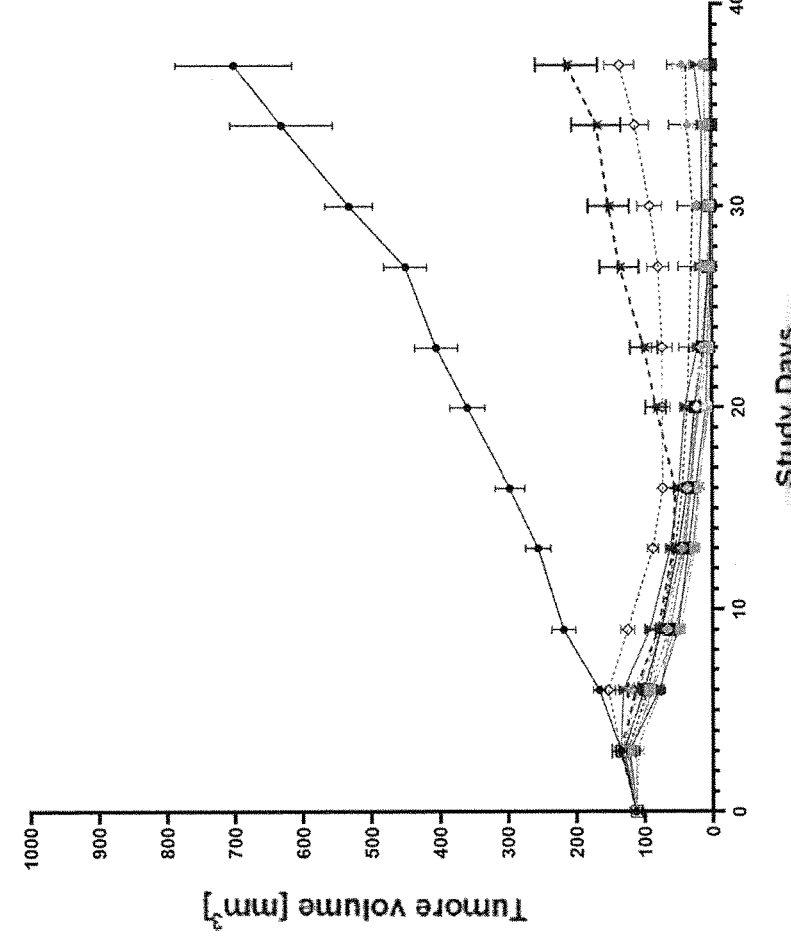
Figure 38:
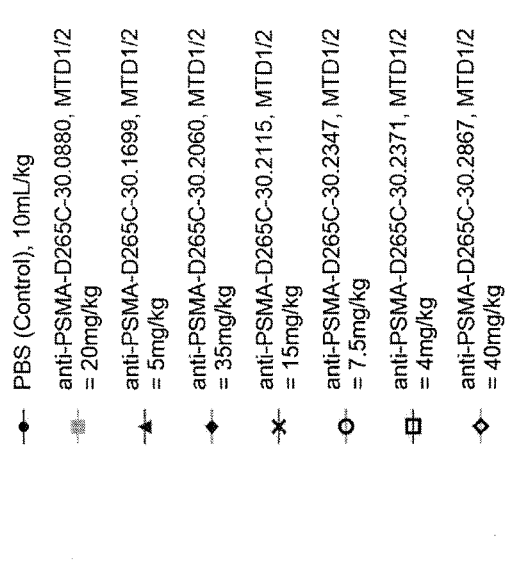
FIG. 38 graphically depicts results of cytotoxic efficacy analysis of various Anti-PSMA-ADCs comprising structurally different amanitin derivatives in an LNCap-cell xenograft tumor mouse model in vivo. Means+/−SEM for all groups at maximum tolerated dose (MTD) ½ are shown.
Figure 38:
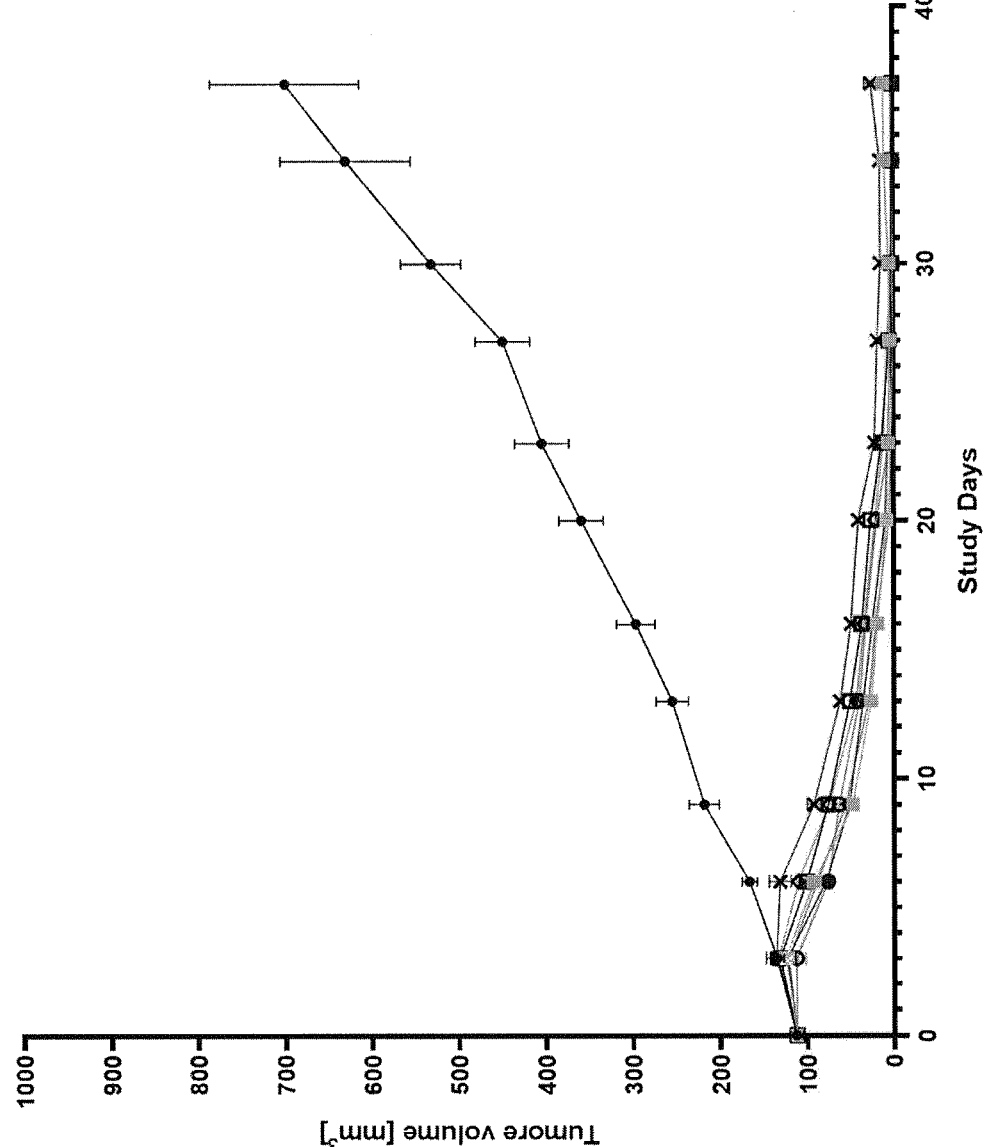
Figure 39:
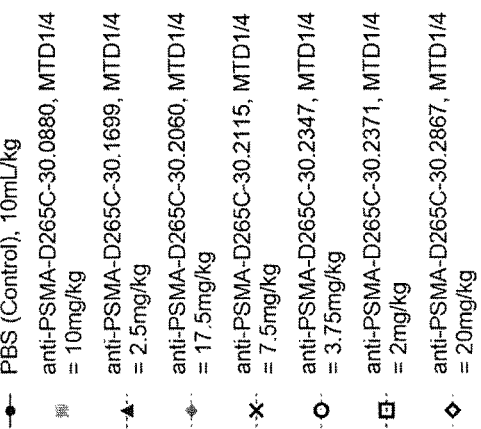
FIG. 39 graphically depicts results of cytotoxic efficacy analysis of various Anti-PSMA-ADCs comprising structurally different amanitin derivatives in an LNCap-cell xenograft tumor mouse model in vivo. Means+/−SEM for all groups at maximum tolerated dose (MTD) ¼ are shown.
Figure 39:
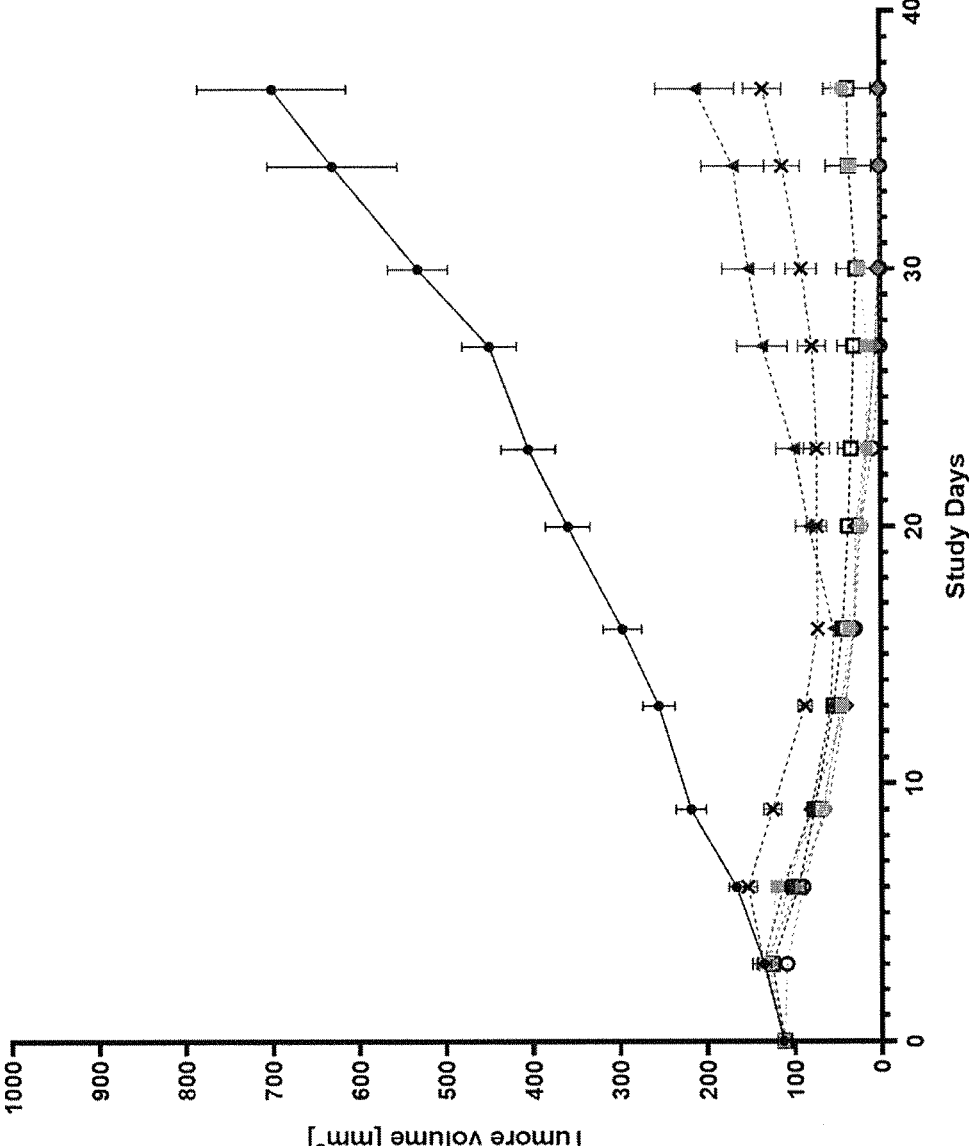
Figure 40:
FIG. 40 graphically depicts results of cytotoxic efficacy analysis of various Anti-PSMA-ADCs comprising structurally different amanitin derivatives in an LNCap-cell xenograft tumor mouse model in vivo. Means+/−SEM for ADCs with linker attachment at amino acid 1 of the amatoxin at maximum tolerated dose (MTD) ½ and ¼ are shown.
Figure 41:
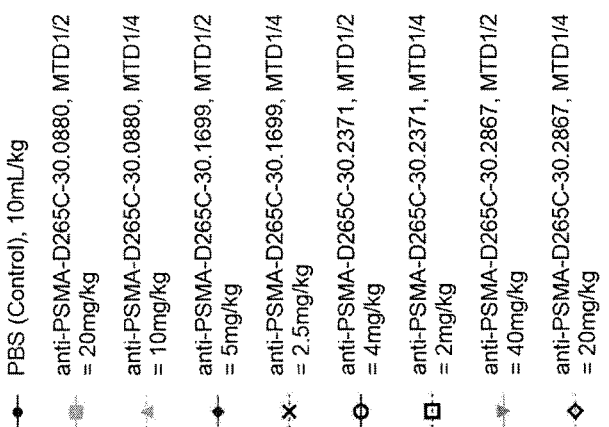
FIG. 41 graphically depicts results of cytotoxic efficacy analysis of various Anti-PSMA-ADCs comprising structurally different amanitin derivatives in an LNCap-cell xenograft tumor mouse model in vivo. Means+/−SEM for ADCs with linker attachment at amino acid 4 of the amatoxin at maximum tolerated dose (MTD) ½ and ¼ are shown.
Figure 41:
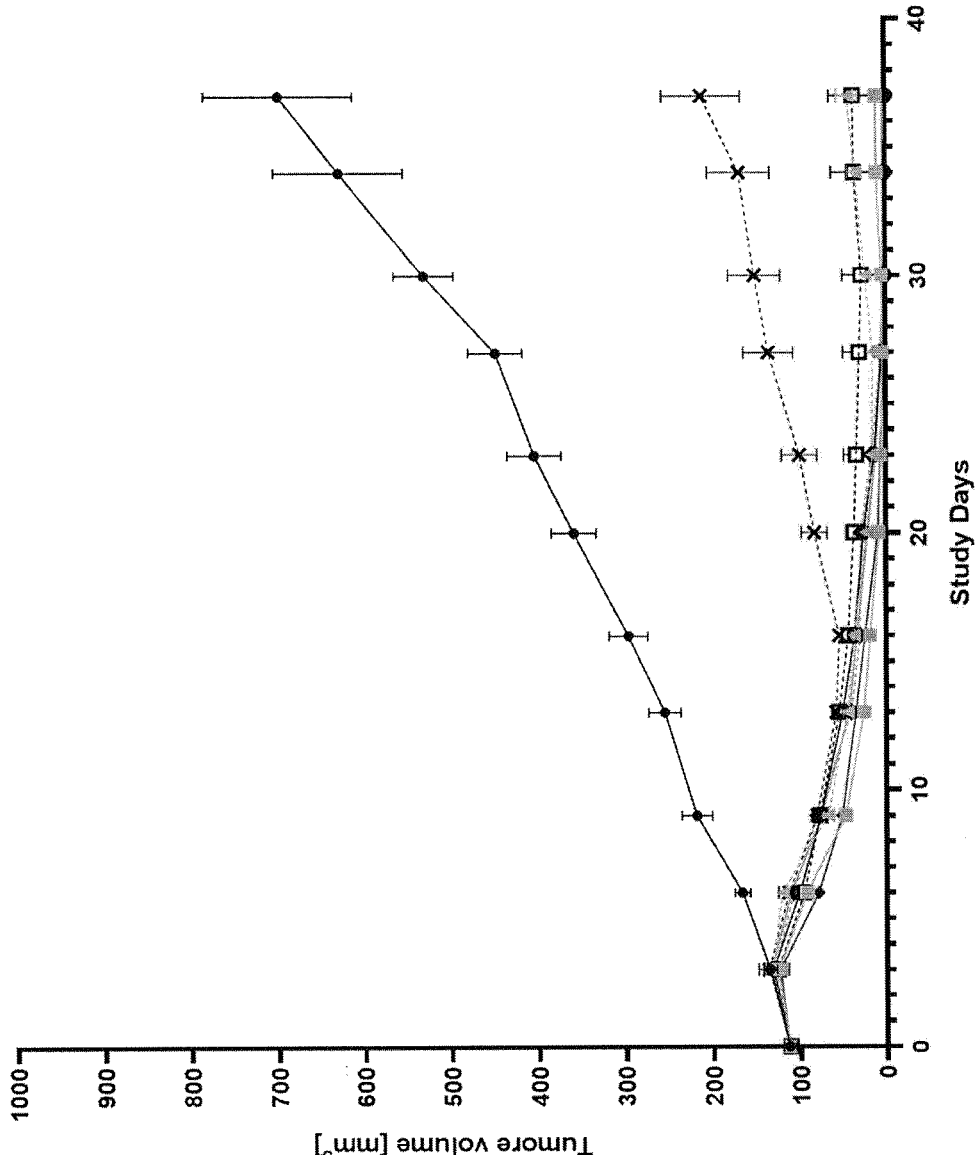
Figure 42:
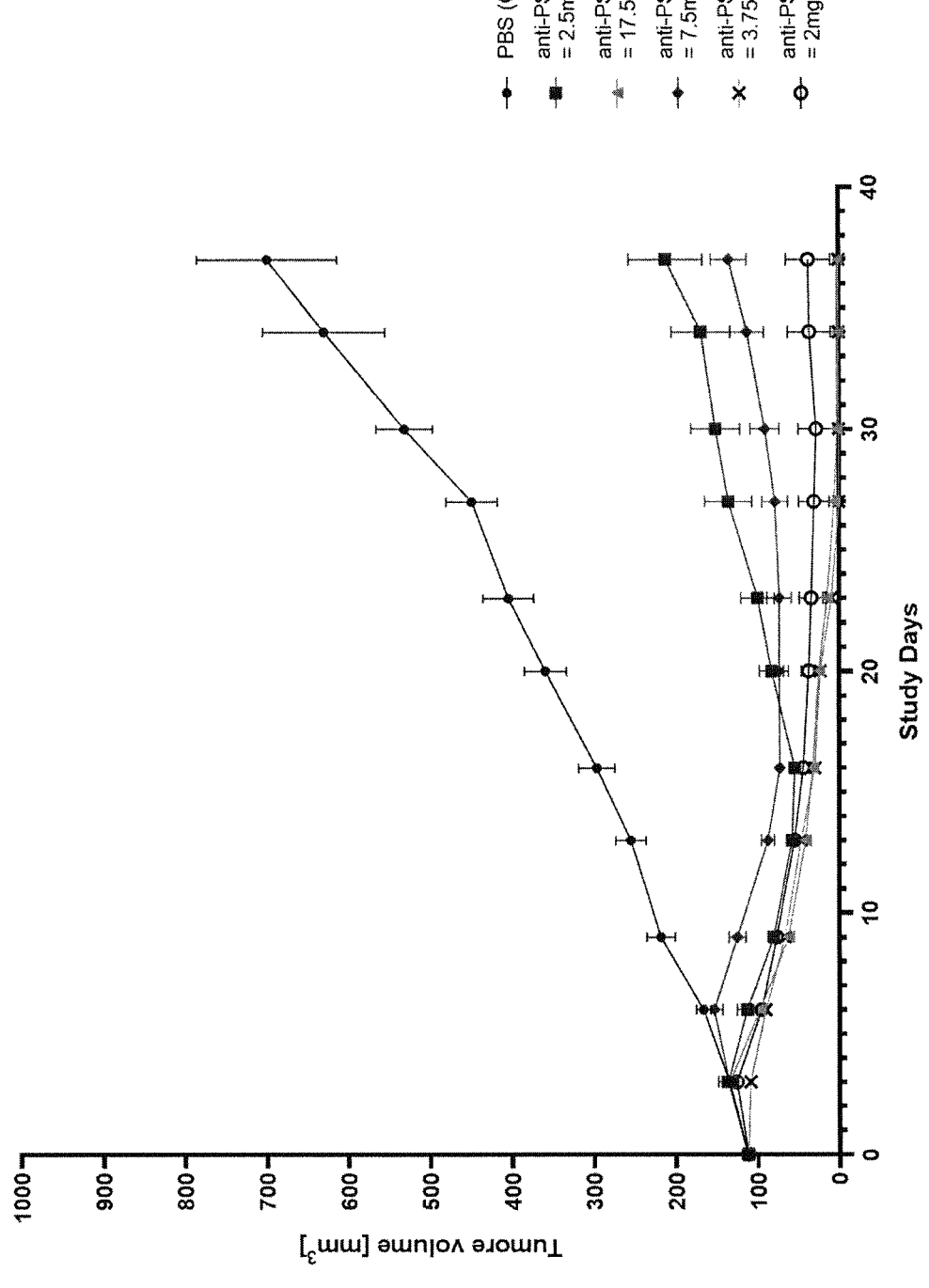
FIG. 42 graphically depicts results of cytotoxic efficacy analysis of various Anti-PSMA-ADCs comprising structurally different amanitin derivatives in an LNCap-cell xenograft tumor mouse model in vivo. Means+/−SEM for ADCs with cleavable linkers at maximum tolerated dose (MTD) % are shown.

Cytotoxic efficacies of respective ADCs on LNCap cells (FIG. 35) and 22RV1 cells (FIG. 36), respectively, are shown in Table 11.

TABLE 11

Cytotoxic activities of PSMA-specific ADCs comprising structurally different amanitin derivatives

| ADC Compound | EC50 [pM] on LNCap | EC50 [pM] on 22RV1 | MTD [mg/kg] |
|---|---|---|---|
| anti-PSMA-D265C-30.2060 | 32 | 193 (20%) | 50< MTD <80 |
| anti-PSMA-D265C-30.2115 | 273 | 357 (40%) | 30 |
| anti-PSMA-D265C-30.2347 | 43 | 163 (20%) | 15 |
| anti-PSMA-D265C-30.1699 | 22 | 110 (10%) | 10 |
| anti-PSMA-D265C-30.2371 | 14 | 71 (10%) | 8 |
| anti-PSMA-D265C-30.0880 | 107 | 569 (30%) | 30 |
| anti-PSMA-D265C-30.2867 | 47 | 486 (30%) | >80 |

Example 18: Efficacy of Anti-PSMA-ADCs Comprising Structurally Different Amanitin Derivatives in Mouse Xenograft Tumor Model In Vivo In the LNCap xenograft tumor mouse model, male CB17 SCID mice were inoculated with $2.5 \times 10^6$ LNCap prostate carcinoma cells per mouse subcutaneously in the right flank. At a mean tumor vol. of ~150 mm$^3$, animals were allocated to groups on day 0. On the same day, the animals received a single intravenous dose of one of the structurally different amanitin-based anti-PSMA antibody drug conjugates (ADCs) listed in Table 6. Tumor volume and body weight were determined twice per week.

Results for the ADCs comprising differently structured amanitin derivatives are shown in FIGS. 37 to 42 and Table 12. ADCs comprising non-cleavable linkers conjugated to the 6'-hydroxy group of tryptophan (amino acid 4) of the amatoxin, in particular h3/F11-D265C-Var16-30.2867 with a thioether bridge between Trp and Cys, were shown to have a high cytotoxic efficacy in vivo, as compared to ADCs comprising cleavable linkers conjugated to either amino acid 4 or amino acid 1 of the amatoxin.

TABLE 12

Survival rate and tumor load

| Treatment Group | Dosing | Alive Animals | Tumor-free Animals |
|---|---|---|---|
| Vehicle control | | 9/10 | 0/9 |
| anti-PSMA-D265C-30.0880 | MTD 1/2 | 10/10 | 5/10 |
| anti-PSMA-D265C-30.0880 | MTD 1/4 | 10/10 | 3/10 |

TABLE 12-continued

| | | Survival rate and tumor load | |
| --- | --- | --- | --- |
| Treatment Group | Dosing | Alive Animals | Tumor-free Animals |
| anti-PSMA-D265C-30.1699 | MTD 1/2 | 10/10 | 10/10 |
| anti-PSMA-D265C-30.1699 | MTD 1/4 | 10/10 | 2/10 |
| anti-PSMA-D265C-30.2060 | MTD 1/2 | 4/10 | 4/4 |
| anti-PSMA-D265C-30.2060 | MTD 1/4 | 10/10 | 9/10 |
| anti-PSMA-D265C-30.2115 | MTD 1/2 | 10/10 | 3/10 |
| anti-PSMA-D265C-30.2115 | MTD 1/4 | 10/10 | 0/10 |
| anti-PSMA-D265C-30.2347 | MTD 1/2 | 10/10 | 10/10 |
| anti-PSMA-D265C-30.2347 | MTD 1/4 | 10/10 | 10/10 |
| anti-PSMA-D265C-30.2371 | MTD 1/2 | 10/10 | 10/10 |
| anti-PSMA-D265C-30.2371 | MTD 1/4 | 9/10 | 7/9 |
| anti-PSMA-D265C-30.2867 | MTD 1/2 | 10/10 | 9/10 |
| anti-PSMA-D265C-30.2867 | MTD 1/4 | 10/10 | 10/10 |

Figure 43:
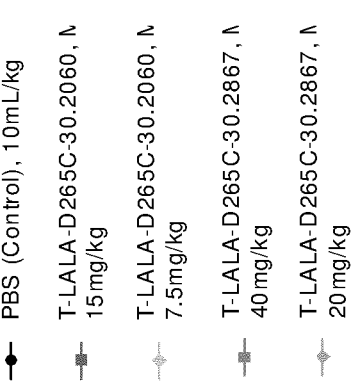
FIG. 43 graphically depicts results of cytotoxic efficacy analysis of anti-Her2 ADCs comprising triple L234A/L235A/D265C mutations and the amatoxin-linker construct HDP30.2060 and HDP30.2867, respectively (T-LALA-D265C-30.2060, T-LALA-D265C-30.2867, respectively) on Her2-positive NCI-N87 cells in a CDX mouse model.
Figure 43:
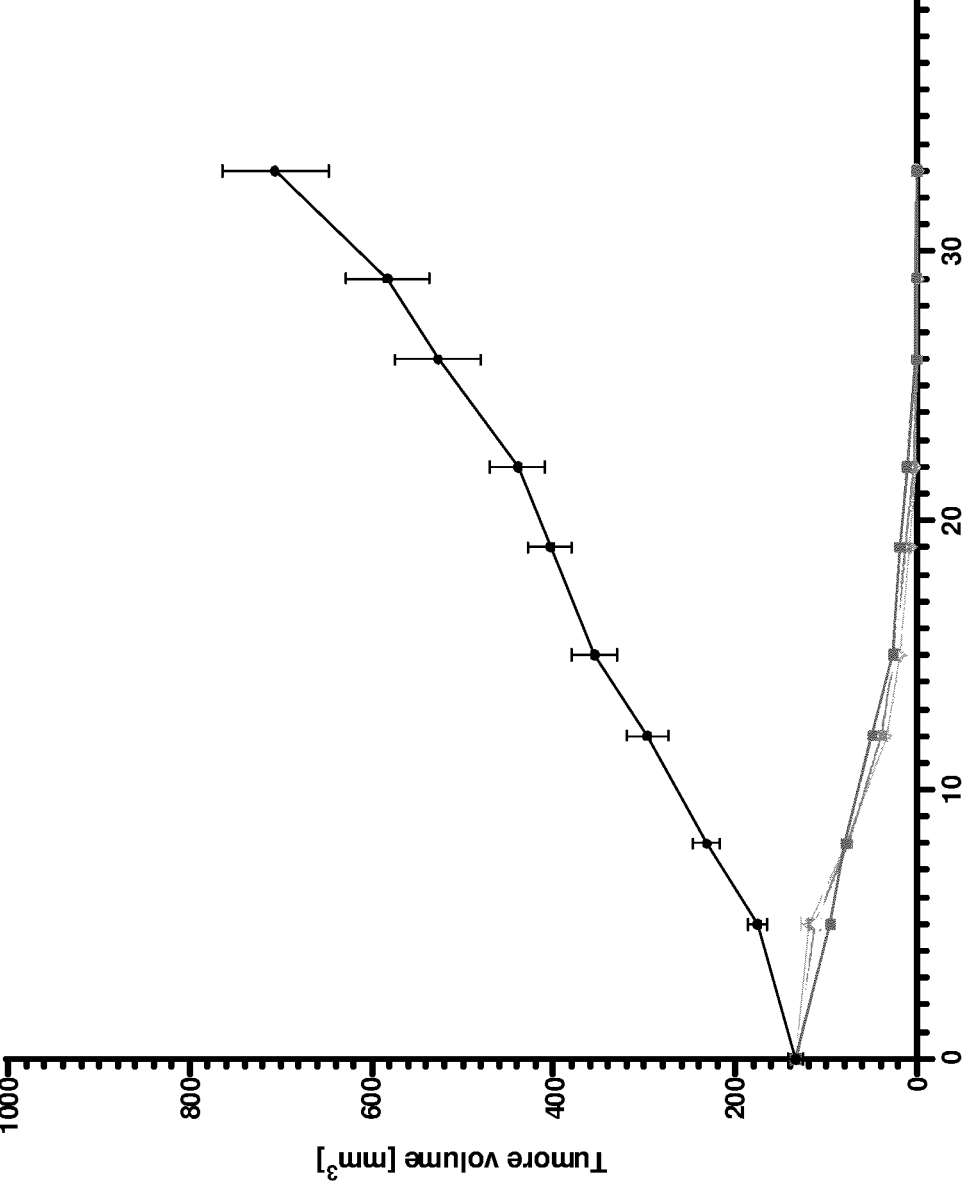
Figure 44:
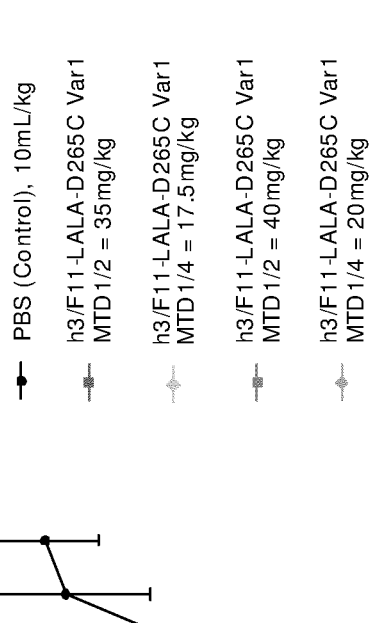
FIG. 44 graphically depicts results of cytotoxic efficacy analysis of anti-PSMA ADCs comprising triple L234A/L235A/D265C mutations and the amatoxin-linker construct HDP30.2060 and HDP30.2867, respectively (h3/F11-LALA-D265C-Var-30.2060, h3/F11-LALA-D265C-Var-30.2867, respectively) on PSMA-positive LNCap cells in a CDX mouse model.
Figure 44:
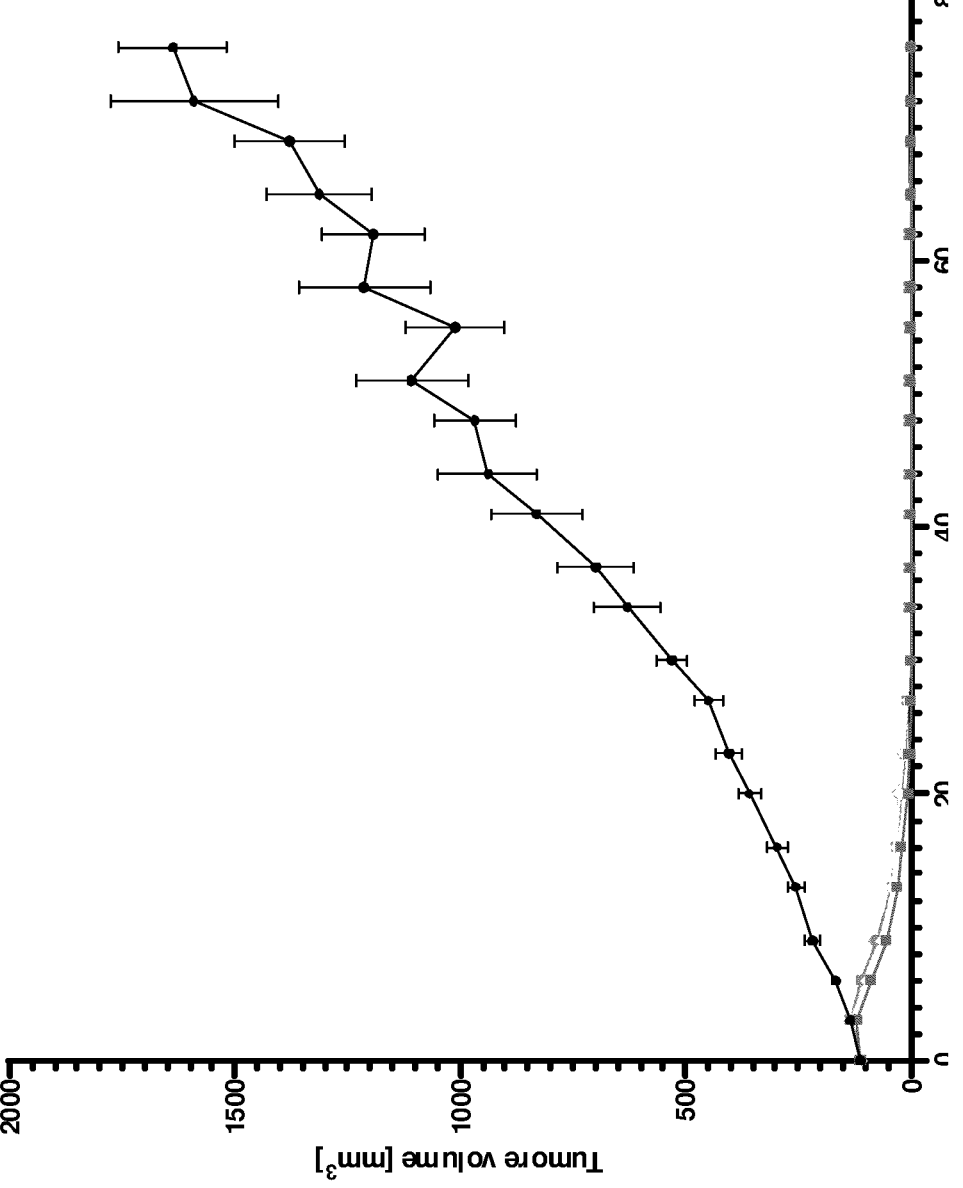
Figure 44:

Example 19: Efficacy of ADCs Comprising Antibodies with LALA and/or D265C Mutation The efficacy of ADCs comprising antibodies having both L234A and L235A mutations and 02650 mutation were tested in cell line-derived tumor xenograft (CDX) mouse models. Anti-Her2 ADCs comprising the triple L234A/L235A/D265C mutations and the amatoxin-linker construct HDP30.2060 and HDP30.2867, respectively (T-LALA-0265C-30.2060 and T-LALA-0265C-30.2867, respectively) were tested on Her2-positive NCI-N87 cells. Results are shown in FIG. 43. Anti-PSMA ADCs comprising the triple L234A/L235A/D265C mutations and the amatoxin-linker construct HDP30.2060 and HDP30.2867, respectively (h3/F11-LALA-D265C Var16-30.2060 and h3/F11-LALA-D265C Var16-30.2867, respectively) were tested on PSMA-positive LNCap cells. Results are shown in FIG. 44. In both studies, the ADCs carrying the triple mutation were shown to be efficient in reducing tumor volumes in the respective CDX mouse models.

As compared to ADCs without the L234A/L235A/D265C mutations, with ADCs comprising antibodies having L234A/L235A mutations and the 02650 mutation, the same range of production yields were obtained. Furthermore, the mutations did not have an impact on the conjugation yields obtained with respective antibodies, as compared to antibodies without the mutations.

Example 20: Cytotoxicity Assay In Vitro on Target-Versus Non-Target Cells

Figure 45:
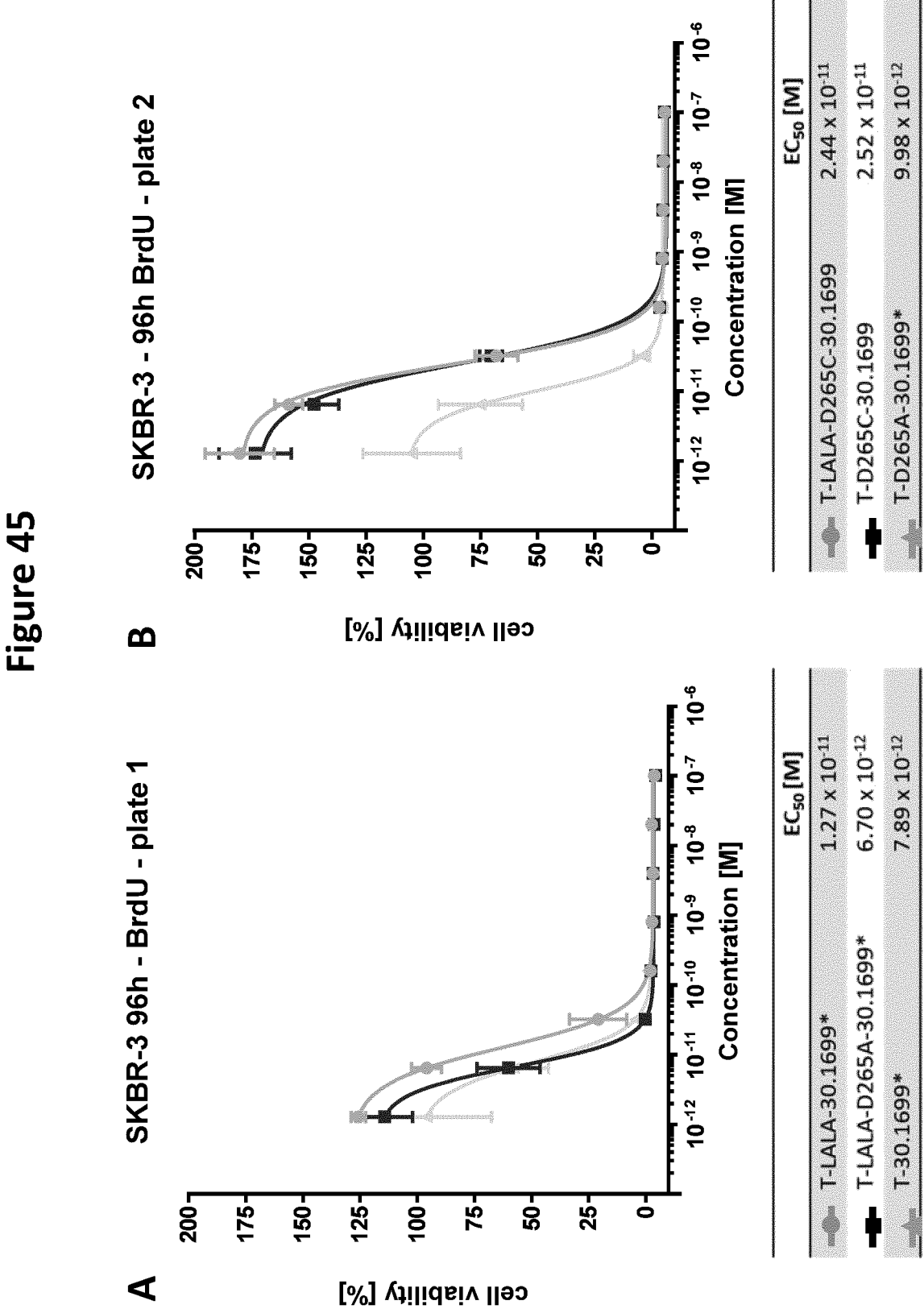
FIG. 45 graphically depicts results of a 96-hour BrdU assay for assessment of the cytotoxic potential in vitro of Her2-specific ADCs comprising an antibody carrying L234A/L235A mutations and/or the D265C mutation, or control mutations, on Her2-positive SKBR-3 cells (A, B, C, D).
Figure 45:
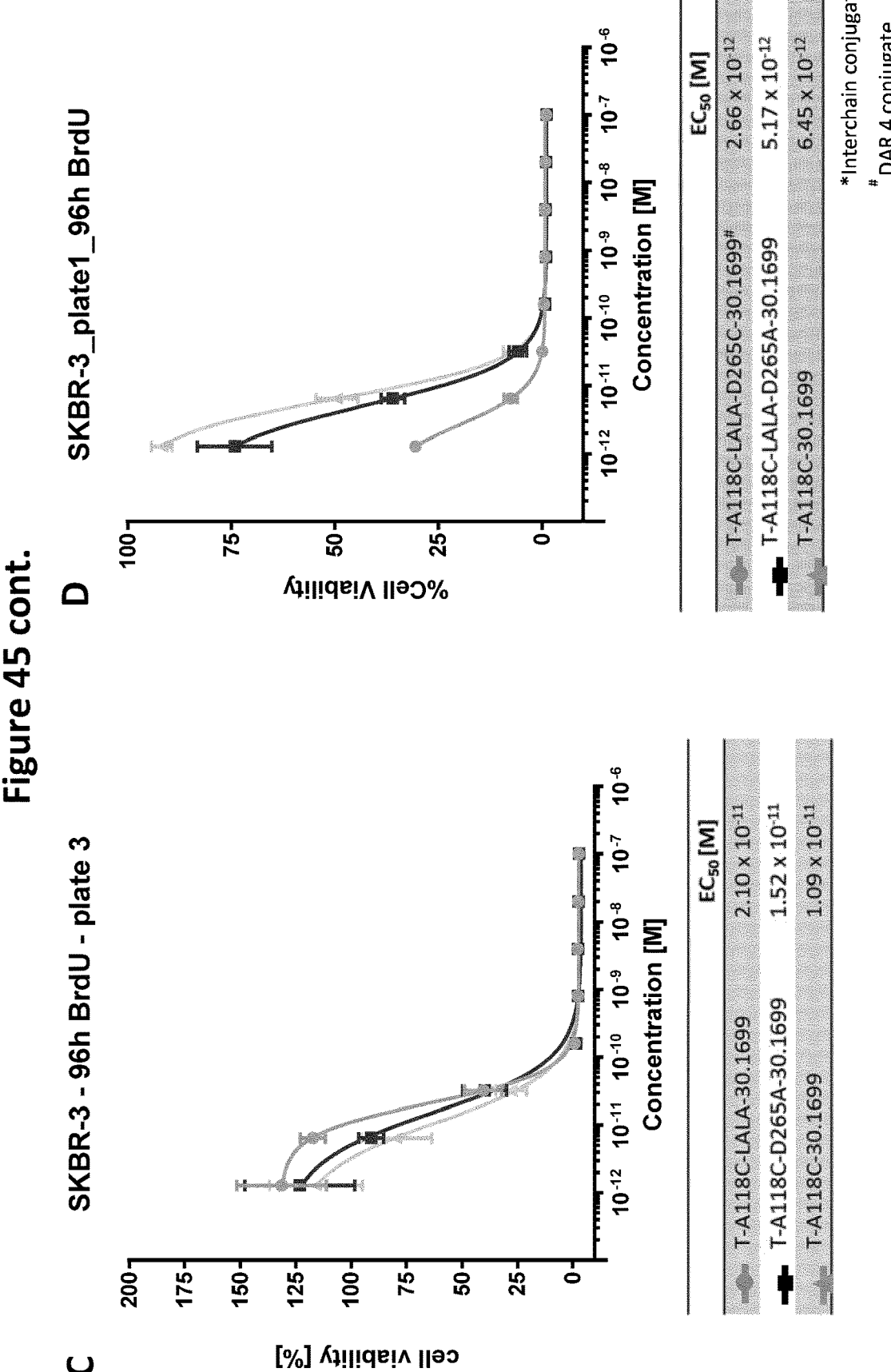

As shown in FIG. 45, the cytotoxic potential in vitro of Her2-specific ADCs comprising an antibody carrying L234A/L235A mutations and/or the D265C mutation, as compared to ADCs without mutation and to control ADCs comprising the same antibody carrying other mutations (A118C, D265A), assessed in a 96-hour BrdU assay on Her2-positive SKBR-3 cells was comparable; full cytotoxicity was observed for all mutants and control ADCs.

Figure 46:
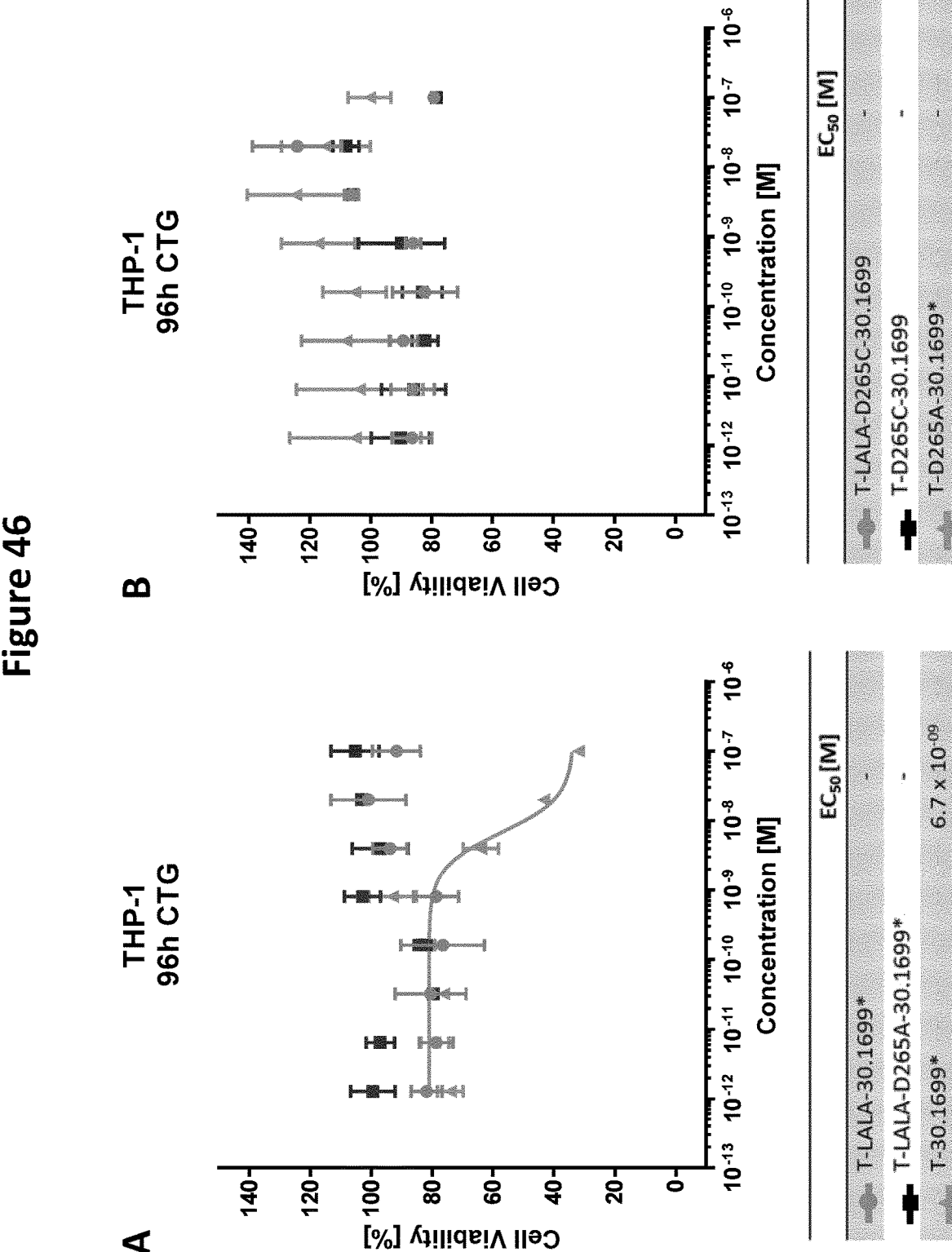
FIG. 46 graphically depicts results of a 96-hour CTG assay for assessment of the cytotoxic potential in vitro of Her2-specific ADCs comprising an antibody carrying L234A/L235A mutations and/or the D265C mutation, or control mutations, on Her2-negative THP-1 cells (A, B, C, D).
Figure 46:
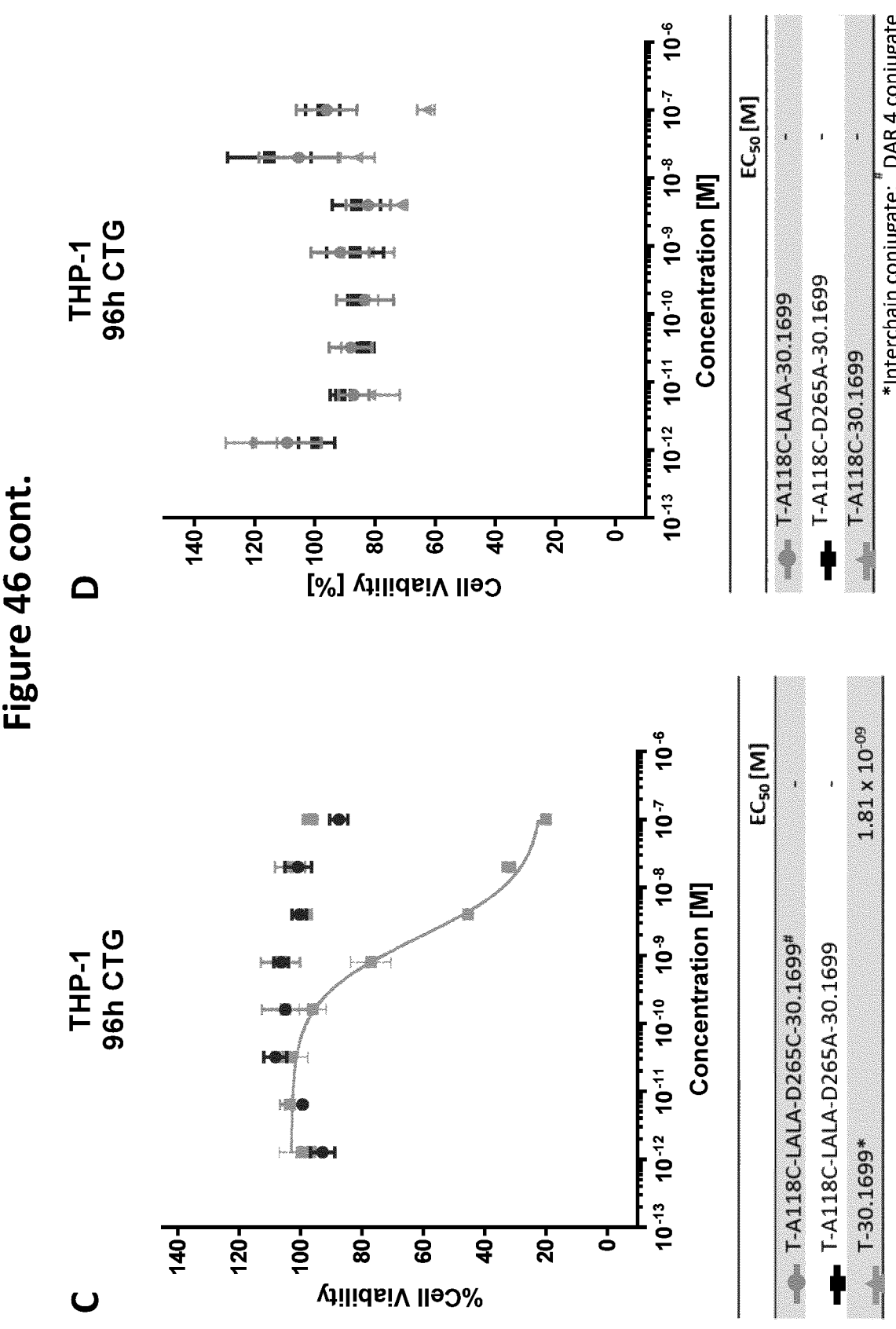
Figure 47:
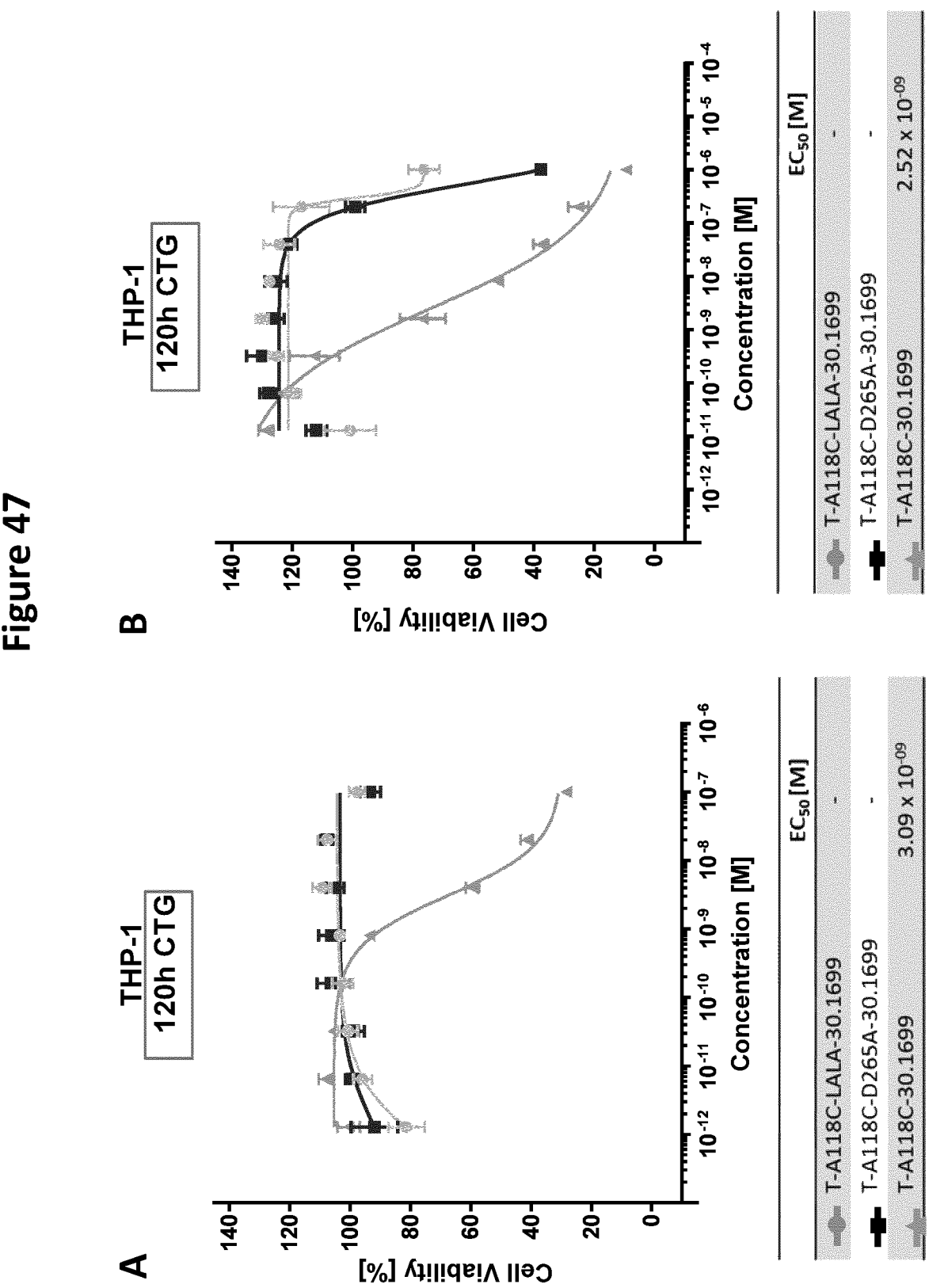
FIG. 47 graphically depicts results of a 120-hour CTG assay for assessment of the cytotoxic potential in vitro of Her2-specific ADCs comprising an antibody carrying L234A/L235A mutations and/or the D265C mutation, or control mutations, on Her2-negative THP-1 cells (A, B, C, D).
Figure 47:
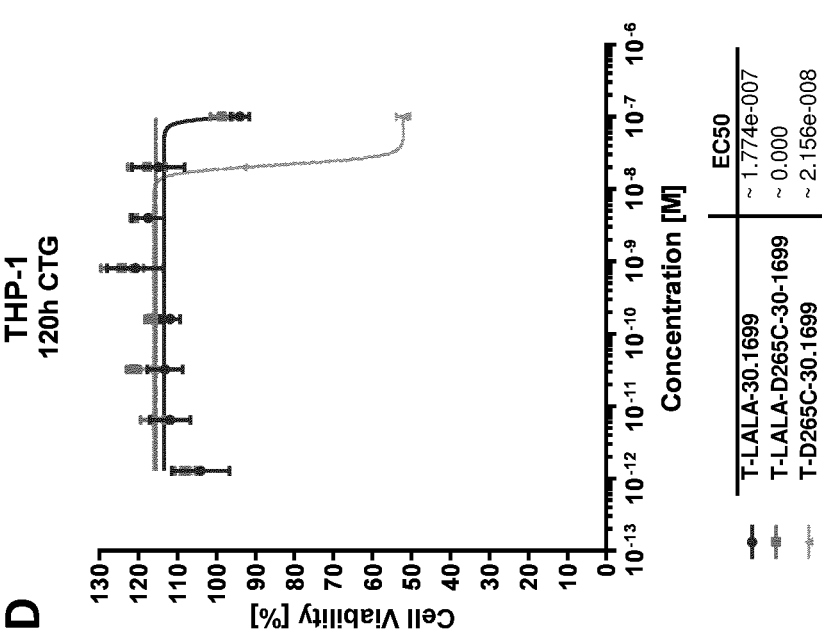
Figure 47:
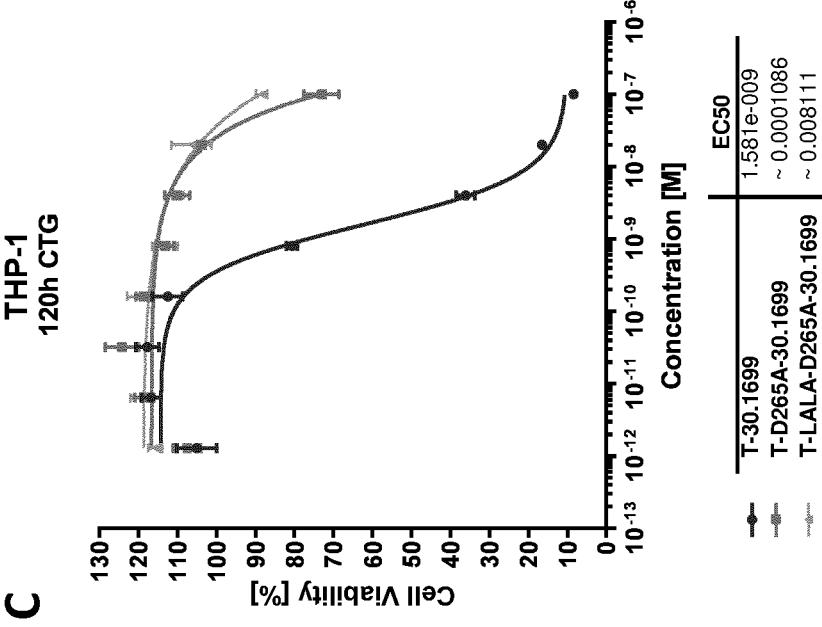

In contrast, when the cytotoxic potential in vitro of Her2-specific ADCs comprising an antibody carrying L234A/L235A mutations and/or the D265C mutation was assessed in a 96-hour CTG assay (FIG. 46) and in a 120-hour CTG assay (FIG. 47) on the Her2-negative macrophage cell line THP-1 in comparison to the respective ADC without mutations in the same antibody backbone, unspecific toxicity was observed with the ADC without mutation in the antibody (T-30.1699, FIG. 46 A, C; FIG. 47 C) at ADC concentrations higher than $10^{10}$ to $10^{-9}$ M. With ADC comprising an antibody carrying L234A/L235A ("LALA") mutations (T-LALA-30.1699), or the D265C mutation (T-D265C), or all three mutations (T-LALA-D265C-30.1699), no such unspecific toxicity on non-target THP-1 cells was observed in the 96-hour CTG assay (FIG. 46 A, B) even at 10- to 100-fold higher ADC concentrations. With ADC comprising an antibody carrying a D265A mutation (T-D265A-30.1699), no unspecific toxicity on non-target THP-1 cells was observed either. In the 120-hour CTG assay, these data were essentially confirmed; the unspecific toxicity of ADC without mutation in the antibody was drastically higher than ADCs comprising an antibody carrying a single or triple mutation (FIG. 47 C). The combination of LALA and D265C (or D265A) mutations appear to have an additive or even synergistic effect in terms of reducing unspecific toxicity on non-target cells (FIG. 47 C, D). Unspecific cytotoxicity on THP-1 cells was shown to be Fcγ receptor mediated which confirms that those ATACs, which do not show cytotoxicity on THP-1 cells (LALA, D265C and D265A variants), have reduced Fcγ receptor interaction and in turn a reduced FcγR mediated uptake.

In summary, L234A/L235A and D265A/C mutation eliminate unspecific toxicity of ADCs on THP-1 cells under tested conditions.

Example 21: Impact of LALA and/or D265C Mutations in ADCs on FcγR Binding

FcγR interaction of ADCs were tested by biolayer interferometry (BLI). Results of these binding studies are shown in Table 13.

TABLE 13

| | FcγR binding of ADCs | | | | | |
| --- | --- | --- | --- | --- | --- | --- |
| | FcγRI | | FcγRIIa$_{H167/R167}$ | | FcγRIIIa$_{V176/F176}$ | |
| ADC/Antibody | K$_D$ [nM] | K$_D$/K$_{D \cdot wt}$ | K$_D$ [μM] | K$_D$/K$_{D \cdot wt}$ | K$_D$ [μM] | K$_D$/K$_{D \cdot wt}$ |
| T-wt | 0.37 | 1 | 1.30/0.68 | 1 | 0.44/1.30 | 1 |
| T-30.1699 | 0.31 | 0.84 | 1.44/0.50 | 1.1/1.36 | 0.65/1.65 | 1.48/1.26 |
| T-D265C-30.1699 | 1.53 | 4.1 | (≈143)/(≈10) | (≈110)/(≈8) | >>10 | >>10 |
| T-D265A-30.1699 | 27.9 | 75 | >>10 | >>1000 | >>10 | >>10 |
| T-LALA-30.1699 | 218 | 590 | >>10/>>10 | >>10/>>10 | 3.7/>>10 | 8.4/>>10 |
| T-LALA-D265C-30.1699 | 2950 | ~8000 | >>10/>>10 | >>10/>>10 | >>10/>>10 | >>10/>>10 |
| T-LALA-D265A-30.1699 | >>5000 | >>5000 | >>10 | >>10 | >>10 | >>10 |

As shown in Table 13, introduction of LALA, D265A or 02650 mutations into the antibody comprised in the ADO significantly reduced the affinity for FcγR, and also reduced binding to FcγRIIa and FcγRIIIa. The combination with D265 mutation (02650, D265A) further drastically decreased FcγRI binding.

Example 22: Impact of LALA and/or D265C Mutations in ADCs on Tolerability In Viva Tolerability of ADCs comprising a Her2- or PSMA-specific antibody, respectively, carrying mutations was assessed in mice. The results are shown in Table 14. All antibodies used had the same backbone and were not cross-reactive in mice.

TABLE 14

Tolerability in mice of ADCs comprising antibodies carrying LALA, D265C mutations

| ADC Compound | MTD, Antibody with D265C | MTD, Antibody with LALA-D265C |
|---|---|---|
| T(Anti-Her2)-30.2060 | 10 mg/kg | 30 mg/kg |
| h3/F11-Var16 (Anti-PSMA)-30.2060 | 40 mg/kg | 70 mg/kg |
| T(Anti-Her2)-30.2867 | ≥80 mg/kg | ≥80 mg/kg |
| h3/F11-Var16 (Anti-PSMA)-30.2867 | ≥80 mg/kg | ≥80 mg/kg |

MTD, maximum tolerated dose

As shown in Tab. 14, with ADCs comprising the ama-toxin/linker compound HOP 30.2060 and antibodies carrying LALA and 02650 mutations the maximum tolerated dose was significantly higher than with ADCs comprising said amatoxin/linker compound and antibodies carrying the D265C mutation only. With ADCs comprising the amatoxin/linker compound HDP 30.2867 and antibodies carrying LALA and D265C mutations the tolerability was even higher.

Tolerability of ADCs comprising antibodies carrying respective mutations was also assessed in non-human primates. All antibodies used had the same backbone and are non-binders in non-human primates. The anti-PSMA ADCs h3/F11-LALA-D265C Var16-30.2060 (carrying LALA and D265C mutations), h3/F11-D265C Var16-30.2060 (carrying D265C mutation only) and the Anti-Digoxigenin ADCs DIG-D265C-30.2060 and DIG-D265C-30.2867 (carrying the D265C mutation only), were assessed for a dose-escalating tolerability study in cynomolgus monkeys.

Groups of 2 female animals were injected with h3/F11-LALA-D265C Var16-30.2060 at days 1 (1 mg/kg), 23 (3 mg/kg), 44 (5 mg/kg), 65 (6 mg/kg), 86 (7.5 mg/kg), 128 (10 mg/kg), with h3/F11-D265C Var16-30.2060 at days 1 (1 mg/kg), 23 (3 mg/kg), and 44 (5 mg/kg), with DIG-D265C-30.2060 at days 1 (1 mg/kg), 22 (3 mg/kg), 43 (5 mg/kg), 64 (7.5 mg/kg), or with DIG-D265C-30.2867 at days 1 (1 mg/kg), 22 (3 mg/kg), 43 (5 mg/kg), 64 (7.5 mg/kg), 106 (10 mg/kg), 148 (15 mg/kg), and 196 (20 mg/kg). Animals were monitored over time for biochemical and haematological blood parameters, body weight, food consumption, clinical signs and mortality. In addition, blood samples were collected for pharmacokinetic studies. At the end of the experiments tissue samples were used for histopathological examinations.

Up to 7.5 mg/kg h3/F11-LALA-D265C Var16-30.2060 (carrying LALA and D265C mutations), 3 mg/kg h3/F11-D265C Var16-30.2060 (carrying D265C mutation only) 5 mg/kg DIG-D265C-30.2060 and 15 mg/kg DIG-D265C-30.2867 (carrying the D265C mutation only) doses were well tolerated with no signs of kidney damage by serum parameters and unaffected body weight and food consumption. Doses of 10 mg/kg h3/F11-LALA-D265C Var16-30.2060, 5 mg/kg h3/F11-D265C Var16-30.2060, 7.5 mg/kg DIG-D265C-30.2060 and 20 mg/kg DIG-D265C-30.2867 resulted in dead animals. The results are shown in Table 15.

TABLE 15

Tolerability in non-human primates of ADCs comprising antibodies carrying LALA, D265C mutations

| Amatoxin/ Linker Compound | MTD, Anti-Digoxigenin Antibody with D265C | MTD, Anti-PSMA Antibody with LALA-D265C | MTD, Anti-PSMA Antibody with D265C |
|---|---|---|---|
| HDP30.2060 | 5 mg/kg | 7.5 mg/kg | 3 mg/kg |
| HDP30.2867 | 15 mg/kg | n.a. | n.a. |

MTD, maximum tolerated dose

The data in non-human primates confirmed that with ADCs comprising antibodies carrying LALA and D265C mutations the maximum tolerated dose was significantly higher than with ADCs comprising antibodies carrying the D265C mutation only. With ADCs comprising the amatoxin/linker compound HDP 30.2867 and antibodies carrying LALA and D265C mutations the tolerability was particularly high.

SEQUENCE TABLE

| Sequence Identifier | Description | Sequence |
|---|---|---|
| SEQ ID NO: 1 | CK6 CDR-H1 | SYWIG |
| SEQ ID NO: 2 | CK6 CDR-H2 | HYPGDSDTRYSPSFQG |
| SEQ ID NO: 3 | CK6 CDR-H3 | HGRGYNGYEGAFDI |
| SEQ ID NO: 4 | CK6 CDR-L1 | RASQGISSALA |
| SEQ ID NO: 5 | CK6 CDR-L2 | DASSLES |
| SEQ ID NO: 6 | CK6 CDR-L3 | CQQFNSYPLT |
| SEQ ID NO: 7 | Consensus human Ab Heavy chain variable domain | EVQLVESGGGLVQPGGSLRLSCAASGFTFSD YAMSWVRQAPGKGLEWVAVISENGSDTYYA DSVKGRFTISRDDSKNTLYLQMNSLRAEDTAV YYCARDRGGAVSYFDVWGQGTLVTVSS |

-continued

| | SEQUENCE TABLE | |
|---|---|---|

| Sequence Identifier | Description | Sequence |
|---|---|---|
| SEQ ID NO: 8 | Consensus human Ab Light chain variable domain | DIQMTQSPSSLSASVGDRVTITCRASQDVSSY LAWYQQKPGKAPKLLIYAASSLESGVPSRFS GSGSGTDFTLTISSLQPEDFATYYCQQYNSLP YTFGQGTKVEIKRT |
| SEQ ID NO: 9 | Ab67 Heavy chain variable region (e.g., as found in HC-67) (CDRs in bold) | EVQLVESGGGLVQPGGSLRLSCAASGFTFSD ADMDWVRQAPGKGLEWVGRTRNKAGSYTTE YAASVKGRFTISRDDSKNSLYLQMNSLKTEDT AVYYCAREPKYWIDFDLWGRGTLVTVSS |
| SEQ ID NO: 10 | Ab67 Light chain variable region (e.g., as found in LC-67) (CDRs in bold) | DIQMTQSPSSLSASVGDRVTITCRASQSISSYL NWYQQKPGKAPKLLIYAASSLQSGVPSRFSG SGSGTDFTLTISSLQPEDFATYYCQQSYIAPYT FGGGTKVEIK |
| SEQ ID NO: 11 | Ab67 CDR-H1 | FTFSDADMD |
| SEQ ID NO: 12 | Ab67 CDR-H2 | RTRNKAGSYIIEYAASVKG |
| SEQ ID NO: 13 | Ab67 CDR-H3 | AREPKYWIDFDL |
| SEQ ID NO: 14 | Ab67 CDR-L1 | RASQSISSYLN |
| SEQ ID NO: 15 | Ab67 CDR-L2 | AASSLQS |
| SEQ ID NO: 16 | Ab67 CDR-L3 | QQSYIAPYT |
| SEQ ID NO: 17 | Ab67 Heavy chain variable region (nucl) | GAGGTGCAGCTGGTGGAGTCTGGGGGAGG CTTGGTCCAGCCTGGAGGGTCCCTGAGACT CTCCTGTGCAGCCTCTGGATTCACCTTCAGT GACGCCGACATGGACTGGGTCCGCCAGGC TCCAGGGAAGGGGCTGGAGTGGGTTGGCC GTACTAGAAACAAAGCAGGAAGTTACACCAC AGAATACGCCGCGTCTGTGAAAGGCAGATT CACCATCTCAAGAGATGATTCAAAGAACTCA CTGTATCTGCAAATGAACAGCCTGAAAACCG AGGACACGGCGGTGTACTACTGCGCCAGAG AGCCTAAATACTGGATCGACTTCGACCTATG GGGGAGAGGTACCTTGGTCACCGTCTCCTC A |
| SEQ ID NO: 18 | Ab67 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAGC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAAGC TACATCGCCCCTTACACTTTTGGCGGAGGG ACCAAGGTTGAGATCAAA |
| SEQ ID NO: 19 | Ab55 Heavy chain variable region (e.g., as found in HC-55) (CDRs in bold) | QVQLVQSGAEVKKPGSSVKVSCKASGGTFRI YAISWVRQAPGQGLEWMGGIIPDFGVANYAQ KFQGRVTITADESTSTAYMELSSLRSEDTAVY YCARGGLDTDEFDLWGRGTLVTVSS |
| SEQ ID NO: 20 | Ab55 Light chain variable region (e.g., as found in LC-55) (CDRs in bold) | DIQMTQSPSSLSASVGDRVTITCRASQSINSYL NWYQQKPGKAPKLLIYAASSLQSGVPSRFSG SGSGTDFTLTISSLQPEDFATYYCQQGVSDITF GGGTKVEIK |
| SEQ ID NO: 21 | Ab55 CDR-H1 | GTFRIYAIS |
| SEQ ID NO: 22 | Ab55 CDR-H2 | GIIPDFGVANYAQKFQG |
| SEQ ID NO: 23 | Ab55 CDR-H3 | ARGGLDTDEFDL |
| SEQ ID NO: 24 | Ab55 CDR-L1 | RASQSINSYLN |
| SEQ ID NO: 25 | Ab55 CDR-L2 | AASSLQS |

| SEQUENCE TABLE | | |
| --- | --- | --- |
| Sequence Identifier | Description | Sequence |
| SEQ ID NO: 26 | Ab55 CDR-L3 | QQGVSDIT |
| SEQ ID NO: 27 | Ab55 Heavy chain variable region (nucl) | CAGGTGCAGCTGGTGCAGTCTGGGGCTGA GGTGAAGAAGCCTGGGTCCTCGGTGAAGGT CTCCTGCAAGGCTTCTGGAGGCACCTTCCG AATCTATGCTATCAGCTGGGTGCGACAGGC CCCTGGACAAGGGCTTGAGTGGATGGGAG GGATCATCCCTGACTTCGGTGTAGCAAACTA CGCACAGAAGTTCCAGGGCAGAGTCACGAT TACCGCGGACGAATCCACGAGCACAGCCTA CATGGAGCTGAGCAGCCTGAGATCTGAGGA CACGGCGGTGTACTACTGCGCCAGAGGTGG ATTGGACACAGACGAGTTCGACCTATGGGG GAGAGGTACCTTGGTCACCGTCTCCTCA |
| SEQ ID NO: 28 | Ab55 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAAC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAGGA GTCAGTGACATCACTTTTGGCGGAGGGACC AAGGTTGAGATCAAA |
| SEQ ID NO: 29 | Ab54 Heavy chain variable region (e.g., as found in HC-54) hIgG1 backbone (CDRs in bold) | QVQLVQSGAEVKKPGSSVKVSCKASGGTFSS YAISWVRQAPGQGLEWMGGIIPIFGTANYAQK FQGRVTITADESTSTAYMELSSLRSEDTAVYY CARGGLDTDEFDLWGRGTLVTVSS |
| SEQ ID NO: 30 | Ab54 Light chain variable region (e.g., as found in LC-54) (CDRs in bold) | DIQMTQSPSSLSASVGDRVTITCRASQSINSYL NWYQQKPGKAPKLLIYAASSLQSGVPSRFSG SGSGTDFTLTISSLQPEDFATYYCQQGVSDITF GGGTKVEIK |
| SEQ ID NO: 31 | Ab54 CDR-H1 | GTFSSYAIS |
| SEQ ID NO: 32 | Ab54 CDR-H2 | GIIPIFGTANYAQKFQG |
| SEQ ID NO: 33 | Ab54 CDR-H3 | ARGGLDTDEFDL |
| SEQ ID NO: 34 | Ab54 CDR-L1 | RASQSINSYLN |
| SEQ ID NO: 35 | Ab54 CDR-L2 | AASSLQS |
| SEQ ID NO: 36 | Ab54 CDR-L3 | QQGVSDIT |
| SEQ ID NO: 37 | Ab54 Heavy chain variable region (nucl) | CAGGTGCAGCTGGTGCAGTCTGGGGCTGA GGTGAAGAAGCCTGGGTCCTCGGTGAAGGT CTCCTGCAAGGCTTCTGGAGGCACCTTCAG CAGCTATGCTATCAGCTGGGTGCGACAGGC CCCTGGACAAGGGCTTGAGTGGATGGGAG GGATCATCCCTATCTTTGGTACAGCAAACTA CGCACAGAAGTTCCAGGGCAGAGTCACGAT TACCGCGGACGAATCCACGAGCACAGCCTA CATGGAGCTGAGCAGCCTGAGATCTGAGGA CACGGCGGTGTACTACTGCGCCAGAGGTGG ATTGGACACAGACGAGTTCGACCTATGGGG GAGAGGTACCTTGGTCACCGTCTCCTCA |
| SEQ ID NO: 38 | Ab54 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAAC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAGGA GTCAGTGACATCACTTTTGGCGGAGGGACC AAGGTTGAGATCAAA |

| SEQUENCE TABLE | | |
| --- | --- | --- |
| Sequence Identifier | Description | Sequence |
| SEQ ID NO: 39 | Ab56 Heavy chain variable region (e.g., as found in HC-56) (CDRs in bold) | QVQLVQSGAEVKKPGSSVKVSCKASGGTFSL YAISWVRQAPGQGLEWMGGIIPAFGTANYAQ KFQGRVTITADESTSTAYMELSSLRSEDTAVY YCARGGLDTDEFDLWGRGTLVTVSS |
| SEQ ID NO: 40 | Ab56 Light chain variable region (e.g., as found in LC-56) (CDRs in bold) | DIQMTQSPSSLSASVGDRVTITCRASQSINSYL NWYQQKPGKAPKLLIYAASSLQSGVPSRFSG SGSGTDFTLTISSLQPEDFATYYCQQGVSDITF GGGTKVEIK |
| SEQ ID NO: 41 | Ab56 CDR-H1 | GTFSLYAIS |
| SEQ ID NO: 42 | Ab56 CDR-H2 | GIIPAFGTANYAQKFQG |
| SEQ ID NO: 43 | Ab56 CDR-H3 | ARGGLDTDEFDL |
| SEQ ID NO: 44 | Ab56 CDR-L1 | RASQSINSYLN |
| SEQ ID NO: 45 | Ab56 CDR-L2 | AASSLQS |
| SEQ ID NO: 46 | Ab56 CDR-L3 | QQGVSDIT |
| SEQ ID NO: 47 | Ab56 Heavy chain variable region (nucl) | CAGGTGCAGCTGGTGCAGTCTGGGGCTGA GGTGAAGAAGCCTGGGTCCTCGGTGAAGGT CTCCTGCAAGGCTTCTGGAGGCACCTTCAG CCTCTATGCTATCTCCTGGGTGCGACAGGC CCCTGGACAAGGGCTTGAGTGGATGGGAG GGATCATCCCTGCCTTCGGTACCGCAAACT ACGCACAGAAGTTCCAGGGCAGAGTCACGA TTACCGCGGACGAATCCACGAGCACAGCCT ACATGGAGCTGAGCAGCCTGAGATCTGAGG ACACGGCGGTGTACTACTGCGCCAGAGGTG GATTGGACACAGACGAGTTCGACCTATGGG GGAGAGGTACCTTGGTCACCGTCTCCTCA |
| SEQ ID NO: 48 | Ab56 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAAC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAGGA GTCAGTGACATCACTTTTGGCGGAGGGACC AAGGTTGAGATCAAA |
| SEQ ID NO: 49 | Ab57 Heavy chain variable region (e.g., as found in HC-57) hIgG1 backbone (CDRs in bold) | QVQLVQSGAEVKKPGSSVKVSCKASGGTFSL YAISWVRQAPGQGLEWMGGIIPHFGLANYAQ KFQGRVTITADESTSTAYMELSSLRSEDTAVY YCARGGLDTDEFDLWGRGTLVTVSS |
| SEQ ID NO: 50 | Ab57 Light chain variable region (e.g., as found in LC-57) hKappa backbone (CDRs in bold) | DIQMTQSPSSLSASVGDRVTITCRASQSINSYL NWYQQKPGKAPKLLIYAASSLQSGVPSRFSG SGSGTDFTLTISSLQPEDFATYYCQQGVSDITF GGGTKVEIK |
| SEQ ID NO: 51 | Ab57 CDR-H1 | GTFSLYAIS |
| SEQ ID NO: 52 | Ab57 CDR-H2 | GIIPHFGLANYAQKFQG |
| SEQ ID NO: 53 | Ab57 CDR-H3 | ARGGLDTDEFDL |
| SEQ ID NO: 54 | Ab57 CDR-L1 | RASQSINSYLN |
| SEQ ID NO: 55 | Ab57 CDR-L2 | AASSLQS |
| SEQ ID NO: 56 | Ab57 CDR-L3 | QQGVSDIT |

-continued

| SEQUENCE TABLE | | |
| --- | --- | --- |
| Sequence<br>Identifier | Description | Sequence |
| SEQ ID NO: 57 | Ab57 Heavy chain<br>variable region<br>(nucl) | CAGGTGCAGCTGGTGCAGTCTGGGGCTGA<br>GGTGAAGAAGCCTGGGTCCTCGGTGAAGGT<br>CTCCTGCAAGGCTTCTGGAGGCACCTTCTC<br>CCTCTATGCTATCAGCTGGGTGCGACAGGC<br>CCCTGGACAAGGGCTTGAGTGGATGGGAG<br>GGATCATCCCTCACTTCGGTCTCGCAAACTA<br>CGCACAGAAGTTCCAGGGCAGAGTCACGAT<br>TACCGCGGACGAATCCACGAGCACAGCCTA<br>CATGGAGCTGAGCAGCCTGAGATCTGAGGA<br>CACGGCGGTGTACTACTGCGCCAGAGGTGG<br>ATTGGACACAGACGAGTTCGACCTATGGGG<br>GAGAGGTACCTTGGTCACCGTCTCCTCA |
| SEQ ID NO: 58 | Ab57 Light chain<br>variable region<br>(nucl) | GACATCCAGATGACCCAGTCTCCATCCTCC<br>CTGTCTGCATCTGTAGGAGACAGAGTCACC<br>ATCACTTGCCGGGCAAGTCAGAGCATTAAC<br>AGCTATTTAAATTGGTATCAGCAGAAACCAG<br>GGAAAGCCCCTAAGCTCCTGATCTATGCTG<br>CATCCAGTTTGCAAAGTGGGGTCCCATCAA<br>GGTTCAGTGGCAGTGGATCTGGGACAGATT<br>TCACTCTCACCATCAGCAGTCTGCAACCTGA<br>AGATTTTGCAACTTACTACTGTCAGCAAGGA<br>GTCAGTGACATCACTTTTGGCGGAGGGACC<br>AAGGTTGAGATCAAA |
| SEQ ID NO: 59 | Ab58 Heavy chain<br>variable region (e.g.,<br>as found in HC-58)<br>(CDRs in bold) | EVQLLESGGGLVQPGGSLRLSCAASGFTFSN<br>YAMSWVRQAPGKGLEWVSAISGSGGSTYYA<br>DSVKGRFTISRDNSKNTLYLQMNSLRAEDTAV<br>YYCAKGPPTYHTNYYYMDVWGKGTTVTVSS |
| SEQ ID NO: 60 | Ab58 Light chain<br>variable region (e.g.,<br>as found in LC-58)<br>(CDRs in bold) | DIQMTQSPSSVSASVGDRVTITCRASQGISSW<br>LAWYQQKPGKAPKLLIYAASSLQSGVPSRFS<br>GSGSGTDFTLTISSLQPEDFATYYCQQTNSFP<br>YTFGGGTKVEIK |
| SEQ ID NO: 61 | Ab58 CDR-H1 | FTFSNYAMS |
| SEQ ID NO: 62 | Ab58 CDR-H2 | AISGSGGSTYYADSVKG |
| SEQ ID NO: 63 | Ab58 CDR-H3 | AKGPPTYHTNYYYMDV |
| SEQ ID NO: 64 | Ab58 CDR-L1 | RASQGISSWLA |
| SEQ ID NO: 65 | Ab58 CDR-L2 | AASSLQS |
| SEQ ID NO: 66 | Ab58 CDR-L3 | QQTNSFPYT |
| SEQ ID NO: 67 | Ab58 Heavy chain<br>variable region<br>(nucl) | GAGGTGCAGCTGTGGAGTCTGGGGGAGG<br>CTTGGTACAGCCTGGGGGGTCCCTGAGACT<br>CTCCTGTGCAGCCTCTGGATTCACCTTTAGC<br>AATTATGCCATGAGCTGGGTCCGCCAGGCT<br>CCAGGGAAGGGGCTGGAGTGGGTCTCAGC<br>TATTAGTGGTAGTGGTGGTAGCACATACTAC<br>GCAGACTCCGTGAAGGGCCGGTTCACCATC<br>TCCAGAGACAATTCCAAGAACACGCTGTATC<br>TGCAAATGAACAGCCTGAGAGCCGAGGACA<br>CGGCGGTGTACTACTGCGCCAAGGGCCCTC<br>CTACATACCACACAAACTACTACTACATGGA<br>CGTATGGGCAAGGGTACAACTGTCACCGT<br>CTCCTCA |
| SEQ ID NO: 68 | Ab58 Light chain<br>variable region<br>(nucl) | GACATCCAGATGACCCAGTCTCCATCTTCCG<br>TGTCTGCATCTGTAGGAGACAGAGTCACCAT<br>CACTTGTCGGGCGAGTCAGGGTATTAGCAG<br>CTGGTTAGCCTGGTATCAGCAGAAACCAGG<br>GAAAGCCCCTAAGCTCCTGATCTATGCTGCA<br>TCCAGTTTGCAAAGTGGGGTCCCATCAAGG<br>TTCAGCGGCAGTGGATCTGGGACAGATTTC<br>ACTCTCACCATCAGCAGCCTGCAGCCTGAA<br>GATTTTGCAACTTATTACTGTCAGCAAACAA<br>ATAGTTTCCCTTACACTTTTGGCGGAGGGAC<br>CAAGGTTGAGATCAAA |

-continued

| SEQUENCE TABLE | | |
|---|---|---|
| Sequence Identifier | Description | Sequence |
| SEQ ID NO: 69 | Ab61 Heavy chain variable region (e.g., as found in HC-61) hIgG1 backbone (CDRs in bold) | EVQLLESGGGLVQPGGSLRLSCAASGFTFSS YVMIWRQAPGKGLEWSSISGDSVTTYYAD SVKGRFTISRDNSKNTLYLQMNSLRAEDTAVY YCAKGPPTYHTNYYYMDVWGKGTTVTVSS |
| SEQ ID NO: 70 | Ab61 Light chain variable region (e.g., as found in LC-61) (CDRs in bold) | DIQMTQSPSSVSASVGDRVTITCRASQGISSW LAWYQQKPGKAPKLLIYAASSLQSGVPSRFS GSGSGTDFTLTISSLQPEDFATYYCQQTNSFP YTFGGGTKVEIK |
| SEQ ID NO: 71 | Ab61 CDR-H1 | FTFSSYVMI |
| SEQ ID NO: 72 | Ab61 CDR-H2 | SISGDSVTTYYADSVKG |
| SEQ ID NO: 73 | Ab61 CDR-H3 | AKGPPTYHTNYYYMDV |
| SEQ ID NO: 74 | Ab61 CDR-L1 | RASQGISSWLA |
| SEQ ID NO: 75 | Ab61 CDR-L2 | AASSLQS |
| SEQ ID NO: 76 | Ab61 CDR-L3 | QQTNSFPYT |
| SEQ ID NO: 77 | Ab61 Heavy chain variable region (nucl) | GAGGTGCAGCTGTTGGAGTCTGGGGGAGG CTTGGTACAGCCTGGGGGGTCCCTGAGACT CTCCTGTGCAGCCTCTGGATTCACCTTTAGC AGCTATGTCATGATCTGGGTCCGCCAGGCT CCAGGGAAGGGGCTGGAGTGGGTCTCAAG CATTAGTGGTGACAGCGTAACAACATACTAC GCAGACTCCGTGAAGGGCCGGTTCACCATC TCCAGAGACAATTCCAAGAACACGCTGTATC TGCAAATGAACAGCCTGAGAGCCGAGGACA CGGCGGTGTACTACTGCGCCAAGGGCCCTC CTACATACCACACAAACTACTACTACATGGA CGTATGGGGCAAGGGTACAACTGTCACCGT CTCCTCA |
| SEQ ID NO: 78 | Ab61 Light chain variable region (nucl) | GACATCCAGATGACCCAGTCTCCATCTTCCG TGTCTGCATCTGTAGGAGACAGAGTCACCAT CACTTGTCGGGCGAGTCAGGGTATTAGCAG CTGGTTAGCCTGGTATCAGCAGAAACCAGG GAAAGCCCCTAAGCTCCTGATCTATGCTGCA TCCAGTTTGCAAAGTGGGGTCCCATCAAGG TTCAGCGGCAGTGGATCTGGGACAGATTTC ACTCTCACCATCAGCAGCCTGCAGCCTGAA GATTTTGCAACTTATTACTGTCAGCAAACAA ATAGTTTCCCTTACACTTTTGGCGGAGGGAC CAAGGTTGAGATCAAA |
| SEQ ID NO: 79 | Ab66 Heavy chain variable region (e.g., as found in HC-66) (CDRs in bold) | EVQLVESGGGLVQPGGSLRLSCAASGFTFSD HYMDWVRQAPGKGLEWVGRTRNKASSYTTE YAASVKGRFTISRDDSKNSLYLQMNSLKTEDT AVYYCAREPKYWIDFDLWGRGTLVTVSS |
| SEQ ID NO: 80 | Ab66 Light chain variable region (e.g., as found in LC-66) hKappa backbone (CDRs in bold) | DIQMTQSPSSLSASVGDRVTITCRASQSISSYL NWYQQKPGKAPKLLIYAASSLQSGVPSRFSG SGSGTDFTLTISSLQPEDFATYYCQQSYIAPYT FGGGTKVEIK |
| SEQ ID NO: 81 | Ab66 CDR-H1 | FTFSDHYMD |
| SEQ ID NO: 82 | Ab66 CDR-H2 | RTRNKASSYTTEYAASVKG |
| SEQ ID NO: 83 | Ab66 CDR-H3 | AREPKYWIDFDL |
| SEQ ID NO: 84 | Ab66 CDR-L1 | RASQSISSYLN |
| SEQ ID NO: 85 | Ab66 CDR-L2 | AASSLQS |
| SEQ ID NO: 86 | Ab66 CDR-L3 | QQSYIAPYT |

SEQUENCE TABLE

| Sequence Identifier | Description | Sequence |
|---|---|---|
| SEQ ID NO: 87 | Ab66 Heavy chain variable region (nucl) | GAGGTGCAGCTGGTGGAGTCTGGGGGAGG CTTGGTCCAGCCTGGAGGGTCCCTGAGACT CTCCTGTGCAGCCTCTGGATTCACCTTCAGT GACCACTACATGGACTGGGTCCGCCAGGCT CCAGGGAAGGGGCTGGAGTGGGTTGGCCG TACTAGAAACAAAGCTAGTAGTTACACCACA GAATACGCCGCGTCTGTGAAAGGCAGATTC ACCATCTCAAGAGATGATTCAAAGAACTCAC TGTATCTGCAAATGAACAGCCTGAAAACCGA GGACACGGCGGTGTACTACTGCGCCAGAGA GCCTAAATACTGGATCGACTTCGACCTATGG GGGAGAGGTACCTTGGTCACCGTCTCCTCA |
| SEQ ID NO: 88 | Ab66 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAGC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAAGC TACATCGCCCCTTACACTTTTGGCGGAGGG ACCAAGGTTGAGATCAAA |
| SEQ ID NO: 89 | Ab68 Heavy chain variable region (e.g., as found in HC-68) (CDRs in bold) | EVQLVESGGGLVQPGRSLRLSCTASGFTFSD HDMNWVRQAPGKGLEWVGRTRNAAGSYTTE YAASVKGRFTISRDDSKNSLYLQMNSLKTEDT AVYYCAREPKYWIDFDLWGRGTLVTVSS |
| SEQ ID NO: 90 | Ab68 Light chain variable region (e.g., as found in LC-68) (CDRs in bold) | DIQMTQSPSSLSASVGDRVTITCRASQSISSYL NWYQQKPGKAPKLLIYAASSLQSGVPSRFSG SGSGTDFTLTISSLQPEDFATYYCQQSYIAPYT FGGGTKVEIK |
| SEQ ID NO: 91 | Ab68 CDR-H1 | FTFSDHDMN |
| SEQ ID NO: 92 | Ab68 CDR-H2 | RTRNAAGSYTTEYAASVKG |
| SEQ ID NO: 93 | Ab68 CDR-H3 | AREPKYWIDFDL |
| SEQ ID NO: 94 | Ab68 CDR-L1 | RASQSISSYLN |
| SEQ ID NO: 95 | Ab68 CDR-L2 | AASSLQS |
| SEQ ID NO: 96 | Ab68 CDR-L3 | QQSYIAPYT |
| SEQ ID NO: 97 | Ab68 Heavy chain variable region (nucl) | GAGGTGCAGCTGGTGGAGTCTGGGGGAGG CTTGGTACAGCCAGGGCGGTCCCTGAGACT CTCCTGTACAGCTTCTGGATTCACCTTCAGT GACCACGACATGAACTGGGTCCGCCAGGCT CCAGGGAAGGGGCTGGAGTGGGTTGGCCG TACTAGAAACGCCGCTGGAAGTTACACCAC AGAATACGCCGCGTCTGTGAAAGGCAGATT CACCATCTCAAGAGATGATTCAAAGAACTCA CTGTATCTGCAAATGAACAGCCTGAAAACCG AGGACACGGCGGTGTACTACTGCGCCAGAG AGCCTAAATACTGGATCGACTTCGACCTATG GGGGAGAGGTACCTTGGTCACCGTCTCCTC A |
| SEQ ID NO: 98 | Ab68 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAGC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAAGC TACATCGCCCCTTACACTTTTGGCGGAGGG ACCAAGGTTGAGATCAAA |

-continued

| Sequence Identifier | Description | Sequence |
|---|---|---|
| SEQ ID NO: 99 | Ab69 Heavy chain variable region (e.g., as found in HC-69) (CDRs in bold) | EVQLVESGGGLVQPGGSLRLSCAASGFTFVD HDMDWVRQAPGKGLEWVGRTRNKLGSYTTE YAASVKGRFTISRDDSKNSLYLQMNSLKTEDT AVYYCAREPKYWIDFDLWGRGTLVTVSS |
| SEQ ID NO: 100 | Ab69 Light chain variable region (e.g., as found in LC-69) (CDRs in bold) | DIQMTQSPSSLSASVGDRVTITCRASQSISSYL NWYQQKPGKAPKLLIYAASSLQSGVPSRFSG SGSGTDFTLTISSLQPEDFATYYCQQSYIAPYT FGGGTKVEIK |
| SEQ ID NO: 101 | Ab69 CDR-H1 | FTFVDHDMD |
| SEQ ID NO: 102 | Ab69 CDR-H2 | RTRNKLGSYTTEYAASVKG |
| SEQ ID NO: 103 | Ab69 CDR-H3 | AREPKYWIDFDL |
| SEQ ID NO: 104 | Ab69 CDR-L1 | RASQSISSYLN |
| SEQ ID NO: 105 | Ab69 CDR-L2 | AASSLQS |
| SEQ ID NO: 106 | Ab69 CDR-L3 | QQSYIAPYT |
| SEQ ID NO: 107 | Ab69 Heavy chain variable region (nucl) | GAGGTGCAGCTGGTGGAGTCTGGGGGAGG CTTGGTCCAGCCTGGAGGGTCCCTGAGACT CTCCTGTGCAGCCTCTGGATTCACCTTCGTA GACCACGACATGGACTGGGTCCGCCAGGCT CCAGGGAAGGGGCTGGAGTGGGTTGGCCG TACTAGAAACAAACTAGGAAGTTACACCACA GAATACGCCGCGTCTGTGAAAGGCAGATTC ACCATCTCAAGAGATGATTCAAAGAACTCAC TGTATCTGCAAATGAACAGCCTGAAAACCGA GGACACGGCGGTGTACTACTGCGCCAGAGA GCCTAAATACTGGATCGACTTCGACCTATGG GGGAGAGGTACCTTGGTCACCGTCTCCTCA |
| SEQ ID NO: 108 | Ab69 Light chain variable region (nucl) | GACATCCAGATGACCCAGTCTCCATCCTCC CTGTCTGCATCTGTAGGAGACAGAGTCACC ATCACTTGCCGGGCAAGTCAGAGCATTAGC AGCTATTTAAATTGGTATCAGCAGAAACCAG GGAAAGCCCCTAAGCTCCTGATCTATGCTG CATCCAGTTTGCAAAGTGGGGTCCCATCAA GGTTCAGTGGCAGTGGATCTGGGACAGATT TCACTCTCACCATCAGCAGTCTGCAACCTGA AGATTTTGCAACTTACTACTGTCAGCAAAGC TACATCGCCCCTTACACTTTTGGCGGAGGG ACCAAGGTTGAGATCAAA |
| SEQ ID NO: 109 | Ab67 Light chain LC constant region underlined | DIQMTQSPSSLSASVGDRVTITCRASQSIS SYLNWYQQKPGKAPKLLIYAASSLQSGVP SRFSGSGSGTDFTLTISSLQPEDFATYYC QQSYIAPYTFGGGTKVEIKRTVAAPSVFIF PPSDEQLKSGTASVVCLLNNFYPREAKVQ WKVDNALQSGNSQESVTEQDSKDSTYSL SSTLTLSKADYEKHKVYACEVTHQGLSSP VTKSFNRGEC |
| SEQ ID NO: 110 | Ab67 Heavy chain HC constant region underlined | EVQLVESGGGLVQPGGSLRLSCAASGFT FSDADMDWVRQAPGKGLEWVGRTRNKA GSYTTEYAASVKGRFTISRDDSKNSLYLQ MNSLKTEDTAVYYCAREPKYWIDFDLWG RGTLVTVSSASTKGPSVFPLAPSSKSTSG GTAALGCLVKDYFPEPVTVSWNSGALTS GVHTFPAVLQSSGLYSLSSVVTVPSSSLG TQTYICNVNHKPSNTKVDKKVEPKSCDKT HTCPPCPAPELLGGPSVFLFPPKPKDTLM ISRTPEVTCVVVDVSHEDPEVKFNWYVD GVEVHNAKTKPREEQYNSTYRVVSVLTVL |

| SEQUENCE TABLE | | |
| --- | --- | --- |
| Sequence Identifier | Description | Sequence |
| | | HQDWLNGKEYKCKVSNKALPAPIEKTISK AKGQPREPQVYTLPPSRDELTKNQVSLT CLVKGFYPSDIAVEWESNGQPENNYKTT PPVLDSDGSFFLYSKLTVDKSRWQQGNV FSCSVMHEALHNHYTQKSLSLSPGK |
| SEQ ID NO: 111 | Ab67 Heavy chain (D265C)* HC constant region underlined | EVQLVESGGGLVQPGGSLRLSCAASGFT FSDADMDWVRQAPGKGLEWVGRTRNKA GSYTTEYAASVKGRFTISRDDSKNSLYLQ MNSLKTEDTAVYYCAREPKYWIDFDLWG RGTLVTVSSASTKGPSVFPLAPSSKSTSG GTAALGCLVKDYFPEPVTVSWNSGALTS GVHTFPAVLQSSGLYSLSSVVTVPSSSLG TQTYICNVNHKPSNTKVDKKVEPKSCDKT HTCPPCPAPELLGGPSVFLFPPKPKDTLM ISRTPEVTCVVVCVSHEDPEVKFNWYVD GVEVHNAKTKPREEQYNSTYRVVSVLTVL HQDWLNGKEYKCKVSNKALPAPIEKTISK AKGQPREPQVYTLPPSRDELTKNQVSLT CLVKGFYPSDIAVEWESNGQPENNYKTT PPVLDSDGSFFLYSKLTVDKSRWQQGNV FSCSVMHEALHNHYTQKSLSLSPGK |
| SEQ ID NO: 112 | Ab67 Heavy chain (L234A/L235A/ D265C)* HC constant region underlined | EVQLVESGGGLVQPGGSLRLSCAASGFT FSDADMDWVRQAPGKGLEWVGRTRNKA GSYTTEYAASVKGRFTISRDDSKNSLYLQ MNSLKTEDTAVYYCAREPKYWIDFDLWG RGTLVTVSSASTKGPSVFPLAPSSKSTSG GTAALGCLVKDYFPEPVTVSWNSGALTS GVHTFPAVLQSSGLYSLSSVVTVPSSSLG TQTYICNVNHKPSNTKVDKKVEPKSCDKT HTCPPCPAPEAAGGPSVFLFPPKPKDTL MISRTPEVTCVVVCVSHEDPEVKFNWYV DGVEVHNAKTKPREEQYNSTYRVVSVLT VLHQDWLNGKEYKCKVSNKALPAPIEKTI SKAKGQPREPQVYTLPPSRDELTKNQVS LTCLVKGFYPSDIAVEWESNGQPENNYKT TPPVLDSDGSFFLYSKLTVDKSRWQQGN VFSCSVMHEALHNHYTQKSLSLSPGK |
| SEQ ID NO: 113 | Ab67 Heavy chain (D265C/H435A)* HC constant region underlined | EVQLVESGGGLVQPGGSLRLSCAASGFT FSDADMDWVRQAPGKGLEWVGRTRNKA GSYTTEYAASVKGRFTISRDDSKNSLYLQ MNSLKTEDTAVYYCAREPKYWIDFDLWG RGTLVTVSSASTKGPSVFPLAPSSKSTSG GTAALGCLVKDYFPEPVTVSWNSGALTS GVHTFPAVLQSSGLYSLSSVVTVPSSSLG TQTYICNVNHKPSNTKVDKKVEPKSCDKT HTCPPCPAPELLGGPSVFLFPPKPKDTLM ISRTPEVTCVVVCVSHEDPEVKFNWYVD GVEVHNAKTKPREEQYNSTYRVVSVLTVL HQDWLNGKEYKCKVSNKALPAPIEKTISK AKGQPREPQVYTLPPSRDELTKNQVSLT CLVKGFYPSDIAVEWESNGQPENNYKTT PPVLDSDGSFFLYSKLTVDKSRWQQGNV FSCSVMHEALHNAYTQKSLSLSPGK |
| SEQ ID NO: 114 | Ab67 Heavy chain (L234A/L235A/ D265C/H435A)* HC constant region underlined | EVQLVESGGGLVQPGGSLRLSCAASGFT FSDADMDWVRQAPGKGLEWVGRTRNKA GSYTTEYAASVKGRFTISRDDSKNSLYLQ MNSLKTEDTAVYYCAREPKYWIDFDLWG RGTLVTVSSASTKGPSVFPLAPSSKSTSG GTAALGCLVKDYFPEPVTVSWNSGALTS GVHTFPAVLQSSGLYSLSSVVTVPSSSLG TQTYICNVNHKPSNTKVDKKVEPKSCDKT HTCPPCPAPEAAGGPSVFLFPPKPKDTL MISRTPEVTCVVVCVSHEDPEVKFNWYV DGVEVHNAKTKPREEQYNSTYRVVSVLT VLHQDWLNGKEYKCKVSNKALPAPIEKTI SKAKGQPREPQVYTLPPSRDELTKNQVS LTCLVKGFYPSDIAVEWESNGQPENNYKT TPPVLDSDGSFFLYSKLTVDKSRWQQGN VFSCSVMHEALHNAYTQKSLSLSPGK |

| | SEQUENCE TABLE | |
|---|---|---|
| Sequence Identifier | Description | Sequence |
| SEQ ID NO: 115 | Ab55 Light chain LC constant region underlined | DIQMTQSPSSLSASVGDRVTITCRASQSINSYL NWYQQKPGKAPKLLIYAASSLQSGVPSRFSG SGSGTDFTLTISSLQPEDFATYYCQQGVSDITF GGGTKVEIKRTVAAPSVFIFPPSDEQLKSG TASVVCLLNNFYPREAKVQWKVDNALQS GNSQESVTEQDSKDSTYSLSSTLTLSKAD YEKHKVYACEVTHQGLSSPVTKSFNRGE C |
| SEQ ID NO: 116 | Ab55 Heavy chain HC constant region underlined | QVQLVQSGAEVKKPGSSVKVSCKASGGTFRI YAISWVRQAPGQGLEWMGGIIPDFGVANYAQ KFQGRVTITADESTSTAYMELSSLRSEDTAVY YCARGGLDTDEFDLWGRGTLVTVSSASTKG PSVFPLAPSSKSTSGGTAALGCLVKDYFP EPVTVSWNSGALTSGVHTFPAVLQSSGL YSLSSVVTVPSSSLGTQTYICNVNHKPSN TKVDKKVEPKSCDKTHTCPPCPAPELLGG PSVFLFPPKPKDTLMISRTPEVTCVVVDV SHEDPEVKFNWYVDGVEVHNAKTKPREE QYNSTYRVVSVLTVLHQDWLNGKEYKCK VSNKALPAPIEKTISKAKGQPREPQVYTLP PSRDELTKNQVSLTCLVKGFYPSDIAVEW ESNGQPENNYKTTPPVLDSDGSFFLYSKL TVDKSRWQQGNVFSCSVMHEALHNHYT QKSLSLSPGK |
| SEQ ID NO: 117 | Ab55 Heavy chain (D265C)* HC constant region underlined | QVQLVQSGAEVKKPGSSVKVSCKASGGTFRI YAISWVRQAPGQGLEWMGGIIPDFGVANYAQ KFQGRVTITADESTSTAYMELSSLRSEDTAVY YCARGGLDTDEFDLWGRGTLVTVSSASTKG PSVFPLAPSSKSTSGGTAALGCLVKDYFP EPVTVSWNSGALTSGVHTFPAVLQSSGL YSLSSVVTVPSSSLGTQTYICNVNHKPSN TKVDKKVEPKSCDKTHTCPPCPAPELLGG PSVFLFPPKPKDTLMISRTPEVTCVVVCV SHEDPEVKFNWYVDGVEVHNAKTKPREE QYNSTYRVVSVLTVLHQDWLNGKEYKCK VSNKALPAPIEKTISKAKGQPREPQVYTLP PSRDELTKNQVSLTCLVKGFYPSDIAVEW ESNGQPENNYKTTPPVLDSDGSFFLYSKL TVDKSRWQQGNVFSCSVMHEALHNHYT QKSLSLSPGK |
| SEQ ID NO: 118 | Ab55 Heavy chain (L234A/L235A/ D265C)* HC constant region underlined | QVQLVQSGAEVKKPGSSVKVSCKASGGTFRI YAISWRQAPGQGLEWMGGIIPDFGVANYAQ KFQGRVTITADESTSTAYMELSSLRSEDTAVY YCARGGLDTDEFDLWGRGTLVTVSSASTKG PSVFPLAPSSKSTSGGTAALGCLVKDYFP EPVTVSWNSGALTSGVHTFPAVLQSSGL YSLSSVVTVPSSSLGTQTYICNVNHKPSN TKVDKKVEPKSCDKTHTCPPCPAPEAAG GPSVFLFPPKPKDTLMISRTPEVTCVVVC VSHEDPEVKFNWYVDGVEVHNAKTKPRE EQYNSTYRVVSVLTVLHQDWLNGKEYKC KVSNKALPAPIEKTISKAKGQPREPQVYTL PPSRDELTKNQVSLTCLVKGFYPSDIAVE WESNGQPENNYKTTPPVLDSDGSFFLYS KLTVDKSRWQQGNVFSCSVMHEALHNHY TQKSLSLSPGK |
| SEQ ID NO: 119 | Ab55 Heavy chain (D265C/H435A)* HC constant region underlined | QVQLVQSGAEVKKPGSSVKVSCKASGGTFRI YAISWRQAPGQGLEWMGGIIPDFGVANYAQ KFQGRVTITADESTSTAYMELSSLRSEDTAVY YCARGGLDTDEFDLWGRGTLVTVSSASTKG PSVFPLAPSSKSTSGGTAALGCLVKDYFP EPVTVSWNSGALTSGVHTFPAVLQSSGL YSLSSVVTVPSSSLGTQTYICNVNHKPSN TKVDKKVEPKSCDKTHTCPPCPAPELLGG PSVFLFPPKPKDTLMISRTPEVTCVVVCV SHEDPEVKFNWYVDGVEVHNAKTKPREE QYNSTYRVVSVLTVLHQDWLNGKEYKCK VSNKALPAPIEKTISKAKGQPREPQVYTLP PSRDELTKNQVSLTCLVKGFYPSDIAVEW ESNGQPENNYKTTPPVLDSDGSFFLYSKL |

| Sequence Identifier | Description | Sequence |
|---|---|---|
| | | TVDKSRWQQGNVFSCSVMHEALHNAYT QKSLSLSPGK |
| SEQ ID NO: 120 | Ab55 Heavy chain (L234A/L235A/ D265C/H435A)* HC constant region underlined | QVQLVQSGAEVKKPGSSVKVSCKASGGTFRI YAISWRQAPGQGLEWMGGIIPDFGVANYAQ KFQGRVTITADESTSTAYMELSSLRSEDTAVY YCARGGLDTDEFDLWGRGTLVTVSSASTKG PSVFPLAPSSKSTSGGTAALGCLVKDYFP EPVTVSWNSGALTSGVHTFPAVLQSSGL YSLSSVVTVPSSSLGTQTYICNVNHKPSN TKVDKKVEPKSCDKTHTCPPCPAPEAAG GPSVFLFPPKPKDTLMISRTPEVTCVVVC VSHEDPEVKFNWYVDGVEVHNAKTKPRE EQYNSTYRVVSVLTVLHQDWLNGKEYKC KVSNKALPAPIEKTISKAKGQPREPQVYTL PPSRDELTKNQVSLTCLVKGFYPSDIAVE WESNGQPENNYKTTPPVLDSDGSFFLYS KLTVDKSRWQQGNVFSCSVMHEALHNAY TQKSLSLSPGK |
| SEQ ID NO: 121 | Light chain constant region of LC-54, LC-55, LC-56, LC-57, LC-58, LC-61, LC-66, LC-67, LC-68, LC-69 | RTVAAPSVFIFPPSDEQLKSGTASVVCLL NNFYPREAKVQWKVDNALQSGNSQESVT EQDSKDSTYSLSSTLTLSKADYEKHKVYA CEVTHQGLSSPVTKSFNRGEC |
| SEQ ID NO: 122 | Heavy chain constant region of WT | ASTKGPSVFPLAPSSKSTSGGTAALGCLV KDYFPEPVTVSWNSGALTSGVHTFPAVL QSSGLYSLSSVVTVPSSSLGTQTYICNVN HKPSNTKVDKKVEPKSCDKTHTCPPCPA PELLGGPSVFLFPPKPKDTLMISRTPEVT CVVVDVSHEDPEVKFNWYVDGVEVHNAK TKPREEQYNSTYRVVSVLTVLHQDWLNG KEYKCKVSNKALPAPIEKTISKAKGQPREP QVYTLPPSRDELTKNQVSLTCLVKGFYPS DIAVEWESNGQPENNYKTTPPVLDSDGS FFLYSKLTVDKSRWQQGNVFSCSVMHEA LHNHYTQKSLSLSPGK |
| SEQ ID NO: 123 | Heavy chain constant region (D265C)* | ASTKGPSVFPLAPSSKSTSGGTAALGCLV KDYFPEPVTVSWNSGALTSGVHTFPAVL QSSGLYSLSSVVTVPSSSLGTQTYICNVN HKPSNTKVDKKVEPKSCDKTHTCPPCPA PELLGGPSVFLFPPKPKDTLMISRTPEVTC VVVCVSHEDPEVKFNWYVDGVEVHNAKT KPREEQYNSTYRVVSVLTVLHQDWLNGK EYKCKVSNKALPAPIEKTISKAKGQPREP QVYTLPPSRDELTKNQVSLTCLVKGFYPS DIAVEWESNGQPENNYKTTPPVLDSDGS FFLYSKLTVDKSRWQQGNVFSCSVMHEA LHNHYTQKSLSLSPGK |
| SEQ ID NO: 124 | Heavy chain constant region (L234A/L235A/ D265C)* | ASTKGPSVFPLAPSSKSTSGGTAALGCLV KDYFPEPVTVSWNSGALTSGVHTFPAVL QSSGLYSLSSVVTVPSSSLGTQTYICNVN HKPSNTKVDKKVEPKSCDKTHTCPPCPA PEAAGGPSVFLFPPKPKDTLMISRTPEVT CVVVCVSHEDPEVKFNWYVDGVEVHNAK TKPREEQYNSTYRVVSVLTVLHQDWLNG KEYKCKVSNKALPAPIEKTISKAKGQPREP QVYTLPPSRDELTKNQVSLTCLVKGFYPS DIAVEWESNGQPENNYKTTPPVLDSDGS FFLYSKLTVDKSRWQQGNVFSCSVMHEA LHNHYTQKSLSLSPGK |
| SEQ ID NO: 125 | Heavy chain constant region (H435A/D265C)* | ASTKGPSVFPLAPSSKSTSGGTAALGCLV KDYFPEPVTVSWNSGALTSGVHTFPAVL QSSGLYSLSSVVTVPSSSLGTQTYICNVN HKPSNTKVDKKVEPKSCDKTHTCPPCPA PELLGGPSVFLFPPKPKDTLMISRTPEVTC VVVCVSHEDPEVKFNWYVDGVEVHNAKT KPREEQYNSTYRVVSVLTVLHQDWLNGK EYKCKVSNKALPAPIEKTISKAKGQPREP |

-continued

| SEQUENCE TABLE | | |
|---|---|---|
| Sequence Identifier | Description | Sequence |
| | | QVYTLPPSRDELTKNQVSLTCLVKGFYPS DIAVEWESNGQPENNYKTTPPVLDSDGS FFLYSKLTVDKSRWQQGNVFSCSVMHEA LHNAYTQKSLSLSPGK |
| SEQ ID NO: 126 | Heavy chain constant region (L234A/L235A/ H435A/D265C)* | ASTKGPSVFPLAPSSKSTSGGTAALGCLV KDYFPEPVTVSWNSGALTSGVHTFPAVL QSSGLYSLSSVVTVPSSSLGTQTYICNVN HKPSNTKVDKKVEPKSCDKTHTCPPCPA PEAAGGPSVFLFPPKPKDTLMISRTPEVT CVVVCVSHEDPEVKFNWYVDGVEVHNAK TKPREEQYNSTYRVVSVLTVLHQDWLNG KEYKCKVSNKALPAPIEKTISKAKGQPREP QVYTLPPSRDELTKNQVSLTCLVKGFYPS DIAVEWESNGQPENNYKTTPPVLDSDGS FFLYSKLTVDKSRWQQGNVFSCSVMHEA LHNAYTQKSLSLSPGK |
| SEQ ID NO: 127 | Consensus sequence of variable heavy chain CDR1 (Abs 54-57) | GTF(S/R)(S/I/L)YAIS |
| SEQ ID NO: 128 | Consensus sequence of variable heavy chain CDR2 (Abs 54-57) | GIIP(I/D/A/H)FG(T/V/L)ANYAQKFQG |
| SEQ ID NO: 129 | Variable heavy chain CDR3 (Abs 54-57) | ARGGLDTDEFDL |
| SEQ ID NO: 130 | Variable light chain CDR1 (Abs 54-57) | RASQSINSYLN |
| SEQ ID NO: 131 | Variable light chain CDR2 (Abs 54-57) | AASSLQS |
| SEQ ID NO: 132 | Variable light chain CDR3 (Abs 54-57) | QQGVSDIT |
| SEQ ID NO: 133 | Consensus sequence of variable heavy chain CDR1 (Abs 58, 61) | FTFS(N/S)Y(A/V)M(S/I) |
| SEQ ID NO: 134 | Consensus sequence of variable heavy chain CDR2 (Abs 58, 61) | (A/S)ISG(S/D)(G/S)(G/V)(S/T) TYYADSVKG |
| SEQ ID NO: 135 | Variable heavy chain CDR3 (Abs 58, 61) | AKGPPTYHTNYYYMDV |
| SEQ ID NO: 136 | Variable light chain CDR1 (Abs 58, 61) | RASQGISSWLA |
| SEQ ID NO: 137 | Variable light chain CDR2 (Abs 58, 61) | AASSLQS |
| SEQ ID NO: 138 | Variable light chain CDR3 (Abs 58, 61) | QQTNSFPYT |
| SEQ ID NO: 139 | Consensus sequence of variable heavy chain CDR1 (Abs 66-69) | FTF(S/V)D(H/A)(Y/D)M(D/N) |
| SEQ ID NO: 140 | Consensus sequence of variable heavy chain CDR2 (Abs 66-69) | RTRN(K/A)(A/L)(S/G)SYIIEYAASVKG |
| SEQ ID NO: 141 | Variable heavy chain CDR3 (Abs 66-69) | AREPKYWIDFDL |

-continued

| SEQUENCE TABLE | | |
| --- | --- | --- |
| Sequence Identifier | Description | Sequence |
| SEQ ID NO: 142 | Variable light chain CDR1 (Abs 66-69) | RASQSISSYLN |
| SEQ ID NO: 143 | Variable light chain CDR2 (Abs 66-69) | AASSLQS |
| SEQ ID NO: 144 | Variable light chain CDR3 (Abs 66-69) | QQSYIAPYT |
| SEQ ID NO: 145 | Human CD117 (mast/stem cell growth factor receptor Kit isoform 1 precursor) Protein NCBI Reference Sequence: NP_000213.1 | MRGARGAWDFLCVLLLLLRVQTGSSQPS VSPGEPSPPSIHPGKSDLIVRVGDEIRLLC TDPGFVKWTFEILDETNENKQNEWITEKA EATNTGKYTCTNKHGLSNSIYVFVRDPAK LFLVDRSLYGKEDNDTLVRCPLTDPEVTN YSLKGCQGKPLPKDLRFIPDPKAGIMIKSV KRAYHRLCLHCSVDQEGKSVLSEKFILKV RPAFKAVPVVSVSKASYLLREGEEFTVTC TIKDVSSSVYSTWKRENSQTKLQEKYNS WHHGDFNYERQATLTISSARVNDSGVFM CYANNTFGSANVTTTLEVVDKGFINIFPMI NTTVFVNDGENVDLIVEYEAFPKPEHQQ WIYMNRTFTDKWEDYPKSENESNIRYVSE LHLTRLKGTEGGTYTFLVSNSDVNAAIAF NVYVNTKPEILTYDRLVNGMLQCVAAGFP EPTIDWYFCPGTEQRCSASVLPVDVQTLN SSGPPFGKLVVQSSIDSSAFKHNGTVECK AYNDVGKTSAYFNFAFKGNNKEQIHPHTL FTPLLIGFVIVAGMMCIIVMILTYKYLQKPM YEVQWKVVEEINGNNYVYIDPTQLPYDHK WEFPRNRLSFGKTLGAGAFGKVVEATAY GLIKSDAAMTVAVKMLKPSAHLTEREALM SELKVLSYLGNHMNIVNLLGACTIGGPTLV ITEYCCYGDLLNFLRRKRDSFICSKQEDH AEAALYKNLLHSKESSCSDSTNEYMDMK PGVSYVVPTKADKRRSVRIGSYIERDVTP AIMEDDELALDLEDLLSFSYQVAKGMAFL ASKNCIHRDLAARNILLTHGRITKICDFGLA RDIKNDSNYVVKGNARLPVKWMAPESIFN CVYTFESDVWSYGIFLWELFSLGSSPYPG MPVDSKFYKMIKEGFRMLSPEHAPAEMY DIMKTCWDADPLKRPTFKQIVQLIEKQISE STNHIYSNLANCSPNRQKPVVDHSVRINS VGSTASSSQPLLVHDDV |
| SEQ ID NO: 146 | Human CD117 (mast/stem cell growth factor receptor Kit isoform 2 precursor) Protein NCBI Reference Sequence: NP_001087241.1 | MRGARGAWDFLCVLLLLLRVQTGSSQPS VSPGEPSPPSIHPGKSDLIVRVGDEIRLLC TDPGFVKWTFEILDETNENKQNEWITEKA EATNTGKYTCTNKHGLSNSIYVFVRDPAK LFLVDRSLYGKEDNDTLVRCPLTDPEVTN YSLKGCQGKPLPKDLRFIPDPKAGIMIKSV KRAYHRLCLHCSVDQEGKSVLSEKFILKV RPAFKAVPVVSVSKASYLLREGEEFTVTC TIKDVSSSVYSTWKRENSQTKLQEKYNS WHHGDFNYERQATLTISSARVNDSGVFM CYANNTFGSANVTTTLEVVDKGFINIFPMI NTTVFVNDGENVDLIVEYEAFPKPEHQQ WIYMNRTFTDKWEDYPKSENESNIRYVSE LHLTRLKGTEGGTYTFLVSNSDVNAAIAF NVYVNTKPEILTYDRLVNGMLQCVAAGFP EPTIDWYFCPGTEQRCSASVLPVDVQTLN SSGPPFGKLVVQSSIDSSAFKHNGTVECK AYNDVGKTSAYFNFAFKEQIHPHTLFTPLL IGFVIVAGMMC11VMILTYKYLQKPMYEVQ WKVVEEINGNNYVYIDPTQLPYDHKWEFP RNRLSFGKTLGAGAFGKVVEATAYGLIKS DAAMTVAVKMLKPSAHLTEREALMSELKV LSYLGNHMNIVNLLGACTIGGPTLVITEYC CYGDLLNFLRRKRDSFICSKQEDHAEAAL YKNLLHSKESSCSDSTNEYMDMKPGVSY VVPTKADKRRSVRIGSYIERDVTPAIMEDD ELALDLEDLLSFSYQVAKGMAFLASKNCI HRDLAARNILLTHGRITKICDFGLARDIKN DSNYVVKGNARLPVKWMAPESIFNCVYT |

SEQUENCE TABLE

| Sequence Identifier | Description | Sequence |
|---|---|---|
| | | FESDVWSYGIFLWELFSLGSSPYPGMPV DSKFYKMIKEGFRMLSPEHAPAEMYDIMK TCWDADPLKRPTFKQIVQLIEKQISESTNH IYSNLANCSPNRQKPVVDHSVRINSVGST ASSSQPLLVHDDV |
| SEQ ID NO: 147 | Heavy chain variable region of HC-1 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 148 | Light chain variable region of LC-1 | AIQLTQSPSSLSASVGDRVTITCRASQGVSSAL AWYQQKPGKAPKLLIYDASSLESGVPSRFSGS GSGTDFTLTISSLQPEDFATYYCQQFNSYPLT FGGGTKVEIK |
| SEQ ID NO: 147 | Heavy chain variable region of HC-2 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 149 | Light chain variable region of LC-2 | DIQLTQSPSSLSASVGDRVTITCRASQGIRTDL GWYQQKPGKAPKLLIYDASSLESGVPSRFSG SGSGTDFTLTISSLQPEDFATYYCQQFNSYPL TFGGGTKVEIK |
| SEQ ID NO: 147 | Heavy chain variable region of HC-3 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 150 | Light chain variable region of LC-3 | AIRMTQSPSSLSASVGDRVTITCRASQGIRNDL AWYQQKPGKTPKLLIYDASSLESGVPSRFSGS GSGTDFTLTISSLQPEDFATYYCQQFNSYPLT FGGGTKVEIK |
| SEQ ID NO: 147 | Heavy chain variable region of HC-4 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 151 | Light chain variable region of LC-4 | AIQMTQSPSSLSASVGDRVTITCRASQGIRND LGWYQQKPGKAPKLLIYDASSLESGVPSRFSG SGSGTDFTLTISSLQPEDFATYYCQQFNSYPL TFGGGTKVDIK |
| SEQ ID NO: 147 | Heavy chain variable region of HC-5 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 152 | Light chain variable region of LC-5 | NIQMTQSPSSLSASVGDRVTITCRASQAISDYL AWFQQKPGKAPKLLIYDASNLETGVPSRFSGS GSGTDFTLTISSLQPEDFATYYCQQLNSYPLTF GGGTKVEIK |
| SEQ ID NO: 147 | Heavy chain variable region of HC-6 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 153 | Light chain variable region of LC-6 | AIRMTQSPSSLSASVGDRVIIACRASQGIGGAL AWYQQKPGNAPKVLVYDASTLESGVPSRFSG GGSGTDFTLTISSLQPEDFATYYCQQFNSYPL TFGGGTKLEIK |
| SEQ ID NO: 147 | Heavy chain variable region of HC-7 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |

-continued

| SEQUENCE TABLE | | |
|---|---|---|
| Sequence Identifier | Description | Sequence |
| SEQ ID NO: 154 | Light chain variable region of LC-7 | DIAMTQSPPSLSAFVGDRVTITCRASQGIISSL AWYQQKPGKAPKLLIYDASSLESGVPSRFSGS GSGTDFTLTIRSLQPEDFATYYCQQFNSYPLT FGGGTKLEIK |
| SEQ ID NO: 147 | Heavy chain variable region of HC-8 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 155 | Light chain variable region of LC-8 | DIQMTQSPSSLSASVGDRVTITCRASQGISSAL AWYQQKAGKAPKVLISDASSLESGVPSRFSG SGSGTDFTLSISSLQPEDFATYYCQQFNGYPL TFGGGTKVDIK |
| SEQ ID NO: 147 | Heavy chain variable region of HC-9 amino acid sequence | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 156 | Light chain variable region of LC-9 | AIRMTQSPSSLSASVGDRVTITCQASQGIRND LGWYQQKPGKAPKLLIYDASNLETGVPSRFSG SGSGTDFTFTISSLQPEDIATYYCQQFNSYPLT FGGGTKLEIK |
| SEQ ID NO: 147 | Heavy chain variable region of HC-10 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 157 | Light chain variable region of LC-10 | NIQMTQSPSSLSTSVGDRVTITCRASQGIGTSL AWYQQKPGKPPKLLIYDASSLESGVPSRLSGS GSGTDFTLTISSLQPEDFATYYCQQSNSYPITF GQGTRLEIK |
| SEQ ID NO: 147 | Heavy chain variable region of HC-11 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 158 | Light chain variable region of LC-11 | AIQLTQSPSSLSASVGDRVTITCRASQSIGDYL TWYQQKPGKAPKVLIYGASSLQSGVPPRFSG SGSGTDFTLTVSSLQPEDFATYYCQQLNSYPL TFGGGTKLEIK |
| SEQ ID NO: 147 | Heavy chain variable region of HC-12 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 159 | Light chain variable region of LC-12 | DIQLTQSPSSLSASVGDRVTITCRASQGVRST LAWYQQKPGKAPKLLIYDASILESGVPSRFSG SGSGTDFTLTISSLQPEDFATYYCQQFNGYPL TFGQGTRLEIK |
| SEQ ID NO: 147 | Heavy chain variable region of HC-13 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 160 | Light chain variable region of LC-13 | DIVMTQSPSSLSASVGDRVTITCRASQGIRND LGWYQQKPGKAPKLLIYDASSLESGVPSRFSG SGSGTDFTLTISSLQPEDFATYYCQQFNSYPL TFGGGTKLEIK |
| SEQ ID NO: 147 | Heavy chain variable region of HC-14 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 161 | Light chain variable region of LC-14 | DIQLTQSPSSLSASVGDRVTITCRASQGISSFL AWYQQKPGKAPKLLIYDASTLQSGVPSRFSG SASGTDFTLTISSLQPEDFATYYCQQLNGYPL TFGGGTKVEIK |

-continued

| Sequence Identifier | Description | Sequence |
|---|---|---|
| SEQ ID NO: 147 | Heavy chain variable region of HC-15 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 162 | Light chain variable region of LC-15 | AIQLTQSPSSLSASVGDRVTITCRASQGIGSAL AWYQQKPGIGPKLLIYDASTLESGVPARFSGS GSRTDFTLTITSLQPEDFATYYCQQFNGYPLT FGGGTKLEIK |
| SEQ ID NO: 147 | Heavy chain variable region of HC-16 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 163 | Light chain variable region of LC-16 | AIQLTQSPSSLSASVGDRVTITCRASQGITSAL AWYQEKPGKAPNLLIYDASSLESGVPSRFSGS GYGTDFTLTISSLQPEDFATYYCQQLNSYPLTF GGGTKVDIK |
| SEQ ID NO: 164 | Heavy chain variable region of HC-17 | QIQLVQSGPELRKPGESVKISCKASGYTFTDY AMYWVKQAPGKGLKWMGWINTYTGKPTYAD DFKGRFVFSLEASANTANLQISNLKNEDTATYF CARARGLVDDYVMDAWGQGTSVTVSS |
| SEQ ID NO: 165 | Light chain variable region of LC-17 | SYELIQPPSASVTLGNTVSLTCVGDELSKRYA QWYQQKPDKTIVSVIYKDSERPSGISDRFSGS SSGTTATLTIHGTLAEDEADYYCLSTYSDDNLP VFGGGTKLTVL |
| SEQ ID NO: 166 | Heavy chain variable region of HC-18 | EVQLQQYGAELGKPGTSVRLSCKVSGYNIRN TYIHWWNQRPGEGLEWIGRIDPTNGNTISAEK FKTKATLTADTSSHTAYLQFSQLKSDDTAIYFC ALNYEGYADYWGQGVMVTGSS |
| SEQ ID NO: 167 | Light chain variable region of LC-18 | DIQMTQSPSFLSASVGDRVTINCKASQNINKYL NWYQQKVGEAPKRLIFKTNSLQTGIPSRFSGS GSGTDYTLTISSLQTEDVATYFCFQYNIGYTFG AGTKVELK |
| SEQ ID NO: 168 | Heavy chain variable region of HC-19 | EVQLQESGPGLVKPSQSLSLTCSVTGYSISSN YRWNWIRKFPGNKVEWMGYINSAGSTNYNPS LKSRISMTRDTSKNQFFLQVNSVTTEDTATYY CARSLRGYITDYSGFFDYWGQGVMVTVSS |
| SEQ ID NO: 169 | Light chain variable region of LC-19 | DIRMTQSPASLSASLGETVNIECLASEDIFSDL AWYQQKPGKSPQLLIYNANSLQNGVPSRFSG SGSGTRYSLKINSLQSEDVATYFCQQYKNYPL TFGSGTKLEIK |
| SEQ ID NO: 170 | Heavy chain variable region of HC-20 | EVQLQQYGAELGKPGTSVRLSCKLSGYKIRNT YIHWVNQRPGKGLEWIGRIDPANGNTIYAEKF KSKVTLTADTSSNTAYMQLSQLKSDDTALYFC AMNYEGYEDYWGQGVMVTVSS |
| SEQ ID NO: 171 | Light chain variable region of LC-20 | DIQMTQSPSFLSASVGDSVTINCKASQNINKYL NWYQQKLGEAPKRLIHKTDSLQTGIPSRFSGS GSGTDYTLTISSLQPEDVATYFCFQYKSGFMF GAGTKLELK |
| SEQ ID NO: 172 | Heavy chain variable region of HC-21 | QIQLVQSGPELKKPGESVKISCKASGYTFTDY AVYWVIQAPGKGLKWMGWINTYTGKPTYADD FKGRFVFSLETSASTANLQISNLKNEDTATYFC ARGAGMTKDYVMDAWGRGVLVTVS |
| SEQ ID NO: 173 | Light chain variable region of LC-21 | SYELIQPPSASVTLGNTVSLTCVGDELSKRYA QWYQQKPDKTIVSVIYKDSERPSDISDRFSGS SSGTTATLTIHGTLAEDEADYYCLSTYSDDNLP VFGGGTKLTVL |

-continued

| SEQUENCE TABLE | | |
| --- | --- | --- |
| Sequence Identifier | Description | Sequence |
| SEQ ID NO: 174 | Heavy chain variable region of HC-22 | QVQLKESGPGLVQPSQTLSLTCTVSGFSLTSY LVHWVRQPPGKTLEWVGLMWNDGDTSYNSA LKSRLSISRDTSKSQVFLKMHSLQAEDTATYY CARESNLGFTYWGHGTLVTVSS |
| SEQ ID NO: 175 | Light chain variable region of LC-22 | DIQMTQSPASLSASLEEIVTITCKASQGIDDDLS WYQQKPGKSPQLLIYDVTRLADGVPSRFSGS RSGTQYSLKISRPQVADSGIYYCLQSYSTPYT FGAGTKLELK |
| SEQ ID NO: 176 | Heavy chain variable region of HC-23 | EVQLQQYGAELGKPGTSVRLSCKVSGYNIRN TYIHWVHQRPGEGLEWIGRIDPTNGNTISAEK FKSKATLTADTSSNTAYMQFSQLKSDDTAIYF CAMNYEGYADYWGQGVMVTVSS |
| SEQ ID NO: 177 | Light chain variable region of LC-23 | DIQMTQSPSFLSASVGDRLTINCKASQNINKYL NWYQQKLGEAPKRLIFKTNSLQTGIPSRFSGS GSGTDYTLTISSLQPEDVATYFCFQYNIGFTFG AGTKLELK |
| SEQ ID NO: 178 | Heavy chain variable region of HC-24 | EVQLVESGGGLVQSGRSLKLSCAASGFTVSD YYMAWVRQAPTKGLEWVATINYDGSTTYHRD SVKGRFTISRDNAKSTLYLQMDSLRSEDTATY YCARHGDYGYHYGAYYFDYWGQGVMVTVSS |
| SEQ ID NO: 179 | Light chain variable region of LC-24 | DIVLTQSPALAVSLGQRATISCRASQTVSLSGY NLIHWYQQRTGQQPKLLIYRASNLAPGIPARF SGSGSGTDFTLTISPVQSDDIATYYCQQSRES WTFGGGTNLEMK |
| SEQ ID NO: 180 | Heavy chain variable region of HC-25 | QIQLVQSGPELKKPGESVKISCKASGYTFTDY AIHWVKQAPGQGLRWMAWINTETGKPTYADD FKGRFVFSLEASASTAHLQISNLKNEDTATFFC AGGSHWFAYWGQGTLVTVSS |
| SEQ ID NO: 181 | Light chain variable region of LC-25 | SYELIQPPSASVTLENTVSITCSGDELSNKYAH WYQQKPDKTILEVIYNDSERPSGISDRFSGSS SGTTAILTIRDAQAEDEADYYCLSTFSDDDLPIF GGGTKLTVL |
| SEQ ID NO: 172 | Heavy chain variable region of HC-26 | QIQLVQSGPELKKPGESVKISCKASGYTFTDY AVYWVIQAPGKGLKWMGWINTYTGKPTYADD FKGRFVFSLETSASTANLQISNLKNEDTATYFC ARGAGMTKDYVMDAWGRGVLVTVS |
| SEQ ID NO: 182 | Light chain variable region of LC-26 | SYELIQPPSTSVTLGNTVSLTCVGNELPKRYAY WFQQKPDQSIVRLIYDDDRRPSGISDRFSGSS SGTTATLTIRDAQAEDEAYYYCHSTYTDDKVPI FGGGTKLTVL |
| SEQ ID NO: 183 | Heavy chain variable region of HC-27 | EVQLVESGGGLVQPGRSMKLSCKASGFTFSN YDMAWVRQAPTRGLEWVASISYDGITAYYRD SVKGRFTISRENAKSTLYLQLVSLRSEDTATYY CTTEGGYVYSGPHYFDYWGQGVMVTVSS |
| SEQ ID NO: 184 | Light chain variable region of LC-27 | DIQMTQSPSSMSVSLGDTVTITCRASQDVGIF VNWFQQKPGRSPRRMIYRATNLADGVPSRFS GSRSGSDYSLTISSLESEDVADYHCLQYDEFP RTFGGGTKLELK |
| SEQ ID NO: 185 | Heavy chain variable region of HC-28 | EVQLQQYGAELGKPGTSVRLSCKVSGYKIRNT YIHWVNQRPGKGLEWIGRIDPANGNTIYAEKF KSKVTLTADTSSNTAYMQLSQLKSDDTALYFC AMNYEGYEDYWGQGVMVTVSS |
| SEQ ID NO: 186 | Light chain variable region of LC-28 | DIQMTQSPSFLSASVGDSVTINCKASQNINKYL NWYQQKLGEAPKRLIHKTNSLQPGFPSRFSG SGSGTDYTLTISSLQPEDVAAYFCFQYNSGFT FGAGTKLELK |

-continued

| SEQUENCE TABLE | | |
|---|---|---|
| Sequence Identifier | Description | Sequence |
| SEQ ID NO: 187 | Heavy chain variable region of HC-29 | QVQLVQSGAEVKKPGASVKVSCKASGYTFTD YYIHWVRQAPGQGLEWMGWMNPHSGDTGY AQKFQGRVTMTRDTSTSTVYMELSSLRSEDT AVYYCARHGRGYNGYEGAFDIWGQGTLVTVS SAS |
| SEQ ID NO: 188 | Light chain variable region of LC-29 | DIQMTQSPSSLSASVGDRVTITCRASQGIGNE LGWYQQKPGKAPKLLIYAASNLQSGVPSRFS GSGSGTDFTLTISSLQPEDFATYYCQQYDNLP LTFGQGTKVEIK |
| SEQ ID NO: 189 | Heavy chain variable region of HC-30 | QVQLVQSGAEVKKPGASVKVSCKASGYTFTG YYLHWVRQAPGQGLEWMGWINPNSGDTNYA QNFQGRVTMTRDTSTSTVYMELSSLRSEDTA VYYCARHGRGYNGYEGAFDIWGQGTLVTVSS AS |
| SEQ ID NO: 190 | Light chain variable region of LC-30 | DIQMTQSPSSLSASVGDRVTITCRASQGIRND LGWYQQKPGKAPKLLIYDASSLESGVPSRFSG SGSGTDFTLTISSLQPEDFATYYCQQLNGYPL TFGGGTKVEIK |
| SEQ ID NO: 191 | Heavy chain variable region of HC-31 | QVQLVQSGAEVKKPGASVKVSCKASGYTFTG YYLHWVRQAPGQGLEWMGWINPNSGGTNYA QKFQGRVTMTRDTSTSTVYMELSSLRSEDTA VYYCARHGRGYEGYEGAFDIWGQGTLVTVSS AS |
| SEQ ID NO: 192 | Light chain variable region of LC-31 | DIQMTQSPSSLSASVGDRVTITCRASQGIRND LGWYQQKPGKAPKLLIYDASELETGVPSRFSG SGSGTDFTLTISSLQPEDFATYYCQQLNGYPIT FGQGTKVEIK |
| SEQ ID NO: 193 | Heavy chain variable region of HC-32 | QVQLVQSGAEVKKPGASVKVSCKASGYTFTS YYIHVWRQAPGQGLEWMGWLNPSGGTSYA QKFQGRVTMTRDTSTSTVYMELSSLRSEDTA VYYCARHGRGYDGYEGAFDIWGQGTLVTVSS AS |
| SEQ ID NO: 194 | Light chain variable region of LC-32 | DIQMTQSPSSLSASVGDRVTITCRASQGIRND LGWYQQKPGKAPKLLIYDASNLETGVPSRFSG SGSGTDFTLTISSLQPEDFATYYCQQLNGYPL TFGGGTKVEIK |
| SEQ ID NO: 195 | Heavy chain variable region of HC-33 | QVQLVQSGAEVKKPGASVKVSCKASGYTFST YYMHVWRQAPGQGLEWMGIINPSGGSTSYA QKFQGRVTMTRDTSTSTVYMKLSSLRSEDTA VYYCARHGRGYEGYEGAFDIWGQGTLVTVSS AS |
| SEQ ID NO: 196 | Light chain variable region of LC-33 | DIQMTQSPSSLSASVGDRVTITCRASQGIRDD LGWYQQKPGKAPKLLIYDASNLETGVPSRFSG SGSGTDFTLTISSLQPEDFATYYCQQANGFPL TFGGGTKVEIK |
| SEQ ID NO: 197 | Heavy chain variable region of HC-34 | QVQLVQSGAEVKKPGASVKVSCKASGYTFTG YYIHWVRQAPGQGLEWMGIINPSGGNTNYAQ NFQGRVTMTRDTSTSTVYMELSSLRSEDTAV YYCARHGRGYNAYEGAFDIWGQGTLVTVSSA S |
| SEQ ID NO: 198 | Light chain variable region of LC-34 | DIQMTQSPSSLSASVGDRVTITCRASQGIRND LGWYQQKPGKAPKLLIYDASNLETGVPSRFSG SGSGTDFTLTISSLQPEDFATYYCQQVNGYPL TFGGGTKVEIK |
| SEQ ID NO: 199 | Heavy chain variable region of HC-35 | QVQLVQSGAEVKKPGASVKVSCKASGGTFSS YAISWVRQAPGQGLEWMGVINPTVGGANYAQ KFQGRVTMTRDTSTSTVYMELSSLRSEDTAV YYCARHGRGYNEYEGAFDIWGQGTLVTVSSA S |

-continued

| SEQUENCE TABLE | | |
| --- | --- | --- |
| Sequence Identifier | Description | Sequence |
| SEQ ID NO: 200 | Light chain variable region of LC-35 | DIQMTQSPSSLSASVGDRVTITCQASQDISDYL NWYQQKPGKAPKLLIYDASNLETGVPSRFSG SGSGTDFTLTISSLQPEDFATYYCQQGNSFPL TFGGGTKLEIK |
| SEQ ID NO: 201 | Heavy chain variable region of HC-36 | QVQLVQSGAEVKKLGASVKVSCKASGYTFSS YYMHWVRQAPGQGLEWMGVINPNGAGTNFA QKFQGRVTMTRDTSTSTVYMELSSLRSEDTA VYYCARHGRGYEGYEGAFDIWGQGTLVTVSS |
| SEQ ID NO: 190 | Light chain variable region of LC-36 | DIQMTQSPSSLSASVGDRVTITCRASQGIRND LGWYQQKPGKAPKLLIYDASSLESGVPSRFSG SGSGTDFTLTISSLQPEDFATYYCQQLNGYPL TFGGGTKVEIK |
| SEQ ID NO: 202 | Heavy chain variable region of HC-37 | QVQLVQSGAEVKKPGASVKVSCKASGYTFTT YYMHWWRQAPGQGLEWMGWINPTGGGTNY AQNFQGRVTMTRDTSTSTVYMELSSLRSEDT AVYYCARHGRGYEGYEGAFDIWGQGTLVTVS SAS |
| SEQ ID NO: 203 | Light chain variable region of LC-37 | DIQMTQSPSSLSASVGDRVTITCRASQGIRND VSWYQQKPGKAPKLLIYDASNLETGVPSRFSG SGSGTDFTLTISSLQPEDFATYYCQQLSGYPIT FGQGTKLEIK |
| SEQ ID NO: 204 | Heavy chain variable region of HC-38 | QVQLVQSGAEVKKPGASVKVSCKASGYTFTS YYIHWVRQAPGQGLEWMGMINPSGGSTNYA QKFQGRVTMTRDTSTSTVYMELSSLRSEDTA VYYCARHGRGYNDYEGAFDIWGQGTLVTVSS AS |
| SEQ ID NO: 205 | Light chain variable region of LC-38 | DIQMTQSPSSLSASVGDRVTITCRASQSISDW LAWYQQKPGKAPKLLIYEASNLEGGVPSRFSG SGSGTDFTLTISSLQPEDFATYYCQQANSFPY TFGQGTKVEIK |
| SEQ ID NO: 206 | Heavy chain variable region of HC-39 | QVQLVQSGAEVKKPGASVKVSCKASGYIFSAY YIHWWRQAPGQGLEWMG11NPSGGSTRYAQK FQGRVTMTRDTSTSTVYMELSSLRSEDTAVY YCARHGRGYGGYEGAFDIWDQGTLVTVSSAS |
| SEQ ID NO: 207 | Light chain variable region of LC-39 | DIQMTQSPSSLSASVGDRVTITCRASQGIGDY VAWYQQKPGKAPKLLIYDASNLETGVPSRFSG SGSGTDFTLTISSLQPEDFATYYCQQLNGYPIT FGQGTRLEIK |
| SEQ ID NO: 208 | Heavy chain variable region of HC-40 | EVQLVQSGAEVKKPGESLKISCKGSGYRFTSY WIGWVRQMPGKGLEWMGIIYPDDSDTRYSPS FQGQVTISVDKSNSTAYLQWSSLKASDTAMY YCARHGRGYNGYEGAFDIWGQGTLVTVSSAS |
| SEQ ID NO: 209 | Light chain variable region of LC-40 | DIQMTQSPSSLSASVGDRVTITCRASQGISSYL AWYQQKPGKAPKLLIYDASNLETGVPSRFSGS GSGTYFTLTISSLQPEDFATYYCQQGASFPITF GQGTKVEIK |
| SEQ ID NO: 210 | Heavy chain variable region of HC-41 | EVQLVQSGAEVKKPGESLKISCKGSGSSFPNS WIAWVRQMPGKGLEWMGIIYPSDSDTRYSPS FQGQVTISADKSISTAYLQWSSLEASDTAMYY CARHGRGYNGYEGAFDIWGQGTLVTVSSAS |
| SEQ ID NO: 211 | Light chain variable region of LC-41 | DIQMTQSPSSLSASVGDRVTITCRASQGIRNY LAWYQQKPGKAPKLLIYDASSLQSGVPSRFSG SGSGTDFTLTISSLQPEDFATYYCQQLNSYPL TFGGGTKVEIK |
| SEQ ID NO: 212 | Heavy chain variable region of HC-42 | EVQLVQSGAEVKKPGESLKISCKGSGYSFDSY WIGWVRQMPGKGLEWMGIMYPGDSDTRYSP SFQGQVTISADKSISTAYLQWSSLKASDTAMY YCARHGRGYNAYEGAFDIWGQGTLVTVSSAS |

-continued

| SEQUENCE TABLE | | |
|---|---|---|
| Sequence Identifier | Description | Sequence |
| SEQ ID NO: 213 | Light chain variable region of LC-42 | DIQMTQSPSSLSASVGDRVTITCRASQSINNW LAWYQQKPGKAPKLLIYDAFILQSGVPSRFSG SGSGTDFTLTISSLQPEDFATYYCLQLNSYPLT FGPGTKVDIK |
| SEQ ID NO: 214 | Heavy chain variable region of HC-43 | EVQLVQSGAEVKKPGESLKISCKGSGYSFTN WIAWVRQMPGKGLEWMGIIYPGDSETRYSPS FQGQVTISADKSISTAYLQWSSLKASDTAMYY CARHGRGYYGYEGAFDIWGQGTLVTVSSAS |
| SEQ ID NO: 215 | Light chain variable region of LC-43 | DIQMTQSPSSLSASVGDRVTITCRASQGISDN LNWYQQKPGKAPKLLIYDASNLETGVPSRFSG SGSGTDFTLTISSLQPEDFATYYCQQAISFPLT FGQGTKVEIK |
| SEQ ID NO: 216 | Heavy chain variable region of HC-44 | EVQLVQSGAEVKKPGESLKISCKGSGYNFTSY WIGWVRQMPGKGLEWMGVIYPDDSETRYSP SFQGQVTISADKSISTAYLQWSSLKASDTAMY YCARHGRGYNGYEGAFDIWGQGTLVTVSSAS |
| SEQ ID NO: 217 | Light chain variable region of LC-44 | DIQMTQSPSSLSASVGDRVTITCRASRDIRDDL GWYQQKPGKAPKLLIYDASNLETGVPSRFSG SGSGTDFTLTISSLQPEDFATYYCQQANSFPL TFGGGTKVEIK |
| SEQ ID NO: 218 | Heavy chain variable region of HC-45 | EVQLVQSGAEVKKPGESLKISCKGSGYTFNTY IGWVRQMPGKGLEWMGIIYPGDSGTRYSPSF QGQVTISADKAISTAYLQWSSLKASDTAMYYC ARHSRGYNGYEGAFDIWGQGTLVTVSSAS |
| SEQ ID NO: 219 | Light chain variable region of LC-45 | DIQMTQSPSSLSASVGDRVTITCRASQGISNYL AWYQQKPGKAPKLLIYDASNLETGVPSRFSGS GSGTDFTLTISSLQPEDFATYYCQQANSFPVT FGQGTKVEIK |
| SEQ ID NO: 220 | Heavy chain variable region of HC-46 | EVQLVQSGAEVKKPGESLKISCKGSGYNFTTY WIGWVRQMPGKGLEWMGIIHPADSDTRYNPS FQGQVTISADKSISTAYLQWSSLKASDTAMYY CARHGRGYNGYEGAFDIWGQGTLVTVSSAS |
| SEQ ID NO: 221 | Light chain variable region of LC-46 | DIQMTQSPSSLSASVGDRVTITCRVSQGISSYL AWYQQKPGKAPKLLIYDASNLETGVPSRFSGS GSGTDFTLTISSLQPEDFATYYCQQANSFPLT FGGGTKVEIK |
| SEQ ID NO: 222 | Heavy chain variable region of HC-47 | EVQLVQSGAEVKKPGESLKISCKGSGYRFSNY WIAWVRQMPGKGLEWMGIIYPDNSDTRYSPS FQGQVTISADKSISTAYLQWSSLKASDTAMYY CARHGRGYDGYEGAFDIWGQGTLVTVSSAS |
| SEQ ID NO: 223 | Light chain variable region of LC-47 | DIQMTQSPSSLSASVGDRVTITCRASQGIRSD LAWYQQKPGKAPKLLIYGASSLQSGVPSRFS GSGSGTDFTLTISSLQPEDFATYYCQQANSFP LSFGQGTKVEIK |
| SEQ ID NO: 224 | Heavy chain variable region of HC-48 | EVQLVQSGAEVKKPGESLKISCKGSGYRFASY WIGWVRQMPGKGLEWMGITYPGDSETRYNP SQGQVTISADKSISTAYLQWSSLKASDTAMYY CARHGRGYGGYEGAFDIWGQGTLVTVSSAS |
| SEQ ID NO: 225 | Light chain variable region of LC-48 | DIQMTQSPSSLSASVGDRVTITCRASQGIRND LGWYQQKPGKAPKLLIYDASNLETGVPSRFSG SGSGTDFTLTISSLQPEDFATYYCQQANSFPL TFGGGTKVEIK |
| SEQ ID NO: 226 | Heavy chain variable region of HC-49 | EVQLVQSGAEVKKPGESLKISCKGSGYSFTSY WIGWVRQMPGKGLEWMGIIYPGDSDTRYSPS FQGQVTISADKSISTAYLQWSSLKASDTAMYY CARHGRGYNGYEGAFDIWGQGTLVTVSSAS |
| SEQ ID NO: 227 | Light chain variable region of LC-49 | DIQMTQSPSSLSASVGDRVTITCRASQSISNW LAWYQQKPGKAPKLLIYDASNLETGVPSRFSG SGSGTDFTLTISSLQPEDFATYYCQQTNSFPL TFGQGTRLEIK |

-continued

| | SEQUENCE TABLE | |
|---|---|---|
| Sequence Identifier | Description | Sequence |
| SEQ ID NO: 147 | Heavy chain variable region of HC-74 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 228 | Light chain variable region of LC-74 | DIQLTQSPSSLSASVGDRVTITCRASQGVISAL AWYQQKPGKAPKLLIYDASSLESGVPSRFSGS GSGTDFTLTISSLQPEDFATYYCQQFNSYPLT FGGGTKVEIK |
| SEQ ID NO: 147 | Heavy chain variable region of HC-75 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 229 | Light chain variable region of LC-75 | DIQLTQSPSSLSASVGDRVTITCRASQGIRSAL AWYQQKPGKAPKLLIYDASSLESGVPSRFSGS GSGTDFTLTISSLQPEDFATYYCQQFNSYPLT FGGGTKVEIK |
| SEQ ID NO: 147 | Heavy chain variable region of HC-76 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 230 | Light chain variable region of LC-76 | DIQLTQSPSSLSASVGDRVTITCRASQGVGSA LAWYQQKPGKAPKLLIYDASSLESGVPSRFSG SGSGTDFTLTISSLQPEDFATYYCQQFNSYPL TFGGGTKVEIK |
| SEQ ID NO: 147 | Heavy chain variable region of HC-77 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 231 | Light chain variable region of LC-77 | DIQLTQSPSSLSASVGDRVTITCRASQGVISAL AWYQQKPGKAPKLLIYDASILESGVPSRFSGS GSGTDFTLTISSLQPEDFATYYCQQFNSYPLT FGGGTKVEIK |
| SEQ ID NO: 147 | Heavy chain variable region of HC-78 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 232 | Light chain variable region of LC-78 | DIQLTQSPSSLSASVGDRVTITCRASQGIRSAL AWYQQKPGKAPKLLIYDASILESGVPSRFSGS GSGTDFTLTISSLQPEDFATYYCQQFNSYPLT FGGGTKVEIK |
| SEQ ID NO: 147 | Heavy chain variable region of HC-79 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 233 | Light chain variable region of LC-79 | DIQLTQSPSSLSASVGDRVTITCRASQGVGSA LAWYQQKPGKAPKLLIYDASILESGVPSRFSG SGSGTDFTLTISSLQPEDFATYYCQQFNSYPL TFGGGTKVEIK |
| SEQ ID NO: 147 | Heavy chain variable region of HC-80 | QVQLVQSGAAVKKPGESLKISCKGSGYRFTTY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 234 | Light chain variable region of LC-80 | DIQLTQSPSSLSASVGDRVTITCRASQGISSAL AWYQQKPGKAPKLLIYDASILESGVPSRFSGS GSGTDFTLTISSLQPEDFATYYCQQFNSYPLT FGGGTKVEIK |

-continued

| SEQUENCE TABLE | | |
|---|---|---|
| Sequence<br>Identifier | Description | Sequence |
| SEQ ID NO:<br>147 | Heavy chain variable<br>region of HC-81 | QVQLVQSGAAVKKPGESLKISCKGSGYRFTTY<br>WIGWVRQMPGKGLEWMGIIYPGDSDTRYSPS<br>FQGQVTISAGKSISTAYLQWSSLKASDTAMYY<br>CARHGRGYNGYEGAFDIWGQGTMVTVSS |
| SEQ ID NO:<br>235 | Light chain variable<br>region of LC-81 | DIQLTQSPSSLSASVGDRVTITCRASQGVISAL<br>AWYQQKPGKAPKLLIYDASTLESGVPSRFSGS<br>GSGTDFTLTISSLQPEDFATYYCQQFNSYPLT<br>FGGGTKVEIK |
| SEQ ID NO:<br>147 | Heavy chain variable<br>region of HC-82 | QVQLVQSGAAVKKPGESLKISCKGSGYRFTTY<br>WIGWVRQMPGKGLEWMGIIYPGDSDTRYSPS<br>FQGQVTISAGKSISTAYLQWSSLKASDTAMYY<br>CARHGRGYNGYEGAFDIWGQGTMVTVSS |
| SEQ ID NO:<br>236 | Light chain variable<br>region of LC-82 | DIQLTQSPSSLSASVGDRVTITCRASQGIRSAL<br>AWYQQKPGKAPKLLIYDASTLESGVPSRFSGS<br>GSGTDFTLTISSLQPEDFATYYCQQFNSYPLT<br>FGGGTKVEIK |
| SEQ ID NO:<br>147 | Heavy chain variable<br>region of HC-83 | QVQLVQSGAAVKKPGESLKISCKGSGYRFTTY<br>WIGWVRQMPGKGLEWMGIIYPGDSDTRYSPS<br>FQGQVTISAGKSISTAYLQWSSLKASDTAMYY<br>CARHGRGYNGYEGAFDIWGQGTMVTVSS |
| SEQ ID NO:<br>237 | Light chain variable<br>region of LC-83 | DIQLTQSPSSLSASVGDRVTITCRASQGVGSA<br>LAWYQQKPGKAPKLLIYDASTLESGVPSRFSG<br>SGSGTDFTLTISSLQPEDFATYYCQQFNSYPL<br>TFGGGTKVEIK |
| SEQ ID NO:<br>147 | Heavy chain variable<br>region of HC-84 | QVQLVQSGAAVKKPGESLKISCKGSGYRFTTY<br>WIGWVRQMPGKGLEWMGIIYPGDSDTRYSPS<br>FQGQVTISAGKSISTAYLQWSSLKASDTAMYY<br>CARHGRGYNGYEGAFDIWGQGTMVTVSS |
| SEQ ID NO:<br>237 | Light chain variable<br>region of LC-84 | DIQLTQSPSSLSASVGDRVTITCRASQGVGSA<br>LAWYQQKPGKAPKLLIYDASTLESGVPSRFSG<br>SGSGTDFTLTISSLQPEDFATYYCQQFNSYPL<br>TFGGGTKVEIK |
| SEQ ID NO:<br>238 | Heavy chain variable<br>region of HC-245 | EVQLVQSGAEVKKPGESLKISCKGSGYRFTTS<br>WIGWVRQMPGKGLEWMGIIYPGDSDTRYSPS<br>FQGQVTISADKSISTAYLQWSSLKASDTAMYY<br>CARHGLGYNGYEGAFDIWGQGTLVTVSS |
| SEQ ID NO:<br>239 | Light chain variable<br>region of LC-245 | DIQMTQSPSSLSASVGDRVTITCRASQGIGSA<br>LAWYQQKPGKAPKLLIYDASTLESGVPSRFSG<br>SGSGTDFTLTISSLQPEDFATYYCQQFNGYPL<br>TFGQGTRLEIK |
| SEQ ID NO:<br>147 | Heavy chain variable<br>region of HC-246 | QVQLVQSGAAVKKPGESLKISCKGSGYRFTTY<br>WIGWVRQMPGKGLEWMGIIYPGDSDTRYSPS<br>FQGQVTISAGKSISTAYLQWSSLKASDTAMYY<br>CARHGRGYNGYEGAFDIWGQGTMVTVSS |
| SEQ ID NO:<br>239 | Light chain variable<br>region of LC-246 | DIQMTQSPSSLSASVGDRVTITCRASQGIGSA<br>LAWYQQKPGKAPKLLIYDASTLESGVPSRFSG<br>SGSGTDFTLTISSLQPEDFATYYCQQFNGYPL<br>TFGQGTRLEIK |
| SEQ ID NO:<br>147 | Heavy chain variable<br>region of HC-247 | QVQLVQSGAAVKKPGESLKISCKGSGYRFTTY<br>WIGWVRQMPGKGLEWMGIIYPGDSDTRYSPS<br>FQGQVTISAGKSISTAYLQWSSLKASDTAMYY<br>CARHGRGYNGYEGAFDIWGQGTMVTVSS |
| SEQ ID NO:<br>240 | Light chain variable<br>region of LC-247 | DIQMTQSPSSLSASVGDRVTITCRASRGISDYL<br>AWYQQKPGKAPKLLIYDASNLETGVPSRFSGS<br>GSGTDFTLTISSLQPEDFATYYCQQANSFPITF<br>GQGTRLEIK |
| SEQ ID NO:<br>238 | Heavy chain variable<br>region of HC-248 | EVQLVQSGAEVKKPGESLKISCKGSGYRFTTS<br>WIGWVRQMPGKGLEWMGIIYPGDSDTRYSPS<br>FQGQVTISADKSISTAYLQWSSLKASDTAMYY<br>CARHGLGYNGYEGAFDIWGQGTLVTVSS |

-continued

| SEQUENCE TABLE | | |
|---|---|---|
| Sequence Identifier | Description | Sequence |
| SEQ ID NO: 241 | Light chain variable region of LC-248 | DIQMTQSPSSLSASVGDRVTITCRASQGIGSA LAWYQQKPGKAPKLLIYDASTLESGVPSRFSG SGSGTDFTLTISSLQPEDFATYYCQQLNGYPL TFGQGTRLEIK |
| SEQ ID NO: 238 | Heavy chain variable region of HC-249 | EVQLVQSGAEVKKPGESLKISCKGSGYRFTTS WIGWVRQMPGKGLEWMGIIYPGDSDTRYSPS FQGQVTISADKSISTAYLQWSSLKASDTAMYY CARHGLGYNGYEGAFDIWGQGTLVTVSS |
| SEQ ID NO: 242 | Light chain variable region of LC-249 | DIQMTQSPSSLSASVGDRVTITCRASQGIGSA LAWYQQKPGKAPKLLIYDASNLETGVPSRFSG SGSGTDFTLTISSLQPEDFATYYCQQLNGYPL TFGQGTRLEIK |
| SEQ ID NO: 243 | Heavy chain variable region of Ab 85 | EVQLVQSGAEVKKPGESLKISCKGSGYSFTNY WIGWVRQMPGKGLEWMAIINPRDSDTRYRPS FQGQVTISADKSISTAYLQWSSLKASDTAMYY CARHGRGYEGYEGAFDIWGQGTLVTVSS |
| SEQ ID NO: 244 | Light chain variable region of Ab 85 | DIQMTQSPSSLSASVGDRVTITCRSSQGIRSD LGWYQQKPGKAPKLLIYDASNLETGVPSRFSG SGSGTDFTLTISSLQPEDFATYYCQQANGFPL TFGGGTKVEIK |
| SEQ ID NO: 245 | Ab85 CDR-H1 | NYWIG |
| SEQ ID NO: 246 | Ab85 CDR-H2 | HNPRDSDTRYRPSFQG |
| SEQ ID NO: 247 | Ab85 CDR-H3 | HGRGYEGYEGAFDI |
| SEQ ID NO: 248 | Ab85 CDR-L1 | RSSQGIRSDLG |
| SEQ ID NO: 249 | Ab85 CDR-L2 Ab249 CDR-L2 | DASNLET |
| SEQ ID NO: 250 | Ab85 CDR-L3 | QQANGFPLT |
| SEQ ID NO: 251 | Heavy chain variable region of Ab 86 | EVQLVQSGAEVKKPGESLKISCKGSGYSFTNY WIGWVRQMPGKGLEWMGIIYPGDSDIRYSPS LQGQVTISVDTSTSTAYLQWNSLKPSDTAMYY CARHGRGYNGYEGAFDIWGQGTLVTVSS |
| SEQ ID NO: 252 | Light chain variable region of Ab 86 | DIQMTQSPSSLSASVGDRVTITCRASQGIGDS LAWYQQKPGKAPKLLIYDASNLETGVPSRFSG SGSGTDFTLTISSLQPEDFATYYCQQLNGYPIT FGQGTKVEIK |
| SEQ ID NO: 245 | Ab86 CDR-H1 | NYWIG |
| SEQ ID NO: 253 | Ab86 CDR-H2 | HYPGDSDIRYSPSLQG |
| SEQ ID NO: 3 | Ab86 CDR-H3 | HGRGYNGYEGAFDI |
| SEQ ID NO: 254 | Ab86 CDR-L1 | RASQGIGDSLA |
| SEQ ID NO: 249 | Ab86 CDR-L2 | DASNLET |
| SEQ ID NO: 255 | Ab86 CDR-L3 | QQLNGYPIT |

-continued

| SEQUENCE TABLE | | |
| --- | --- | --- |
| Sequence Identifier | Description | Sequence |
| SEQ ID NO: 243 | Heavy chain variable region of Ab 87 | EVQLVQSGAEVKKPGESLKISCKGSGYSFTNY WIGWVRQMPGKGLEWMAIINPRDSDTRYRPS FQGQVTISADKSISTAYLQWSSLKASDTAMYY CARHGRGYEGYEGAFDIWGQGTLVTVSS |
| SEQ ID NO: 256 | Light chain variable region of Ab 87 | DIQMTQSPSSLSASVGDRVTITCRASQGIRND LGWYQQKPGKAPKLLIYDASSLESGVPSRFSG SGSGTDFTLTISSLQPEDFATYYCQQLNGYPIT FGQGTKVEIK |
| SEQ ID NO: 245 | Ab87 CDR-H1 | NYWIG |
| SEQ ID NO: 246 | Ab87 CDR-H2 | HNPRDSDTRYRPSFQG |
| SEQ ID NO: 247 | Ab87 CDR-H3 | HGRGYEGYEGAFDI |
| SEQ ID NO: 257 | Ab87 CDR-L1 | RASQGIRNDLG |
| SEQ ID NO: 5 | Ab87 CDR-L2 | DASSLES |
| SEQ ID NO: 255 | Ab87 CDR-L3 | QQLNGYPIT |
| SEQ ID NO: 258 | Heavy chain variable region of Ab 88 | EVQLVQSGAEVKKPGESLKISCKGSGYSFTNY WIGWVRQMPGKGLEWMGIIYPGDSLTRYSPS FQGQVTISADKSISTAYLQWSSLKASDTAMYY CARHGRGYNGYEGAFDIWGQGTLVTVSS |
| SEQ ID NO: 256 | Light chain variable region of Ab 88 | DIQMTQSPSSLSASVGDRVTITCRASQGIRND LGWYQQKPGKAPKLLIYDASSLESGVPSRFSG SGSGTDFTLTISSLQPEDFATYYCQQLNGYPIT FGQGTKVEIK |
| SEQ ID NO: 245 | Ab88 CDR-H1 | NYWIG |
| SEQ ID NO: 259 | Ab88 CDR-H2 | IIYPGDSLTRYSPSFQG |
| SEQ ID NO: 3 | Ab88 CDR-H3 | HGRGYNGYEGAFDI |
| SEQ ID NO: 257 | Ab88 CDR-L1 | RASQGIRNDLG |
| SEQ ID NO: 5 | Ab88 CDR-L2 | DASSLES |
| SEQ ID NO: 255 | Ab88 CDR-L3 | QQLNGYPIT |
| SEQ ID NO: 260 | Heavy chain variable region of Ab89 | EVQLVQSGAEVKKPGESLKISCKGSGYSFTNY WIGWVRQMPGKGLEWMGIIYPGDSDTRYSPS FQGQVTISADKSISTAYLQWSSLKASDTAMYY CARHGRGYNGYEGAFDIWGQGTLVTVSS |
| SEQ ID NO: 252 | Light chain variable region of Ab89 | DIQMTQSPSSLSASVGDRVTITCRASQGIGDS LAWYQQKPGKAPKLLIYDASNLETGVPSRFSG SGSGTDFTLTISSLQPEDFATYYCQQLNGYPIT FGQGTKVEIK |
| SEQ ID NO: 245 | Ab89 CDR-H1 | NYWIG |
| SEQ ID NO: 2 | Ab89 CDR-H2 | HYPGDSDTRYSPSFQG |
| SEQ ID NO: 3 | Ab89 CDR-H3 | HGRGYNGYEGAFDI |
| SEQ ID NO: 254 | Ab89 CDR-L1 | RASQGIGDSLA |

SEQUENCE TABLE

| Sequence Identifier | Description | Sequence |
|---|---|---|
| SEQ ID NO: 249 | Ab89 CDR-L2 | DASNLET |
| SEQ ID NO: 255 | Ab89 CDR-L3 | QQLNGYPIT |
| SEQ ID NO: 261 | Heavy chain variable region amino acid sequence of CK6 | QVQLVQSGAAVKKPGESLKISCKGSGYRFTSY WIGWVRQMPGKGLEWMGIIYPGDSDTRYSPS FQGQVTISAGKSISTAYLQWSSLKASDTAMYY CARHGRGYNGYEGAFDIWGQGTMVTVSS |
| SEQ ID NO: 262 | Light chain variable region amino acid sequence of CK6 | AIQLTQSPSSLSASVGDRVTITCRASQGISSAL AWYQQKPGKAPKLLIYDASSLESGVPSRFSGS GSGTDFTLTISSLQPEDFATYYCQQFNSYPLT FGGGTKVEIK |
| SEQ ID NO: 263 | Ab77 CDR-H1 | TYWIG |
| SEQ ID NO: 2 | Ab77 CDR-H2 | HYPGDSDTRYSPSFQG |
| SEQ ID NO: 3 | Ab77 CDR-H3 | HGRGYNGYEGAFDI |
| SEQ ID NO: 264 | Ab77 CDR-L1 | RASQGVISALA |
| SEQ ID NO: 265 | Ab77 CDR-L2 | DASILES |
| SEQ ID NO: 266 | Ab77 CDR-L3 | QQFNSYPLT |
| SEQ ID NO: 263 | Ab79 CDR-H1 | TYWIG |
| SEQ ID NO: 2 | Ab79 CDR-H2 | HYPGDSDTRYSPSFQG |
| SEQ ID NO: 3 | Ab79 CDR-H3 | HGRGYNGYEGAFDI |
| SEQ ID NO: 267 | Ab79 CDR-L1 | RASQGVGSALA |
| SEQ ID NO: 265 | Ab79 CDR-L2 | DASILES |
| SEQ ID NO: 266 | Ab79 CDR-L3 | QQFNSYPLT |
| SEQ ID NO: 263 | Ab81 CDR-H1 | TYWIG |
| SEQ ID NO: 2 | Ab81 CDR-H2 | HYPGDSDTRYSPSFQG |
| SEQ ID NO: 3 | Ab81 CDR-H3 | HGRGYNGYEGAFDI |
| SEQ ID NO: 264 | Ab81 CDR-L1 | RASQGVISALA |
| SEQ ID NO: 268 | Ab81 CDR-L2 | DASTLES |
| SEQ ID NO: 266 | Ab81 CDR-L3 | QQFNSYPLT |
| SEQ ID NO: 269 | Heavy chain constant region (Wild type (WT)) | ASTKGPSVFPLAPSSKSTSGGTAALGCLVKDY FPEPVTVSWNSGALTSGVHTFPAVLQSSGLY SLSSVVTVPSSSLGTQTYICNVNHKPSNTKVD KKVEPKSCDKTHTCPPCPAPELLGGPSVFLFP PKPKDTLMISRTPEVTCVVVDVSHEDPEVKFN WYVDGVEVHNAKTKPREEQYNSTYRVVSVLT VLHQDWLNGKEYKCKVSNKALPAPIEKTISKA |

SEQUENCE TABLE

| Sequence Identifier | Description | Sequence |
|---|---|---|
| | | KGQPREPQVYTLPPSRDELTKNQVSLTCLVK GFYPSDIAVEWESNGQPENNYKTTPPVLDSD GSFFLYSKLTVDKSRWQQGNVFSCSVMHEAL HNHYTQKSLSLSPGK |
| SEQ ID NO: 270 | Heavy chain constant region with L234A, L235A (LALA) mutations (mutations in bold)* | ASTKGPSVFPLAPSSKSTSGGTAALGCLVKDY FPEPVTVSWNSGALTSGVHTFPAVLQSSGLY SLSSVVTVPSSSLGTQTYICNVNHKPSNTKVD KKVEPKSCDKTHTCPPCPAPEAAGGPSVFLF PPKPKDTLMISRTPEVTCVVVDVSHEDPEVKF NWYVDGVEVHNAKTKPREEQYNSTYRVVSVL TVLHQDWLNGKEYKCKVSNKALPAPIEKTISK AKGQPREPQVYTLPPSRDELTKNQVSLTCLVK GFYPSDIAVEWESNGQPENNYKTTPPVLDSD GSFFLYSKLTVDKSRWQQGNVFSCSVMHEAL HNHYTQKSLSLSPGK |
| SEQ ID NO: 271 | Heavy chain constant region with D265C mutation (mutation in bold)* | ASTKGPSVFPLAPSSKSTSGGTAALGCLVKDY FPEPVTVSWNSGALTSGVHTFPAVLQSSGLY SLSSVVTVPSSSLGTQTYICNVNHKPSNTKVD KKVEPKSCDKTHTCPPCPAPELLGGPSVFLFP PKPKDTLMISRTPEVTCVVVCVSHEDPEVKFN WYVDGVEVHNAKTKPREEQYNSTYRVVSVLT VLHQDWLNGKEYKCKVSNKALPAPIEKTISKA KGQPREPQVYTLPPSRDELTKNQVSLTCLVK GFYPSDIAVEWESNGQPENNYKTTPPVLDSD GSFFLYSKLTVDKSRWQQGNVFSCSVMHEAL HNHYTQKSLSLSPGK |
| SEQ ID NO: 272 | Heavy chain constant region with H435A mutation (mutation in bold)* | ASTKGPSVFPLAPSSKSTSGGTAALGCLVKDY FPEPVTVSWNSGALTSGVHTFPAVLQSSGLY SLSSVVTVPSSSLGTQTYICNVNHKPSNTKVD KKVEPKSCDKTHTCPPCPAPELLGGPSVFLFP PKPKDTLMISRTPEVTCVVVDVSHEDPEVKFN WYVDGVEVHNAKTKPREEQYNSTYRVVSVLT VLHQDWLNGKEYKCKVSNKALPAPIEKTISKA KGQPREPQVYTLPPSRDELTKNQVSLTCLVK GFYPSDIAVEWESNGQPENNYKTTPPVLDSD GSFFLYSKLTVDKSRWQQGNVFSCSVMHEAL HNAYTQKSLSLSPGK |
| SEQ ID NO: 273 | Heavy chain constant region: modified Fc region with L234A, L235A, D265C mutations (mutations in bold)* | ASTKGPSVFPLAPSSKSTSGGTAALGCLVKDY FPEPVTVSWNSGALTSGVHTFPAVLQSSGLY SLSSVVTVPSSSLGTQTYICNVNHKPSNTKVD KKVEPKSCDKTHTCPPCPAPEAAGGPSVFLF PPKPKDTLMISRTPEVTCVVVCVSHEDPEVKF NWYVDGVEVHNAKTKPREEQYNSTYRVVSVL TVLHQDWLNGKEYKCKVSNKALPAPIEKTISK AKGQPREPQVYTLPPSRDELTKNQVSLTCLVK GFYPSDIAVEWESNGQPENNYKTTPPVLDSD GSFFLYSKLTVDKSRWQQGNVFSCSVMHEAL HNHYTQKSLSLSPGK |
| SEQ ID NO: 274 | Heavy chain constant region: modified Fc region with L234A, L235A, D265C, H435A mutations (mutations in bold)* | ASTKGPSVFPLAPSSKSTSGGTAALGCLVKDY FPEPVTVSWNSGALTSGVHTFPAVLQSSGLY SLSSVVTVPSSSLGTQTYICNVNHKPSNTKVD KKVEPKSCDKTHTCPPCPAPEAAGGPSVFLF PPKPKDTLMISRTPEVTCVVVCVSHEDPEVKF NWYVDGVEVHNAKTKPREEQYNSTYRVVSVL TVLHQDWLNGKEYKCKVSNKALPAPIEKTISK AKGQPREPQVYTLPPSRDELTKNQVSLTCLVK GFYPSDIAVEWESNGQPENNYKTTPPVLDSD GSFFLYSKLTVDKSRWQQGNVFSCSVMHEAL HNAYTQKSLSLSPGK |
| SEQ ID NO: 275 | Ab85 full length heavy chain sequence; constant region underlined | EVQLVQSGAEVKKPGESLKISCKGSGYSFTNY WIGWVRQMPGKGLEWMAIINPRDSDTRYRPS FQGQVTISADKSISTAYLQWSSLKASDTAMYY CARHGRGYEGYEGAFDIWGQGTLVTVSS<u>AST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPELLGGPSVFLFPPKPK DTLMISRTPEVTCVVVDVSHEDPEVKFNWYVD</u> |

-continued

| SEQUENCE TABLE | | |
|---|---|---|
| Sequence Identifier | Description | Sequence |
| | | GVEVHNAKTKPREEQYNSTYRVVSVLTVLHQ DWLNGKEYKCKVSNKALPAPIEKTISKAKGQP REPQVYTLPPSRDELTKNQVSLTCLVKGFYPS DIAVEWESNGQPENNYKTTPPVLDSDGSFFLY SKLTVDKSRWQQGNVFSCSVMHEALHNHYT QKSLSLSPGK |
| SEQ ID NO: 276 | Ab85 full length heavy chain sequence; constant region underlined; modified Fc region with L234A, L235A mutations (mutations in bold)* | EVQLVQSGAEVKKPGESLKISCKGSGYSFTNY WIGWVRQMPGKGLEWMAIINPRDSDTRYRPS FQGQVTISADKSISTAYLQWSSLKASDTAMYY CARHGRGYEGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKP KDTLMISRTPEVTCVVVDVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFFL YSKLTVDKSRWQQGNVFSCSVMHEALHNHYT QKSLSLSPGK |
| SEQ ID NO: 277 | Ab85 full length heavy chain sequence: constant region underlined; modified Fc region with L234A, L235A, D265C mutations (mutations in bold)* | EVQLVQSGAEVKKPGESLKISCKGSGYSFTNY WIGWVRQMPGKGLEWMAIINPRDSDTRYRPS FQGQVTISADKSISTAYLQWSSLKASDTAMYY CARHGRGYEGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKP KDTLMISRTPEVTCVVVCVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFFL YSKLTVDKSRWQQGNVFSCSVMHEALHNHYT QKSLSLSPGK |
| SEQ ID NO: 278 | Ab85 full length heavy chain sequence (LALA-D265C-H435A mutant); constant region underlined | EVQLVQSGAEVKKPGESLKISCKGSGYSFTNY WIGWVRQMPGKGLEWMAIINPRDSDTRYRPS FQGQVTISADKSISTAYLQWSSLKASDTAMYY CARHGRGYEGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKP KDTLMISRTPEVTCVVVCVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFFL YSKLTVDKSRWQQGNVFSCSVMHEALHNAYT QKSLSLSPGK |
| SEQ ID NO: 279 | Ab249 full length heavy chain sequence; constant region underlined | EVQLVQSGAEVKKPGESLKISCKGSGYRFTTS WIGWVRQMPGKGLEWMGIIYPGDSDTRYSPS FQGQVTISADKSISTAYLQWSSLKASDTAMYY CARHGLGYNGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPELLGGPSVFLFPPKPK DTLMISRTPEVTCVVVDVSHEDPEVKFNWYVD GVEVHNAKTKPREEQYNSTYRVVSVLTVLHQ DWLNGKEYKCKVSNKALPAPIEKTISKAKGQP REPQVYTLPPSRDELTKNQVSLTCLVKGFYPS DIAVEWESNGQPENNYKTTPPVLDSDGSFFLY SKLTVDKSRWQQGNVFSCSVMHEALHNHYT QKSLSLSPGK |
| SEQ ID NO: 280 | Ab249 full length heavy chain sequence; constant | EVQLVQSGAEVKKPGESLKISCKGSGYRFTTS WIGWVRQMPGKGLEWMGIIYPGDSDTRYSPS FQGQVTISADKSISTAYLQWSSLKASDTAMYY |

SEQUENCE TABLE

| Sequence Identifier | Description | Sequence |
|---|---|---|
| | region underlined (LALA mutations)* | CARHGLGYNGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKP KDTLMISRTPEVTCVVVDVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFFL YSKLTVDKSRWQQGNVFSCSVMHEALHNHYT QKSLSLSPGK |
| SEQ ID NO: 281 | Ab249 full length heavy chain sequence; constant region underlined (LALA-D265C mutations)* | EVQLVQSGAEVKKPGESLKISCKGSGYRFTTS WIGWVRQMPGKGLEWMGIIYPGDSDTRYSPS FQGQVTISADKSISTAYLQWSSLKASDTAMYY CARHGLGYNGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKP KDTLMISRTPEVTCVVVCVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFFL YSKLTVDKSRWQQGNVFSCSVMHEALHNHYT QKSLSLSPGK |
| SEQ ID NO: 282 | Ab249 full length heavy chain sequence; constant region underlined; (LALA-D265C-H435A mutations)* | EVQLVQSGAEVKKPGESLKISCKGSGYRFTTS WIGWVRQMPGKGLEWMGIIYPGDSDTRYSPS FQGQVTISADKSISTAYLQWSSLKASDTAMYY CARHGLGYNGYEGAFDIWGQGTLVTVSSAST KGPSVFPLAPSSKSTSGGTAALGCLVKDYFPE PVTVSWNSGALTSGVHTFPAVLQSSGLYSLSS VVTVPSSSLGTQTYICNVNHKPSNTKVDKKVE PKSCDKTHTCPPCPAPEAAGGPSVFLFPPKP KDTLMISRTPEVTCVVVCVSHEDPEVKFNWYV DGVEVHNAKTKPREEQYNSTYRVVSVLTVLH QDWLNGKEYKCKVSNKALPAPIEKTISKAKGQ PREPQVYTLPPSRDELTKNQVSLTCLVKGFYP SDIAVEWESNGQPENNYKTTPPVLDSDGSFFL YSKLTVDKSRWQQGNVFSCSVMHEALHNAYT QKSLSLSPGK |
| SEQ ID NO: 283 | Light chain constant region | RTVAAPSVFIFPPSDEQLKSGTASVVCLLNNFY PREAKVQWKVDNALQSGNSQESVTEQDSKD STYSLSSTLTLSKADYEKHKVYACEVTHQGLS SPVTKSFNRGEC |
| SEQ ID NO: 284 | Ab85 full length light chain; constant region underlined | DIQMTQSPSSLSASVGDRVTITCRSSQGIRSD LGWYQQKPGKAPKLLIYDASNLETGVPSRFSG SGSGTDFTLTISSLQPEDFATYYCQQANGFPL TFGGGTKVEIKRTVAAPSVFIFPPSDEQLKSGT ASVVCLLNNFYPREAKVQWKVDNALQSGNSQ ESVTEQDSKDSTYSLSSTLTLSKADYEKHKVY ACEVTHQGLSSPVTKSFNRGEC |
| SEQ ID NO: 285 | Ab249 light chain; constant region underlined | DIQMTQSPSSLSASVGDRVTITCRASQGIGSA LAWYQQKPGKAPKLLIYDASNLETGVPSRFSG SGSGTDFTLTISSLQPEDFATYYCQQLNGYPL TFGQGTRLEIKRTVAAPSVFIFPPSDEQLKSGT ASVVCLLNNFYPREAKVQWKVDNALQSGNSQ ESVTEQDSKDSTYSLSSTLTLSKADYEKHKVY ACEVTHQGLSSPVTKSFNRGEC |
| SEQ ID NO: 286 | Ab249 HC-CDR1 | TSWIG |
| SEQ ID NO: 287 | Ab249 HC-CDR3 | HGLGYNGYEGAFDI |
| SEQ ID NO: 288 | Ab249 LC-CDR1 | RASQGIGSALA |

| | | SEQUENCE TABLE | |
|---|---|---|

| Sequence Identifier | Description | Sequence |
|---|---|---|
| SEQ ID NO: 289 | Ab249 LC-CDR3 | CQQLNGYPLT |
| SEQ ID NO: 290 | ch-BBK2 Heavy Chain (Variable region italicized) | *QVQLQQPGAELVRPGASVKLSCKASGYTFTSYWI* *NWVKQRPGQGLEWIGNIYPSDSYTNYNQKFKDKA* *TLTVDKSSNTVYMQLNSPTSEDSAVYYCTRNGVE* *GYPHYYAMEYWGQGTSVTVSS*ASTKGPSVFPLAP SSKSTSGGTAALGCLVKDYFPEPVTVSWNSGALTS GVHTFPAVLQSSGLYSLSSVVTVPSSSLGTQTYICN VNHKPSNTKVDKKVEPKSCDKTHTCPPCPAPELLG GPSVFLFPPKPKDTLMISRTPEVTCVVVDVSHEDP EVKFNWYVDGVEVHNAKTKPREEQYNSTYRWSV LTVLHQDWLNGKEYKCKVSNKALPAPIEKTISKAKG QPREPQVYTLPPSRDELTKNQVSLTCLVKGFYPSD IAVEWESNGQPENNYKTTPPVLDSDGSFFLYSKLT VDKSRWQQGNVFSCSVMHEALHNHYTQKSLSLSP GK |
| SEQ ID NO: 291 | ch-BBK2 Light Chain (Variable region italicized) | *DIQMTQTTSALSASLGDRVTIGCRASQDLSNHLYW* *YQQKPDGTVKLLIYYTSRLHSGVPSRFSGSGSGTD* *YSLTIRNLEQEDVATYFCQQGYTLPYTFGGGTKLEI* KRTVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFNR GEC |
| SEQ ID NO: 292 | ch-BBK2 VH CDR1 | SYWIN |
| SEQ ID NO: 293 | ch-BBK2 VH CDR2 | NIYPSDSYTNYNQKFKD |
| SEQ ID NO: 294 | ch-BBK2 VH CDR3 | NGVEGYPHYYAMEY |
| SEQ ID NO: 295 | ch-BBK2 VL CDR1 | RASQDLSNHLY |
| SEQ ID NO: 296 | ch-BBK2 VL CDR2 | YTSRLHS |
| SEQ ID NO: 297 | ch-BBK2 VL CDR3 | QQGYTLPYT |
| SEQ ID NO: 298 | ch-BBK2 Light Chain Variable Region | QVQLQQPGAELVRPGASVKLSCKASGYTFTSYWI NWVKQRPGQGLEWIGNIYPSDSYTNYNQKFKDKA TLTVDKSSNTVYMQLNSPTSEDSAVYYCTRNGVE GYPHYYAMEYWGQGTSVTVSS |
| SEQ ID NO: 299 | ch-BBK2 Heavy Chain Variable Region | DIQMTQTTSALSASLGDRVTIGCRASQDLSNHLYW YQQKPDGTVKLLIYYTSRLHSGVPSRFSGSGSGTD YSLTIRNLEQEDVATYFCQQGYTLPYTFGGGTKLEI K. |
| SEQ ID NO: 300 | Anti CD2 Ab1 CDR-H1 | EYYMY |
| SEQ ID NO: 301 | Ab1 CDR-H2 | RIDPEDGSIDYVEKFKK |
| SEQ ID NO: 302 | Ab1 CDR-H3 | GKFNYRFAY |
| SEQ ID NO: 303 | Ab1 CDR-L1 | RSSQSLLHSSGNTYLN |
| SEQ ID NO: 304 | Ab1 CDR-L2 | LVSKLES |
| SEQ ID NO: 305 | Ab1 CDR-L3 | MQFTHYPYT |

-continued

| Sequence Identifier | Description | Sequence |
|---|---|---|
| SEQ ID NO: 306 | Ab1 Heavy chain variable region | QVQLVQSGAEVKKPGASVKVSCKASGYTFTE YYMYWVRQAPGQGLELMGRIDPEDGSIDYVE KFKKKVTLTADTSSSTAYMELSSLTSDDTAVY YCARGKFNYRFAYWGQGTLVTVSS |
| SEQ ID NO: 307 | Ab1 Light chain variable region | DVVMTQSPPSLLVTLGQPASISCRSSQSLLHS SGNTYLNWLLQRPGQSPQPLIYLVSKLESGVP DRFSGSGSGTDFTLKISGVEAEDVGVYYCMQ FTHYPYTFGQGTKLE IK |
| SEQ ID NO: 308 | Ab1a Heavy chain variable region | QVQLVQSGAEVQRPGASVKVSCKASGYIFTE YYMYWVRQAPGQGLELVGRIDPEDGSIDYVE KFKKKVTLTADTSSSTAYMELSSLTSDDTAVY YCARGKFNYRFAYWGQGTLVTVSS |
| SEQ ID NO: 309 | Ab1a Light chain variable region | DVVMTQSPPSLLVTLGQPASISCRSSQSLLHS SGNTYLNWLLQRPGQSPQPLIYLVSKLESGVP DRFSGSGSGTDFTLKISGVEAEDVGVYYCMQ FTHYPYTFGQGTKLEIK |
| SEQ ID NO: 310 | Consensus human Ab Heavy chain variable domain | EVQLVESGGGLVQPGGSLRLSCAASGFTFSD YAMSWVRQAPGKGLEWVAVISENGSDTYYA DSVKGRFTISRDDSKNTLYLQMNSLRAEDTAV YYCARDRGGAVSYFDVWGQGTLVTVSS |
| SEQ ID NO: 311 | Consensus human Ab Light chain variable domain | DIQMTQSPSSLSASVGDRVTITCRASQDVSSY LAWYQQKPGKAPKLLIYAASSLESGVPSRFS GSGSGTDFTLTISSLQPEDFATYYCQQYNSLP YTFGQGTKVEIKRT |
| SEQ ID NO: 312 | Human CD2 sequence | MSFPCKFVASFLLIFNVSSKGAVSKEITNALET WGALGQDINLDIPSFQMSDDIDDIKWEKTSDK KKIAQFRKEKETFKEKDTYKLFKNGTLKIKHLK TDDQDIYKVSIYDTKGKNVLEKIFDLKIQERVSK PKISWTCINTTLTCEVMNGTDPELNLYQDGKH LKLSQRVITHKWTTSLSAKFKCTAGNKVSKES SVEPVSCPEKGLDIYLIIGICGGGSLLMVFVALL VFYITKRKKQRSRRNDEELETRAHRVATEERG RKPHQIPASTPQNPATSQHPPPPPGHRSQAP SHRPPPPGHRVQHQPQKRPPAPSGTQVHQQ KGPPLPRPRVQPKPPHGAAENSLSPSSN |
| SEQ ID NO: 313 | RPA-2.10 CDR-H1 | GFTFSSY |
| SEQ ID NO: 314 | Anti-CD2 RPA-2.10 CDR-H2 | SGGGF |
| SEQ ID NO: 315 | RPA-2.10 CDR-H3 Variant 1 | SSYGEIMDY |
| SEQ ID NO: 316 | RPA-2.10 CDR-H3 Variant 2 | SSYGELMDY |
| SEQ ID NO: 317 | RPA-2.10 CDR-L1 | RASQRIGTSIH |
| SEQ ID NO: 318 | RPA-2.10 CDR-L2 | YASESIS |
| SEQ ID NO: 319 | RPA-2.10 CDR-L3 | QQSHGWPFTF |
| SEQ ID NO: 320 | RPA-2.10 Heavy chain variable region Variant 1 | EVKLVESGGGLVKPGGSLKLSCAASGFTFSSY DMSWVRQTPEKRLEWVASISGGGFLYYLDSV KGRFTISRDNARNILYLHMTSLRSEDTAMYYC ARSSYGEIMDYWGQGTSVTVSS |
| SEQ ID NO: 321 | RPA-2.10 Heavy chain variable region Variant 2 | EVKLVESGGGLVKPGGSLKLSCAASGFTFSSY DMSWVRQTPEKRLEWVASISGGGFLYYLDSV KGRFTISRDNARNILYLHMTSLRSEDTAMYYC ARSSYGELMDYWGQGTSVTVSS |

-continued

| SEQUENCE TABLE |
| --- |

| Sequence Identifier | Description | Sequence |
| --- | --- | --- |
| SEQ ID NO: 322 | RPA-2.10 Light chain variable region | DILLTQSPAILSVSPGERVSFSCRASQRIGTSIH WYQQRTTGSPRLLIKYASESISGIPSRFSGSG SGTDFTLSINSVESEDVADYYCQQSHGWPFT FGGGTKLEIE |
| SEQ ID NO: 323 | RPA-2.10 Heavy chain constant region | AKTTPPSVYPLAPGSAAQTNSMVTLGCLVKGY FPEPVTVTWNSGSLSSGVHTFPAVLQSDLYTL SSSVTVPSSTWPSETVTCNVAHPASSTKVDK KIVPRDCGCKPCICTVPEVSSVFIFPPKPKDVL TITLTPKVTCVVVDISKDDPEVQFSWFVDDVEV HTAQTQPREEQFNSTFRSVSELPIMHQDWLN GKEFKCRVNSAAFPAPIEKTISKTKGRPKAPQ VYTIPPPKEQMAKDKVSLTCMITDFFPEDITVE WQWNGQPAENYKNTQPIMDTDGSYFVYSKL NVQKSNWEAGNTFTCSVLHEGLHNHHTEKSL SHSPGK |
| SEQ ID NO: 324 | RPA-2.10 Light chain constant region | RADAAPTVSIFPPSSEQLTSGGASVVCFLNNF YPKDINVKWKIDGSERQNGVLNSWTDQDSKD STYSMSSTLTLTKDEYERHNSYTCEATHKTST SPIVKSFNRNEC |
| SEQ ID NO: 325 | Anti-CD5 antibody Light chain variable region | DIQMTQSPSSMSASLGDRVTITCRASQDINSY LSWFQQKPGKSPKTLIYRANRLVDGVPSRFS GSGSGTDYTLTISSLQYEDFGIYYCQQYDESP WTFGGGTKLEIK |
| SEQ ID NO: 326 | Heavy chain variable region | QIQLVQSGPGLKKPGGSVRISCAASGYTFTNY GMNWVKQAPGKGLRWMGWINTHTGEPTYAD DFKGRFTFSLDTSKSTAYLQINSLRAEDTATYF CTRRGYDWY FDVWGQGTTVTSS |
| SEQ ID NO: 327 | CDR-H1 | GYTFTNY |
| SEQ ID NO: 328 | CDR-H2 | NTHTGE |
| SEQ ID NO: 329 | CDR-H3 | RGYDWYFDV |
| SEQ ID NO: 330 | CDR-L1 | RASQDINSYLS |
| SEQ ID NO: 331 | CDR-L2 | RANRLVD |
| SEQ ID NO: 332 | CDR-L3 | QQYDESPWT |
| SEQ ID NO: 333 | Light chain variable region | DIQMTQSPSSLSASVGDRVTITCRASQDINSYL SWFQQKPGKAPKTLIYRANRLESGVPSRFSG SGSGTDYTLTISSLQYEDFGIYYCQQYDESPW TFGGGTKLEIK |
| SEQ ID NO: 334 | Heavy chain variable region | EIQLVQSGGGLVKPGGSVRISCAASGYTFTNY GMNWVRQAPGKGLEWMGWINTHYGEPTYAD SFKGTRTFSLDDSKNTAYLQINSLRAEDTAVYF CTRRGYDWYFDVWGQGGTTVTVSS |
| SEQ ID NO: 335 | CDR-H1 | GYTFTNY |
| SEQ ID NO: 336 | CDR-H2 | NTHYGE |
| SEQ ID NO: 337 | CDR-H3 | RRGYDWYFDV |
| SEQ ID NO: 338 | CDR-L1 | RASQDINSYLS |
| SEQ ID NO: 339 | CDR-L2 | RANRLES |

-continued

| | SEQUENCE TABLE | |
|---|---|---|

| Sequence Identifier | Description | Sequence |
|---|---|---|
| SEQ ID NO: 340 | CDR-L3 | QQYDESPWT |
| SEQ ID NO: 341 | CDR-H1 | GYSITSGYY |
| SEQ ID NO: 342 | CDR-H2 | ISYSGFT |
| SEQ ID NO: 343 | CDR-H3 | AGDRTGSWFAY |
| SEQ ID NO: 344 | CDR-L1 | QDISNY |
| SEQ ID NO: 345 | CDR-L2 | ATS |
| SEQ ID NO: 346 | CDR-L3 | LQYASYPFT |
| SEQ ID NO: 347 | CDR-H1 | GYIFTNYG |
| SEQ ID NO: 348 | CDR-H2 | INTYNGEP |
| SEQ ID NO: 349 | CDR-H3 | ARGDYYGYEDY |
| SEQ ID NO: 350 | CDR-L1 | QGISNY |
| SEQ ID NO: 351 | CDR-L2 | YTS |
| SEQ ID NO: 352 | CDR-L3 | QQYSKLPWT |
| SEQ ID NO: 353 | 5D7CDR-H1 | FSLSTSGMG |
| SEQ ID NO: 354 | 5D7 CDR-H2 | WWDDD |
| SEQ ID NO: 355 | 5D7 CDR-H3 | RRATGTGFDY |
| SEQ ID NO: 356 | 5D7 CDR-L1 | QDVGTA |
| SEQ ID NO: 357 | 5D7 CDR-L2 | WTSTRHT |
| SEQ ID NO: 358 | 5D7 CDR-L3 | YNSYNT |
| SEQ ID NO: 359 | Humanized 5D7 Heavy chain variable region (CDRs in bold) | QVTLKESGPVLVKPTETLTLTCTFSGFSLSTSG MGVGWIRQAPGKGLEWVAHIWWDDDVYYNP SLKSRLTITKDASKDQVSLKLSSVTAADTAVYY CVRRRATGTGFDYWGQGTLVTVSS |
| SEQ ID NO: 360 | Humanized 5D7 Light chain variable region (CDRs in bold) | NIVMTQSPSSLSASVGDRVTITCQASQDVGTA VAWYQQKPDQSPKLLIYWTSTRHTGVPDRFT GSGSGTDFTLTISSLQPEDIATYFCHQYNSYNT FGSGTKLEIK |
| SEQ ID NO: 361 | Consensus human Heavy chain variable domain (CDRs in bold) | EVQLVESGGGLVQPGGSLRLSCAASGFTFSD YAMSWVRQAPGKGLEWVAVISENGSDTYYA DSVKGRFTISRDDSKNTLYLQMNSLRAEDTAV YYCARDRGGAVSYFDVWGQGTLVTVSS |

-continued

| SEQUENCE TABLE | | |
|---|---|---|
| Sequence Identifier | Description | Sequence |
| SEQ ID NO: 362 | Consensus human Light chain variable domain (CDRs in bold) | DIQMTQSPSSLSASVGDRVTITCRASQDVSSY LAWYQQKPGKAPKLLIYAASSLESGVPSRFS GSGSGTDFTLTISSLQPEDFATYYCQQYNSLP YTFGQGTKVEIKRT |
| SEQ ID NO: 363 | Human CD5 amino acid sequence | MVCSQSWGRS SKQWEDPSQA SKVCQRLNCG VPLSLGPFLV TYTPQSSIIC YGQLGSFSNCSHSRNDMCHS LGLTCLEPQK TTPPTTRPPP TTTPEPTAPP RLQLVAQSGG QHCAGVVEFYSGSLGGTISY EAQDKTQDLE NFLCNNLQCG SFLKHLPETE AGRAQDPGEP REHQPLPIQWKIQNSSCTSL EHCFRKIKPQ KSGRVLALLC SGFQPKVQSR LVGGSSICEG TVEVRQGAQWAALCDSSSAR SSLRWEEVCR EQQCGSVNSY RVLDAGDPTS RGLFCPHQKL SQCHELWERNSYCKKVFVTC QDPNPAGLAA GTVASIILAL VLLVVLLVVC GPLAYKKLVK KFRQKKQRQWIGPTGMNQNM SFHRNHTATV RSHAENPTAS HVDNEYSQPP RNSHLSAYPA LEGALHRSSMQPDNSSDSDY DLHGAQRL |
| SEQ ID NO: 364 | Trastuzumab HC | EVQLVESGGGLVQPGGSLRLSCAASGFNIKDTYIH WVRQAPGKGLEWVARIYPTNGYTRYADSVKGRFTI SADTSKNTAYLQMNSLRAEDTAVYYCSRWGGDGF YAMDYWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVDVSHEDPEVKFN WYVDGVEVHNAKTKPREEQYNSTYRWSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDK SRWQQGNVFSCSVMHEALHNHYTQKSLSLSPGK |
| SEQ ID NO: 365 | Trastuzumab D265C HC | EVQLVESGGGLVQPGGSLRLSCAASGFNIKDTYIH WVRQAPGKGLEWVARIYPTNGYTRYADSVKGRFTI SADTSKNTAYLQMNSLRAEDTAVYYCSRWGGDGF YAMDYWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVCVSHEDPEVKFN WYVDGVEVHNAKTKPREEQYNSTYRWSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDK SRWQQGNVFSCSVMHEALHNHYTQKSLSLSPGK |
| SEQ ID NO: 366 | Trastuzumab LALA HC | EVQLVESGGGLVQPGGSLRLSCAASGFNIKDTYIH WVRQAPGKGLEWVARIYPTNGYTRYADSVKGRFTI SADTSKNTAYLQMNSLRAEDTAVYYCSRWGGDGF YAMDYWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPEAAGGPS VFLFPPKPKDTLMISRTPEVTCVVVDVSHEDPEVKF NWYVDGVEVHNAKTKPREEQYNSTYRWSVLTVL HQDWLNGKEYKCKVSNKALPAPIEKTISKAKGQPR EPQVYTLPPSREEMTKNQVSLTCLVKGFYPSDIAV EWESNGQPENNYKTTPPVLDSDGSFFLYSKLTVD KSRWQQGNVFSCSVMHEALHNHYTQKSLSLSPGK |
| SEQ ID NO: 367 | Trastuzumab LALA D265C HC | EVQLVESGGGLVQPGGSLRLSCAASGFNIKDTYIH WVRQAPGKGLEWVARIYPTNGYTRYADSVKGRFTI SADTSKNTAYLQMNSLRAEDTAVYYCSRWGGDGF YAMDYWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPEAAGGPS VFLFPPKPKDTLMISRTPEVTCVVVCVSHEDPEVKF NWYVDGVEVHNAKTKPREEQYNSTYRWSVLTVL HQDWLNGKEYKCKVSNKALPAPIEKTISKAKGQPR EPQVYTLPPSREEMTKNQVSLTCLVKGFYPSDIAV |

-continued

| SEQUENCE TABLE | | |
|---|---|---|
| Sequence Identifier | Description | Sequence |
| | | EWESNGQPENNYKTTPPVLDSDGSFFLYSKLTVD KSRWQQGNVFSCSVMHEALHNHYTQKSLSLSPGK |
| SEQ ID NO: 368 | Trastuzumab HC Variable Region | EVQLVESGGGLVQPGGSLRLSCAASGFNIKDTYIH WVRQAPGKGLEWVARIYPTNGYTRYADSVKGRFTI SADTSKNTAYLQMNSLRAEDTAVYYCSRWGGDGF YAMDYWGQGTLVTVSS |
| SEQ ID NO: 369 | Trastuzumab LC | DIQMTQSPSSLSASVGDRVTITCRASQDVNTAVAW YQQKPGKAPKLLIYSASFLYSGVPSRFSGSRSGTD FTLTISSLQPEDFATYYCQQHYTTPPTFGQGTKVEI KRTVAAPSVFIFPPSDEQLKSGTASVVCLLNNFYPR EAKVQWKVDNALQSGNSQESVTEQDSKDSTYSLS STLTLSKADYEKHKVYACEVTHQGLSSPVTKSFNR GEC |
| SEQ ID NO: 370 | Trastuzumab LC Variable Region | DIQMTQSPSSLSASVGDRVTITCRASQDVNTAVAW YQQKPGKAPKLLIYSASFLYSGVPSRFSGSRSGTD FTLTISSLQPEDFATYYCQQHYTTPPTFGQGTKVEI K |
| SEQ ID NO: 371 | Anti-PSMA Antibody h3/F11-Var16 HC | QVQLVQSGAEVKKPGASVKVSCKASGYTFTYFDIN WLRQAPGQGLEWMGGISPGDSNVNYAQKFQGRV TLTIDTSTSTAYMELSSLRSEDTAVYYCARDGNFPY YAMDSWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVDVSHEDPEVKFN WYVDGVEVHNAKTKPREEQYNSTYRWSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDK SRWQQGNVFSCSVMHEALHNHYTQKSLSLSPGK |
| SEQ ID NO: 372 | Anti-PSMA Antibody h3/F11-Var16 D265C HC | QVQLVQSGAEVKKPGASVKVSCKASGYTFTYFDIN WLRQAPGQGLEWMGGISPGDSNVNYAQKFQGRV TLTIDTSTSTAYMELSSLRSEDTAVYYCARDGNFPY YAMDSWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPELLGGPSV FLFPPKPKDTLMISRTPEVTCVVVCVSHEDPEVKFN WYVDGVEVHNAKTKPREEQYNSTYRWSVLTVLH QDWLNGKEYKCKVSNKALPAPIEKTISKAKGQPRE PQVYTLPPSREEMTKNQVSLTCLVKGFYPSDIAVE WESNGQPENNYKTTPPVLDSDGSFFLYSKLTVDK SRWQQGNVFSCSVMHEALHNHYTQKSLSLSPGK |
| SEQ ID NO: 373 | Anti-PSMA Antibody h3/F11-Var16 LALA HC | QVQLVQSGAEVKKPGASVKVSCKASGYTFTYFDIN WLRQAPGQGLEWMGGISPGDSNVNYAQKFQGRV TLTIDTSTSTAYMELSSLRSEDTAVYYCARDGNFPY YAMDSWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPEAAGGPS VFLFPPKPKDTLMISRTPEVTCVVVDVSHEDPEVKF NWYVDGVEVHNAKTKPREEQYNSTYRWSVLTVL HQDWLNGKEYKCKVSNKALPAPIEKTISKAKGQPR EPQVYTLPPSREEMTKNQVSLTCLVKGFYPSDIAV EWESNGQPENNYKTTPPVLDSDGSFFLYSKLTVD KSRWQQGNVFSCSVMHEALHNHYTQKSLSLSPGK |
| SEQ ID NO: 374 | Anti-PSMA Antibody h3/F11-Var16 LALA D265C HC | QVQLVQSGAEVKKPGASVKVSCKASGYTFTYFDIN WLRQAPGQGLEWMGGISPGDSNVNYAQKFQGRV TLTIDTSTSTAYMELSSLRSEDTAVYYCARDGNFPY YAMDSWGQGTLVTVSSASTKGPSVFPLAPSSKST SGGTAALGCLVKDYFPEPVTVSWNSGALTSGVHT FPAVLQSSGLYSLSSVVTVPSSSLGTQTYICNVNHK PSNTKVDKKVEPKSCDKTHTCPPCPAPEAAGGPS VFLFPPKPKDTLMISRTPEVTCVVVCVSHEDPEVKF NWYVDGVEVHNAKTKPREEQYNSTYRWSVLTVL HQDWLNGKEYKCKVSNKALPAPIEKTISKAKGQPR EPQVYTLPPSREEMTKNQVSLTCLVKGFYPSDIAV |

-continued

SEQUENCE TABLE

| Sequence Identifier | Description | Sequence |
|---|---|---|
| | | EWESNGQPENNYKTTPPVLDSDGSFFLYSKLTVD KSRWQQGNVFSCSVMHEALHNHYTQKSLSLSPGK |
| SEQ ID NO: 375 | Anti-PSMA Antibody h3/F11-Var16 HC Variable Region | QVQLVQSGAEVKKPGASVKVSCKASGYTFTYFDIN WLRQAPGQGLEWMGGISPGDSNVNYAQKFQGRV TLTIDTSTSTAYMELSSLRSEDTAVYYCARDGNFPY YAMDSWGQGTLVTVSS |
| SEQ ID NO: 376 | Anti-PSMA Antibody h3/F11-Var16 LC | DIVMTQSPLSLPVTPGEPASISCRSSQSLVHSSGQ TYLHWYQQKPGQSPQLLIYTVSNRASGVPDRFSG SGSGTDFTLKISRVEAEDVGTYYCSQSTHVPTFGG GTKVEIKRTVAAPSVFIFPPSDEQLKSGTASWCLL NNFYPREAKVQWKVDNALQSGNSQESVTEQDSK DSTYSLSSTLTLSKADYEKHKVYACEVTHQGLSSP VTKSFNRGEC |
| SEQ ID NO: 377 | Anti-PSMA Antibody h3/F11-Var16 LC Variable Region | DIVMTQSPLSLPVTPGEPASISCRSSQSLVHSSGQ TYLHWYQQKPGQSPQLLIYTVSNRASGVPDRFSG SGSGTDFTLKISRVEAEDVGTYYCSQSTHVPTFGG GTKVEIK |
| SEQ ID NO: 378 | Anti-PSMA Antibody h3/F11-Var16 CDRH1 | GYTFTYF |
| SEQ ID NO: 379 | Anti-PSMA Antibody h3/F11-Var16 CDRH2 | GISPGDSNVNYAQKFQG |
| SEQ ID NO: 380 | Anti-PSMA Antibody h3/F11-Var16 CDRH3 | DGNFPYYAMDS |
| SEQ ID NO: 381 | Anti-PSMA Antibody h3/F11-Var16 CDRL1 | RSSQSLVHSSGQTYLH |
| SEQ ID NO: 382 | Anti-PSMA Antibody h3/F11-Var16 CDRL2 | TVSNRAS |
| SEQ ID NO: 383 | Anti-PSMA Antibody h3/F11-Var16 CDRL3 | SQSTHVPT |

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

The invention claimed is:

1. An amatoxin comprising the structure of Formula (A) (HDP 30.2867):

Formula (A)

(HDP 30.2867)

(Ia)

or a stereoisomer thereof, wherein

Q is S;

L is a linker;

Z is a chemical moiety formed by a coupling reaction between a reactive substituent present on L and a reactive substituent present within the antibody, or antigen-binding fragment thereof; and Ab is the antibody or the antigen binding fragment thereof;

wherein Ab, Z, and L, taken together as Ab-Z-L, is represented by the formula:

2. A method of preparing an antibody-drug conjugate (ADC) comprising conjugating an antibody, or an antigen-binding fragment thereof, to the amatoxin according to claim 1.

3. An antibody-drug conjugate (ADC) comprising an antibody, or an antigen-binding fragment thereof, conjugated to an amatoxin via a linker, the ADC having the structure of Formula (Ia):

wherein S is the sulfur atom of a cysteine residue present in the antibody, or the antigen-binding fragment thereof.

4. The ADC according to claim 3, wherein L is a non-cleavable linker.

5. An antibody drug conjugate (ADC) comprising an antibody, or an antigen-binding fragment thereof, conjugated to an amatoxin via a linker, the ADC having the structure of Formula (IIa):

(IIa)

6. The ADC according to claim 5, wherein the antibody, or the antigen binding fragment thereof, specifically binds to human Her2, PSMA, CD37, or CD123.

7. The ADC according to claim 5, wherein the antibody, or the antigen binding fragment thereof, comprises an Fc region comprising at least one mutation selected from the group consisting of D265C, D265A, A118C, L234A, or L235A (according to EU index).

8. The ADC according to claim 5, wherein the antibody, or antigen binding fragment thereof, specifically binds to PSMA and comprises a CDRH1 according to SEQ ID NO. 378, a CDRH2 according to SEQ ID NO. 379, a CDRH3 according to SEQ ID NO. 380, a CDRL1 according to SEQ ID NO. 381, a CDRL2 according to SEQ ID NO. 382, and a CDRL3 according to SEQ ID NO. 383.

9. The ADC according to claim 8, wherein the antibody, or antigen binding fragment thereof, comprises a heavy chain variable region according to SEQ ID NO. 375 and a light chain variable region according to SEQ ID NO. 377.

10. The ADC according to claim 9, wherein the antibody comprises a heavy chain according to SEQ ID NO. 371, SEQ ID NO. 372, SEQ ID NO. 373, or SEQ ID NO. 374, and a light chain according to SEQ ID NO. 376, or an antigen binding fragment thereof.

11. An antibody-drug conjugate (ADC), wherein the antibody-drug conjugate comprises an antibody, or an antigen-binding fragment thereof, which specifically binds to human PSMA, and comprises a heavy chain having an amino acid sequence according to SEQ ID NO. 374 and a light chain having an amino acid sequence according to SEQ ID NO. 376, and which is conjugated to compound HDP30.2867.

12. The antibody-drug conjugate (ADC) according to claim 11, wherein the drug antibody ratio (DAR) is about 1, 2, 3, or 4.

13. A pharmaceutical composition comprising the ADC according to claim 5 and at least a pharmaceutically acceptable carrier.

14. A pharmaceutical composition comprising the ADC according to claim 11 and at least a pharmaceutically acceptable carrier.

15. A method of treating cancer, the method comprising administering a therapeutically effective amount of the ADC of claim 5, or a pharmaceutical composition comprising a therapeutically effective amount of the ADC, to a patient, wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, hematological cancer, leukemia, and malignant lymphoma.

16. The method according to claim 15, wherein the cancer is prostate cancer.

17. A method of treating cancer, the method comprising administering a therapeutically effective amount of the ADC of claim 11, or a pharmaceutical composition comprising a therapeutically effective amount of the ADC, to a patient, wherein the cancer is selected from the group consisting of breast cancer, pancreatic cancer, cholangiocarcinoma, colorectal cancer, lung cancer, prostate cancer, ovarian cancer, prostate cancer, stomach cancer, kidney cancer, malignant melanoma, hematological cancer, leukemia, and malignant lymphoma.

18. The method according to claim 17, wherein the cancer is prostate cancer.

* * * * *

SEQUENCE LISTING

<160> NUMBER OF SEQ ID NOS: 564

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

```
Ser Tyr Trp Ile Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Synthetic

<400> SEQUENCE: 3

His Gly Arg Gly Tyr Asn Gly Tyr Glu Gly Ala Phe Asp Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Ala Ser Gln Gly Ile Ser Ser Ala Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Asp Ala Ser Ser Leu Glu Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Cys Gln Gln Phe Asn Ser Tyr Pro Leu Thr
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7
```

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120

<210> SEQ ID NO 8
<211> LENGTH: 109
<212> TYPE: PRT
<213> ORGANISM: Artificial Sequence
<220> FEATURE:
<223> OTHER INFORMATION: Synthetic

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105

<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser

-continued

```
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120
```

```
<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                85                  90                  95

Thr Phe Gly Gly Gly Thr Lys Val Glu Ile Lys
            100                 105
```

```
<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Phe Thr Phe Ser Asp Ala Asp Met Asp
1               5
```

```
<210> SEQ ID NO 12
<211> LENGTH: 19
<212> TYPE: PRT
<213> ORGANISM: Artificial Sequence
<220> FEATURE:
<223> OTHER INFORMATION: Synthetic

<400> SEQUENCE: 12

Arg Thr Arg Asn Lys Ala Gly Ser Tyr Thr Thr Glu Tyr Ala Ala Ser
1               5                   10                  15

Val Lys Gly
```

```
<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13
```

-continued

Ala Arg Glu Pro Lys Tyr Trp Ile Asp Phe Asp Leu
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

Arg Ala Ser Gln Ser Ile Ser Ser Tyr Leu Asn
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic

<400> SEQUENCE: 15

Ala Ala Ser Ser Leu Gln Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Ile Ala Pro Tyr Thr
1               5

<210> SEQ ID NO 17
<211> LENGTH: 363
<212> TYPE: DNA
<213> ORGANISM: Artificial Sequence
<220> FEATURE:
<223> OTHER INFORMATION: Synthetic

<400> SEQUENCE: 17
gaggtgcagc tggtggagtc tgggggaggc ttggtccagc ctggagggtc cctgagactc      60
tcctgtgcag cctctggatt caccttcagt gacgccgaca tggactgggt ccgccaggct     120
ccagggaagg ggctggagtg ggttggccgt actagaaaca aagcaggaag ttacaccaca     180
gaatacgccg cgtctgtgaa aggcagattc accatctcaa gagatgattc aaagaactca     240
ctgtatctgc aaatgaacag cctgaaaacc gaggacacgg cggtgtacta ctgcgccaga     300
gagcctaaat actggatcga cttcgaccta tggggagag  gtaccttggt caccgtctcc     360
tca                                                                   363

<210> SEQ ID NO 18
<211> LENGTH: 321
<212> TYPE: DNA
<213> ORGANISM: Artificial Sequence
<220> FEATURE:
<223> OTHER INFORMATION: Synthetic

<400> SEQUENCE: 18
gacatccaga tgacccagtc tccatcctcc ctgtctgcat ctgtaggaga cagagtcacc      60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcagcaa agctacatcg cccccttacac ttttggcgga      300 gggaccaagg ttgagatcaa a                                                 321

<210> SEQ ID NO 19
<211> LENGTH: 119
<212> TYPE: PRT
<213> ORGANISM: Artificial Sequence
<220> FEATURE:
<223> OTHER INFORMATION: Synthetic

<400> SEQUENCE: 19

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: Synthetic

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

Phe Gly Gly Gly Thr Lys Val Glu Ile Lys
            100                 105

<210> SEQ ID NO 21
<211> LENGTH: 9
<212> TYPE: PRT

```
<213> ORGANISM: Artificial Sequence
<220> FEATURE:
<223> OTHER INFORMATION: Synthetic

<400> SEQUENCE: 21

Gly Thr Phe Arg Ile Tyr Ala Ile Ser
1               5

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Gly Ile Ile Pro Asp Phe Gly Val Ala Asn Tyr Ala Gln Lys Phe Gln
1               5                   10                  15

Gly

<210> SEQ ID NO 23
<211> LENGTH: 12
<212> TYPE: PRT
<213> ORGANISM: Artificial Sequence
<220> FEATURE:
<223> OTHER INFORMATION: Synthetic

<400> SEQUENCE: 23

Ala Arg Gly Gly Leu Asp Thr Asp Glu Phe Asp Leu
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic

<400> SEQUENCE: 24

Arg Ala Ser Gln Ser Ile Asn Ser Tyr Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic

<400> SEQUENCE: 25

Ala Ala Ser Ser Leu Gln Ser
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Gln Gln Gly Val Ser Asp Ile Thr
1               5

<210> SEQ ID NO 27
<211> LENGTH: 357
```

<212> TYPE: DNA
<213> ORGANISM: Artificial Sequence
<220> FEATURE:
<223> OTHER INFORMATION: Synthetic

<400> SEQUENCE: 27
caggtgcagc tggtgcagtc tggggctgag gtgaagaagc ctgggtcctc ggtgaaggtc      60
tcctgcaagg cttctggagg caccttccga atctatgcta tcagctgggt gcgacaggcc     120
cctggacaag ggcttgagtg gatgggaggg atcatccctg acttcggtgt agcaaactac     180
gcacagaagt tccagggcag agtcacgatt accgcggacg aatccacgag cacagcctac     240
atggagctga gcagcctgag atctgaggac acggcggtgt actactgcgc cagaggtgga     300
ttggacacag acgagttcga cctatggggg agaggtacct tggtcaccgt ctcctca        357

<210> SEQ ID NO 28
<211> LENGTH: 318
<212> TYPE: DNA
<213> ORGANISM: Artificial Sequence
<220> FEATURE:
<223> OTHER INFORMATION: Synthetic

<400> SEQUENCE: 28
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ggagtcagtg acatcacttt tggcggaggg     300
accaaggttg agatcaaa                                                   318

<210> SEQ ID NO 29
<211> LENGTH: 119
<212> TYPE: PRT
<213> ORGANISM: Artificial Sequence
<220> FEATURE:
<223> OTHER INFORMATION: Synthetic

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 30
<211> LENGTH: 106
<212> TYPE: PRT

<213> ORGANISM: Artificial Sequence
<220> FEATURE:
<223> OTHER INFORMATION: Synthetic

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

Phe Gly Gly Gly Thr Lys Val Glu Ile Lys
            100                 105

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Gly Thr Phe Ser Ser Tyr Ala Ile Ser
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

Gly Ile Ile Pro Ile Phe Gly Thr Ala Asn Tyr Ala Gln Lys Phe Gln
1               5                   10                  15

Gly

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Ala Arg Gly Gly Leu Asp Thr Asp Glu Phe Asp Leu
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic

<400> SEQUENCE: 34

Arg Ala Ser Gln Ser Ile Asn Ser Tyr Leu Asn 1                5                10

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Ala Ala Ser Ser Leu Gln Ser
1                5

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gln Gln Gly Val Ser Asp Ile Thr
1                5

<210> SEQ ID NO 37
<211> LENGTH: 357
<212> TYPE: DNA
<213> ORGANISM: Artificial Sequence
<220> FEATURE:
<223> OTHER INFORMATION: Synthetic

<400> SEQUENCE: 37
caggtgcagc tggtgcagtc tggggctgag gtgaagaagc ctgggtcctc ggtgaaggtc        60
tcctgcaagg cttctggagg caccttcagc agctatgcta tcagctgggt gcgacaggcc       120
cctggacaag ggcttgagtg gatgggaggg atcatcccta tctttggtac agcaaactac       180
gcacagaagt tccagggcag agtcacgatt accgcggacg aatccacgag cacagcctac       240
atggagctga gcagcctgag atctgaggac acggcggtgt actactgcgc cagaggtgga       300
ttggacacag acgagttcga cctatggggg agaggtacct tggtcaccgt ctcctca         357

<210> SEQ ID NO 38
<211> LENGTH: 318
<212> TYPE: DNA
<213> ORGANISM: Artificial Sequence
<220> FEATURE:
<223> OTHER INFORMATION: Synthetic

<400> SEQUENCE: 38
gacatccaga tgacccagtc tccatcctcc ctgtctgcat ctgtaggaga cagagtcacc        60
atcacttgcc gggcaagtca gagcattaac agctatttaa attggtatca gcagaaacca       120
gggaaagccc ctaagctcct gatctatgct gcatccagtt tgcaaagtgg ggtcccatca       180
aggttcagtg gcagtggatc tgggacagat ttcactctca ccatcagcag tctgcaacct       240
gaagattttg caacttacta ctgtcagcaa ggagtcagtg acatcacttt tggcggaggg       300
accaaggttg agatcaaa                                                     318

<210> SEQ ID NO 39
<211> LENGTH: 119
<212> TYPE: PRT
<213> ORGANISM: Artificial Sequence
<220> FEATURE:
<223> OTHER INFORMATION: Synthetic

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Leu Tyr
            20                  25                  30

Ala Ile Ser Trp Val Arg Gln Ala Pro Gly Gln Gly Leu Glu Trp Met
        35                  40                  45

Gly Gly Ile Ile Pro Ala Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115

<210> SEQ ID NO 40
<211> LENGTH: 106
<212> TYPE: PRT
<213> ORGANISM: Artificial Sequence
<220> FEATURE:
<223> OTHER INFORMATION: Synthetic

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

Phe Gly Gly Gly Thr Lys Val Glu Ile Lys
            100                 105

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Gly Thr Phe Ser Leu Tyr Ala Ile Ser
1               5

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Gly Ile Ile Pro Ala Phe Gly Thr Ala Asn Tyr Ala Gln Lys Phe Gln
1               5                   10                  15

Gly

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

Ala Arg Gly Gly Leu Asp Thr Asp Glu Phe Asp Leu
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Arg Ala Ser Gln Ser Ile Asn Ser Tyr Leu Asn
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Synthetic

<400> SEQUENCE: 45

Ala Ala Ser Ser Leu Gln Ser
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic

<400> SEQUENCE: 46

Gln Gln Gly Val Ser Asp Ile Thr
1               5

<210> SEQ ID NO 47
<211> LENGTH: 357
<212> TYPE: DNA
<213> ORGANISM: Artificial Sequence
<220> FEATURE:
<223> OTHER INFORMATION: Synthetic

<400> SEQUENCE: 47
caggtgcagc tggtgcagtc tggggctgag gtgaagaagc ctgggtcctc ggtgaaggtc      60
tcctgcaagg cttctggagg caccttcagc ctctatgcta tctcctgggt gcgacaggcc     120
cctggacaag ggcttgagtg gatgggaggg atcatccctg ccttcggtac cgcaaactac     180
gcacagaagt tccagggcag agtcacgatt accgcggacg aatccacgag cacagcctac     240
atggagctga gcagcctgag atctgaggac acggcggtgt actactgcgc cagaggtgga     300

-continued

```
ttggacacag acgagttcga cctatggggg agaggtacct tggtcaccgt ctcctca          357
```

```
<210> SEQ ID NO 48
<211> LENGTH: 318
<212> TYPE: DNA
<213> ORGANISM: Artificial Sequence
<220> FEATURE:
<223> OTHER INFORMATION: Synthetic

<400> SEQUENCE: 48
gacatccaga tgacccagtc tccatcctcc ctgtctgcat ctgtaggaga cagagtcacc           60
atcacttgcc gggcaagtca gagcattaac agctatttaa attggtatca gcagaaacca          120
gggaaagccc ctaagctcct gatctatgct gcatccagtt tgcaaagtgg ggtcccatca          180
aggttcagtg gcagtggatc tgggacagat ttcactctca ccatcagcag tctgcaacct          240
gaagattttg caacttacta ctgtcagcaa ggagtcagtg acatcacttt tggcggaggg          300
accaaggttg agatcaaa                                                         318
```

```
<210> SEQ ID NO 49
<211> LENGTH: 119
<212> TYPE: PRT
<213> ORGANISM: Artificial Sequence
<220> FEATURE:
<223> OTHER INFORMATION: Synthetic

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Leu Tyr
            20                  25                  30

Ala Ile Ser Trp Val Arg Gln Ala Pro Gly Gln Gly Leu Glu Trp Met
        35                  40                  45

Gly Gly Ile Ile Pro His Phe Gly Leu Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser
        115
```

```
<210> SEQ ID NO 50
<211> LENGTH: 106
<212> TYPE: PRT
<213> ORGANISM: Artificial Sequence
<220> FEATURE:
<223> OTHER INFORMATION: Synthetic

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Asp Ile Thr
                85                  90                  95

Phe Gly Gly Gly Thr Lys Val Glu Ile Lys
            100                 105

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Gly Thr Phe Ser Leu Tyr Ala Ile Ser
1               5

<210> SEQ ID NO 52
<211> LENGTH: 17
<212> TYPE: PRT
<213> ORGANISM: Artificial Sequence
<220> FEATURE:
<223> OTHER INFORMATION: Synthetic

<400> SEQUENCE: 52

Gly Ile Ile Pro His Phe Gly Leu Ala Asn Tyr Ala Gln Lys Phe Gln
1               5                   10                  15

Gly

<210> SEQ ID NO 53
<211> LENGTH: 12
<212> TYPE: PRT
<213> ORGANISM: Artificial Sequence
<220> FEATURE:
<223> OTHER INFORMATION: Synthetic

<400> SEQUENCE: 53

Ala Arg Gly Gly Leu Asp Thr Asp Glu Phe Asp Leu
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic

<400> SEQUENCE: 54

Arg Ala Ser Gln Ser Ile Asn Ser Tyr Leu Asn
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Synthetic

<400> SEQUENCE: 55

Ala Ala Ser Ser Leu Gln Ser
1               5

<210> SEQ ID NO 56
```

```
<211> LENGTH: 8
<212> TYPE: PRT
<213> ORGANISM: Artificial Sequence
<220> FEATURE:
<223> OTHER INFORMATION: Synthetic

<400> SEQUENCE: 56

Gln Gln Gly Val Ser Asp Ile Thr
1               5

<210> SEQ ID NO 57
<211> LENGTH: 357
<212> TYPE: DNA
<213> ORGANISM: Artificial Sequence
<220> FEATURE:
<223> OTHER INFORMATION: Synthetic

<400> SEQUENCE: 57
caggtgcagc tggtgcagtc tggggctgag gtgaagaagc ctgggtcctc ggtgaaggtc      60
tcctgcaagg cttctggagg caccttctcc ctctatgcta tcagctgggt gcgacaggcc     120
cctggacaag ggcttgagtg gatgggaggg atcatccctc acttcggtct cgcaaactac     180
gcacagaagt tccagggcag agtcacgatt accgcggacg aatccacgag cacagcctac     240
atggagctga gcagcctgag atctgaggac acggcggtgt actactgcgc cagaggtgga     300
ttggacacag acgagttcga cctatggggg agaggtacct tggtcaccgt ctcctca       357

<210> SEQ ID NO 58
<211> LENGTH: 318
<212> TYPE: DNA
<213> ORGANISM: Artificial Sequence
<220> FEATURE:
<223> OTHER INFORMATION: Synthetic

<400> SEQUENCE: 58
gacatccaga tgacccagtc tccatcctcc ctgtctgcat ctgtaggaga cagagtcacc      60
atcacttgcc gggcaagtca gagcattaac agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa ggagtcagtg acatcacttt tggcggaggg     300
accaaggttg agatcaaa                                                   318

<210> SEQ ID NO 59
<211> LENGTH: 123
<212> TYPE: PRT
<213> ORGANISM: Artificial Sequence
<220> FEATURE:
<223> OTHER INFORMATION: Synthetic

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Pro Pro Thr Tyr His Thr Asn Tyr Tyr Tyr Met Asp Val
            100                 105                 110

Trp Gly Lys Gly Thr Thr Val Thr Val Ser Ser
        115                 120
```

```
<210> SEQ ID NO 60
<211> LENGTH: 107
<212> TYPE: PRT
<213> ORGANISM: Artificial Sequence
<220> FEATURE:
<223> OTHER INFORMATION: Synthetic

<400> SEQUENCE: 60

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Tyr
                85                  90                  95

Thr Phe Gly Gly Gly Thr Lys Val Glu Ile Lys
            100                 105
```

```
<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Phe Thr Phe Ser Asn Tyr Ala Met Ser
1               5
```

```
<210> SEQ ID NO 62
<211> LENGTH: 17
<212> TYPE: PRT
<213> ORGANISM: Artificial Sequence
<220> FEATURE:
<223> OTHER INFORMATION: Synthetic

<400> SEQUENCE: 62

Ala Ile Ser Gly Ser Gly Gly Ser Thr Tyr Tyr Ala Asp Ser Val Lys
1               5                   10                  15

Gly
```

```
<210> SEQ ID NO 63
<211> LENGTH: 16
<212> TYPE: PRT
<213> ORGANISM: Artificial Sequence
<220> FEATURE:
<223> OTHER INFORMATION: Synthetic

<400> SEQUENCE: 63
```

```
Ala Lys Gly Pro Pro Thr Tyr His Thr Asn Tyr Tyr Tyr Met Asp Val
1               5                   10                  15
```

<210> SEQ ID NO 64
<211> LENGTH: 11
<212> TYPE: PRT
<213> ORGANISM: Artificial Sequence
<220> FEATURE:
<223> OTHER INFORMATION: Synthetic

<400> SEQUENCE: 64

```
Arg Ala Ser Gln Gly Ile Ser Ser Trp Leu Ala
1               5                   10
```

<210> SEQ ID NO 65
<211> LENGTH: 7
<212> TYPE: PRT
<213> ORGANISM: Artificial Sequence
<220> FEATURE:
<223> OTHER INFORMATION: Synthetic

<400> SEQUENCE: 65

```
Ala Ala Ser Ser Leu Gln Ser
1               5
```

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

```
Gln Gln Thr Asn Ser Phe Pro Tyr Thr
1               5
```

<210> SEQ ID NO 67
<211> LENGTH: 369
<212> TYPE: DNA
<213> ORGANISM: Artificial Sequence
<220> FEATURE:
<223> OTHER INFORMATION: Synthetic

<400> SEQUENCE: 67

```
gaggtgcagc tgttggagtc tgggggaggc ttggtacagc ctggggggtc cctgagactc      60
tcctgtgcag cctctggatt cacctttagc aattatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggcggtgt actactgcgc caagggccct     300
cctacatacc acacaaacta ctactacatg gacgtatggg gcaagggtac aactgtcacc     360
gtctcctca                                                             369
```

<210> SEQ ID NO 68
<211> LENGTH: 321
<212> TYPE: DNA
<213> ORGANISM: Artificial Sequence
<220> FEATURE:
<223> OTHER INFORMATION: Synthetic

<400> SEQUENCE: 68

```
gacatccaga tgacccagtc tccatcttcc gtgtctgcat ctgtaggaga cagagtcacc      60
atcacttgtc gggcgagtca gggtattagc agctggttag cctggtatca gcagaaacca     120
```

-continued gggaaagccc ctaagctcct gatctatgct gcatccagtt tgcaaagtgg ggtcccatca      180
aggttcagcg gcagtggatc tgggacagat ttcactctca ccatcagcag cctgcagcct      240
gaagattttg caacttatta ctgtcagcaa acaaatagtt cccttacac ttttggcgga       300 gggaccaagg ttgagatcaa a                                                 321

<210> SEQ ID NO 69
<211> LENGTH: 123
<212> TYPE: PRT
<213> ORGANISM: Artificial Sequence
<220> FEATURE:
<223> OTHER INFORMATION: Synthetic

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ile Trp Val Arg Gln Ala Pro Gly Lys Gly Leu Glu Trp Val
        35                  40                  45

Ser Ser Ile Ser Gly Asp Ser Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Pro Thr Tyr His Thr Asn Tyr Tyr Tyr Met Asp Val
            100                 105                 110

Trp Gly Lys Gly Thr Thr Val Thr Val Ser Ser
        115                 120

<210> SEQ ID NO 70
<211> LENGTH: 107
<212> TYPE: PRT
<213> ORGANISM: Artificial Sequence
<220> FEATURE:
<223> OTHER INFORMATION: Synthetic

<400> SEQUENCE: 70

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Tyr
                85                  90                  95

Thr Phe Gly Gly Gly Thr Lys Val Glu Ile Lys
            100                 105

<210> SEQ ID NO 71
<211> LENGTH: 9
<212> TYPE: PRT
<213> ORGANISM: Artificial Sequence -continued

```
<220> FEATURE:
<223> OTHER INFORMATION: Synthetic

<400> SEQUENCE: 71

Phe Thr Phe Ser Ser Tyr Val Met Ile
1               5

<210> SEQ ID NO 72
<211> LENGTH: 17
<212> TYPE: PRT
<213> ORGANISM: Artificial Sequence
<220> FEATURE:
<223> OTHER INFORMATION: Synthetic

<400> SEQUENCE: 72

Ser Ile Ser Gly Asp Ser Val Thr Thr Tyr Tyr Ala Asp Ser Val Lys
1               5                   10                  15

Gly

<210> SEQ ID NO 73
<211> LENGTH: 16
<212> TYPE: PRT
<213> ORGANISM: Artificial Sequence
<220> FEATURE:
<223> OTHER INFORMATION: Synthetic

<400> SEQUENCE: 73

Ala Lys Gly Pro Pro Thr Tyr His Thr Asn Tyr Tyr Tyr Met Asp Val
1               5                   10                  15

<210> SEQ ID NO 74
<211> LENGTH: 11
<212> TYPE: PRT
<213> ORGANISM: Artificial Sequence
<220> FEATURE:
<223> OTHER INFORMATION: Synthetic

<400> SEQUENCE: 74

Arg Ala Ser Gln Gly Ile Ser Ser Trp Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic

<400> SEQUENCE: 75

Ala Ala Ser Ser Leu Gln Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Gln Gln Thr Asn Ser Phe Pro Tyr Thr
1               5

<210> SEQ ID NO 77
<211> LENGTH: 369
<212> TYPE: DNA
```

<213> ORGANISM: Artificial Sequence
<220> FEATURE:
<223> OTHER INFORMATION: Synthetic

<400> SEQUENCE: 77
gaggtgcagc tgttggagtc tggggggaggc ttggtacagc ctggggggtc cctgagactc      60
tcctgtgcag cctctggatt cacctttagc agctatgtca tgatctgggt ccgccaggct     120
ccagggaagg ggctggagtg ggtctcaagc attagtggtg acagcgtaac aacatactac     180
gcagactccg tgaagggccg gttcaccatc tccagagaca attccaagaa cacgctgtat     240
ctgcaaatga acagcctgag agccgaggac acggcggtgt actactgcgc caagggccct     300
cctacatacc acacaaacta ctactacatg gacgtatggg gcaagggtac aactgtcacc     360
gtctcctca                                                             369

<210> SEQ ID NO 78
<211> LENGTH: 321
<212> TYPE: DNA
<213> ORGANISM: Artificial Sequence
<220> FEATURE:
<223> OTHER INFORMATION: Synthetic

<400> SEQUENCE: 78
gacatccaga tgacccagtc tccatcttcc gtgtctgcat ctgtaggaga cagagtcacc      60
atcacttgtc gggcgagtca gggtattagc agctggttag cctggtatca gcagaaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgtcagcaa acaaatagtt tcccttacac ttttggcgga     300
gggaccaagg ttgagatcaa a                                               321

<210> SEQ ID NO 79
<211> LENGTH: 121
<212> TYPE: PRT
<213> ORGANISM: Artificial Sequence
<220> FEATURE:
<223> OTHER INFORMATION: Synthetic

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Ser Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120

<210> SEQ ID NO 80
<211> LENGTH: 107

-continued

```
<212> TYPE: PRT
<213> ORGANISM: Artificial Sequence
<220> FEATURE:
<223> OTHER INFORMATION: Synthetic

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                85                  90                  95

Thr Phe Gly Gly Gly Thr Lys Val Glu Ile Lys
            100                 105

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Phe Thr Phe Ser Asp His Tyr Met Asp
1               5

<210> SEQ ID NO 82
<211> LENGTH: 19
<212> TYPE: PRT
<213> ORGANISM: Artificial Sequence
<220> FEATURE:
<223> OTHER INFORMATION: Synthetic

<400> SEQUENCE: 82

Arg Thr Arg Asn Lys Ala Ser Ser Tyr Thr Thr Glu Tyr Ala Ala Ser
1               5                   10                  15

Val Lys Gly

<210> SEQ ID NO 83
<211> LENGTH: 12
<212> TYPE: PRT
<213> ORGANISM: Artificial Sequence
<220> FEATURE:
<223> OTHER INFORMATION: Synthetic

<400> SEQUENCE: 83

Ala Arg Glu Pro Lys Tyr Trp Ile Asp Phe Asp Leu
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic

<400> SEQUENCE: 84
```

Arg Ala Ser Gln Ser Ile Ser Ser Tyr Leu Asn
1               5                   10

<210> SEQ ID NO 85
<211> LENGTH: 7
<212> TYPE: PRT
<213> ORGANISM: Artificial Sequence
<220> FEATURE:
<223> OTHER INFORMATION: Synthetic

<400> SEQUENCE: 85

Ala Ala Ser Ser Leu Gln Ser
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

Gln Gln Ser Tyr Ile Ala Pro Tyr Thr
1               5

<210> SEQ ID NO 87
<211> LENGTH: 363
<212> TYPE: DNA
<213> ORGANISM: Artificial Sequence
<220> FEATURE:
<223> OTHER INFORMATION: Synthetic

<400> SEQUENCE: 87
gaggtgcagc tggtggagtc tggggggaggc ttggtccagc ctggagggtc cctgagactc      60
tcctgtgcag cctctggatt caccttcagt gaccactaca tggactgggt ccgccaggct     120
ccagggaagg ggctggagtg ggttggccgt actagaaaca aagctagtag ttacaccaca     180
gaatacgccg cgtctgtgaa aggcagattc accatctcaa gagatgattc aaagaactca     240
ctgtatctgc aaatgaacag cctgaaaacc gaggacacgg cggtgtacta ctgcgccaga     300
gagcctaaat actggatcga cttcgaccta tggggggagag gtaccttggt caccgtctcc     360
tca                                                                    363

<210> SEQ ID NO 88
<211> LENGTH: 321
<212> TYPE: DNA
<213> ORGANISM: Artificial Sequence
<220> FEATURE:
<223> OTHER INFORMATION: Synthetic

<400> SEQUENCE: 88
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agctacatcg cccccttacac ttttggcgga     300 gggaccaagg ttgagatcaa a                                                321

<210> SEQ ID NO 89
<211> LENGTH: 121
<212> TYPE: PRT

-continued

<213> ORGANISM: Artificial Sequence
<220> FEATURE:
<223> OTHER INFORMATION: Synthetic

<400> SEQUENCE: 89

Glu Val Gln Leu Val Glu Ser Gly Gly Gly Leu Val Gln Pro Gly Arg
1                   5                   10                  15

Ser Leu Arg Leu Ser Cys Thr Ala Ser Gly Phe Thr Phe Ser Asp His
            20                  25                  30

Asp Met Asn Trp Val Arg Gln Ala Pro Gly Lys Gly Leu Glu Trp Val
        35                  40                  45

Gly Arg Thr Arg Asn Ala Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                85                  90                  95

Thr Phe Gly Gly Gly Thr Lys Val Glu Ile Lys
            100                 105

<210> SEQ ID NO 91
<211> LENGTH: 9
<212> TYPE: PRT
<213> ORGANISM: Artificial Sequence
<220> FEATURE:
<223> OTHER INFORMATION: Synthetic

<400> SEQUENCE: 91

Phe Thr Phe Ser Asp His Asp Met Asn
1                   5

<210> SEQ ID NO 92
<211> LENGTH: 19
<212> TYPE: PRT
<213> ORGANISM: Artificial Sequence
<220> FEATURE:
<223> OTHER INFORMATION: Synthetic

<400> SEQUENCE: 92

Arg Thr Arg Asn Ala Ala Gly Ser Tyr Thr Thr Glu Tyr Ala Ala Ser
1               5                   10                  15

Val Lys Gly

<210> SEQ ID NO 93
<211> LENGTH: 12
<212> TYPE: PRT
<213> ORGANISM: Artificial Sequence
<220> FEATURE:
<223> OTHER INFORMATION: Synthetic

<400> SEQUENCE: 93

Ala Arg Glu Pro Lys Tyr Trp Ile Asp Phe Asp Leu
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthetic

<400> SEQUENCE: 94

Arg Ala Ser Gln Ser Ile Ser Ser Tyr Leu Asn
1               5                   10

<210> SEQ ID NO 95
<211> LENGTH: 7
<212> TYPE: PRT
<213> ORGANISM: Artificial Sequence
<220> FEATURE:
<223> OTHER INFORMATION: Synthetic

<400> SEQUENCE: 95

Ala Ala Ser Ser Leu Gln Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ile Ala Pro Tyr Thr
1               5

<210> SEQ ID NO 97
<211> LENGTH: 363
<212> TYPE: DNA
<213> ORGANISM: Artificial Sequence
<220> FEATURE:
<223> OTHER INFORMATION: Synthetic

<400> SEQUENCE: 97
gaggtgcagc tggtggagtc tggggggaggc ttggtacagc cagggcggtc cctgagactc        60
tcctgtacag cttctggatt caccttcagt gaccacgaca tgaactgggt ccgccaggct       120
ccagggaagg ggctggagtg ggttggccgt actagaaacg ccgctggaag ttacaccaca       180
gaatacgccg cgtctgtgaa aggcagattc accatctcaa gagatgattc aaagaactca       240

```
ctgtatctgc aaatgaacag cctgaaaacc gaggacacgg cggtgtacta ctgcgccaga        300
gagcctaaat actggatcga cttcgaccta tggggagag gtaccttggt caccgtctcc          360
tca                                                                       363
```

<210> SEQ ID NO 98
<211> LENGTH: 321
<212> TYPE: DNA
<213> ORGANISM: Artificial Sequence
<220> FEATURE:
<223> OTHER INFORMATION: Synthetic

<400> SEQUENCE: 98

```
gacatccaga tgacccagtc tccatcctcc ctgtctgcat ctgtaggaga cagagtcacc         60
atcacttgcc gggcaagtca gagcattagc agctatttaa attggtatca gcagaaacca        120
gggaaagccc ctaagctcct gatctatgct gcatccagtt tgcaaagtgg ggtcccatca        180
aggttcagtg gcagtggatc tgggacagat ttcactctca ccatcagcag tctgcaacct        240
gaagattttg caacttacta ctgtcagcaa agctacatcg ccccttacac ttttggcgga        300
gggaccaagg ttgagatcaa a                                                   321
```

<210> SEQ ID NO 99
<211> LENGTH: 121
<212> TYPE: PRT
<213> ORGANISM: Artificial Sequence
<220> FEATURE:
<223> OTHER INFORMATION: Synthetic

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Val Asp His
            20                  25                  30

Asp Met Asp Trp Val Arg Gln Ala Pro Gly Lys Gly Leu Glu Trp Val
        35                  40                  45

Gly Arg Thr Arg Asn Lys Leu Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser
        115                 120
```

<210> SEQ ID NO 100
<211> LENGTH: 107
<212> TYPE: PRT
<213> ORGANISM: Artificial Sequence
<220> FEATURE:
<223> OTHER INFORMATION: Synthetic

<400> SEQUENCE: 100

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

-continued

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Ala Pro Tyr
                 85                  90                  95

Thr Phe Gly Gly Gly Thr Lys Val Glu Ile Lys
                 100                 105
```

<210> SEQ ID NO 101
<211> LENGTH: 9
<212> TYPE: PRT
<213> ORGANISM: Artificial Sequence
<220> FEATURE:
<223> OTHER INFORMATION: Synthetic

<400> SEQUENCE: 101

```
Phe Thr Phe Val Asp His Asp Met Asp
1               5
```

<210> SEQ ID NO 102
<211> LENGTH: 19
<212> TYPE: PRT
<213> ORGANISM: Artificial Sequence
<220> FEATURE:
<223> OTHER INFORMATION: Synthetic

<400> SEQUENCE: 102

```
Arg Thr Arg Asn Lys Leu Gly Ser Tyr Thr Thr Glu Tyr Ala Ala Ser
1               5                   10                  15

Val Lys Gly
```

<210> SEQ ID NO 103
<211> LENGTH: 12
<212> TYPE: PRT
<213> ORGANISM: Artificial Sequence
<220> FEATURE:
<223> OTHER INFORMATION: Synthetic

<400> SEQUENCE: 103

```
Ala Arg Glu Pro Lys Tyr Trp Ile Asp Phe Asp Leu
1               5                   10
```

<210> SEQ ID NO 104
<211> LENGTH: 11
<212> TYPE: PRT
<213> ORGANISM: Artificial Sequence
<220> FEATURE:
<223> OTHER INFORMATION: Synthetic

<400> SEQUENCE: 104

```
Arg Ala Ser Gln Ser Ile Ser Ser Tyr Leu Asn
1               5                   10
```

<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105

-continued

```
Ala Ala Ser Ser Leu Gln Ser
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic

<400> SEQUENCE: 106

Gln Gln Ser Tyr Ile Ala Pro Tyr Thr
1               5

<210> SEQ ID NO 107
<211> LENGTH: 363
<212> TYPE: DNA
<213> ORGANISM: Artificial Sequence
<220> FEATURE:
<223> OTHER INFORMATION: Synthetic

<400> SEQUENCE: 107
gaggtgcagc tggtggagtc tggggggaggc ttggtccagc ctggagggtc cctgagactc      60
tcctgtgcag cctctggatt caccttcgta gaccacgaca tggactgggt ccgccaggct     120
ccagggaagg ggctggagtg ggttggccgt actagaaaca aactaggaag ttacaccaca     180
gaatacgccg cgtctgtgaa aggcagattc accatctcaa gagatgattc aaagaactca     240
ctgtatctgc aaatgaacag cctgaaaacc gaggacacgg cggtgtacta ctgcgccaga     300
gagcctaaat actggatcga cttcgaccta tgggggagag gtaccttggt caccgtctcc     360
tca                                                                    363

<210> SEQ ID NO 108
<211> LENGTH: 321
<212> TYPE: DNA
<213> ORGANISM: Artificial Sequence
<220> FEATURE:
<223> OTHER INFORMATION: Synthetic

<400> SEQUENCE: 108
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcaa agctacatcg ccccttacac ttttggcgga     300
gggaccaagg ttgagatcaa a                                                321

<210> SEQ ID NO 109
<211> LENGTH: 214
<212> TYPE: PRT
<213> ORGANISM: Artificial Sequence
<220> FEATURE:
<223> OTHER INFORMATION: Synthetic

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
```

-continued

```
              35                    40                    45
Tyr Ala Ala Ser Ser Leu Gln Ser Gly Val Pro Ser Arg Phe Ser Gly
    50                    55                    60
Ser Gly Ser Gly Thr Asp Phe Thr Leu Thr Ile Ser Ser Leu Gln Pro
65                    70                    75                    80
Glu Asp Phe Ala Thr Tyr Tyr Cys Gln Gln Ser Tyr Ile Ala Pro Tyr
                  85                    90                    95
Thr Phe Gly Gly Gly Thr Lys Val Glu Ile Lys Arg Thr Val Ala Ala
                  100                   105                   110
Pro Ser Val Phe Ile Phe Pro Pro Ser Asp Glu Gln Leu Lys Ser Gly
                  115                   120                   125
Thr Ala Ser Val Val Cys Leu Leu Asn Asn Phe Tyr Pro Arg Glu Ala
    130                   135                   140
Lys Val Gln Trp Lys Val Asp Asn Ala Leu Gln Ser Gly Asn Ser Gln
145                   150                   155                   160
Glu Ser Val Thr Glu Gln Asp Ser Lys Asp Ser Thr Tyr Ser Leu Ser
                  165                   170                   175
Ser Thr Leu Thr Leu Ser Lys Ala Asp Tyr Glu Lys His Lys Val Tyr
                  180                   185                   190
Ala Cys Glu Val Thr His Gln Gly Leu Ser Ser Pro Val Thr Lys Ser
                  195                   200                   205
Phe Asn Arg Gly Glu Cys
    210

<210> SEQ ID NO 110
<211> LENGTH: 451
<212> TYPE: PRT
<213> ORGANISM: Artificial Sequence
<220> FEATURE:
<223> OTHER INFORMATION: Synthetic

<400> SEQUENCE: 110

Glu Val Gln Leu Val Glu Ser Gly Gly Gly Leu Val Gln Pro Gly Gly
1               5                   10                    15
Ser Leu Arg Leu Ser Cys Ala Ala Ser Gly Phe Thr Phe Ser Asp Ala
              20                    25                    30
Asp Met Asp Trp Val Arg Gln Ala Pro Gly Lys Gly Leu Glu Trp Val
              35                    40                    45
Gly Arg Thr Arg Asn Lys Ala Gly Ser Tyr Thr Thr Glu Tyr Ala Ala
    50                    55                    60
Ser Val Lys Gly Arg Phe Thr Ile Ser Arg Asp Asp Ser Lys Asn Ser
65                    70                    75                    80
Leu Tyr Leu Gln Met Asn Ser Leu Lys Thr Glu Asp Thr Ala Val Tyr
                  85                    90                    95
Tyr Cys Ala Arg Glu Pro Lys Tyr Trp Ile Asp Phe Asp Leu Trp Gly
                  100                   105                   110
Arg Gly Thr Leu Val Thr Val Ser Ser Ala Ser Thr Lys Gly Pro Ser
              115                   120                   125
Val Phe Pro Leu Ala Pro Ser Ser Lys Ser Thr Ser Gly Gly Thr Ala
    130                   135                   140
Ala Leu Gly Cys Leu Val Lys Asp Tyr Phe Pro Glu Pro Val Thr Val
145                   150                   155                   160
Ser Trp Asn Ser Gly Ala Leu Thr Ser Gly Val His Thr Phe Pro Ala
                  165                   170                   175
Val Leu Gln Ser Ser Gly Leu Tyr Ser Leu Ser Ser Val Val Thr Val
```

-continued

```
                180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445

Pro Gly Lys
    450
```

```
<210> SEQ ID NO 111
<211> LENGTH: 451
<212> TYPE: PRT
<213> ORGANISM: Artificial Sequence
<220> FEATURE:
<223> OTHER INFORMATION: Synthetic

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
            35                  40                  45

Gly Arg Thr Arg Asn Lys Ala Gly Ser Tyr Thr Thr Glu Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
```

-continued

```
                  85                  90                  95
Tyr Cys Ala Arg Glu Pro Lys Tyr Trp Ile Asp Phe Asp Leu Trp Gly
            100                 105                 110
Arg Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Lys Val Glu Pro Lys Ser Cys
            210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Cys Val Ser His
            260                 265                 270
Glu Asp Pro Glu Val Lys Phe Asn Trp Tyr Val Asp Gly Val Glu Val
            275                 280                 285
His Asn Ala Lys Thr Lys Pro Arg Glu Glu Gln Tyr Asn Ser Thr Tyr
            290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
            435                 440                 445
Pro Gly Lys
    450
```

<210> SEQ ID NO 112
<211> LENGTH: 451
<212> TYPE: PRT
<213> ORGANISM: Artificial Sequence
<220> FEATURE:
<223> OTHER INFORMATION: Synthetic

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
                20                  25                  30

Asp Met Asp Trp Val Arg Gln Ala Pro Gly Lys Gly Leu Glu Trp Val
            35                  40                  45

Gly Arg Thr Arg Asn Lys Ala Gly Ser Tyr Thr Thr Glu Tyr Ala Ala
        50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Cys Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 113
<211> LENGTH: 451
<212> TYPE: PRT
<213> ORGANISM: Artificial Sequence
<220> FEATURE:
<223> OTHER INFORMATION: Synthetic

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
            35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Cys Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn Ala Tyr Thr Gln Lys Ser Leu Ser Leu Ser
        435                 440                 445

Pro Gly Lys
    450

<210> SEQ ID NO 114
<211> LENGTH: 451
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ala
            20                  25                  30

Asp Met Asp Trp Val Arg Gln Ala Pro Gly Lys Gly Leu Glu Trp Val
        35                  40                  45

Gly Arg Thr Arg Asn Lys Ala Gly Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Glu Pro Lys Tyr Trp Ile Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Ala Ala Gly
225                 230             235             240

Gly Pro Ser Val Phe Leu Phe Pro Pro Lys Pro Lys Asp Thr Leu Met
                245                 250             255

Ile Ser Arg Thr Pro Glu Val Thr Cys Val Val Val Cys Val Ser His
                260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
        290             295             300

Arg Val Val Ser Val Leu Thr Val Leu His Gln Asp Trp Leu Asn Gly
305                 310             315             320

Lys Glu Tyr Lys Cys Lys Val Ser Asn Lys Ala Leu Pro Ala Pro Ile
                325             330             335

Glu Lys Thr Ile Ser Lys Ala Lys Gly Gln Pro Arg Glu Pro Gln Val
                340             345             350

Tyr Thr Leu Pro Pro Ser Arg Asp Glu Leu Thr Lys Asn Gln Val Ser
            355             360             365

Leu Thr Cys Leu Val Lys Gly Phe Tyr Pro Ser Asp Ile Ala Val Glu
        370             375             380

Trp Glu Ser Asn Gly Gln Pro Glu Asn Asn Tyr Lys Thr Thr Pro Pro
385                 390             395             400

Val Leu Asp Ser Asp Gly Ser Phe Phe Leu Tyr Ser Lys Leu Thr Val
                405             410             415

Asp Lys Ser Arg Trp Gln Gln Gly Asn Val Phe Ser Cys Ser Val Met
            420             425             430

His Glu Ala Leu His Asn Ala Tyr Thr Gln Lys Ser Leu Ser Leu Ser
        435             440             445

Pro Gly Lys
    450
```

```
<210> SEQ ID NO 115
<211> LENGTH: 213
<212> TYPE: PRT
<213> ORGANISM: Artificial Sequence
<220> FEATURE:
<223> OTHER INFORMATION: Synthetic

<400> SEQUENCE: 115
```

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Asn Ser Tyr
                20              25              30

Leu Asn Trp Tyr Gln Gln Lys Pro Gly Lys Ala Pro Lys Leu Leu Ile
            35              40              45

Tyr Ala Ala Ser Ser Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Gly Val Ser Asp Ile Thr
                85              90              95

Phe Gly Gly Gly Thr Lys Val Glu Ile Lys Arg Thr Val Ala Ala Pro
            100             105             110

Ser Val Phe Ile Phe Pro Pro Ser Asp Glu Gln Leu Lys Ser Gly Thr
            115             120             125
```

```
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 116
<211> LENGTH: 449
<212> TYPE: PRT
<213> ORGANISM: Artificial Sequence
<220> FEATURE:
<223> OTHER INFORMATION: Synthetic

<400> SEQUENCE: 116

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
                20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270
```

```
Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

<210> SEQ ID NO 117
<211> LENGTH: 449
<212> TYPE: PRT
<213> ORGANISM: Artificial Sequence
<220> FEATURE:
<223> OTHER INFORMATION: Synthetic

<400> SEQUENCE: 117

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
                20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
                100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys
```

<210> SEQ ID NO 118
<211> LENGTH: 449
<212> TYPE: PRT
<213> ORGANISM: Artificial Sequence
<220> FEATURE:
<223> OTHER INFORMATION: Synthetic

<400> SEQUENCE: 118

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
```

-continued

```
                    85                    90                    95

Ala Arg Gly Gly Leu Asp Thr Asp Glu Phe Asp Leu Trp Gly Arg Gly
                100                   105                   110

Thr Leu Val Thr Val Ser Ser Ala Ser Thr Lys Gly Pro Ser Val Phe
            115                   120                   125

Pro Leu Ala Pro Ser Ser Lys Ser Thr Ser Gly Gly Thr Ala Ala Leu
        130                   135                   140

Gly Cys Leu Val Lys Asp Tyr Phe Pro Glu Pro Val Thr Val Ser Trp
145                   150                   155                   160

Asn Ser Gly Ala Leu Thr Ser Gly Val His Thr Phe Pro Ala Val Leu
                165                   170                   175

Gln Ser Ser Gly Leu Tyr Ser Leu Ser Ser Val Val Thr Val Pro Ser
            180                   185                   190

Ser Ser Leu Gly Thr Gln Thr Tyr Ile Cys Asn Val Asn His Lys Pro
        195                   200                   205

Ser Asn Thr Lys Val Asp Lys Lys Val Glu Pro Lys Ser Cys Asp Lys
    210                   215                   220

Thr His Thr Cys Pro Pro Cys Pro Ala Pro Glu Ala Ala Gly Gly Pro
225                   230                   235                   240

Ser Val Phe Leu Phe Pro Pro Lys Pro Lys Asp Thr Leu Met Ile Ser
                245                   250                   255

Arg Thr Pro Glu Val Thr Cys Val Val Val Cys Val Ser His Glu Asp
            260                   265                   270

Pro Glu Val Lys Phe Asn Trp Tyr Val Asp Gly Val Glu Val His Asn
        275                   280                   285

Ala Lys Thr Lys Pro Arg Glu Glu Gln Tyr Asn Ser Thr Tyr Arg Val
    290                   295                   300

Val Ser Val Leu Thr Val Leu His Gln Asp Trp Leu Asn Gly Lys Glu
305                   310                   315                   320

Tyr Lys Cys Lys Val Ser Asn Lys Ala Leu Pro Ala Pro Ile Glu Lys
                325                   330                   335

Thr Ile Ser Lys Ala Lys Gly Gln Pro Arg Glu Pro Gln Val Tyr Thr
            340                   345                   350

Leu Pro Pro Ser Arg Asp Glu Leu Thr Lys Asn Gln Val Ser Leu Thr
        355                   360                   365

Cys Leu Val Lys Gly Phe Tyr Pro Ser Asp Ile Ala Val Glu Trp Glu
    370                   375                   380

Ser Asn Gly Gln Pro Glu Asn Asn Tyr Lys Thr Thr Pro Pro Val Leu
385                   390                   395                   400

Asp Ser Asp Gly Ser Phe Phe Leu Tyr Ser Lys Leu Thr Val Asp Lys
                405                   410                   415

Ser Arg Trp Gln Gln Gly Asn Val Phe Ser Cys Ser Val Met His Glu
            420                   425                   430

Ala Leu His Asn His Tyr Thr Gln Lys Ser Leu Ser Leu Ser Pro Gly
        435                   440                   445

Lys
```

<210> SEQ ID NO 119
<211> LENGTH: 449
<212> TYPE: PRT
<213> ORGANISM: Artificial Sequence
<220> FEATURE:
<223> OTHER INFORMATION: Synthetic

<400> SEQUENCE: 119

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
                20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

-continued

```
Ser Arg Trp Gln Gln Gly Asn Val Phe Ser Cys Ser Val Met His Glu
        420                 425                 430

Ala Leu His Asn Ala Tyr Thr Gln Lys Ser Leu Ser Leu Ser Pro Gly
        435                 440                 445

Lys

<210> SEQ ID NO 120
<211> LENGTH: 449
<212> TYPE: PRT
<213> ORGANISM: Artificial Sequence
<220> FEATURE:
<223> OTHER INFORMATION: Synthetic

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ile Tyr
            20                  25                  30

Ala Ile Ser Trp Val Arg Gln Ala Pro Gly Gln Gly Leu Glu Trp Met
        35                  40                  45

Gly Gly Ile Ile Pro Asp Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Leu Asp Thr Asp Glu Phe Asp Leu Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Cys Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                    325              330              335
Thr Ile Ser Lys Ala Lys Gly Gln Pro Arg Glu Pro Gln Val Tyr Thr
            340              345              350

Leu Pro Pro Ser Arg Asp Glu Leu Thr Lys Asn Gln Val Ser Leu Thr
            355              360              365

Cys Leu Val Lys Gly Phe Tyr Pro Ser Asp Ile Ala Val Glu Trp Glu
        370              375              380

Ser Asn Gly Gln Pro Glu Asn Asn Tyr Lys Thr Thr Pro Pro Val Leu
385              390              395              400

Asp Ser Asp Gly Ser Phe Phe Leu Tyr Ser Lys Leu Thr Val Asp Lys
                405              410              415

Ser Arg Trp Gln Gln Gly Asn Val Phe Ser Cys Ser Val Met His Glu
            420              425              430

Ala Leu His Asn Ala Tyr Thr Gln Lys Ser Leu Ser Leu Ser Pro Gly
            435              440              445

Lys
```

```
<210> SEQ ID NO 121
<211> LENGTH: 107
<212> TYPE: PRT
<213> ORGANISM: Artificial Sequence
<220> FEATURE:
<223> OTHER INFORMATION: Synthetic

<400> SEQUENCE: 121

Arg Thr Val Ala Ala Pro Ser Val Phe Ile Phe Pro Pro Ser Asp Glu
1               5               10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
            35              40              45

Ser Gly Asn Ser Gln Glu Ser Val Thr Glu Gln Asp Ser Lys Asp Ser
        50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
                85              90              95

Pro Val Thr Lys Ser Phe Asn Arg Gly Glu Cys
            100              105
```

```
<210> SEQ ID NO 122
<211> LENGTH: 330
<212> TYPE: PRT
<213> ORGANISM: Homo sapiens

<400> SEQUENCE: 122

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
        50              55              60

Leu Ser Ser Val Val Thr Val Pro Ser Ser Ser Leu Gly Thr Gln Thr
65              70              75              80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 123
<211> LENGTH: 330
<212> TYPE: PRT
<213> ORGANISM: Artificial Sequence
<220> FEATURE:
<223> OTHER INFORMATION: Synthetic

<400> SEQUENCE: 123

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 124
<211> LENGTH: 330
<212> TYPE: PRT
<213> ORGANISM: Artificial Sequence
<220> FEATURE:
<223> OTHER INFORMATION: Synthetic

<400> SEQUENCE: 124
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140
```

```
Val Val Val Cys Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
        210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
                245             250             255

Pro Ser Asp Ile Ala Val Glu Trp Glu Ser Asn Gly Gln Pro Glu Asn
                260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
        290             295             300

Val Phe Ser Cys Ser Val Met His Glu Ala Leu His Asn His Tyr Thr
305             310             315             320

Gln Lys Ser Leu Ser Leu Ser Pro Gly Lys
                325             330

<210> SEQ ID NO 125
<211> LENGTH: 330
<212> TYPE: PRT
<213> ORGANISM: Artificial Sequence
<220> FEATURE:
<223> OTHER INFORMATION: Synthetic

<400> SEQUENCE: 125

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
        130             135             140

Val Val Val Cys Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Ala Tyr Thr
305                 310                 315                 320

Gln Lys Ser Leu Ser Leu Ser Pro Gly Lys
                325                 330

<210> SEQ ID NO 126
<211> LENGTH: 330
<212> TYPE: PRT
<213> ORGANISM: Artificial Sequence
<220> FEATURE:
<223> OTHER INFORMATION: Synthetic

<400> SEQUENCE: 126

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205
```

-continued

```
Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
        275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn Ala Tyr Thr
305             310             315             320

Gln Lys Ser Leu Ser Leu Ser Pro Gly Lys
            325             330
```

```
<210> SEQ ID NO 127
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(9)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (4)..(4)
<223> OTHER INFORMATION: /replace="Arg"
<220> FEATURE:
<221> NAME/KEY: VARIANT
<222> LOCATION: (5)..(5)
<223> OTHER INFORMATION: /replace="Ile" or "Leu"

<400> SEQUENCE: 127

Gly Thr Phe Ser Ser Tyr Ala Ile Ser
1               5
```

```
<210> SEQ ID NO 128
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(17)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (5)..(5)
<223> OTHER INFORMATION: /replace="Asp" or "Ala" or "His"
<220> FEATURE:
<221> NAME/KEY: VARIANT
<222> LOCATION: (8)..(8)
<223> OTHER INFORMATION: /replace="Val" or "Leu"

<400> SEQUENCE: 128

Gly Ile Ile Pro Ile Phe Gly Thr Ala Asn Tyr Ala Gln Lys Phe Gln
1               5               10              15

Gly
```

-continued

```
<210> SEQ ID NO 129
<211> LENGTH: 12
<212> TYPE: PRT
<213> ORGANISM: Artificial Sequence
<220> FEATURE:
<223> OTHER INFORMATION: Synthetic

<400> SEQUENCE: 129

Ala Arg Gly Gly Leu Asp Thr Asp Glu Phe Asp Leu
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Synthetic

<400> SEQUENCE: 130

Arg Ala Ser Gln Ser Ile Asn Ser Tyr Leu Asn
1               5                   10

<210> SEQ ID NO 131
<211> LENGTH: 7
<212> TYPE: PRT
<213> ORGANISM: Artificial Sequence
<220> FEATURE:
<223> OTHER INFORMATION: Synthetic

<400> SEQUENCE: 131

Ala Ala Ser Ser Leu Gln Ser
1               5

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gln Gln Gly Val Ser Asp Ile Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(9)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (9)..(9)
<223> OTHER INFORMATION: /replace="Ile"
```

```
<400> SEQUENCE: 133

Phe Thr Phe Ser Asn Tyr Ala Met Ser
1               5

<210> SEQ ID NO 134
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)..(1)
<223> OTHER INFORMATION: /replace="Ser"
<220> FEATURE:
<221> NAME/KEY: SITE
<222> LOCATION: (1)..(17)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (5)..(5)
<223> OTHER INFORMATION: /replace="Asp"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Val"
<220> FEATURE:
<221> NAME/KEY: VARIANT
<222> LOCATION: (8)..(8)
<223> OTHER INFORMATION: /replace="Thr"

<400> SEQUENCE: 134

Ala Ile Ser Gly Ser Gly Gly Ser Thr Tyr Tyr Ala Asp Ser Val Lys
1               5                   10                  15

Gly

<210> SEQ ID NO 135
<211> LENGTH: 16
<212> TYPE: PRT
<213> ORGANISM: Artificial Sequence
<220> FEATURE:
<223> OTHER INFORMATION: Synthetic

<400> SEQUENCE: 135

Ala Lys Gly Pro Pro Thr Tyr His Thr Asn Tyr Tyr Tyr Met Asp Val
1               5                   10                  15

<210> SEQ ID NO 136
<211> LENGTH: 11
<212> TYPE: PRT
<213> ORGANISM: Artificial Sequence
<220> FEATURE:
<223> OTHER INFORMATION: Synthetic

<400> SEQUENCE: 136

Arg Ala Ser Gln Gly Ile Ser Ser Trp Leu Ala
1               5                   10

<210> SEQ ID NO 137
<211> LENGTH: 7
<212> TYPE: PRT
<213> ORGANISM: Artificial Sequence
<220> FEATURE:
<223> OTHER INFORMATION: Synthetic
```

<400> SEQUENCE: 137

Ala Ala Ser Ser Leu Gln Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic

<400> SEQUENCE: 138

Gln Gln Thr Asn Ser Phe Pro Tyr Thr
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(9)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (4)..(4)
<223> OTHER INFORMATION: /replace="Val"
<220> FEATURE:
<221> NAME/KEY: VARIANT
<222> LOCATION: (6)..(6)
<223> OTHER INFORMATION: /replace="Ala"
<220> FEATURE:
<221> NAME/KEY: VARIANT
<222> LOCATION: (7)..(7)
<223> OTHER INFORMATION: /replace="Asp"
<220> FEATURE:
<221> NAME/KEY: VARIANT
<222> LOCATION: (9)..(9)
<223> OTHER INFORMATION: /replace="Asn"

<400> SEQUENCE: 139

Phe Thr Phe Ser Asp His Tyr Met Asp
1               5

<210> SEQ ID NO 140
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(19)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (5)..(5)
<223> OTHER INFORMATION: /replace="Ala"
<220> FEATURE:
<221> NAME/KEY: VARIANT
<222> LOCATION: (6)..(6)
<223> OTHER INFORMATION: /replace="Leu"
<220> FEATURE:
<221> NAME/KEY: VARIANT
<222> LOCATION: (7)..(7)
<223> OTHER INFORMATION: /replace="Gly"

<400> SEQUENCE: 140

Arg Thr Arg Asn Lys Ala Ser Ser Tyr Thr Thr Glu Tyr Ala Ala Ser
1               5                   10                  15

Val Lys Gly

<210> SEQ ID NO 141
<211> LENGTH: 12
<212> TYPE: PRT
<213> ORGANISM: Artificial Sequence
<220> FEATURE:
<223> OTHER INFORMATION: Synthetic

<400> SEQUENCE: 141

Ala Arg Glu Pro Lys Tyr Trp Ile Asp Phe Asp Leu
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Synthetic

<400> SEQUENCE: 142

Arg Ala Ser Gln Ser Ile Ser Ser Tyr Leu Asn
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Synthetic

<400> SEQUENCE: 143

Ala Ala Ser Ser Leu Gln Ser
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Ser Tyr Ile Ala Pro Tyr Thr
1               5

<210> SEQ ID NO 145
<211> LENGTH: 976
<212> TYPE: PRT
<213> ORGANISM: Homo sapiens

<400> SEQUENCE: 145

Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

-continued

```
Lys Trp Thr Phe Glu Ile Leu Asp Glu Thr Asn Glu Asn Lys Gln Asn
65                  70              75              80

Glu Trp Ile Thr Glu Lys Ala Glu Ala Thr Asn Thr Gly Lys Tyr Thr
                85              90              95

Cys Thr Asn Lys His Gly Leu Ser Asn Ser Ile Tyr Val Phe Val Arg
            100             105             110

Asp Pro Ala Lys Leu Phe Leu Val Asp Arg Ser Leu Tyr Gly Lys Glu
            115             120             125

Asp Asn Asp Thr Leu Val Arg Cys Pro Leu Thr Asp Pro Glu Val Thr
            130             135             140

Asn Tyr Ser Leu Lys Gly Cys Gln Gly Lys Pro Leu Pro Lys Asp Leu
145             150             155             160

Arg Phe Ile Pro Asp Pro Lys Ala Gly Ile Met Ile Lys Ser Val Lys
                165             170             175

Arg Ala Tyr His Arg Leu Cys Leu His Cys Ser Val Asp Gln Glu Gly
            180             185             190

Lys Ser Val Leu Ser Glu Lys Phe Ile Leu Lys Val Arg Pro Ala Phe
            195             200             205

Lys Ala Val Pro Val Val Ser Val Ser Lys Ala Ser Tyr Leu Leu Arg
            210             215             220

Glu Gly Glu Glu Phe Thr Val Thr Cys Thr Ile Lys Asp Val Ser Ser
225             230             235             240

Ser Val Tyr Ser Thr Trp Lys Arg Glu Asn Ser Gln Thr Lys Leu Gln
                245             250             255

Glu Lys Tyr Asn Ser Trp His His Gly Asp Phe Asn Tyr Glu Arg Gln
            260             265             270

Ala Thr Leu Thr Ile Ser Ser Ala Arg Val Asn Asp Ser Gly Val Phe
            275             280             285

Met Cys Tyr Ala Asn Asn Thr Phe Gly Ser Ala Asn Val Thr Thr Thr
            290             295             300

Leu Glu Val Val Asp Lys Gly Phe Ile Asn Ile Phe Pro Met Ile Asn
305             310             315             320

Thr Thr Val Phe Val Asn Asp Gly Glu Asn Val Asp Leu Ile Val Glu
                325             330             335

Tyr Glu Ala Phe Pro Lys Pro Glu His Gln Gln Trp Ile Tyr Met Asn
                340             345             350

Arg Thr Phe Thr Asp Lys Trp Glu Asp Tyr Pro Lys Ser Glu Asn Glu
            355             360             365

Ser Asn Ile Arg Tyr Val Ser Glu Leu His Leu Thr Arg Leu Lys Gly
            370             375             380

Thr Glu Gly Gly Thr Tyr Thr Phe Leu Val Ser Asn Ser Asp Val Asn
385             390             395             400

Ala Ala Ile Ala Phe Asn Val Tyr Val Asn Thr Lys Pro Glu Ile Leu
                405             410             415

Thr Tyr Asp Arg Leu Val Asn Gly Met Leu Gln Cys Val Ala Ala Gly
            420             425             430

Phe Pro Glu Pro Thr Ile Asp Trp Tyr Phe Cys Pro Gly Thr Glu Gln
            435             440             445

Arg Cys Ser Ala Ser Val Leu Pro Val Asp Val Gln Thr Leu Asn Ser
            450             455             460

Ser Gly Pro Pro Phe Gly Lys Leu Val Val Gln Ser Ser Ile Asp Ser
465             470             475             480
```

-continued

```
Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
                565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
                645                 650                 655

Leu Gly Ala Cys Thr Ile Gly Gly Pro Thr Leu Val Ile Thr Glu Tyr
                660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
            690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
            755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
                820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
            850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
```

-continued

```
                900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
            930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 146
<211> LENGTH: 972
<212> TYPE: PRT
<213> ORGANISM: Homo sapiens

<400> SEQUENCE: 146

Met Arg Gly Ala Arg Gly Ala Trp Asp Phe Leu Cys Val Leu Leu Leu
1                   5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
            115                 120                 125

Asp Asn Asp Thr Leu Val Arg Cys Pro Leu Thr Asp Pro Glu Val Thr
        130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
            195                 200                 205

Lys Ala Val Pro Val Val Ser Val Ser Lys Ala Ser Tyr Leu Leu Arg
        210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
        290                 295                 300
```

-continued

```
Leu Glu Val Val Asp Lys Gly Phe Ile Asn Ile Phe Pro Met Ile Asn
305             310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
                340             345                 350

Arg Thr Phe Thr Asp Lys Trp Glu Asp Tyr Pro Lys Ser Glu Asn Glu
            355             360             365

Ser Asn Ile Arg Tyr Val Ser Glu Leu His Leu Thr Arg Leu Lys Gly
        370             375                 380

Thr Glu Gly Gly Thr Tyr Thr Phe Leu Val Ser Asn Ser Asp Val Asn
385             390                 395                 400

Ala Ala Ile Ala Phe Asn Val Tyr Val Asn Thr Lys Pro Glu Ile Leu
                405             410                 415

Thr Tyr Asp Arg Leu Val Asn Gly Met Leu Gln Cys Val Ala Ala Gly
            420             425                 430

Phe Pro Glu Pro Thr Ile Asp Trp Tyr Phe Cys Pro Gly Thr Glu Gln
            435             440                 445

Arg Cys Ser Ala Ser Val Leu Pro Val Asp Val Gln Thr Leu Asn Ser
    450             455             460

Ser Gly Pro Pro Phe Gly Lys Leu Val Val Gln Ser Ser Ile Asp Ser
465             470             475                 480

Ser Ala Phe Lys His Asn Gly Thr Val Glu Cys Lys Ala Tyr Asn Asp
            485             490                 495

Val Gly Lys Thr Ser Ala Tyr Phe Asn Phe Ala Phe Lys Glu Gln Ile
            500             505             510

His Pro His Thr Leu Phe Thr Pro Leu Leu Ile Gly Phe Val Ile Val
        515             520             525

Ala Gly Met Met Cys Ile Ile Val Met Ile Leu Thr Tyr Lys Tyr Leu
    530             535             540

Gln Lys Pro Met Tyr Glu Val Gln Trp Lys Val Val Glu Glu Ile Asn
545             550             555             560

Gly Asn Asn Tyr Val Tyr Ile Asp Pro Thr Gln Leu Pro Tyr Asp His
            565             570             575

Lys Trp Glu Phe Pro Arg Asn Arg Leu Ser Phe Gly Lys Thr Leu Gly
            580             585             590

Ala Gly Ala Phe Gly Lys Val Val Glu Ala Thr Ala Tyr Gly Leu Ile
        595             600             605

Lys Ser Asp Ala Ala Met Thr Val Ala Val Lys Met Leu Lys Pro Ser
    610             615             620

Ala His Leu Thr Glu Arg Glu Ala Leu Met Ser Glu Leu Lys Val Leu
625             630             635             640

Ser Tyr Leu Gly Asn His Met Asn Ile Val Asn Leu Leu Gly Ala Cys
            645             650             655

Thr Ile Gly Gly Pro Thr Leu Val Ile Thr Glu Tyr Cys Cys Tyr Gly
            660             665             670

Asp Leu Leu Asn Phe Leu Arg Arg Lys Arg Asp Ser Phe Ile Cys Ser
            675             680             685

Lys Gln Glu Asp His Ala Glu Ala Ala Leu Tyr Lys Asn Leu Leu His
        690             695             700

Ser Lys Glu Ser Ser Cys Ser Asp Ser Thr Asn Glu Tyr Met Asp Met
705             710             715             720

Lys Pro Gly Val Ser Tyr Val Val Pro Thr Lys Ala Asp Lys Arg Arg
```

-continued

```
                725                 730                 735
Ser Val Arg Ile Gly Ser Tyr Ile Glu Arg Asp Val Thr Pro Ala Ile
                740                 745                 750

Met Glu Asp Asp Glu Leu Ala Leu Asp Leu Glu Asp Leu Leu Ser Phe
                755                 760                 765

Ser Tyr Gln Val Ala Lys Gly Met Ala Phe Leu Ala Ser Lys Asn Cys
                770                 775                 780

Ile His Arg Asp Leu Ala Ala Arg Asn Ile Leu Leu Thr His Gly Arg
785                 790                 795                 800

Ile Thr Lys Ile Cys Asp Phe Gly Leu Ala Arg Asp Ile Lys Asn Asp
                805                 810                 815

Ser Asn Tyr Val Val Lys Gly Asn Ala Arg Leu Pro Val Lys Trp Met
                820                 825                 830

Ala Pro Glu Ser Ile Phe Asn Cys Val Tyr Thr Phe Glu Ser Asp Val
                835                 840                 845

Trp Ser Tyr Gly Ile Phe Leu Trp Glu Leu Phe Ser Leu Gly Ser Ser
                850                 855                 860

Pro Tyr Pro Gly Met Pro Val Asp Ser Lys Phe Tyr Lys Met Ile Lys
865                 870                 875                 880

Glu Gly Phe Arg Met Leu Ser Pro Glu His Ala Pro Ala Glu Met Tyr
                885                 890                 895

Asp Ile Met Lys Thr Cys Trp Asp Ala Asp Pro Leu Lys Arg Pro Thr
                900                 905                 910

Phe Lys Gln Ile Val Gln Leu Ile Glu Lys Gln Ile Ser Glu Ser Thr
                915                 920                 925

Asn His Ile Tyr Ser Asn Leu Ala Asn Cys Ser Pro Asn Arg Gln Lys
                930                 935                 940

Pro Val Val Asp His Ser Val Arg Ile Asn Ser Val Gly Ser Thr Ala
945                 950                 955                 960

Ser Ser Ser Gln Pro Leu Leu Val His Asp Asp Val
                965                 970

<210> SEQ ID NO 147
<211> LENGTH: 123
<212> TYPE: PRT
<213> ORGANISM: Artificial Sequence
<220> FEATURE:
<223> OTHER INFORMATION: Synthetic

<400> SEQUENCE: 147

Gln Val Gln Leu Val Gln Ser Gly Ala Ala Val Lys Lys Pro Gly Glu
1               5                   10                  15

Ser Leu Lys Ile Ser Cys Lys Gly Ser Gly Tyr Arg Phe Thr Thr Tyr
                20                  25                  30

Trp Ile Gly Trp Val Arg Gln Met Pro Gly Lys Gly Leu Glu Trp Met
                35                  40                  45

Gly Ile Ile Tyr Pro Gly Asp Ser Asp Thr Arg Tyr Ser Pro Ser Phe
                50                  55                  60

Gln Gly Gln Val Thr Ile Ser Ala Gly Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
                100                 105                 110

Trp Gly Gln Gly Thr Met Val Thr Val Ser Ser
```

-continued

```
                115                 120

<210> SEQ ID NO 148
<211> LENGTH: 107
<212> TYPE: PRT
<213> ORGANISM: Artificial Sequence
<220> FEATURE:
<223> OTHER INFORMATION: Synthetic

<400> SEQUENCE: 148

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ser Ser Ala
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 149
<211> LENGTH: 107
<212> TYPE: PRT
<213> ORGANISM: Artificial Sequence
<220> FEATURE:
<223> OTHER INFORMATION: Synthetic

<400> SEQUENCE: 149

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Thr Asp
                20                  25                  30

Leu Gly Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 150
<211> LENGTH: 107
<212> TYPE: PRT
<213> ORGANISM: Artificial Sequence
<220> FEATURE:
<223> OTHER INFORMATION: Synthetic

<400> SEQUENCE: 150

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30
```

Leu Ala Trp Tyr Gln Gln Lys Pro Gly Lys Thr Pro Lys Leu Leu Ile
        35                      40                      45

Tyr Asp Ala Ser Ser Leu Glu Ser Gly Val Pro Ser Arg Phe Ser Gly
        50                      55                      60

Ser Gly Ser Gly Thr Asp Phe Thr Leu Thr Ile Ser Ser Leu Gln Pro
65                      70                      75                      80

Glu Asp Phe Ala Thr Tyr Tyr Cys Gln Gln Phe Asn Ser Tyr Pro Leu
                85                      90                      95

Thr Phe Gly Gly Gly Thr Lys Val Glu Ile Lys
            100                     105

<210> SEQ ID NO 151
<211> LENGTH: 107
<212> TYPE: PRT
<213> ORGANISM: Artificial Sequence
<220> FEATURE:
<223> OTHER INFORMATION: Synthetic

<400> SEQUENCE: 151

Ala Ile Gln Met Thr Gln Ser Pro Ser Ser Leu Ser Ala Ser Val Gly
1                       5                       10                      15

Asp Arg Val Thr Ile Thr Cys Arg Ala Ser Gln Gly Ile Arg Asn Asp
                20                      25                      30

Leu Gly Trp Tyr Gln Gln Lys Pro Gly Lys Ala Pro Lys Leu Leu Ile
        35                      40                      45

Tyr Asp Ala Ser Ser Leu Glu Ser Gly Val Pro Ser Arg Phe Ser Gly
        50                      55                      60

Ser Gly Ser Gly Thr Asp Phe Thr Leu Thr Ile Ser Ser Leu Gln Pro
65                      70                      75                      80

Glu Asp Phe Ala Thr Tyr Tyr Cys Gln Gln Phe Asn Ser Tyr Pro Leu
                85                      90                      95

Thr Phe Gly Gly Gly Thr Lys Val Asp Ile Lys
            100                     105

<210> SEQ ID NO 152
<211> LENGTH: 107
<212> TYPE: PRT
<213> ORGANISM: Artificial Sequence
<220> FEATURE:
<223> OTHER INFORMATION: Synthetic

<400> SEQUENCE: 152

Asn Ile Gln Met Thr Gln Ser Pro Ser Ser Leu Ser Ala Ser Val Gly
1                       5                       10                      15

Asp Arg Val Thr Ile Thr Cys Arg Ala Ser Gln Ala Ile Ser Asp Tyr
                20                      25                      30

Leu Ala Trp Phe Gln Gln Lys Pro Gly Lys Ala Pro Lys Leu Leu Ile
        35                      40                      45

Tyr Asp Ala Ser Asn Leu Glu Thr Gly Val Pro Ser Arg Phe Ser Gly
        50                      55                      60

Ser Gly Ser Gly Thr Asp Phe Thr Leu Thr Ile Ser Ser Leu Gln Pro
65                      70                      75                      80

Glu Asp Phe Ala Thr Tyr Tyr Cys Gln Gln Leu Asn Ser Tyr Pro Leu
                85                      90                      95

Thr Phe Gly Gly Gly Thr Lys Val Glu Ile Lys
            100                     105

```
<210> SEQ ID NO 153
<211> LENGTH: 107
<212> TYPE: PRT
<213> ORGANISM: Artificial Sequence
<220> FEATURE:
<223> OTHER INFORMATION: Synthetic

<400> SEQUENCE: 153

Ala Ile Arg Met Thr Gln Ser Pro Ser Ser Leu Ser Ala Ser Val Gly
1               5                   10                  15

Asp Arg Val Ile Ile Ala Cys Arg Ala Ser Gln Gly Ile Gly Gly Ala
            20                  25                  30

Leu Ala Trp Tyr Gln Gln Lys Pro Gly Asn Ala Pro Lys Val Leu Val
        35                  40                  45

Tyr Asp Ala Ser Thr Leu Glu Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Ala Met Thr Gln Ser Pro Pro Ser Leu Ser Ala Phe Val Gly
1               5                   10                  15

Asp Arg Val Thr Ile Thr Cys Arg Ala Ser Gln Gly Ile Ile Ser Ser
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 155
<211> LENGTH: 107
<212> TYPE: PRT
<213> ORGANISM: Artificial Sequence
<220> FEATURE:
<223> OTHER INFORMATION: Synthetic

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Ala Gly Lys Ala Pro Lys Val Leu Ile
        35                  40                  45
```

```
Ser Asp Ala Ser Ser Leu Glu Ser Gly Val Pro Ser Arg Phe Ser Gly
    50              55              60

Ser Gly Ser Gly Thr Asp Phe Thr Leu Ser Ile Ser Ser Leu Gln Pro
65              70              75              80

Glu Asp Phe Ala Thr Tyr Tyr Cys Gln Gln Phe Asn Gly Tyr Pro Leu
                85              90              95

Thr Phe Gly Gly Gly Thr Lys Val Asp Ile Lys
            100             105
```

```
<210> SEQ ID NO 156
<211> LENGTH: 107
<212> TYPE: PRT
<213> ORGANISM: Artificial Sequence
<220> FEATURE:
<223> OTHER INFORMATION: Synthetic

<400> SEQUENCE: 156
```

```
Ala Ile Arg Met Thr Gln Ser Pro Ser Ser Leu Ser Ala Ser Val Gly
1               5               10              15

Asp Arg Val Thr Ile Thr Cys Gln Ala Ser Gln Gly Ile Arg Asn Asp
                20              25              30

Leu Gly Trp Tyr Gln Gln Lys Pro Gly Lys Ala Pro Lys Leu Leu Ile
            35              40              45

Tyr Asp Ala Ser Asn Leu Glu Thr Gly Val Pro Ser Arg Phe Ser Gly
    50              55              60

Ser Gly Ser Gly Thr Asp Phe Thr Phe Thr Ile Ser Ser Leu Gln Pro
65              70              75              80

Glu Asp Ile Ala Thr Tyr Tyr Cys Gln Gln Phe Asn Ser Tyr Pro Leu
                85              90              95

Thr Phe Gly Gly Gly Thr Lys Leu Glu Ile Lys
            100             105
```

```
<210> SEQ ID NO 157
<211> LENGTH: 107
<212> TYPE: PRT
<213> ORGANISM: Artificial Sequence
<220> FEATURE:
<223> OTHER INFORMATION: Synthetic

<400> SEQUENCE: 157
```

```
Asn Ile Gln Met Thr Gln Ser Pro Ser Ser Leu Ser Thr Ser Val Gly
1               5               10              15

Asp Arg Val Thr Ile Thr Cys Arg Ala Ser Gln Gly Ile Gly Thr Ser
                20              25              30

Leu Ala Trp Tyr Gln Gln Lys Pro Gly Lys Pro Pro Lys Leu Leu Ile
            35              40              45

Tyr Asp Ala Ser Ser Leu Glu Ser Gly Val Pro Ser Arg Leu Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Asn Ser Tyr Pro Ile
                85              90              95

Thr Phe Gly Gln Gly Thr Arg Leu Glu Ile Lys
            100             105
```

```
<210> SEQ ID NO 158
<211> LENGTH: 107
<212> TYPE: PRT
```

<213> ORGANISM: Artificial Sequence
<220> FEATURE:
<223> OTHER INFORMATION: Synthetic

<400> SEQUENCE: 158

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Gly Asp Tyr
            20                  25                  30

Leu Thr Trp Tyr Gln Gln Lys Pro Gly Lys Ala Pro Lys Val Leu Ile
        35                  40                  45

Tyr Gly Ala Ser Ser Leu Gln Ser Gly Val Pro Pro Arg Phe Ser Gly
    50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Leu Glu Ile Lys
            100                 105

<210> SEQ ID NO 159
<211> LENGTH: 107
<212> TYPE: PRT
<213> ORGANISM: Artificial Sequence
<220> FEATURE:
<223> OTHER INFORMATION: Synthetic

<400> SEQUENCE: 159

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Arg Ser Thr
            20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gln Gly Thr Arg Leu Glu Ile Lys
            100                 105

<210> SEQ ID NO 160
<211> LENGTH: 107
<212> TYPE: PRT
<213> ORGANISM: Artificial Sequence
<220> FEATURE:
<223> OTHER INFORMATION: Synthetic

<400> SEQUENCE: 160

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Leu Glu Ile Lys
            100                 105

<210> SEQ ID NO 161
<211> LENGTH: 107
<212> TYPE: PRT
<213> ORGANISM: Artificial Sequence
<220> FEATURE:
<223> OTHER INFORMATION: Synthetic

<400> SEQUENCE: 161

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Phe
                20                  25                  30

Leu Ala Trp Tyr Gln Gln Lys Pro Gly Lys Ala Pro Lys Leu Leu Ile
            35                  40                  45

Tyr Asp Ala Ser Thr Leu Gln Ser Gly Val Pro Ser Arg Phe Ser Gly
        50                  55                  60

Ser Ala Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gly Gly Thr Lys Val Glu Ile Lys
            100                 105

<210> SEQ ID NO 162
<211> LENGTH: 107
<212> TYPE: PRT
<213> ORGANISM: Artificial Sequence
<220> FEATURE:
<223> OTHER INFORMATION: Synthetic

<400> SEQUENCE: 162

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
                20                  25                  30

Leu Ala Trp Tyr Gln Gln Lys Pro Gly Ile Gly Pro Lys Leu Leu Ile
            35                  40                  45

Tyr Asp Ala Ser Thr Leu Glu Ser Gly Val Pro Ala Arg Phe Ser Gly
        50                  55                  60

Ser Gly Ser Arg Thr Asp Phe Thr Leu Thr Ile Thr Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gly Gly Thr Lys Leu Glu Ile Lys
            100                 105

<210> SEQ ID NO 163
<211> LENGTH: 107
<212> TYPE: PRT
<213> ORGANISM: Artificial Sequence
<220> FEATURE:
<223> OTHER INFORMATION: Synthetic
```

<400> SEQUENCE: 163

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Thr Ser Ala
            20                  25                  30

Leu Ala Trp Tyr Gln Glu Lys Pro Gly Lys Ala Pro Asn Leu Leu Ile
        35                  40                  45

Tyr Asp Ala Ser Ser Leu Glu Ser Gly Val Pro Ser Arg Phe Ser Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Asp Ile Lys
            100                 105

<210> SEQ ID NO 164
<211> LENGTH: 121
<212> TYPE: PRT
<213> ORGANISM: Artificial Sequence
<220> FEATURE:
<223> OTHER INFORMATION: Synthetic

<400> SEQUENCE: 164

Gln Ile Gln Leu Val Gln Ser Gly Pro Glu Leu Arg Lys Pro Gly Glu
1               5                   10                  15

Ser Val Lys Ile Ser Cys Lys Ala Ser Gly Tyr Thr Phe Thr Asp Tyr
            20                  25                  30

Ala Met Tyr Trp Val Lys Gln Ala Pro Gly Lys Gly Leu Lys Trp Met
        35                  40                  45

Gly Trp Ile Asn Thr Tyr Thr Gly Lys Pro Thr Tyr Ala Asp Asp Phe
    50                  55                  60

Lys Gly Arg Phe Val Phe Ser Leu Glu Ala Ser Ala Asn Thr Ala Asn
65                  70                  75                  80

Leu Gln Ile Ser Asn Leu Lys Asn Glu Asp Thr Ala Thr Tyr Phe Cys
                85                  90                  95

Ala Arg Ala Arg Gly Leu Val Asp Asp Tyr Val Met Asp Ala Trp Gly
            100                 105                 110

Gln Gly Thr Ser Val Thr Val Ser Ser
        115                 120

<210> SEQ ID NO 165
<211> LENGTH: 108
<212> TYPE: PRT
<213> ORGANISM: Artificial Sequence
<220> FEATURE:
<223> OTHER INFORMATION: Synthetic

<400> SEQUENCE: 165

Ser Tyr Glu Leu Ile Gln Pro Pro Ser Ala Ser Val Thr Leu Gly Asn
1               5                   10                  15

Thr Val Ser Leu Thr Cys Val Gly Asp Glu Leu Ser Lys Arg Tyr Ala
            20                  25                  30

Gln Trp Tyr Gln Gln Lys Pro Asp Lys Thr Ile Val Ser Val Ile Tyr
        35                  40                  45

Lys Asp Ser Glu Arg Pro Ser Gly Ile Ser Asp Arg Phe Ser Gly Ser
    50                  55                  60

-continued

Ser Ser Gly Thr Thr Ala Thr Leu Thr Ile His Gly Thr Leu Ala Glu
65                  70                  75                  80

Asp Glu Ala Asp Tyr Tyr Cys Leu Ser Thr Tyr Ser Asp Asp Asn Leu
                85                  90                  95

Pro Val Phe Gly Gly Gly Thr Lys Leu Thr Val Leu
            100                 105

<210> SEQ ID NO 166
<211> LENGTH: 117
<212> TYPE: PRT
<213> ORGANISM: Artificial Sequence
<220> FEATURE:
<223> OTHER INFORMATION: Synthetic

<400> SEQUENCE: 166

Glu Val Gln Leu Gln Gln Tyr Gly Ala Glu Leu Gly Lys Pro Gly Thr
1                   5                   10                  15

Ser Val Arg Leu Ser Cys Lys Val Ser Gly Tyr Asn Ile Arg Asn Thr
                20                  25                  30

Tyr Ile His Trp Val Asn Gln Arg Pro Gly Glu Gly Leu Glu Trp Ile
            35                  40                  45

Gly Arg Ile Asp Pro Thr Asn Gly Asn Thr Ile Ser Ala Glu Lys Phe
        50                  55                  60

Lys Thr Lys Ala Thr Leu Thr Ala Asp Thr Ser Ser His Thr Ala Tyr
65                  70                  75                  80

Leu Gln Phe Ser Gln Leu Lys Ser Asp Asp Thr Ala Ile Tyr Phe Cys
                85                  90                  95

Ala Leu Asn Tyr Glu Gly Tyr Ala Asp Tyr Trp Gly Gln Gly Val Met
            100                 105                 110

Val Thr Gly Ser Ser
        115

<210> SEQ ID NO 167
<211> LENGTH: 106
<212> TYPE: PRT
<213> ORGANISM: Artificial Sequence
<220> FEATURE:
<223> OTHER INFORMATION: Synthetic

<400> SEQUENCE: 167

Asp Ile Gln Met Thr Gln Ser Pro Ser Phe Leu Ser Ala Ser Val Gly
1                   5                   10                  15

Asp Arg Val Thr Ile Asn Cys Lys Ala Ser Gln Asn Ile Asn Lys Tyr
                20                  25                  30

Leu Asn Trp Tyr Gln Gln Lys Val Gly Glu Ala Pro Lys Arg Leu Ile
            35                  40                  45

Phe Lys Thr Asn Ser Leu Gln Thr Gly Ile Pro Ser Arg Phe Ser Gly
        50                  55                  60

Ser Gly Ser Gly Thr Asp Tyr Thr Leu Thr Ile Ser Ser Leu Gln Thr
65                  70                  75                  80

Glu Asp Val Ala Thr Tyr Phe Cys Phe Gln Tyr Asn Ile Gly Tyr Thr
                85                  90                  95

Phe Gly Ala Gly Thr Lys Val Glu Leu Lys
            100                 105

<210> SEQ ID NO 168
<211> LENGTH: 124
<212> TYPE: PRT

<213> ORGANISM: Artificial Sequence
<220> FEATURE:
<223> OTHER INFORMATION: Synthetic

<400> SEQUENCE: 168

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Ser Ser Asn
            20                  25                  30

Tyr Arg Trp Asn Trp Ile Arg Lys Phe Pro Gly Asn Lys Val Glu Trp
        35                  40                  45

Met Gly Tyr Ile Asn Ser Ala Gly Ser Thr Asn Tyr Asn Pro Ser Leu
    50                  55                  60

Lys Ser Arg Ile Ser Met Thr Arg Asp Thr Ser Lys Asn Gln Phe Phe
65                  70                  75                  80

Leu Gln Val Asn Ser Val Thr Thr Glu Asp Thr Ala Thr Tyr Tyr Cys
                85                  90                  95

Ala Arg Ser Leu Arg Gly Tyr Ile Thr Asp Tyr Ser Gly Phe Phe Asp
            100                 105                 110

Tyr Trp Gly Gln Gly Val Met Val Thr Val Ser Ser
        115                 120

<210> SEQ ID NO 169
<211> LENGTH: 107
<212> TYPE: PRT
<213> ORGANISM: Artificial Sequence
<220> FEATURE:
<223> OTHER INFORMATION: Synthetic

<400> SEQUENCE: 169

Asp Ile Arg Met Thr Gln Ser Pro Ala Ser Leu Ser Ala Ser Leu Gly
1               5                   10                  15

Glu Thr Val Asn Ile Glu Cys Leu Ala Ser Glu Asp Ile Phe Ser Asp
            20                  25                  30

Leu Ala Trp Tyr Gln Gln Lys Pro Gly Lys Ser Pro Gln Leu Leu Ile
        35                  40                  45

Tyr Asn Ala Asn Ser Leu Gln Asn Gly Val Pro Ser Arg Phe Ser Gly
    50                  55                  60

Ser Gly Ser Gly Thr Arg Tyr Ser Leu Lys Ile Asn Ser Leu Gln Ser
65                  70                  75                  80

Glu Asp Val Ala Thr Tyr Phe Cys Gln Gln Tyr Lys Asn Tyr Pro Leu
                85                  90                  95

Thr Phe Gly Ser Gly Thr Lys Leu Glu Ile Lys
            100                 105

<210> SEQ ID NO 170
<211> LENGTH: 117
<212> TYPE: PRT
<213> ORGANISM: Artificial Sequence
<220> FEATURE:
<223> OTHER INFORMATION: Synthetic

<400> SEQUENCE: 170

Glu Val Gln Leu Gln Gln Tyr Gly Ala Glu Leu Gly Lys Pro Gly Thr
1               5                   10                  15

Ser Val Arg Leu Ser Cys Lys Leu Ser Gly Tyr Lys Ile Arg Asn Thr
            20                  25                  30

Tyr Ile His Trp Val Asn Gln Arg Pro Gly Lys Gly Leu Glu Trp Ile
        35                  40                  45

-continued

```
Gly Arg Ile Asp Pro Ala Asn Gly Asn Thr Ile Tyr Ala Glu Lys Phe
    50                  55                  60

Lys Ser Lys Val Thr Leu Thr Ala Asp Thr Ser Ser Asn Thr Ala Tyr
65                  70                  75                  80

Met Gln Leu Ser Gln Leu Lys Ser Asp Asp Thr Ala Leu Tyr Phe Cys
                85                  90                  95

Ala Met Asn Tyr Glu Gly Tyr Glu Asp Tyr Trp Gly Gln Gly Val Met
                100                 105                 110

Val Thr Val Ser Ser
        115
```

```
<210> SEQ ID NO 171
<211> LENGTH: 106
<212> TYPE: PRT
<213> ORGANISM: Artificial Sequence
<220> FEATURE:
<223> OTHER INFORMATION: Synthetic

<400> SEQUENCE: 171
```

```
Asp Ile Gln Met Thr Gln Ser Pro Ser Phe Leu Ser Ala Ser Val Gly
1               5                   10                  15

Asp Ser Val Thr Ile Asn Cys Lys Ala Ser Gln Asn Ile Asn Lys Tyr
                20                  25                  30

Leu Asn Trp Tyr Gln Gln Lys Leu Gly Glu Ala Pro Lys Arg Leu Ile
            35                  40                  45

His Lys Thr Asp Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Lys Ser Gly Phe Met
                85                  90                  95

Phe Gly Ala Gly Thr Lys Leu Glu Leu Lys
            100                 105
```

```
<210> SEQ ID NO 172
<211> LENGTH: 120
<212> TYPE: PRT
<213> ORGANISM: Artificial Sequence
<220> FEATURE:
<223> OTHER INFORMATION: Synthetic

<400> SEQUENCE: 172
```

```
Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ala Val Tyr Trp Val Ile Gln Ala Pro Gly Lys Gly Leu Lys Trp Met
            35                  40                  45

Gly Trp Ile Asn Thr Tyr Thr Gly Lys Pro Thr Tyr Ala Asp Asp Phe
    50                  55                  60

Lys Gly Arg Phe Val Phe Ser Leu Glu Thr Ser Ala Ser Thr Ala Asn
65                  70                  75                  80

Leu Gln Ile Ser Asn Leu Lys Asn Glu Asp Thr Ala Thr Tyr Phe Cys
                85                  90                  95

Ala Arg Gly Ala Gly Met Thr Lys Asp Tyr Val Met Asp Ala Trp Gly
            100                 105                 110

Arg Gly Val Leu Val Thr Val Ser
```

-continued

```
            115                 120

<210> SEQ ID NO 173
<211> LENGTH: 108
<212> TYPE: PRT
<213> ORGANISM: Artificial Sequence
<220> FEATURE:
<223> OTHER INFORMATION: Synthetic

<400> SEQUENCE: 173

Ser Tyr Glu Leu Ile Gln Pro Pro Ser Ala Ser Val Thr Leu Gly Asn
1               5                   10                  15

Thr Val Ser Leu Thr Cys Val Gly Asp Glu Leu Ser Lys Arg Tyr Ala
            20                  25                  30

Gln Trp Tyr Gln Gln Lys Pro Asp Lys Thr Ile Val Ser Val Ile Tyr
        35                  40                  45

Lys Asp Ser Glu Arg Pro Ser Asp Ile Ser Asp Arg Phe Ser Gly Ser
    50                  55                  60

Ser Ser Gly Thr Thr Ala Thr Leu Thr Ile His Gly Thr Leu Ala Glu
65                  70                  75                  80

Asp Glu Ala Asp Tyr Tyr Cys Leu Ser Thr Tyr Ser Asp Asp Asn Leu
                85                  90                  95

Pro Val Phe Gly Gly Gly Thr Lys Leu Thr Val Leu
            100                 105

<210> SEQ ID NO 174
<211> LENGTH: 116
<212> TYPE: PRT
<213> ORGANISM: Artificial Sequence
<220> FEATURE:
<223> OTHER INFORMATION: Synthetic

<400> SEQUENCE: 174

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Tyr
            20                  25                  30

Leu Val His Trp Val Arg Gln Pro Pro Gly Lys Thr Leu Glu Trp Val
        35                  40                  45

Gly Leu Met Trp Asn Asp Gly Asp Thr Ser Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met His Ser Leu Gln Ala Glu Asp Thr Ala Thr Tyr Tyr Cys Ala
                85                  90                  95

Arg Glu Ser Asn Leu Gly Phe Thr Tyr Trp Gly His Gly Thr Leu Val
            100                 105                 110

Thr Val Ser Ser
        115

<210> SEQ ID NO 175
<211> LENGTH: 107
<212> TYPE: PRT
<213> ORGANISM: Artificial Sequence
<220> FEATURE:
<223> OTHER INFORMATION: Synthetic

<400> SEQUENCE: 175

Asp Ile Gln Met Thr Gln Ser Pro Ala Ser Leu Ser Ala Ser Leu Glu
1               5                   10                  15
```

-continued

```
Glu Ile Val Thr Ile Thr Cys Lys Ala Ser Gln Gly Ile Asp Asp Asp
            20                  25                  30

Leu Ser Trp Tyr Gln Gln Lys Pro Gly Lys Ser Pro Gln Leu Leu Ile
            35                  40                  45

Tyr Asp Val Thr Arg Leu Ala Asp Gly Val Pro Ser Arg Phe Ser Gly
    50                  55                  60

Ser Arg Ser Gly Thr Gln Tyr Ser Leu Lys Ile Ser Arg Pro Gln Val
65                  70                  75                  80

Ala Asp Ser Gly Ile Tyr Tyr Cys Leu Gln Ser Tyr Ser Thr Pro Tyr
                85                  90                  95

Thr Phe Gly Ala Gly Thr Lys Leu Glu Leu Lys
            100                 105
```

```
<210> SEQ ID NO 176
<211> LENGTH: 117
<212> TYPE: PRT
<213> ORGANISM: Artificial Sequence
<220> FEATURE:
<223> OTHER INFORMATION: Synthetic

<400> SEQUENCE: 176
```

```
Glu Val Gln Leu Gln Gln Tyr Gly Ala Glu Leu Gly Lys Pro Gly Thr
1               5                   10                  15

Ser Val Arg Leu Ser Cys Lys Val Ser Gly Tyr Asn Ile Arg Asn Thr
            20                  25                  30

Tyr Ile His Trp Val His Gln Arg Pro Gly Glu Gly Leu Glu Trp Ile
            35                  40                  45

Gly Arg Ile Asp Pro Thr Asn Gly Asn Thr Ile Ser Ala Glu Lys Phe
    50                  55                  60

Lys Ser Lys Ala Thr Leu Thr Ala Asp Thr Ser Ser Asn Thr Ala Tyr
65                  70                  75                  80

Met Gln Phe Ser Gln Leu Lys Ser Asp Asp Thr Ala Ile Tyr Phe Cys
                85                  90                  95

Ala Met Asn Tyr Glu Gly Tyr Ala Asp Tyr Trp Gly Gln Gly Val Met
            100                 105                 110

Val Thr Val Ser Ser
        115
```

```
<210> SEQ ID NO 177
<211> LENGTH: 106
<212> TYPE: PRT
<213> ORGANISM: Artificial Sequence
<220> FEATURE:
<223> OTHER INFORMATION: Synthetic

<400> SEQUENCE: 177
```

```
Asp Ile Gln Met Thr Gln Ser Pro Ser Phe Leu Ser Ala Ser Val Gly
1               5                   10                  15

Asp Arg Leu Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
            35                  40                  45

Phe Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Phe Gln Tyr Asn Ile Gly Phe Thr
```

-continued

```
                    85              90              95
Phe Gly Ala Gly Thr Lys Leu Glu Leu Lys
                100             105
```

<210> SEQ ID NO 178
<211> LENGTH: 124
<212> TYPE: PRT
<213> ORGANISM: Artificial Sequence
<220> FEATURE:
<223> OTHER INFORMATION: Synthetic

<400> SEQUENCE: 178

```
Glu Val Gln Leu Val Glu Ser Gly Gly Gly Leu Val Gln Ser Gly Arg
1               5               10              15

Ser Leu Lys Leu Ser Cys Ala Ala Ser Gly Phe Thr Val Ser Asp Tyr
            20              25              30

Tyr Met Ala Trp Val Arg Gln Ala Pro Thr Lys Gly Leu Glu Trp Val
        35              40              45

Ala Thr Ile Asn Tyr Asp Gly Ser Thr Thr Tyr His Arg Asp Ser Val
    50              55              60

Lys Gly Arg Phe Thr Ile Ser Arg Asp Asn Ala Lys Ser Thr Leu Tyr
65              70              75              80

Leu Gln Met Asp Ser Leu Arg Ser Glu Asp Thr Ala Thr Tyr Tyr Cys
            85              90              95

Ala Arg His Gly Asp Tyr Gly Tyr His Tyr Gly Ala Tyr Tyr Phe Asp
            100             105             110

Tyr Trp Gly Gln Gly Val Met Val Thr Val Ser Ser
        115             120
```

<210> SEQ ID NO 179
<211> LENGTH: 109
<212> TYPE: PRT
<213> ORGANISM: Artificial Sequence
<220> FEATURE:
<223> OTHER INFORMATION: Synthetic

<400> SEQUENCE: 179

```
Asp Ile Val Leu Thr Gln Ser Pro Ala Leu Ala Val Ser Leu Gly Gln
1               5               10              15

Arg Ala Thr Ile Ser Cys Arg Ala Ser Gln Thr Val Ser Leu Ser Gly
            20              25              30

Tyr Asn Leu Ile His Trp Tyr Gln Gln Arg Thr Gly Gln Gln Pro Lys
        35              40              45

Leu Leu Ile Tyr Arg Ala Ser Asn Leu Ala Pro Gly Ile Pro Ala Arg
    50              55              60

Phe Ser Gly Ser Gly Ser Gly Thr Asp Phe Thr Leu Thr Ile Ser Pro
65              70              75              80

Val Gln Ser Asp Asp Ile Ala Thr Tyr Tyr Cys Gln Gln Ser Arg Glu
            85              90              95

Ser Trp Thr Phe Gly Gly Gly Thr Asn Leu Glu Met Lys
        100             105
```

<210> SEQ ID NO 180
<211> LENGTH: 116
<212> TYPE: PRT
<213> ORGANISM: Artificial Sequence
<220> FEATURE:
<223> OTHER INFORMATION: Synthetic

<400> SEQUENCE: 180

-continued

```
Gln Ile Gln Leu Val Gln Ser Gly Pro Glu Leu Lys Lys Pro Gly Glu
1               5                   10                  15

Ser Val Lys Ile Ser Cys Lys Ala Ser Gly Tyr Thr Phe Thr Asp Tyr
                20                  25                  30

Ala Ile His Trp Val Lys Gln Ala Pro Gly Gln Gly Leu Arg Trp Met
            35                  40                  45

Ala Trp Ile Asn Thr Glu Thr Gly Lys Pro Thr Tyr Ala Asp Asp Phe
        50                  55                  60

Lys Gly Arg Phe Val Phe Ser Leu Glu Ala Ser Ala Ser Thr Ala His
65                  70                  75                  80

Leu Gln Ile Ser Asn Leu Lys Asn Glu Asp Thr Ala Thr Phe Phe Cys
                85                  90                  95

Ala Gly Gly Ser His Trp Phe Ala Tyr Trp Gly Gln Gly Thr Leu Val
            100                 105                 110

Thr Val Ser Ser
        115
```

```
<210> SEQ ID NO 181
<211> LENGTH: 108
<212> TYPE: PRT
<213> ORGANISM: Artificial Sequence
<220> FEATURE:
<223> OTHER INFORMATION: Synthetic

<400> SEQUENCE: 181
```

```
Ser Tyr Glu Leu Ile Gln Pro Pro Ser Ala Ser Val Thr Leu Glu Asn
1               5                   10                  15

Thr Val Ser Ile Thr Cys Ser Gly Asp Glu Leu Ser Asn Lys Tyr Ala
                20                  25                  30

His Trp Tyr Gln Gln Lys Pro Asp Lys Thr Ile Leu Glu Val Ile Tyr
            35                  40                  45

Asn Asp Ser Glu Arg Pro Ser Gly Ile Ser Asp Arg Phe Ser Gly Ser
        50                  55                  60

Ser Ser Gly Thr Thr Ala Ile Leu Thr Ile Arg Asp Ala Gln Ala Glu
65                  70                  75                  80

Asp Glu Ala Asp Tyr Tyr Cys Leu Ser Thr Phe Ser Asp Asp Asp Leu
                85                  90                  95

Pro Ile Phe Gly Gly Gly Thr Lys Leu Thr Val Leu
            100                 105
```

```
<210> SEQ ID NO 182
<211> LENGTH: 108
<212> TYPE: PRT
<213> ORGANISM: Artificial Sequence
<220> FEATURE:
<223> OTHER INFORMATION: Synthetic

<400> SEQUENCE: 182
```

```
Ser Tyr Glu Leu Ile Gln Pro Pro Ser Thr Ser Val Thr Leu Gly Asn
1               5                   10                  15

Thr Val Ser Leu Thr Cys Val Gly Asn Glu Leu Pro Lys Arg Tyr Ala
                20                  25                  30

Tyr Trp Phe Gln Gln Lys Pro Asp Gln Ser Ile Val Arg Leu Ile Tyr
            35                  40                  45

Asp Asp Asp Arg Arg Pro Ser Gly Ile Ser Asp Arg Phe Ser Gly Ser
        50                  55                  60

Ser Ser Gly Thr Thr Ala Thr Leu Thr Ile Arg Asp Ala Gln Ala Glu
```

-continued

```
65              70              75              80

Asp Glu Ala Tyr Tyr Tyr Cys His Ser Thr Tyr Thr Asp Asp Lys Val
                85              90              95

Pro Ile Phe Gly Gly Gly Thr Lys Leu Thr Val Leu
                100             105
```

<210> SEQ ID NO 183
<211> LENGTH: 123
<212> TYPE: PRT
<213> ORGANISM: Artificial Sequence
<220> FEATURE:
<223> OTHER INFORMATION: Synthetic

<400> SEQUENCE: 183

```
Glu Val Gln Leu Val Glu Ser Gly Gly Gly Leu Val Gln Pro Gly Arg
1               5               10              15

Ser Met Lys Leu Ser Cys Lys Ala Ser Gly Phe Thr Phe Ser Asn Tyr
                20              25              30

Asp Met Ala Trp Val Arg Gln Ala Pro Thr Arg Gly Leu Glu Trp Val
                35              40              45

Ala Ser Ile Ser Tyr Asp Gly Ile Thr Ala Tyr Tyr Arg Asp Ser Val
                50              55              60

Lys Gly Arg Phe Thr Ile Ser Arg Glu Asn Ala Lys Ser Thr Leu Tyr
65              70              75              80

Leu Gln Leu Val Ser Leu Arg Ser Glu Asp Thr Ala Thr Tyr Tyr Cys
                85              90              95

Thr Thr Glu Gly Gly Tyr Val Tyr Ser Gly Pro His Tyr Phe Asp Tyr
                100             105             110

Trp Gly Gln Gly Val Met Val Thr Val Ser Ser
                115             120
```

<210> SEQ ID NO 184
<211> LENGTH: 107
<212> TYPE: PRT
<213> ORGANISM: Artificial Sequence
<220> FEATURE:
<223> OTHER INFORMATION: Synthetic

<400> SEQUENCE: 184

```
Asp Ile Gln Met Thr Gln Ser Pro Ser Ser Met Ser Val Ser Leu Gly
1               5               10              15

Asp Thr Val Thr Ile Thr Cys Arg Ala Ser Gln Asp Val Gly Ile Phe
                20              25              30

Val Asn Trp Phe Gln Gln Lys Pro Gly Arg Ser Pro Arg Arg Met Ile
                35              40              45

Tyr Arg Ala Thr Asn Leu Ala Asp Gly Val Pro Ser Arg Phe Ser Gly
                50              55              60

Ser Arg Ser Gly Ser Asp Tyr Ser Leu Thr Ile Ser Ser Leu Glu Ser
65              70              75              80

Glu Asp Val Ala Asp Tyr His Cys Leu Gln Tyr Asp Glu Phe Pro Arg
                85              90              95

Thr Phe Gly Gly Gly Thr Lys Leu Glu Leu Lys
                100             105
```

<210> SEQ ID NO 185
<211> LENGTH: 117
<212> TYPE: PRT
<213> ORGANISM: Artificial Sequence
<220> FEATURE:

<223> OTHER INFORMATION: Synthetic

<400> SEQUENCE: 185

Glu Val Gln Leu Gln Gln Tyr Gly Ala Glu Leu Gly Lys Pro Gly Thr
1               5                   10                  15

Ser Val Arg Leu Ser Cys Lys Val Ser Gly Tyr Lys Ile Arg Asn Thr
            20                  25                  30

Tyr Ile His Trp Val Asn Gln Arg Pro Gly Lys Gly Leu Glu Trp Ile
        35                  40                  45

Gly Arg Ile Asp Pro Ala Asn Gly Asn Thr Ile Tyr Ala Glu Lys Phe
    50                  55                  60

Lys Ser Lys Val Thr Leu Thr Ala Asp Thr Ser Ser Asn Thr Ala Tyr
65                  70                  75                  80

Met Gln Leu Ser Gln Leu Lys Ser Asp Asp Thr Ala Leu Tyr Phe Cys
            85                  90                  95

Ala Met Asn Tyr Glu Gly Tyr Glu Asp Tyr Trp Gly Gln Gly Val Met
            100                 105                 110

Val Thr Val Ser Ser
        115

<210> SEQ ID NO 186
<211> LENGTH: 106
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Phe Leu Ser Ala Ser Val Gly
1               5                   10                  15

Asp Ser Val Thr Ile Asn Cys Lys Ala Ser Gln Asn Ile Asn Lys Tyr
            20                  25                  30

Leu Asn Trp Tyr Gln Gln Lys Leu Gly Glu Ala Pro Lys Arg Leu Ile
        35                  40                  45

His Lys Thr Asn Ser Leu Gln Pro Gly Phe Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Ala Tyr Phe Cys Phe Gln Tyr Asn Ser Gly Phe Thr
            85                  90                  95

Phe Gly Ala Gly Thr Lys Leu Glu Leu Lys
            100                 105

<210> SEQ ID NO 187
<211> LENGTH: 125
<212> TYPE: PRT
<213> ORGANISM: Artificial Sequence
<220> FEATURE:
<223> OTHER INFORMATION: Synthetic

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Met Asn Pro His Ser Gly Asp Thr Gly Tyr Ala Gln Lys Phe

-continued

```
                50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Gly Tyr Glu Gly Ala Phe Asp Ile
                100                 105                 110

Trp Gly Gln Gly Thr Leu Val Thr Val Ser Ser Ala Ser
        115                 120                 125

<210> SEQ ID NO 188
<211> LENGTH: 107
<212> TYPE: PRT
<213> ORGANISM: Artificial Sequence
<220> FEATURE:
<223> OTHER INFORMATION: Synthetic

<400> SEQUENCE: 188

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Gly Ile Gly Asn Glu
                20                  25                  30

Leu Gly Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Leu Pro Leu
                85                  90                  95

Thr Phe Gly Gln Gly Thr Lys Val Glu Ile Lys
                100                 105

<210> SEQ ID NO 189
<211> LENGTH: 125
<212> TYPE: PRT
<213> ORGANISM: Artificial Sequence
<220> FEATURE:
<223> OTHER INFORMATION: Synthetic

<400> SEQUENCE: 189

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Thr Gly Tyr
                20                  25                  30

Tyr Leu His Trp Val Arg Gln Ala Pro Gly Gln Gly Leu Glu Trp Met
        35                  40                  45

Gly Trp Ile Asn Pro Asn Ser Gly Asp Thr Asn Tyr Ala Gln Asn Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Gly Tyr Glu Gly Ala Phe Asp Ile
                100                 105                 110

Trp Gly Gln Gly Thr Leu Val Thr Val Ser Ser Ala Ser
        115                 120                 125
```

-continued

```
<210> SEQ ID NO 190
<211> LENGTH: 107
<212> TYPE: PRT
<213> ORGANISM: Artificial Sequence
<220> FEATURE:
<223> OTHER INFORMATION: Synthetic

<400> SEQUENCE: 190

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gly Gly Thr Lys Val Glu Ile Lys
            100                 105

<210> SEQ ID NO 191
<211> LENGTH: 125
<212> TYPE: PRT
<213> ORGANISM: Artificial Sequence
<220> FEATURE:
<223> OTHER INFORMATION: Synthetic

<400> SEQUENCE: 191

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Leu His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser
            115                 120                 125

<210> SEQ ID NO 192
<211> LENGTH: 107
<212> TYPE: PRT
<213> ORGANISM: Artificial Sequence
<220> FEATURE:
<223> OTHER INFORMATION: Synthetic

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
```

-continued

```
                20              25              30

Leu Gly Trp Tyr Gln Gln Lys Pro Gly Lys Ala Pro Lys Leu Leu Ile
        35              40              45

Tyr Asp Ala Ser Glu Leu Glu Thr Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Leu Asn Gly Tyr Pro Ile
                85              90              95

Thr Phe Gly Gln Gly Thr Lys Val Glu Ile Lys
            100             105

<210> SEQ ID NO 193
<211> LENGTH: 125
<212> TYPE: PRT
<213> ORGANISM: Artificial Sequence
<220> FEATURE:
<223> OTHER INFORMATION: Synthetic

<400> SEQUENCE: 193

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Ser Tyr
                20              25              30

Tyr Ile His Trp Val Arg Gln Ala Pro Gly Gln Gly Leu Glu Trp Met
        35              40              45

Gly Trp Leu Asn Pro Ser Gly Gly Gly Thr Ser Tyr Ala Gln Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg His Gly Arg Gly Tyr Asp Gly Tyr Glu Gly Ala Phe Asp Ile
            100             105             110

Trp Gly Gln Gly Thr Leu Val Thr Val Ser Ser Ala Ser
        115             120             125

<210> SEQ ID NO 194
<211> LENGTH: 107
<212> TYPE: PRT
<213> ORGANISM: Artificial Sequence
<220> FEATURE:
<223> OTHER INFORMATION: Synthetic

<400> SEQUENCE: 194

Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Arg Asn Asp
                20              25              30

Leu Gly Trp Tyr Gln Gln Lys Pro Gly Lys Ala Pro Lys Leu Leu Ile
        35              40              45

Tyr Asp Ala Ser Asn Leu Glu Thr Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Leu Asn Gly Tyr Pro Leu
                85              90              95
```

```
Thr Phe Gly Gly Gly Thr Lys Val Glu Ile Lys
            100                 105
```

<210> SEQ ID NO 195
<211> LENGTH: 125
<212> TYPE: PRT
<213> ORGANISM: Artificial Sequence
<220> FEATURE:
<223> OTHER INFORMATION: Synthetic

<400> SEQUENCE: 195

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Lys Leu Ser Ser Leu Arg Ser Glu Asp Thr Ala Val Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser
        115                 120                 125
```

<210> SEQ ID NO 196
<211> LENGTH: 107
<212> TYPE: PRT
<213> ORGANISM: Artificial Sequence
<220> FEATURE:
<223> OTHER INFORMATION: Synthetic

<400> SEQUENCE: 196

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Leu
                85                  90                  95

Thr Phe Gly Gly Gly Thr Lys Val Glu Ile Lys
            100                 105
```

<210> SEQ ID NO 197
<211> LENGTH: 125
<212> TYPE: PRT
<213> ORGANISM: Artificial Sequence
<220> FEATURE:
<223> OTHER INFORMATION: Synthetic

<400> SEQUENCE: 197

```
Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Ile Ile Asn Pro Ser Gly Gly Asn Thr Asn Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Ala Tyr Glu Gly Ala Phe Asp Ile
            100                 105                 110

Trp Gly Gln Gly Thr Leu Val Thr Val Ser Ser Ala Ser
        115                 120                 125
```

<210> SEQ ID NO 198
<211> LENGTH: 107
<212> TYPE: PRT
<213> ORGANISM: Artificial Sequence
<220> FEATURE:
<223> OTHER INFORMATION: Synthetic

<400> SEQUENCE: 198

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Asn Gly Tyr Pro Leu
                85                  90                  95

Thr Phe Gly Gly Gly Thr Lys Val Glu Ile Lys
            100                 105
```

<210> SEQ ID NO 199
<211> LENGTH: 125
<212> TYPE: PRT
<213> ORGANISM: Artificial Sequence
<220> FEATURE:
<223> OTHER INFORMATION: Synthetic

<400> SEQUENCE: 199

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Asn Pro Thr Val Gly Gly Ala Asn Tyr Ala Gln Lys Phe
    50                  55                  60

Gln Gly Arg Val Thr Met Thr Arg Asp Thr Ser Thr Ser Thr Val Tyr
65                  70                  75                  80
```

-continued

```
Met Glu Leu Ser Ser Leu Arg Ser Glu Asp Thr Ala Val Tyr Tyr Cys
                85                  90                  95

Ala Arg His Gly Arg Gly Tyr Asn Glu Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 200
<211> LENGTH: 107
<212> TYPE: PRT
<213> ORGANISM: Artificial Sequence
<220> FEATURE:
<223> OTHER INFORMATION: Synthetic

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Leu
                85                  90                  95

Thr Phe Gly Gly Gly Thr Lys Leu Glu Ile Lys
            100                 105

<210> SEQ ID NO 201
<211> LENGTH: 125
<212> TYPE: PRT
<213> ORGANISM: Artificial Sequence
<220> FEATURE:
<223> OTHER INFORMATION: Synthetic

<400> SEQUENCE: 201

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Val Ile Asn Pro Asn Gly Ala Gly Thr Asn Phe Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 202
<211> LENGTH: 125
<212> TYPE: PRT
<213> ORGANISM: Artificial Sequence
```

-continued

```
<220> FEATURE:
<223> OTHER INFORMATION: Synthetic

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Met His Trp Val Arg Gln Ala Pro Gly Gln Gly Leu Glu Trp Met
        35                  40                  45

Gly Trp Ile Asn Pro Thr Gly Gly Thr Asn Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 203
<211> LENGTH: 107
<212> TYPE: PRT
<213> ORGANISM: Artificial Sequence
<220> FEATURE:
<223> OTHER INFORMATION: Synthetic

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Val Ser Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Ser Gly Tyr Pro Ile
            85                  90                  95

Thr Phe Gly Gln Gly Thr Lys Leu Glu Ile Lys
        100                 105

<210> SEQ ID NO 204
<211> LENGTH: 125
<212> TYPE: PRT
<213> ORGANISM: Artificial Sequence
<220> FEATURE:
<223> OTHER INFORMATION: Synthetic

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45
```

```
Gly Met Ile Asn Pro Ser Gly Gly Ser Thr Asn Tyr Ala Gln Lys Phe
    50              55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Asn Asp Tyr Glu Gly Ala Phe Asp Ile
                100                 105                 110

Trp Gly Gln Gly Thr Leu Val Thr Val Ser Ser Ala Ser
        115                 120                 125

<210> SEQ ID NO 205
<211> LENGTH: 107
<212> TYPE: PRT
<213> ORGANISM: Artificial Sequence
<220> FEATURE:
<223> OTHER INFORMATION: Synthetic

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Glu Ala Ser Asn Leu Glu Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Val Glu Ile Lys
            100                 105

<210> SEQ ID NO 206
<211> LENGTH: 125
<212> TYPE: PRT
<213> ORGANISM: Artificial Sequence
<220> FEATURE:
<223> OTHER INFORMATION: Synthetic

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Ala Tyr
                20                  25                  30

Tyr Ile His Trp Val Arg Gln Ala Pro Gly Gln Gly Leu Glu Trp Met
            35                  40                  45

Gly Ile Ile Asn Pro Ser Gly Gly Ser Thr Arg Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg His Gly Arg Gly Tyr Gly Gly Tyr Glu Gly Ala Phe Asp Ile
                100                 105                 110

Trp Asp Gln Gly Thr Leu Val Thr Val Ser Ser Ala Ser
        115                 120                 125
```

```
<210> SEQ ID NO 207
<211> LENGTH: 107
<212> TYPE: PRT
<213> ORGANISM: Artificial Sequence
<220> FEATURE:
<223> OTHER INFORMATION: Synthetic

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Tyr
            20                  25                  30

Val Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Ile
                85                  90                  95

Thr Phe Gly Gln Gly Thr Arg Leu Glu Ile Lys
            100                 105

<210> SEQ ID NO 208
<211> LENGTH: 125
<212> TYPE: PRT
<213> ORGANISM: Artificial Sequence
<220> FEATURE:
<223> OTHER INFORMATION: Synthetic

<400> SEQUENCE: 208

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Val Asp Lys Ser Asn Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 209
<211> LENGTH: 107
<212> TYPE: PRT
<213> ORGANISM: Artificial Sequence
<220> FEATURE:
<223> OTHER INFORMATION: Synthetic

<400> SEQUENCE: 209

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln Gln Gly Ala Ser Phe Pro Ile
                85                  90                  95

Thr Phe Gly Gln Gly Thr Lys Val Glu Ile Lys
            100                 105
```

```
<210> SEQ ID NO 210
<211> LENGTH: 125
<212> TYPE: PRT
<213> ORGANISM: Artificial Sequence
<220> FEATURE:
<223> OTHER INFORMATION: Synthetic

<400> SEQUENCE: 210
```

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Ser Ser Phe Pro Asn Ser
            20                  25                  30

Trp Ile Ala Trp Val Arg Gln Met Pro Gly Lys Gly Leu Glu Trp Met
        35                  40                  45

Gly Ile Ile Tyr Pro Ser Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Glu Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125
```

```
<210> SEQ ID NO 211
<211> LENGTH: 107
<212> TYPE: PRT
<213> ORGANISM: Artificial Sequence
<220> FEATURE:
<223> OTHER INFORMATION: Synthetic

<400> SEQUENCE: 211
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95
```

Thr Phe Gly Gly Gly Thr Lys Val Glu Ile Lys
            100                 105

<210> SEQ ID NO 212
<211> LENGTH: 125
<212> TYPE: PRT
<213> ORGANISM: Artificial Sequence
<220> FEATURE:
<223> OTHER INFORMATION: Synthetic

<400> SEQUENCE: 212

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Ser Tyr
            20                  25                  30

Trp Ile Gly Trp Val Arg Gln Met Pro Gly Lys Gly Leu Glu Trp Met
        35                  40                  45

Gly Ile Met Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
            85                  90                  95

Ala Arg His Gly Arg Gly Tyr Asn Ala Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 213
<211> LENGTH: 107
<212> TYPE: PRT
<213> ORGANISM: Artificial Sequence
<220> FEATURE:
<223> OTHER INFORMATION: Synthetic

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Lys Leu Leu Ile
        35                  40                  45

Tyr Asp Ala Phe Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Leu Asn Ser Tyr Pro Leu
            85                  90                  95

Thr Phe Gly Pro Gly Thr Lys Val Asp Ile Lys
            100                 105

<210> SEQ ID NO 214
<211> LENGTH: 124
<212> TYPE: PRT
<213> ORGANISM: Artificial Sequence
<220> FEATURE:
<223> OTHER INFORMATION: Synthetic

<400> SEQUENCE: 214

Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Ser Phe Thr Asn Trp
                20                  25                  30

Ile Ala Trp Val Arg Gln Met Pro Gly Lys Gly Leu Glu Trp Met Gly
            35                  40                  45

Ile Ile Tyr Pro Gly Asp Ser Glu Thr Arg Tyr Ser Pro Ser Phe Gln
        50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg His Gly Arg Gly Tyr Tyr Gly Tyr Glu Gly Ala Phe Asp Ile Trp
            100                 105                 110

Gly Gln Gly Thr Leu Val Thr Val Ser Ser Ala Ser
            115                 120

<210> SEQ ID NO 215
<211> LENGTH: 107
<212> TYPE: PRT
<213> ORGANISM: Artificial Sequence
<220> FEATURE:
<223> OTHER INFORMATION: Synthetic

<400> SEQUENCE: 215

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Gly Ile Ser Asp Asn
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Ser Phe Pro Leu
                85                  90                  95

Thr Phe Gly Gln Gly Thr Lys Val Glu Ile Lys
            100                 105

<210> SEQ ID NO 216
<211> LENGTH: 125
<212> TYPE: PRT
<213> ORGANISM: Artificial Sequence
<220> FEATURE:
<223> OTHER INFORMATION: Synthetic

<400> SEQUENCE: 216

Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Asn Phe Thr Ser Tyr
                20                  25                  30

Trp Ile Gly Trp Val Arg Gln Met Pro Gly Lys Gly Leu Glu Trp Met
            35                  40                  45

Gly Val Ile Tyr Pro Asp Asp Ser Glu Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 217
<211> LENGTH: 107
<212> TYPE: PRT
<213> ORGANISM: Artificial Sequence
<220> FEATURE:
<223> OTHER INFORMATION: Synthetic

<400> SEQUENCE: 217

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Asp Ile Arg Asp Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 218
<211> LENGTH: 124
<212> TYPE: PRT
<213> ORGANISM: Artificial Sequence
<220> FEATURE:
<223> OTHER INFORMATION: Synthetic

<400> SEQUENCE: 218

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Asn Thr Tyr
            20                  25                  30

Ile Gly Trp Val Arg Gln Met Pro Gly Lys Gly Leu Glu Trp Met Gly
        35                  40                  45

Ile Ile Tyr Pro Gly Asp Ser Gly Thr Arg Tyr Ser Pro Ser Phe Gln
    50                  55                  60

Gly Gln Val Thr Ile Ser Ala Asp Lys Ala Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg His Ser Arg Gly Tyr Asn Gly Tyr Glu Gly Ala Phe Asp Ile Trp
            100                 105                 110

Gly Gln Gly Thr Leu Val Thr Val Ser Ser Ala Ser
        115                 120

<210> SEQ ID NO 219
<211> LENGTH: 107
<212> TYPE: PRT

<213> ORGANISM: Artificial Sequence
<220> FEATURE:
<223> OTHER INFORMATION: Synthetic

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Val
                85                  90                  95

Thr Phe Gly Gln Gly Thr Lys Val Glu Ile Lys
            100                 105

<210> SEQ ID NO 220
<211> LENGTH: 125
<212> TYPE: PRT
<213> ORGANISM: Artificial Sequence
<220> FEATURE:
<223> OTHER INFORMATION: Synthetic

<400> SEQUENCE: 220

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Thr Tyr
            20                  25                  30

Trp Ile Gly Trp Val Arg Gln Met Pro Gly Lys Gly Leu Glu Trp Met
        35                  40                  45

Gly Ile Ile His Pro Ala Asp Ser Asp Thr Arg Tyr Asn Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125

<210> SEQ ID NO 221
<211> LENGTH: 107
<212> TYPE: PRT
<213> ORGANISM: Artificial Sequence
<220> FEATURE:
<223> OTHER INFORMATION: Synthetic

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Arg Val Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

```
Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 222
<211> LENGTH: 125
<212> TYPE: PRT
<213> ORGANISM: Artificial Sequence
<220> FEATURE:
<223> OTHER INFORMATION: Synthetic

<400> SEQUENCE: 222

Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Arg Phe Ser Asn Tyr
                20                  25                  30

Trp Ile Ala Trp Val Arg Gln Met Pro Gly Lys Gly Leu Glu Trp Met
            35                  40                  45

Gly Ile Ile Tyr Pro Asp Asn Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asp Gly Tyr Glu Gly Ala Phe Asp Ile
            100                 105                 110

Trp Gly Gln Gly Thr Leu Val Thr Val Ser Ser Ala Ser
            115                 120                 125

<210> SEQ ID NO 223
<211> LENGTH: 107
<212> TYPE: PRT
<213> ORGANISM: Artificial Sequence
<220> FEATURE:
<223> OTHER INFORMATION: Synthetic

<400> SEQUENCE: 223

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Gly Ile Arg Ser Asp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Ser Phe Gly Gln Gly Thr Lys Val Glu Ile Lys
            100                 105
```

-continued

```
<210> SEQ ID NO 224
<211> LENGTH: 124
<212> TYPE: PRT
<213> ORGANISM: Artificial Sequence
<220> FEATURE:
<223> OTHER INFORMATION: Synthetic

<400> SEQUENCE: 224

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Ala Ser Tyr
            20                  25                  30

Trp Ile Gly Trp Val Arg Gln Met Pro Gly Lys Gly Leu Glu Trp Met
        35                  40                  45

Gly Ile Thr Tyr Pro Gly Asp Ser Glu Thr Arg Tyr Asn Pro Ser Gln
    50                  55                  60

Gly Gln Val Thr Ile Ser Ala Asp Lys Ser Ile Ser Thr Ala Tyr Leu
65                  70                  75                  80

Gln Trp Ser Ser Leu Lys Ala Ser Asp Thr Ala Met Tyr Tyr Cys Ala
                85                  90                  95

Arg His Gly Arg Gly Tyr Gly Gly Tyr Glu Gly Ala Phe Asp Ile Trp
            100                 105                 110

Gly Gln Gly Thr Leu Val Thr Val Ser Ser Ala Ser
        115                 120

<210> SEQ ID NO 225
<211> LENGTH: 107
<212> TYPE: PRT
<213> ORGANISM: Artificial Sequence
<220> FEATURE:
<223> OTHER INFORMATION: Synthetic

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 226
<211> LENGTH: 125
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

-continued

```
Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser Ala Ser
        115                 120                 125
```

<210> SEQ ID NO 227
<211> LENGTH: 107
<212> TYPE: PRT
<213> ORGANISM: Artificial Sequence
<220> FEATURE:
<223> OTHER INFORMATION: Synthetic

<400> SEQUENCE: 227

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gln Gly Thr Arg Leu Glu Ile Lys
            100                 105
```

<210> SEQ ID NO 228
<211> LENGTH: 107
<212> TYPE: PRT
<213> ORGANISM: Artificial Sequence
<220> FEATURE:
<223> OTHER INFORMATION: Synthetic

<400> SEQUENCE: 228

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
```

-continued

```
              100                 105

<210> SEQ ID NO 229
<211> LENGTH: 107
<212> TYPE: PRT
<213> ORGANISM: Artificial Sequence
<220> FEATURE:
<223> OTHER INFORMATION: Synthetic

<400> SEQUENCE: 229

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 230
<211> LENGTH: 107
<212> TYPE: PRT
<213> ORGANISM: Artificial Sequence
<220> FEATURE:
<223> OTHER INFORMATION: Synthetic

<400> SEQUENCE: 230

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 231
<211> LENGTH: 107
<212> TYPE: PRT
<213> ORGANISM: Artificial Sequence
<220> FEATURE:
<223> OTHER INFORMATION: Synthetic

<400> SEQUENCE: 231

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ile Ser Ala
            20                  25                  30
```

-continued

```
Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 232
<211> LENGTH: 107
<212> TYPE: PRT
<213> ORGANISM: Artificial Sequence
<220> FEATURE:
<223> OTHER INFORMATION: Synthetic

<400> SEQUENCE: 232

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
                20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 233
<211> LENGTH: 107
<212> TYPE: PRT
<213> ORGANISM: Artificial Sequence
<220> FEATURE:
<223> OTHER INFORMATION: Synthetic

<400> SEQUENCE: 233

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Gly Ser Ala
                20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105
```

-continued

```
<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ile Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 235
<211> LENGTH: 107
<212> TYPE: PRT
<213> ORGANISM: Artificial Sequence
<220> FEATURE:
<223> OTHER INFORMATION: Synthetic

<400> SEQUENCE: 235

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Val Ile Ser Ala
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 236
<211> LENGTH: 107
<212> TYPE: PRT
<213> ORGANISM: Artificial Sequence
<220> FEATURE:
<223> OTHER INFORMATION: Synthetic

<400> SEQUENCE: 236

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Ala Trp Tyr Gln Gln Lys Pro Gly Lys Ala Pro Lys Leu Leu Ile
        35                  40                  45
```

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 237
<211> LENGTH: 107
<212> TYPE: PRT
<213> ORGANISM: Artificial Sequence
<220> FEATURE:
<223> OTHER INFORMATION: Synthetic

<400> SEQUENCE: 237

Asp Ile Gln Leu Thr Gln Ser Pro Ser Ser Leu Ser Ala Ser Val Gly
1                   5                   10                  15

Asp Arg Val Thr Ile Thr Cys Arg Ala Ser Gln Gly Val Gly Ser Ala
                20                  25                  30

Leu Ala Trp Tyr Gln Gln Lys Pro Gly Lys Ala Pro Lys Leu Leu Ile
            35                  40                  45

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 238
<211> LENGTH: 123
<212> TYPE: PRT
<213> ORGANISM: Artificial Sequence
<220> FEATURE:
<223> OTHER INFORMATION: Synthetic

<400> SEQUENCE: 238

Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Arg Phe Thr Thr Ser
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Leu Gly Tyr Asn Gly Tyr Glu Gly Ala Phe Asp Ile
            100                 105                 110

Trp Gly Gln Gly Thr Leu Val Thr Val Ser Ser
            115                 120

```
<210> SEQ ID NO 239
<211> LENGTH: 107
<212> TYPE: PRT
<213> ORGANISM: Artificial Sequence
<220> FEATURE:
<223> OTHER INFORMATION: Synthetic

<400> SEQUENCE: 239

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Gly Tyr Pro Leu
                85                  90                  95

Thr Phe Gly Gln Gly Thr Arg Leu Glu Ile Lys
            100                 105

<210> SEQ ID NO 240
<211> LENGTH: 107
<212> TYPE: PRT
<213> ORGANISM: Artificial Sequence
<220> FEATURE:
<223> OTHER INFORMATION: Synthetic

<400> SEQUENCE: 240

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Ser Asp Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 241
<211> LENGTH: 107
<212> TYPE: PRT
<213> ORGANISM: Artificial Sequence
<220> FEATURE:
<223> OTHER INFORMATION: Synthetic

<400> SEQUENCE: 241

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45
```

Tyr Asp Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gln Gly Thr Arg Leu Glu Ile Lys
            100                 105

<210> SEQ ID NO 242
<211> LENGTH: 107
<212> TYPE: PRT
<213> ORGANISM: Artificial Sequence
<220> FEATURE:
<223> OTHER INFORMATION: Synthetic

<400> SEQUENCE: 242

Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Gly Ile Gly Ser Ala
                20                  25                  30

Leu Ala Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gln Gly Thr Arg Leu Glu Ile Lys
            100                 105

<210> SEQ ID NO 243
<211> LENGTH: 123
<212> TYPE: PRT
<213> ORGANISM: Artificial Sequence
<220> FEATURE:
<223> OTHER INFORMATION: Synthetic

<400> SEQUENCE: 243

Glu Val Gln Leu Val Gln Ser Gly Ala Glu Val Lys Lys Pro Gly Glu
1                   5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser
            115                 120

<210> SEQ ID NO 244
<211> LENGTH: 107
<212> TYPE: PRT
<213> ORGANISM: Artificial Sequence
<220> FEATURE:
<223> OTHER INFORMATION: Synthetic

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Arg Ser Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Leu
                85                  90                  95

Thr Phe Gly Gly Gly Thr Lys Val Glu Ile Lys
            100                 105

<210> SEQ ID NO 245
<211> LENGTH: 5
<212> TYPE: PRT
<213> ORGANISM: Artificial Sequence
<220> FEATURE:
<223> OTHER INFORMATION: Synthetic

<400> SEQUENCE: 245

Asn Tyr Trp Ile Gly
1               5

<210> SEQ ID NO 246
<211> LENGTH: 17
<212> TYPE: PRT
<213> ORGANISM: Artificial Sequence
<220> FEATURE:
<223> OTHER INFORMATION: Synthetic

<400> SEQUENCE: 246

Ile Ile Asn Pro Arg Asp Ser Asp Thr Arg Tyr Arg Pro Ser Phe Gln
1               5                   10                  15

Gly

<210> SEQ ID NO 247
<211> LENGTH: 14
<212> TYPE: PRT
<213> ORGANISM: Artificial Sequence
<220> FEATURE:
<223> OTHER INFORMATION: Synthetic

<400> SEQUENCE: 247

His Gly Arg Gly Tyr Glu Gly Tyr Glu Gly Ala Phe Asp Ile
1               5                   10

<210> SEQ ID NO 248
<211> LENGTH: 11
<212> TYPE: PRT
<213> ORGANISM: Artificial Sequence
<220> FEATURE:
<223> OTHER INFORMATION: Synthetic

<400> SEQUENCE: 248

Arg Ser Ser Gln Gly Ile Arg Ser Asp Leu Gly
1               5                   10

<210> SEQ ID NO 249
<211> LENGTH: 7
<212> TYPE: PRT
<213> ORGANISM: Artificial Sequence
<220> FEATURE:
<223> OTHER INFORMATION: Synthetic

<400> SEQUENCE: 249

Asp Ala Ser Asn Leu Glu Thr
1               5

<210> SEQ ID NO 250
<211> LENGTH: 9
<212> TYPE: PRT
<213> ORGANISM: Artificial Sequence
<220> FEATURE:
<223> OTHER INFORMATION: Synthetic

<400> SEQUENCE: 250

Gln Gln Ala Asn Gly Phe Pro Leu Thr
1               5

<210> SEQ ID NO 251
<211> LENGTH: 123
<212> TYPE: PRT
<213> ORGANISM: Artificial Sequence
<220> FEATURE:
<223> OTHER INFORMATION: Synthetic

<400> SEQUENCE: 251

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Ile Arg Tyr Ser Pro Ser Leu
    50                  55                  60

Gln Gly Gln Val Thr Ile Ser Val Asp Thr Ser Thr Ser Thr Ala Tyr
65                  70                  75                  80

Leu Gln Trp Asn Ser Leu Lys Pro Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser
        115                 120

<210> SEQ ID NO 252
<211> LENGTH: 107
<212> TYPE: PRT
<213> ORGANISM: Artificial Sequence
<220> FEATURE:
<223> OTHER INFORMATION: Synthetic

<400> SEQUENCE: 252

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Ser

-continued

```
                20                   25                   30

Leu Ala Trp Tyr Gln Gln Lys Pro Gly Lys Ala Pro Lys Leu Leu Ile
        35                   40                   45

Tyr Asp Ala Ser Asn Leu Glu Thr Gly Val Pro Ser Arg Phe Ser Gly
        50                   55                   60

Ser Gly Ser Gly Thr Asp Phe Thr Leu Thr Ile Ser Ser Leu Gln Pro
65                   70                   75                   80

Glu Asp Phe Ala Thr Tyr Tyr Cys Gln Gln Leu Asn Gly Tyr Pro Ile
                85                   90                   95

Thr Phe Gly Gln Gly Thr Lys Val Glu Ile Lys
            100                   105

<210> SEQ ID NO 253
<211> LENGTH: 17
<212> TYPE: PRT
<213> ORGANISM: Artificial Sequence
<220> FEATURE:
<223> OTHER INFORMATION: Synthetic

<400> SEQUENCE: 253

Ile Ile Tyr Pro Gly Asp Ser Asp Ile Arg Tyr Ser Pro Ser Leu Gln
1                   5                   10                   15

Gly

<210> SEQ ID NO 254
<211> LENGTH: 11
<212> TYPE: PRT
<213> ORGANISM: Artificial Sequence
<220> FEATURE:
<223> OTHER INFORMATION: Synthetic

<400> SEQUENCE: 254

Arg Ala Ser Gln Gly Ile Gly Asp Ser Leu Ala
1                   5                   10

<210> SEQ ID NO 255
<211> LENGTH: 9
<212> TYPE: PRT
<213> ORGANISM: Artificial Sequence
<220> FEATURE:
<223> OTHER INFORMATION: Synthetic

<400> SEQUENCE: 255

Gln Gln Leu Asn Gly Tyr Pro Ile Thr
1                   5

<210> SEQ ID NO 256
<211> LENGTH: 107
<212> TYPE: PRT
<213> ORGANISM: Artificial Sequence
<220> FEATURE:
<223> OTHER INFORMATION: Synthetic

<400> SEQUENCE: 256

Asp Ile Gln Met Thr Gln Ser Pro Ser Ser Leu Ser Ala Ser Val Gly
1                   5                   10                   15

Asp Arg Val Thr Ile Thr Cys Arg Ala Ser Gln Gly Ile Arg Asn Asp
                20                   25                   30

Leu Gly Trp Tyr Gln Gln Lys Pro Gly Lys Ala Pro Lys Leu Leu Ile
        35                   40                   45

Tyr Asp Ala Ser Ser Leu Glu Ser Gly Val Pro Ser Arg Phe Ser Gly
        50                   55                   60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Ile
                85                  90                  95

Thr Phe Gly Gln Gly Thr Lys Val Glu Ile Lys
            100                 105
```

<210> SEQ ID NO 257
<211> LENGTH: 11
<212> TYPE: PRT
<213> ORGANISM: Artificial Sequence
<220> FEATURE:
<223> OTHER INFORMATION: Synthetic

<400> SEQUENCE: 257

```
Arg Ala Ser Gln Gly Ile Arg Asn Asp Leu Gly
1               5                   10
```

<210> SEQ ID NO 258
<211> LENGTH: 123
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Leu Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser
        115                 120
```

<210> SEQ ID NO 259
<211> LENGTH: 17
<212> TYPE: PRT
<213> ORGANISM: Artificial Sequence
<220> FEATURE:
<223> OTHER INFORMATION: Synthetic

<400> SEQUENCE: 259

```
Ile Ile Tyr Pro Gly Asp Ser Leu Thr Arg Tyr Ser Pro Ser Phe Gln
1               5                   10                  15

Gly
```

<210> SEQ ID NO 260
<211> LENGTH: 123
<212> TYPE: PRT
<213> ORGANISM: Artificial Sequence
<220> FEATURE:
<223> OTHER INFORMATION: Synthetic

<400> SEQUENCE: 260

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Leu Val Thr Val Ser Ser
            115                 120

<210> SEQ ID NO 261
<211> LENGTH: 123
<212> TYPE: PRT
<213> ORGANISM: Artificial Sequence
<220> FEATURE:
<223> OTHER INFORMATION: Synthetic

<400> SEQUENCE: 261

Gln Val Gln Leu Val Gln Ser Gly Ala Ala Val Lys Lys Pro Gly Glu
1               5                   10                  15

Ser Leu Lys Ile Ser Cys Lys Gly Ser Gly Tyr Arg Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Gly Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Asn Gly Tyr Glu Gly Ala Phe Asp Ile
            100                 105                 110

Trp Gly Gln Gly Thr Met Val Thr Val Ser Ser
            115                 120

<210> SEQ ID NO 262
<211> LENGTH: 107
<212> TYPE: PRT
<213> ORGANISM: Artificial Sequence
<220> FEATURE:
<223> OTHER INFORMATION: Synthetic

<400> SEQUENCE: 262

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
                20                  25                  30

Leu Ala Trp Tyr Gln Gln Lys Pro Gly Lys Ala Pro Lys Leu Leu Ile
            35                  40                  45

```
Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys
            100                 105

<210> SEQ ID NO 263
<211> LENGTH: 5
<212> TYPE: PRT
<213> ORGANISM: Artificial Sequence
<220> FEATURE:
<223> OTHER INFORMATION: Synthetic

<400> SEQUENCE: 263

Thr Tyr Trp Ile Gly
1               5

<210> SEQ ID NO 264
<211> LENGTH: 11
<212> TYPE: PRT
<213> ORGANISM: Artificial Sequence
<220> FEATURE:
<223> OTHER INFORMATION: Synthetic

<400> SEQUENCE: 264

Arg Ala Ser Gln Gly Val Ile Ser Ala Leu Ala
1               5                   10

<210> SEQ ID NO 265
<211> LENGTH: 7
<212> TYPE: PRT
<213> ORGANISM: Artificial Sequence
<220> FEATURE:
<223> OTHER INFORMATION: Synthetic

<400> SEQUENCE: 265

Asp Ala Ser Ile Leu Glu Ser
1               5

<210> SEQ ID NO 266
<211> LENGTH: 9
<212> TYPE: PRT
<213> ORGANISM: Artificial Sequence
<220> FEATURE:
<223> OTHER INFORMATION: Synthetic

<400> SEQUENCE: 266

Gln Gln Phe Asn Ser Tyr Pro Leu Thr
1               5

<210> SEQ ID NO 267
<211> LENGTH: 11
<212> TYPE: PRT
<213> ORGANISM: Artificial Sequence
<220> FEATURE:
<223> OTHER INFORMATION: Synthetic

<400> SEQUENCE: 267

Arg Ala Ser Gln Gly Val Gly Ser Ala Leu Ala
1               5                   10
```

<210> SEQ ID NO 268
<211> LENGTH: 7
<212> TYPE: PRT
<213> ORGANISM: Artificial Sequence
<220> FEATURE:
<223> OTHER INFORMATION: Synthetic

<400> SEQUENCE: 268

Asp Ala Ser Thr Leu Glu Ser
1               5

<210> SEQ ID NO 269
<211> LENGTH: 330
<212> TYPE: PRT
<213> ORGANISM: Homo sapiens

<400> SEQUENCE: 269

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

```
Gln Lys Ser Leu Ser Leu Ser Pro Gly Lys
            325                 330

<210> SEQ ID NO 270
<211> LENGTH: 330
<212> TYPE: PRT
<213> ORGANISM: Artificial Sequence
<220> FEATURE:
<223> OTHER INFORMATION: Synthetic

<400> SEQUENCE: 270

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 271
```

-continued

```
<211> LENGTH: 330
<212> TYPE: PRT
<213> ORGANISM: Artificial Sequence
<220> FEATURE:
<223> OTHER INFORMATION: Synthetic

<400> SEQUENCE: 271

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Cys Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 272
<211> LENGTH: 330
<212> TYPE: PRT
<213> ORGANISM: Artificial Sequence
<220> FEATURE:
<223> OTHER INFORMATION: Synthetic
```

```
<400> SEQUENCE: 272

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Ala Tyr Thr
305                 310                 315                 320

Gln Lys Ser Leu Ser Leu Ser Pro Gly Lys
                325                 330

<210> SEQ ID NO 273
<211> LENGTH: 330
<212> TYPE: PRT
<213> ORGANISM: Artificial Sequence
<220> FEATURE:
<223> OTHER INFORMATION: Synthetic

<400> SEQUENCE: 273

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
            20              25              30
Phe Pro Glu Pro Val Thr Val Ser Trp Asn Ser Gly Ala Leu Thr Ser
         35              40              45

Gly Val His Thr Phe Pro Ala Val Leu Gln Ser Ser Gly Leu Tyr Ser
     50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
             85              90              95

Lys Val Glu Pro Lys Ser Cys Asp Lys Thr His Thr Cys Pro Pro Cys
             100             105             110

Pro Ala Pro Glu Ala Ala Gly Gly Pro Ser Val Phe Leu Phe Pro Pro
         115             120             125

Lys Pro Lys Asp Thr Leu Met Ile Ser Arg Thr Pro Glu Val Thr Cys
     130             135             140

Val Val Val Cys Val Ser His Glu Asp Pro Glu Val Lys Phe Asn Trp
145             150             155             160

Tyr Val Asp Gly Val Glu Val His Asn Ala Lys Thr Lys Pro Arg Glu
             165             170             175

Glu Gln Tyr Asn Ser Thr Tyr Arg Val Val Ser Val Leu Thr Val Leu
         180             185             190

His Gln Asp Trp Leu Asn Gly Lys Glu Tyr Lys Cys Lys Val Ser Asn
         195             200             205

Lys Ala Leu Pro Ala Pro Ile Glu Lys Thr Ile Ser Lys Ala Lys Gly
     210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
             245             250             255

Pro Ser Asp Ile Ala Val Glu Trp Glu Ser Asn Gly Gln Pro Glu Asn
         260             265             270

Asn Tyr Lys Thr Thr Pro Pro Val Leu Asp Ser Asp Gly Ser Phe Phe
     275             280             285

Leu Tyr Ser Lys Leu Thr Val Asp Lys Ser Arg Trp Gln Gln Gly Asn
     290             295             300

Val Phe Ser Cys Ser Val Met His Glu Ala Leu His Asn His Tyr Thr
305             310             315             320

Gln Lys Ser Leu Ser Leu Ser Pro Gly Lys
             325             330

<210> SEQ ID NO 274
<211> LENGTH: 330
<212> TYPE: PRT
<213> ORGANISM: Artificial Sequence
<220> FEATURE:
<223> OTHER INFORMATION: Synthetic

<400> SEQUENCE: 274

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
             20              25              30

Phe Pro Glu Pro Val Thr Val Ser Trp Asn Ser Gly Ala Leu Thr Ser
         35              40              45

Gly Val His Thr Phe Pro Ala Val Leu Gln Ser Ser Gly Leu Tyr Ser
```

-continued

```
             50                   55                   60

Leu Ser Ser Val Val Thr Val Pro Ser Ser Leu Gly Thr Gln Thr
65                   70                   75                   80

Tyr Ile Cys Asn Val Asn His Lys Pro Ser Asn Thr Lys Val Asp Lys
                 85                   90                   95

Lys Val Glu Pro Lys Ser Cys Asp Lys Thr His Thr Cys Pro Pro Cys
                 100                  105                  110

Pro Ala Pro Glu Ala Ala Gly Gly Pro Ser Val Phe Leu Phe Pro Pro
                 115                  120                  125

Lys Pro Lys Asp Thr Leu Met Ile Ser Arg Thr Pro Glu Val Thr Cys
                 130                  135                  140

Val Val Val Cys Val Ser His Glu Asp Pro Glu Val Lys Phe Asn Trp
145                  150                  155                  160

Tyr Val Asp Gly Val Glu Val His Asn Ala Lys Thr Lys Pro Arg Glu
                 165                  170                  175

Glu Gln Tyr Asn Ser Thr Tyr Arg Val Val Ser Val Leu Thr Val Leu
                 180                  185                  190

His Gln Asp Trp Leu Asn Gly Lys Glu Tyr Lys Cys Lys Val Ser Asn
                 195                  200                  205

Lys Ala Leu Pro Ala Pro Ile Glu Lys Thr Ile Ser Lys Ala Lys Gly
                 210                  215                  220

Gln Pro Arg Glu Pro Gln Val Tyr Thr Leu Pro Pro Ser Arg Asp Glu
225                  230                  235                  240

Leu Thr Lys Asn Gln Val Ser Leu Thr Cys Leu Val Lys Gly Phe Tyr
                 245                  250                  255

Pro Ser Asp Ile Ala Val Glu Trp Glu Ser Asn Gly Gln Pro Glu Asn
                 260                  265                  270

Asn Tyr Lys Thr Thr Pro Pro Val Leu Asp Ser Asp Gly Ser Phe Phe
                 275                  280                  285

Leu Tyr Ser Lys Leu Thr Val Asp Lys Ser Arg Trp Gln Gln Gly Asn
                 290                  295                  300

Val Phe Ser Cys Ser Val Met His Glu Ala Leu His Asn Ala Tyr Thr
305                  310                  315                  320

Gln Lys Ser Leu Ser Leu Ser Pro Gly Lys
                 325                  330

<210> SEQ ID NO 275
<211> LENGTH: 453
<212> TYPE: PRT
<213> ORGANISM: Artificial Sequence
<220> FEATURE:
<223> OTHER INFORMATION: Synthetic

<400> SEQUENCE: 275

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Ala Ile Ile Asn Pro Arg Asp Ser Asp Thr Arg Tyr Arg Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
```

-continued

```
                        85                      90                      95

Ala Arg His Gly Arg Gly Tyr Glu Gly Tyr Glu Gly Ala Phe Asp Ile
            100                     105                     110

Trp Gly Gln Gly Thr Leu Val Thr Val Ser Ser Ala Ser Thr Lys Gly
            115                     120                     125

Pro Ser Val Phe Pro Leu Ala Pro Ser Ser Lys Ser Thr Ser Gly Gly
            130                     135                     140

Thr Ala Ala Leu Gly Cys Leu Val Lys Asp Tyr Phe Pro Glu Pro Val
145                     150                     155                     160

Thr Val Ser Trp Asn Ser Gly Ala Leu Thr Ser Gly Val His Thr Phe
                165                     170                     175

Pro Ala Val Leu Gln Ser Ser Gly Leu Tyr Ser Leu Ser Ser Val Val
                180                     185                     190

Thr Val Pro Ser Ser Ser Leu Gly Thr Gln Thr Tyr Ile Cys Asn Val
                195                     200                     205

Asn His Lys Pro Ser Asn Thr Lys Val Asp Lys Lys Val Glu Pro Lys
            210                     215                     220

Ser Cys Asp Lys Thr His Thr Cys Pro Pro Cys Pro Ala Pro Glu Leu
225                     230                     235                     240

Leu Gly Gly Pro Ser Val Phe Leu Phe Pro Pro Lys Pro Lys Asp Thr
                245                     250                     255

Leu Met Ile Ser Arg Thr Pro Glu Val Thr Cys Val Val Val Asp Val
                260                     265                     270

Ser His Glu Asp Pro Glu Val Lys Phe Asn Trp Tyr Val Asp Gly Val
                275                     280                     285

Glu Val His Asn Ala Lys Thr Lys Pro Arg Glu Glu Gln Tyr Asn Ser
            290                     295                     300

Thr Tyr Arg Val Val Ser Val Leu Thr Val Leu His Gln Asp Trp Leu
305                     310                     315                     320

Asn Gly Lys Glu Tyr Lys Cys Lys Val Ser Asn Lys Ala Leu Pro Ala
                325                     330                     335

Pro Ile Glu Lys Thr Ile Ser Lys Ala Lys Gly Gln Pro Arg Glu Pro
                340                     345                     350

Gln Val Tyr Thr Leu Pro Pro Ser Arg Asp Glu Leu Thr Lys Asn Gln
                355                     360                     365

Val Ser Leu Thr Cys Leu Val Lys Gly Phe Tyr Pro Ser Asp Ile Ala
                370                     375                     380

Val Glu Trp Glu Ser Asn Gly Gln Pro Glu Asn Asn Tyr Lys Thr Thr
385                     390                     395                     400

Pro Pro Val Leu Asp Ser Asp Gly Ser Phe Phe Leu Tyr Ser Lys Leu
                405                     410                     415

Thr Val Asp Lys Ser Arg Trp Gln Gln Gly Asn Val Phe Ser Cys Ser
                420                     425                     430

Val Met His Glu Ala Leu His Asn His Tyr Thr Gln Lys Ser Leu Ser
            435                     440                     445

Leu Ser Pro Gly Lys
    450
```

<210> SEQ ID NO 276
<211> LENGTH: 453
<212> TYPE: PRT
<213> ORGANISM: Artificial Sequence
<220> FEATURE:
<223> OTHER INFORMATION: Synthetic -continued

<400> SEQUENCE: 276

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Ala Ile Ile Asn Pro Arg Asp Ser Asp Thr Arg Tyr Arg Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
        370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415
```

```
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 277
<211> LENGTH: 453
<212> TYPE: PRT
<213> ORGANISM: Artificial Sequence
<220> FEATURE:
<223> OTHER INFORMATION: Synthetic

<400> SEQUENCE: 277

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Ala Ile Ile Asn Pro Arg Asp Ser Asp Thr Arg Tyr Arg Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Arg Gly Tyr Glu Gly Tyr Glu Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Cys Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320
```

-continued

```
Asn Gly Lys Glu Tyr Lys Cys Lys Val Ser Asn Lys Ala Leu Pro Ala
                325             330             335

Pro Ile Glu Lys Thr Ile Ser Lys Ala Lys Gly Gln Pro Arg Glu Pro
                340             345             350

Gln Val Tyr Thr Leu Pro Pro Ser Arg Asp Glu Leu Thr Lys Asn Gln
                355             360             365

Val Ser Leu Thr Cys Leu Val Lys Gly Phe Tyr Pro Ser Asp Ile Ala
        370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
                405             410             415

Thr Val Asp Lys Ser Arg Trp Gln Gln Gly Asn Val Phe Ser Cys Ser
                420             425             430

Val Met His Glu Ala Leu His Asn His Tyr Thr Gln Lys Ser Leu Ser
        435             440             445

Leu Ser Pro Gly Lys
    450

<210> SEQ ID NO 278
<211> LENGTH: 453
<212> TYPE: PRT
<213> ORGANISM: Artificial Sequence
<220> FEATURE:
<223> OTHER INFORMATION: Synthetic

<400> SEQUENCE: 278

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Ser Phe Thr Asn Tyr
                20              25              30

Trp Ile Gly Trp Val Arg Gln Met Pro Gly Lys Gly Leu Glu Trp Met
            35              40              45

Ala Ile Ile Asn Pro Arg Asp Ser Asp Thr Arg Tyr Arg Pro Ser Phe
        50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
                85              90              95

Ala Arg His Gly Arg Gly Tyr Glu Gly Tyr Glu Gly Ala Phe Asp Ile
            100             105             110

Trp Gly Gln Gly Thr Leu Val Thr Val Ser Ser Ala Ser Thr Lys Gly
            115             120             125

Pro Ser Val Phe Pro Leu Ala Pro Ser Ser Lys Ser Thr Ser Gly Gly
        130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
                165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220
```

```
Ser Cys Asp Lys Thr His Thr Cys Pro Pro Cys Pro Ala Pro Glu Ala
225             230             235             240

Ala Gly Gly Pro Ser Val Phe Leu Phe Pro Pro Lys Pro Lys Asp Thr
                245             250             255

Leu Met Ile Ser Arg Thr Pro Glu Val Thr Cys Val Val Val Cys Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
        290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
                325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
        370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
                405             410             415

Thr Val Asp Lys Ser Arg Trp Gln Gln Gly Asn Val Phe Ser Cys Ser
                420             425             430

Val Met His Glu Ala Leu His Asn Ala Tyr Thr Gln Lys Ser Leu Ser
            435             440             445

Leu Ser Pro Gly Lys
        450

<210> SEQ ID NO 279
<211> LENGTH: 453
<212> TYPE: PRT
<213> ORGANISM: Artificial Sequence
<220> FEATURE:
<223> OTHER INFORMATION: Synthetic

<400> SEQUENCE: 279

Glu Val Gln Leu Val Gln Ser Gly Ala Glu Val Lys Lys Pro Gly Glu
1               5               10              15

Ser Leu Lys Ile Ser Cys Lys Gly Ser Gly Tyr Arg Phe Thr Thr Ser
            20              25              30

Trp Ile Gly Trp Val Arg Gln Met Pro Gly Lys Gly Leu Glu Trp Met
            35              40              45

Gly Ile Ile Tyr Pro Gly Asp Ser Asp Thr Arg Tyr Ser Pro Ser Phe
        50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
                85              90              95

Ala Arg His Gly Leu Gly Tyr Asn Gly Tyr Glu Gly Ala Phe Asp Ile
            100             105             110

Trp Gly Gln Gly Thr Leu Val Thr Val Ser Ser Ala Ser Thr Lys Gly
            115             120             125
```

-continued

```
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys
    450
```

```
<210> SEQ ID NO 280
<211> LENGTH: 453
<212> TYPE: PRT
<213> ORGANISM: Artificial Sequence
<220> FEATURE:
<223> OTHER INFORMATION: Synthetic

<400> SEQUENCE: 280

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
                20                  25                  30
```

```
Trp Ile Gly Trp Val Arg Gln Met Pro Gly Lys Gly Leu Glu Trp Met
    35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Ala Arg His Gly Leu Gly Tyr Asn Gly Tyr Glu Gly Ala Phe Asp Ile
            100             105             110

Trp Gly Gln Gly Thr Leu Val Thr Val Ser Ser Ala Ser Thr Lys Gly
            115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Ala
225             230             235             240

Ala Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445
```

```
Leu Ser Pro Gly Lys
    450

<210> SEQ ID NO 281
<211> LENGTH: 453
<212> TYPE: PRT
<213> ORGANISM: Artificial Sequence
<220> FEATURE:
<223> OTHER INFORMATION: Synthetic

<400> SEQUENCE: 281

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Thr Ser
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Gly Leu Gly Tyr Asn Gly Tyr Glu Gly Ala Phe Asp Ile
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Cys Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350
```

```
Gln Val Tyr Thr Leu Pro Pro Ser Arg Asp Glu Leu Thr Lys Asn Gln
        355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
        435             440             445

Leu Ser Pro Gly Lys
    450
```

```
<210> SEQ ID NO 282
<211> LENGTH: 453
<212> TYPE: PRT
<213> ORGANISM: Artificial Sequence
<220> FEATURE:
<223> OTHER INFORMATION: Synthetic

<400> SEQUENCE: 282
```

```
Glu Val Gln Leu Val Gln Ser Gly Ala Glu Val Lys Lys Pro Gly Glu
1               5               10              15

Ser Leu Lys Ile Ser Cys Lys Gly Ser Gly Tyr Arg Phe Thr Thr Ser
            20              25              30

Trp Ile Gly Trp Val Arg Gln Met Pro Gly Lys Gly Leu Glu Trp Met
        35              40              45

Gly Ile Ile Tyr Pro Gly Asp Ser Asp Thr Arg Tyr Ser Pro Ser Phe
    50              55              60

Gln Gly Gln Val Thr Ile Ser Ala Asp Lys Ser Ile Ser Thr Ala Tyr
65              70              75              80

Leu Gln Trp Ser Ser Leu Lys Ala Ser Asp Thr Ala Met Tyr Tyr Cys
            85              90              95

Ala Arg His Gly Leu Gly Tyr Asn Gly Tyr Glu Gly Ala Phe Asp Ile
        100             105             110

Trp Gly Gln Gly Thr Leu Val Thr Val Ser Ser Ala Ser Thr Lys Gly
        115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
        180             185             190

Thr Val Pro Ser Ser Ser Leu Gly Thr Gln Thr Tyr Ile Cys Asn Val
        195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Ala
225             230             235             240

Ala Gly Gly Pro Ser Val Phe Leu Phe Pro Pro Lys Pro Lys Asp Thr
            245             250             255
```

-continued

```
Leu Met Ile Ser Arg Thr Pro Glu Val Thr Cys Val Val Val Cys Val
            260             265             270

Ser His Glu Asp Pro Glu Val Lys Phe Asn Trp Tyr Val Asp Gly Val
            275             280             285

Glu Val His Asn Ala Lys Thr Lys Pro Arg Glu Glu Gln Tyr Asn Ser
            290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
            370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn Ala Tyr Thr Gln Lys Ser Leu Ser
            435             440             445

Leu Ser Pro Gly Lys
            450
```

```
<210> SEQ ID NO 283
<211> LENGTH: 107
<212> TYPE: PRT
<213> ORGANISM: Artificial Sequence
<220> FEATURE:
<223> OTHER INFORMATION: Synthetic

<400> SEQUENCE: 283
```

```
Arg Thr Val Ala Ala Pro Ser Val Phe Ile Phe Pro Pro Ser Asp Glu
1               5               10              15

Gln Leu Lys Ser Gly Thr Ala Ser Val Val Cys Leu Leu Asn Asn Phe
            20              25              30

Tyr Pro Arg Glu Ala Lys Val Gln Trp Lys Val Asp Asn Ala Leu Gln
            35              40              45

Ser Gly Asn Ser Gln Glu Ser Val Thr Glu Gln Asp Ser Lys Asp Ser
            50              55              60

Thr Tyr Ser Leu Ser Ser Thr Leu Thr Leu Ser Lys Ala Asp Tyr Glu
65              70              75              80

Lys His Lys Val Tyr Ala Cys Glu Val Thr His Gln Gly Leu Ser Ser
            85              90              95

Pro Val Thr Lys Ser Phe Asn Arg Gly Glu Cys
            100             105
```

```
<210> SEQ ID NO 284
<211> LENGTH: 214
<212> TYPE: PRT
<213> ORGANISM: Artificial Sequence
<220> FEATURE:
<223> OTHER INFORMATION: Synthetic

<400> SEQUENCE: 284
```

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Arg Ser Asp
            20                  25                  30

Leu Gly Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Gly Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

```
<210> SEQ ID NO 285
<211> LENGTH: 214
<212> TYPE: PRT
<213> ORGANISM: Artificial Sequence
<220> FEATURE:
<223> OTHER INFORMATION: Synthetic

<400> SEQUENCE: 285
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Ser Ala
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Gly Tyr Pro Leu
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 286
<211> LENGTH: 5
<212> TYPE: PRT
<213> ORGANISM: Artificial Sequence
<220> FEATURE:
<223> OTHER INFORMATION: Synthetic

<400> SEQUENCE: 286

Thr Ser Trp Ile Gly
1               5

<210> SEQ ID NO 287
<211> LENGTH: 14
<212> TYPE: PRT
<213> ORGANISM: Artificial Sequence
<220> FEATURE:
<223> OTHER INFORMATION: Synthetic

<400> SEQUENCE: 287

His Gly Leu Gly Tyr Asn Gly Tyr Glu Gly Ala Phe Asp Ile
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Synthetic

<400> SEQUENCE: 288

Arg Ala Ser Gln Gly Ile Gly Ser Ala Leu Ala
1               5                   10

<210> SEQ ID NO 289
<211> LENGTH: 10
<212> TYPE: PRT
<213> ORGANISM: Artificial Sequence
<220> FEATURE:
<223> OTHER INFORMATION: Synthetic

<400> SEQUENCE: 289

Cys Gln Gln Leu Asn Gly Tyr Pro Leu Thr
1               5                   10

<210> SEQ ID NO 290
<211> LENGTH: 453
<212> TYPE: PRT
<213> ORGANISM: Artificial Sequence
<220> FEATURE:
<223> OTHER INFORMATION: Synthetic

<400> SEQUENCE: 290

Gln Val Gln Leu Gln Gln Pro Gly Ala Glu Leu Val Arg Pro Gly Ala
```

-continued

```
1                5                    10                   15
Ser Val Lys Leu Ser Cys Lys Ala Ser Gly Tyr Thr Phe Thr Ser Tyr
            20              25                   30

Trp Ile Asn Trp Val Lys Gln Arg Pro Gly Gln Gly Leu Glu Trp Ile
            35              40                   45

Gly Asn Ile Tyr Pro Ser Asp Ser Tyr Thr Asn Tyr Asn Gln Lys Phe
            50              55                   60

Lys Asp Lys Ala Thr Leu Thr Val Asp Lys Ser Ser Asn Thr Val Tyr
65                      70              75                   80

Met Gln Leu Asn Ser Pro Thr Ser Glu Asp Ser Ala Val Tyr Tyr Cys
                85              90                   95

Thr Arg Asn Gly Val Glu Gly Tyr Pro His Tyr Tyr Ala Met Glu Tyr
            100             105                  110

Trp Gly Gln Gly Thr Ser Val Thr Val Ser Ser Ala Ser Thr Lys Gly
            115             120                  125

Pro Ser Val Phe Pro Leu Ala Pro Ser Ser Lys Ser Thr Ser Gly Gly
            130             135                  140

Thr Ala Ala Leu Gly Cys Leu Val Lys Asp Tyr Phe Pro Glu Pro Val
145                 150             155                  160

Thr Val Ser Trp Asn Ser Gly Ala Leu Thr Ser Gly Val His Thr Phe
                165             170                  175

Pro Ala Val Leu Gln Ser Ser Gly Leu Tyr Ser Leu Ser Ser Val Val
                180             185                  190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Thr Cys Pro Pro Cys Pro Ala Pro Glu Leu
225                 230             235                  240

Leu Gly Gly Pro Ser Val Phe Leu Phe Pro Pro Lys Pro Lys Asp Thr
                245             250             255

Leu Met Ile Ser Arg Thr Pro Glu Val Thr Cys Val Val Val Asp Val
                260             265             270

Ser His Glu Asp Pro Glu Val Lys Phe Asn Trp Tyr Val Asp Gly Val
    275             280             285

Glu Val His Asn Ala Lys Thr Lys Pro Arg Glu Glu Gln Tyr Asn Ser
    290             295             300

Thr Tyr Arg Val Val Ser Val Leu Thr Val Leu His Gln Asp Trp Leu
305             310             315                  320

Asn Gly Lys Glu Tyr Lys Cys Lys Val Ser Asn Lys Ala Leu Pro Ala
            325             330             335

Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
                405             410             415

Thr Val Asp Lys Ser Arg Trp Gln Gln Gly Asn Val Phe Ser Cys Ser
            420             425             430
```

Val Met His Glu Ala Leu His Asn His Tyr Thr Gln Lys Ser Leu Ser
        435                 440                 445

Leu Ser Pro Gly Lys
    450

<210> SEQ ID NO 291
<211> LENGTH: 214
<212> TYPE: PRT
<213> ORGANISM: Artificial Sequence
<220> FEATURE:
<223> OTHER INFORMATION: Synthetic

<400> SEQUENCE: 291

Asp Ile Gln Met Thr Gln Thr Thr Ser Ala Leu Ser Ala Ser Leu Gly
1               5                   10                  15

Asp Arg Val Thr Ile Gly Cys Arg Ala Ser Gln Asp Leu Ser Asn His
            20                  25                  30

Leu Tyr Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Val Ala Thr Tyr Phe Cys Gln Gln Gly Tyr Thr Leu Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 292
<211> LENGTH: 5
<212> TYPE: PRT
<213> ORGANISM: Artificial Sequence
<220> FEATURE:
<223> OTHER INFORMATION: Synthetic

<400> SEQUENCE: 292

Ser Tyr Trp Ile Asn
1               5

<210> SEQ ID NO 293
<211> LENGTH: 17
<212> TYPE: PRT
<213> ORGANISM: Artificial Sequence
<220> FEATURE:
<223> OTHER INFORMATION: Synthetic

<400> SEQUENCE: 293

Asn Ile Tyr Pro Ser Asp Ser Tyr Thr Asn Tyr Asn Gln Lys Phe Lys
1               5                   10                  15

Asp

<210> SEQ ID NO 294
<211> LENGTH: 14
<212> TYPE: PRT
<213> ORGANISM: Artificial Sequence
<220> FEATURE:
<223> OTHER INFORMATION: Synthetic

<400> SEQUENCE: 294

Asn Gly Val Glu Gly Tyr Pro His Tyr Tyr Ala Met Glu Tyr
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Synthetic

<400> SEQUENCE: 295

Arg Ala Ser Gln Asp Leu Ser Asn His Leu Tyr
1               5                   10

<210> SEQ ID NO 296
<211> LENGTH: 7
<212> TYPE: PRT
<213> ORGANISM: Artificial Sequence
<220> FEATURE:
<223> OTHER INFORMATION: Synthetic

<400> SEQUENCE: 296

Tyr Thr Ser Arg Leu His Ser
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic

<400> SEQUENCE: 297

Gln Gln Gly Tyr Thr Leu Pro Tyr Thr
1               5

<210> SEQ ID NO 298
<211> LENGTH: 123
<212> TYPE: PRT
<213> ORGANISM: Artificial Sequence
<220> FEATURE:
<223> OTHER INFORMATION: Synthetic

<400> SEQUENCE: 298

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
                20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50              55                  60

Lys Asp Lys Ala Thr Leu Thr Val Asp Lys Ser Ser Asn Thr Val Tyr
65              70                  75                  80

Met Gln Leu Asn Ser Pro Thr Ser Glu Asp Ser Ala Val Tyr Tyr Cys
                85                  90                  95

Thr Arg Asn Gly Val Glu Gly Tyr Pro His Tyr Tyr Ala Met Glu Tyr
            100                 105                 110

Trp Gly Gln Gly Thr Ser Val Thr Val Ser Ser
        115                 120

<210> SEQ ID NO 299
<211> LENGTH: 107
<212> TYPE: PRT
<213> ORGANISM: Artificial Sequence
<220> FEATURE:
<223> OTHER INFORMATION: Synthetic

<400> SEQUENCE: 299

Asp Ile Gln Met Thr Gln Thr Thr Ser Ala Leu Ser Ala Ser Leu Gly
1               5                   10                  15

Asp Arg Val Thr Ile Gly Cys Arg Ala Ser Gln Asp Leu Ser Asn His
            20                  25                  30

Leu Tyr Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Arg Asn Leu Glu Gln
65                  70                  75                  80

Glu Asp Val Ala Thr Tyr Phe Cys Gln Gln Gly Tyr Thr Leu Pro Tyr
                85                  90                  95

Thr Phe Gly Gly Gly Thr Lys Leu Glu Ile Lys
            100                 105

<210> SEQ ID NO 300
<211> LENGTH: 5
<212> TYPE: PRT
<213> ORGANISM: Artificial Sequence
<220> FEATURE:
<223> OTHER INFORMATION: Synthetic

<400> SEQUENCE: 300

Glu Tyr Tyr Met Tyr
1               5

<210> SEQ ID NO 301
<211> LENGTH: 17
<212> TYPE: PRT
<213> ORGANISM: Artificial Sequence
<220> FEATURE:
<223> OTHER INFORMATION: Synthetic

<400> SEQUENCE: 301

Arg Ile Asp Pro Glu Asp Gly Ser Ile Asp Tyr Val Glu Lys Phe Lys
1               5                   10                  15

Lys

<210> SEQ ID NO 302
<211> LENGTH: 9
<212> TYPE: PRT
<213> ORGANISM: Artificial Sequence
<220> FEATURE:
<223> OTHER INFORMATION: Synthetic

<400> SEQUENCE: 302

Gly Lys Phe Asn Tyr Arg Phe Ala Tyr
1               5

<210> SEQ ID NO 303
<211> LENGTH: 16
<212> TYPE: PRT
<213> ORGANISM: Artificial Sequence
<220> FEATURE:
<223> OTHER INFORMATION: Synthetic

<400> SEQUENCE: 303

Arg Ser Ser Gln Ser Leu Leu His Ser Ser Gly Asn Thr Tyr Leu Asn
1               5                   10                  15

<210> SEQ ID NO 304
<211> LENGTH: 7
<212> TYPE: PRT
<213> ORGANISM: Artificial Sequence
<220> FEATURE:
<223> OTHER INFORMATION: Synthetic

<400> SEQUENCE: 304

Leu Val Ser Lys Leu Glu Ser
1               5

<210> SEQ ID NO 305
<211> LENGTH: 9
<212> TYPE: PRT
<213> ORGANISM: Artificial Sequence
<220> FEATURE:
<223> OTHER INFORMATION: Synthetic

<400> SEQUENCE: 305

Met Gln Phe Thr His Tyr Pro Tyr Thr
1               5

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Tyr Met Tyr Trp Val Arg Gln Ala Pro Gly Gln Gly Leu Glu Leu Met
        35                  40                  45

Gly Arg Ile Asp Pro Glu Asp Gly Ser Ile Asp Tyr Val Glu Lys Phe
    50                  55                  60

Lys Lys Lys Val Thr Leu Thr Ala Asp Thr Ser Ser Ser Thr Ala Tyr
65                  70                  75                  80

Met Glu Leu Ser Ser Leu Thr Ser Asp Asp Thr Ala Val Tyr Tyr Cys
                85                  90                  95

Ala Arg Gly Lys Phe Asn Tyr Arg Phe Ala Tyr Trp Gly Gln Gly Thr
            100                 105                 110

Leu Val Thr Val Ser Ser

115

<210> SEQ ID NO 307
<211> LENGTH: 112
<212> TYPE: PRT
<213> ORGANISM: Artificial Sequence
<220> FEATURE:
<223> OTHER INFORMATION: Synthetic

<400> SEQUENCE: 307

Asp Val Val Met Thr Gln Ser Pro Pro Ser Leu Leu Val Thr Leu Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Asn Trp Leu Leu Gln Arg Pro Gly Gln Ser
        35                  40                  45

Pro Gln Pro Leu Ile Tyr Leu Val Ser Lys Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Val Tyr Tyr Cys Met Gln Phe
                85                  90                  95

Thr His Tyr Pro Tyr Thr Phe Gly Gln Gly Thr Lys Leu Glu Ile Lys
            100                 105                 110

<210> SEQ ID NO 308
<211> LENGTH: 118
<212> TYPE: PRT
<213> ORGANISM: Artificial Sequence
<220> FEATURE:
<223> OTHER INFORMATION: Synthetic

<400> SEQUENCE: 308

Gln Val Gln Leu Val Gln Ser Gly Ala Glu Val Gln Arg Pro Gly Ala
1               5                   10                  15

Ser Val Lys Val Ser Cys Lys Ala Ser Gly Tyr Ile Phe Thr Glu Tyr
            20                  25                  30

Tyr Met Tyr Trp Val Arg Gln Ala Pro Gly Gln Gly Leu Glu Leu Val
        35                  40                  45

Gly Arg Ile Asp Pro Glu Asp Gly Ser Ile Asp Tyr Val Glu Lys Phe
    50                  55                  60

Lys Lys Lys Val Thr Leu Thr Ala Asp Thr Ser Ser Ser Thr Ala Tyr
65                  70                  75                  80

Met Glu Leu Ser Ser Leu Thr Ser Asp Asp Thr Ala Val Tyr Tyr Cys
                85                  90                  95

Ala Arg Gly Lys Phe Asn Tyr Arg Phe Ala Tyr Trp Gly Gln Gly Thr
            100                 105                 110

Leu Val Thr Val Ser Ser
        115

<210> SEQ ID NO 309
<211> LENGTH: 112
<212> TYPE: PRT
<213> ORGANISM: Artificial Sequence
<220> FEATURE:
<223> OTHER INFORMATION: Synthetic

<400> SEQUENCE: 309

Asp Val Val Met Thr Gln Ser Pro Pro Ser Leu Leu Val Thr Leu Gly
1               5                   10                  15

-continued

```
Gln Pro Ala Ser Ile Ser Cys Arg Ser Ser Gln Ser Leu Leu His Ser
            20                  25                  30

Ser Gly Asn Thr Tyr Leu Asn Trp Leu Leu Gln Arg Pro Gly Gln Ser
            35                  40                  45

Pro Gln Pro Leu Ile Tyr Leu Val Ser Lys Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Val Gly Val Tyr Tyr Cys Met Gln Phe
                85                  90                  95

Thr His Tyr Pro Tyr Thr Phe Gly Gln Gly Thr Lys Leu Glu Ile Lys
            100                 105                 110
```

<210> SEQ ID NO 310
<211> LENGTH: 120
<212> TYPE: PRT
<213> ORGANISM: Artificial Sequence
<220> FEATURE:
<223> OTHER INFORMATION: Synthetic

<400> SEQUENCE: 310

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
            35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

Gly Thr Leu Val Thr Val Ser Ser
        115                 120
```

<210> SEQ ID NO 311
<211> LENGTH: 109
<212> TYPE: PRT
<213> ORGANISM: Artificial Sequence
<220> FEATURE:
<223> OTHER INFORMATION: Synthetic

<400> SEQUENCE: 311

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
```

-continued

```
                        85                    90                    95
Thr Phe Gly Gln Gly Thr Lys Val Glu Ile Lys Arg Thr
                100                   105

<210> SEQ ID NO 312
<211> LENGTH: 351
<212> TYPE: PRT
<213> ORGANISM: Homo sapiens

<400> SEQUENCE: 312

Met Ser Phe Pro Cys Lys Phe Val Ala Ser Phe Leu Leu Ile Phe Asn
1                   5                    10                   15

Val Ser Ser Lys Gly Ala Val Ser Lys Glu Ile Thr Asn Ala Leu Glu
                20                   25                   30

Thr Trp Gly Ala Leu Gly Gln Asp Ile Asn Leu Asp Ile Pro Ser Phe
            35                   40                   45

Gln Met Ser Asp Asp Ile Asp Asp Ile Lys Trp Glu Lys Thr Ser Asp
        50                   55                   60

Lys Lys Lys Ile Ala Gln Phe Arg Lys Glu Lys Glu Thr Phe Lys Glu
65                  70                   75                   80

Lys Asp Thr Tyr Lys Leu Phe Lys Asn Gly Thr Leu Lys Ile Lys His
                85                   90                   95

Leu Lys Thr Asp Asp Gln Asp Ile Tyr Lys Val Ser Ile Tyr Asp Thr
                100                  105                  110

Lys Gly Lys Asn Val Leu Glu Lys Ile Phe Asp Leu Lys Ile Gln Glu
            115                  120                  125

Arg Val Ser Lys Pro Lys Ile Ser Trp Thr Cys Ile Asn Thr Thr Leu
        130                  135                  140

Thr Cys Glu Val Met Asn Gly Thr Asp Pro Glu Leu Asn Leu Tyr Gln
145                 150                  155                  160

Asp Gly Lys His Leu Lys Leu Ser Gln Arg Val Ile Thr His Lys Trp
                165                  170                  175

Thr Thr Ser Leu Ser Ala Lys Phe Lys Cys Thr Ala Gly Asn Lys Val
                180                  185                  190

Ser Lys Glu Ser Ser Val Glu Pro Val Ser Cys Pro Glu Lys Gly Leu
            195                  200                  205

Asp Ile Tyr Leu Ile Ile Gly Ile Cys Gly Gly Gly Ser Leu Leu Met
        210                  215                  220

Val Phe Val Ala Leu Leu Val Phe Tyr Ile Thr Lys Arg Lys Lys Gln
225                 230                  235                  240

Arg Ser Arg Arg Asn Asp Glu Glu Leu Glu Thr Arg Ala His Arg Val
                245                  250                  255

Ala Thr Glu Glu Arg Gly Arg Lys Pro His Gln Ile Pro Ala Ser Thr
                260                  265                  270

Pro Gln Asn Pro Ala Thr Ser Gln His Pro Pro Pro Pro Gly His
            275                  280                  285

Arg Ser Gln Ala Pro Ser His Arg Pro Pro Pro Gly His Arg Val
            290                  295                  300

Gln His Gln Pro Gln Lys Arg Pro Pro Ala Pro Ser Gly Thr Gln Val
305                 310                  315                  320

His Gln Gln Lys Gly Pro Pro Leu Pro Arg Pro Arg Val Gln Pro Lys
                325                  330                  335

Pro Pro His Gly Ala Ala Glu Asn Ser Leu Ser Pro Ser Ser Asn
            340                  345                  350
```

-continued

```
<210> SEQ ID NO 313
<211> LENGTH: 7
<212> TYPE: PRT
<213> ORGANISM: Artificial Sequence
<220> FEATURE:
<223> OTHER INFORMATION: Synthetic

<400> SEQUENCE: 313

Gly Phe Thr Phe Ser Ser Tyr
1               5

<210> SEQ ID NO 314
<211> LENGTH: 5
<212> TYPE: PRT
<213> ORGANISM: Artificial Sequence
<220> FEATURE:
<223> OTHER INFORMATION: Synthetic

<400> SEQUENCE: 314

Ser Gly Gly Gly Phe
1               5

<210> SEQ ID NO 315
<211> LENGTH: 9
<212> TYPE: PRT
<213> ORGANISM: Artificial Sequence
<220> FEATURE:
<223> OTHER INFORMATION: Synthetic

<400> SEQUENCE: 315

Ser Ser Tyr Gly Glu Ile Met Asp Tyr
1               5

<210> SEQ ID NO 316
<211> LENGTH: 9
<212> TYPE: PRT
<213> ORGANISM: Artificial Sequence
<220> FEATURE:
<223> OTHER INFORMATION: Synthetic

<400> SEQUENCE: 316

Ser Ser Tyr Gly Glu Leu Met Asp Tyr
1               5

<210> SEQ ID NO 317
<211> LENGTH: 11
<212> TYPE: PRT
<213> ORGANISM: Artificial Sequence
<220> FEATURE:
<223> OTHER INFORMATION: Synthetic

<400> SEQUENCE: 317

Arg Ala Ser Gln Arg Ile Gly Thr Ser Ile His
1               5                   10

<210> SEQ ID NO 318
<211> LENGTH: 7
<212> TYPE: PRT
<213> ORGANISM: Artificial Sequence
<220> FEATURE:
<223> OTHER INFORMATION: Synthetic

<400> SEQUENCE: 318

Tyr Ala Ser Glu Ser Ile Ser
1               5
```

```
<210> SEQ ID NO 319
<211> LENGTH: 10
<212> TYPE: PRT
<213> ORGANISM: Artificial Sequence
<220> FEATURE:
<223> OTHER INFORMATION: Synthetic

<400> SEQUENCE: 319

Gln Gln Ser His Gly Trp Pro Phe Thr Phe
1               5                   10

<210> SEQ ID NO 320
<211> LENGTH: 117
<212> TYPE: PRT
<213> ORGANISM: Artificial Sequence
<220> FEATURE:
<223> OTHER INFORMATION: Synthetic

<400> SEQUENCE: 320

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Arg Leu Glu Trp Val
            35                  40                  45

Ala Ser Ile Ser Gly Gly Gly Phe Leu Tyr Tyr Leu Asp Ser Val Lys
            50                  55                  60

Gly Arg Phe Thr Ile Ser Arg Asp Asn Ala Arg Asn Ile Leu Tyr Leu
65                  70                  75                  80

His Met Thr Ser Leu Arg Ser Glu Asp Thr Ala Met Tyr Tyr Cys Ala
                85                  90                  95

Arg Ser Ser Tyr Gly Glu Ile Met Asp Tyr Trp Gly Gln Gly Thr Ser
                100                 105                 110

Val Thr Val Ser Ser
            115

<210> SEQ ID NO 321
<211> LENGTH: 117
<212> TYPE: PRT
<213> ORGANISM: Artificial Sequence
<220> FEATURE:
<223> OTHER INFORMATION: Synthetic

<400> SEQUENCE: 321

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Asp Met Ser Trp Val Arg Gln Thr Pro Glu Lys Arg Leu Glu Trp Val
            35                  40                  45

Ala Ser Ile Ser Gly Gly Gly Phe Leu Tyr Tyr Leu Asp Ser Val Lys
            50                  55                  60

Gly Arg Phe Thr Ile Ser Arg Asp Asn Ala Arg Asn Ile Leu Tyr Leu
65                  70                  75                  80

His Met Thr Ser Leu Arg Ser Glu Asp Thr Ala Met Tyr Tyr Cys Ala
                85                  90                  95

Arg Ser Ser Tyr Gly Glu Leu Met Asp Tyr Trp Gly Gln Gly Thr Ser
                100                 105                 110

Val Thr Val Ser Ser
            115
```

<210> SEQ ID NO 322
<211> LENGTH: 107
<212> TYPE: PRT
<213> ORGANISM: Artificial Sequence
<220> FEATURE:
<223> OTHER INFORMATION: Synthetic

<400> SEQUENCE: 322

```
Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Arg Ile Gly Thr Ser
            20                  25                  30

Ile His Trp Tyr Gln Gln Arg Thr Thr Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Val Ala Asp Tyr Tyr Cys Gln Gln Ser His Gly Trp Pro Phe
                85                  90                  95

Thr Phe Gly Gly Gly Thr Lys Leu Glu Ile Glu
            100                 105
```

<210> SEQ ID NO 323
<211> LENGTH: 324
<212> TYPE: PRT
<213> ORGANISM: Artificial Sequence
<220> FEATURE:
<223> OTHER INFORMATION: Synthetic

<400> SEQUENCE: 323

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
```

-continued

```
          195                200                205

Ile Glu Lys Thr Ile Ser Lys Thr Lys Gly Arg Pro Lys Ala Pro Gln
    210                215                220

Val Tyr Thr Ile Pro Pro Lys Glu Gln Met Ala Lys Asp Lys Val
225                230                235                240

Ser Leu Thr Cys Met Ile Thr Asp Phe Phe Pro Glu Asp Ile Thr Val
                245                250                255

Glu Trp Gln Trp Asn Gly Gln Pro Ala Glu Asn Tyr Lys Asn Thr Gln
                260                265                270

Pro Ile Met Asp Thr Asp Gly Ser Tyr Phe Val Tyr Ser Lys Leu Asn
                275                280                285

Val Gln Lys Ser Asn Trp Glu Ala Gly Asn Thr Phe Thr Cys Ser Val
    290                295                300

Leu His Glu Gly Leu His Asn His His Thr Glu Lys Ser Leu Ser His
305                310                315                320

Ser Pro Gly Lys
```

<210> SEQ ID NO 324
<211> LENGTH: 107
<212> TYPE: PRT
<213> ORGANISM: Artificial Sequence
<220> FEATURE:
<223> OTHER INFORMATION: Synthetic

<400> SEQUENCE: 324

```
Arg Ala Asp Ala Ala Pro Thr Val Ser Ile Phe Pro Pro Ser Ser Glu
1                5                10                15

Gln Leu Thr Ser Gly Gly Ala Ser Val Val Cys Phe Leu Asn Asn Phe
                20                25                30

Tyr Pro Lys Asp Ile Asn Val Lys Trp Lys Ile Asp Gly Ser Glu Arg
                35                40                45

Gln Asn Gly Val Leu Asn Ser Trp Thr Asp Gln Asp Ser Lys Asp Ser
    50                55                60

Thr Tyr Ser Met Ser Ser Thr Leu Thr Leu Thr Lys Asp Glu Tyr Glu
65                70                75                80

Arg His Asn Ser Tyr Thr Cys Glu Ala Thr His Lys Thr Ser Thr Ser
                85                90                95

Pro Ile Val Lys Ser Phe Asn Arg Asn Glu Cys
                100                105
```

<210> SEQ ID NO 325
<211> LENGTH: 107
<212> TYPE: PRT
<213> ORGANISM: Artificial Sequence
<220> FEATURE:
<223> OTHER INFORMATION: Synthetic

<400> SEQUENCE: 325

```
Asp Ile Gln Met Thr Gln Ser Pro Ser Ser Met Ser Ala Ser Leu Gly
1                5                10                15

Asp Arg Val Thr Ile Thr Cys Arg Ala Ser Gln Asp Ile Asn Ser Tyr
                20                25                30

Leu Ser Trp Phe Gln Gln Lys Pro Gly Lys Ser Pro Lys Thr Leu Ile
                35                40                45

Tyr Arg Ala Asn Arg Leu Val Asp Gly Val Pro Ser Arg Phe Ser Gly
    50                55                60

Ser Gly Ser Gly Thr Asp Tyr Thr Leu Thr Ile Ser Ser Leu Gln Tyr
```

-continued

```
65                70                75                80

Glu Asp Phe Gly Ile Tyr Tyr Cys Gln Gln Tyr Asp Glu Ser Pro Trp
                    85                90                95

Thr Phe Gly Gly Gly Thr Lys Leu Glu Ile Lys
            100               105

<210> SEQ ID NO 326
<211> LENGTH: 118
<212> TYPE: PRT
<213> ORGANISM: Artificial Sequence
<220> FEATURE:
<223> OTHER INFORMATION: Synthetic

<400> SEQUENCE: 326

Gln Ile Gln Leu Val Gln Ser Gly Pro Gly Leu Lys Lys Pro Gly Gly
1               5                10                15

Ser Val Arg Ile Ser Cys Ala Ala Ser Gly Tyr Thr Phe Thr Asn Tyr
                20                25                30

Gly Met Asn Trp Val Lys Gln Ala Pro Gly Lys Gly Leu Arg Trp Met
        35                40                45

Gly Trp Ile Asn Thr His Thr Gly Glu Pro Thr Tyr Ala Asp Asp Phe
    50                55                60

Lys Gly Arg Phe Thr Phe Ser Leu Asp Thr Ser Lys Ser Thr Ala Tyr
65                70                75                80

Leu Gln Ile Asn Ser Leu Arg Ala Glu Asp Thr Ala Thr Tyr Phe Cys
                85                90                95

Thr Arg Arg Gly Tyr Asp Trp Tyr Phe Asp Val Trp Gly Gln Gly Thr
            100               105               110

Thr Val Thr Val Ser Ser
        115

<210> SEQ ID NO 327
<211> LENGTH: 7
<212> TYPE: PRT
<213> ORGANISM: Artificial Sequence
<220> FEATURE:
<223> OTHER INFORMATION: Synthetic

<400> SEQUENCE: 327

Gly Tyr Thr Phe Thr Asn Tyr
1               5

<210> SEQ ID NO 328
<211> LENGTH: 6
<212> TYPE: PRT
<213> ORGANISM: Artificial Sequence
<220> FEATURE:
<223> OTHER INFORMATION: Synthetic

<400> SEQUENCE: 328

Asn Thr His Thr Gly Glu
1               5

<210> SEQ ID NO 329
<211> LENGTH: 9
<212> TYPE: PRT
<213> ORGANISM: Artificial Sequence
<220> FEATURE:
<223> OTHER INFORMATION: Synthetic

<400> SEQUENCE: 329

Arg Gly Tyr Asp Trp Tyr Phe Asp Val
```

1                 5

<210> SEQ ID NO 330
<211> LENGTH: 11
<212> TYPE: PRT
<213> ORGANISM: Artificial Sequence
<220> FEATURE:
<223> OTHER INFORMATION: Synthetic

<400> SEQUENCE: 330

Arg Ala Ser Gln Asp Ile Asn Ser Tyr Leu Ser
1               5                   10

<210> SEQ ID NO 331
<211> LENGTH: 7
<212> TYPE: PRT
<213> ORGANISM: Artificial Sequence
<220> FEATURE:
<223> OTHER INFORMATION: Synthetic

<400> SEQUENCE: 331

Arg Ala Asn Arg Leu Val Asp
1               5

<210> SEQ ID NO 332
<211> LENGTH: 9
<212> TYPE: PRT
<213> ORGANISM: Artificial Sequence
<220> FEATURE:
<223> OTHER INFORMATION: Synthetic

<400> SEQUENCE: 332

Gln Gln Tyr Asp Glu Ser Pro Trp Thr
1               5

<210> SEQ ID NO 333
<211> LENGTH: 107
<212> TYPE: PRT
<213> ORGANISM: Artificial Sequence
<220> FEATURE:
<223> OTHER INFORMATION: Synthetic

<400> SEQUENCE: 333

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Glu Ser Gly Val Pro Ser Arg Phe Ser Gly
    50                  55                  60

Ser Gly Ser Gly Thr Asp Tyr Thr Leu Thr Ile Ser Ser Leu Gln Tyr
65                  70                  75                  80

Glu Asp Phe Gly Ile Tyr Tyr Cys Gln Gln Tyr Asp Glu Ser Pro Trp
                85                  90                  95

Thr Phe Gly Gly Gly Thr Lys Leu Glu Ile Lys
            100                 105

<210> SEQ ID NO 334
<211> LENGTH: 119
<212> TYPE: PRT
<213> ORGANISM: Artificial Sequence
<220> FEATURE:
<223> OTHER INFORMATION: Synthetic

<400> SEQUENCE: 334

Glu Ile Gln Leu Val Gln Ser Gly Gly Gly Leu Val Lys Pro Gly Gly
1               5                   10                  15

Ser Val Arg Ile Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Met
        35                  40                  45

Gly Trp Ile Asn Thr His Tyr Gly Glu Pro Thr Tyr Ala Asp Ser Phe
    50                  55                  60

Lys Gly Thr Arg Thr Phe Ser Leu Asp Asp Ser Lys Asn Thr Ala Tyr
65                  70                  75                  80

Leu Gln Ile Asn Ser Leu Arg Ala Glu Asp Thr Ala Val Tyr Phe Cys
                85                  90                  95

Thr Arg Arg Gly Tyr Asp Trp Tyr Phe Asp Val Trp Gly Gln Gly Gly
            100                 105                 110

Thr Thr Val Thr Val Ser Ser
        115

<210> SEQ ID NO 335
<211> LENGTH: 7
<212> TYPE: PRT
<213> ORGANISM: Artificial Sequence
<220> FEATURE:
<223> OTHER INFORMATION: Synthetic

<400> SEQUENCE: 335

Gly Tyr Thr Phe Thr Asn Tyr
1               5

<210> SEQ ID NO 336
<211> LENGTH: 6
<212> TYPE: PRT
<213> ORGANISM: Artificial Sequence
<220> FEATURE:
<223> OTHER INFORMATION: Synthetic

<400> SEQUENCE: 336

Asn Thr His Tyr Gly Glu
1               5

<210> SEQ ID NO 337
<211> LENGTH: 10
<212> TYPE: PRT
<213> ORGANISM: Artificial Sequence
<220> FEATURE:
<223> OTHER INFORMATION: Synthetic

<400> SEQUENCE: 337

Arg Arg Gly Tyr Asp Trp Tyr Phe Asp Val
1               5                   10

<210> SEQ ID NO 338
<211> LENGTH: 11
<212> TYPE: PRT
<213> ORGANISM: Artificial Sequence
<220> FEATURE:
<223> OTHER INFORMATION: Synthetic

<400> SEQUENCE: 338

Arg Ala Ser Gln Asp Ile Asn Ser Tyr Leu Ser
1               5                   10

```
<210> SEQ ID NO 339
<211> LENGTH: 7
<212> TYPE: PRT
<213> ORGANISM: Artificial Sequence
<220> FEATURE:
<223> OTHER INFORMATION: Synthetic

<400> SEQUENCE: 339

Arg Ala Asn Arg Leu Glu Ser
1               5

<210> SEQ ID NO 340
<211> LENGTH: 9
<212> TYPE: PRT
<213> ORGANISM: Artificial Sequence
<220> FEATURE:
<223> OTHER INFORMATION: Synthetic

<400> SEQUENCE: 340

Gln Gln Tyr Asp Glu Ser Pro Trp Thr
1               5

<210> SEQ ID NO 341
<211> LENGTH: 9
<212> TYPE: PRT
<213> ORGANISM: Artificial Sequence
<220> FEATURE:
<223> OTHER INFORMATION: Synthetic

<400> SEQUENCE: 341

Gly Tyr Ser Ile Thr Ser Gly Tyr Tyr
1               5

<210> SEQ ID NO 342
<211> LENGTH: 7
<212> TYPE: PRT
<213> ORGANISM: Artificial Sequence
<220> FEATURE:
<223> OTHER INFORMATION: Synthetic

<400> SEQUENCE: 342

Ile Ser Tyr Ser Gly Phe Thr
1               5

<210> SEQ ID NO 343
<211> LENGTH: 11
<212> TYPE: PRT
<213> ORGANISM: Artificial Sequence
<220> FEATURE:
<223> OTHER INFORMATION: Synthetic

<400> SEQUENCE: 343

Ala Gly Asp Arg Thr Gly Ser Trp Phe Ala Tyr
1               5                   10

<210> SEQ ID NO 344
<211> LENGTH: 6
<212> TYPE: PRT
<213> ORGANISM: Artificial Sequence
<220> FEATURE:
<223> OTHER INFORMATION: Synthetic

<400> SEQUENCE: 344

Gln Asp Ile Ser Asn Tyr
1               5
```

```
<210> SEQ ID NO 345
<211> LENGTH: 3
<212> TYPE: PRT
<213> ORGANISM: Artificial Sequence
<220> FEATURE:
<223> OTHER INFORMATION: Synthetic

<400> SEQUENCE: 345

Ala Thr Ser
1

<210> SEQ ID NO 346
<211> LENGTH: 9
<212> TYPE: PRT
<213> ORGANISM: Artificial Sequence
<220> FEATURE:
<223> OTHER INFORMATION: Synthetic

<400> SEQUENCE: 346

Leu Gln Tyr Ala Ser Tyr Pro Phe Thr
1               5

<210> SEQ ID NO 347
<211> LENGTH: 8
<212> TYPE: PRT
<213> ORGANISM: Artificial Sequence
<220> FEATURE:
<223> OTHER INFORMATION: Synthetic

<400> SEQUENCE: 347

Gly Tyr Ile Phe Thr Asn Tyr Gly
1               5

<210> SEQ ID NO 348
<211> LENGTH: 8
<212> TYPE: PRT
<213> ORGANISM: Artificial Sequence
<220> FEATURE:
<223> OTHER INFORMATION: Synthetic

<400> SEQUENCE: 348

Ile Asn Thr Tyr Asn Gly Glu Pro
1               5

<210> SEQ ID NO 349
<211> LENGTH: 11
<212> TYPE: PRT
<213> ORGANISM: Artificial Sequence
<220> FEATURE:
<223> OTHER INFORMATION: Synthetic

<400> SEQUENCE: 349

Ala Arg Gly Asp Tyr Tyr Gly Tyr Glu Asp Tyr
1               5                   10

<210> SEQ ID NO 350
<211> LENGTH: 6
<212> TYPE: PRT
<213> ORGANISM: Artificial Sequence
<220> FEATURE:
<223> OTHER INFORMATION: Synthetic

<400> SEQUENCE: 350

Gln Gly Ile Ser Asn Tyr
1               5

<210> SEQ ID NO 351
```

```
<211> LENGTH: 3
<212> TYPE: PRT
<213> ORGANISM: Artificial Sequence
<220> FEATURE:
<223> OTHER INFORMATION: Synthetic

<400> SEQUENCE: 351

Tyr Thr Ser
1

<210> SEQ ID NO 352
<211> LENGTH: 9
<212> TYPE: PRT
<213> ORGANISM: Artificial Sequence
<220> FEATURE:
<223> OTHER INFORMATION: Synthetic

<400> SEQUENCE: 352

Gln Gln Tyr Ser Lys Leu Pro Trp Thr
1               5

<210> SEQ ID NO 353
<211> LENGTH: 9
<212> TYPE: PRT
<213> ORGANISM: Artificial Sequence
<220> FEATURE:
<223> OTHER INFORMATION: Synthetic

<400> SEQUENCE: 353

Phe Ser Leu Ser Thr Ser Gly Met Gly
1               5

<210> SEQ ID NO 354
<211> LENGTH: 5
<212> TYPE: PRT
<213> ORGANISM: Artificial Sequence
<220> FEATURE:
<223> OTHER INFORMATION: Synthetic

<400> SEQUENCE: 354

Trp Trp Asp Asp Asp
1               5

<210> SEQ ID NO 355
<211> LENGTH: 10
<212> TYPE: PRT
<213> ORGANISM: Artificial Sequence
<220> FEATURE:
<223> OTHER INFORMATION: Synthetic

<400> SEQUENCE: 355

Arg Arg Ala Thr Gly Thr Gly Phe Asp Tyr
1               5                   10

<210> SEQ ID NO 356
<211> LENGTH: 6
<212> TYPE: PRT
<213> ORGANISM: Artificial Sequence
<220> FEATURE:
<223> OTHER INFORMATION: Synthetic

<400> SEQUENCE: 356

Gln Asp Val Gly Thr Ala
1               5

<210> SEQ ID NO 357
<211> LENGTH: 7
```

```
<212> TYPE: PRT
<213> ORGANISM: Artificial Sequence
<220> FEATURE:
<223> OTHER INFORMATION: Synthetic

<400> SEQUENCE: 357

Trp Thr Ser Thr Arg His Thr
1               5

<210> SEQ ID NO 358
<211> LENGTH: 6
<212> TYPE: PRT
<213> ORGANISM: Artificial Sequence
<220> FEATURE:
<223> OTHER INFORMATION: Synthetic

<400> SEQUENCE: 358

Tyr Asn Ser Tyr Asn Thr
1               5

<210> SEQ ID NO 359
<211> LENGTH: 120
<212> TYPE: PRT
<213> ORGANISM: Artificial Sequence
<220> FEATURE:
<223> OTHER INFORMATION: Synthetic

<400> SEQUENCE: 359

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Ala Pro Gly Lys Gly Leu Glu
            35                  40                  45

Trp Val Ala His Ile Trp Trp Asp Asp Asp Val Tyr Tyr Asn Pro Ser
        50                  55                  60

Leu Lys Ser Arg Leu Thr Ile Thr Lys Asp Ala Ser Lys Asp Gln Val
65                  70                  75                  80

Ser Leu Lys Leu Ser Ser Val Thr Ala Ala Asp Thr Ala Val Tyr Tyr
                85                  90                  95

Cys Val Arg Arg Arg Ala Thr Gly Thr Gly Phe Asp Tyr Trp Gly Gln
            100                 105                 110

Gly Thr Leu Val Thr Val Ser Ser
            115                 120

<210> SEQ ID NO 360
<211> LENGTH: 106
<212> TYPE: PRT
<213> ORGANISM: Artificial Sequence
<220> FEATURE:
<223> OTHER INFORMATION: Synthetic

<400> SEQUENCE: 360

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
                20                  25                  30

Val Ala Trp Tyr Gln Gln Lys Pro Asp Gln Ser Pro Lys Leu Leu Ile
            35                  40                  45

Tyr Trp Thr Ser Thr Arg His Thr Gly Val Pro Asp Arg Phe Thr Gly
        50                  55                  60
```

```
Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys
                100                 105
```

```
<210> SEQ ID NO 361
<211> LENGTH: 120
<212> TYPE: PRT
<213> ORGANISM: Artificial Sequence
<220> FEATURE:
<223> OTHER INFORMATION: Synthetic

<400> SEQUENCE: 361

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
                35                  40                  45

Ala Val Ile Ser Glu Asn Gly Ser Asp Thr Tyr Tyr Ala Asp Ser Val
        50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
                100                 105                 110

Gly Thr Leu Val Thr Val Ser Ser
        115                 120
```

```
<210> SEQ ID NO 362
<211> LENGTH: 109
<212> TYPE: PRT
<213> ORGANISM: Artificial Sequence
<220> FEATURE:
<223> OTHER INFORMATION: Synthetic

<400> SEQUENCE: 362

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
                20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
                100                 105
```

```
<210> SEQ ID NO 363
<211> LENGTH: 438
<212> TYPE: PRT
<213> ORGANISM: Homo sapiens
```

-continued

<400> SEQUENCE: 363

```
Met Val Cys Ser Gln Ser Trp Gly Arg Ser Ser Lys Gln Trp Glu Asp
1               5                   10                  15

Pro Ser Gln Ala Ser Lys Val Cys Gln Arg Leu Asn Cys Gly Val Pro
                20                  25                  30

Leu Ser Leu Gly Pro Phe Leu Val Thr Tyr Thr Pro Gln Ser Ser Ile
            35                  40                  45

Ile Cys Tyr Gly Gln Leu Gly Ser Phe Ser Asn Cys Ser His Ser Arg
        50                  55                  60

Asn Asp Met Cys His Ser Leu Gly Leu Thr Cys Leu Glu Pro Gln Lys
65                  70                  75                  80

Thr Thr Pro Pro Thr Thr Arg Pro Pro Thr Thr Thr Pro Glu Pro
                85                  90                  95

Thr Ala Pro Pro Arg Leu Gln Leu Val Ala Gln Ser Gly Gly Gln His
            100                 105                 110

Cys Ala Gly Val Val Glu Phe Tyr Ser Gly Ser Leu Gly Gly Thr Ile
            115                 120                 125

Ser Tyr Glu Ala Gln Asp Lys Thr Gln Asp Leu Glu Asn Phe Leu Cys
        130                 135                 140

Asn Asn Leu Gln Cys Gly Ser Phe Leu Lys His Leu Pro Glu Thr Glu
145                 150                 155                 160

Ala Gly Arg Ala Gln Asp Pro Gly Glu Pro Arg Glu His Gln Pro Leu
                165                 170                 175

Pro Ile Gln Trp Lys Ile Gln Asn Ser Ser Cys Thr Ser Leu Glu His
            180                 185                 190

Cys Phe Arg Lys Ile Lys Pro Gln Lys Ser Gly Arg Val Leu Ala Leu
            195                 200                 205

Leu Cys Ser Gly Phe Gln Pro Lys Val Gln Ser Arg Leu Val Gly Gly
        210                 215                 220

Ser Ser Ile Cys Glu Gly Thr Val Glu Val Arg Gln Gly Ala Gln Trp
225                 230                 235                 240

Ala Ala Leu Cys Asp Ser Ser Ser Ala Arg Ser Ser Leu Arg Trp Glu
                245                 250                 255

Glu Val Cys Arg Glu Gln Gln Cys Gly Ser Val Asn Ser Tyr Arg Val
            260                 265                 270

Leu Asp Ala Gly Asp Pro Thr Ser Arg Gly Leu Phe Cys Pro His Gln
        275                 280                 285

Lys Leu Ser Gln Cys His Glu Leu Trp Glu Arg Asn Ser Tyr Cys Lys
        290                 295                 300

Lys Val Phe Val Thr Cys Gln Asp Pro Asn Pro Ala Gly Leu Ala Ala
305                 310                 315                 320

Gly Thr Val Ala Ser Ile Ile Leu Ala Leu Val Leu Leu Val Val Leu
            325                 330                 335

Leu Val Val Cys Gly Pro Leu Ala Tyr Lys Lys Leu Val Lys Lys Phe
            340                 345                 350

Arg Gln Lys Lys Gln Arg Gln Trp Ile Gly Pro Thr Gly Met Asn Gln
        355                 360                 365

Asn Met Ser Phe His Arg Asn His Thr Ala Thr Val Arg Ser His Ala
        370                 375                 380

Glu Asn Pro Thr Ala Ser His Val Asp Asn Glu Tyr Ser Gln Pro Pro
385                 390                 395                 400

Arg Asn Ser His Leu Ser Ala Tyr Pro Ala Leu Glu Gly Ala Leu His
```

-continued

```
                    405                 410                 415

Arg Ser Ser Met Gln Pro Asp Asn Ser Ser Asp Ser Asp Tyr Asp Leu
            420                 425                 430

His Gly Ala Gln Arg Leu
        435

<210> SEQ ID NO 364
<211> LENGTH: 450
<212> TYPE: PRT
<213> ORGANISM: Artificial Sequence
<220> FEATURE:
<223> OTHER INFORMATION: Synthetic

<400> SEQUENCE: 364

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

-continued

```
                325             330             335
Lys Thr Ile Ser Lys Ala Lys Gly Gln Pro Arg Glu Pro Gln Val Tyr
        340             345             350

Thr Leu Pro Pro Ser Arg Glu Glu Met Thr Lys Asn Gln Val Ser Leu
        355             360             365

Thr Cys Leu Val Lys Gly Phe Tyr Pro Ser Asp Ile Ala Val Glu Trp
    370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

```
<210> SEQ ID NO 365
<211> LENGTH: 450
<212> TYPE: PRT
<213> ORGANISM: Artificial Sequence
<220> FEATURE:
<223> OTHER INFORMATION: Synthetic

<400> SEQUENCE: 365
```

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Asn Ile Lys Asp Thr
        20              25              30

Tyr Ile His Trp Val Arg Gln Ala Pro Gly Lys Gly Leu Glu Trp Val
        35              40              45

Ala Arg Ile Tyr Pro Thr Asn Gly Tyr Thr Arg Tyr Ala Asp Ser Val
    50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
            85              90              95

Ser Arg Trp Gly Gly Asp Gly Phe Tyr Ala Met Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
```

```
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Cys Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 366
<211> LENGTH: 450
<212> TYPE: PRT
<213> ORGANISM: Artificial Sequence
<220> FEATURE:
<223> OTHER INFORMATION: Synthetic

<400> SEQUENCE: 366

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

-continued

```
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 367
<211> LENGTH: 450
<212> TYPE: PRT
<213> ORGANISM: Artificial Sequence
<220> FEATURE:
<223> OTHER INFORMATION: Synthetic

<400> SEQUENCE: 367

Glu Val Gln Leu Val Glu Ser Gly Gly Gly Leu Val Gln Pro Gly Gly
1                   5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
```

-continued

```
              35                  40                  45
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Cys Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450
```

```
<210> SEQ ID NO 368
<211> LENGTH: 120
<212> TYPE: PRT
<213> ORGANISM: Artificial Sequence
<220> FEATURE:
<223> OTHER INFORMATION: Synthetic

<400> SEQUENCE: 368

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 369
<211> LENGTH: 214
<212> TYPE: PRT
<213> ORGANISM: Artificial Sequence
<220> FEATURE:
<223> OTHER INFORMATION: Synthetic

<400> SEQUENCE: 369

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

-continued

```
              180             185             190
Ala Cys Glu Val Thr His Gln Gly Leu Ser Ser Pro Val Thr Lys Ser
          195             200             205

Phe Asn Arg Gly Glu Cys
          210

<210> SEQ ID NO 370
<211> LENGTH: 107
<212> TYPE: PRT
<213> ORGANISM: Artificial Sequence
<220> FEATURE:
<223> OTHER INFORMATION: Synthetic

<400> SEQUENCE: 370

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100             105

<210> SEQ ID NO 371
<211> LENGTH: 450
<212> TYPE: PRT
<213> ORGANISM: Artificial Sequence
<220> FEATURE:
<223> OTHER INFORMATION: Synthetic

<400> SEQUENCE: 371

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Ser Asn Val Asn Tyr Ala Gln Lys Phe
    50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100             105             110

Gly Thr Leu Val Thr Val Ser Ser Ala Ser Thr Lys Gly Pro Ser Val
            115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160
```

```
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 372
<211> LENGTH: 450
<212> TYPE: PRT
<213> ORGANISM: Artificial Sequence
<220> FEATURE:
<223> OTHER INFORMATION: Synthetic

<400> SEQUENCE: 372

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
            35                  40                  45

Gly Gly Ile Ser Pro Gly Asp Ser Asn Val Asn Tyr Ala Gln Lys Phe
    50                  55                  60
```

-continued

```
Gln Gly Arg Val Thr Leu Thr Ile Asp Thr Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100             105             110

Gly Thr Leu Val Thr Val Ser Ser Ala Ser Thr Lys Gly Pro Ser Val
        115             120             125

Phe Pro Leu Ala Pro Ser Ser Lys Ser Thr Ser Gly Gly Thr Ala Ala
    130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Gln Thr Tyr Ile Cys Asn Val Asn His Lys
            195             200             205

Pro Ser Asn Thr Lys Val Asp Lys Lys Val Glu Pro Lys Ser Cys Asp
    210             215             220

Lys Thr His Thr Cys Pro Pro Cys Pro Ala Pro Glu Leu Leu Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Cys Val Ser His Glu
            260             265             270

Asp Pro Glu Val Lys Phe Asn Trp Tyr Val Asp Gly Val Glu Val His
    275             280             285

Asn Ala Lys Thr Lys Pro Arg Glu Glu Gln Tyr Asn Ser Thr Tyr Arg
    290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
            370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

<210> SEQ ID NO 373
<211> LENGTH: 450
<212> TYPE: PRT

-continued

```
<213> ORGANISM: Artificial Sequence
<220> FEATURE:
<223> OTHER INFORMATION: Synthetic

<400> SEQUENCE: 373

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
                20                  25                  30

Asp Ile Asn Trp Leu Arg Gln Ala Pro Gly Gln Gly Leu Glu Trp Met
            35                  40                  45

Gly Gly Ile Ser Pro Gly Asp Ser Asn Val Asn Tyr Ala Gln Lys Phe
        50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
        435                 440                 445
Gly Lys
    450
```

```
<210> SEQ ID NO 374
<211> LENGTH: 450
<212> TYPE: PRT
<213> ORGANISM: Artificial Sequence
<220> FEATURE:
<223> OTHER INFORMATION: Synthetic

<400> SEQUENCE: 374

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Tyr Phe
                20                  25                  30
Asp Ile Asn Trp Leu Arg Gln Ala Pro Gly Gln Gly Leu Glu Trp Met
            35                  40                  45
Gly Gly Ile Ser Pro Gly Asp Ser Asn Val Asn Tyr Ala Gln Lys Phe
        50                  55                  60
Gln Gly Arg Val Thr Leu Thr Ile Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Gly Asn Phe Pro Tyr Tyr Ala Met Asp Ser Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
        210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Cys Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
```

```
            290             295             300
Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
                325             330             335

Lys Thr Ile Ser Lys Ala Lys Gly Gln Pro Arg Glu Pro Gln Val Tyr
                340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
            370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
                405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
            435             440             445

Gly Lys
    450
```

```
<210> SEQ ID NO 375
<211> LENGTH: 120
<212> TYPE: PRT
<213> ORGANISM: Artificial Sequence
<220> FEATURE:
<223> OTHER INFORMATION: Synthetic

<400> SEQUENCE: 375

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Tyr Phe
                20              25              30

Asp Ile Asn Trp Leu Arg Gln Ala Pro Gly Gln Gly Leu Glu Trp Met
            35              40              45

Gly Gly Ile Ser Pro Gly Asp Ser Asn Val Asn Tyr Ala Gln Lys Phe
        50              55              60

Gln Gly Arg Val Thr Leu Thr Ile Asp Thr Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg Asp Gly Asn Phe Pro Tyr Tyr Ala Met Asp Ser Trp Gly Gln
            100             105             110

Gly Thr Leu Val Thr Val Ser Ser
        115             120
```

```
<210> SEQ ID NO 376
<211> LENGTH: 218
<212> TYPE: PRT
<213> ORGANISM: Artificial Sequence
<220> FEATURE:
<223> OTHER INFORMATION: Synthetic

<400> SEQUENCE: 376

Asp Ile Val Met Thr Gln Ser Pro Leu Ser Leu Pro Val Thr Pro Gly
1               5               10              15
```

-continued

```
Glu Pro Ala Ser Ile Ser Cys Arg Ser Ser Gln Ser Leu Val His Ser
        20                  25                  30

Ser Gly Gln Thr Tyr Leu His Trp Tyr Gln Gln Lys Pro Gly Gln Ser
        35                  40                  45

Pro Gln Leu Leu Ile Tyr Thr Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ser Gln Ser
                85                  90                  95

Thr His Val Pro Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215
```

```
<210> SEQ ID NO 377
<211> LENGTH: 111
<212> TYPE: PRT
<213> ORGANISM: Artificial Sequence
<220> FEATURE:
<223> OTHER INFORMATION: Synthetic

<400> SEQUENCE: 377
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
        20                  25                  30

Ser Gly Gln Thr Tyr Leu His Trp Tyr Gln Gln Lys Pro Gly Gln Ser
        35                  40                  45

Pro Gln Leu Leu Ile Tyr Thr Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ser Gln Ser
                85                  90                  95

Thr His Val Pro Thr Phe Gly Gly Gly Thr Lys Val Glu Ile Lys
            100                 105                 110
```

```
<210> SEQ ID NO 378
<211> LENGTH: 7
<212> TYPE: PRT
<213> ORGANISM: Artificial Sequence
<220> FEATURE:
<223> OTHER INFORMATION: Synthetic

<400> SEQUENCE: 378
```

-continued

```
Gly Tyr Thr Phe Thr Tyr Phe
1               5

<210> SEQ ID NO 379
<211> LENGTH: 17
<212> TYPE: PRT
<213> ORGANISM: Artificial Sequence
<220> FEATURE:
<223> OTHER INFORMATION: Synthetic

<400> SEQUENCE: 379

Gly Ile Ser Pro Gly Asp Ser Asn Val Asn Tyr Ala Gln Lys Phe Gln
1               5                   10                  15

Gly

<210> SEQ ID NO 380
<211> LENGTH: 11
<212> TYPE: PRT
<213> ORGANISM: Artificial Sequence
<220> FEATURE:
<223> OTHER INFORMATION: Synthetic

<400> SEQUENCE: 380

Asp Gly Asn Phe Pro Tyr Tyr Ala Met Asp Ser
1               5                   10

<210> SEQ ID NO 381
<211> LENGTH: 16
<212> TYPE: PRT
<213> ORGANISM: Artificial Sequence
<220> FEATURE:
<223> OTHER INFORMATION: Synthetic

<400> SEQUENCE: 381

Arg Ser Ser Gln Ser Leu Val His Ser Ser Gly Gln Thr Tyr Leu His
1               5                   10                  15

<210> SEQ ID NO 382
<211> LENGTH: 7
<212> TYPE: PRT
<213> ORGANISM: Artificial Sequence
<220> FEATURE:
<223> OTHER INFORMATION: Synthetic

<400> SEQUENCE: 382

Thr Val Ser Asn Arg Ala Ser
1               5

<210> SEQ ID NO 383
<211> LENGTH: 8
<212> TYPE: PRT
<213> ORGANISM: Artificial Sequence
<220> FEATURE:
<223> OTHER INFORMATION: Synthetic

<400> SEQUENCE: 383

Ser Gln Ser Thr His Val Pro Thr
1               5

<210> SEQ ID NO 384
<211> LENGTH: 450
<212> TYPE: PRT
<213> ORGANISM: Artificial Sequence
<220> FEATURE:
<223> OTHER INFORMATION: Synthetic
```

<400> SEQUENCE: 384

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

-continued

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 385
<211> LENGTH: 450
<212> TYPE: PRT
<213> ORGANISM: Artificial Sequence
<220> FEATURE:
<223> OTHER INFORMATION: Synthetic

<400> SEQUENCE: 385

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Cys Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 386
<211> LENGTH: 450
<212> TYPE: PRT
<213> ORGANISM: Artificial Sequence
<220> FEATURE:
<223> OTHER INFORMATION: Synthetic

<400> SEQUENCE: 386

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220
```

```
Lys Thr His Thr Cys Pro Pro Cys Pro Ala Pro Glu Ala Ala Gly Gly
225             230             235             240

Pro Ser Val Phe Leu Phe Pro Pro Lys Pro Lys Asp Thr Leu Met Ile
            245             250             255

Ser Arg Thr Pro Glu Val Thr Cys Val Val Val Asp Val Ser His Glu
            260             265             270

Asp Pro Glu Val Lys Phe Asn Trp Tyr Val Asp Gly Val Glu Val His
            275             280             285

Asn Ala Lys Thr Lys Pro Arg Glu Glu Gln Tyr Asn Ser Thr Tyr Arg
        290             295             300

Val Val Ser Val Leu Thr Val Leu His Gln Asp Trp Leu Asn Gly Lys
305             310             315             320

Glu Tyr Lys Cys Lys Val Ser Asn Lys Ala Leu Pro Ala Pro Ile Glu
            325             330             335

Lys Thr Ile Ser Lys Ala Lys Gly Gln Pro Arg Glu Pro Gln Val Tyr
            340             345             350

Thr Leu Pro Pro Ser Arg Glu Glu Met Thr Lys Asn Gln Val Ser Leu
            355             360             365

Thr Cys Leu Val Lys Gly Phe Tyr Pro Ser Asp Ile Ala Val Glu Trp
        370             375             380

Glu Ser Asn Gly Gln Pro Glu Asn Asn Tyr Lys Thr Thr Pro Pro Val
385             390             395             400

Leu Asp Ser Asp Gly Ser Phe Phe Leu Tyr Ser Lys Leu Thr Val Asp
            405             410             415

Lys Ser Arg Trp Gln Gln Gly Asn Val Phe Ser Cys Ser Val Met His
            420             425             430

Glu Ala Leu His Asn His Tyr Thr Gln Lys Ser Leu Ser Leu Ser Pro
        435             440             445

Gly Lys
    450
```

<210> SEQ ID NO 387
<211> LENGTH: 450
<212> TYPE: PRT
<213> ORGANISM: Artificial Sequence
<220> FEATURE:
<223> OTHER INFORMATION: Synthetic

<400> SEQUENCE: 387

```
Glu Val Gln Leu Val Glu Ser Gly Gly Gly Leu Val Gln Pro Gly Gly
1               5               10              15

Ser Leu Arg Leu Ser Cys Ala Ala Ser Gly Phe Asn Ile Lys Asp Thr
            20              25              30

Tyr Ile His Trp Val Arg Gln Ala Pro Gly Lys Gly Leu Glu Trp Val
            35              40              45

Ala Arg Ile Tyr Pro Thr Asn Gly Tyr Thr Arg Tyr Ala Asp Ser Val
        50              55              60

Lys Gly Arg Phe Thr Ile Ser Ala Asp Thr Ser Lys Asn Thr Ala Tyr
65              70              75              80

Leu Gln Met Asn Ser Leu Arg Ala Glu Asp Thr Ala Val Tyr Tyr Cys
                85              90              95

Ser Arg Trp Gly Gly Asp Gly Phe Tyr Ala Met Asp Tyr Trp Gly Gln
            100             105             110

Gly Thr Leu Val Thr Val Ser Ser Ala Ser Thr Lys Gly Pro Ser Val
            115             120             125
```

```
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Ala Ala Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Cys Val Ser His Glu
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
                355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
Gly Lys
    450

<210> SEQ ID NO 388
<211> LENGTH: 120
<212> TYPE: PRT
<213> ORGANISM: Artificial Sequence
<220> FEATURE:
<223> OTHER INFORMATION: Synthetic

<400> SEQUENCE: 388

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
        115                 120
```

```
<210> SEQ ID NO 389
<211> LENGTH: 214
<212> TYPE: PRT
<213> ORGANISM: Artificial Sequence
<220> FEATURE:
<223> OTHER INFORMATION: Synthetic

<400> SEQUENCE: 389
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
        20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210
```

```
<210> SEQ ID NO 390
<211> LENGTH: 107
<212> TYPE: PRT
<213> ORGANISM: Artificial Sequence
<220> FEATURE:
<223> OTHER INFORMATION: Synthetic
```

-continued

<400> SEQUENCE: 390

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 391
<211> LENGTH: 450
<212> TYPE: PRT
<213> ORGANISM: Artificial Sequence
<220> FEATURE:
<223> OTHER INFORMATION: Synthetic

<400> SEQUENCE: 391

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
            20                  25                  30

Asp Ile Asn Trp Leu Arg Gln Ala Pro Gly Gln Gly Leu Glu Trp Met
        35                  40                  45

Gly Gly Ile Ser Pro Gly Asp Ser Asn Val Asn Tyr Ala Gln Lys Phe
    50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile

-continued

```
                    245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                    325                 330                 335

Lys Thr Ile Ser Lys Ala Lys Gly Gln Pro Arg Glu Pro Gln Val Tyr
                    340                 345                 350

Thr Leu Pro Pro Ser Arg Glu Glu Met Thr Lys Asn Gln Val Ser Leu
                    355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                    420                 425                 430

Glu Ala Leu His Asn His Tyr Thr Gln Lys Ser Leu Ser Leu Ser Pro
                    435                 440                 445

Gly Lys
    450
```

```
<210> SEQ ID NO 392
<211> LENGTH: 450
<212> TYPE: PRT
<213> ORGANISM: Artificial Sequence
<220> FEATURE:
<223> OTHER INFORMATION: Synthetic

<400> SEQUENCE: 392

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
                20                  25                  30

Asp Ile Asn Trp Leu Arg Gln Ala Pro Gly Gln Gly Leu Glu Trp Met
            35                  40                  45

Gly Gly Ile Ser Pro Gly Asp Ser Asn Val Asn Tyr Ala Gln Lys Phe
        50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
```

```
145              150              155              160

Trp Asn Ser Gly Ala Leu Thr Ser Gly Val His Thr Phe Pro Ala Val
             165              170              175

Leu Gln Ser Ser Gly Leu Tyr Ser Leu Ser Ser Val Val Thr Val Pro
             180              185              190

Ser Ser Ser Leu Gly Thr Gln Thr Tyr Ile Cys Asn Val Asn His Lys
             195              200              205

Pro Ser Asn Thr Lys Val Asp Lys Lys Val Glu Pro Lys Ser Cys Asp
    210              215              220

Lys Thr His Thr Cys Pro Pro Cys Pro Ala Pro Glu Leu Leu Gly Gly
225              230              235              240

Pro Ser Val Phe Leu Phe Pro Pro Lys Pro Lys Asp Thr Leu Met Ile
             245              250              255

Ser Arg Thr Pro Glu Val Thr Cys Val Val Val Cys Val Ser His Glu
             260              265              270

Asp Pro Glu Val Lys Phe Asn Trp Tyr Val Asp Gly Val Glu Val His
             275              280              285

Asn Ala Lys Thr Lys Pro Arg Glu Glu Gln Tyr Asn Ser Thr Tyr Arg
    290              295              300

Val Val Ser Val Leu Thr Val Leu His Gln Asp Trp Leu Asn Gly Lys
305              310              315              320

Glu Tyr Lys Cys Lys Val Ser Asn Lys Ala Leu Pro Ala Pro Ile Glu
             325              330              335

Lys Thr Ile Ser Lys Ala Lys Gly Gln Pro Arg Glu Pro Gln Val Tyr
             340              345              350

Thr Leu Pro Pro Ser Arg Glu Glu Met Thr Lys Asn Gln Val Ser Leu
             355              360              365

Thr Cys Leu Val Lys Gly Phe Tyr Pro Ser Asp Ile Ala Val Glu Trp
    370              375              380

Glu Ser Asn Gly Gln Pro Glu Asn Asn Tyr Lys Thr Thr Pro Pro Val
385              390              395              400

Leu Asp Ser Asp Gly Ser Phe Phe Leu Tyr Ser Lys Leu Thr Val Asp
             405              410              415

Lys Ser Arg Trp Gln Gln Gly Asn Val Phe Ser Cys Ser Val Met His
             420              425              430

Glu Ala Leu His Asn His Tyr Thr Gln Lys Ser Leu Ser Leu Ser Pro
             435              440              445

Gly Lys
    450

<210> SEQ ID NO 393
<211> LENGTH: 450
<212> TYPE: PRT
<213> ORGANISM: Artificial Sequence
<220> FEATURE:
<223> OTHER INFORMATION: Synthetic

<400> SEQUENCE: 393

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Tyr Phe
             20              25              30

Asp Ile Asn Trp Leu Arg Gln Ala Pro Gly Gln Gly Leu Glu Trp Met
             35              40              45

Gly Gly Ile Ser Pro Gly Asp Ser Asn Val Asn Tyr Ala Gln Lys Phe
```

-continued

```
       50                 55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450
```

<210> SEQ ID NO 394

<211> LENGTH: 450
<212> TYPE: PRT
<213> ORGANISM: Artificial Sequence
<220> FEATURE:
<223> OTHER INFORMATION: Synthetic

<400> SEQUENCE: 394

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
                20                  25                  30

Asp Ile Asn Trp Leu Arg Gln Ala Pro Gly Gln Gly Leu Glu Trp Met
            35                  40                  45

Gly Gly Ile Ser Pro Gly Asp Ser Asn Val Asn Tyr Ala Gln Lys Phe
        50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Cys Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 395
<211> LENGTH: 120
<212> TYPE: PRT
<213> ORGANISM: Artificial Sequence
<220> FEATURE:
<223> OTHER INFORMATION: Synthetic

<400> SEQUENCE: 395

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Phe
                20                  25                  30

Asp Ile Asn Trp Leu Arg Gln Ala Pro Gly Gln Gly Leu Glu Trp Met
            35                  40                  45

Gly Gly Ile Ser Pro Gly Asp Ser Asn Val Asn Tyr Ala Gln Lys Phe
        50                  55                  60

Gln Gly Arg Val Thr Leu Thr Ile Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Asn Phe Pro Tyr Tyr Ala Met Asp Ser Trp Gly Gln
            100                 105                 110

Gly Thr Leu Val Thr Val Ser Ser
        115                 120

<210> SEQ ID NO 396
<211> LENGTH: 218
<212> TYPE: PRT
<213> ORGANISM: Artificial Sequence
<220> FEATURE:
<223> OTHER INFORMATION: Synthetic

<400> SEQUENCE: 396

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Ser Gly Gln Thr Tyr Leu His Trp Tyr Gln Gln Lys Pro Gly Gln Ser
            35                  40                  45

Pro Gln Leu Leu Ile Tyr Thr Val Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ser Gln Ser
                85                  90                  95

Thr His Val Pro Thr Phe Gly Gly Gly Thr Lys Val Glu Ile Lys Arg
```

-continued

```
                    100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

```
<210> SEQ ID NO 397
<211> LENGTH: 111
<212> TYPE: PRT
<213> ORGANISM: Artificial Sequence
<220> FEATURE:
<223> OTHER INFORMATION: Synthetic

<400> SEQUENCE: 397

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Val His Ser
            20                  25                  30

Ser Gly Gln Thr Tyr Leu His Trp Tyr Gln Gln Lys Pro Gly Gln Ser
        35                  40                  45

Pro Gln Leu Leu Ile Tyr Thr Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Thr Tyr Tyr Cys Ser Gln Ser
                85                  90                  95

Thr His Val Pro Thr Phe Gly Gly Gly Thr Lys Val Glu Ile Lys
            100                 105                 110
```

```
<210> SEQ ID NO 398
<211> LENGTH: 7
<212> TYPE: PRT
<213> ORGANISM: Artificial Sequence
<220> FEATURE:
<223> OTHER INFORMATION: Synthetic

<400> SEQUENCE: 398

Gly Tyr Thr Phe Thr Tyr Phe
1               5
```

```
<210> SEQ ID NO 399
<211> LENGTH: 17
<212> TYPE: PRT
<213> ORGANISM: Artificial Sequence
<220> FEATURE:
<223> OTHER INFORMATION: Synthetic

<400> SEQUENCE: 399

Gly Ile Ser Pro Gly Asp Ser Asn Val Asn Tyr Ala Gln Lys Phe Gln
1               5                  10                  15
```

-continued

Gly

```
<210> SEQ ID NO 400
<211> LENGTH: 11
<212> TYPE: PRT
<213> ORGANISM: Artificial Sequence
<220> FEATURE:
<223> OTHER INFORMATION: Synthetic

<400> SEQUENCE: 400

Asp Gly Asn Phe Pro Tyr Tyr Ala Met Asp Ser
1               5                   10

<210> SEQ ID NO 401
<211> LENGTH: 16
<212> TYPE: PRT
<213> ORGANISM: Artificial Sequence
<220> FEATURE:
<223> OTHER INFORMATION: Synthetic

<400> SEQUENCE: 401

Arg Ser Ser Gln Ser Leu Val His Ser Ser Gly Gln Thr Tyr Leu His
1               5                   10                  15

<210> SEQ ID NO 402
<211> LENGTH: 7
<212> TYPE: PRT
<213> ORGANISM: Artificial Sequence
<220> FEATURE:
<223> OTHER INFORMATION: Synthetic

<400> SEQUENCE: 402

Thr Val Ser Asn Arg Ala Ser
1               5

<210> SEQ ID NO 403
<211> LENGTH: 8
<212> TYPE: PRT
<213> ORGANISM: Artificial Sequence
<220> FEATURE:
<223> OTHER INFORMATION: Synthetic

<400> SEQUENCE: 403

Ser Gln Ser Thr His Val Pro Thr
1               5

<210> SEQ ID NO 404
<211> LENGTH: 15
<212> TYPE: PRT
<213> ORGANISM: Artificial Sequence
<220> FEATURE:
<223> OTHER INFORMATION: Synthetic

<400> SEQUENCE: 404

Glu Pro Lys Ser Ser Asp Lys Thr His Thr Ser Pro Pro Ser Pro
1               5                   10                  15

<210> SEQ ID NO 405
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(8)
<223> OTHER INFORMATION: /note="Variant residues given in the sequence
```

-continued

```
      have no preference with respect to those in the annotations for
      variant positions"
<220> FEATURE:
<221> NAME/KEY: VARIANT
<222> LOCATION: (7)..(7)
<223> OTHER INFORMATION: /replace="Asp"

<400> SEQUENCE: 405

Ile Trp Gly Ile Gly Cys Asn Pro
1               5

<210> SEQ ID NO 406
<211> LENGTH: 10
<212> TYPE: PRT
<213> ORGANISM: Artificial Sequence
<220> FEATURE:
<223> OTHER INFORMATION: Synthetic

<400> SEQUENCE: 406

Ser Gly Tyr Ser Phe Thr Gly Tyr Thr Met
1               5                   10

<210> SEQ ID NO 407
<211> LENGTH: 10
<212> TYPE: PRT
<213> ORGANISM: Artificial Sequence
<220> FEATURE:
<223> OTHER INFORMATION: Synthetic

<400> SEQUENCE: 407

Ser Gly Tyr Ser Phe Thr Asp Tyr Thr Met
1               5                   10

<210> SEQ ID NO 408
<211> LENGTH: 10
<212> TYPE: PRT
<213> ORGANISM: Artificial Sequence
<220> FEATURE:
<223> OTHER INFORMATION: Synthetic

<400> SEQUENCE: 408

Ser Gly Phe Thr Phe Ser Asn Tyr Ala Met
1               5                   10

<210> SEQ ID NO 409
<211> LENGTH: 10
<212> TYPE: PRT
<213> ORGANISM: Artificial Sequence
<220> FEATURE:
<223> OTHER INFORMATION: Synthetic

<400> SEQUENCE: 409

Ser Gly Phe Thr Phe Ser Ser Tyr Ala Met
1               5                   10

<210> SEQ ID NO 410
<211> LENGTH: 10
<212> TYPE: PRT
<213> ORGANISM: Artificial Sequence
<220> FEATURE:
<223> OTHER INFORMATION: Synthetic

<400> SEQUENCE: 410

Ser Gly Tyr Ser Phe Thr Ala Tyr Asn Ile
1               5                   10

<210> SEQ ID NO 411
```

-continued

```
<211> LENGTH: 10
<212> TYPE: PRT
<213> ORGANISM: Artificial Sequence
<220> FEATURE:
<223> OTHER INFORMATION: Synthetic

<400> SEQUENCE: 411

Ser Gly Tyr Ser Phe Thr Ala Tyr Ser Met
1               5                   10

<210> SEQ ID NO 412
<211> LENGTH: 10
<212> TYPE: PRT
<213> ORGANISM: Artificial Sequence
<220> FEATURE:
<223> OTHER INFORMATION: Synthetic

<400> SEQUENCE: 412

Ser Gly Tyr Thr Phe Thr Asn Phe Ala Ile
1               5                   10

<210> SEQ ID NO 413
<211> LENGTH: 10
<212> TYPE: PRT
<213> ORGANISM: Artificial Sequence
<220> FEATURE:
<223> OTHER INFORMATION: Synthetic

<400> SEQUENCE: 413

Ser Gly Phe Asn Ile Lys Asp Thr Tyr Met
1               5                   10

<210> SEQ ID NO 414
<211> LENGTH: 10
<212> TYPE: PRT
<213> ORGANISM: Artificial Sequence
<220> FEATURE:
<223> OTHER INFORMATION: Synthetic

<400> SEQUENCE: 414

Ser Gly Tyr Ser Phe Thr Ser Tyr Trp Met
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Synthetic

<400> SEQUENCE: 415

Ser Gly Phe Ser Leu Thr Asn Tyr Asp Val
1               5                   10

<210> SEQ ID NO 416
<211> LENGTH: 10
<212> TYPE: PRT
<213> ORGANISM: Artificial Sequence
<220> FEATURE:
<223> OTHER INFORMATION: Synthetic

<400> SEQUENCE: 416

Ser Gly Phe Thr Phe Ser Asn Tyr Gly Met
1               5                   10

<210> SEQ ID NO 417
<211> LENGTH: 10
```

-continued

```
<212> TYPE: PRT
<213> ORGANISM: Artificial Sequence
<220> FEATURE:
<223> OTHER INFORMATION: Synthetic

<400> SEQUENCE: 417

Ser Gly Tyr Ile Phe Ala Asn Tyr Gly Met
1               5                   10

<210> SEQ ID NO 418
<211> LENGTH: 10
<212> TYPE: PRT
<213> ORGANISM: Artificial Sequence
<220> FEATURE:
<223> OTHER INFORMATION: Synthetic

<400> SEQUENCE: 418

Ser Gly Tyr Asn Phe Thr Asn Tyr Gly Met
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Synthetic

<400> SEQUENCE: 419

Ser Gly Tyr Thr Phe Thr Asn Tyr Gly Met
1               5                   10

<210> SEQ ID NO 420
<211> LENGTH: 10
<212> TYPE: PRT
<213> ORGANISM: Artificial Sequence
<220> FEATURE:
<223> OTHER INFORMATION: Synthetic

<400> SEQUENCE: 420

Ser Gly Tyr Thr Phe Thr Asp Tyr Tyr Ile
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Synthetic

<400> SEQUENCE: 421

Ser Gly Asn Thr Phe Thr Asn Phe Tyr Leu
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Synthetic

<400> SEQUENCE: 422

Ser Glu Phe Thr Phe Ser Asn Tyr Ala Met
1               5                   10

<210> SEQ ID NO 423
<211> LENGTH: 10
<212> TYPE: PRT
```

<213> ORGANISM: Artificial Sequence
<220> FEATURE:
<223> OTHER INFORMATION: Synthetic

<400> SEQUENCE: 423

Ser Gly Tyr Thr Phe Thr Ser Tyr Arg Met
1               5                   10

<210> SEQ ID NO 424
<211> LENGTH: 10
<212> TYPE: PRT
<213> ORGANISM: Artificial Sequence
<220> FEATURE:
<223> OTHER INFORMATION: Synthetic

<400> SEQUENCE: 424

Ser Gly Tyr Met Phe Thr Asn His Gly Met
1               5                   10

<210> SEQ ID NO 425
<211> LENGTH: 10
<212> TYPE: PRT
<213> ORGANISM: Artificial Sequence
<220> FEATURE:
<223> OTHER INFORMATION: Synthetic

<400> SEQUENCE: 425

Ser Gly Tyr Met Phe Thr Asn Tyr Gly Met
1               5                   10

<210> SEQ ID NO 426
<211> LENGTH: 10
<212> TYPE: PRT
<213> ORGANISM: Artificial Sequence
<220> FEATURE:
<223> OTHER INFORMATION: Synthetic

<400> SEQUENCE: 426

Ser Gly Tyr Ile Phe Thr Asn Tyr Gly Met
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Synthetic

<400> SEQUENCE: 427

Ser Gly Phe Asn Ile Lys Asp Tyr Tyr Ile
1               5                   10

<210> SEQ ID NO 428
<211> LENGTH: 10
<212> TYPE: PRT
<213> ORGANISM: Artificial Sequence
<220> FEATURE:
<223> OTHER INFORMATION: Synthetic

<400> SEQUENCE: 428

Ser Gly Tyr Thr Phe Ile Asn Tyr Gly Met
1               5                   10

<210> SEQ ID NO 429
<211> LENGTH: 10
<212> TYPE: PRT
<213> ORGANISM: Artificial Sequence
<220> FEATURE:
<223> OTHER INFORMATION: Synthetic

<400> SEQUENCE: 429

Ser Gly Tyr Thr Phe Thr Asp Tyr Phe Ile
1               5                   10

<210> SEQ ID NO 430
<211> LENGTH: 10
<212> TYPE: PRT
<213> ORGANISM: Artificial Sequence
<220> FEATURE:
<223> OTHER INFORMATION: Synthetic

<400> SEQUENCE: 430

Ser Gly Tyr Ile Phe Thr Gly Tyr Asn Ile
1               5                   10

<210> SEQ ID NO 431
<211> LENGTH: 10
<212> TYPE: PRT
<213> ORGANISM: Artificial Sequence
<220> FEATURE:
<223> OTHER INFORMATION: Synthetic

<400> SEQUENCE: 431

Leu Ile Asn Pro Tyr Asn Gly Gly Thr Thr
1               5                   10

<210> SEQ ID NO 432
<211> LENGTH: 10
<212> TYPE: PRT
<213> ORGANISM: Artificial Sequence
<220> FEATURE:
<223> OTHER INFORMATION: Synthetic

<400> SEQUENCE: 432

Leu Ile Asn Pro Tyr Asn Gly Gly Thr Met
1               5                   10

<210> SEQ ID NO 433
<211> LENGTH: 9
<212> TYPE: PRT
<213> ORGANISM: Artificial Sequence
<220> FEATURE:
<223> OTHER INFORMATION: Synthetic

<400> SEQUENCE: 433

Ser Ile Ser Ser Gly Gly Asn Thr Phe
1               5

<210> SEQ ID NO 434
<211> LENGTH: 9
<212> TYPE: PRT
<213> ORGANISM: Artificial Sequence
<220> FEATURE:
<223> OTHER INFORMATION: Synthetic

<400> SEQUENCE: 434

Ser Ile Ser Ser Gly Gly Ser Thr Tyr
1               5

<210> SEQ ID NO 435
<211> LENGTH: 10
<212> TYPE: PRT
<213> ORGANISM: Artificial Sequence
<220> FEATURE:

-continued

```
<223> OTHER INFORMATION: Synthetic

<400> SEQUENCE: 435

Ser Ile Asp Pro Tyr Tyr Gly Asp Thr Lys
1               5                   10

<210> SEQ ID NO 436
<211> LENGTH: 10
<212> TYPE: PRT
<213> ORGANISM: Artificial Sequence
<220> FEATURE:
<223> OTHER INFORMATION: Synthetic

<400> SEQUENCE: 436

Leu Ile Ser Ser Asn Ser Gly Asp Val Ser
1               5                   10

<210> SEQ ID NO 437
<211> LENGTH: 10
<212> TYPE: PRT
<213> ORGANISM: Artificial Sequence
<220> FEATURE:
<223> OTHER INFORMATION: Synthetic

<400> SEQUENCE: 437

Leu Ile Ser Thr Ser Ser Gly Asp Val Ser
1               5                   10

<210> SEQ ID NO 438
<211> LENGTH: 10
<212> TYPE: PRT
<213> ORGANISM: Artificial Sequence
<220> FEATURE:
<223> OTHER INFORMATION: Synthetic

<400> SEQUENCE: 438

Arg Ile Asp Pro Ala Asn Gly Asn Thr Lys
1               5                   10

<210> SEQ ID NO 439
<211> LENGTH: 10
<212> TYPE: PRT
<213> ORGANISM: Artificial Sequence
<220> FEATURE:
<223> OTHER INFORMATION: Synthetic

<400> SEQUENCE: 439

Met Ile His Pro Ser Asp Ser Glu Thr Arg
1               5                   10

<210> SEQ ID NO 440
<211> LENGTH: 9
<212> TYPE: PRT
<213> ORGANISM: Artificial Sequence
<220> FEATURE:
<223> OTHER INFORMATION: Synthetic

<400> SEQUENCE: 440

Val Ile Trp Ser Gly Gly Asn Thr Asp
1               5

<210> SEQ ID NO 441
<211> LENGTH: 10
<212> TYPE: PRT
<213> ORGANISM: Artificial Sequence
<220> FEATURE:
<223> OTHER INFORMATION: Synthetic
```

<400> SEQUENCE: 441

Ala Ile Asn Ser Asn Gly Asp Ile Thr Tyr
1               5                   10

<210> SEQ ID NO 442
<211> LENGTH: 10
<212> TYPE: PRT
<213> ORGANISM: Artificial Sequence
<220> FEATURE:
<223> OTHER INFORMATION: Synthetic

<400> SEQUENCE: 442

Leu Ile Asn Pro Tyr Asn Gly Gly Thr Arg
1               5                   10

<210> SEQ ID NO 443
<211> LENGTH: 10
<212> TYPE: PRT
<213> ORGANISM: Artificial Sequence
<220> FEATURE:
<223> OTHER INFORMATION: Synthetic

<400> SEQUENCE: 443

Trp Ile Asn Thr Tyr Thr Gly Glu Pro Thr
1               5                   10

<210> SEQ ID NO 444
<211> LENGTH: 10
<212> TYPE: PRT
<213> ORGANISM: Artificial Sequence
<220> FEATURE:
<223> OTHER INFORMATION: Synthetic

<400> SEQUENCE: 444

Trp Ile Tyr Pro Gly Gly Gly Asn Thr Arg
1               5                   10

<210> SEQ ID NO 445
<211> LENGTH: 10
<212> TYPE: PRT
<213> ORGANISM: Artificial Sequence
<220> FEATURE:
<223> OTHER INFORMATION: Synthetic

<400> SEQUENCE: 445

Cys Ile Tyr Pro Gly Asn Val Lys Thr Lys
1               5                   10

<210> SEQ ID NO 446
<211> LENGTH: 10
<212> TYPE: PRT
<213> ORGANISM: Artificial Sequence
<220> FEATURE:
<223> OTHER INFORMATION: Synthetic

<400> SEQUENCE: 446

Thr Ile Ser Ser Gly Gly Ser Tyr Thr Tyr
1               5                   10

<210> SEQ ID NO 447
<211> LENGTH: 10
<212> TYPE: PRT
<213> ORGANISM: Artificial Sequence
<220> FEATURE:
<223> OTHER INFORMATION: Synthetic -continued

```
<400> SEQUENCE: 447

Arg Ile Asp Pro Tyr Asp Ser Gly Thr His
1               5                   10

<210> SEQ ID NO 448
<211> LENGTH: 10
<212> TYPE: PRT
<213> ORGANISM: Artificial Sequence
<220> FEATURE:
<223> OTHER INFORMATION: Synthetic

<400> SEQUENCE: 448

Trp Ile Asp Pro Glu Asn Gly Arg Thr Glu
1               5                   10

<210> SEQ ID NO 449
<211> LENGTH: 10
<212> TYPE: PRT
<213> ORGANISM: Artificial Sequence
<220> FEATURE:
<223> OTHER INFORMATION: Synthetic

<400> SEQUENCE: 449

Glu Ile Tyr Pro Gly Ser Ser Asn Thr Tyr
1               5                   10

<210> SEQ ID NO 450
<211> LENGTH: 10
<212> TYPE: PRT
<213> ORGANISM: Artificial Sequence
<220> FEATURE:
<223> OTHER INFORMATION: Synthetic

<400> SEQUENCE: 450

Ala Val Tyr Pro Gly Asn Gly Asp Thr Ser
1               5                   10

<210> SEQ ID NO 451
<211> LENGTH: 15
<212> TYPE: PRT
<213> ORGANISM: Artificial Sequence
<220> FEATURE:
<223> OTHER INFORMATION: Synthetic

<400> SEQUENCE: 451

Cys Ala Arg Asp Tyr Tyr Gly Ser Ser Pro Asp Phe Asp Tyr Trp
1               5                   10                  15

<210> SEQ ID NO 452
<211> LENGTH: 15
<212> TYPE: PRT
<213> ORGANISM: Artificial Sequence
<220> FEATURE:
<223> OTHER INFORMATION: Synthetic

<400> SEQUENCE: 452

Cys Ala Arg Asp Asn Tyr Gly Ser Ser Pro Asp Phe Asp Tyr Trp
1               5                   10                  15

<210> SEQ ID NO 453
<211> LENGTH: 15
<212> TYPE: PRT
<213> ORGANISM: Artificial Sequence
<220> FEATURE:
<223> OTHER INFORMATION: Synthetic

<400> SEQUENCE: 453
```

```
Cys Ala Arg Asp Asn Tyr Gly Ser Ser Pro Tyr Phe Asp Tyr Trp
1               5                   10                  15
```

<210> SEQ ID NO 454
<211> LENGTH: 16
<212> TYPE: PRT
<213> ORGANISM: Artificial Sequence
<220> FEATURE:
<223> OTHER INFORMATION: Synthetic

<400> SEQUENCE: 454

```
Cys Val Arg Tyr Tyr Tyr Gly Val Thr Tyr Trp Tyr Phe Asp Val Trp
1               5                   10                  15
```

<210> SEQ ID NO 455
<211> LENGTH: 16
<212> TYPE: PRT
<213> ORGANISM: Artificial Sequence
<220> FEATURE:
<223> OTHER INFORMATION: Synthetic

<400> SEQUENCE: 455

```
Cys Val Arg Tyr Tyr Tyr Gly Ile Arg Tyr Trp Tyr Phe Asp Val Trp
1               5                   10                  15
```

<210> SEQ ID NO 456
<211> LENGTH: 16
<212> TYPE: PRT
<213> ORGANISM: Artificial Sequence
<220> FEATURE:
<223> OTHER INFORMATION: Synthetic

<400> SEQUENCE: 456

```
Cys Ala Arg Arg Met Ile Thr Met Gly Asp Trp Tyr Phe Asp Val Trp
1               5                   10                  15
```

<210> SEQ ID NO 457
<211> LENGTH: 16
<212> TYPE: PRT
<213> ORGANISM: Artificial Sequence
<220> FEATURE:
<223> OTHER INFORMATION: Synthetic

<400> SEQUENCE: 457

```
Cys Ala Arg Arg Met Ile Thr Thr Gly Asp Trp Tyr Phe Asp Val Trp
1               5                   10                  15
```

<210> SEQ ID NO 458
<211> LENGTH: 14
<212> TYPE: PRT
<213> ORGANISM: Artificial Sequence
<220> FEATURE:
<223> OTHER INFORMATION: Synthetic

<400> SEQUENCE: 458

```
Cys Ala Arg His Tyr Gly Ala His Asn Tyr Phe Asp Tyr Trp
1               5                   10
```

<210> SEQ ID NO 459
<211> LENGTH: 14
<212> TYPE: PRT
<213> ORGANISM: Artificial Sequence
<220> FEATURE:
<223> OTHER INFORMATION: Synthetic

<400> SEQUENCE: 459

-continued

```
Cys Ala Arg His Tyr Gly Ala Asn Asn Tyr Phe Asp Tyr Trp
1               5                   10

<210> SEQ ID NO 460
<211> LENGTH: 16
<212> TYPE: PRT
<213> ORGANISM: Artificial Sequence
<220> FEATURE:
<223> OTHER INFORMATION: Synthetic

<400> SEQUENCE: 460

Cys Ala Arg Glu Glu Asn Tyr Tyr Gly Thr Tyr Tyr Phe Asp Tyr Trp
1               5                   10                  15

<210> SEQ ID NO 461
<211> LENGTH: 14
<212> TYPE: PRT
<213> ORGANISM: Artificial Sequence
<220> FEATURE:
<223> OTHER INFORMATION: Synthetic

<400> SEQUENCE: 461

Cys Ala Arg Trp Gly Asp His Asp Asp Ala Met Asp Phe Trp
1               5                   10

<210> SEQ ID NO 462
<211> LENGTH: 17
<212> TYPE: PRT
<213> ORGANISM: Artificial Sequence
<220> FEATURE:
<223> OTHER INFORMATION: Synthetic

<400> SEQUENCE: 462

Cys Ala Arg Asn His Gly Asp Gly Tyr Phe Asn Trp Tyr Phe Asp Val
1               5                   10                  15

Trp

<210> SEQ ID NO 463
<211> LENGTH: 17
<212> TYPE: PRT
<213> ORGANISM: Artificial Sequence
<220> FEATURE:
<223> OTHER INFORMATION: Synthetic

<400> SEQUENCE: 463

Cys Ala Arg Asn His Gly Asp Gly Tyr Tyr Asn Trp Tyr Phe Asp Val
1               5                   10                  15

Trp

<210> SEQ ID NO 464
<211> LENGTH: 11
<212> TYPE: PRT
<213> ORGANISM: Artificial Sequence
<220> FEATURE:
<223> OTHER INFORMATION: Synthetic

<400> SEQUENCE: 464

Cys Ala Arg Gly Thr Ala Trp Phe Thr Tyr Trp
1               5                   10

<210> SEQ ID NO 465
<211> LENGTH: 14
<212> TYPE: PRT
<213> ORGANISM: Artificial Sequence
<220> FEATURE:
<223> OTHER INFORMATION: Synthetic
```

<400> SEQUENCE: 465

Cys Ala Arg Asp Gly Asp Asp Gly Trp Asp Ile Asp Val Trp
1               5                   10

<210> SEQ ID NO 466
<211> LENGTH: 13
<212> TYPE: PRT
<213> ORGANISM: Artificial Sequence
<220> FEATURE:
<223> OTHER INFORMATION: Synthetic

<400> SEQUENCE: 466

Cys Ala Arg Arg Gly Thr Tyr Trp His Phe Asp Val Trp
1               5                   10

<210> SEQ ID NO 467
<211> LENGTH: 13
<212> TYPE: PRT
<213> ORGANISM: Artificial Sequence
<220> FEATURE:
<223> OTHER INFORMATION: Synthetic

<400> SEQUENCE: 467

Cys Ala Arg Arg Gly Ser Tyr Trp His Phe Asp Val Trp
1               5                   10

<210> SEQ ID NO 468
<211> LENGTH: 12
<212> TYPE: PRT
<213> ORGANISM: Artificial Sequence
<220> FEATURE:
<223> OTHER INFORMATION: Synthetic

<400> SEQUENCE: 468

Cys Ala Arg Arg Ser Thr Leu Val Phe Asp Tyr Trp
1               5                   10

<210> SEQ ID NO 469
<211> LENGTH: 12
<212> TYPE: PRT
<213> ORGANISM: Artificial Sequence
<220> FEATURE:
<223> OTHER INFORMATION: Synthetic

<400> SEQUENCE: 469

Cys Ala Arg Asn Gly Tyr Trp Tyr Phe Asp Val Trp
1               5                   10

<210> SEQ ID NO 470
<211> LENGTH: 16
<212> TYPE: PRT
<213> ORGANISM: Artificial Sequence
<220> FEATURE:
<223> OTHER INFORMATION: Synthetic

<400> SEQUENCE: 470

Cys Ala Lys Glu Gly Asp Tyr Asp Gly Thr Ala Tyr Phe Asp Tyr Trp
1               5                   10                  15

<210> SEQ ID NO 471
<211> LENGTH: 12
<212> TYPE: PRT
<213> ORGANISM: Artificial Sequence
<220> FEATURE:
<223> OTHER INFORMATION: Synthetic

<400> SEQUENCE: 471

Cys Ala Arg Arg Arg Asp Gly Asn Phe Asp Tyr Trp
1               5                   10

<210> SEQ ID NO 472
<211> LENGTH: 10
<212> TYPE: PRT
<213> ORGANISM: Artificial Sequence
<220> FEATURE:
<223> OTHER INFORMATION: Synthetic

<400> SEQUENCE: 472

Cys Val Arg His Gly Tyr Phe Asp Val Trp
1               5                   10

<210> SEQ ID NO 473
<211> LENGTH: 9
<212> TYPE: PRT
<213> ORGANISM: Artificial Sequence
<220> FEATURE:
<223> OTHER INFORMATION: Synthetic

<400> SEQUENCE: 473

Cys Ala Phe Tyr Asp Gly Ala Tyr Trp
1               5

<210> SEQ ID NO 474
<211> LENGTH: 9
<212> TYPE: PRT
<213> ORGANISM: Artificial Sequence
<220> FEATURE:
<223> OTHER INFORMATION: Synthetic

<400> SEQUENCE: 474

Cys Ala Ser Tyr Asp Pro Asp Tyr Trp
1               5

<210> SEQ ID NO 475
<211> LENGTH: 14
<212> TYPE: PRT
<213> ORGANISM: Artificial Sequence
<220> FEATURE:
<223> OTHER INFORMATION: Synthetic

<400> SEQUENCE: 475

Cys Ala Arg Asp Thr Thr Ala Thr Tyr Tyr Phe Asp Tyr Trp
1               5                   10

<210> SEQ ID NO 476
<211> LENGTH: 12
<212> TYPE: PRT
<213> ORGANISM: Artificial Sequence
<220> FEATURE:
<223> OTHER INFORMATION: Synthetic

<400> SEQUENCE: 476

Cys Ala Arg Arg Val Ala Thr Tyr Phe Asp Val Trp
1               5                   10

<210> SEQ ID NO 477
<211> LENGTH: 12
<212> TYPE: PRT
<213> ORGANISM: Artificial Sequence
<220> FEATURE:
<223> OTHER INFORMATION: Synthetic

<400> SEQUENCE: 477

-continued

```
Cys Thr Arg Arg Ser His Ile Thr Leu Asp Tyr Trp
1               5                   10

<210> SEQ ID NO 478
<211> LENGTH: 12
<212> TYPE: PRT
<213> ORGANISM: Artificial Sequence
<220> FEATURE:
<223> OTHER INFORMATION: Synthetic

<400> SEQUENCE: 478

Cys Ala Arg Arg Arg Thr Thr Ala Phe Asp Tyr Trp
1               5                   10

<210> SEQ ID NO 479
<211> LENGTH: 15
<212> TYPE: PRT
<213> ORGANISM: Artificial Sequence
<220> FEATURE:
<223> OTHER INFORMATION: Synthetic

<400> SEQUENCE: 479

Cys Asn Asn Gly Asn Tyr Val Arg His Tyr Tyr Phe Asp Tyr Trp
1               5                   10                  15

<210> SEQ ID NO 480
<211> LENGTH: 12
<212> TYPE: PRT
<213> ORGANISM: Artificial Sequence
<220> FEATURE:
<223> OTHER INFORMATION: Synthetic

<400> SEQUENCE: 480

Cys Thr Arg Arg Arg Glu Ile Thr Phe Asp Tyr Trp
1               5                   10

<210> SEQ ID NO 481
<211> LENGTH: 12
<212> TYPE: PRT
<213> ORGANISM: Artificial Sequence
<220> FEATURE:
<223> OTHER INFORMATION: Synthetic

<400> SEQUENCE: 481

Cys Ala Arg Ser Gly Ile Ser Pro Phe Thr Tyr Trp
1               5                   10

<210> SEQ ID NO 482
<211> LENGTH: 11
<212> TYPE: PRT
<213> ORGANISM: Artificial Sequence
<220> FEATURE:
<223> OTHER INFORMATION: Synthetic

<400> SEQUENCE: 482

Cys Ala Lys Tyr Asp Arg Phe Phe Ala Ser Trp
1               5                   10

<210> SEQ ID NO 483
<211> LENGTH: 8
<212> TYPE: PRT
<213> ORGANISM: Artificial Sequence
<220> FEATURE:
<223> OTHER INFORMATION: Synthetic

<400> SEQUENCE: 483
```

Ser Gln Gly Ile Ser Asn His Leu
1               5

<210> SEQ ID NO 484
<211> LENGTH: 8
<212> TYPE: PRT
<213> ORGANISM: Artificial Sequence
<220> FEATURE:
<223> OTHER INFORMATION: Synthetic

<400> SEQUENCE: 484

Ser Gln Gly Ile Arg Asn Tyr Leu
1               5

<210> SEQ ID NO 485
<211> LENGTH: 8
<212> TYPE: PRT
<213> ORGANISM: Artificial Sequence
<220> FEATURE:
<223> OTHER INFORMATION: Synthetic

<400> SEQUENCE: 485

Ser Gln Gly Ile Asn Asn Tyr Leu
1               5

<210> SEQ ID NO 486
<211> LENGTH: 12
<212> TYPE: PRT
<213> ORGANISM: Artificial Sequence
<220> FEATURE:
<223> OTHER INFORMATION: Synthetic

<400> SEQUENCE: 486

Ser Gln Ser Val Asp His Asp Gly Asp Ser Tyr Met
1               5                   10

<210> SEQ ID NO 487
<211> LENGTH: 12
<212> TYPE: PRT
<213> ORGANISM: Artificial Sequence
<220> FEATURE:
<223> OTHER INFORMATION: Synthetic

<400> SEQUENCE: 487

Ser Gln Ser Val Asp Tyr Asp Gly Asp Ser Tyr Met
1               5                   10

<210> SEQ ID NO 488
<211> LENGTH: 8
<212> TYPE: PRT
<213> ORGANISM: Artificial Sequence
<220> FEATURE:
<223> OTHER INFORMATION: Synthetic

<400> SEQUENCE: 488

Ser Gln Asp Ile Ser Asn Tyr Leu
1               5

<210> SEQ ID NO 489
<211> LENGTH: 8
<212> TYPE: PRT
<213> ORGANISM: Artificial Sequence
<220> FEATURE:
<223> OTHER INFORMATION: Synthetic

<400> SEQUENCE: 489

Ser Gln Asp Ile Ser Thr Tyr Leu

```
1               5

<210> SEQ ID NO 490
<211> LENGTH: 9
<212> TYPE: PRT
<213> ORGANISM: Artificial Sequence
<220> FEATURE:
<223> OTHER INFORMATION: Synthetic

<400> SEQUENCE: 490

Thr Ser Ser Ile Ser Ser Ser Tyr Leu
1               5

<210> SEQ ID NO 491
<211> LENGTH: 9
<212> TYPE: PRT
<213> ORGANISM: Artificial Sequence
<220> FEATURE:
<223> OTHER INFORMATION: Synthetic

<400> SEQUENCE: 491

Asn Ser Ser Val Ser Ser Ser Tyr Leu
1               5

<210> SEQ ID NO 492
<211> LENGTH: 8
<212> TYPE: PRT
<213> ORGANISM: Artificial Sequence
<220> FEATURE:
<223> OTHER INFORMATION: Synthetic

<400> SEQUENCE: 492

Ser Glu Asn Ile Tyr Tyr Asn Leu
1               5

<210> SEQ ID NO 493
<211> LENGTH: 8
<212> TYPE: PRT
<213> ORGANISM: Artificial Sequence
<220> FEATURE:
<223> OTHER INFORMATION: Synthetic

<400> SEQUENCE: 493

Ser Glu Asn Ile Tyr Gly Tyr Phe
1               5

<210> SEQ ID NO 494
<211> LENGTH: 8
<212> TYPE: PRT
<213> ORGANISM: Artificial Sequence
<220> FEATURE:
<223> OTHER INFORMATION: Synthetic

<400> SEQUENCE: 494

Ser Gln Asp Ile Asn Asn Tyr Ile
1               5

<210> SEQ ID NO 495
<211> LENGTH: 8
<212> TYPE: PRT
<213> ORGANISM: Artificial Sequence
<220> FEATURE:
<223> OTHER INFORMATION: Synthetic

<400> SEQUENCE: 495

Ser Gln Asp Ile Asn Lys Tyr Ile
1               5
```

-continued

```
<210> SEQ ID NO 496
<211> LENGTH: 8
<212> TYPE: PRT
<213> ORGANISM: Artificial Sequence
<220> FEATURE:
<223> OTHER INFORMATION: Synthetic

<400> SEQUENCE: 496

Ser Glu Asn Ile Tyr Ser Tyr Leu
1               5

<210> SEQ ID NO 497
<211> LENGTH: 8
<212> TYPE: PRT
<213> ORGANISM: Artificial Sequence
<220> FEATURE:
<223> OTHER INFORMATION: Synthetic

<400> SEQUENCE: 497

Ser Gln Asp Val Arg Thr Asp Val
1               5

<210> SEQ ID NO 498
<211> LENGTH: 8
<212> TYPE: PRT
<213> ORGANISM: Artificial Sequence
<220> FEATURE:
<223> OTHER INFORMATION: Synthetic

<400> SEQUENCE: 498

Ser Gln Asp Val Ile Thr Ala Val
1               5

<210> SEQ ID NO 499
<211> LENGTH: 8
<212> TYPE: PRT
<213> ORGANISM: Artificial Sequence
<220> FEATURE:
<223> OTHER INFORMATION: Synthetic

<400> SEQUENCE: 499

Ser Gln Ser Ile Gly Thr Ser Ile
1               5

<210> SEQ ID NO 500
<211> LENGTH: 12
<212> TYPE: PRT
<213> ORGANISM: Artificial Sequence
<220> FEATURE:
<223> OTHER INFORMATION: Synthetic

<400> SEQUENCE: 500

Ser Ser Gln Ser Leu Leu Asn Gln Lys Asn Tyr Leu
1               5                   10

<210> SEQ ID NO 501
<211> LENGTH: 9
<212> TYPE: PRT
<213> ORGANISM: Artificial Sequence
<220> FEATURE:
<223> OTHER INFORMATION: Synthetic

<400> SEQUENCE: 501

Ser Ser Ser Val Ser Ser Ser Tyr Leu
1               5
```

<210> SEQ ID NO 502
<211> LENGTH: 8
<212> TYPE: PRT
<213> ORGANISM: Artificial Sequence
<220> FEATURE:
<223> OTHER INFORMATION: Synthetic

<400> SEQUENCE: 502

Ser Gln Thr Ile Gly Thr Ser Ile
1               5

<210> SEQ ID NO 503
<211> LENGTH: 14
<212> TYPE: PRT
<213> ORGANISM: Artificial Sequence
<220> FEATURE:
<223> OTHER INFORMATION: Synthetic

<400> SEQUENCE: 503

Ser Gln Ser Leu Leu Tyr Ser Ser Asp Gln Lys Asn Tyr Leu
1               5                   10

<210> SEQ ID NO 504
<211> LENGTH: 7
<212> TYPE: PRT
<213> ORGANISM: Artificial Sequence
<220> FEATURE:
<223> OTHER INFORMATION: Synthetic

<400> SEQUENCE: 504

Asn Ser Ser Val Ser Tyr Met
1               5

<210> SEQ ID NO 505
<211> LENGTH: 7
<212> TYPE: PRT
<213> ORGANISM: Artificial Sequence
<220> FEATURE:
<223> OTHER INFORMATION: Synthetic

<400> SEQUENCE: 505

Ser Ser Ser Leu Ser Tyr Met
1               5

<210> SEQ ID NO 506
<211> LENGTH: 8
<212> TYPE: PRT
<213> ORGANISM: Artificial Sequence
<220> FEATURE:
<223> OTHER INFORMATION: Synthetic

<400> SEQUENCE: 506

Ser Gln Arg Ile Gly Thr Ser Met
1               5

<210> SEQ ID NO 507
<211> LENGTH: 8
<212> TYPE: PRT
<213> ORGANISM: Artificial Sequence
<220> FEATURE:
<223> OTHER INFORMATION: Synthetic

<400> SEQUENCE: 507

Ser Gln Asn Ile Gly Thr Ser Ile
1               5

-continued

```
<210> SEQ ID NO 508
<211> LENGTH: 7
<212> TYPE: PRT
<213> ORGANISM: Artificial Sequence
<220> FEATURE:
<223> OTHER INFORMATION: Synthetic

<400> SEQUENCE: 508

Ile Ser Ser Val Ser Tyr Met
1               5

<210> SEQ ID NO 509
<211> LENGTH: 8
<212> TYPE: PRT
<213> ORGANISM: Artificial Sequence
<220> FEATURE:
<223> OTHER INFORMATION: Synthetic

<400> SEQUENCE: 509

Ser Gln Thr Ile Ala Thr Ser Ile
1               5

<210> SEQ ID NO 510
<211> LENGTH: 13
<212> TYPE: PRT
<213> ORGANISM: Artificial Sequence
<220> FEATURE:
<223> OTHER INFORMATION: Synthetic

<400> SEQUENCE: 510

Ser Gln Ser Leu Val His Ser Asn Gly Asn Thr Tyr Leu
1               5                   10

<210> SEQ ID NO 511
<211> LENGTH: 12
<212> TYPE: PRT
<213> ORGANISM: Artificial Sequence
<220> FEATURE:
<223> OTHER INFORMATION: Synthetic

<400> SEQUENCE: 511

Asn Glu Ser Val Glu Tyr Ser Gly Thr Ser Leu Met
1               5                   10

<210> SEQ ID NO 512
<211> LENGTH: 5
<212> TYPE: PRT
<213> ORGANISM: Artificial Sequence
<220> FEATURE:
<223> OTHER INFORMATION: Synthetic

<400> SEQUENCE: 512

Tyr Phe Thr Ser Ser
1               5

<210> SEQ ID NO 513
<211> LENGTH: 5
<212> TYPE: PRT
<213> ORGANISM: Artificial Sequence
<220> FEATURE:
<223> OTHER INFORMATION: Synthetic

<400> SEQUENCE: 513

Tyr Tyr Thr Ser Ser
1               5

<210> SEQ ID NO 514
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 514

Tyr Ala Ala Ser Asn
1               5

<210> SEQ ID NO 515
<211> LENGTH: 5
<212> TYPE: PRT
<213> ORGANISM: Artificial Sequence
<220> FEATURE:
<223> OTHER INFORMATION: Synthetic

<400> SEQUENCE: 515

Tyr Tyr Thr Ser Arg
1               5

<210> SEQ ID NO 516
<211> LENGTH: 5
<212> TYPE: PRT
<213> ORGANISM: Artificial Sequence
<220> FEATURE:
<223> OTHER INFORMATION: Synthetic

<400> SEQUENCE: 516

Phe Tyr Thr Ser Arg
1               5

<210> SEQ ID NO 517
<211> LENGTH: 5
<212> TYPE: PRT
<213> ORGANISM: Artificial Sequence
<220> FEATURE:
<223> OTHER INFORMATION: Synthetic

<400> SEQUENCE: 517

Tyr Gly Thr Ser Asn
1               5

<210> SEQ ID NO 518
<211> LENGTH: 5
<212> TYPE: PRT
<213> ORGANISM: Artificial Sequence
<220> FEATURE:
<223> OTHER INFORMATION: Synthetic

<400> SEQUENCE: 518

Tyr Asn Ala Asn Ser
1               5

<210> SEQ ID NO 519
<211> LENGTH: 5
<212> TYPE: PRT
<213> ORGANISM: Artificial Sequence
<220> FEATURE:
<223> OTHER INFORMATION: Synthetic

<400> SEQUENCE: 519

Tyr Asn Ala Lys Thr
1               5

<210> SEQ ID NO 520
<211> LENGTH: 5
```

-continued

```
<212> TYPE: PRT
<213> ORGANISM: Artificial Sequence
<220> FEATURE:
<223> OTHER INFORMATION: Synthetic

<400> SEQUENCE: 520

His Tyr Thr Ser Thr
1               5

<210> SEQ ID NO 521
<211> LENGTH: 5
<212> TYPE: PRT
<213> ORGANISM: Artificial Sequence
<220> FEATURE:
<223> OTHER INFORMATION: Synthetic

<400> SEQUENCE: 521

Tyr His Thr Ser Thr
1               5

<210> SEQ ID NO 522
<211> LENGTH: 5
<212> TYPE: PRT
<213> ORGANISM: Artificial Sequence
<220> FEATURE:
<223> OTHER INFORMATION: Synthetic

<400> SEQUENCE: 522

Tyr Ser Ala Ser Phe
1               5

<210> SEQ ID NO 523
<211> LENGTH: 5
<212> TYPE: PRT
<213> ORGANISM: Artificial Sequence
<220> FEATURE:
<223> OTHER INFORMATION: Synthetic

<400> SEQUENCE: 523

Tyr Ser Ala Ser Tyr
1               5

<210> SEQ ID NO 524
<211> LENGTH: 5
<212> TYPE: PRT
<213> ORGANISM: Artificial Sequence
<220> FEATURE:
<223> OTHER INFORMATION: Synthetic

<400> SEQUENCE: 524

Lys Ser Ala Ser Glu
1               5

<210> SEQ ID NO 525
<211> LENGTH: 5
<212> TYPE: PRT
<213> ORGANISM: Artificial Sequence
<220> FEATURE:
<223> OTHER INFORMATION: Synthetic

<400> SEQUENCE: 525

Tyr Trp Ala Ser Thr
1               5

<210> SEQ ID NO 526
<211> LENGTH: 5
<212> TYPE: PRT
```

-continued

```
<213> ORGANISM: Artificial Sequence
<220> FEATURE:
<223> OTHER INFORMATION: Synthetic

<400> SEQUENCE: 526

Tyr Ser Thr Ser Asn
1               5

<210> SEQ ID NO 527
<211> LENGTH: 5
<212> TYPE: PRT
<213> ORGANISM: Artificial Sequence
<220> FEATURE:
<223> OTHER INFORMATION: Synthetic

<400> SEQUENCE: 527

Lys Asn Ala Ser Glu
1               5

<210> SEQ ID NO 528
<211> LENGTH: 5
<212> TYPE: PRT
<213> ORGANISM: Artificial Sequence
<220> FEATURE:
<223> OTHER INFORMATION: Synthetic

<400> SEQUENCE: 528

Tyr Asp Thr Ser Lys
1               5

<210> SEQ ID NO 529
<211> LENGTH: 5
<212> TYPE: PRT
<213> ORGANISM: Artificial Sequence
<220> FEATURE:
<223> OTHER INFORMATION: Synthetic

<400> SEQUENCE: 529

Tyr Asp Thr Ser Asn
1               5

<210> SEQ ID NO 530
<211> LENGTH: 5
<212> TYPE: PRT
<213> ORGANISM: Artificial Sequence
<220> FEATURE:
<223> OTHER INFORMATION: Synthetic

<400> SEQUENCE: 530

Lys Asp Ala Ser Glu
1               5

<210> SEQ ID NO 531
<211> LENGTH: 5
<212> TYPE: PRT
<213> ORGANISM: Artificial Sequence
<220> FEATURE:
<223> OTHER INFORMATION: Synthetic

<400> SEQUENCE: 531

Tyr Ala Thr Ser Asn
1               5

<210> SEQ ID NO 532
<211> LENGTH: 5
<212> TYPE: PRT
<213> ORGANISM: Artificial Sequence
```

<220> FEATURE:
<223> OTHER INFORMATION: Synthetic

<400> SEQUENCE: 532

Tyr Lys Val Ser Asn
1               5

<210> SEQ ID NO 533
<211> LENGTH: 5
<212> TYPE: PRT
<213> ORGANISM: Artificial Sequence
<220> FEATURE:
<223> OTHER INFORMATION: Synthetic

<400> SEQUENCE: 533

Ser Ala Ala Ser Asn
1               5

<210> SEQ ID NO 534
<211> LENGTH: 11
<212> TYPE: PRT
<213> ORGANISM: Artificial Sequence
<220> FEATURE:
<223> OTHER INFORMATION: Synthetic

<400> SEQUENCE: 534

Cys Gln Gln Tyr Ser Asn Leu Pro Tyr Thr Phe
1               5                   10

<210> SEQ ID NO 535
<211> LENGTH: 11
<212> TYPE: PRT
<213> ORGANISM: Artificial Sequence
<220> FEATURE:
<223> OTHER INFORMATION: Synthetic

<400> SEQUENCE: 535

Cys Gln Gln Tyr Ser Lys Ile Pro Tyr Thr Cys
1               5                   10

<210> SEQ ID NO 536
<211> LENGTH: 10
<212> TYPE: PRT
<213> ORGANISM: Artificial Sequence
<220> FEATURE:
<223> OTHER INFORMATION: Synthetic

<400> SEQUENCE: 536

Cys Gln Gln Asn Tyr Glu Asp Pro Thr Phe
1               5                   10

<210> SEQ ID NO 537
<211> LENGTH: 10
<212> TYPE: PRT
<213> ORGANISM: Artificial Sequence
<220> FEATURE:
<223> OTHER INFORMATION: Synthetic

<400> SEQUENCE: 537

Cys Gln Gln Ser Asn Glu Asp Pro Thr Phe
1               5                   10

<210> SEQ ID NO 538
<211> LENGTH: 11
<212> TYPE: PRT
<213> ORGANISM: Artificial Sequence
<220> FEATURE:

<223> OTHER INFORMATION: Synthetic

<400> SEQUENCE: 538

Cys Gln Gln Gly Asp Ala Leu Pro Trp Thr Phe
1               5                   10

<210> SEQ ID NO 539
<211> LENGTH: 11
<212> TYPE: PRT
<213> ORGANISM: Artificial Sequence
<220> FEATURE:
<223> OTHER INFORMATION: Synthetic

<400> SEQUENCE: 539

Cys Gln Gln Gly Asn Ser Leu Pro Phe Thr Phe
1               5                   10

<210> SEQ ID NO 540
<211> LENGTH: 11
<212> TYPE: PRT
<213> ORGANISM: Artificial Sequence
<220> FEATURE:
<223> OTHER INFORMATION: Synthetic

<400> SEQUENCE: 540

Cys Gln Gln Trp Ser Ser Arg Pro Pro Thr Phe
1               5                   10

<210> SEQ ID NO 541
<211> LENGTH: 11
<212> TYPE: PRT
<213> ORGANISM: Artificial Sequence
<220> FEATURE:
<223> OTHER INFORMATION: Synthetic

<400> SEQUENCE: 541

Cys Gln Gln Tyr Ser Gly Tyr Pro Leu Thr Phe
1               5                   10

<210> SEQ ID NO 542
<211> LENGTH: 11
<212> TYPE: PRT
<213> ORGANISM: Artificial Sequence
<220> FEATURE:
<223> OTHER INFORMATION: Synthetic

<400> SEQUENCE: 542

Cys Gln Gln Tyr Ser Asp Tyr Pro Leu Thr Phe
1               5                   10

<210> SEQ ID NO 543
<211> LENGTH: 11
<212> TYPE: PRT
<213> ORGANISM: Artificial Sequence
<220> FEATURE:
<223> OTHER INFORMATION: Synthetic

<400> SEQUENCE: 543

Cys Gln Gln Arg Ser Tyr Phe Pro Phe Thr Phe
1               5                   10

<210> SEQ ID NO 544
<211> LENGTH: 11
<212> TYPE: PRT
<213> ORGANISM: Artificial Sequence
<220> FEATURE:
<223> OTHER INFORMATION: Synthetic

<400> SEQUENCE: 544

Cys Lys Gln Val Tyr Asp Val Pro Phe Thr Phe
1               5                   10

<210> SEQ ID NO 545
<211> LENGTH: 11
<212> TYPE: PRT
<213> ORGANISM: Artificial Sequence
<220> FEATURE:
<223> OTHER INFORMATION: Synthetic

<400> SEQUENCE: 545

Cys Gln His His Tyr Gly Thr Pro Phe Thr Phe
1               5                   10

<210> SEQ ID NO 546
<211> LENGTH: 10
<212> TYPE: PRT
<213> ORGANISM: Artificial Sequence
<220> FEATURE:
<223> OTHER INFORMATION: Synthetic

<400> SEQUENCE: 546

Cys Leu Gln Tyr Asp Asn Leu Trp Thr Phe
1               5                   10

<210> SEQ ID NO 547
<211> LENGTH: 11
<212> TYPE: PRT
<213> ORGANISM: Artificial Sequence
<220> FEATURE:
<223> OTHER INFORMATION: Synthetic

<400> SEQUENCE: 547

Cys Gln His His Tyr Gly Tyr Pro Tyr Thr Phe
1               5                   10

<210> SEQ ID NO 548
<211> LENGTH: 11
<212> TYPE: PRT
<213> ORGANISM: Artificial Sequence
<220> FEATURE:
<223> OTHER INFORMATION: Synthetic

<400> SEQUENCE: 548

Cys Gln Gln Tyr Ser Asn Leu Pro Leu Thr Phe
1               5                   10

<210> SEQ ID NO 549
<211> LENGTH: 11
<212> TYPE: PRT
<213> ORGANISM: Artificial Sequence
<220> FEATURE:
<223> OTHER INFORMATION: Synthetic

<400> SEQUENCE: 549

Cys Gln Gln His Tyr Thr Ser Pro Trp Thr Phe
1               5                   10

<210> SEQ ID NO 550
<211> LENGTH: 11
<212> TYPE: PRT
<213> ORGANISM: Artificial Sequence
<220> FEATURE:
<223> OTHER INFORMATION: Synthetic

```
<400> SEQUENCE: 550

Cys Gln Gln His Tyr Ser Thr Pro Trp Thr Phe
1               5                   10

<210> SEQ ID NO 551
<211> LENGTH: 11
<212> TYPE: PRT
<213> ORGANISM: Artificial Sequence
<220> FEATURE:
<223> OTHER INFORMATION: Synthetic

<400> SEQUENCE: 551

Cys Gln Gln Ser Asn Arg Trp Pro Leu Thr Phe
1               5                   10

<210> SEQ ID NO 552
<211> LENGTH: 11
<212> TYPE: PRT
<213> ORGANISM: Artificial Sequence
<220> FEATURE:
<223> OTHER INFORMATION: Synthetic

<400> SEQUENCE: 552

Cys Gln Asn Asp Tyr Asp Tyr Pro Tyr Thr Phe
1               5                   10

<210> SEQ ID NO 553
<211> LENGTH: 11
<212> TYPE: PRT
<213> ORGANISM: Artificial Sequence
<220> FEATURE:
<223> OTHER INFORMATION: Synthetic

<400> SEQUENCE: 553

Cys His Gln Tyr His Arg Ser Pro Leu Thr Phe
1               5                   10

<210> SEQ ID NO 554
<211> LENGTH: 11
<212> TYPE: PRT
<213> ORGANISM: Artificial Sequence
<220> FEATURE:
<223> OTHER INFORMATION: Synthetic

<400> SEQUENCE: 554

Cys Gln Gln Thr Phe Asp Val Pro Trp Thr Phe
1               5                   10

<210> SEQ ID NO 555
<211> LENGTH: 11
<212> TYPE: PRT
<213> ORGANISM: Artificial Sequence
<220> FEATURE:
<223> OTHER INFORMATION: Synthetic

<400> SEQUENCE: 555

Cys Gln Gln Ser Asn Ser Trp Pro Leu Thr Tyr
1               5                   10

<210> SEQ ID NO 556
<211> LENGTH: 11
<212> TYPE: PRT
<213> ORGANISM: Artificial Sequence
<220> FEATURE:
<223> OTHER INFORMATION: Synthetic

<400> SEQUENCE: 556
```

-continued

```
Cys Gln Gln Tyr Tyr Asn Tyr Pro Leu Thr Phe
1               5                   10

<210> SEQ ID NO 557
<211> LENGTH: 11
<212> TYPE: PRT
<213> ORGANISM: Artificial Sequence
<220> FEATURE:
<223> OTHER INFORMATION: Synthetic

<400> SEQUENCE: 557

Cys Gln Gln Trp Ser Ser Asn Pro Phe Thr Phe
1               5                   10

<210> SEQ ID NO 558
<211> LENGTH: 11
<212> TYPE: PRT
<213> ORGANISM: Artificial Sequence
<220> FEATURE:
<223> OTHER INFORMATION: Synthetic

<400> SEQUENCE: 558

Cys Lys Gln Ala Tyr Asp Val Pro Trp Thr Phe
1               5                   10

<210> SEQ ID NO 559
<211> LENGTH: 11
<212> TYPE: PRT
<213> ORGANISM: Artificial Sequence
<220> FEATURE:
<223> OTHER INFORMATION: Synthetic

<400> SEQUENCE: 559

Cys Gln Gln Trp Ser Ser Phe Pro Pro Thr Phe
1               5                   10

<210> SEQ ID NO 560
<211> LENGTH: 11
<212> TYPE: PRT
<213> ORGANISM: Artificial Sequence
<220> FEATURE:
<223> OTHER INFORMATION: Synthetic

<400> SEQUENCE: 560

Cys Gln Gln Ser Asn Ser Trp Pro Leu Thr Phe
1               5                   10

<210> SEQ ID NO 561
<211> LENGTH: 11
<212> TYPE: PRT
<213> ORGANISM: Artificial Sequence
<220> FEATURE:
<223> OTHER INFORMATION: Synthetic

<400> SEQUENCE: 561

Cys Gln Gln Ser Asp Ser Trp Pro Leu Thr Phe
1               5                   10

<210> SEQ ID NO 562
<211> LENGTH: 11
<212> TYPE: PRT
<213> ORGANISM: Artificial Sequence
<220> FEATURE:
<223> OTHER INFORMATION: Synthetic

<400> SEQUENCE: 562
```

-continued

```
Cys Gln Gln Trp Ser Ser Asn Pro Arg Thr Phe
1               5               10

<210> SEQ ID NO 563
<211> LENGTH: 11
<212> TYPE: PRT
<213> ORGANISM: Artificial Sequence
<220> FEATURE:
<223> OTHER INFORMATION: Synthetic

<400> SEQUENCE: 563

Cys Trp Gln Asn Thr His Phe Pro Gln Thr Phe
1               5               10

<210> SEQ ID NO 564
<211> LENGTH: 11
<212> TYPE: PRT
<213> ORGANISM: Artificial Sequence
<220> FEATURE:
<223> OTHER INFORMATION: Synthetic

<400> SEQUENCE: 564

Cys Gln Gln Ser Arg Gln Val Pro Leu Thr Phe
1               5               10
```